US012116412B2

(12) United States Patent
Meruelo et al.

(10) Patent No.: US 12,116,412 B2
(45) Date of Patent: Oct. 15, 2024

(54) INDUCTION AND ENHANCEMENT OF ANTITUMOR IMMUNITY INVOLVING VIRUS VECTORS EXPRESSING MULTIPLE EPITOPES OF TUMOR ASSOCIATED ANTIGENS AND IMMUNE CHECKPOINT INHIBITORS OR PROTEINS

(71) Applicant: NEW YORK UNIVERSITY, New York, NY (US)

(72) Inventors: Daniel Meruelo, Scarborough, NY (US); Alicia Hurtado Martinez, New York, NY (US); Christine Pampeno, New York, NY (US); Iris Scherwitzl, Hoboken, NJ (US)

(73) Assignee: New York University, New York, NY (US)

( * ) Notice: Subject to any disclaimer, the term of this patent is extended or adjusted under 35 U.S.C. 154(b) by 944 days.

(21) Appl. No.: 16/489,769

(22) PCT Filed: Mar. 5, 2018

(86) PCT No.: PCT/US2018/020985
§ 371 (c)(1),
(2) Date: Aug. 29, 2019

(87) PCT Pub. No.: WO2018/161092
PCT Pub. Date: Sep. 7, 2018

(65) Prior Publication Data

US 2020/0377598 A1 Dec. 3, 2020

Related U.S. Application Data

(60) Provisional application No. 62/575,179, filed on Oct. 20, 2017, provisional application No. 62/466,761, filed on Mar. 3, 2017.

(51) Int. Cl.

| | |
|---|---|
| ***C07K 16/28*** | (2006.01) |
| ***A61K 39/00*** | (2006.01) |
| ***A61P 35/00*** | (2006.01) |
| ***C07K 14/705*** | (2006.01) |
| ***C12N 15/86*** | (2006.01) |

(52) U.S. Cl.
CPC .......... *C07K 16/2818* (2013.01); *A61P 35/00* (2018.01); *C07K 14/705* (2013.01); *C12N 15/86* (2013.01); *A61K 39/00* (2013.01); *A61K 2039/505* (2013.01); *C12N 2770/36133* (2013.01); *C12N 2770/36134* (2013.01); *C12N 2770/36143* (2013.01); *C12N 2770/36171* (2013.01)

(58) Field of Classification Search
CPC .......... C12N 15/86; C12N 2770/36134; C12N 2770/36171; C12N 2770/36133; C12N 2770/36122; C12N 2770/36141; C12N 2770/36143; A61P 35/00; A61P 35/02; A61P 35/04; A61K 2039/505; A61K 2300/00
See application file for complete search history.

(56) References Cited

U.S. PATENT DOCUMENTS

| | | | |
|---|---|---|---|
| 4,946,778 | A | 8/1990 | Ladner et al. |
| 5,399,346 | A | 3/1995 | Anderson et al. |
| 6,432,699 | B1 | 8/2002 | Meruelo et al. |
| 7,303,898 | B2 | 12/2007 | Hurtado et al. |
| 7,306,792 | B2 | 12/2007 | Meruelo |
| 8,084,026 | B2 | 12/2011 | Glaser et al. |
| 8,093,021 | B2 | 1/2012 | Hurtado et al. |
| 8,178,346 | B2 | 5/2012 | Mancebo et al. |
| 8,282,916 | B2 | 10/2012 | Meruelo et al. |
| 8,530,232 | B2 | 9/2013 | Hurtado et al. |
| 9,423,401 | B2 | 8/2016 | Varki et al. |

(Continued)

FOREIGN PATENT DOCUMENTS

| | | | |
|---|---|---|---|
| WO | WO-9953938 A1 * | 10/1999 | ............. A61P 35/00 |
| WO | WO 02/094994 | 11/2002 | |

(Continued)

OTHER PUBLICATIONS

Kelly et al (Recent Patents on Anti-Cancer Drug Design, 2007, vol. 2, pp. 159-166) (Year: 2007).*

(Continued)

*Primary Examiner* — Karen A. Canella
(74) *Attorney, Agent, or Firm* — Hodgson Russ LLP

(57) ABSTRACT

Provided are polynucleotides and viral vectors, e.g., alphavirus or Sindbis viral vectors, encoding multiple, e.g., two or more, epitopes of at least one tumor associated antigen, in which each epitope is separated by a processing or enzyme cleavage site. The encoded epitopes may be the same or different. Also provided are polynucleotides and viral vectors, particularly, alphavirus or Sindbis viral vectors, encoding an immune checkpoint protein, or a ligand binding portion thereof. The immune checkpoint protein or ligand binding portion thereof may be fused to immunoglobulin domains, e.g., an Ig hinge domain and an Ig heavy chain constant domain. Methods of treating subjects having a cancer or tumor, e.g., a TAA-expressing tumor, with the described viral vectors are provided. Treatment of subjects with the vectors, the checkpoint inhibitor molecules and/or other immunomodulatory components, generate an anti-cancer or anti-tumor immune response resulting in increased survivability of tumored subjects and epitope spreading.

1 Claim, 67 Drawing Sheets

Specification includes a Sequence Listing.

(56) References Cited

U.S. PATENT DOCUMENTS

| | | | | |
|---|---|---|---|---|
| 2013/0251744 A1* | 9/2013 | Ueno | A61P 35/00 435/69.3 |
| 2016/0000843 A1 | 1/2016 | Lowe et al. | |
| 2016/0008431 A1 | 1/2016 | Meruelo et al. | |
| 2016/0264643 A1 | 9/2016 | Lazar et al. | |
| 2017/0233450 A1 | 8/2017 | Akahata et al. | |
| 2018/0000912 A1 | 1/2018 | Meruelo et al. | |
| 2021/0000946 A1 | 1/2021 | Meruelo et al. | |

FOREIGN PATENT DOCUMENTS

| | | | |
|---|---|---|---|
| WO | WO-2014047350 A1 * | 3/2014 | A61K 35/761 |
| WO | WO 2015/035213 | 3/2015 | |
| WO | WO-2015153417 A1 * | 10/2015 | A61K 35/761 |
| WO | WO 2016/149643 | 9/2016 | |
| WO | WO-2017083291 A1 * | 5/2017 | A61K 31/675 |
| WO | WO-2017120670 A1 * | 7/2017 | A61K 35/766 |
| WO | WO 2017/152042 | 9/2017 | |
| WO | WO 2018/161092 | 9/2018 | |

OTHER PUBLICATIONS

Molloy et al (Journal of Biological Chemistry, 1992, vol. 267, pp. 16396-16402) (Year: 1992).*

The abstract of Smothers et al (Annals of Oncology, 2103, vol. 24, supplement, abstract No. L02.04) (Year: 2013).*

The abstract of Quetglas et al (Cancer Research, 2015, vol. 75, No. 15, suppl. 1, abstract No. 281) (Year: 2015).*

The abstract of Fourcade et al (Journal of Immunology, 2014, vol. 192, No. 1, suppl 1, abstract No. VAC3P.944) (Year: 2014).*

Gibney et al (Clinical Cancer Research, 2015, vol. 21, pp. 712-720 (Year: 2015).*

Sato et al (BMC, 2021, 21:1222, 12 pages) (Year: 2021).*

Esfandiary and Ghafouri-Fard (Future Medicine, 2015, vol. 7, pp. 411-439) (Year: 2015).*

Dos Santos, Cancer Immunology, Immunotherapy, 2015, vol. 64, pp. 311-323 (Year: 2015).*

Dos Santos, Cancer Immunology, Immunotherapy, 2015, vol. 64, supplemental, 4 pages (Year: 2015).*

Albershardt et al., "LV305, a dendritic cell-targeting integration-deficient ZVex™-based lentiviral vector encoding NY-ESO-1, induces potent anti-tumor immune response," Molecular Therapy—Oncolytics, 2016, 3:16010, XP055373918.

Ding et al., "Activation of $CD4^+$ T cells by delivery of the B7 costimulatory signal on bystander antigen-presenting cells (trans-costimulation)," European Journal of Immunology, 1994, 24(4):859-866.

EP Office Action in European Appln. No. 18717142.6, dated Jul. 28, 2021, 9 pages.

Foks et al., "Immune checkpoint proteins: exploring their therapeutic potential to regulate atherosclerosis," British Journal of Pharmacology, 2017, 174(22):3940-3955.

GenBank Accession No. AK155610.1, "Mus musculus B6-derived CD11 +ve dendritic cells cDNA, RIKEN full-length enriched library, clone:F730022K13 product:tumor necrosis factor (ligand) superfamily, member 9, full insert sequence," dated Oct. 6, 2010, 4 pages.

GenBank Accession No. BC104807.1, "*Homo sapiens* tumor necrosis factor (ligand) superfamily, member 9, mRNA (cDNA clone MGC:132467 IMAGE:8143810), complete cds," dated Jan. 19, 2006, 2 pages.

GenBank Accession No. NM_005018.2, "*Homo sapiens* programmed cell death 1 (PDCD1), mRNA," dated Sep. 15, 2016, 4 pages.

GenBank Accession No. NP_005009.2, "programmed cell death protein 1 precursor [*Homo sapiens*]," dated Sep. 15, 2016, 3 pages.

GenBank Accession No. P01857.1, "RecName: Full=Ig gamma-1 chain C region," dated Feb. 15, 2017, 8 pages.

Gnjatic et al., "NY-ESO-1: Review of an Immunogenic Tumor Antigen," Immunotherapy of Cancer In: Advances in Cancer Research, 2006, 95:1-30, XP008073732.

Granot et al., "Sindbis Viral Vectors Transiently Deliver Tumor-associated Antigens to Lymph Nodes and Elicit Diversified Anti-tumor $CD8^+$ T-cell Immunity," Molecular Therapy, 2014, 22(1):112-122, XP-002767391.

Holland's Cancer Medicine, 6th ed. BC Decker Inc., 2003, Zarour et al., "Tumor Antigens," Section 2, Chapter 12, 22 pages.

Lechner et al., "Immunogenicity of murine solid tumor models as a defining feature of in vivo behavior and response to immunotherapy," Journal of Immunotherapy, 2013 36(9):477-489.

Liu et al., "Cells that present both specific ligand and costimulatory activity are the most efficient inducers of clonal expansion of normal CD4 T cells," Proceedings of the National Academy of Sciences, 1992. 89(9):3845-3849.

Melero et al., "Monoclonal antibodies against the 4-1BB T-cell activation molecule eradicate established tumors," Nature Medicine, 1997, 3(6):682-685.

Mellman et al., "Cancer immunotherapy comes of age," Nature, 2011, 480(7378):480-489.

Morris et al., "Development and characterization of recombinant human Fc: OX40L fusion protein linked via a coiled-coil trimerization domain," Molecular Immunology, 2007, 44(12):3112-3121.

Roska et al., "Dissection of the functions of antigen-presenting cells in the induction of T cell activation," The Journal of Immunology, 1985, 135(5):2953-2961.

Sanmamed et al., "Agonists of co-stimulation in cancer immunotherapy directed against CD137, OX40, GITR, CD27, CD28, and ICOS," Seminars in Oncology, 2015, 42(4):640-655.

UniProt Accession No. P41273, "Tumor necrosis factor ligand superfamily member 9," dated Feb. 15, 2017, 3 pages.

UniProt Accession No. P01857, "Immunoglobulin heavy constant gamma 1," dated Feb. 15, 2017, 11 pages.

Wülfing et al., "A receptor/cytoskeletal movement triggered by costimulation during T cell activation," Science, 1998, 282(5397):2266-2269.

Aarnoudse et al., "Interleukin-2-induced, Melanoma-Specific T Cells Recognize CAMEL, an Unexpected Translation Product of LAGE-1," Int J Cancer., 1999, 82(3):442-8.

Adair et al. "The TAG Family of Cancer/Testis Antigens Is Widely Expressed in a Variety of Malignancies and Gives Rise to HLA-A2-restricted Epitopes," J Immunother., 2008, 31(1):7-17.

Albershardt et al., "LV305, a dendritic cell-targeting integration-deficient ZVex TM-based lentiviral vector encoding NY-ESO-1, induces potent anti-tumor immune response," Molecular Therapy Oncolytics, 2016, 3(16010): 11 pages.

Alexander, J. et al., "Development of High Potency Universal DR-restricted Helper Epitopes by Modification of High Affinity DR-blocking Peptides," Immunity, 1994, 1(9):751-761.

Alisa et al., "Analysis of CD4+ T-Cell Responses to a Novel Alpha-Fetoprotein-Derived Epitope in Hepatocellular Carcinoma Patients," Clin. Cancer Res., 2005, 11(18):6686-94.

Altman, J.D. et al., "Phenotypic Analysis of Antigen-Specific T Lymphocytes," Science, 1996, 274(5284):94-96.

Andersen et al., "Identification of a Cyclin B1-derived CTL Epitope Eliciting Spontaneous Responses in Both Cancer Patients and Healthy Donors," Cancer Immunol Immunother, 2011, 60(2):227-34.

Anderson et al., "Endogenously Synthesized Peptide With an Endoplasmic Reticulum Signal Sequence Sensitizes Antigen Processing Mutant Cells to Class I-restricted Cell-Mediated Lysis," J Exp Med., 1991, 174(2):489-492.

Anderson et al., "Identification of MAGE-C1 (CT-7) Epitopes for T-cell Therapy of Multiple Myeloma," Cancer Immunol Immunother, 2011, 60(7):985-97.

Anderson, "Prospects for Human Gene Therapy," Science, 1984, 226(4673):401-409.

Andtbacka et al., "Talimogene Laherparepvec Improves Durable Response Rate in Patients With Advanced Melanoma," J Clin Oneal, 2015, 33(25):2780-2788.

Asai et al., "In Vitro Generated Cytolytic T Lymphocytes Reactive Against Head and Neck Cancer Recognize Multiple Epitopes Presented by HLA-A2, Including Peptides Derived From the p53 and MDM-2 Proteins," Cancer Immun., Apr. 16, 2002, 2(3): 17 pages.

(56) References Cited

OTHER PUBLICATIONS

Asemissen et al., "Identification of a Highly Immunogenic HLA-A*01-binding T Cell Epitope of WT1," Clin. Cancer Res., 2006, 12(24):7476-82.
Aurisicchio et al., "A Novel Minigene Scaffold for Therapeutic Cancer Vaccines," Oncoimmunology, Oct. 27, 2014, 3(e27529): 14 pages.
Ayyoub et al., "An Immunodominant SSX-2-derived Epitope Recognized by CD4+ T Cells in Association With HLA-DR," J Clin Invest., 2004, 113(8):1225-33.
Ayyoub et al., "Assessment of Vaccine-Induced CD4 T Cell Responses to the 119-143 Immunodominant Region of the Tumor-Specific Antigen NY-ESO-1 Using DRB1*0101 Tetramers," Clin Cancer Res., 2010, 16(18):4607-15.
Ayyoub et al., "CD4+ T Cell Responses to SSX-4 in Melanoma Patients," J Immunol., 2005, 174(8):5092-9.
Ayyoub et al., "Distinct but Overlapping T Helper Epitopes in the 37-58 Region of SSX-2," Clin Immunol., 2005, 114(1):70-8.
Ayyoub et al., "Identification of an SSX-2 Epitope Presented by Dendritic Cells to Circulating Autologous CD4+ T Cells," J Immunol., 2004, 172(11):7206-11.
Ayyoub et al., "Proteasome-assisted Identification of a SSX-2-derived Epitope Recognized by Tumor-Reactive CTL Infiltrating Metastatic Melanoma," J Immunol., 2002, 168(4):1717-22.
Backert et al., "Immunoinformatics and Epitope Prediction in the Age of Genomic Medicine," Genome Medicine, 2015, 7(119): 12 pages.
Bagnoli et al., "A Step Further in Understanding the Biology of the Folate Receptor in Ovarian Carcinoma," Gynecol. Oncol., 2003, 88:S140-4.
Bakker et al., "Identification of a Novel Peptide Derived From the Melanocyte-Specific gp100 Antigen as the Dominant Epitope Recognized by an HLA-A2.1-restricted Anti-Melanoma CTL Line," Int J Cancer., 1995, 62(1):97-102.
Bast et al., "CA 125 and the Detection of Recurrent Ovarian Cancer: A Reasonably Accurate Biomarker for a Difficult Disease," Cancer, 2010, 116(12):2850-2853.
Bast et al., "Monitoring Human Ovarian Carcinoma With a Combination of CA 125, CA 19-9, and Carcinoembryonic Antigen," Am. J. Obstet. Gynecol., 1984, 149(5):553-9.
Baurain et al., "High Frequency of Autologous Anti-Melanoma CTL Directed Against an Antigen Generated by a Point Mutation in a New Helicase Gene," J. Immunol., 2000, 164(11):6057-66.
Bei et al., "TAA polywpitope DNA-based vaccines: a potential tool for cancer therapy," Journal of Biomedicine and Biotechnology, Jan. 2010, 2010: 12 pages.
Bellone et al., "Induction of Human Tumor-Associated Differentially Expressed gene-12 (TADG-12/TMPRSS3)-specific Cytotoxic T Lymphocytes in Human Lymphocyte antigen-A2.1-positive Healthy Donors and Patients With Advanced Ovarian Cancer," Cancer, 2009, 115(4):800-811.
Benlalam et al., "Identification of Five New HLA-B*3501-restricted Epitopes Derived From Common Melanoma-Associated Antigens, Spontaneously Recognized by Tumor-Infiltrating Lymphocytes," J. Immunol., 2003, 171:(11):6283-6289.
Benton et al., "Screening Lambdagt Recombinant Clones by Hybridization to Single Plaques in Situ," Science, 1977, 196(4286):180-182.
Bertino et al., "The Immune System in Hepatocellular Carcinoma and Potential New Immunotherapeutic Strategies," Biomed. Res. Int., 2015, 2015(731469): 13 pages.
Bilsborough et al., "A MAGE-3 Peptide Presented by HLA-B44 Is Also Recognized by Cytolytic T Lymphocytes on HLA-B18," Tissue Antigens, 2002, 60(1):16-24.
Bioley et al., "Vaccination With Recombinant NY-ESO-1 Protein Elicits Immunodominant HLA-DR52b-restricted CD4+ T Cell Responses With a Conserved T Cell Receptor Repertoire," Clin Cancer Res., 2009, 15(13):4467-74.
Bloomer et al., "Highly Efficient and Sustained Gene Transfer in Adult Neurons With a Lentivirus Vector," J. Virol., 1997, 71(9):6641-6649.
Boel et al., "BAGE: A New Gene Encoding an Antigen Recognized on Human Melanomas by Cytolytic T Lymphocytes," Immunity, 1995, 2(2):167-75.
Bosch et al., "Recognition of BCR-ABL Positive Leukemic Blasts by Human CD4+ T Cells Elicited by Primary in Vitro Immunization With a BCR-ABL Breakpoint Peptide," Blood, 1996, 88(9):3522-7.
Breckpot et al., "Identification of New Antigenic Peptide Presented by HLA-Cw7 and Encoded by Several MAGE Genes Using Dendritic Cells Transduced With Lentiviruses," J Immunol, 2004, 172(4):2232-7.
Breckpot et al., "Lentiviral Vectors for Cancer Immunotherapy: Transforming Infectious Particles Into Therapeutics," Gene Ther., 2007, 14(11):847-862.
Bredenbeek et al., "Sindbis Virus Expression Vectors: Packaging of RNA Replicons by Using Defective Helper RNAs," Journal od Virology, Nov. 1993, 67(11):6439-6446.
Brichard et al., "A Tyrosinase Nonapeptide Presented by HLA-B44 Is Recognized on a Human Melanoma by Autologous Cytolytic T Lymphocytes," Eur. J. Immunol., 1996, 26(1):224-30.
Brigham et al., "In Vivo Transfection of Murine Lungs With a Functioning Prokaryotic Gene Using a Liposome Vehicle," Am. J. Med.. Sci., 1989, 298(4):278-81.
Bright et al., "Overexpressed Oncogenic Tumor-Self Antigens," Hum Vaccin. Immunother., 2014, 10(11):3297-3305.
Brossart et al., "Her-2/neu-derived Peptides Are Tumor-Associated Antigens Expressed by Human Renal Cell and Colon Carcinoma Lines and Are Recognized by in Vitro Induced Specific Cytotoxic T Lymphocytes," Cancer Res., 1998, 58(4):732-6.
Brossart et al., "Identification of HLA-A2-restricted T-cell Epitopes Derived From the MUC1 Tumor Antigen for Broadly Applicable Vaccine Therapies," Blood, 1999, 93(12):4309-4317.
Butterfield et al., "Generation of Human T-cell Responses to an HLA-A2.1-restricted Peptide Epitope Derived From Alpha-Fetoprotein," Cancer Res., 1999, 59(13):3134-42.
Campi et al., "CD4(+) T Cells From Healthy Subjects and Colon Cancer Patients Recognize a Carcinoembryonic Antigen-Specific Immunodominant Epitope," Cancer Res., 2003, 63(23):8481-6.
Cancer Medicine, 6th ed., Kufe et al. (ed)., 2003 Section 2: Cancer Immunology, Chapter 12: Tumor Antigens, 18 pages.
cancerimmunitv.org [online], "T cell-defined tumor antigens," available on or before Oct. 20, 2013, via Internet Archive: Wayback Machine URL <https://web.archive.org/web/20131020055211/http://www.cancerimmunity.org/peptide//>, retrieved on Jul. 8, 2020, URL <http://www.cancerimmunity.org/peptide//>, 4 pages.
Castelli et al., "Novel HLA-Cw8-restricted T Cell Epitopes Derived From Tyrosinase-Related protein-2 and gp100 Melanoma Antigens," J. Immunol., 1999, 162(3):1739-48.
Castle et al., "Immunomic, Genomic and Transcriptomic Characterization of CT26 Colorectal Carcinoma," BMC Genomics, 2014, 15(190): 12 pages.
Cayouette et al., "Adenovirus-mediated Gene Transfer of Ciliary Neurotrophic Factor Can Prevent Photoreceptor Degeneration in the Retinal Degeneration (Rd) Mouse," Human Gene Therapy, 1997, 8(4):423-430.
Cesson et al., "MAGE-A3 and MAGE-A4 Specific CD4(+) T Cells in Head and Neck Cancer Patients: Detection of Naturally Acquired Responses and Identification of New Epitopes," Cancer Immunol Immunother., 60(1):23-35.
Chang et al., "Peptide Length-Based Prediction of peptide-MHC Class II Binding," Bioinformatics, 2006, 22(22):2761-2767.
Chaux et al., "A MAGE-1 Peptide Recognized on HLA-DR15 by CD4(+) T Cells," Eur J Immunol., 2001, 31(6):1910-6.
Chaux et al., "Identification of Five MAGE-A1 Epitopes Recognized by Cytolytic T Lymphocytes Obtained by in Vitro Stimulation With Dendritic Cells Transduced With MAGE-A1," J Immunol., 1999, 163(5):2928-36.
Chaux et al., "Identification of MAGE-3 Epitopes Presented by HLA-DR Molecules to CD4(+) T Lymphocytes," J Exp Med., 1999, 189(5):767-78.

(56) References Cited

OTHER PUBLICATIONS

Cheever et al., "The Prioritization of Cancer Antigens: A National Cancer Institute Pilot Project for the Acceleration of Translational Research," Clin Cancer Res., 2009, 15(17):5323-5337.
Chekmasova et al., "Successful Eradication of Established Peritoneal Ovarian Tumors in SCID-Beige Mice Following Adoptive Transfer of T Cells Genetically Targeted to the MUC16 Antigen," Clin. Cancer Res., 2010, 16(14):3594-606.
Chen et al., "Immunodominant CD4+ Responses Identified in a Patient Vaccinated With Full-Length NY-ESO-1 Formulated With ISCOMATRIX Adjuvant," Proc Natl Acad Sci USA., 2004, 101(25):9363-8.
Chen et al., "Identification of NY-ESO-1 Peptide Analogues Capable of Improved Stimulation of Tumor-Reactive CTL," J Immunol., 2000, 165(2):948-55.
Chester et al., "Immunotherapeutic Approaches to Ovarian Cancer Treatment," J Immunother., 2015, Cancer 3(7): 10 pages.
Chiari et al., "Two Antigens Recognized by Autologous Cytolytic T Lymphocytes on a Melanoma Result From a Single Point Mutation in an Essential Housekeeping Gene," Cancer Res., 1999, 59(22):5785-92.
Chiriva-Inernati et al., "Sperm Protein 17 Is a Suitable Target for Adoptive T-cell-based Immunotherapy in Human Ovarian Cancer," J. Immunother., 2008, 31(8):693-703.
Chiriva-Internati et al., "Identification of a Sperm Protein 17 CTL Epitope Restricted by HLA-A1," Int J Cancer, 2003, 107(5):863-5.
Cole et al., "The EBV-hybridoma technique and its application to human lung cancer," Paper, Presentated at Monoclonal Antibodies and Cancer Therapy, Jan. 26-Feb. 2, 1985, 12 pages.
Consogno et al., "Identification of Immunodominant Regions Among Promiscuous HLA-DR-restricted CD4+ T-cell Epitopes on the Tumor Antigen MAGE-3," Blood., 2003, 101(3):1038-44.
Corbiere et al., "Antigen Spreading Contributes to MAGE Vaccination-Induced Regression of Melanoma Metastases," Cancer Res., 2011, 71(4):1253-62.
Corbiere et al., "Identification of a MAGE-1 Peptide Recognized by Cytolytic T Lymphocytes on HLA-B*5701 Tumors," Tissue Antigens, 2004, 63(5):453-7.
Cornetta et al., "Gene Transfer Into Primates and Prospects for Gene Therapy in Humans," Prog. Nucleic. Acid Research and Molecular Biology, 1989, 36:311-322.
Correale et al., "In Vitro Generation of Human Cytotoxic T Lymphocytes Specific for Peptides Derived From Prostate-Specific Antigen," J Natl. Cancer Inst., 1997, 89(4):293-300.
Coulie et al., "A Mutated Intron Sequence Codes for an Antigenic Peptide Recognized by Cytolytic T Lymphocytes on a Human Melanoma," Proc. Natl. Acad. Sci. U.S.A., 1995, 92(17):7976-80.
Cox et al., "Identification of a Peptide Recognized by Five Melanoma-Specific Human Cytotoxic T Cell Lines," Science, 1994, 264(5159):716-719.
Criscitiello, "Tumor-associated Antigens in Breast Cancer," Breast Care, 2012, 7(4):262-266.
Crosti et al., "Identification of Novel Subdominant Epitopes on the Carcinoembryonic Antigen Recognized by CD4+ T Cells of Lung Cancer Patients," J Immunol., 2006, 176(8):5093-9.
Dalet et al., "An Antigenic Peptide Produced by Reverse Splicing and Double Asparagine Deamidation," Proc. Natl. Acad. Sci., U.S.A., 2011, 108(29):E323-31.
De Backer et al., "Characterization of the GAGE Genes That Are Expressed in Various Human Cancers and in Normal Testis," Cancer Res., 1999, 59(13):3157-65.
Di Modugno et al., "Human Mena Protein, a Serex-Defined Antigen Overexpressed in Breast Cancer Eliciting Both Humoral and CD8+ T-cell Immune Response," Int. J Cancer, 2004, 109(6):909-18.
Djenidi et al., "CD8+CD103+ Tumor-Infiltrating Lymphocytes Are Tumor-Specific Tissue-Resident Memory T Cells and a Prognostic Factor for Survival in Lung Cancer Patients," J Immunol., 2015, 194(7):3475-3486.
Duffour et al., "A MAGE-A4 Peptide Presented by HLA-A2 Is Recognized by Cytolytic T Lymphocytes," Eur J Immunol., 1999, 29(10):3329-37.
Duffy, "Carcinoembryonic Antigen as a Marker for Colorectal Cancer: Is It Clinically Useful?," Clin. Chem., 2001, 47(4):624-30.
Ebert et al., "A Long, Naturally Presented Immunodominant Epitope From NY-ESO-1 Tumor Antigen: Implications for Cancer Vaccine Design," Cancer Res., 2009, 69(3):1046-54.
Echchakir et al., "A Point Mutation in the alpha-actinin-4 Gene Generates an Antigenic Peptide Recognized by Autologous Cytolytic T Lymphocytes on a Human Lung Carcinoma," Cancer Res., 2001, 61(10):4078-83.
Eglitis et al., "Retroviral Vectors for Introduction of Genes Into Mammalian Cells," Biotechniques, 1988, 6(7):608-614.
Eikawa et al., "Induction of CD8 T-cell Responses Restricted to Multiple HLA Class I Alleles in a Cancer Patient by Immunization With a 20-mer NY-ESO-1f (NY-ESO-1 91-110) Peptide," Int J Cancer, 2013, 132(2):345-54.
El Hage et al., "Preprocalcitonin Signal Peptide Generates a Cytotoxic T Lymphocyte-Defined Tumor Epitope Processed by a Proteasome-Independent Pathway," Proc. Natl. Acad. Sci. U.S.A., 2008, 105(29):10119-24.
Enamorado et al., "Enhanced anti-tumor immunity requires the interplay between resident and circulating memory CD8+ T Cell," Nat Commun, Jul. 17, 2017, 8(6073): 11 pages.
EP Extended Search Report in Euroepean Appln. No. 18717142.6, dated Sep. 27, 2019.
Facciabene et al., "DNA and Adenoviral Vectors Encoding Carcinoembryonic Antigen Fused to Immunoenhancing Sequences Augment Antigen-Specific Immune Response and Confer Tumor Protection," Hum Gene Ther., 2006, 17(1):81-92.
Facciabene et al., "Vectors Encoding Carcinoembryonic Antigen Fused to the B Subunit of Heat-Labile Enterotoxin Elicit Antigen-Specific Immune Responses and Antitumor Effects," Vaccine, 2007, 26:47-58.
Felgner et al., "Lipofection: A Highly Efficient, Lipid-Mediated DNA-transfection Procedure," Proc. Natl. Acad. Sci., 1987, 84(21):7413.
Fikes et al., "Design of multi-epitope, analogue-bassed cancer vaccines," Expert Opinion on Biological Therapy, Jan. 1, 2003, 3(6):985-993.
Fisk et , "Identification of an Immunodominant Peptide of HER-2/neu Protooncogene Recognized by Ovarian Tumor-Specific Cytotoxic T Lymphocyte Lines," J Exp Med., 1995, 181(6):2109-17.
Fossum et al., "Overlapping Epitopes Encompassing a Point Mutation (12 Gly-->Arg) in p21 Ras Can Be Recognized by HLA-DR, —DP and—DQ Restricted T Cells," J Immunol., 1993, 23(10):2687-2691.
Friedman, "Progress Toward Human Gene Therapy," Science, 1989, 244(4910):1275-1281.
Fuertes et al., "Host Type I IFN Signals Are Required for Antitumor CD8+ T Cell Responses Through CD8 {alpha}+ Dendritic Cells," J Exp Med, 2011,208(10):2005-2016.
Fujiki et al., "Identification and Characterization of a WTI (Wilms Tumor Gene) Protein-Derived HLA-DRB1*0405-restricted 16-mer Helper Peptide That Promotes the Induction and Activation of WT1-specific Cytotoxic T Lymphocytes," J. Immunother., 2007, 30(3):282-93.
Fukuyama et al., "Identification of a New Cancer/Germline Gene, KK-LC-1, Encoding an Antigen Recognized by Autologous CTL Induced on Human Lung Adenocarcinoma," Cancer Res., 2006, 66(9):4922-8.
Galanis et al., "Phase I Trial of Intraperitoneal Administration of an Oncolytic Measles Virus Strain Engineered to Express Carcinoembryonic Antigen for Recurrent Ovarian Cancer," Cancer Res., 2010, 70(3):875-82.
Gambacorti-Passerini et al., "Human CD4 Lymphocytes Specifically Recognize a Peptide Representing the Fusion Region of the Hybrid Protein pml/RAR Alpha Present in Acute Promyelocytic Leukemia Cells," Blood., 1993, 81(5):1369-75.
Garoff et al., "The Signal Sequence of the p62 Protein of Semliki Forest Virus Is Involved in Initiation but Not in Completing Chain Translocation," J Cell. Biol., 1990, 111(3):867-876.

(56) References Cited

OTHER PUBLICATIONS

Garon et al., "Pembrolizumab for the Treatment of Non-Small-Cell Lung Cancer," N Engl J Med, 2015, 372(21):2018-2028.
Gastl et al., "Ep-CAM Overexpression in Breast Cancer as a Predictor of Survival," Lancet, 2000, 356(9246):1981-2.
Gaudin et al., "A hsp70-2 Mutation Recognized by CTL on a Human Renal Cell Carcinoma," J. Immunol., 1999, 162(3):1730-8.
Gaugler et al., "Human Gene MAGE-3 Codes for an Antigen Recognized on a Melanoma by Autologous Cytolytic T Lymphocytes," J Exp Med., 1994, 179(3):921-30.
Gjertsen et al., "Cytotoxic CD4+ and CD8+ T Lymphocytes, Generated by Mutant p21-ras (12Val) Peptide Vaccination of a Patient, Recognize 12Val-dependent Nested Epitopes Present Within the Vaccine Peptide and Kill Autologous Tumour Cells Carrying This Mutation," Int. J. Cancer, 72(5):784-90.
Gnjactic et al., "NY-ESO-1: Review of an Immunogenic Tumor Antigen," Immunotherapy of Cancer In: Advances in Cancer Research, 2006, 95:1-30.
Gnjatic et al., "Strategy for monitoring T cell responses to NY_ESO-1 in patients with any HLA class I allele," Proceedings of the National Academy of Sciences of the United States of America, Sep. 26, 2000, 97(20):10917-10922.
Godelaine et al. "A New Tumor-Specific Antigen Encoded by MAGE-C2 and Presented to Cytolytic T Lymphocytes by HLA-B44," Cancer Immunol Immunother., 2007, 56(6):753-9.
Goodyear et al., "Dominant Responses With Conservation of T-cell Receptor Usage in the CD8+ T-cell Recognition of a Cancer Testis Antigen Peptide Presented Through HLA-Cw7 in Patients With Multiple Myeloma," Cancer Immunol Immunother., 2011, 60(12):1751-61.
Graf et al., "A Neoepitope Generated by an FLT3 Internal Tandem Duplication (FLT3-ITD) Is Recognized by Leukemia-Reactive Autologous CD8+ T Cells," Blood, 2007, 109(7):2985-8.
Granot et al., "Activation of Cytotoxic and Regulatory Functions of NK Cells by Sindbis Viral Vectors," PLoS One, 2011, 6(6):e20598, 14 pages.
Granot et al., "Sindbis Viral Vectors Transiently Deliver Tumor-Associated Antigens to Lymph Nodes and Elicit Diversified Antitumor CD8+ T-cell Immunity," Mol. Ther., 2014, 22(1):112-122.
Granot et al., "The Role of Natural Killer Cells in Combinatorial Anti-Cancer Therapy Using Sindbis Viral Vectors and Irinotecan," Cancer Gene Ther., 2012, 19(8):588-591.
Grunstein et al., "Colony Hybridization: A Method for the Isolation of Cloned DNAs That Contain a Specific Gene," Proc. Nat Acad. Sci., USA, 1975, 72(10):3961-3975.
Guillaume et al., "Soluble MHC-peptide complexes: tools for the monitoring of T cell responses in clinical trials and basic research," Cancer Immunity, 2009, 9:7, 6 pages.
Guilloux et al., "A Peptide Recognized by Human Cytolytic T Lymphocytes on HLA-A2 Melanomas Is Encoded by an Intron Sequence of the N-acetylglucosaminyltransferase V Gene," J Exp Med., 1996, 183(3):1173-83.
Guo et al., "Direct Recognition and Lysis of Leukemia Cells by WT1-specific CD4+ T Lymphocytes in an HLA Class II-restricted Manner," Blood, 2005, 106(4):1415-8.
Guo et al., "Editorial of the Special Issue: Oncolytic Viruses as a Novel Form of Immunotherapy for Cancer," Biomedicines, Aug. 24, 2017, 5(52): 5 pages.
Guo et al., "HLA-A2-restricted Cytotoxic T Lymphocyte Epitopes From Human Hepsin as Novel Targets for Prostate Cancer Immunotherapy," Scand J Immunol., 2013, 78(3):248-57.
Hanada et al., "Immune Recognition of a Human Renal Cancer Antigen Through Post-Translational Protein Splicing," Nature, 2004, 427(6971):252-6.
Harvard.edu [online], "TANTIGEN: Tumor T cell Antigen Database," available on or before Sep. 5, 2016, via Internet Archive: Wayback Machine URL <https://web.archive.org/web/20160905170314/http://cvc.dfci.harvard.edu/tadb/> retrieved on Sep. 9, 2020, URL <http://cvc.dfci.harvard.edu/tadb/>, 1 page.
Hasegawa et al., "In Vitro Stimulation of CD8 and CD4 T Cells by Dendritic Cells Loaded With a Complex of Cholesterol-Bearing Hydrophobized Pullulan and NY-ESO-1 Protein: Identification of a New HLA-DR15-binding CD4 T-cell Epitope," Clin Cancer Res., 2006, 12(6):1921-7.
Hassan et al., "Localization of Mesothelin in Epithelial Ovarian Cancer," Appl. Immunohistochem. Mol. Morphol., 2005, 13(3):243-7.
Heidecker et al., Cytolytic T Lymphocytes Raised Against a Human Bladder Carcinoma Recognize an Antigen Encoded by Gene MAGE-A12, J Immunol., 2000, 164(11):6041-5.
Helm et al., "Targeting c-MYC With T-cells," PLoS ONE, 2013, 8(10):e77375, 14 pages.
Herbst et al., "Predictive correlates of response to the anti-PD-L1 antibody MPDL3280A in cancer patients," Nature, 2014, 515(7528):563-567.
Herman et al., "A Peptide Encoded by the Human MAGE3 Gene and Presented by HLA-B44 Induces Cytolytic T Lymphocytes That Recognize Tumor Cells Expressing MAGE3," Immunogenetics, 1996, 43(6):377-83.
Hiltbold et al., "Naturally Processed Class II Epitope From the Tumor Antigen MUC1 Primes Human CD4+ T Cells," Cancer Res., 1998, 58(22):5066-70.
Hogan et al., "The Peptide Recognized by HLA-A68.2-restricted, Squamous Cell Carcinoma of the Lung-Specific Cytotoxic T Lymphocytes Is Derived From a Mutated Elongation Factor 2 Gene," Cancer Res., 1998, 58(22):5144-50.
Hong et al., "Diverse Solid Tumors Expressing a Restricted Epitope of LI-CAM Can Be Targeted by Chimeric Antigen Receptor Redirected T Lymphocytes," J. Immunother., 2014, 37(2):93-104.
Horiguchi et al., "Screening of HLA-A24-restricted Epitope Peptides From Prostate-Specific Membrane Antigen That Induce Specific Antitumor Cytotoxic T Lymphocytes," Clin Cancer Res., 2002, 8(12):3885-92.
Horton et al., "Gene Splicing by Overlap Extension: Tailor-Made Genes Using the Polymerase Chain Reaction," BioTechniques, 1990, 8(5):528-535.
Huang et al., "Cytolytic T Lymphocytes Recognize an Antigen Encoded by MAGE-A10 on a Human Melanoma," J Immunol., 1999, 162(11):6849-54.
Huang et al., "T Cells Associated With Tumor Regression Recognize Frameshifted Products of the CDKN2A Tumor Suppressor Gene Locus and a Mutated HLA Class I Gene Product," J Immunol., 2004, 172(10):6057-64.
Hung et al., "Antigen-specific Immunotherapy of Cervical and Ovarian Cancer," Immunol. Rev., 2008, 222:43-69.
Hural et al., "Identification of naturally processed CD4 T cell epitopes from the prostate-specific antigen kallikrein 4 using peptide-based in vitro stimulation," J. Immunol., Jul. 1, 2002, 169(1):557-565.
Hurtado et al., "Identification of Amino Acids of Sindbis Virus E2 Protein Involved in Targeting Tumor Metastases in Vivo," Mol Ther, 2005, 12(5):813-82.
Ikeda et al., "Characterization of an Antigen That Is Recognized on a Melanoma Showing Partial HLA Loss by CTL Expressing an NK Inhibitory Receptor," Immunity, 1997, 6(2):199-208.
Ito et al., "Immunological Characterization of Missense Mutations Occurring Within Cytotoxic T Cell-Defined p53 Epitopes in HLA-A*0201+ Squamous Cell Carcinomas of the Head and Neck," Int. J Cancer, 2007, 120(12):2618-2624.
Jager et al., "Identification of a Naturally Processed NY-ESO-1 Peptide Recognized by CD8+ T Cells in the Context of HLA-B51," Cancer Immun., 2002, 2(12): 13 pages.
Jager et al., "Identification of NY-ESO-1 Epitopes Presented by Human Histocompatibility Antigen (HLA)-DRB4*0101-0103 and Recognized by CD4(+) T Lymphocytes of Patients With NY-ESO-1-expressing Melanoma," J Exp Med., 2000, 191(4):625-30.
Jager et al., "Recombinant Vaccinia/Fowlpox NY-ESO-1 Vaccines Induce Both Humoral and Cellular NY-ESO-1-specific Immune Responses in Cancer Patients," Proc. Natl. Acad. Sci. U.S.A., 2006, 103(39):14453-8.
Jager et al., "Simultaneous Humoral and Cellular Immune Response Against Cancer-Testis Antigen NY-ESO-1: Definition of Human

(56) References Cited

OTHER PUBLICATIONS

Histocompatibility Leukocyte Antigen (HLA)-A2-binding Peptide Epitopes," J Exp Med., 1998, 187(2):265-70.
Janjic et al., "Spontaneous CD4+ T Cell Responses Against TRAG-3 in Patients With Melanoma and Breast Cancers," J Immunol., 2006, 177(4):2717-27.
Jaramillo et al., "Identification of HLA-A3-restricted CD8+ T Cell Epitopes Derived From mammaglobin-A, a Tumor-Associated Antigen of Human Breast Cancer," Int. J. Cancer, 2002, 102(5):499-506.
Jerome et al., "Tumor-specific Cytotoxic T Cell Clones From Patients With Breast and Pancreatic Adenocarcinoma Recognize EBV-immortalized B Cells Transfected With Polymorphic Epithelial Mucin Complementary DNA," J Immunol., Aug. 1, 1993, 151(3):1654-62 (Abstract Only).
Jin et al., "Construction and Characterization of a CTLA-4-targeted scFv-melittin Fusion Protein as a Potential Immunosuppressive Agent for Organ Transplant," Cell Biochem Biophys, 2013, 67(3):1067-74.
Johnson, "Gene Therapy for Cystic Fibrosis," Chest, 1995, 107(2 Suppl):77S-83S.
Jose et al., "A Structural and Functional Perspective of Alphavirus Replication and Assembly," Future Microbiol., 2009, 4(7):837-856.
Kang et al., "Identification of a Tyrosinase Epitope Recognized by HLA-A24-restricted, Tumor-Infiltrating Lymphocytes," J. Immunol., 1995, 155(3):1343-8.
Karanikas et al., "High Frequency of Cytolytic T Lymphocytes Directed Against a Tumor-Specific Mutated Antigen Detectable With HLA Tetramers in the Blood of a Lung Carcinoma Patient With Long Survival," Cancer Res., 2001, 61(9):3718-24.
Kaufman et al., "Oncolytic Viruses: A New Class of Immunotherapy Drugs," Nat Rev Drug Discov., 14:642-662.
Kawakami et al., "Identification of New Melanoma Epitopes on Melanosomal Proteins Recognized by Tumor Infiltrating T Lymphocytes Restricted by HLA-A1,—A2, and—A3 Alleles," J Immunol., 1998, 161(12):6985-92.
Kawakami et al., "Isolation of a New Melanoma Antigen, MART-2, Containing a Mutated Epitope Recognized by Autologous Tumor-Infiltrating T Lymphocytes," J Immunol., 2001, 166(4):2871-7.
Kawakami et al., "Recognition of Multiple Epitopes in the Human Melanoma Antigen gp100 by Tumor-Infiltrating T Lymphocytes Associated With in Vivo Tumor Regression," J Immunol., Apr. 15, 1995, 154(8):3961-3968 (Abstract Only).
Kawashima et al., "Identification of HLA-A3-restricted Cytotoxic T Lymphocyte Epitopes From Carcinoembryonic Antigen and HER-2/neu by Primary in Vitro Immunization With Peptide-Pulsed Dendritic Cells," Cancer Res., 1999, 59(2):431-5.
Kawashima et al., "The Multi-Epitope Approach for Immunotherapy for Cancer: Identification of Several CTL Epitopes From Various Tumor-Associated Antigens Expressed on Solid Epithelial Tumors," Hum Immunol., 1998, 59(1):1-14.
Kenter et al., "Vaccination against HPV-16 Oncoproteins for Vulvar Intraepithelial Neoplasia," N Engl J Med., 2009, 361:1838-1847.
Kessler et al., "Efficient Identification of Novel HLA-A(*)0201-presented Cytotoxic T Lymphocyte Epitopes in the Widely Expressed Tumor Antigen PRAME by Proteasome-Mediated Digestion Analysis," J. Exp. Med., 2001, 193(1):73-88.
Kho et al., "Prognostic Variables for Patient Return-to-Work Interval Following Carpal Tunnel Release in a Workers' Compensation Population," Hand (NY), 2017, 12(3):246-251.
Kido et al., "Use of a Retroviral Vector With an Internal Opsin Promoter to Direct Gene Expression to Retinal Photoreceptor Cells," Current Eye Research, 1996, 15:833-844.
Kimmel, "Identification and Characterization of Specific Clones: Strategy for Confirming the Validity of Presumptive Clones," Methods Enzymol., 1987, 152:507-511.
Kittlesen et al., "Human Melanoma Patients Recognize an HLA-A1-restricted CTL Epitope From Tyrosinase Containing Two Cysteine Residues: Implications for Tumor Vaccine Development," J. Immunol., 1998, 160(5):2099-106.
Knappik et al., "Fully Synthetic Human Combinatorial Antibody Libraries (HuCAL) Based on Modular Consensus Frameworks and CDRs Randomized With Trinucleotides," J Mol. Biol., 2000, 296(1):57-86.
Knights et al., "Modified Tumour Antigen-Encoding mRNA Facilitates the Analysis of Naturally Occurring and Vaccine-Induced CD4 and CD8 T Cells in Cancer Patients," Cancer Immunol Immunother., 2009, 58(3):325-38.
Knudsen et al., "Kinetic and Phenotypic Analysis of CD8+ T Cell Responses After Priming With Alphavirus Replicons and Homologous or Heterologous Booster Immunizations," J Virology, 2014, 8(21):12438-12451.
Kobayashi et al., "New MAGE-4 Antigenic Peptide Recognized by Cytolytic T Lymphocytes on HLA-A1 Tumor Cells," Tissue Antigens., 2003, 62(5):426-32.
Kobayashi et al., "CD4+ T Cells From Peripheral Blood of a Melanoma Patient Recognize Peptides Derived From Nonmutated Tyrosinase," Cancer Res., 1998, 58(2):296-301.
Kobayashi et al., "Identification of an Antigenic Epitope for Helper T Lymphocytes From Carcinoembryonic Antigen," Clin Cancer Res., 2002, 8(10):3219-25.
Kobayashi et al., "Recognition of Prostate and Melanoma Tumor Cells by Six-Transmembrane Epithelial Antigen of Prostate-Specific Helper T Lymphocytes in a Human Leukocyte Antigen Class II-restricted Manner," Cancer Res., 2007, 67(11):5498-504.
Kobayashi et al., "Tumor-reactive T Helper Lymphocytes Recognize a Promiscuous MAGE-A3 Epitope Presented by Various Major Histocompatibility Complex Class II Alleles," Cancer Res., 2001, 61(12):4773-8.
Kohler et al., "Continuous Cultures of Fused Cells Secreting Antibody of Predefined Specificity," Nature, 1975, 256(5517):495-497.
Kozbor et al., "The Production of Monoclonal Antibodies From Human Lymphocytes," Immunology Today, 1983, 4(3):72-9.
La Salle et al., "An Adenovirus Vector for Gene Transfer Into Neurons and Glia in the Brain," Science, 1993, 259(5097):988-990.
Lapointe et al., "Retrovirally Transduced Human Dendritic Cells Can Generate T Cells Recognizing Multiple MHC Class I and Class II Epitopes From the Melanoma Antigen Glycoprotein 100," J Immunol., 2001, 167(8):4758-64.
Larkin et al., "Combined Nivolumab and Ipilimumab or Monotherapy in Untreated Melanoma," N Engl J Med, 373:23-34.
Le et al., "A Live-Attenuated Listeria Vaccine (ANZ-100) and a Live-Attenuated Listeria Vaccine Expressing Mesothelin (CRS-207) for Advanced Cancers: Phase I Studies of Safety and Immune Induction," Clin. Cancer Res., 2012, 18(3):858-68.
Lennerz et al., "The Response of Autologous T Cells to a Human Melanoma Is Dominated by Mutated Neoantigens," Proc. Natl. Acad. Sci. U.S.A., 2005, 102(44):16013-8.
Li et al., "Detection of Autoantibodies to Multiple Tumor-Associated Antigens in the Immunodiagnosis of Ovarian Cancer," Mol. Med. Report, 2008, 1(4):589-594.
Li et al., "Identification of a WT1 Protein-Derived Peptide, WT1, as a HLA-A 0206-restricted, WT1-specific CTL Epitope," Microbial. Immunol., 2008, 52(11):551-558.
Lin et al., "HLA-DPB1*05: 01-restricted WT1332-specific TCR-transduced CD4+ T Lymphocytes Display a Helper Activity for WTI-specific CTL Induction and a Cytotoxicity Against Leukemia Cells," J. Immunother., 2013, 36(3):159-70.
Linard et al., "A Ras-Mutated Peptide Targeted by CTL Infiltrating a Human Melanoma Lesion," J. Immunol., 2002, 168(9):4802-8.
Linnebacher et al., "Frameshift Peptide-Derived T-cell Epitopes: A Source of Novel Tumor-Specific Antigens," Int. J. Cancer., 2001, 93(1):6-11.
Liu et al., "Ovarian Cancer Immunotherapy: Opportunities, Progresses and Challenges," J Hematol., Oncol., 2010, 3(7): 11 pages.
Loveland et al., "Mannan-MUC1-pulsed Dendritic Cell Immunotherapy: A Phase I Trial in Patients With Adenocarcinoma," Clin. Cancer Res., 2006, 12(3 Pt 1):869-77.
Lu et al., "Mutated PPP1R3B Is Recognized by T Cells Used to Treat a Melanoma Patient Who Experienced a Durable Complete Tumor Regression," J Immunol., 2013, 190(12):6034-42.

(56) References Cited

OTHER PUBLICATIONS

Luiten et al., "A MAGE-A1 peptide is recognized on HLA-B7 human tumors by cytolytic T lymphocytes," Tissue Antigens, 2000, 55(2):149-152.
Luiten et al., "A MAGE-A1 peptide presented to cytolytic T lymphocytes by both HLA-B35 and HLA-A1 molecules," Tissue Antigens, 2000, 56(1):77-81.
Lupetti et al., "Translation of a Retained Intron in Tyrosinase-Related Protein (TRP) 2 mRNA Generates a New Cytotoxic T Lymphocyte (CTL)-defined and Shared Human Melanoma Antigen Not Expressed in Normal Cells of the Melanocytic Lineage," J Exp Med., 1998, 188(6):1005-16.
Ma et al., "A MAGE-C2 Antigenic Peptide Processed by the Immunoproteasome Is Recognized by Cytolytic T Cells Isolated From a Melanoma Patient After Successful Immunotherapy," Int J Cancer, 2011, 129(10):2427-3.
Ma et al., "Two New Tumor-Specific Antigenic Peptides Encoded by Gene MAGE-C2 and Presented to Cytolytic T Lymphocytes by HLA-A2," Int J Cancer, 2004, 109(5):698-702.
Maccalli et al., "Identification of a Colorectal Tumor-Associated Antigen (COA-1) Recognized by CD4(+) T Lymphocytes," Cancer Res., 2003, 63(20):6735-43.
Maier et al., "Peptide Motifs of HLA-A3,—A24, and—B7 Molecules as Determined by Pool Sequencing," Immunogenetics, 1994, 40(4):306-3.
Makita et al., "Leukemia-associated Fusion Proteins, Dek-Can and Ber-Ab1, Represent Immunogenic HLA-DR-restricted Epitopes Recognized by Fusion Peptide-Specific CD4+ T Lymphocytes," Leukemia, 2002, 16(12):2400-7.
Malik et al., "Resident Memory T Cells in the Skin Mediate Durable Immunity to Melanoma," Sci Immunol, Apr. 14, 2017, 2(eaam6346):12 pages.
Mandic et al., "One NY-ESO-1-derived Epitope That Promiscuously Binds to Multiple HLA-DR and HLA-DP4 Molecules and Stimulates Autologous CD4+ T Cells From Patients With NY-ESO-1-expressing Melanoma," J Immunol., 2005, 174(3):1751-9.
Mandruzzato et al., "A CASP-8 Mutation Recognized by Cytolytic T Lymphocytes on a Human Head and Neck Carcinoma," J. Exp. Med., 1997, 186(5):785-93.
Manici et al., "Melanoma Cells Present a MAGE-3 Epitope to CD4(+) Cytotoxic T Cells in Association With Histocompatibility Leukocyte Antigen DR11," J Exp Med., 1999, 189(5):871-6.
Marks et al., "By-passing immunization: building high affinity human antibodies by chain shuffling," Biotechnology, Jul. 1992, 10(7):779-783.
Massari et al., "Immune Checkpoint Inhibitors for Metastatic Bladder Cancer," Cancer Treat Rev., 2018, 64:11-20.
Matsuzaki et al., "Recognition of Naturally Processed and Ovarian Cancer Reactive CD8+ T Cell Epitopes Within a Promiscuous HLA Class II T-helper Region of NY-ESO-1," Cancer Immunol Immunother., 2008, 57(8)1185-95.
McCafferty et al., "Phage antibodies: filamentous phage displaying antibody variable domains," Nature, 1990, 348(6301):552-554.
Meng et al., "Identification of an HLA-DPB1*0501 Restricted Melan-A/MART-1 Epitope Recognized by CD4+ T Lymphocytes: Prevalence for Immunotherapy in Asian Populations," J. Immunother., 2011, 23(7):525-534.
Michaux et al., "A Spliced Antigenic Peptide Comprising a Single Spliced Amino Acid Is Produced in the Proteasome by Reverse Splicing of a Longer Peptide Fragment Followed by Trimming," J Immunol., 2014, 192(4):1962-71.
Miller et al., "Improved Retroviral Vectors for Gene Transfer and Expression," Biotechnology, 1989, 7(9):980-990.
Miller, "Retrovirus Packaging Cells ," Human Gene Therapy, 1990, 1:5-14.
Minev et al. "Cytotoxic T cell immunity againist telomerase reverse transscriptase in humans," Proceedings of the National Academy of Sciences of the United States of America, Apr. 25, 2000, 97(9):4796-4801.
Miwa et al., "Expression of the Wilms' tumor gene (WT1) in human leukemias," Leukemia, May 1992, 6(5):405-409 (Abstract Only).
Miyagawa et al., "A Newly Identified MAGE-3-derived, HLA-A24-restricted Peptide Is Naturally Processed and Presented as a CTL Epitope on MAGE-3-expressing Gastrointestinal Cancer Cells," Oncology, 2006, 70(1):54-62.
Miyahara et al., "Determination of Cellularly Processed HLA-A2402-restricted Novel CTL Epitopes Derived From Two Cancer Germ Line Genes, MAGE-A4 and SAGE," Clin Cancer Res., 2005, 11(15):5581-9.
Miyoshi et al., "Stable and Efficient Gene Transfer Into the Retina Using an HIV-based Lentiviral Vector," Proc. Natl. Acad Sci. US.A., 94(19):10319-10323.
Mizote et al., "Three Novel NY-ESO-1 Epitopes Bound to DRB1*0803, DQB1*0401 and DRB1*0901 Recognized by CD4 T Cells From CHP-NY-ESO-1-vaccinated Patients," Vaccine, 2010, 28(32):5338-46.
Moen, "Directions in Gene Therapy," Blood Cells, 1991, 17(2):407-416 (Abstract Only).
Moesta et al., "Local Delivery of OncoVEX mGM-CSF Generates Systemic Antitumor Immune Responses Enhanced by Cytotoxic T-Lymphocyte-Associated Protein Blockade," Clin Cancer Res., 2017, 23(20):6190-6202.
Monji et al., "Identification of a Novel Human Cancer/Testis Antigen, KM-HN-1, Recognized by Cellular and Humoral Immune Responses," Clin Cancer Res., Sep. 15, 2004, 10:6047-57.
Moreau-Aubry et al., "A Processed Pseudogene Codes for a New Antigen Recognized by a CD8(+) T Cell Clone on Melanoma," J Exp Med., 2000, 191(9):1617-24.
Morel et al., "A Tyrosinase Peptide Presented by HLA-B35 Is Recognized on a Human Melanoma by Autologous Cytotoxic T Lymphocytes," Int. J. Cancer, 1999, 83(6):755-9.
Morgan et al., "High Efficiency TCR Gene Transfer Into Primary Human Lymphocytes Affords Avid Recognition of Melanoma Tumor Antigen Glycoprotein 100 and Does Not Alter the Recognition of Autologous Melanoma Antigens," J. Immunol., 2003, 171(6):3287-3295.
Morizono et al., "Redirecting Lentiviral Vectors Pseudotyped With Sindbis Virus-Derived Envelope Proteins to DC-SIGN by Modification of N-linked Glycans of Envelope Proteins," J Viral., 2010, 84(14):6923-693.
Motzer et al., "Nivolumab for Metastatic Renal Cell Carcinoma: Results of a Randomized Phase II Trial," J Clin Oneal, 2015, 33(13):1430-1437.
Munir et al., "HLA-restricted CTL That Are Specific for the Immune Checkpoint Ligand PD-L1 Occur With High Frequency in Cancer Patients," Cancer Res., 2013, 73(6):1764-76.
Muraoka et al., "Establishment of Animal Models to Analyze the Kinetics and Distribution of Human Tumor Antigen-Specific CD8+ T Cells," Vaccine, 2013, 31(17):2110-2118.
Nakatsuka et al., "Immunohistochemical Detection of WT1 Protein in a Variety of Cancer Cells," Mod. Pathol., 2006, 19(6):804-814.
Naldini et al., "In Vivo Gene Delivery and Stable Transduction of Nondividing Cells by a Lentiviral Vector," Science, 1996, 272(5259):263-267.
Needleman et al., "A General Method Applicable to the Search for Similarities in the Amino Acid Sequence of Two Proteins," J. Mol. Biol., 1970, 48:443-453.
Neumann et al., "A Peptide Epitope Derived From the Cancer Testis Antigen HOM-MEL-40/SSX2 Capable of Inducing $CD4^+$ and $CD8^+$ T-cell as Well as B-cell Responses," Cancer Immunol Immunother., 2011, 60(9):1333-46.
Neumann et al., "Identification of an HLA-DR-restricted Peptide Epitope With a Promiscuous Binding Pattern Derived From the Cancer Testis Antigen HOM-MEL-40/SSX2," Int J Cancer, 2004, 112(4):661-8.
Nezafat et al., "A novel multi-epitode peptide vaccine against cancer: An in silico approach," Journal of Theoretical Biology, Feb. 7, 2014, 349:121-134.
Nielsen et al., "MHC Class II Epitope Predictive Algorithms," Immunology, 2010, 130(3):319-328.

(56) References Cited

OTHER PUBLICATIONS

Noppen et al., "Naturally Processed and Concealed HLA-A2.1-restricted Epitopes From Tumor-Associated Antigen Tyrosinase-Related protein-2," Int. J. Cancer, 2000, 87(2):241-6.
Novellino et al., "Identification of a Mutated Receptor-Like Protein Tyrosine Phosphatase Kappa as a Novel, Class II HLA-restricted Melanoma Antigen," J. Immunol., 2003, 170(12):6363-70.
Nuber et al., "Fine Analysis of Spontaneous MAGE-C1/CT7-specific Immunity in Melanoma Patients," Proc Natl Acad Sci U.S.A. 107(34):15187-92.
Ochsenreither et al., "Cyclin-A1 Represents a New Immunogenic Targetable Antigen Expressed in Acute Myeloid Leukemia Stem Cells With Characteristics of a Cancer-Testis Antigen," Blood, 2012, 119(23):5492-501.
Oehlrich et al., "Generation of RAGE-1 and MAGE-9 Peptide-Specific Cytotoxic T-lymphocyte Lines for Transfer in Patients With Renal Cell Carcinoma," Int. J. Cancer, 2005, 117(2):256-64.
Ohminami et al., "HLA Class I-restricted Lysis of Leukemia Cells by a CD8(+) Cytotoxic T-lymphocyte Clone Specific for WTI Peptide," Blood, 2000, 95(1):286-93.
Ohue et al., "Spontaneous Antibody, and CD4 and CD8 T-cell Responses Against XAGE-1b (GAGED2a) in Non-Small Cell Lung Cancer Patients," Int J Cancer, 2012, 131(5):E649-58.
Oiso et al., "A Newly Identified MAGE-3-derived Epitope Recognized by HLA-A24-restricted Cytotoxic T Lymphocytes," Int J Cancer, 1999, 81(3):387-94.
Oji et al., "Expression of the wilms' tumor gene WTI in solid tumors and its involvement intumor cell growth," Japan J Cancer. Res., Feb. 1999, 90(19):194-204.
Oka et al., "Cancer Immunotherapy Targeting Wilms' Tumor Gene WT1 Product," J Immunol., 2000, 164(4):1873-80.
Okugawa et al., "A Novel Human HER2-derived Peptide Homologous to the Mouse K(d)-restricted Tumor Rejection Antigen Can Induce HLA-A24-restricted Cytotoxic T Lymphocytes in Ovarian Cancer Patients and Healthy Individuals," Eur J Immunol., 2000, 30(11):3338-46.
Oliveira et al., "Alternative antigen processing for MHC class I: mutiple roads lead to rome," Frontiers in Immunology, Jun. 5, 2015, 6(298): 10 pages.
Olson et al., "HLA-A2-restricted T-cell epitopes specific for prostatic acid phosphatase," Cancer Immunol Immunother., 2010, 59(6):943-53.
Olson et al., "The Androgen Receptor: A Biologically Relevant Vaccine Target for the Treatment of Prostate Cancer," Cancer Immunol., 2010, Immunother., 62(3):585-596.
Ono et al., "Plasmid DNAs directly injected into mouse brain with lipofectin can be incorporated and expressed by brain cells," Neuroscience Letters, 1990, 117(3): 259-263.
Osen et al., "Screening of Human Tumor Antigens for CD4 T Cell Epitopes by Combination of HLA-transgenic Mice, Recombinant Adenovirus and Antigen Peptide Libraries," PLoS One., 2010, 5(11):e14137, 13 pages.
Ottaviani et al., "A MAGE-1 Antigenic Peptide Recognized by Human Cytolytic T Lymphocytes on HLA-A2 Tumor Cells," Cancer Immunol Immunother., 2005, 54(12):1214-20.
Ottaviani et al., "A New MAGE-4 Antigenic Peptide Recognized by Cytolytic T Lymphocytes on HLA-A24 Carcinoma Cells," Cancer Immunol Immunother., 2006, 55(7):867-72.
Panelli et al., "A Tumor-Infiltrating Lymphocyte From a Melanoma Metastasis With Decreased Expression of Melanoma Differentiation Antigens Recognizes MAGE-12," J Immunol., 2000, 164(8):4382-92.
Pardoll, "The Blockade of Immune Checkpoints in Cancer Immunotherapy," Nat Rev Cancer, 2012, 12(4):252-264.
Parker et al., "Scheme for Ranking Potential HLA-A2 Binding Peptides Based on Independent Binding of Individual Peptide Side-Chains," J Immunol., 1994, 152(1):163-175.
Parkhurst et al., "Identification of a Shared HLA-A*0201-restricted T-cell Epitope From the Melanoma Antigen Tyrosinase-Related Protein 2 (TRP2)," Cancer Res., 1998, 58(21):4895-901.
Parkhurst et al., "Induction of CD4+ Th1 Lymphocytes That Recognize Known and Novel Class II MHC Restricted Epitopes From the Melanoma Antigen gp100 by Stimulation With Recombinant Protein," J Immunother., 2004, 27(2):79-91.
Parkhurst et al., "T Cells Targeting Carcinoembryonic Antigen Can Mediate Regression of Metastatic Colorectal Cancer but Induce Severe Transient Colitis," Mol. Ther., 2011, 19(3):620-6.
Parmiani et al., "Cancer Immunotherapy With Peptide-Based Vaccines: What Have We Achieved? Where Are We Going?," J. Nat. Cancer Inst., 94(11):805-818.
Paschen et al., "Detection of Spontaneous CD4+ T-cell Responses in Melanoma Patients Against a Tyrosinase-Related protein-2-derived Epitope Identified in HLA-DRB1*0301 Transgenic Mice," Clin. Cancer Res., 2005, (14):5241-7.
Pascolo et al., "A MAGE-A1 HLA-A A*0201 Epitope Identified by Mass Spectrometry," Cancer Res., 2001, 61(10):4072-7.
PCT International Preliminary Report on Patentability in International Appln. PCT/US2019/020562, dated Sep. 17, 2020, 10 pages.
PCT International Search Report and Written Opinion in International Appln. No. PCT/US2018/020985, dated Aug. 20, 2018, 22 pages.
PCT International Search Report and Written Opinion in International Appln. No. PCT/US2019/020562, dated Jun. 6, 2019, 13 pages.
Pettitt et al., "CAR-T Cells: A Systematic Review and Mixed Methods Analysis of the Clinical Trial Landscape," Mol. Ther., 2018, 26(2):342-35.
Pichard et al., "Detection, Isolation, and Characterization of Alpha-Fetoprotein-Specific T Cell Populations and Clones Using MHC Class I Multimer Magnetic Sorting," J Immunother., 2008, 31(3):246-53.
Pieper et al., "Biochemical Identification of a Mutated Human Melanoma Antigen Recognized by CD4(+) T Cells," J Exp Med., 1999, 189(5):757-66.
Pils et al., "In Ovarian Cancer the Prognostic Influence of HER2/neu Is Not Dependent on the CXCR4/SDF-1 Signalling Pathway," Br. J. Cancer, 96(3):485-91.
Powers et al., "Evolutionary Relationships and Systematics of the Alphaviruses," J Viral., 2001, 75(21):10118-10131.
Principals and Practice of the Biologic Therapy for Cancer, 3rd ed., Resenberg (ed)., 2000, Chapter 16.7: Identification of Human Tumor antigens by Serological Expression Cloning, p. 557-570.
Probst-Kepper et al., "An Alternative Open Reading Frame of the Human Macrophage Colony-Stimulating Factor Gene Is Independently Translated and Codes for an Antigenic Peptide of 14 Amino Acids Recognized by Tumor-Infiltrating CD8 T Lymphocytes," J Exp Med. 193(10):1189-98.
Qian et al., "Dickkopf-1 (DKK1) Is a Widely Expressed and Potent Tumor-Associated Antigen in Multiple Myeloma," Blood, 2007, 110(5):1587-94.
Raghavan et al., "Extended Repertoire of Permissible Peptide Ligands for HLA-B*2702," Protein Science, 1996, 5(10):2080-208.
Rajasagi et al., "Systematic Identification of Personal Tumor-Specific Neoantigens in Chronic Lymphocytic Leukemia," Blood, 2014, 124(3):453-62.
Rammensee et al., "SYFPEITHI: database for MHC ligands and peptide motifs," Immunogenetics, 1999, 50:213-219.
Reche et al., "Enhancement to the RANKPEP Resource for the Prediction of Peptide Binding to MHC Molecules Using Profiles," Immunogenetics, 2004, 56:405-419.
Reche et al., "Prediction of MHC Class I Binding Peptides Using Profile Motifs," Human Immunol., 2002, 63(9):701-709.
Reche et al., "Prediction of peptide-MHC Binding Using Profiles," Methods Mol. Biol., 2007, 409:185-200.
Reuschenbach et al., "A systematic review of humoral immune responses against tumor antigens," Cancer Immunol. Immunother., Oct. 2009, 58(10):1535-1544.
Ribas, "Adaptive Immune Resistance: How Cancer Protects From Immune Attack," Cancer Discov, 2015, 5(9):915-919.
Riley et al., "Identification of a New Shared HLA-A2.1 Restricted Epitope From the Melanoma Antigen Tyrosinase," J. Immunother., 2001, 24(3):212-220.

(56) References Cited

OTHER PUBLICATIONS

Rimoldi et al., "Efficient Simultaneous Presentation of NY-ESO-1/LAGE-1 Primary and Nonprimary Open Reading Frame-Derived CTL Epitopes in Melanoma," The Journal of Immunology, 2000, 165(12):7253-7261.

Ripberger et al., "Identification of an HLA-A0201-restricted CTL Epitope Generated by a Tumor-Specific Frameshift Mutation in a Coding Microsatellite of the OGT Gene," J Clin Immunol., Sep. 2003, 23(5):415-423.

Robbins et al., "A Mutated f3-Catenin Gene Encodes a Melanoma-specific Antigen Recognized by Tumor Infiltrating Lymphocytes," J. Exp. Med., 1996, 183(3):1185-1192.

Robbins et al., "Mining exomic sequencing data to identify mutated antigens recognized by adoptively transferred tumor-reactive T cells," Nature Med., Jun. 2013, 19(6):747-752.

Robbins et al., "Multiple HLA class II-restricted melanocyte differentiation antigens are recognized by tumor-infiltrating lymphocytes from a patient with melanoma," J. Immunol., 2002, 169(10):6036-6047.

Robbins et al., "The intronic region of an incompletely spliced gp100 gene transcript encodes an epitope recognized by melanoma-reactive tumor-infiltrating lymphocytes," J Immunol., Jul. 1, 1997, 159(1):303-308.

Rodeberg et al., "Recognition of six-transmembrane epithelial antigen of the prostate-expressing tumor cells by peptide antigen-induced cytotoxic T lymphocytes," Clin. Cancer Res., 2005, 11(12):4545-4552.

Rongcun et al., "Identification of New HER2/neu-Derived Peptide Epitopes That Can Elicit Specific CTL Against Autologous and Allogeneic Carcinomas and Melanomas," J Immunol., 1999, 163(2):1037-1044.

Ronsin et al., "A Non-AUG-Defined Alternative Open Reading Frame of the Intestinal Carboxyl Esterase mRNA Generates an Epitope Recognized by Renal Cell Carcinoma-Reactive Tumor-Infiltrating Lymphocytes In Situ," J Immunol., 1999, 163(1):483-490.

Rosenberg et al., "Gene Transfer into Humans—Immunotherapy of Patients with Advanced Melanoma, Using Tumor-Infiltrating Lymphocytes Modified by Retroviral Gene Transduction," The New England Journal of Medicine, Aug. 30, 1990, 323(9):570-578.

Russo et al., "Dendritic cells acquire the MAGE-3 human tumor antigen from apoptotic cells and induce a class I-restricted T cell response," Proceedings of the National Academy of Sciences of the United States of America, 2000, 97(5):2185-2190.

Sanders, "No False Start for Novel Pseudotyped Vectors," Curr. Opin. Biotechnol., 2002, 13(5):437-442.

Scardino et al., "HER-2/neu and hTERT cryptic epitopes as novel targets for broad spectrum tumor immunotherapy," J Immunol., 2002, 168(11):5900-5906.

Scardino et al., "Identification of HER-2/neu immunogenic epitopes presented by renal cell carcinoma and other human epithelial tumors," Eur J Immunol., Nov. 2001, 31(11):3261-3270.

Scherwitzl et al., "Systemically administered Sindbis virus in combination with immune checkpoint blockade induces curative anti-tumor immunity," Molecular Therapy: Oncolytics, Jun. 2018, 9:51-63.

Schiavetti et al., "A human endogenous retroviral sequence encoding an antigen recognized on melanoma by cytolytic T lymphocytes," Cancer Res., Oct. 2002, 62(19):5510-5516.

Schmitz et al., "Generation of survivin-specific CD8+ T effector cells by dendritic cells pulsed with protein or selected peptides," Cancer Res., 2000, 60(17):4845-4849.

Schroers et al., "Human telomerase reverse transcriptase-specific T-helper responses induced by promiscuous major histocompatibility complex class II-restricted epitopes," Clin. Cancer Res., 2003, 9(13):4743-4755.

Schroers et al., "Identification of HLA DR7-restricted epitopes from human telomerase reverse transcriptase recognized by CD4+ T-helper cells," Cancer Res., 2002, 62(9):2600-2605.

Schultz et al., "A MAGE-3 peptide recognized on HLA-B35 and HLA-A1 by cytolytic T lymphocytes," Tissue Antigens, 2001, 57(2):103-109.

Schultz et al., "A MAGE-A3 peptide presented by HLA-DP4 is recognized on tumor cells by CD4+ cytolytic T lymphocytes," Cancer Res., 2000, 60(22):6272-6275.

Schultz et al., "Functional analysis of tumor-specific Th cell responses detected in melanoma patients after dendritic cell-based immunotherapy," J Immunol., 2004, 172(2):1304-1310.

Schultz et al., "The production of a new MAGE-3 peptide presented to cytolytic T lymphocytes by HLA-B40 requires the immunoproteasome," J Exp Med., 2002, 195(4):391-399.

Schwab et al., "Past, present and future targets for immunotherapy in ovarian cancer," Immunotherapy, 2014, 6(12):1279-1293.

Schwitalle et al., "Immunogenic peptides generated by frameshift mutations in DNA mismatch repair-deficient cancer cells," Cancer Immun., 2004, 4(1):14.

Seidah et al., "The Biology and Therapeutic Targeting of the Proprotein Convertases," Nature Reviews Drug Discovery, 2012, 11(5):367-38.

Sensi et al., "Identification of a novel gp100/pMel17 peptide presented by HLA-A*6801 and recognized on human melanoma by cytolytic T cell clones," Tissue Antigens., 2002, 59(4):273-279.

Sensi et al., "Immunogenicity without Immunoselection: A Mutant but Functional Antioxidant Enzyme Retained in a Human Metastatic Melanoma and Targeted by CD8+ T Cells with a Memory Phenotype," Cancer Res., 2005, 65(2):632-640.

Sharkey et al., "CD4(+) T-cell recognition of mutated B-RAF in melanoma patients harboring the V599E mutation," Cancer Res., 2004, 64(5):1595-1599.

Sharkey et al., "Ross River virus glycoprotein-pseudotyped retroviruses and stable cell lines for their production," J Virology, Mar. 2001, 75(6):2653-2659.

Sharma et al., "Immune Checkpoint Targeting in Cancer Therapy: Toward Combination Strategies With Curative Potential," Cell, 2015, 161:205-214.

Sharp, "Gene Therapy," The Lancet, May 1991, 337:1277-1278.

Shimono et al., "Identification of DR9-restricted XAGE antigen on lung adenocarcinoma recognized by autologous CD4 T-cells," Int J Oncol., Apr. 2007, 30(4):835-840.

Siegel et al., "Induction of antitumour immunity using survivin peptide-pulsed dendritic cells in a murine lymphoma model," Br. J. Haematology, Sep. 2003, 122(6):911-914.

Skipper et al., "An HLA-A2-restricted Tyrosinase Antigen on Melanoma Cells Results from Posttranslational Modification and Suggests a Novel Pathway for Processing of Membrane Proteins," J. Exp. Med., Feb. 1996, 183(2):527-534.

Skipper et al., "Shared epitopes for HLA-A3-restricted melanoma-reactive human CTL include a naturally processed epitope from Pmel-17/gp100.," J Immunol., Dec. 1, 1996, 157(11):5027-5033.

Slager et al., "CD4+ Th2 Cell Recognition of HLA-DR-Restricted Epitopes Derived from CAMEL: A Tumor Antigen Translated in an Alternative Open Reading Frame," J Immunol., Feb. 2003, 170(3):1490-1497.

Slager et al., "Identification of multiple HLA-DR-restricted epitopes of the tumor-associated antigen CAMEL by CD4+ Th1/Th2 lymphocytes," J Immunol., 2004, 172(8):5095-5102.

Slager et al., "Induction of CAMEL/NY-ESO-ORF2-specific CD8 p T cells upon stimulation with dendritic cells infected with a modified Ad5 vector expressing a chimeric Ad5/35 fiber," Cancer Gene Ther., 2004, 11(3):227-236.

Slansky et al., "Enhanced antigen-specific antitumor immunity with altered peptide ligands that stabilize the MHC-peptide-TCR complex," Immunity, Oct. 2000, 13(4):529-538.

Spizzo et al., "Overexpression of epithelial cell adhesion molecule (Ep-CAM) is an independent prognostic marker for reduced survival of patients with epithelial ovarian cancer," Gynecology Oncology, 2006, 103(2):483-488.

Spranger et al., "Up-regulation of PD-L1, IDO, and Tregs in the Melanoma tumor microenvironment is driven by CD8+ T cells," Sci Transl Med, 2013, 5(200ra116):1-10.

Staubinger et al., "Liposomes as carriers for intracellular delivery of nucleic acids," Methods in Enzymology, 1983, 101:512-527.

(56) References Cited

OTHER PUBLICATIONS

Stroobant et al., "Inefficient exogenous loading of a tapasin-dependent peptide onto HLA-B*44:02 can be improved by acid treatment or fixation of target cells," Eur J Immunol., 2012, 42(6):1417-1428.
Suda et al., "Identification of human leukocyte antigen-A24-restricted epitope peptides derived from gene products upregulated in lung and esophageal cancers as novel targets for immunotherapy," Cancer Sci., Nov. 2007, 98(11):1803-1808.
Sun et al., "A new LAGE-1 peptide recognized by cytolytic T lymphocytes on HLA-A68 tumors," Cancer Immunol Immunother., 2006, 55(6):644-652.
Suri et al., "Targeting cancer testis antigens for biomarkers and immunotherapy in colorectal cancer: Current status and challenges," World J Gastrointestinal Oncology, Dec. 2015, 7(12):492-502.
Taglimonte et al., "Antigen-specific vaccines for cancer treatment," Human Vaccines and Immunotherapeutics, Oct. 31, 2014, 10(11):3332-3346.
Tahara et al., "Identification of a MAGE-2-encoded Human Leukocyte AntigenA24-binding Synthetic Peptide That Induces Specific Antitumor Cytotoxic T Lymphocytes," Clin Cancer Res., Aug. 1999, 5(8):2236-2241.
Tajima et al., "Identification of an epitope from the epithelial cell adhesion molecule eliciting HLA-A*2402-restricted cytotoxic T-lymphocyte responses," Tissue Antigens, Dec. 2004, 64(6):650-659.
Takenoyama et al., "A point mutation in the NFYC gene generates an antigenic peptide recognized by autologous cytolytic T lymphocytes on a human squamous cell lung carcinoma," Int. J Cancer, 2006, 118(8):1992-1997.
Tandon et al., "Emerging strategies for EphA2 receptor targeting for cancer therapeutics," Expert Opin. Ther. Targets, Dec. 2010, 15(1):31-51.
Tanzarella et al., "Identification of a Promiscuous T-Cell Epitope Encoded by Multiple Members of the MAGE Family," Cancer Res., Jun. 1999, 59(11):2668-2674.
Thomas et al., "Mesothelin-specific CD8(+) T Cell Responses Provide Evidence of in Vivo Cross-Priming by Antigen-Presenting Cells in Vaccinated Pancreatic Cancer Patients," J Exp Med., 200(3):297-306.
Thomson et al., "Delivery of Multiple CD8 Cytotoxic T Cell Epitopes by DNA Vaccination," J. Immunol., Feb. 1998, 160(4):1717-1723.
Tolstoshev et al., "Gene expression using retroviral vectors," Current Opinion in Biotechnology, Oct. 1990, 1(1):55-61.
Tomita et al., "A novel tumor-associated antigen, cell division cycle 45-like can induce cytotoxic T-lymphocytes reactive to tumor cells," Cancer Sci., Apr. 2011, 102(4):697-705.
Tomita et al., "Identification of immunogenic LY6K long peptide encompassing both CD4+ and CD8+ T-cell epitopes and eliciting CD4+ T-cell immunity in patients with malignant disease," Oncoimmunology, Feb. 2014 3(e28100):1-15.
Topalian et al., "Melanoma-specific CD4+ T cells recognize nonmutated HLA-DR-restricted tyrosinase epitopes," J. Exp. Med., May 1, 1996, 183(5):1965-1971.
Topalian et al., "Revelation of a Cryptic Major Histocompatibility Complex Class II-restricted Tumor Epitope in a Novel RNA-processing Enzyme," Cancer Res., Oct. 1, 2002, 62(19):5505-5509.
Topalian et al., "Safety, Activity, and Immune Correlates of Anti-PD-I Antibody in Cancer," N Engl. J Med., 2012, 366(26):2443-2454.
Touloukian et al., "Expression of a "Self-" Antigen by Human Tumor Cells Enhances Tumor Antigen-specific CD4+ T-Cell Function," Cancer Res., Sep. 2002, 62(18):5144-5147.
Touloukian et al., "Identification of a MHC class II-restricted human gp100 epitope using DR4-IE transgenic mice," J Immunol., Apr. 1, 2000, 164(7):3535-3542.
Touloukian et al., "Normal Tissue Depresses While Tumor Tissue Enhances Human T Cell Responses In Vivo to a Novel Self/Tumor Melanoma Antigen, OA1," J. Immunol., Feb. 1, 2003, 170(3):1579-1585.
Traversari et al., "A nonapeptide encoded by human gene MAGE-1 is recognized on HLA-A1 by cytolytic T lymphocytes directed against tumor antigen MZ2-English," J Exp Med., Nov. 1, 1992, 176(5):1453-1457.
Tsai et al., "Identification of Subdominant CTL Epitopes of the GP100 Melanoma-Associated Tumor Antigen by Primary in Vitro Immunization with Peptide-Pulsed Dendritic Cells," J Immunol., Feb. 15, 1997, 158(4):1796-1802 (Abstract Only).
Tseng et al., "In Vivo Antitumor Activity of Sindbis Viral Vectors," J Natl Cancer Inst., Dec. 4, 2002, 94(23):1790-1802.
Tseng et al., "Systemic Tumor Targeting and Killing by Sindbis Viral Vectors," Nat Biotechnol., 2004, 22(1):70-77.
Tseng et al., "Using Sindbis Viral Vectors for Specific Detection and Suppression of Advanced Ovarian Cancer in Animal Models," Cancer Res., Sep. 15, 2004, 64(18):6684-6692.
Tsukahara et al., "Identification of Human Autologous Cytotoxic T-Lymphocyte-Defined Osteosarcoma Gene That Encodes a Transcriptional Regulator, Papillomavirus Binding Factor," Cancer Research, Aug. 1, 2004, 64(15):5442-5448.
Tumeh et al., "PD-1 Blockade Induces Responses by Inhibiting Adaptive Immune Resistance," Nature, 2014, 515(7528):568-571.
Underwood et al., "Ovarian Tumor Cells Express a Novel Multi-Domain Cell Surface Serine Protease," BBA Mol. Basis of Disease, 2000, 1502(3):337-350.
Valmori et al., "Expression of synovial sarcoma X (SSX) antigens in epithelial ovarian cancer and identification of SSX-4 epitopes recognized by CD4+ T cells," Clin Cancer Res. Jan. 15, 2006, 12(2):398-404.
Valmori et al., "Naturally Occuring Human Lymphocyte Antigen-A2 Restricted CD8+ T-Cell Response to the Cancer Testis Antigen NY-ESO-1 in Melanoma Patients," Cancer Res., Aug. 2000, 60(16):4499-4506.
Van Den Eynde et al., "A new antigen recognized by cytolytic T lymphocytes on a human kidney tumor results from reverse strand transcription," J. Exp. Med., Dec. 20, 1999, 190(12):1793-1800.
Van den Eynde et al., "A new family of genes coding for an antigen recognized by autologous cytolytic T lymphocytes on a human melanoma," J Exp Med., Sep. 1, 1995, 182(3):689-698.
Van der Bruggen et al., "A peptide encoded by human gene MAGE-3 and presented by HLA-A2 induces cytolytic T lymphocytes that recognize tumor cells expressing MAGE-3," Eur J Immunol., Dec. 1994, 24(12):3038-3043.
Van der Bruggen et al., Autologous cytolytic T lymphocytes recognize a MAGE-1 nonapeptide on melanomas expressing HLA-Cw* 1601, Eur J Immunol. Sep. 1994, 24(9):2134-2140.
Vantomme et al., "A new tumor-specific antigenic peptide encoded by MAGE-6 is presented to cytolytic T lymphocytes by HLA-Cw16," Cancer Immun., Dec. 10, 2003, 3(17):1-8.
Vauchy et al., "CD20 alternative splicing isoform generates immunogenic CD4helper T epitopes," Int J Cancer, Jul. 1, 2015, 137(1):116-126.
Vigneron et al., "A peptide derived from melanocytic protein gp100 and presented by HLA-B35 is recognized by autologous cytolytic T lymphocytes on melanoma cells," Tissue Antigens, 2005, 65(2):156-162.
Vigneron et al., "Database of T cell-defined human tumor antigens: the 2013 update," Cancer Immun., Jul. 15, 2013, 13(15):1-6.
Vigneron et al., "Identification of a new peptide recognized by autologous cytolytic T lymphocytes on a human melanoma," Cancer Immunity, Jul. 2002, 2(9): 10 pages.
Vissers et al., "The Renal Cell Carcinoma-associated Antigen G250 Encodes a Human Leukocyte Antigen (HLA)-A2.1-restricted Epitope Recognized by Cytotoxic T Lymphocytes," Cancer Research, Nov. 1, 1999, 59(21):5554-5559.
Vonderheide et al., "The Telomerase Catalytic Subunit Is aWidely Expressed Tumor-Associated AntigenRecognized by Cytotoxic T Lymphocytes," Immunity, Jun. 1999, 10(6):673-679.

(56) References Cited

OTHER PUBLICATIONS

Wahl et al., "Molecular hybridization of immobilized nucleic acids: theoretical concepts and practical considerations," Methods Enzymol., 1987, 152:399-407.
Walton et al., "Spontaneous CD8 T cell responses against the melanocyte differentiation antigen RAB38/NY-MEL-1 in melanoma patients," J Immunol., Dec. 1, 2006, 177(11):8212-8218.
Wang et al., "A Breast and Melanoma-Shared Tumor Antigen: T Cell Responses to Antigenic Peptides Translated from Different Open Reading Frames," Journal of Immunology, Oct. 1, 1998, 161(7):3596-3606.
Wang et al. "Identification of TRP-2 as a Human Tumor Antigen Recognized by Cytotoxic T Lymphocytes," Journal of Experimental Medicine, Dec. 1, 1996, 184(6):2207-2216.
Wang et al., "A systematic assessment of MHC class II peptide beinding predictions and evaluation of a consensus approach," PLoS Comput. Biol., Apr. 2008, 4(4):e10000048, 10 pages.
Wang et al., "Calreticulin promotes tumor lymphocyte infiltration and enhances the antitumor effects of immunotherapy by up-regulating the endothelial expression of adhesion molecules," Int. J Cancer, Jul. 29, 2011, 130(12):2892-2902.
Wang et al., "Cloning genes encoding MHC class II-restricted antigens: mutated CDC27 as a tumor antigen," Science, May 21, 1999, 284(5418):1351-1354.
Wang et al., "Identification of a Mutated Fibronectin As a Tumor Antigen Recognized by CD4 T Cells: Its Role in Extracellular Matrix Formation and Tumor Metastasis," Journal of Experimental Medicine, Jun. 3, 2002, 195(11):1397-1406.
Wang et al., "Identification of a novel major histocompatibility complex class II-restricted tumor antigen resulting from a chromosomal rearrangement recognized by CD4(+) T cells," J Exp Med., May 17, 1999, 189(10):1659-1668.
Wang et al., "Peptide binding predictions for HLA DR, DP and DQ molecules," BMC Bioinformatics, Nov. 2010, 11(568): 12 pages.
Wang et al., "Recognition of a New ARTC1 Peptide Ligand Uniquely Expressed in Tumor Cells by Antigen-Specific CD4 Regulatory T Cells," J Immunol., Apr. 2005, 174(5):2661-2670.
Wang et al., "Recognition of an antigenic peptide derived from tyrosinase-related protein-2 by CTL in the context of HLA-A31 and—A33," J. Immunol., Jan. 15, 1998, 160(2):890-897.
Wang et al., "Recognition of Breast Cancer Cells by CD8+ Cytotoxic T-Cell Clones Specific for NY-BR-1," Cancer Res., Jul. 1, 2006, 66(13):6826-6833.
Wang et al., "Selective identification of HLA-DP4 binding T cell epitopes encoded by the MAGE-A gene family," Cancer Immunol Immunother., 2007, 56(6):807-818.
Wang et al., "Tumor-Specific Human CD4+ Regulatory T Cells and Their Ligands: Implications for Immunotherapy," Immunity, Jan. 2004, 20(1):107-118.
Webb et al., "Tumor-infiltrating Lymphocytes Expressing the Tissue Resident Memory Marker CD103 Are Associated With Increased Survival in High-Grade Serous Ovarian Cancer," Clin Cancer Res., 20(2):434-444.
Wen et al., "Identification of promiscuous HLA-DR-restricted CD4+ T-cell epitopes on the cancer-testis antigen HCA587," Cancer Sci., Aug. 2011, 102(8):1455-1461.
Wick et al., "Surveillance of the Tumor Mutanome by T Cells During Progression From Primary to Recurrent Ovarian Cancer," Clin. Cancer Res., Mar. 1, 2014, 20(5):1125-1134.
Wilkinson et al., "Human kallikrein 4 signle peptide induces cytotoxis T cell responses in healthy donors and prostate cancer patients," Cancer Immunol., Immunother., 2012, 61(2):169-179.
Wolchok et al., "Overall Survival With Combined Nivolumab and Ipilimumab in Advanced Melanoma," N Engl J Med., 2017, 377(14):1345-1356.
Wolfel et al., "A p16INK4a-insensitive CDK4 mutant targeted by cytolytic T lymphocytes in a human melanoma," Science, Sep. 1, 1995, 269(5228):1281-1284.
Wolfel et al., "Two tyrosinase nonpeptides recognized on HLA-A2 melanomas by autologous cytolytic T lymphocytes," Eur. J. Immunol., 1994, 24(3):759-764.
Wolff et al., "Direct gene transfer into mouse muscle in vivo," Science, Mar. 23, 1990, 247(4949):1465-1468.
Woodland, "Jump-starting the immune system: prime-boosting comes of age," TRENDS in Immunology, Feb. 2004, 25(2):98-104.
Wu et al., "Receptor-mediated gene delivery and expression in vivo," Journal of Biological Chemistry, Oct. 15, 1989, 263(29):14621-14624.
Wu et al., "Targeting genes: delivery and persistent expression of a foreign gene driven by mammalian regulatory elements in vivo," Journal of Biological Chemistry, Oct. 15, 1989, 264(29):16985-16987.
Wurz et al., "Novel cancer antigens for personalized immunotherapies: latest evidence and clinical potential," Therapeutic Advances in Medical Oncology, Jan. 2016, 8(1):4-31.
Yang et al., "A novel mimovirus vaccine containing survivin epitope with adjuvant IL-15 induces long-lasting cellular immunity and high antitumor efficiency," Mol. Immunol., Mar. 2008, 45(6):1674-1681.
Yang et al., "An introduction to epitope prediction methods and software," Rev. Med. Viral., Dec. 19, 2008, 19(2):77-96.
Yotnda et al., "Cytotoxic T Cell Response against the Chimeric ETV6-AMLI Protein in Childhood Acute Lymphoblastic Leukemia," J. Clin. Invest. Jul. 1998, 102(2):455-462.
Yotnda et al., "Cytotoxic T Cell Response Against the Chimeric p210 BCR-ABL Protein in Patients with Chronic Myelogenous Leukemia," J. Clin. Invest., May 1998, 101(10):2290-2296.
Yun et al., "Augmentation of immune response by altered peptide ligands of the antigenic peptide in a human CD4+ T-cell clone reacting to TEL/AMLI fusion protein," Tissue Antigens, Aug. 1999, 54(2):153-161.
Zamarin et al., "Localized Oncolytic Virotherapy Overcomes Systemic Tumor Resistance to Immune Checkpoint Blockade Immunotherapy," Sci Transl. Med., Mar. 5, 2014, 6(226):226ra23, 12 pages.
Zarour et al., "NY-ESO-1 119-143 is a promiscuous major histocompatibility complex class II T-helper epitope recognized by Th1- and Th2-type tumor-reactive CD4+ T cells," Cancer Res., Jan. 1, 2002, 62(1):213-218.
Zarour et al., "NY-ESO-I encodes DRB1*0401-restricted epitopes recognized by melanoma-reactive CD4+ T cells," Cancer Res., Sep. 1, 2000, 60(17):4946-4952.
Zeng et al., "CD4(+) T cell recognition of MHC class II-restricted epitopes from NY-ESO-1 presented by a prevalent HLA DP4 allele: association with NY-ESO-1 antibody production," Proceedings of the National Academy of Sciences of the United States of America, Mar. 27, 2001, 98(7):3964-3969.
Zeng et al., "Identification of CD4+ T Cell Epitopes from NY-ESO-1 Presented by HLA-DR Molecules," J Immunol., 165(2):1153-1159.
Zhang et al., "A MAGE-3 peptide presented by HLA-DR1 to CD4+ T cells that were isolated from a melanoma patient vaccinated with a MAGE-3 protein," J Immunol., Jul. 1, 2003, 171(1):219-225.
Zhang et al., "A MAGE-A4 peptide presented by HLA-B37 is recognized on human tumors by cytolytic T lymphocytes," Tissue Antigens., Nov. 2002, 60(5):365-371.
Zorn et al., "A MAGE-6-encoded peptide is recognized by expanded lymphocytes infiltrating a spontaneously regressing human primary melanoma lesion," Eur J Immunol., Feb. 1999, 29(2):602-607.
Zorn et al., "A natural cytotoxic T cell response in a spontaneously regressing human melanoma targets a neoantigen resulting from a somatic point mutation," Eur. J. Immunol., Feb. 1999, 29(2):592-601.

* cited by examiner

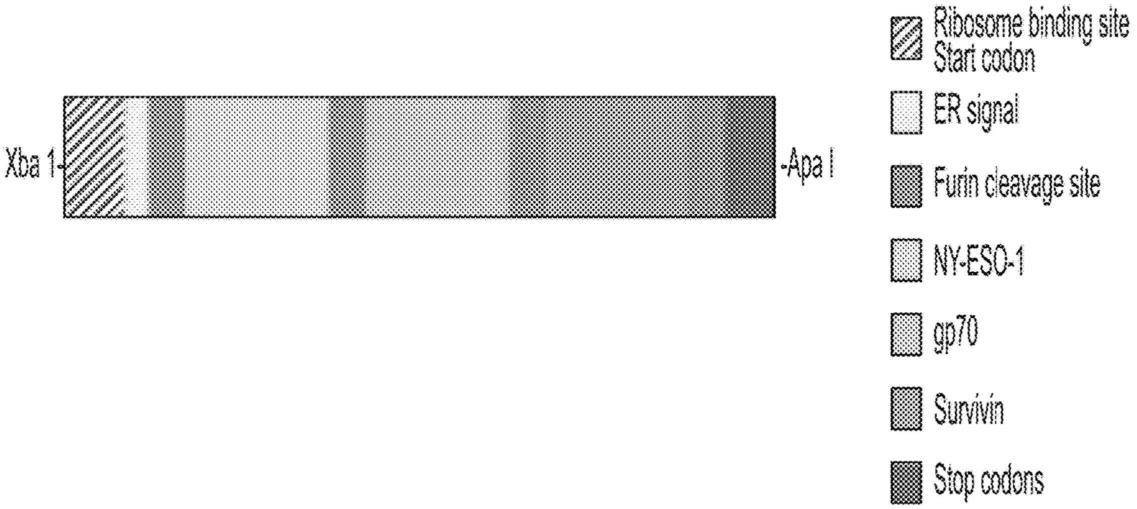

FIG. 1A

```
                    M  L  V  T  A  M  C  L  L  G  N  V  S  F  V  R  S  K  R
TCTAGAGCCACCATGCTGGTGACAGCCATGTGTCTGCTGGGCAATGTCAGCTTCGTCCGGAGCAAGCG
      L  R  G  P  E  S  R  L  L  E  V  R  S  K  R  L  S  P  S  Y  A  Y  H
GCTGCGGGGACCAGAGTCTCGGCTCCTGGAGGTGCGGAGCAAGCGGCTGTCCCCATCTTACGCCTACC
      Q  F  V  R  S* K  R  L  G  C  A  F  L  T  V  K  Q  M  R  S  K  R
ACCAGTTCGTCCGGAGCAAGCGGCTGGGCTGTGCCTTCCTGACCGTGAAGCAGATGCGGAGCAAGCGG
L  * (SEQ ID NO: 11)
CTGTGAGGGCCC (SEQ ID NO: 10)
```

— start — RBS — ER signal — Furin site — NY-Eso1 — gp70 — Survivin  TCTAGA xbaI  GGGCCC ApaI
(SEQ ID NO: 8) (SEQ ID NO: 9)

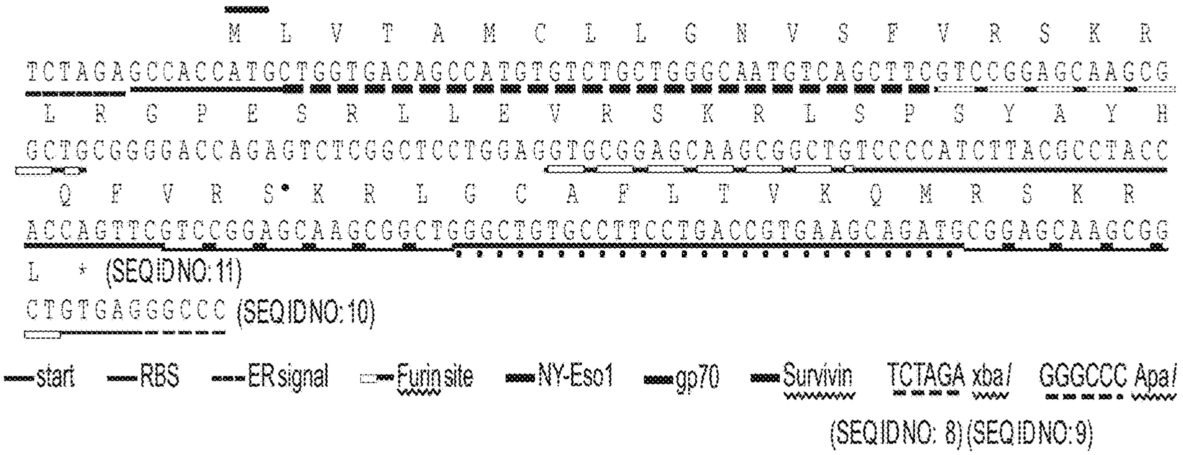

FIG. 1B

| | Day -1 | Day 6 | Day 13 | Day 21 |
|---|---|---|---|---|
| —◇— Control | 1.0 | 57.4 | 538.9 | 1883.3 |
| —□— SV_LacZ | 1.0 | 15.8 | 61.2 | 801.7 |
| —△— SV_NYESO1 | 1.0 | 0.7 | 3.9 | 42.1 |
| - ○ - -SV_MinigeneCT26 | 1.0 | 1.3 | 6.1 | 39.9 |

Days after treatment

Therapeutic effect of Sindbis/LacZ on s.c. tumor could not be observed in T cell-depleted mice.

anti-CTLA-4 + anti-PD-1 + SV/NY-ESO-1

| | Day -1 | Day 6 | Day 13 | Day 20 | Day 27 |
|---|---|---|---|---|---|
| Control-1 | 1.0 | 20.2 | 149.4 | 389.2 | |
| Control-2 | 1.0 | 53.8 | 288.2 | 1284.9 | |
| Control-3 | 1.0 | 2.1 | 41.9 | 307.6 | 353.2 |
| Control-4 | 1.0 | 22.0 | 297.3 | 807.2 | |
| Control-5 | 1.0 | 20.8 | 168.2 | 378.5 | |

Days after treatment

| | Day -1 | Day 6 | Day 13 | Day 20 | Day 27 | Day 34 | Day 41 | Day 48 | Day 55 | Day 62 |
|---|---|---|---|---|---|---|---|---|---|---|
| aCTL4-1 | 1.0 | 0.5 | 0.6 | 0.7 | 0.5 | 0.5 | 0.4 | 0.6 | 0.4 | 0.5 |
| aCTL4-2 | 1.0 | 0.4 | 0.5 | 0.4 | 0.4 | 0.3 | 0.3 | 0.4 | 0.3 | 0.3 |
| aCTL4-3 | 1.0 | 19.2 | 108.1 | | | | | | | |
| aCTL4-4 | 1.0 | 1.1 | 5.4 | 7.0 | 34.3 | 65.7 | 35.6 | 644.7 | | |
| aCTL4-5 | 1.0 | 0.5 | 0.6 | 0.5 | 0.5 | 0.5 | 0.4 | 0.4 | 0.4 | 0.4 |

Days after Sindbis treatment

| | Day -1 | Day 6 | Day 13 | Day 20 | Day 27 | Day 34 | Day 41 | Day 48 | Day 55 | Day 62 |
|---|---|---|---|---|---|---|---|---|---|---|
| aCTLA4_SVNYESO_1 | 1.0 | 0.5 | 0.4 | 0.5 | 0.5 | 0.4 | 0.5 | 0.5 | 0.5 | 0.5 |
| aCTLA4_SVNYESO_2 | 1.0 | 0.5 | 0.4 | 0.4 | 0.4 | 0.4 | 0.4 | 0.5 | 0.4 | 0.5 |
| aCTLA4_SVNYESO_3 | 1.0 | 0.6 | 0.6 | 0.6 | 0.5 | 0.5 | 0.7 | 0.6 | 0.6 | 0.6 |
| aCTLA4_SVNYESO_4 | 1.0 | 0.4 | 0.4 | 0.4 | 0.4 | 0.4 | 0.4 | 0.4 | 0.4 | 0.4 |
| aCTLA4_SVNYESO_5 | 1.0 | 0.6 | 0.5 | 0.6 | 0.6 | 0.5 | 0.5 | 0.5 | 0.6 | 0.5 |

Days after treatment

| | Day -1 | Day 6 | Day 13 | Day 20 | Day 27 | Day 34 | Day 41 | Day 48 | Day 55 | Day 62 |
|---|---|---|---|---|---|---|---|---|---|---|
| aPD1-1 | 1.0 | 4.6 | 1.9 | 226.6 | | | | | | |
| aPD1-2 | 1.0 | 16.7 | 332.9 | 619.2 | 432.9 | | | | | |
| aPD1-3 | 1.0 | 17.5 | 137.7 | 385.1 | 602.1 | | | | | |
| aPD1-4 | 1.0 | 1.8 | 40.2 | 205.8 | 297.2 | | | | | |
| aPD1-5 | 1.0 | 0.4 | 0.7 | 2.8 | 7.3 | 0.3 | 0.4 | 0.4 | 0.3 | 0.3 |

Days after Sindbis treatment

| | Day -1 | Day 6 | Day 13 | Day 20 | Day 27 | Day 34 | Day 41 | Day 48 | Day 55 | Day 62 |
|---|---|---|---|---|---|---|---|---|---|---|
| aPD1_SVNYESO_1 | 1.0 | 0.7 | 0.3 | 0.3 | 0.3 | 0.3 | 0.3 | 0.4 | 0.4 | 0.3 |
| aPD1_SVNYESO_2 | 1.0 | 0.9 | 0.6 | 0.7 | 0.5 | 0.7 | 0.6 | 0.8 | 0.7 | 0.7 |
| aPD1_SVNYESO_3 | 1.0 | 0.5 | 0.4 | 0.5 | 0.4 | 0.5 | 0.5 | 0.5 | 0.5 | 0.5 |
| aPD1_SVNYESO_4 | 1.0 | 0.5 | 0.4 | 1.0 | 1.7 | 22.4 | 20.4 | 93.1 | | |
| aPD1_SVNYESO_5 | 1.0 | 0.6 | 0.5 | 0.6 | 0.5 | 0.5 | 0.6 | 0.6 | 0.6 | 0.6 |

Days after Sindbis treatment

GAGGAATTCATGCAGGTGCAGCTGGTGGAGTCTGGGGGAGGCGTGGTCCAGCCTG
GGAGG
TCCCTGAGACTCTCCTGTGTGGCTTCTGGATTCACCTTCAGCAGCCATGGCATGC
ACTGG
GTCCGCCAGGCTCCAGGCAAGGGACTGGAGTGGGTGGCAGTTATCTGGTATGATG
GAAGA
AATAAATACTATGCAGACTCCGTGAAGGGCCGGTTCACCATCTCCAGAGACAATT
CCAAG
AACACACTGTTTCTGCAGATGAACAGCCTGAGAGCCGAGGACACTGCTGTGTATT
ACTGT
GCTAGAGGAGGCCACTTCGGTCCTTTTGACTACTGGGGCCAGGGAACCCTGGTCA
CCGTC
TCCTCTGGAGGCGGTGGCAGCGGAGGCGGAGGCAGCGGAGGCGGCGGCAGCCAGT
CTCCA
GGCACCCTGTCTCTGTCTCCAGGGGAAAGAGCCACCCTGTCCTGCAGGGCCAGCC
AGAGC
ATTAGCAGCAGCTTCCTGGCCTGGTACCAGCAGAGACCTGGCCAGGCTCCCAGGC
TGCTT
ATCTATGGTGCATCCAGCAGGGCCACTGGCATCCCAGACAGGTTCAGCGGCAGCG
GGTCT
GGGACAGACTTCACTCTCACCATCAGCAGACTGGAGCCTGAAGATTTTGCAGTGT
ATTAC
TGTCAGCAGTATGGCACCTCTCCCTGGACATTCGGCCAAGGGACCAAGGTGGAAA
TCAAA
AGATGA

MQVQLVESGGGVVQPGRSLRLSCVASGFTFSSHGMHWVRQAPGKGLEWVAVIWYD
GRNKYYADSVKGRFTISRDNSKNTLFLQMNSLRAEDTAVYYCARGGHFGPFDYWG
QGTLVTVSSGGGGSGGGGSGGGGSQSPGTLSLSPGERATLSCRASQSISSSFLAW
YQQRPGQAPRLLIYGASSRATGIPDRFSGSGSGTDFTLTISRLEPEDFAVYYCQQ
YGTSPWTFGQGTKVEIKR

FIG. 23A

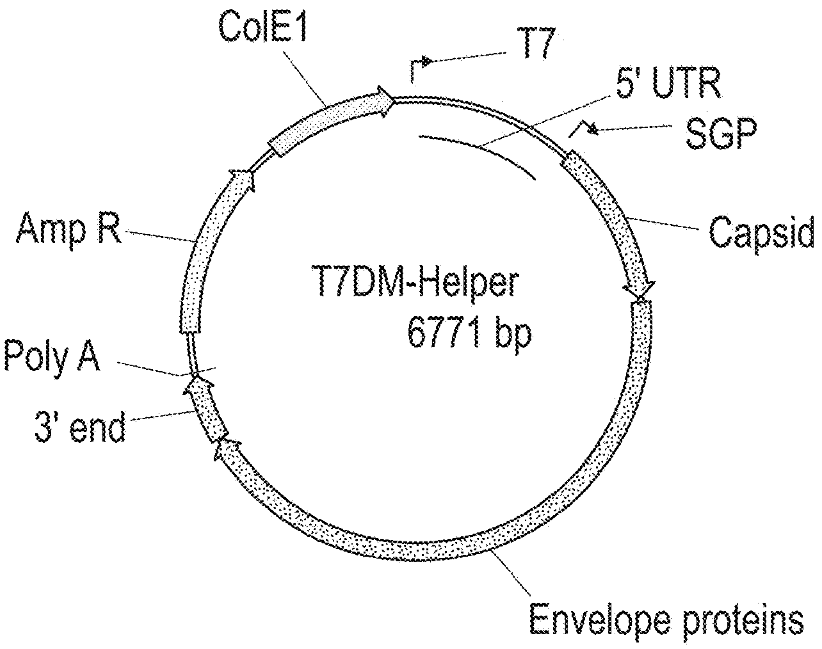
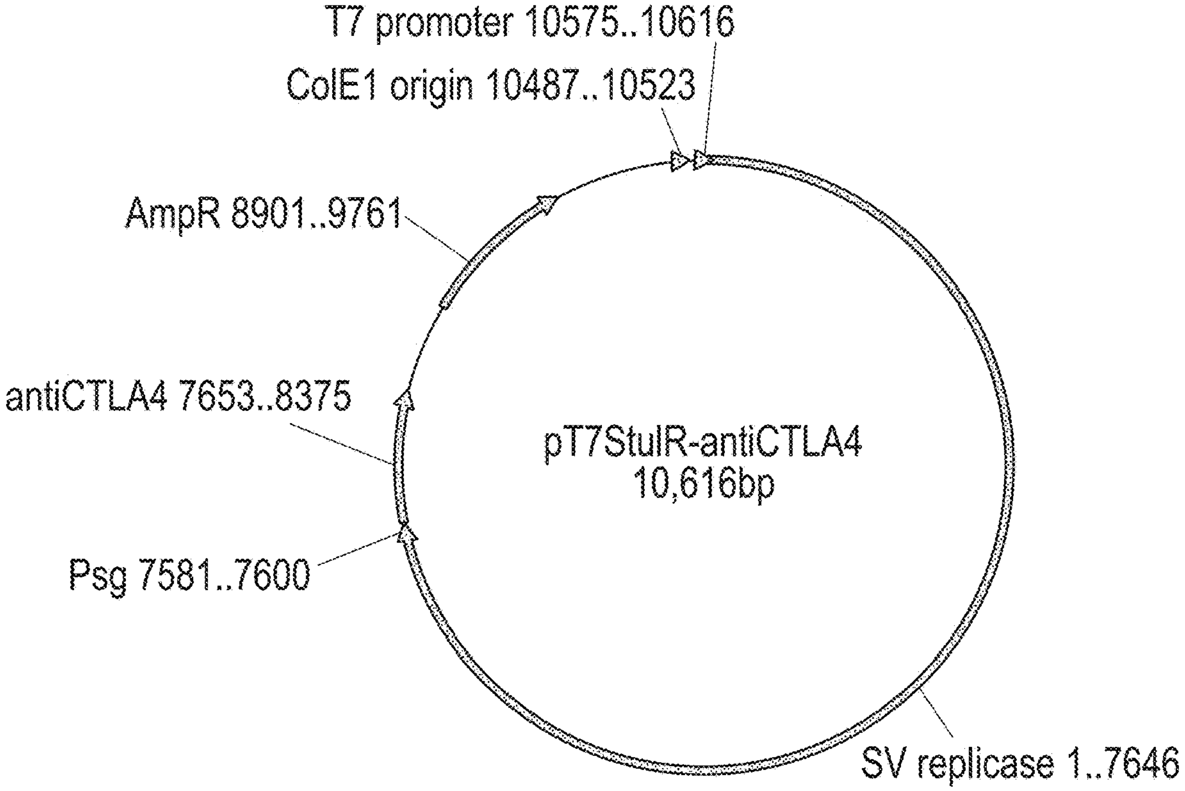
FIG. 23B

| | day -2 | Day 6 | Day 13 | Day 20 |
|---|---|---|---|---|
| Control | 1.0 | 32.1 | 207.0 | 354.8 |
| SV_CTLA4 | 1.0 | 16.3 | 57.4 | 69.2 |

Days after Sindbis treatment

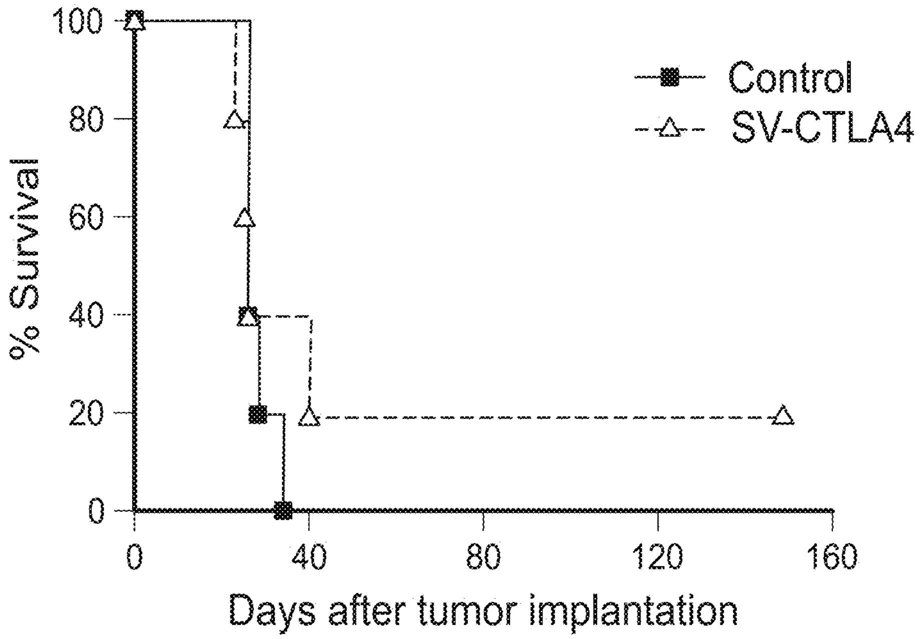

FIG. 24C tctagaGCCGGCATGGGTGCCCCGACGTTGCCCCCTGCCTGGCAGCCCTTTCTCA
AGGACCACCGCATCTCTACATTCAAGAACTGGCCCTTCTTGGAGGGCTGCGCCTG
CACCCCGGAGCGGATGGCCGAGGCTGGCTTCATCCACTGCCCCACTGAGAACGAG
CCAGACTTGGCCCAGTGTTTCTTCTGCTTCAAGGAGCTGGAAGGCTGGGAGCCAG
ATGACGACCCCATTGGGCCGGGCACGGTGGCTTACGCCTGTAATACCAGCACTTT
GGGAGGCCGAGGCGGGCGGATCACGAGAGAGGAACATAAAAAGCATTCGTCCGGT
TGCGCTTTCCTTTCTGTCAAGAAGCAGTTTGAAGAATTAACCCTTGGTGAATTTT
TGAAACTGGACAGAGAAAGAGCCAAGAACAAAATTGCAAAGGAAACCAACAATAA
GAAGAAAGAATTTGAGGAAACTGCGGAGAAAGTGCGCCGTGCCATCGAGCAGCTG
GCTGCCATGGATTGAgggccc (underlined bases in lower case indicate added restriction sites)

MGAPTLPPAWQPFLKDHRISTFKNWPFLEGCACTPERMAEAGFIHCPTENEPDLA
QCFFC
FKELEGWEPDDDPIGPGTVAYACNTSTLGGRGGRITREEHKKHSSGCAFLSVKKQ
FEELT
LGEFLKLDRERAKNKIAKETNNKKKEFEETAEKVRRAIEQLAAMD*

FIG. 25A

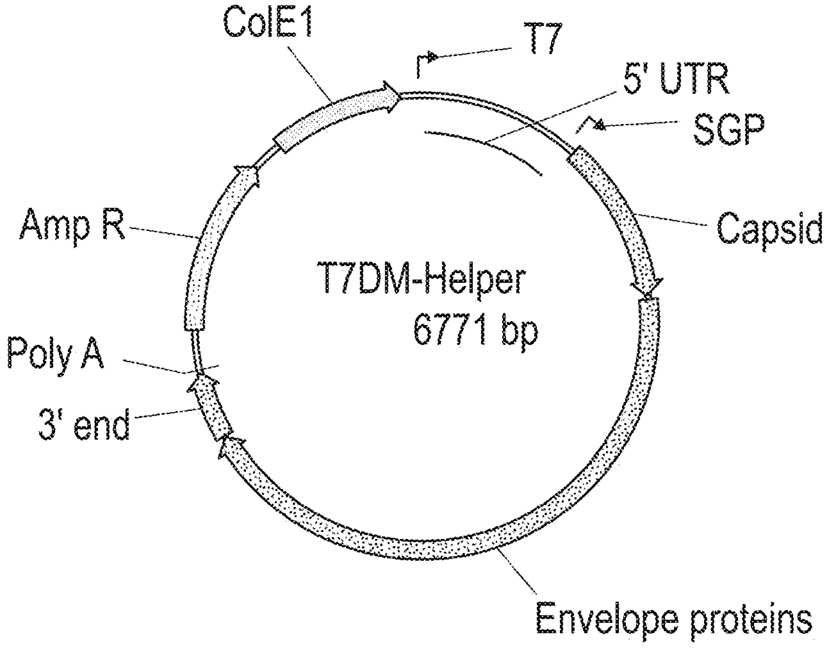
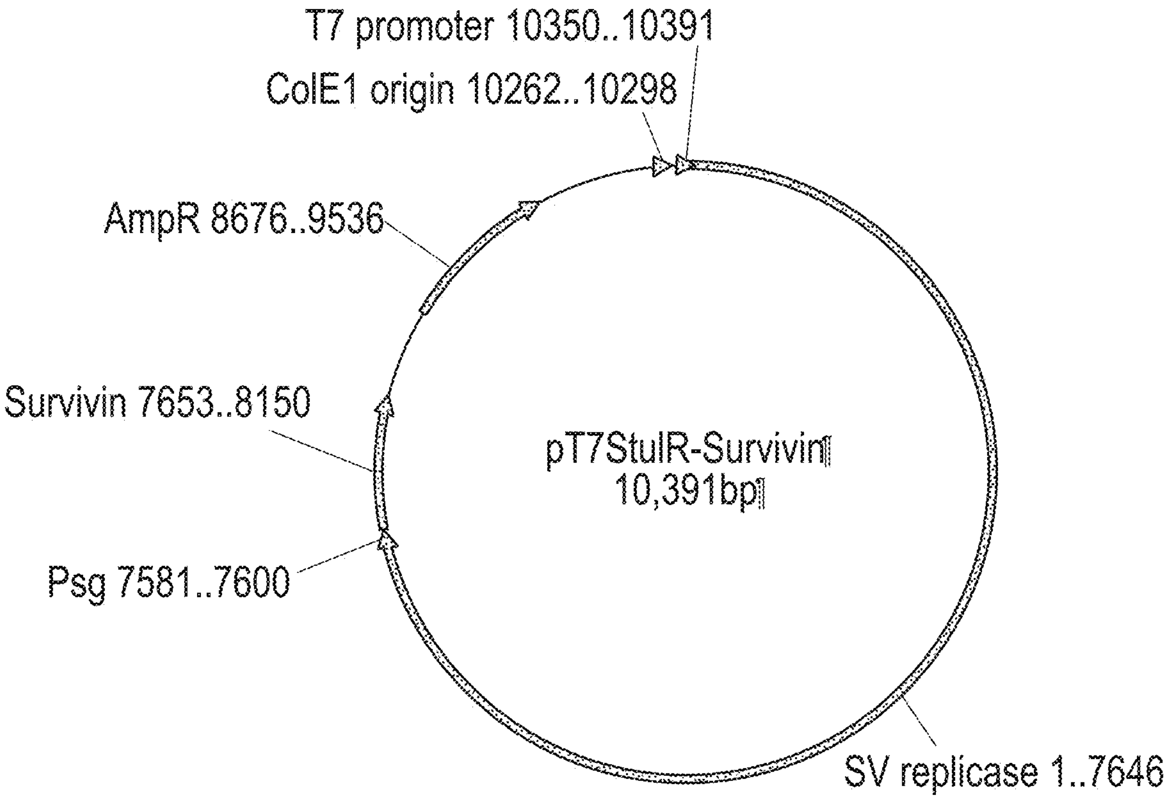
FIG. 25B

| | Day 0 | Day 7 | Day 14 | Day 21 | Day 28 |
|---|---|---|---|---|---|
| CONTROL | 1.0 | 25.2 | 229.0 | | |
| SV_Survivin | 1.0 | 1.6 | 7.8 | 43.3 | 67.9 |

Days after treatment gccaccATGCAGATCCCACAGGCGCCCTGGCCAGTCGTCTGGGCGGTGCTACAACTGGGCTGGC
GGCCAGGATGGTTCTTAGACTCCCCAGACAGGCCCTGGAACCCCCCCACCTTCTCCCCAGCCC
TGCTCGTGGTGACCGAAGGGGACAACGCCACCTTCACCTGCAGCTTCTCCAACACATCGGAGA
GCTTCGTGCTAAACTGGTACCGCATGAGCCCCAGCAACCAGACGGACAAGCTGGCCGCCTTCC
CCGAGGACCGCAGCCAGCCCGGCCAGGACTGCCGCTTCCGTGTCACACAACTGCCCAACGGG
CGTGACTTCCACATGAGCGTGGTCAGGGCCCGGCGCAATGACAGCGGCACCTACCTCTGTGG
GGCCATCTCCCTGGCCCCCAAGGCGCAGATCAAAGAGAGCCTGCGGGCAGAGCTCAGGGTGA
CAGAGAGAAGGGCAGAAGTGCCCACAGCCCACCCCAGCCCCTCACCCAGGCCAGCCGGCCA
GTTCCAAACCCTGGTGG AGCCTAAGAGCTGCGACAAAACACACACTTGCCCACCCTGC
*GGAGGAGGCTCTAGCGGAGGAGGGTCTGGA*GGCCAGCCAAGAGAGCCCCAGGTGTACACACT
GCCTCCCTCTCGAGACGAGCTTACAAAGAACCAGGTGTCTCTGACCTGTCTGGTTAAAGGCTTC
TATCCTAGCGACATTGCTGTGGAGTGGGAAAGCAACGGCCAGCCAGAGAATAACTACAAGACT
ACACCACCTGTGCTGGACTCTGATGGCAGCTTCTTTCTTTACAGCAAACTGACAGTTGACAAGT
CTAGGTGGCAGCAAGGCAACGTGTTCTCTTGCAGCGTGATGCACAACCACTACACACAGAAGT
CTCTTAGCCTGAGCCCTGGCAAATGA M Q I P Q A P W P V V W A V L Q L G W R P G W F L D S P D R P W N P P T F S P A L L V V T E G
D N A T F T C S F S N T S E S F V L N W Y R M S P S N Q T D K L A A F P E D R S Q P G Q D C R
F R V T Q L P N G R D F H M S V V R A R R N D S G T Y L C G A I S L A P K A Q I K E S L R A E L
R V T E R R A E V P T A H P S P S P R P A G Q F Q T L V E P K S C D K T H T C P P C *G G G S S*
*G G G S G G* Q P R E P Q V Y T L P P S R D E L T K N Q V S L T C L V K G F Y P S D I A V E W E
S N G Q P E N N Y K T T P P V L D S D G S F F L Y S K L T V D K S R W Q Q G N V F S C S V M H
N H Y T Q K S L S L S P G K Stop

FIG. 27A

```
Mouse   MWVRQVPWSFTWAVLQLSWQSGWLLEVPNGPWRSLTFYPAWLTVSEGANATFTCSLSNWS
Human   MQIPQAPWPVVWAVLQLGWRPGWFLDSPDRPWNPPTFSPALLVVTEGDNATFTCSFSNTS
Monkey  MQIPQAPWPVVWAVLQLGWRPGWFLESPDRPWNPPTFSPALLLVTEGDNATFTCSFSNAS
        * : *.** ..******.*: **:*: *: **.  ** ** * *:** *******:** *

Mouse   EDLMLNWNRLSPSNQTEKQAAFCNGLSQPVQDARFQIIQLPNRHDFHMNILDTRRNDSGI
Human   ESFVLNWYRMSPSNQTDKLAAFPEDRSQPGQDCRFRVTQLPNGRDFHMSVVRARRNDSGT
Monkey  ESFVLNWYRMSPSNQTDKLAAFPEDRSQPGQDCRFRVTQLPNGRDFHMSVVRARRNDSGT
        *.::*** *:******:* **** :. *** **.**:: **** :**** .:: :******

Mouse   YLCGAISLHPKAKIEESPGAELVVTERILETSTRYPSPSPKPEGRFQGMVIGIMSALVGI
Human   YLCGAISLAPKAQIKESLRAELRVTERRAEVPTAHPSPSPRPAGQFQTLVVGVVGGLLGS
Monkey  YLCGAISLAPKAQIKESLRAELRVTERRAEVPTAHPSPSPRPAGQFQALVVGVVGGLLGS
        ******** *** :*:** *** **** *. * :*****:* *:** :* :*::.:*:*

Mouse   PVLLLLAWALAVFCSTSMSEARGAGSKDDTLKEEPSAAPVPSVAYEELDFQGREKTPELP
Human   - LVLLVWVLAVICSRAARGTIGARRTGQPLKEDPSAVPVFSVDYGELDFQWREKTPEPP
Monkey  --LVLLVWVLAVICSRAAQGTIEARRTGQPLKEDPSAVPVFSVDYGELDFQWREKTPEPP
        *:**.*.***:**:** :   :   ***:***.** ** * ***** ****** *

Mouse   TACV--HTEYATIVFTEGLGASAMGRRGSADGLQGPRPPRHEDGHCSWPL
Human   VPCVPEQTEYATIVFPSGMGTSSPARRGSADGPRSAQPLRPEDGHCSWPL
Monkey  APCVPEQTEYATIVFPSGLGTSSPARRGSADGPRSPRPLRPEDGHCSWPL
        . ** :******** .*:*:*: .******* :. :* * ***********
```

Sequences aligned by Clustal Omega [ebi.ac.uk]

Percent Identity Matrix

| | | | |
|---|---|---|---|
| Mouse [GenPept Mus Musculus CAA48113.1] | 100.00 | 60.14 | 61.19 |
| Human [GenPept Homo Sapiens NP_005009.2] | 60.14 | 100.00 | 96.53 |
| Monkey[GenPept Macaca nemestrina ABR15757.1] | 61.19 | 96.53 | 100.00 |

*, amino acid identity; :high amino acid similarity; ., amino acid similarity

FIG. 27B

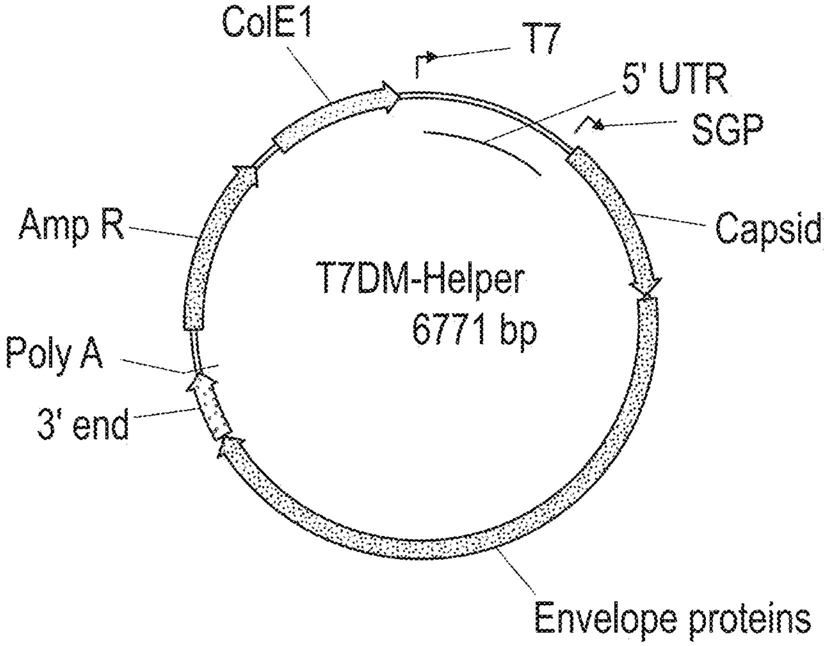
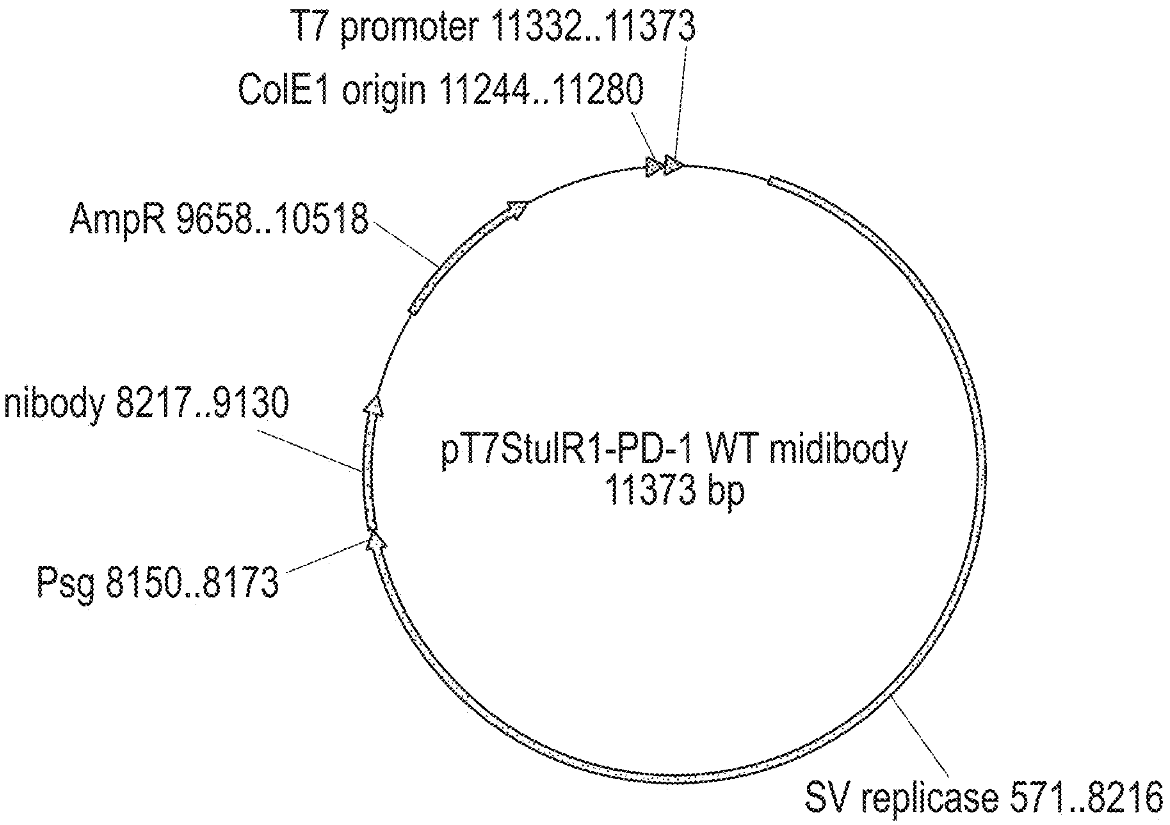
FIG. 28

| | Day -1 | Day 6 | Day 13 | Day 20 |
|---|---|---|---|---|
| Control | 1.0 | 19.3 | 197.8 | |
| aPD1 (P) | 1.0 | 25.2 | 114.3 | |
| SV_WTPD1 | 1.0 | 2.0 | 16.2 | 33.7 |

DAYS AFTER SINDBIS TREATMENT

Control

Antibody aPD1

SV_PD-1WT

Day 4

Day 11

Day 18

INDUCTION AND ENHANCEMENT OF ANTITUMOR IMMUNITY INVOLVING VIRUS VECTORS EXPRESSING MULTIPLE EPITOPES OF TUMOR ASSOCIATED ANTIGENS AND IMMUNE CHECKPOINT INHIBITORS OR PROTEINS

STATEMENT OF PRIORITY

This application claims benefit of provisional patent application No. 62/575,179, filed Oct. 20, 2017, and provisional patent application No. 62/466,761, filed Mar. 3, 2017, the contents of each of which are incorporated herein in their entireties.

STATEMENT REGARDING FEDERALLY SPONSORED RESEARCH

This invention was made with government support under Grant Number 5R44CA206606 awarded by The National Institutes of Health. The government has certain rights in the invention.

SEQUENCE LISTING

The instant application contains a Sequence Listing which has been submitted in .txt format and is hereby incorporated by reference in its entirety. Said .txt copy was created on Oct. 28, 2022, is named "Sequence_Listing_October_28_2022_ST25.txt", and is 115,356 bytes in size.

BACKGROUND OF THE INVENTION

Despite available cancer treatments, which may include aggressive surgical approaches and combination chemotherapeutic regimens, implemented over the past two decades, a variety of cancers routinely evade detection and destruction by cells of the immune system and offer a grim prognosis for patients afflicted with such cancers. Anticancer immunity, including protective immunity, is thought to be based both on the magnitude of the immune response and on the phenotype of the memory immune responses, including T central memory cells (Tcm) and T effector memory cells (Tem). Tcm are characterized by a $CD62L^+$ $CD127^+$ phenotype, whereas Tem are defined by a $CD62L^-$ $CD127^+$ phenotype. Tem traffic through non-lymphoid tissues and exert immediate effector functions in the periphery, while Tcm localize to the secondary lymphoid organs, where they constitute a secondary line of defense by massively expanding upon encounter with antigens presented by dendritic cells. Induction of T cell memory immune responses is dependent on a variety of factors, such as cytokine milieu, length of antigen stimulation, and dose of antigen. $CD8^+$ T cell memory inflation is characterized by the accumulation of high-frequency, functional Ag-specific $CD8^+$ T cell pools with an effector-memory phenotype and enrichment in peripheral organs. This type of response is more vigorous and desirable, for an effective immune response against cancer growth and recurrence.

Sindbis virus (SV) is an oncolytic alphavirus with a positive-stranded RNA genome that has the ability to travel systemically through the circulation and is capable of killing tumor cells through apoptosis. To date, cancer treatment approaches using oncolytic viruses have not generally led to complete cancer or tumor remission. Moreover, some tumor cells may not be efficiently targeted by viruses used in cancer treatments to date, thus underscoring the need to develop new therapies and additional ways to enhance anticancer treatment.

Immune checkpoint inhibitors, including antibodies against CTLA-4 and PD-1, have been used to block immune inhibitory receptors on activated T-cells, thereby amplifying the immune response. Unfortunately, many patients treated with checkpoint inhibitors ultimately develop resistance to the inhibitors and suffer from disease progression. Given the many hurdles that currently exist in the treatment and prevention of many types of cancers, there exists a profound need for new and improved anti-cancer therapeutic agents, especially those that elicit an immune response directed against tumor and cancer cells, as well as methods for administering such agents to augment the immune response in the treatment and eradication of tumors and cancers in mammals.

SUMMARY OF THE INVENTION

The present invention features a therapeutic combination that includes a polynucleotide that encodes an alphavirus protein or a fragment thereof (e.g., Sindbis virus protein or a fragment thereof), one or more tumor associated antigens (TAAs), and a checkpoint inhibitor molecule (e.g., anti-PD-1 antibody, anti-PD-L1 antibody, anti-CTLA-4 antibody). The one or more checkpoint inhibitor molecules may be administered at the same time as (simultaneously), or at different times from, the administration of the polynucleotides, viral vectors, or viral particles, or pharmaceutical compositions thereof, as described herein. In an embodiment, a checkpoint inhibitor molecule, such as an antibody specifically directed against an immune checkpoint protein, or a fragment thereof that specifically binds to the immune checkpoint protein, is co-administered to a subject in conjunction with the polynucleotides, viral vectors, viral particles, or compositions thereof, particularly, in the methods described herein.

The invention further features a viral vector or a virus particle, which comprises a polynucleotide that encodes multiple (e.g., two or more) epitopes of one or more tumor associated antigens (TAA), wherein each epitope is separated by an enzyme cleavage site. In an embodiment, the viral vector is an alphavirus vector or a pseudotyped alphavirus vector. In a particular embodiment, the viral vector is a Sindbis viral vector. In other embodiments, the viral vector is a retrovirus or lentivirus pseudotyped with one or more alphavirus envelope proteins, e.g., E1, E2, or E3. In other embodiments, the viral vector is a retrovirus or lentivirus pseudotyped with Sindbis virus envelope proteins, such as E1-E3 or ZZ E2. In an embodiment, the epitopes of the tumor associated antigen comprise 5-50 amino acids. In other embodiments, the epitopes of the tumor associated antigen comprise 5-30 amino acids, 5-25 amino acids, 5-20 amino acids, 7-25 amino acids, 7-20, or 7-14 amino acids. In an embodiment, the enzyme cleavage sites comprise sequences that are recognized by an enzyme as described infra.

In an aspect, the invention provides a polynucleotide which encodes two or more epitopes of one or more tumor associated antigens (TAAs), wherein each epitope is separated by an enzyme cleavage site. In embodiments, the polynucleotide comprises DNA or RNA, which can be single stranded (ss) RNA. In an embodiment, the polynucleotide is carried in a viral vector or viral particle as described infra. In an embodiment, the polynucleotide comprises two or more epitopes which comprise 5-50 amino acids. In an embodiment, the polynucleotide comprises two or more epitopes which comprise 5-30 amino acids. In an embodiment, the one or more tumor associated antigens are expressed on the surface of a cancer or tumor cell (e.g., extracellularly) or are expressed intracellularly inside a cancer or tumor cell. In an embodiment, the two or more epitopes encoded by the polynucleotide comprise an amino acid sequence of a tumor associated antigen listed in any one of Tables 1-28.

In embodiments, two or more epitopes of the one or more of the following tumor associated antigens may be encoded by the polynucleotides, viral vectors, or viral particles described herein: kallikrein 4, papillomavirus binding factor (PBF), preferentially expressed antigen of melanoma (PRAME), Wilms' tumor-1 (WT1), Hydroxysteroid Dehydrogenase Like 1 (HSDL1), mesothelin, cancer testis antigen (NY-ESO-1), carcinoembryonic antigen (CEA), p53, human epidermal growth factor receptor 2/neuro receptor tyrosine kinase (Her2/Neu), carcinoma-associated epithelial cell adhesion molecule (EpCAM), ovarian and uterine carcinoma antigen (CA125), folate receptor a, sperm protein 17, tumor-associated differentially expressed gene-12 (TADG-12), mucin-16 (MUC-16), L1 cell adhesion molecule (LiCAM), mannan-MUC-1, Human endogenous retrovirus K (HERV-K-MEL), Kita-kyushu lung cancer antigen-1 (KK-LC-1), human cancer/testis antigen (KM-HN-1), cancer testis antigen (LAGE-1), melanoma antigen-A1 (MAGE-A1), Sperm surface zona pellucida binding protein (Sp17), Synovial Sarcoma, X Breakpoint 4 (SSX-4), Transient axonal glycoprotein-1 (TAG-1), Transient axonal glycoprotein-2 (TAG-2), Enabled Homolog (ENAH), mammoglobin-A, NY-BR-1, Breast Cancer Antigen, (BAGE-1), B melanoma antigen, melanoma antigen-A1 (MAGE-A1), melanoma antigen-A2 (MAGE-A2), mucin k, synovial sarcoma, X breakpoint 2 (SSX-2), Taxol-resistance-associated gene-3 (TRAG-3), Avian Myelocytomatosis Viral Oncogene (c-myc), cyclin B1, mucin 1 (MUC1), p62, survivin, lymphocyte common antigen (CD45), Dickkopf WNT Signaling Pathway Inhibitor 1 (DKK1), telomerase, Kirsten rat sarcoma viral oncogene homolog (K-ras), G250, intestinal carboxyl esterase, alpha-fetoprotein, Macrophage Colony-Stimulating Factor (M-CSF), Prostate-specific membrane antigen (PSMA), caspase 5 (CASP-5), Cytochrome C Oxidase Assembly Factor 1 Homolog (COA-1), O-linked β-N-acetylglucosamine transferase (OGT), Osteosarcoma Amplified 9, Endoplasmic Reticulum Lectin (OS-9), Transforming Growth Factor Beta Receptor 2 (TGF-betaRII), murine leukemia glycoprotein 70 (gp70), Calcitonin Related Polypeptide Alpha (CALCA), Programmed cell death 1 ligand 1 (CD274), Mouse Double Minute 2Homolog (mdm-2), alpha-actinin-4, elongation factor 2, Malic Enzyme 1 (MEI), Nuclear Transcription Factor Y Subunit C (NFYC), G Antigen 1,3 (GAGE-1,3), melanoma antigen-A6 (MAGE-A6), cancer testis antigen XAGE-1b, six transmembrane epithelial antigen of the prostate 1 (STEAP1), PAP, prostate specific antigen (PSA), Fibroblast Growth Factor 5 (FGF5), heat shock protein hsp70-2, melanoma antigen-A9 (MAGE-A9), Arg-specific ADP-ribosyltransferase family C (ARTC1), B-Raf Proto-Oncogene (B-RAF), Serine/Threonine Kinase, beta-catenin, Cell Division Cycle 27 homolog (Cdc27), cyclin dependent kinase 4 (CDK4), cyclin dependent kinase 12 (CDK12), Cyclin Dependent Kinase Inhibitor 2A (CDKN2A), Casein Kinase 1 Alpha 1 (CSNKIA1), Fibronectin 1 (FN1), Growth Arrest Specific 7 (GAS7), Glycoprotein nonmetastatic melanoma protein B (GPNMB), HAUS Augmin Like Complex Subunit 3 (HAUS3), LDLR-fucosyltransferase, Melanoma Antigen Recognized By T-Cells 2 (MART2), myostatin (MSTN), Melanoma Associated Antigen (Mutated) 1 (MUM-1-2-3), Poly(A) polymerase gamma (neo-PAP), myosin class I, Protein phosphatase 1 regulatory subunit 3B (PPPIR3B), Peroxiredoxin-5 (PRDX5), Receptor-type tyrosine-protein phosphatase kappa (PTPRK), Transforming protein N-Ras (N-ras), retinoblastoma-associated factor 600 (RBAF600), sirtuin-2 (SIRT2), SNRPD1, triosephosphate isomerase, Ocular Albinism Type 1 Protein (OA1), member RAS oncogene family (RAB38), Tyrosinase related protein 1-2 (TRP-1-2), Melanoma Antigen Gp75 (gp75), tyrosinase, Melan-A (MART-1), Glycoprotein 100 melanoma antigen (gp100), N-acetylglucosaminyltransferase V gene (GnTVf), Lymphocyte Antigen 6 Complex Locus K (LY6K), melanoma antigen-A10 (MAGE-A10), melanoma antigen-A12 (MAGE-A12), melanoma antigen-C2 (MAGE-C2), melanoma antigen NA88-A, Taxol-resistant-associated protein 3 (TRAG-3), PDZ binding kinase (pbk), caspase 8 (CASP-8), sarcoma antigen 1 (SAGE), Breakpoint Cluster Region-Abelson oncogene (BCR-ABL), fusion protein in leukemia, dek-can, Elongation Factor Tu GTP Binding Domain Containing 2 (EFTUD2), ETS Variant gene 6/acute myeloid leukemia fusion protein (ETV6-AML1), FMS-like tyrosine kinase-3 internal tandem duplications (FLT3-ITD), cyclin-A1, Fibronectin Type III Domain Containing 3B (FDNC3B,) promyelocytic leukemia/retinoic acid receptor alpha fusion protein (pml-RARalpha), melanoma antigen-C1 (MAGE-C1), membrane protein alternative spliced isoform (D393-CD20), melanoma antigen-A4 (MAGE-A4), or melanoma antigen-A3 (MAGE-A3).

In some embodiments, at least one of the two or more epitopes encoded by the polynucleotide is from the tumor associated antigen NY-ESO-1, the tumor associated antigen MAGE-A3 and/or the tumor associated antigen pbk. In a particular embodiment, the polynucleotide encodes an epitope from the tumor associated antigen NY-ESO-1 comprising the amino acid sequence LLMWITQCF (SEQ ID NO: 1) and an epitope from the tumor associated antigen pbk comprising the amino acid sequence GSPFPAAVI (SEQ ID NO: 2). In an embodiment, one of the two or more epitopes encoded by the polynucleotide is from the tumor associated antigen NY-ESO-1 and one of the two or more epitopes is from the tumor associated antigen survivin. In a particular embodiment, the polynucleotide encodes an epitope from the tumor associated antigen NY-ESO-1 comprising the amino acid sequence RGPESRLLE (SEQ ID NO: 3) and an epitope from the tumor associated antigen survivin comprising the amino acid sequence AFLTVKKQM (SEQ ID NO: 4). In an embodiment, the polynucleotide encodes three or more epitopes of one or more tumor associated antigens. In certain embodiments, the three or more epitopes are of the same tumor associated antigen. In other embodiments, the three or more epitopes are from at least one different tumor associated antigen. In certain embodiments, the polynucleotide encodes eight or more epitopes of one or more tumor associated antigens. In embodiments, the polypeptide as described encodes epitopes, particularly, two or more epitopes, of tumor associated antigens expressed on the surface of a cancer or tumor cell or in the cytosol of a cancer or tumor cell of a/an ovarian cancer, breast cancer, testicular cancer, pancreatic cancer, liver cancer, colon cancer, colorectal cancer, thyroid cancer, lung cancer, prostate cancer, kidney cancer, melanoma, squamous cell carcinoma, chronic myeloid leukemia, acute lymphoblastic leukemia, acute myelogenous leukemia, chronic lymphocytic leukemia, promyelocytic leukemia, multiple myeloma, B-cell lymphoma, bladder carcinoma, head and neck cancer, esophageal cancer, brain cancer, pharynx cancer, tongue cancer, synovial cell carcinoma, neuroblastoma, uterine cancer, fibrosarcoma, myxosarcoma, liposarcoma, chondrosarcoma, osteogenic sarcoma, chordoma, angiosarcoma, endotheliosarcoma. lymphangiosarcoma, synovioma, mesothelioma, Ewing's tumor, leiomyosarcoma, rhabdomyosarcoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroglioma, or retinoblastoma.

In some embodiment, the polynucleotide further encodes a processing site or an enzyme cleavage site which is a protease cleavage site. In an embodiment, the enzyme cleavage site is a serine protease cleavage site. In a particular embodiment, the serine protease cleavage site is cleaved by a protein selected from furin, PC1, PC2, PC4, PC5, PACE4, PC7 or a combination thereof. In another particular embodiment, the serine protease cleavage site is cleaved by furin. In an embodiment, the enzyme cleavage site encoded by the polynucleotide comprises the amino acid sequence XRSKRX, (SEQ ID NO: 5), wherein X represents a hydrophobic amino acid. In another embodiment, the enzyme cleavage site encoded by the polynucleotide comprises the amino acid sequence (R/K)Xn(R/K), (SEQ ID NO: 6), wherein X represents an amino acid and n is an integer from 0 to 6. In an embodiment, the polynucleotide comprises a 5' endoplasmic reticulum signal sequence. In certain embodiments, the polynucleotide comprises a 5' endoplasmic reticulum signal sequence derived from alphavirus, influenza virus matrix protein-derived peptide M57-68 or tissue plasminogen activator peptide. In an embodiment, the polynucleotide comprises a 3' sequence encoding an immunogenic protein selected from heat shock protein 70, IgG1 Fc domain, lysosome-associated membrane protein (LAMP), tetanus toxin universal helper T (Th) epitope, or *E. coli* heat-labile enterotoxin B subunit. In another embodiment, the polynucleotide encodes one or more immunostimulatory proteins. By way of example, such proteins include, without limitation, one or more of IL-1, IL-2, IL-3, IL-4, IL-5, IL-6 IL-7, IL-8, IL-9, IL-10, IL-11, IL-12, IL-13, IL-14, IL-15, IL-16, IL-17, IL-18, IL-19, IL-20 through IL-36, chemokine CCL1 through CCL27, CC chemokine CXCL1 through CXCL13, a CXC chemokine, a C chemokine, a CX3C chemokine, a cytokine or chemokine receptor, a soluble receptor, Transforming Growth Factor-beta (TGF-β), a checkpoint inhibitor, or Tumor Necrosis Factor-alpha (TNFα). In a particular embodiment, the polynucleotide encodes the immunostimulatory protein IL-12. In another embodiment, the polynucleotide further comprises one or more suicide genes, which are capable of converting an inert prodrug, such as, without limitation, ganciclovir, acyclovir, 1-(2-deoxy-2-fluoro-β-D-arabinofuranosyl)-5-iodouracil (FIAU), 6-methoxypurine arabinoside, or 5-fluorocytosine, into a cytotoxic metabolite. In an embodiment, the one or more suicide genes encode cytosine deaminase or thymidine kinase which can be derived from Herpes Simplex Virus (HSVtk) or Varicella Zoster Virus (VZV-tk). As will be appreciated by one skilled in the art, derived from refers to obtaining from, originating from, or producing from, all or a portion of, (typically a functional or active portion of), a polynucleotide, a polypeptide, or a peptide from a source, e.g., a virus, bacterium, microorganism, or biological source.

The present invention also features a polynucleotide that encodes an alphavirus, lentivirus, or retrovirus protein or a fragment thereof, and an immune checkpoint molecule, such as, PD-1 or a cognate ligand binding portion or fragment thereof. In an embodiment, the polynucleotide encodes an alphavirus (e.g., Sindbis virus protein or a fragment thereof) and an immune checkpoint molecule or a cognate ligand binding portion or fragment thereof. In an embodiment, the alphavirus is Sindbis virus, a Sindbis virus vector, or viral particle. In an embodiment, the virus is a Sindbis virus vector which contains a polynucleotide that encodes one or more immune checkpoint proteins, or a fragment or portion of the immune checkpoint protein that binds to its cognate ligand, for example and without limitation, the PD-1 immune checkpoint protein or a fragment or portion of PD-1 that binds to its cognate ligand PD-L1. In an embodiment, the checkpoint protein is the extracellular domain of the protein.

Another feature provided herein is an alphavirus vector, e.g., a Sindbis virus vector, containing a polynucleotide that encodes an immune checkpoint protein, or more than one immune checkpoint protein, or a fragment or portion of the immune checkpoint protein that binds to its cognate ligand. In an embodiment, the immune checkpoint protein comprises all, or a portion, e.g., the extracellular domain, of a checkpoint protein (also called a "checkpoint molecule" herein). In an embodiment, the checkpoint protein is in the form of a fusion protein, also called a "minibody" herein, in which checkpoint protein or a ligand binding portion of the checkpoint protein, e.g., the extracellular domain, is fused to an immunoglobulin (Ig) hinge region, and an Ig heavy chain constant region domain, such as the CH1, CH2, or CH3 domain of an Ig heavy chain. In embodiments, the Ig is of the IgG, IgM, IgA, IgD, or IgE class. In an embodiment, the hinge and/or the heavy chain constant region domain is derived from an IgG class selected from IgG1, IgG2a, IgG2b, IgG2c, IgG3, or IgG4. In certain embodiments, the hinge and/or the heavy chain constant region domain is derived from an IgG subclass selected from the human IgG1, IgG2, IgG3, or IgG4 subclass. In certain embodiments, the hinge and/or the heavy chain constant region domain is derived from an IgG subclass selected from the mouse IgG1, IgG2a, IgG2b, IgG2c, or IgG3 subclass. In certain embodiments, the hinge and/or the heavy chain constant region domain is derived from an IgG subclass selected from the rat IgG1, IgG2a, IgG2b, or IgG2c subclass. In a particular embodiment, the immunoglobulin chain is the human IgG1 heavy chain and the Ig constant region domain is the IgG1 CH3 domain. In an embodiment, a glycine-rich spacer (or linker) sequence is inserted between the hinge region and the Ig heavy chain CH domain for flexibility. In an embodiment, the spacer (or linker) sequence is or comprises the sequence GGGSSGGGSGG (SEQ ID NO: 19).

In an embodiment, the alphavirus vector, e.g., Sindbis virus vector or viral particles, encoding an immune checkpoint protein, or a binding portion thereof, is administered to a subject in need, e.g., a subject having a cancer or tumor, e.g., a solid tumor, according to the methods described herein. In an embodiment, the Sindbis virus vector encoding an immune checkpoint protein, or a binding portion thereof, is in a pharmaceutical composition or formulation. In an embodiment, the pharmaceutical composition or formulation comprising the Sindbis virus vector encoding a immune checkpoint protein, or a binding portion thereof, is administered to a subject in need, e.g., a subject having a cancer or tumor, according to the methods described herein. In an embodiment, the Sindbis virus vector encoding an immune checkpoint molecule, or a binding portion thereof, or a pharmaceutical composition comprising the Sindbis virus vector encoding an immune checkpoint molecule, or a binding portion thereof, is administered to a subject in conjunction with another anti-cancer, anti-tumor or chemotherapeutic agent.

In an embodiment, the alphavirus vector, e.g. a Sindbis virus vector, encoding an immune checkpoint molecule, or a binding portion thereof, is administered to a subject in conjunction with one or more checkpoint inhibitor molecules. The one or more checkpoint inhibitor molecules may be administered at the same time as (simultaneously), or at different times from, the administration of the polynucleotides, viral vectors, or viral particles, or pharmaceutical compositions thereof, as described herein. In an embodiment, a checkpoint inhibitor molecule, such as an antibody specifically directed against an immune checkpoint protein, or a fragment thereof that specifically binds to the immune checkpoint protein, is co-administered to a subject in conjunction with the polynucleotides, viral vectors, viral particles, or compositions thereof, particularly, in the methods described herein.

In another embodiment, the alphavirus vector, e.g., Sindbis virus vector, comprises a polynucleotide encoding one or more tumor associated antigens (TAAs) and an immune checkpoint molecule (e.g., PD-1) or a binding portion thereof. In an embodiment, the checkpoint protein is the extracellular domain of the protein.

In embodiments, the virus vector contains a polynucleotide that encodes a checkpoint protein that binds to a cognate ligand (a receptor protein) that is expressed on the surface of a cancer or tumor cell, or in the cytosol of a cancer or tumor cell, of a/an ovarian cancer, breast cancer, testicular cancer, pancreatic cancer, liver cancer, colon cancer, colorectal cancer, thyroid cancer, lung cancer, prostate cancer, kidney cancer, melanoma, squamous cell carcinoma, chronic myeloid leukemia, acute lymphoblastic leukemia, acute myelogenous leukemia, chronic lymphocytic leukemia, promyelocytic leukemia, multiple myeloma, B-cell lymphoma, bladder carcinoma, head and neck cancer, esophageal cancer, brain cancer, pharynx cancer, tongue cancer, synovial cell carcinoma, neuroblastoma, uterine cancer, fibrosarcoma, myxosarcoma, liposarcoma, chondrosarcoma, osteogenic sarcoma, chordoma, angiosarcoma, endotheliosarcoma. lymphangiosarcoma, synovioma, mesothelioma, Ewing's tumor, leiomyosarcoma, rhabdomyosarcoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroglioma, or retinoblastoma.

In another of its aspects, the present invention is directed to a viral vector comprising the polynucleotide as described supra and infra. In embodiments, the viral vector is selected from an alphavirus, a lentivirus, or a retrovirus. In an embodiment, the viral vector is pseudotyped with one or more alphavirus virus envelope proteins. In an embodiment, the viral vector is pseudotyped with alphavirus E1 protein, E2 protein, both the E1 and the E2 proteins, or a fragment thereof. In a particular embodiment, the viral vector is a Sindbis viral vector or is derived from Sindbis virus. In an embodiment, the viral vector is pseudotyped with one or more Sindbis virus envelope proteins. In an embodiment, the viral vector is pseudotyped with Sindbis-ZZ E2 protein or a fragment thereof. In a particular embodiment, the viral vector is a lentivirus pseudotyped with one or more Sindbis virus envelope proteins, which may include the Sindbis-ZZ E2 protein. In a particular embodiment, the viral vector is a retrovirus pseudotyped with one or more Sindbis virus envelope proteins, which may include the Sindbis-ZZ E2 protein. In an embodiment, the viral vector is a replication-defective viral vector. In an embodiment, the viral vector is a replication-competent viral vector. In an embodiment, the viral vector is a non-integrating viral vector. In an embodiment, the viral vector is capable of eliciting an immune response against a tumor or cancer expressing the two or more epitopes of one or more tumor associated antigens following administration to a subject, preferably a human subject or patient who has a cancer or tumor. In an embodiment, the immune response generates cytotoxic T cells that specifically kill the cancer or tumor cells expressing the tumor associated antigen epitopes. In all of the above embodiments, the viral vector contains the polynucleotide described supra and infra (also called a minigene) whose encoded products are expressed in cells following contact of the viral vector with cells in vitro and in vivo.

In a particular aspect, a Sindbis viral vector is provided which comprises a polynucleotide encoding two or more epitopes comprising 5-30 amino acids of a tumor associated antigen, wherein each epitope is separated by a furin enzyme cleavage site. In another particular aspect, a viral vector pseudotyped with one or more Sindbis virus envelope proteins is provided, wherein the viral vector comprises a polynucleotide encoding two or more epitopes comprising 5-30 amino acids of a tumor associated antigen, wherein each epitope is separated by a furin enzyme cleavage site. In embodiments, the two or more epitopes of the above viral vectors comprise an amino acid sequence of a tumor associated antigen listed in any one of Tables 1-28. In an embodiment, the two or more epitopes are of one or more tumor associated antigens selected from the group consisting of kallikrein 4, PBF, PRAME, WT1, HSDL1, mesothelin, NY-ESO-1, CEA, p53, Her2/Neu, EpCAM, CA125, folate receptor a, sperm protein 17, TADG-12, MUC-16, LiCAM, mannan-MUC-1, HERV-K-MEL, KK-LC-1, KM-HN-1, LAGE-1, MAGE-A4, Spi17, SSX-4, TAG-1, TAG-2, ENAH, mammoglobin-A, NY-BR-1, BAGE-1, MAGE-A1, MAGE-A2, mucink, SSX-2, TRAG-3, c-myc, cyclin B1, MUC1, p62, survivin, CD45, DKK1, RU2AS, telomerase, K-ras, G250, hepsin, intestinal carboxyl esterase, alpha-foetoprotein, M-CSF, PSMA, CASP-5, COA-1, OGT, OS-9, TGF-betaRII, gp70, CALCA, CD274, mdm-2, alpha-actinin-4, elongation factor 2, ME1, NFYC, GAGE-1, MAGE-A6, XAGE-1b, PSMA, STEAP1, PAP, PSA, GAGE3, FGF5, hepsin, hsp70-2, MAGE-A9, ARTC1, B-RAF, beta-catenin, Cdc27, CDK4, CDK12, CDKN2A, CLLP, CSNKIA1, FN1, GAS7, GPNMB, HAUS3, LDLR-fucosyltransferase, MART2, MATN, MUM-1, MUM-2, MUM-3, neo-PAP, myosin class I, PPPIR3B, PRDX5, PTPRK, N-ras, RBAF600, SIRT2, SNRPD1, triosephosphate isomerase, OA1, RAB38, TRP-1, gp75, TRP2, tyrosinase, MART-1, gp100, GnTVf, LY6K, MAGE-A10, MAGE-A12, MAGE-C2, NA88-A, TRAG-3, TRP2-INT2g, pbk, CASP-8, SAGE, BCR-ABL, dek-can, EFTUD2, ETV6-AML1, FLT3-ITD, cyclin-A1, FDNC3B, pml-RARalpha, MAGE-C1, D393-

CD20, MAGE-A4, and MAGE-A3. In a particular embodiment, at least one of the two or more epitopes is from the tumor associated antigen NY-ESO-1 and at least one of the two or more epitopes is from the tumor associated antigen survivin or pbk. In a particular embodiment, the epitope from the tumor associated antigen NY-ESO-1 comprises the amino acid sequence LLMWITQCF (SEQ ID NO: 1) or the amino acid sequence (RGPESRLLE) (SEQ ID NO: 3), the epitope from the tumor associated antigen survivin comprises the amino acid sequence AFLTVKKQM (SEQ ID NO: 4), and the epitope from the tumor associated antigen pbk comprises the amino acid sequence GSPFPAAVI (SEQ ID NO: 2). In another embodiment, one of the two or more epitopes is from the tumor associated antigens NY-ESO-1 and one of the two or more epitopes encoded by the viral vector is from the tumor associated antigen survivin. In another embodiment, the epitope from the tumor associated antigen NY-ESO-1 comprises the amino acid sequence RGPESRLLE (SEQ ID NO: 3) and the epitope from the tumor associated antigen survivin comprises the amino acid sequence AFLTVKKQM (SEQ ID NO: 4). In an embodiment, the polynucleotide contained in the viral vector encodes three or more epitopes or eight or more epitopes of one or more tumor associated antigens. In embodiment, the viral vector encodes epitopes, particularly, two or more epitopes, of tumor associated antigens expressed on the surface of a cancer or tumor cell or in the cytosol of a cancer or tumor cell of a/an ovarian cancer, breast cancer, testicular cancer, pancreatic cancer, liver cancer, colorectal cancer, thyroid cancer, lung cancer, prostate cancer, kidney cancer, melanoma, squamous cell carcinoma, chronic myeloid leukemia, acute lymphoblastic leukemia, acute myelogenous leukemia, chronic lymphocytic leukemia, promyelocytic leukemia, multiple myeloma, B-cell lymphoma, bladder carcinoma, head and neck cancer, esophageal cancer, brain cancer, pharynx cancer, tongue cancer, synovial cell carcinoma, neuroblastoma, uterine cancer, fibrosarcoma, myxosarcoma, liposarcoma, chondrosarcoma, osteogenic sarcoma, chordoma, angiosarcoma, endotheliosarcoma. lymphangiosarcoma, synovioma, mesothelioma, Ewing's tumor, leiomyosarcoma, rhabdomyosarcoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroglioma, or retinoblastoma. In an embodiment, the above Sindbis or pseudotyped viral vector comprises a 5' endoplasmic reticulum signal sequence, which sequence is optionally derived from an alphavirus, influenza virus matrix protein-derived peptide M57-68 or tissue plasminogen activator peptide. In an embodiment, the viral vector comprises a 3' sequence encoding an immunogenic protein selected from heat shock protein 70, IgG1 Fc domain, lysosome-associated membrane protein (LAMP), tetanus toxin universal helper T (Th) epitope, or *E. coli* heat-labile enterotoxin B subunit. In embodiments, the polynucleotide contained in the viral vector encodes one or more immunostimulatory proteins selected from IL-1, IL-2, IL-3, TL-4, IL-5, IL-6 IL-7, IL-8, IL-9, IL-10, IL-11, IL-12, IL-13, IL-14, IL-15, IL-16, IL-17, IL-18, IL-19, IL-20 through IL-36, chemokine CCL1 through CCL27, CC chemokine CXCL1 through CXCL13, a CXC chemokine, a C chemokine, a CX3C chemokine, a cytokine or chemokine receptor, a soluble receptor, a checkpoint inhibitor, Transforming Growth Factor-beta (TGF-β), or Tumor Necrosis Factor-alpha (TNFα). In an embodiment, the viral vector comprises one or more suicide genes, which is capable of converting an inert prodrug into a cytotoxic metabolite. By way of example, the inert prodrug may be ganciclovir, acyclovir, 1-(2-deoxy-2-fluoro-β-D-arabinofuranosyl)-5-iodouracil (FIAU), 6-methoxypurine arabinoside, or 5-fluorocytosine. In an embodiment, the one or more suicide genes encode cytosine deaminase or thymidine kinase, which is optionally derived from Herpes Simplex Virus (HSVtk) or Varicella Zoster Virus (VZV-tk). In an embodiment, the viral vector is capable of eliciting an immune response against a tumor or cancer expressing the two or more epitopes of the one or more tumor associated antigens following administration to a subject, preferably a human subject or patient who has a cancer or tumor. In an embodiment, the immune response generates cytotoxic T cells that specifically kill the cancer or tumor cells expressing the tumor associated antigen epitopes. In all of the above embodiments, the Sindbis viral vector or the pseudotyped viral vector contains the polynucleotide described supra and infra (also called a minigene) whose encoded products are expressed in cells following contact of the viral vector with cells in vitro and in vivo.

In an embodiment, the viral vector, e.g., the Sindbis virus vector, encoding a checkpoint protein, or a cognate ligand binding portion thereof, elicits an immune response against a tumor or cancer following administration to a subject, preferably a human subject or patient who has a cancer or tumor. In an embodiment, the administration of the viral vector, e.g., the Sindbis virus vector, encoding a checkpoint protein, or a cognate ligand binding portion thereof increases the survivability of the subject having cancer or a tumor. In an embodiment, the Sindbis viral vector or the pseudotyped viral vector contains the polynucleotide described supra and infra. In an embodiment, the Sindbis viral vector or the pseudotyped viral vector contains a polynucleotide sequence encoding a minibody which comprises a checkpoint protein fusion molecule, or a ligand binding portion thereof, as described herein, whose encoded products are expressed in cells and secreted by cells following contact of the viral vector with cells in vitro and in vivo.

Provided as another aspect of the invention is a lentiviral vector pseudotyped with one or more genetically engineered Sindbis virus envelope proteins, in which the lentiviral vector comprises the polynucleotide as described supra and infra. Also provided by the invention is a lentiviral vector pseudotyped with one or more genetically engineered Sindbis virus envelope proteins, said lentiviral vector comprising the polynucleotide as described supra and infra, wherein the polynucleotide encodes an epitope of one or more tumor associated antigen selected from NY-ESO-1, MAGE-A3, pbk, survivin, or a combination thereof. Also provided by the invention is a lentiviral vector pseudotyped with one or more genetically engineered Sindbis virus envelope proteins, said lentiviral vector comprising the polynucleotide as described supra and infra, wherein the polynucleotide encodes a checkpoint protein or a ligand binding portion thereof.

In another aspect, the invention provides a viral particle comprising the viral vector, such as the Sindbis viral vector or the pseudotyped viral vector as described supra and infra. In another aspect, the invention provides a viral particle comprising an alphavirus vector, a lentiviral vector, a retroviral vector, or a pseudotyped vector thereof as described supra and infra.

In another aspect, the invention provides a cell comprising a polynucleotide as described supra and infra. In other aspects, the invention further provides a cell comprising a viral vector or a lentiviral vector as described supra and infra. In an aspect, the invention provides a cell comprising a viral particle as described supra and infra.

In yet another aspect, pharmaceutical compositions are provided which comprise a polynucleotide, viral particle, and/or viral vector as described supra and infra, and a pharmaceutically acceptable vehicle, carrier, or diluent. In an embodiment, the pharmaceutical composition is in liquid dosage form.

In another aspect, a method of inducing an immune response against a cancer or tumor cell, e.g., a cancer or tumor cell that expresses one or more tumor associated antigens or epitopes thereof, is provided in which the method involves contacting the cancer or tumor cell with an effective amount of a polynucleotide, viral particle, viral vector, and/or pharmaceutical composition as described supra and infra, such as a Sinbbis viral vector containing a polynucleotide that encodes a checkpoint protein or a ligand binding fragment thereof, or a checkpoint protein minibody as described herein, to induce an immune response against the cancer or tumor cell. In an embodiment, the immune response involves the generation of activated cytotoxic T cells that specifically kill the cancer or tumor cells that express the cognate ligand (e.g., protein receptor) that interacts with the vector-encoded checkpoint protein, such asPD-1 or a cognate ligand binding portion thereof. In an embodiment of the foregoing, the checkpoint protein is the extracellular domain of the protein.

In another aspect, a method of inducing an immune response against a cancer or tumor cell expressing one or more epitopes of two or more tumor associated antigens is provided in which the method involves contacting the cancer or tumor cell with an effective amount of a polynucleotide, viral particle, viral vector, and/or pharmaceutical composition as described supra and infra to induce the immune response against the cancer or tumor cell. In an embodiment, the immune response generates cytotoxic T cells that specifically kill the cancer or tumor cells expressing the tumor associated antigen epitopes. In another aspect, a method of treating cancer in a subject who has, or is at risk or having, cancer or tumorigenesis is provided, in which the method involves administering to the subject a therapeutically effective amount of a polynucleotide, viral particle, viral vector, and/or pharmaceutical composition as described supra and infra to treat cancer in the subject. In an embodiment of the method, the subject is preferably a human patient having or at risk of having a cancer or tumor selected from one or more of a/an ovarian cancer, cervical cancer, uterine cancer, breast cancer, testicular cancer, pancreatic cancer, liver cancer, colorectal cancer, thyroid cancer, lung cancer, prostate cancer, kidney cancer, melanoma, squamous cell carcinoma, chronic myeloid leukemia, acute lymphoblastic leukemia, acute myelogenous leukemia, chronic lymphocytic leukemia, promyelocytic leukemia, multiple myeloma, B-cell lymphoma, bladder carcinoma, head and neck cancer, esophageal cancer, brain cancer, pharynx cancer, tongue cancer, synovial cell carcinoma, neuroblastoma, fibrosarcoma, myxosarcoma, liposarcoma, chondrosarcoma, osteogenic sarcoma, chordoma, angiosarcoma, endotheliosarcoma. lymphangiosarcoma, synovioma, mesothelioma, Ewing's tumor, leiomyosarcoma, rhabdomyosarcoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroglioma, or retinoblastoma. In a particular embodiment of the methods, the subject's cancer is one or more of ovarian cancer, cervical cancer, breast cancer, or colon cancer. In embodiments of the methods, the polynucleotide, viral particle, viral vector, or pharmaceutical composition encodes two or more epitopes of one or more of the tumor associated antigens NY-ESO-1, p53, sp17, survivin, pbk, CEA, CA125, or WT1. In an embodiment of the methods, the polynucleotide, viral particle, viral vector, or pharmaceutical composition is administered parenterally or as a prophylactic. In an embodiment, one or more checkpoint inhibitor molecules, such as an antibody specifically directed against an immune checkpoint protein, or a fragment thereof that specifically binds to the immune checkpoint protein, may be co-administered to a subject in conjunction with the polynucleotides, viral vectors, viral particles, or compositions thereof, in the methods described herein. In embodiments of the methods, the subject is further treated with chemotherapy or radiation. In an embodiment of the methods, a booster is administered to the subject following a decline in the subject's immune response as assessed by determining levels of the subject's effector T-cells. In an embodiment, the booster is a heterologous booster comprising a replication-defective adenoviral vector, such as adenovirus or adeno-associated virus. In an embodiment, the adenoviral booster vector comprises a polynucleotide encoding one or more epitopes of two or more tumor associated antigens, wherein each epitope is separated by a processing site, such as an enzyme cleavage site. In an embodiment, the epitopes comprise an amino acid sequence of a tumor associated antigen listed in any one of Tables 1-28, illustratively, kallikrein 4, PBF, PRAME, WT1, HSDL1, mesothelin, NY-ESO-1, CEA, p53, Her2/Neu, EpCAM, CA125, folate receptor a, sperm protein 17, TADG-12, MUC-16, L1CAM, mannan-MUC-1, HERV-K-MEL, KK-LC-1, KM-HN-1, LAGE-1, MAGE-A4, Spi17, SSX-4, TAG-1, TAG-2, ENAH, mammoglobin-A, NY-BR-1, BAGE-1, MAGE-A1, MAGE-A2, mucink, SSX-2, TRAG-3, c-myc, cyclin B1, MUC1, p62, survivin, CD45, DKK1, RU2AS, telomerase, K-ras, G250, hepsin, intestinal carboxyl esterase, alpha-fetoprotein, M-CSF, PSMA, CASP-5, COA-1, OGT, OS-9, TGF-betaRII, gp70, CALCA, CD274, mdm-2, alpha-actinin-4, elongation factor 2, ME1, NFYC, GAGE-1, MAGE-A6, XAGE-1b, PSMA, STEAP1, PAP, PSA, GAGE3, FGF5, hepsin, hsp70-2, MAGE-A9, ARTC1, B-RAF, beta-catenin, Cdc27, CDK4, CDK12, CDKN2A, CLLP, CSNK1A1, FN1, GAS7, GPNMB, HAUS3, LDLR-fucosyltransferase, MART2, MATN, MUM-1, MUM-2, MUM-3, neo-PAP, myosin class I, PPP1R3B, PRDX5, PTPRK, N-ras, RBAF600, SIRT2, SNRPD1, triosephosphate isomerase, OA1, RAB38, TRP-1, gp75, TRP2, tyrosinase, MART-1, gp100, GnTVf, LY6K, MAGE-A10, MAGE-A12, MAGE-C2, NA88-A, TRAG-3, TRP2-INT2g, pbk, CASP-8, SAGE, BCR-ABL, dek-can, EFTUD2, ETV6-AML1, FLT3-ITD, cyclin-A1, FDNC3B, pml-RARalpha, MAGE-C1, D393-CD20, MAGE-A4, or MAGE-A3. In an embodiment, the booster is administered to the subject at least one day to at least two weeks after administration of the polynucleotide, viral particle, viral vector, or pharmaceutical composition. In an embodiment of the methods, the administering of the polynucleotide, viral particle, viral vector, or pharmaceutical composition as described supra and infra, or the boosting, if utilized, causes epitope spreading in the subject. In embodiments, the polynucleotide the viral particle, or the viral vector as described supra and infra further comprise a nucleic acid sequence encoding the amino acid sequence AKFVAAWTLKAAA (SEQ ID NO: 7) for inducing a CD4+ T cell response.

A particular aspect of the invention provides a non-integrating alphavirus vector (e.g., a Sindbis viral vector) molecularly engineered to contain a polynucleotide which encodes at least one immune checkpoint protein, or a cognate ligand binding portion thereof, or a checkpoint protein-Ig fusion protein (called a minibody) as described and exemplified herein. In an embodiment, the vector also contains a polynucleotide which encodes a tumor associated antigen (TAA) or one or more epitopes thereof. By way of example, the TAA epitope may comprise 5-50 amino acids or 5-30 amino acids. In an embodiment, if more than one tumor associated antigen or epitope thereof is encoded by the vector, each epitope sequence may be separated by a processing site, such as an enzyme cleavage site, e.g., a furin enzyme cleavage site, for reproducibility in intracellular processing of the tumor associated antigen epitope polypeptide and peptide products. In some embodiments, the viral vector also contains one or more nucleic acid sequences which encode one or more neo-antigens, cytokines, chemokines, antibodies, mutated oncogenes, or overexpressed oncogenes, for enhancing and improving the immune response against the tumor associated antigen epitopes that is elicited by the viral vectors and viral particles described herein, as well as the therapeutic and/or prophylactic uses thereof.

Provided by the invention are therapeutic, prophylactic, or combined therapeutic and prophylactic treatments of mammalian cancers or tumors using the polynucleotides, viral vectors viral particles and pharmaceutical compositions as described supra and infra. In embodiments, one or more checkpoint inhibitor molecules, such as an antibody specifically directed against an immune checkpoint protein, or a fragment thereof that specifically binds to the immune checkpoint protein, are co-administered to a subject in conjunction with the polynucleotides, viral vectors, viral particles, or pharmaceutical compositions thereof, in the methods described herein. Nonlimiting examples of checkpoint inhibitors include anti-PD-1 antibody, anti-PD-L1 antibody, anti-CTLA-4 antibody, and the like, as described herein, or a fragment of such antibodies that specifically binds to the immune checkpoint protein and interrupts or blocks the suppressive interaction resulting from the binding of cognate checkpoint proteins on different cells, for example, PD-1 on T cells and PD-L1 on tumor cells. The one or more checkpoint inhibitor molecules may be administered at the same time as (simultaneously), or at different times from, the administration of the polynucleotides, viral vectors, or viral particles, or pharmaceutical compositions thereof, as described herein.

A particular aspect of the invention provides a non-integrating alphavirus vector (e.g., a Sindbis viral vector) molecularly engineered to contain a polynucleotide which encodes two or more epitopes comprising, for example, 5-50 amino acids or 5-30 amino acids, of one or more tumor associated antigens, in which each epitope sequence is separated by processing site, such as an enzyme cleavage site, e.g., a furin enzyme cleavage site, for reproducibility in intracellular processing of the tumor associated antigen epitope polypeptide and peptide products. In some embodiments, the viral vector also contains one or more nucleic acid sequences which encode one or more neo-antigens, cytokines, chemokines, antibodies, checkpoint inhibitors, mutated oncogenes, or overexpressed oncogenes, for enhancing and improving the immune response against the tumor associated antigen epitopes that is elicited by the viral vectors and viral particles described herein, as well as the therapeutic and/or prophylactic uses thereof.

In an aspect, because the Sindbis viral vectors as described herein elicit strong T cell responses, including CD8+ T cell responses, against multiple epitopes of tumor associated antigens, combining checkpoint inhibitor sequences with the multi-epitope sequences in the described polynucleotides and alphavirus and Sindbis virus vectors offers advantageous and augmented anti-tumor efficacy for the T cells generated by the viral vectors as described and exemplified herein.

In another aspect, the alphavirus protein or a fragment thereof of the polynucleotides, viral vectors, or viral particles as described herein is derived from one or more of Barmah Forest virus, Barmah Forest virus complex, Eastern equine encephalitis virus (EEEV), Eastern equine encephalitis virus complex, Middelburg virus, Middelburg virus complex, Ndumu virus, Ndumu virus complex, Semliki Forest virus, Semliki Forest virus complex, Bebaru virus, Chikungunya virus, Mayaro virus, Subtype Una virus, O'Nyong Nyong virus, Subtype Igbo-Ora virus, Ross River virus, Subtype Getah virus, Subtype Bebaru virus, Subtype Sagiyama virus, Subtype Me Tri virus, Venezuelan equine encephalitis virus (VEEV), VEEV complex, Cabassou virus, Everglades virus, Mosso das Pedras virus, Mucambo virus, Paramana virus, Pixuna virus, Western equine encephalitis virus (WEEV), Rio Negro virus, Trocara virus, Subtype Bijou Bridge virus, Western equine encephalitis virus complex, Aura virus, Babanki virus, Kyzylagach virus, Sindbis virus, Ockelbo virus, Whataroa virus, Buggy Creek virus, Fort Morgan virus, Highlands J virus, Eilat virus, Salmon pancreatic disease virus (SPDV), Southern elephant seal virus (SESV), Tai Forest virus, or Tonate virus.

In yet another aspect, a Sindbis viral vector encoding a checkpoint inhibitor molecule is provided. In an embodiment, the checkpoint inhibitor molecule encoded by the Sindbis viral vector is selected from the group consisting of anti-PD-1 antibody, an anti-PD-L1 antibody, an CTLA-4 antibody, an anti-LAG-3 antibody, an anti-KIR antibody, an anti-IDO1 antibody, an anti-4-1BB antibody, and anti-TIM-3 antibody, and anti-OX40 antibody, an anti-A2AR antibody, an anti-B7-H3 antibody, an anti-B7-H4 antibody, an anti-B7-1/B7-2 antibody, an anti-BTLA antibody, an anti-VISTA antibody, or a fragment of each of the antibodies that retains specific checkpoint protein binding activity. In an embodiment, the checkpoint inhibitor molecule is a single chain antibody. Also provided is a method of treating cancer or a tumor in a subject in which the method comprises administering to the subject an effective amount of the above-described Sindbis viral vector.

In another aspect, a pharmaceutical composition comprising a Sindbis viral vector encoding a checkpoint inhibitor molecule is provided. In an embodiment of the pharmaceutical composition, the checkpoint inhibitor molecule encoded by the Sindbis virus vector is selected from the group consisting of anti-PD-1 antibody, an anti-PD-L1 antibody, an CTLA-4 antibody, an anti-LAG-3 antibody, an anti-KIR antibody, an anti-IDO1 antibody, an anti-4-1BB antibody, and anti-TIM-3 antibody, and anti-OX40 antibody, an anti-A2AR antibody, an anti-B7-H3 antibody, an anti-B7-H4 antibody, an anti-B7-1/B7-2 antibody, an anti-BTLA antibody, an anti-VISTA antibody, or a fragment of each of the antibodies that retains specific checkpoint protein binding activity. In an embodiment, the checkpoint inhibitor molecule is a single chain antibody. Also provided is a method of treating cancer or a tumor in a subject in which the method comprises administering to the subject an effective amount of the above-described pharmaceutical composition.

In another aspect, a pharmaceutical composition comprising a Sindbis viral vector encoding a tumor associated antigen and a Sindbis viral vector encoding a checkpoint inhibitor molecule is provided. In an embodiment of the pharmaceutical composition, the checkpoint inhibitor molecule encoded by the Sindbis viral vector is selected from the group consisting of anti-PD-1 antibody, an anti-PD-L1 antibody, an CTLA-4 antibody, an anti-LAG-3 antibody, an anti-KIR antibody, an anti-IDO1 antibody, an anti-4-1BB antibody, and anti-TIM-3 antibody, and anti-OX40 antibody, an anti-A2AR antibody, an anti-B7-H3 antibody, an anti-B7-H4 antibody, an anti-B7-1/B7-2 antibody, an anti-BTLA antibody, an anti-VISTA antibody, or a fragment of each of the antibodies that retains specific checkpoint protein binding activity. In an embodiment, the checkpoint inhibitor molecule is a single chain antibody.

In another aspect is provided a method of treating cancer or a tumor in a subject, the method comprising administering to the subject a Sindbis viral vector encoding a tumor associated antigen and a Sindbis viral vector encoding a checkpoint inhibitor molecule. In an embodiment of the method, the checkpoint inhibitor molecule encoded by the Sindbis virus vector is selected from the group consisting of anti-PD-1 antibody, an anti-PD-L1 antibody, an CTLA-4 antibody, an anti-LAG-3 antibody, an anti-KIR antibody, an anti-IDO1 antibody, an anti-4-1BB antibody, and anti-TIM-3 antibody, and anti-OX40 antibody, an anti-A2AR antibody, an anti-B7-H3 antibody, an anti-B7-H4 antibody, an anti-B7-1/B7-2 antibody, an anti-BTLA antibody, an anti-VISTA antibody, or a fragment of each of the antibodies that retains specific checkpoint protein binding activity. In an embodiment, the checkpoint inhibitor molecule is a single chain antibody.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "NY-ESO-1 protein" is meant a polypeptide having at least 85% amino acid sequence identity to UniProtKB-P78358 (CTG1B_Human) or a fragment thereof. An exemplary NY-ESO-1 amino acid sequence is provided below:

```
                                                   (SEQ ID NO: 21)
MQAEGRGTGG STGDADGPGG PGIPDGPGGN AGGPGEAGAT GGRGPRGAGA

ARASGPGGGA PRGPHGGAAS GLNGCCRCGA RGPESRLLEF YLAMPFATPM

EAELARRSLA QDAPPLPVPG VLLKEFTVSG NILTIRLTAA DHRQLQLSIS

SCLQQLSLLM WITQCFLPVF LAQPPSGQRR
```

By "NY-ESO-1 polynucleotide" is meant a nucleic acid molecule encoding an NY-ESO-1 protein. An exemplary NY-ESO-1 polynucleotide sequence is provided below:

```
                                                               (SEQ ID NO: 20)
  1 atcctcgtgg gccctgacct tctctctgag agccgggcag aggctccgga gccatgcagg

 61 ccgaaggccg ggcacagggg ggttcgacgg gcgatgctga tggcccagga ggccctggca

121 ttcctgatgg cccagggggc aatgctggcg gcccaggaga ggcgggtgcc acgggcggca

181 gaggtccccg gggcgcaggg gcagcaaggg cctcggggcc gggaggaggc gccccgcggg

241 gtccgcatgg cggcgcggct tcagggctga atggatgctg cagatgcggg gccagggggc

301 cggagagccg cctgcttgag ttctacctcg ccatgccttt cgcgacaccc atggaagcag

361 agctggcccg caggagcctg gcccaggatg ccccaccgct tcccgtgcca ggggtgcttc

421 tgaaggagtt cactgtgtcc ggcaacatac tgactatccg actgactgct gcagaccacc

481 gccaactgca gctctccatc agctcctgtc tccagcagct ttccctgttg atgtggatca

541 cgcagtgctt tctgcccgtg tttttggctc agcctccctc agggcagagg cgctaagccc
```

-continued

```
601 agcctggcgc cccttcctag gtcatgcctc ctcccctagg gaatggtccc agcacgagtg

661 gccagttcat tgtgggggcc tgattgtttg tcgctggagg aggacggctt acatgtttgt

721 ttctgtagaa aataaaactg agctacgaaa aa
```

By "agent" is meant a peptide, polypeptide, nucleic acid molecule, or small molecule chemical compound, antibody, or a fragment thereof. In one embodiment, the agent is a Sindbis virus, is a checkpoint inhibitor (e.g., an anti-PD1 antibody or anti-CTLA4 antibody), or is a therapeutic composition comprising a Sindbis virus (e.g., a Sindbis virus encoding a tumor associated antigen or fragment thereof (e.g., epitope) and a checkpoint inhibitor.

By "alteration" is meant a change (increase or decrease) in an analyte. In one embodiment an alteration is in the expression levels or activity of a gene or polypeptide as detected by standard art known methods such as those described herein. As used herein, an alteration includes a 10% change in expression levels, a 25% change, a 40% change, or a 50% or greater change in expression levels.

By "ameliorate" and "amelioration" is meant decrease, suppress, attenuate, diminish, arrest, or stabilize the development or progression of a disease.

By "analog" or "derivative" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

As used herein, the term "antigen" refers to a substance capable of eliciting a humoral or cell-mediated immune response. An antigen may be capable, e.g., of inducing the generation of antibodies or stimulating T-cell activity through activation of a T-cell receptor.

Antigens are typically proteins or polysaccharides, and may be components of bacteria, viruses, and other microorganisms (e.g., coats, capsules, cell walls, capsids, flagella, and toxins). The term as used herein encompasses all substances that can be recognized by the adaptive and innate immune system and by an antibody or antibody fragment in vitro or in vivo.

The term "antibody" refers to a polypeptide encoded by an immunoglobulin gene or fragments thereof that specifically bind a cognate antigen. Immunoglobulin genes typically include variable region genes of the light and heavy chains; the kappa and lambda light chain constant region genes, and the alpha, gamma, delta, epsilon, and mu heavy chain constant region genes, which correspond to the immunoglobulin classes, IgA, IgG, IgD, IgE and IgM, respectively. An exemplary immunoglobulin (antibody) structural unit comprises a tetramer. Each tetramer is composed of two identical pairs of polypeptide chains, each pair having one "light" (about 2 kDa) and one "heavy" chain (up to about 70 kDa). Antibodies exist, for example, as intact immunoglobulins or as a number of well-characterized fragments produced by digestion with various peptidases. While various antibody fragments are defined in terms of the digestion of an intact antibody, one of skill in the art will appreciate that such fragments may be synthesized de novo chemically or via recombinant DNA methodologies. Thus, the term antibody, as used herein, also includes antibody fragments produced by the modification of whole antibodies, those synthesized de novo using recombinant DNA methodologies (for example, single chain Fv), monoclonal antibodies or humanized antibodies, and those identified using phage display libraries (see, for example, McCafferty et al., *Nature,* 348:2-4, 1990), for example. For preparation of antibodies, e.g., recombinant or monoclonal antibodies, any technique known in the art can be used, for example, Kohler & Milstein, *Nature,* 256(5517):495-497, 1975; Kozbor et al., *Immunology Today,* 4:72, 1983; Cole et al., pp. 77-96 in *Monoclonal Antibodies and Cancer Therapy*, Alan R. Liss, Inc., 1998). In addition, techniques for the production of single chain antibodies (See, U.S. Pat. No. 4,946,778) can be adapted to produce antibodies to proteins and polypeptides, such as anti-immune checkpoint protein molecules. Transgenic mice, or other organisms, for example, other mammals, can be used to express humanized antibodies. Phage display technology also can be used to identify antibodies and heteromeric Fab fragments that specifically bind to selected proteins, e.g., checkpoint inhibitor proteins (see, e.g., McCafferty et al., 1990, *Nature,* 348:2-4; Marks et al., 1992, *Biotechnology,* 10(7):779-783; and Knappik et al., 2000, *J. Mol. Biol.,* 296:57-86.

As used herein, the term "at risk" as it applies to a cell proliferation disease, such as cancer (e.g., a cancer described herein), refers to patients who have undergone tumor debulking surgery or individuals who have a family history of cancer and/or have been diagnosed as having genetic risk factor genes.

As used herein, the term "carrier" refers to a diluent, adjuvant, excipient, or vehicle with which a composition or pharmaceutical composition, e.g., comprising a polynucleotide, viral vector, or viral particle) can be administered. Pharmaceutical and pharmaceutically acceptable carriers include sterile liquids, such as water and oils, including those of petroleum, animal, vegetable or synthetic origin, such as peanut oil, soybean oil, mineral oil, sesame oil, and the like. Water or aqueous saline solutions and aqueous dextrose and glycerol solutions may be employed as carriers, particularly for injectable solutions. Carriers may also include solid dosage forms, including, but not limited to, one or more of a binder (for compressed pills), a glidant, an encapsulating agent, a flavorant, and a colorant. Suitable pharmaceutical carriers are described in "Remington's Pharmaceutical Sciences" by E. W. Martin.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As will be appreciated by one skilled in the art, "derived from" refers to obtaining from, originating from, or producing from, all or a portion of, (typically a functional or active portion of), a polynucleotide, a polypeptide, or a peptide from a source, e.g., a virus, bacterium, microorganism, or a biological source.

By "immune checkpoint protein" or "immune checkpoint molecule," or simply, "checkpoint protein or molecule" is meant a protein or molecule that hinders or stops a particular process in a cellular or immune system pathway, e.g., to prevent errors or an abnormal or pathological activity or condition. Checkpoint proteins are regulators of the immune system and frequently bound by or interact with ligands (cognate ligands), which may cause a given effect, e.g., cell stimulation, anergy, or apoptosis. In a specific embodiment, the immune checkpoint protein is PD-1 or a cognate ligand binding portion thereof. In an embodiment, the checkpoint protein is the extracellular domain of the protein.

The term "cognate ligand" refers to the specific binding partner, binding member, or ligand with which a checkpoint protein specifically interacts or with which it specifically binds. For example, a specific ligand to which a receptor protein binds or with which it interacts is a "cognate ligand" for that receptor protein. Similarly, the receptor protein is a cognate ligand for a specific ligand molecule or protein.

By "checkpoint inhibitor" is meant an agent that enhances an anti-cancer immune response by blocking, reducing or disrupting the activity of a checkpoint protein. Examples of checkpoint proteins found on T cells or cancer cells include PD-1/PD-L1 and CTLA.-4/B7-1/B7-2. Exemplary checkpoint inhibitors include agents (e.g., antibodies) that bind to such proteins. Checkpoint protein inhibitors (also called "immune checkpoint protein inhibitors") are typically proteins or small molecules, e.g., druggable proteins or small molecules, that block or interrupt the interaction of certain proteins expressed by some types of immune cells in the body (e.g., T cells) with cognate proteins expressed by some cancer cells. In a particular embodiment, checkpoint protein inhibitors include antibodies and fragments of the antibodies that retain binding to checkpoint protein molecules, which prevent certain checkpoint proteins expressed on cells, particularly immune cells (e.g. T cells), from becoming inactive or anergic such that they do not attack and kill foreign or "non-self" cells in the body. Such inactivation of T-cells can occur when tumor cells that express ligands, such as PD-L1, bind to the cognate checkpoint proteins on T cells, e.g., PD-1. In embodiments, a checkpoint protein inhibitor is an antibody, such as a monoclonal antibody, a humanized antibody, a human antibody, a single chain antibody, etc., or a fragment thereof that binds to a checkpoint protein (cognate ligand). As noted above, checkpoint protein inhibitors target certain immune checkpoint proteins. Without limitation, PD-1, programmed cell-death protein 1, is a checkpoint protein targeted by checkpoint inhibitors (for example, nivoumab (Optivo, Bristol-Myers Squibb); pembrolizumab (Keytruda, Merck & Co.); Pidilizumab (CT-011, CureTech); MEDI0680 (AMP-514)); PD-L1, programmed cell-death ligand 1, is a checkpoint protein targeted by checkpoint inhibitors, (for example, MEDI4736 (AstraZeneca); MPDL3280A, Roche/Genentech; Tecentriq, Genentech); MSB-0010718C (Merck KGaA)). Other checkpoint proteins and their targeting checkpoint inhitors include CTLA-4 (cytotoxic T-lymphocyte protein 4, also called CD152) checkpoint inhibitors, (for example, Tremelimumab (AstraZeneca); LAG-3, lymphocyte activation gene 3 protein, checkpoint inhibitors (for example, BNS-986016, Bristol-Myers Squibb); KIR, killer cell immunoglobulin-like receptor, checkpoint inhibitors, (for example, Lirilumab (BMS-986015), Bristol-Myers Squibb); IDO1, indoleamine 2,3-dioxygenase 1, checkpoint inhibitors (for example, Indoximod (NLG-9189, NewLink Genetics); NLG-919 (NewLink Genetics); INCB024360 (Incyte)); 4-1BB, a tumor necrosis factor receptor superfamily member 9, (also known as CD137), checkpoint inhibitors, (for example, PF-05082566 (Pfizer); Urelumab (BMS-663513), Bristol-Myers Squibb); TIM-3, "T-cell immunoglobulin domain and mucin domain," checkpoint inhibitors; OX40, tumor necrosis factor receptor superfamily member 4, (also known as CD134) checkpoint inhibitors, (for example, MEDI6469 (AztraZeneca)); A2aR, adenosine A2A receptor, checkpoint inhibitors, B7-H3 (also called CD276) checkpoint inhibitors, B7-114 (also called VTCN1) checkpoint inhibitors, B7-1/B7-2 checkpoint inhibitors, BTLA (also called CD272) checkpoint inhibitors, VISTA, "V-domain Ig suppressor of T cell activation," checkpoint inhibitors, and the like.

"Detect" refers to identifying the presence, absence or amount of a molecule, compound, or agent to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that adversely affects, damages or interferes with the normal function of a cell, tissue, organ, or part of the body, such as cancer or tumorigenesis.

By "effective amount" is meant the amount of a required to ameliorate the symptoms of a disease relative to an untreated patient. The effective amount of active compound (s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. In one embodiment, an effective amount is the amount of an agent of the invention required to reduce or stabilize the rate of proliferation of a cancer cell. In another embodiment, an effective amount is the amount of an agent of the invention required to reduce the survival of a cancer cell. In another embodiment, an effective amount is the amount of an agent of the invention required to induce the death of a cancer cell.

As used herein, the term "endogenous" describes a molecule (e.g., a polypeptide, peptide, nucleic acid, or cofactor) that is found naturally in a particular organism (e.g., a human) or in a particular location within an organism (e.g., an organ, a tissue, or a cell, such as a human cell).

As used herein, the term "epitope" or "antigenic determinant" refers to a site, e.g., an amino acid sequence, on an antigen (e.g., a tumor-associated antigen) to which a ligand, an antibody, or T-cell receptor is capable of binding (e.g., during the induction of an immune response) that can be formed from either contiguous amino acids or discontinuous amino acids that are rendered spatially proximal by the tertiary folding of a protein. Other epitopes are formed by quaternary structures, e.g., by the assembly of several polypeptides. Epitopes formed from contiguous amino acids are typically retained on exposure to denaturing solvents, while epitopes formed by tertiary or quaternary folding are typically lost on treatment with denaturing solvents. An epitope may include, e.g., from 3-30 amino acid residues, or from 5 to 30 or from 5 to 25 amino acid residues, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues, which may be in a distinct spatial conformation. Methods of determining spatial conformation of epitopes are known in the art and include, e.g., x-ray crystallography and 2-dimensional nuclear magnetic resonance (NMR). Such methods are described in detail, e.g., in Morris, *Epitope Mapping Protocols in Methods in Molecular Biology*, Vol. 66, (1996).

As used herein, the term "epitope spreading" (also called "antigen spreading") refers to the diversification of epitope specificity from an initial focused, epitope-specific immune response (e.g., by cytotoxic T cells) directed against a self or foreign antigen or protein, to subdominant and/or cryptic, or mutated epitopes on the protein (intramolecular spreading) or on other proteins (intermolecular spreading). Epitope spreading may enable a patient's immune system to mount an immune response against additional epitopes not initially recognized by cells (e.g., cytotoxic T cells) of the immune system while reducing the possibility of escape variants in the tumor population, and may thus attenuate progression of disease (cancer). In one embodiment, after vaccination with a vector described herein, T cells are generated that respond to tumor associated antigens that were not in the original vaccine formulation, indicating that a secondary round of T cell priming has occurred with antigens derived from tumor cells.

As used herein, the term "exogenous" refers to a molecule (e.g., a polypeptide, peptide nucleic acid, or cofactor) that is not found naturally or endogenously in a particular organism (e.g., a human) or in a particular location within an organism (e.g., an organ, a tissue, or a cell, such as a human cell). Exogenous materials include those that are provided from an external source to an organism or to cultured matter extracted therefrom.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

As used herein, the term "immune response" refers to a subject's immune system response or reaction to one or more antigens, (e.g., an immunogenic protein or peptide), and/or the epitopes of the antigens, recognized by the immune system as foreign or heterologous. Immune responses include both cell-mediated immune responses (i.e., responses mediated by effector T cells, such as antigen-specific or non-specific T-cells, such as $CD8^+$ T-cells, Th1 cells, Th2 cells, and Th17 cells) as well as humoral immune responses (i.e., responses characterized by B-cell activation and the production of antigen-specific antibodies). The term "immune response" encompasses both the innate immune responses to an antigen or immunogen (e.g., a tumor-associated antigen and/or its associated epitopes) as well as memory responses that are a result of acquired immunity and can involve either B cells or T cells, or both.

The terms "isolated," "purified," or "biologically pure" refer to material that is free to varying degrees from components which normally accompany or are associated with it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid, protein, or peptide gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide that has been separated from components that naturally accompany it. Typically, a polypeptide is isolated when it is at least 60%, by weight, free from the proteins and naturally-occurring organic molecules with which it is naturally associated. Preferably, the preparation is at least 75%, or at least 85%, or at least 90%, or at least 99%, by weight, a desired polypeptide. An isolated polypeptide may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

A "neo-epitope" as referred to herein is a newly formed (or neo) epitope (e.g., antigenic determinant) that has not been previously recognized by the immune system. Neo-epitopes encompass epitopes on a neoantigen, which is a newly formed antigen. Neoantigens, which are often associated with tumor antigens, are found in oncogenic cells. Within the described viral vectors, large quantities of proteins with the mutated neo-epitope can be generated and secreted into the cytoplasm of antigen-presenting cells of the immune system, where they are processed and used to activate tumor-specific T cells, which can then target the cancer cells and destroy them.

As used herein, "obtaining" as in "obtaining an agent" includes synthesizing, purchasing, or otherwise acquiring the agent.

By "polynucleotide" is meant a nucleic acid molecule, e.g., a double-stranded (ds) DNA polynucleotide, a single-stranded (ss) DNA polynucleotide, a dsRNA polynucleotide, or a ssRNA polynucleotide, that encodes one or more polypeptides. The term encompasses positive-sense (i.e., protein-coding) DNA polynucleotides, which are capable of being transcribed to form an RNA transcript, which can be subsequently translated to produce a polypeptide following one or more optional RNA processing events (e.g., intron excision by RNA splicing, or ligation of a 5' cap or a 3' polyadenyl tail). The term additionally encompasses positive-sense RNA polynucleotides, capable of being directly translated to produce a polypeptide following one or more optional RNA processing events. As used herein, a polynucleotide may be contained within a viral vector, such as a Sindbis viral vector.

A "minigene" as used herein refers to a molecularly engineered polynucleotide, e.g., a multigene construct containing sequences encoding different components, which is designed to encode at least one, preferably, two or more, epitopes of an antigen, such as a tumor associated antigen (TAA), or one or more, preferably, two or more, epitopes of two or more tumor associated antigens. The two or more epitopes may be from the same tumor associated antigen or from different tumor associated antigens. A minigene polynucleotide may further comprise nucleic acid sequences in addition to the epitope-encoding sequences, including, without limitation, framework or motif sequences (e.g., one or more enzyme cleavage sites) and processing sequences, such as a ribosome binding site, a signal sequence (e.g., an endoplasmic reticulum signal sequence), a 5' flanking region and a 3' stop codon sequence. The polynucleotide may also contain nucleic acid sequences that encode other antigens (e.g., tumor associated antigens), cell receptors and immunostimulatory or immunomodulatory molecules, such as cytokines, chemokines, cell signaling molecules, checkpoint inhibitor molecules (e.g., antibodies and binding fragments thereof), and the like. Some or all of the foregoing sequences may be included in the polynucleotide. A minigene may be a polynucleotide, such as a negative-sense DNA or RNA polynucleotide, which serves as a template for the production of a positive-sense polynucleotide.

As used herein, the phrase "pharmaceutically acceptable" refers to molecular entities, biological products and compositions that are physiologically tolerable and do not typically produce an allergic or other adverse reactions, such as gastric upset, dizziness and the like, when administered to a patient (e.g., a human patient).

As used herein, the terms "prevent," "preventing," "prevention," "prophylactic treatment" and the like refer to reducing the probability of developing a disorder or condition in a subject, who does not have, but who is at risk of or susceptible to developing a disorder or condition.

As used herein, the term "pseudotyped" refers to a viral vector that contains one or more foreign viral structural proteins, e.g., envelope glycoproteins. A pseudotyped virus may be one in which the envelope glycoproteins of an enveloped virus or the capsid proteins of a non-enveloped virus originate from a virus that differs from the source of the original virus genome and the genome replication apparatus. (D. A. Sanders, 2002, *Curr. Opin. Biotechnol.*, 13:437-442). The foreign viral envelope proteins of a pseudotyped virus can be utilized to alter host tropism or to increase or decrease the stability of the virus particles. Examples of pseudotyped viral vectors include a retrovirus or lentivirus that contains one or more envelope glycoproteins that do not naturally occur on the exterior of the wild-type retrovirus or lentivirus, such as one or more proteins derived from an alphavirus (e.g., Sindbis virus, such as Sindbis-ZZ E2 protein (Morizono, K. et al., 2010, *J. Virol.*, 84(14):6923-6934), or Sindbis E1, E2 and/or E3 proteins). Pseudotyped viral vectors can infect cells and express and produce proteins encoded by polynucleotides, e.g., "minigenes", contained within the viral vectors.

By "reduces" is meant a negative alteration of at least 5%, 10%, 25%, 50%, 75%, or 100%.

By "reference" is meant a standard or control condition. In one embodiment, a standard of comparison is an untreated control cell (e.g., cancer cell) or an untreated subject having cancer.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "subject" is meant a mammal, including, but not limited to, a human or non-human mammal, such as a non-human primate, bovine, equine, canine, ovine, or feline mammal. A subject is typically a patient, such as a human patient, who receives treatment for a particular disease or condition as described herein (e.g., a cell proliferation disease, such as cancer or tumor). Examples of subjects and patients include mammals, such as humans, receiving treatment for such diseases or conditions or who are at risk of having such diseases or conditions.

As used herein, the term "suicide gene" refers to a gene encoding a polypeptide capable of inducing cell death, e.g., by apoptosis. Suicide genes may function by encoding a protein or peptide capable of converting a prodrug into a cytotoxic molecule. Exemplary suicide genes include, without limitation, Herpes simplex virus thymidine kinase (HSV-TK), cytosine deaminase, nitroreductase, carboxylesterase, cytochrome P450, and purine nucleoside phosphorylase (PNP), among others.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the term "therapeutically effective amount" refers to a quantity of a therapeutic agent that is sufficient to treat, diagnose, prevent, and/or delay the onset of one or more symptoms of a disease, disorder, and/or condition upon administration to a patient in need of treatment. In some cases, a therapeutically effective amount may also refer to a quantity of a therapeutic agent that is administered prophylactically (e.g., in advance of the development of full-blown disease) to a subject who is at risk of developing a disease or the symptoms thereof, such as cancer or a tumor.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. "Treat" or "treatment" may refer to therapeutic treatment, in which the object is to prevent or slow down (lessen or reduce) an undesired physiological change or disorder, such as the progression of a cell proliferation disorder, such as cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder, as well as those prone to have the condition or disorder or those in whom the condition or disorder is to be prevented.

As used herein, the term "tumor-associated antigen" or "TAA" refers to a protein, polypeptide, or peptide that is expressed by cancer cell, such as a cell within a solid tumor. Tumor-associated antigens include protein or peptide antigens that are expressed on the surface of a cancer cell or that are overexpressed relative to a non-cancerous cell, as well as proteins that arise from mutations of wild-type proteins. Proteins that arise from mutations of wild-type cellular proteins embrace neo-epitopes and neo-antigens that occur in cancer or tumor cells, e.g., mutated k-Ras proteins. Tumor associated antigens thus embrace cell surface receptor proteins, e.g., membrane bound proteins, that are expressed on the surface of a cancer or tumor cell. Tumor associated antigens also embrace intracellular, e.g., cytoplasmic, nuclear, or membrane-bound proteins that are expressed within a cancer or tumor cell. A tumor-associated antigen may be tumor-specific, in which case the expression of the antigen is restricted to a particular type of cancer cell. Alternatively, a tumor-associated antigen may be common to several cancers and thus expressed on the surface of a variety of cancer cell types.

As used herein, the term "vector" refers to a nucleic acid (e.g., a DNA vector, such as a plasmid), a RNA vector, virus or other suitable replicon (e.g., viral vector). A variety of vectors have been developed for the delivery of polynucleotides encoding exogenous proteins into a prokaryotic or eukaryotic cell. A vector may contain a polynucleotide sequence that includes gene of interest (e.g., a gene encoding a tumor-associated antigen and/or an epitope thereof) as well as, for example, additional sequence elements capable of regulating transcription, translation, and/or the integration of these polynucleotide sequences into the genome of a cell. A vector may contain regulatory sequences, such as a promoter, e.g., a subgenomic promoter, region and an enhancer region, which direct gene transcription. A vector may contain polynucleotide sequences that enhance the rate of translation of these genes or improve the stability or nuclear export of the mRNA that results from gene transcription. These sequence elements may include, e.g., 5' and 3' untranslated regions, an internal ribosomal entry site (IRES), and/or a polyadenylation signal site in order to direct efficient transcription of a gene carried on the expression vector.

As used herein, the term "vehicle" refers to a solvent, diluent, or carrier component of a pharmaceutical composition.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, preferably at least 70%, more preferably 80% or 85%, and most preferably 90%, 95% or even 99% identical at the amino acid level or nucleic acid to the sequence used for comparison, for example, over a specified comparison window. Optimal alignment may be conducted using the homology alignment algorithm of Needleman and Wunsch, 1970, *J. Mol. Biol.,* 48:443. An indication that two peptide or polypeptide sequences are substantially identical is that one peptide or polypeptide is immunologically reactive with specific antibodies raised against the second peptide or polypeptide, although such cross-reactivity is not required for two polypeptides to be deemed substantially identical. Thus, a peptide or polypeptide is substantially identical to a second peptide or polypeptide, for example, where the two differ only by a conservative substitution. Peptides or polypeptides that are "substantially similar" share sequences as noted above except that residue positions which are not identical may differ by conservative amino acid changes. Conservative substitutions typically include, but are not limited to, substitutions within the following groups: glycine and alanine; valine, isoleucine, and leucine; aspartic acid and glutamic acid; asparagine and glutamine; serine and threonine; lysine and arginine; and phenylalanine and tyrosine, and others as known to the skilled person in the art.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Polynucleotides and viral nucleic acid molecules useful in the methods of the invention include any nucleic acid molecule that encodes the components of viral vectors described herein and the polypeptide products encoded by the viral vectors, such as alphavirus vectors, Sindbis viral vectors and the like, as well as peptides or fragments thereof. Such nucleic acid molecules need not be 100% identical with the viral vector nucleic acid sequence, but will typically exhibit substantial identity. Polynucleotides having substantial identity to the viral vector sequences are typically capable of hybridizing with at least one strand of the viral vector nucleic acid molecule. Nucleic acid molecules useful in the methods of the invention include any nucleic acid molecule that encodes a polypeptide of the invention or a fragment thereof. Polynucleotides having "substantial identity" to an endogenous sequence are typically capable of hybridizing with at least one strand of a double-stranded nucleic acid molecule. By "hybridize" is meant the pair of nucleic acid molecules to form a double-stranded molecule between complementary polynucleotide sequences (e.g., a gene or nucleic acid sequence described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Nonlimiting examples of "moderately stringent hybridization conditions" include a hybridization in a buffer of 40% formamide, 1 M NaCl, 1% SDS at 37 C, and a wash in 1×SSC at 45 C. A positive hybridization is at least twice background. Those of ordinary skill will readily recognize that alternative hybridization and wash conditions can be utilized to provide conditions of similar stringency.

By "ortholog" is meant any polypeptide or nucleic acid molecule of an organism that is highly related to a reference protein or nucleic acid sequence from another organism. The degree of relatedness may be expressed as the probability that a reference protein would identify a sequence, for example, in a blast search. The probability that a reference sequence would identify a random sequence as an ortholog is extremely low, less than $e^{-10}$, $e^{-20}$, $e^{-30}$, $e^{-4}$ $e^{-50}$, $e^{-75}$, $e^{-100}$. The skilled artisan understands that an ortholog is likely to be functionally related to the reference protein or nucleic acid sequence. In other words, the ortholog and its reference molecule would be expected to fulfill similar, if not equivalent, functional roles in their respective organisms, e.g., mouse and human orthologs.

It is not required that an ortholog, when aligned with a reference sequence, have a particular degree of amino acid sequence identity to the reference sequence. A protein ortholog might share significant amino acid sequence identity over the entire length of the protein, for example, or, alternatively, might share significant amino acid sequence identity over only a single functionally important domain of the protein. Such functionally important domains may be defined by genetic mutations or by structure-function assays. Orthologs may be identified using methods practiced in the art. The functional role of an ortholog may be assayed using methods well known to the skilled artisan. For example, function might be assayed in vivo or in vitro using a biochemical, immunological, or enzymatic assay; or transformation rescue. Alternatively, bioassays may be carried out in tissue culture; function may also be assayed by gene inactivation (e.g., by RNAi, siRNA, or gene knockout), or gene over-expression, as well as by other methods.

Unless specifically stated or obvious from context, as used herein, the term "or" is understood to be inclusive. Unless specifically stated or obvious from context, as used herein, the terms "a", "an", and "the" are understood to be singular or plural.

As used herein, the term "about" or "approximately" means within an acceptable error range for the type of value described and the method used to measure the value. For example, these terms can signify within 20%, more preferably within 10%, and most preferably still within 5% of a given value or range. More specifically, "about" can be understood as within 20%, 10%, 9%, 8%, 7%, 6%, 5%, 4%, 3%, 2%, 1%, 0.5%, 0.100, 0.05%, or 0.01% of the stated value or range. Alternatively, especially in biological systems, the term "about" means within one log unit (i.e., one order of magnitude), preferably within a factor of two of a given value. Unless specifically stated or obvious from context, as used herein, the term "about" is understood as within a range of normal tolerance in the art, for example within 2 standard deviations of the mean. Unless otherwise clear from context, all numerical values provided herein are modified by the term about.

Any compositions or methods provided herein can be combined with one or more of any of the other compositions, or components thereof, and methods provided herein.

BRIEF DESCRIPTION OF THE DRAWINGS

FIGS. 1A and 1B depict schematic representations of the design and sequence of a polynucleotide (minigene) encoding various components, including two or more, e.g., 3, epitopes, of one or more, e.g., 3, tumor associated antigens separated by enzyme cleavage sites (e.g., furin enzyme) as described herein. FIG. 1A shows a schematic representation of the polynucleotide for constructing a Sindbis viral vector encoding multiple (3) epitopes of 3 tumor associated antigens. The polynucleotide construct, named "SV/MG" in FIG. 1A, contains an Xba1 restriction enzyme site (TCTAGA) at its 5' end and an Apa1 restriction enzyme site (GGGCCC) at its 3' end for insertion of the polynucleotide into a Sindbis virus vector 'backbone.' From 5' to 3', the polynucleotide contains a ribosome binding site start codon, an endoplasmic reticulum signal sequence, an epitope of the NY-ESO-1 tumor associated antigen, an epitope of the gp70 glycoprotein tumor associated antigen, an epitope of survivin tumor associated antigen, a furin cleavage site separating each of the tumor associated antigen epitopes and a stop codon. FIG. 1B sets forth the polynucleotide sequence of the polynucleotide (minigene) described in FIG. 1A and the corresponding amino acid sequences of the polypeptide and peptide components encoded by the polynucleotide. The component genes and encoded polypeptides/peptides of the polynucleotide are identified below the sequences in FIG. 1B (SEQ ID NO: 10 and SEQ ID NO: 11).

FIG. 2A depicts the therapeutic treatment protocol for administering the Sindbis viral vector containing the polynucleotide of FIGS. 1A and 1B to mice harboring growing tumors in the CT26 tumor mouse model. FIG. 2B presents a graph showing tumor growth as a function of days after treatment of tumored animals with the Sindbis viral vector encoding multiple epitopes, i.e., SV/MA of FIG. 1A (in which the multiple TAAs include NY-ESO-1, survivin and gp70), versus controls, as described in Example 2, infra. Compared with the controls (Control: mice not receiving any Sindbis viral vector; SV/LacZ: Sindbis viral vector encoding β-galactosidase, an irrelevant bacterial enzyme; and SV/NY-ESO-1, a positive control encoding the NY-ESO-1 tumor associated antigen), the SV/MG viral vector encoding multiple tumor associated antigen epitopes of NY-ESO-1, survivin and gp70 were very effective in inhibiting the growth of CT26 tumor cells following injection into tumored animals (FIG. 2B). Shown below the graph in FIG. 2B are the relative light unit (RLU) values indicating tumor growth in the control and experimental groups of mice treated as described above.

FIG. 4A shows that LacZ+ CT26 tumor-bearing mice were treated with either the SV/LacZ Sindbis viral vector, a control SV vector encoding the GFP protein (SV/GFP), or medium/PBS (Mock) and that only the SV/LacZ Sindbis viral vector induced complete tumor remission (100% animal survival) for at least 60 days. The data are presented as Kaplan-Meier survival plots. Significant values between curves are shown $P<0.05$; $^{**}P<0.01$. FIG. 4B demonstrated using tetramers (Altman, J. D. et al., 1996, *Science,* 274 (5284):94-96) that splenocytes from SV/LacZ-treated mice contained $CD8^+$ T cells specific for both LacZ (not shown) and gp70, an endogenous tumor associated antigen expressed by CT26 cells, thus indicating that epitope spreading had occurred. FIG. 4C presents photographs of a control mouse ("Naïve") and a mouse that survived its tumors following injection with the SV/LacZ viral vector as described in FIG. 4A ("SV/LacZ survivor") demonstrating that LacZ (−) CT26 tumors grew in naïve mice, but not in mice treated with the SV/LacZ viral vector encoding LacZ (SV/LacZ survivor mice). These results support the finding that SV/LacZ-induced epitope spreading successfully countered the loss of tumor associated antigen (i.e., LacZ) expression.

FIG. 5A shows the results of in vivo imaging used to non-invasively and longitudinally determine the sites of expression of a representative tumor associated antigen, firefly luciferase, after the injection of animals with a Sindbis viral vector encoding luciferase as the tumor associated antigen. As demonstrated by T-cell activation marker CD69 expression levels assessed in the animals, the mediastinal lymph node (MLN), identified as a site of luciferase (as TAA) delivery, was also found to be a site of potent $CD8^+$ T cell activation. ILN=control inguinal lymph nodes (FIG. 5B). The use of encoded luciferase allows the measurement of tumor growth in animal models in which tumor cells are molecularly engineered (e.g., transfected) to express the luciferase gene, which permits imaging of tumor cells and assessing the growth of the tumors comprising these cells.

FIGS. 11A-11C show schematic depictions of a genetic map of the helper replicon, SV-LacZ and SV-NYESO-1 plasmids. FIG. 11D: To verify NYESO-1 expression by SV-NYESO-1 containing the gene encoding NYESO-1, proteins were extracted from SV-NYESO1 infected BHK cells and NYESO-1 expression was detected by Western Blot. As positive and negative controls, recombinant NYESO-1 and uninfected BHK cells, respectively, were used. FIG. 11E: NYESO-1 expression in CT26.Fluc.NYESO1 was verified by Western blot. CT26.Fluc.LacZ was used as a negative control. FIG. 11F: To verify LacZ expression of SV-LacZ, proteins were extracted from SV-LacZ infected BHK cells, and LacZ expression was detected using the mammalian β-galactosidase assay kit. As a negative control, uninfected BHK cells were used. FIG. 11G: LacZ expression of the mouse colon carcinoma cell line CT26.Fluc.LacZ was verified using the mammalian β-galactosidase assay kit. As a negative control, CT26.Fluc.NYESO1 cells were used.

FIG. 12A: Treatment schema. BALB/c mice were injected i.p. (day −4) with CT26.Fluc.NYESO1 cells ($7\times10^4$) on the right side of the abdomen. Five days later (day 1), SV-LacZ or SV-NYESO1 was injected into the left side of the abdomen for 4 consecutive days for a total of 4 weeks. Tumor growth was measured once a week using noninvasive bioluminescence imaging. FIG. 12B: Tumor growth curves are shown as fold changes relative to the luminescence of the same mouse on day 0. Left graph: animals received no treatment (Control, n=40); Middle graph: animals were treated with SV-LacZ (SV-LacZ, n=33); Right graph: animals were treated with SV-NYESO1 (SV-NYESO1, n=43); FIG. 12C: Representative bioluminescence images of control and SV treated mice bearing CT26.Fluc.NYESO1 tumors. FIG. 12D: Survival plots of untreated (Control, n=35) and SV-NYESO1 (n=35) or SV-LacZ (n=34) treated mice. Statistical significance between SV-LacZ and SV-NYESO1 was determined with the Mantel-Cox Text. Results are representatives of at least two independent experiments. ****P≤; 0.0001.

FIG. 13A: PD-L1 expression on the surface of tumor cells CT26.Fluc.NYESO1 in vivo. PD-L1 expression was analyzed by flow cytometry in untreated (C, Control) and SV-NYESO (SV) treated mice on day 14 and shown as histogram and bar graph. FIG. 13B: PD-1 expression on T cells was analyzed by flow cytometry by gating on CD3+ cells. Top graph: Splenocytes from naive (n=3) and untreated (C, n=9) or SV-NYESO1 treated (SV, n=9) tumor bearing mice on day 7. Bottom graph: T cells from tumor of untreated (C, n=4) or SV-NYESO1 treated (SV, n=8) tumor bearing mice on day 14. Representative flow cytometry plots are shown as histograms. FIG. 13C: Regulatory T cell frequency (TREG) in tumors from control and SV-NYESO1 treated mice on day 14. Frequency was analyzed by flow cytometry and results are shown as dot plots and bar graph. FIG. 13D: Treatment schema used in FIGS. 13D and 13E. Tumor bearing mice were left untreated or were treated with SV with or without anti-PD-1. FIG. 13E: Tumor growth curves are shown as fold changes relative to the luminescence of the same mouse on day 0. Left to right: untreated (Control, n=40), anti-PD-1 antibody (αPD-1, n=23), SV-NYESO1 (n=43), SV-NYESO1 in combination with anti-PD-1 antibody ($\text{SV-NYESO1}^{+}\alpha\text{PD-1}$, n=23) and SV-LacZ in combination with anti-PD-1 antibody (SV-LacZ+αPD-1, n=10) treated mice. FIG. 13F: Survival plots of untreated and treated mice. Statistical significance between SV-NYESO1 and SV-NYESO1+αPD-1 was determined with the Mantel-Cox Text. FIGS. 13A-C: Lines represent means, and statistical significance was determined with the Mann-Whitney test or with the Kurskal-Wallis test followed by the Dunns' test. FIGS. 13D and 13E: Results are representatives of at least two independent experiments. *P 0.05, **P≤0.01.

FIG. 15A: Treatment schema—Tumor bearing mice were left untreated or were treated with one injection of anti-PD-1 antibody and/or SV-NYESO1 On day 2, organs and blood were collected from mice for flow cytometry and multiplex analyses, respectively. FIGS. 15B and C: Plasma samples from naïve, control and SV-NYESO1 treated mice were collected on day 2. Cytokine (FIG. 15B) and chemokine (FIG. 15C) levels in plasma samples were determined by multiplex assay (FIGS. 15E, G, I). Representative flow cytometry plots of the mediastinal lymph node (FIGS. 15D to G). Percentage of CD69 expression by $CD4^{+}$ T cells (FIGS. 15D and E) and CD8+ T cells (FIGS. 15F and G). Left to right: spleen, mediastinal (LN med), inguinal (LN ing) and axillary lymph nodes (LN ax). (FIGS. 15H and 15I). T cell frequency was analyzed in naive mice and control or treated tumor bearing mice. Results are representatives from two independent experiments. (FIGS. 15B-I). Lines represent means, and statistical significance was determined with the Kurskal-Wallis test followed by the Dunns' test and with the Mann-Whitney test (FIG. 15B). n.s>0.05, *P 0.05, **P≤0.01.

FIGS. 16A and B: Flow cytometry gating strategy to define NK cells (FIG. 16A) and B cells (FIG. 16B). FIGS. 16C and D: Percentage of CD69 expression by NK cells (FIG. 16(C) and B cells (FIG. 16D). Left to right: spleen, mediastinal (LN med), inguinal (LN ing) and axillary lymph nodes (LN ax). Results are representatives from two independent experiments. Lines represent means, and statistical significance was determined with the Kurskal-Wallis test followed by the Dunns' test.

FIGS. 17A-1.7F demonstrate results showing that the presence of anti-PD-1 antibody enhanced T cell activation and function during treatment of animals with SV-NYESO1 vector as anti-tumor therapy. FIG. 17A: Treatment schema—Tumor bearing mice were left untreated or were treated with SV with or without anti-PD-1 antibody. Mice were sacrificed on day 7, 14 or 21 to analyze the T cell immune response in spleen. FIG. 1F: Cytotoxic activity of splenocytes harvested on day 14 from control and treated mice (n=5 mice per group). Splenocytes were co-cultured with either CT26.Fluc.NYESO1 (left column) or CT26.Fluc.LacZ (right column) at various ratios for 2 days. Cytotoxic activity was assessed based on the viability of CT26 cells, which was determined by measuring the luciferase activity and is shown relative to naive splenocytes. Results are representatives from two independent experiments. (FIGS. 17B, C, E, F) Bars or symbols represent means±SEB.M and statistical significance was determined with the Mann-Whitney test (FIGS. 171B, C, E) or with the Kurskal-Wallis test followed by the Dunns' test (FIG. 17F). n.s >0.05, *P<0.05, P≤0.01, *P≤0.001 ****P≤0.0001.

FIGS. 18A and B: Percentage of CD44 (FIG. 18A) and Ki-67 (FIG. 18B) expression by CD4+ T cells and CD8+ T cells in naive mice, as well as control or treated tumor bearing mice using flow cytometry (n=8 mice per group). Left graphs: CD4+ T cells. Right graphs: CD8+ T cells. Symbols summarize data from two independent experiments. Statistical significance between groups treated with SV vector in the presence or absence of anti-PD-1 antibody was determined with the Mann-Whitney test. FIG. 18C: Correlation of splenic CD4+ T cells' or CD8+ T cells' Ki-67 expression against tumor growth on day 14 by the Spearman-rank correlation test. Results are representatives from two independent experiments. n.s >0.05, *P<0.05, **P≤0.01.

FIGS. 19A and 19H: T cell immune response from indicated groups was assessed by flow cytometry. FIG. 19A: Left Graph: T cell frequency. Middle graph: Percentage of CD69 expression by T cells. Right graph: Percentage of Ki-67 expression by T cells. FIG. 19B: Representative flow cytometry plots. FIG. 19C: Interferon-γ (IFN-γ) enzyme-linked immunospot analysis of tumor infiltrating cells from control and treated mice. FIG. 19D: Resident-memory T cell frequency from indicated groups was assessed by flow cytometry and shown in dot plots and bar graph. FIGS. 19E-G: Frequencies of various myeloid cells in tumors from indicated groups were assessed by flow cytometry. FIG. 19E: Granulocytic-myeloid derived suppressor cell (gMDSC) frequency. FIG. 19F: Tumor-associated macrophage (TAM) frequency. FIG. 19G: Frequency of CD206+M-CII− cell as a proportion of TAMs. Results are representatives from two independent experiments. Bars and lines represent means±S.E M, and statistical significance was determined with the Kurskal-Wallis test followed by the Dunns' test (FIGS. 19A-G) or the Mann-Whitney test (FIG. 19C) ms>0.05, *P<0.05, P≤0.01, *P≤0.001.

FIG. 20A: Gating strategy of granulocytic-myeloid derived suppressor cells (gMDSC) by flow cytometry. FIG. 20B: Gating strategy of tumor-associated macrophages by flow cytometry. FIG. 20C: Representative flow cytometry plots of the frequencies of gMDSCs, TAMs and macrophage type 2 like cells from indicated groups.

FIGS. 21A and 21B: Memory phenotype of T cells was characterized in spleen and tumor from animals in the indicated groups by flow cytometry by gating on CD3+ cells. The percentage of T cells expressing CD62L and/or CD44 was analyzed and shown as contour plots and pie charts, summarizing data from two independent experiments. FIG. 21A: Splenocytes were harvested from indicated groups (n=8 mice per group) at 3 and 13 weeks after the beginning of treatment. FIG. 21B: Tumors were harvested from animals in the indicated groups (n=5-8 mice per group) at 3 weeks after the beginning of treatment. FIG. 21C: Treatment schema—Tumor-cured mice after SV vector (SV NYESO1) treatment/therapy were rechallenged with the same cancer cells, CT26.Fluc.NYESO1, at more than 150 days after the last SV vector treatment, and tumor growth was analyzed every day by noninvasive bioluminescent imaging. FIG. 21D: Survival plots of naïve (control, n=5) and tumor-cured mice (n=11) after rechallenge with CT26.Fluc.NYESO1 tumor cells (n===7) or CT26.Fluc, LacZ control cells (n=4). Statistical significance between tumor-cured and control (naïve) mice was determined with the Mantel-Cox Text. n.s >0.05, *P<0.05, ***P≤0.01.

FIGS. 23A and 23B present polynucleotide and amino acid sequences and schematic depictions of Sindbis virus vector encoding a single chain anti-CTLA4 binding molecule (aCTLA4) as described herein. FIG. 23A: Polynucleotide sequence (top) (SEQ ID NO: 8) encoding the anti-CTLA4 binding molecule cloned into Sindbis virus pT7StuIR replicon plasmid. The polynucleotide sequence is adapted from Jin et.al., 2013, *Cell Biochem Biophys,* 67:1067. The encoding nucleotides were optimized for expression in mouse cells; the changes are shown in grey. Delineated elements in the sequence from 5'end: anti-CTLA4 $V_H$ human (Double underline), Linker, and Immunoglobulin (Ig) light chain, kappa isotype (Single underline). The amino acid sequence (SEQ ID NO: 9) of the encoded protein is shown beneath the polynucleotide sequence. FIG. 23B: Helper and Replicon DNA plasmids used to make the SV-aCTLA4 vector for in vivo experiments as described in Example 9 herein.

FIGS. 24A-24C: Schematic depiction of the in vivo experimental design, graph of tumor growth and survival curves as described in Example 9 herein. FIG. 24A: Schematic in vivo experimental design: For mice that received treatment with the SV_aCTLA4 Sindbis vector, Sindbis vector treatment was administered 4 times a week for 4 weeks, at days 6, 7, 8, 9 (Week one); 13, 14, 15, 16 (week 2); 21, 22, 23, 24 (week 3); and 28, 29, 30, 31 (week 4) after animals were inoculated with tumor cells. FIG. 24B: Tumor growth curves of SV_aCTLA4 treated and untreated (control) mice. Tumor growth curves are shown as fold changes relative to the bioluminescence in the first image taken of the same mouse 2 days before the start of SV_aCTLA4 virus vector treatment: (day −2/day −2); (day 6/day −2); (day 13/day −2) and (day 20/day −2). Each time point shows the average of tumor growth in 5 mice of each group. Day 20 was the last day on which bioluminescence was measured in the control (untreated) group (5 mice in the control (untreated)group) and in the SV_CTLA4-treated group (5 mice in the SV-CTLA4-treated group). FIG. 24C: Survival curves of mice in the untreated Control group (n=5) and mice in the SV_CTLA4 treated group (n=5).

FIGS. 25A and 25B present polynucleotide (SEQ ID NO: 12) and amino acid sequences (SEQ ID NO: 13) and schematic depictions of Sindbis virus vector containing a polynucleotide sequence encoding the survivin protein as described herein. FIG. 25A: Polynucleotide sequence (top) comprising survivin sequence cloned into the Sindbis pT7StuIR replicon plasmid. The mouse survivin sequence was derived from the GenBank protein sequence having Accession No. AAD34225. Nucleotides that encode the sequence were optimized for expression in mouse cells. FIG. 25B: Helper and Replicon DNA plasmids used to make the SV-Survivin vector for in vivo experiments as described in Example 10 herein.

FIG. 26A: Schematic in vivo experimental design: For mice that received treatment with the SV_Survivin vector, Sindbis vector treatment was administered 4 times a week for 4 weeks, at days 5, 6, 7, 8 (Week one); 12, 13, 14, 15 (week 2); 20, 21, 22, 23 (week 3); and 27, 28, 29, 30 (week 4) after animals were inoculated with tumor cells. FIG. 26B: Tumor growth curves of SV_Survivin treated and untreated (control) mice. Tumor growth curves are shown as fold changes relative to the bioluminescence in the first image taken of the same mouse: (day0/day0); (day 7/day 0); (day 14/day 0); (day 21/day 0) and (day 28/day 0). The first image was taken before first dose of the SV_Survivin vector in the same day, day 0. Each time point shows the average of tumor growth in 5 mice of each group. Day 14 was the last day on which bioluminescence was measured in the untreated (control) group (5 mice in control (untreated) group). Day 28 was the last day on which bioluminescence was measured in the SV_survivin vector-treated group (5 mice in the SV_Survivin-treated group). FIG. 26C: Survival curves of animals in the untreated Control group (n=5) and animals in the SV_Survivin treated group (n=5).

FIGS. 27A and 27B present polynucleotide sequences and amino acid sequences related to the PD-1 checkpoint protein. FIG. 27A presents the polynucleotide sequence (top) (SEQ ID NO: 14) and the encoded amino acid (aa) sequence (SEQ ID NO: 15) of PD-1 (Programmed cell death protein 1) precursor [*Homo sapiens*]. The PD-1 polynucleotide sequence was cloned into the T7StuI-R vector (Accession No. NP_005009 VERSION NP_005009.2). The elements delineated in the sequences and depicted from the 5' end of the sequences are as follows: The soluble PD-1 amino acid (aa) sequence (1-169 aa) is shown in gray; the Hinge region is shown by double underlining; the Linker sequence is shown in Italics; and the Ig CH3 domain is shown by single underlining. The CH3 and hinge domains are from human IgG1 (Accession: P01857.1). The Linker is synthetically produced. FIG. 27B shows an amino acid sequence comparison (alignment) of the human WT-PD-1 amino acid sequence (SEQ ID NO: 16) to PD-1 amino acid sequences of other species, namely, mouse (SEQ ID NO: 17) and monkey (SEQ ID NO: 18).

FIG. 28 presents Helper and Replicon DNA plasmids used to make the SV-PD-IWT vector for in vivo experiments as described herein.

DETAILED DESCRIPTION OF THE INVENTION

Figure 2A:
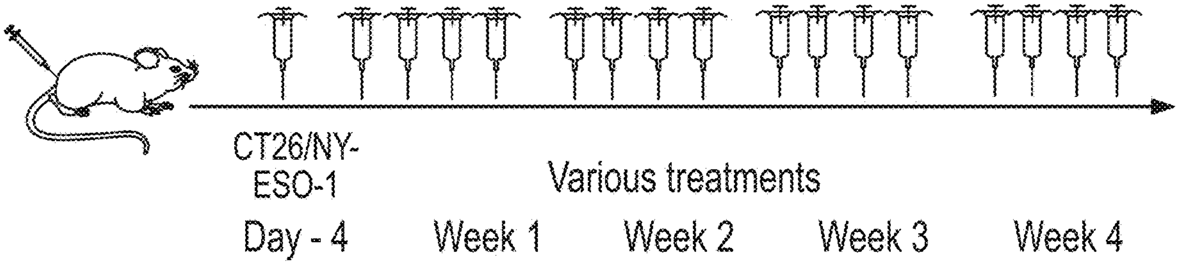
FIGS. 2A and 2B present a treatment protocol and a plot of tumor growth following treatment of mice bearing CT26-derived tumors with a Sindbis viral vector encoding multiple epitopes of tumor associated antigens.

Provided by the present invention are polynucleotides and viral vectors, particularly, alphavirus vectors, that encode multiple epitopes of one or more tumor associated antigens (TAAs) to induce a potent immune response in a subject against the multiple tumor associated antigens expressed by the subject's cancer or tumor, optimally in the context of HLA/MHC antigens. The polynucleotides and viral vectors as described also result in epitope spreading following administration, which serves to enhance the immune response against the multiple TAAs.

As reported in more detail below, the invention is based, at least in part, on the discovery that a Sindbis vector encoding multiple tumor associated antigens (e.g., NY-1 ESO, survivin, gp70) resulted in the long-term survival of tumor-bearing mice and to the generation of long-lasting $CD8^+$ T cells against multiple tumor antigens. Significantly, therapy with a Sindbis vector encoding multiple tumor associated antigens led to epitope spreading, providing a promising solution to the problem of tumor escape by tumor associated antigen loss or modification. As the gp70 is a murine retroviral glycoprotein, it is particularly useful for preclinical studies. Examples of glycoproteins that may similarly stimulate immune cells, but which derive or originate from a human virus (lentivirus), include, without limitation, the gp120 and gp41 envelope proteins of the human immunodeficiency virus (HIV), or fragments thereof.

The molecularly engineered viral vectors described herein provide an efficient and effective delivery system designed to harbor the genetic information of one or more tumor antigens (also called tumor associated antigens) as multiple selected epitopes of the tumor associated antigen, including neo-epitopes, and to initiate and perpetuate a specific immune response, which ultimately generates cytotoxic T cells (e.g., effector $CD8^+$ T cells) that are activated to specifically kill the cancer or tumor.

Provided by the present invention are polynucleotides and viral vectors, particularly, alphavirus vectors, that encode an immune checkpoint protein, or a portion thereof that binds to the cognate ligand of the checkpoint protein, which induce a potent immune response in a subject against the subject's cancer or tumor.

The present invention further provides a polynucleotide that encodes an alphavirus, lentivirus, or retrovirus protein or a fragment thereof, and an immune checkpoint molecule, or a cognate ligand binding portion or fragment thereof. In embodiments, the immune checkpoint protein molecule is, without limitation, PD-1. In a particular embodiment, the immune checkpoint protein molecule is PD-1 or the extracellular domain of PD-1. In an embodiment, the polynucleotide encodes an alphavirus (e.g., Sindbis virus protein or a fragment thereof) and an immune checkpoint molecule or a cognate ligand binding portion or fragment thereof. In an embodiment, the alphavirus is Sindbis virus, a Sindbis virus vector, or Sindbis viral particle. In a particular embodiment, the Sindbis virus vector contains a polynucleotide that encodes one or more immune checkpoint proteins, or a fragment or portion of the immune checkpoint protein that binds to its cognate ligand, for example and without limitation, the PD-1 immune checkpoint protein or a fragment or portion of PD-1 that binds to its cognate ligand PD-L1. In a particular embodiment, the Sindbis virus vector contains a polynucleotide that encodes the PD-1 immune checkpoint protein, or an extracellular domain of PD-1, that binds to its cognate ligand PD-L1.

In an embodiment, the checkpoint protein encoded by the Sindbis virus vector is in the form of a "minibody," as described herein, in which checkpoint protein or a portion of the checkpoint protein, e.g., the extracellular domain, is fused to portions of an immunoglobulin (Ig) molecule, thereby forming a fusion protein. In particular, checkpoint protein or a ligand binding portion of the checkpoint protein, e.g., the extracellular domain, is fused to an Ig hinge region, and an Ig heavy chain constant region domain, such as the CH1, CH2, or CH3 domain of an Ig heavy chain. In an embodiment, a spacer (or linker) sequence is inserted between the hinge region and the Ig heavy chain CH domain for flexibility. In an embodiment, the spacer (or linker) sequence is glycine-rich and is or comprises the sequence GGGSSGGGSGG (SEQ ID NO: 19). In an embodiment, the Ig is of the IgG, IgM, IgA, IgD, or IgE class. In an embodiment, the Ig is of the IgG class. In embodiments, the Ig is an IgG subclass selected from IgG1, IgG2a, IgG2b, or IgG4., IgM, IgA, IgD, or IgE type. In a specific embodiment, the Ig chain is the IgG1 heavy chain and the Ig constant region domain is the CH3 domain. In an embodiment, a glycine-rich spacer (or linker) sequence is inserted between the hinge region and the Ig heavy chain CH domain for flexibility. In an embodiment, the spacer (or linker) sequence is or comprises the sequence GGGSSGGGSGG (SEQ ID NO: 19). In embodiments of the foregoing, the checkpoint protein is PD-1, a cognate ligand binding portion thereof, or extracellular domain thereof. In a particular embodiment of the foregoing, the checkpoint protein is PD-1 or the extracellular domain of PD-1.

The invention is based, at least in part, on the discovery that a Sindbis virus vector encoding an immune checkpoint protein, such as the extracellular domain of a checkpoint protein, e.g., PD-1, resulted in a significant decrease in tumor growth and the long-term survival of tumor-bearing mice following treatment of the animals with a Sindbis virus vector encoding the checkpoint protein or a ligand binding portion thereof. In particular, treatment of animals with a Sindbis virus vector encoding the extracellular portion of wild-type PD-1 checkpoint protein significantly reduced tumor growth in tumored animals relative to control animals for over 2 weeks, e.g., at least 20 days. Treatment of tumored animals with this vector also resulted in a greater survival of animals following implantation of tumors, for example, by day 40 after tumor implantation, percent survival of tumored animals was approximately 3-times greater for animals that had been treated with the Sindbis virus vector encoding the PD-1 checkoint protein compared with control animals.

Surprisingly and unexpectedly, treatment of tumored animals with the Sindbis virus vector encoding the checkoint protein (e.g., WT PD-1), as exemplified herein, resulted in a significant reduction in tumor growth compared with tumored animals that had been treated with an anti-PD-1 antibody, e.g., a more conventional checkpoint protein inhibitor treatment, and also compared with untreated control animals. In addition, and also surprisingly, a significantly higher percentage of tumored animals survived following treatment with the Sindbis virus vector encoding the checkoint protein (e.g., WT PD-1) compared with tumored animals that were treated with checkpoint inhibitor treatment with anti-PD-1 antibody.

Without wishing or intending to be bound by theory, following the administration of a Sindbis virus vector encoding an immune checkpoint protein, such as, e.g., PD-1, to a subject, large quantities of the checkpoint protein are expressed by the virus vector and soluble checkpoint protein is secreted systemically. Such large quantities of the checkpoint protein then circulate in a treated subject and are available to bind the cognate ligand, such as PD-L1, on tumor cells. The large amount of the checkpoint protein produced following administration of the Sindbis viral vector may thus directly compete with the binding of tumor cell-expressed cognate ligand (e.g., PD-L1) to T-cell expressed checkpoint protein (e.g., PD-1), thereby effectively blocking the binding of T-cell-expressed checkpoint protein to the tumor cell-expressed, interacting ligand. In such a system, the checkpoint protein encoded by the Sindbis virus vector, expressed in and produced from infected cells, may "flood" the tumor environment with soluble checkpoint protein that binds to the interacting ligand on tumor cells. Because of the occupation of the tumor-cell expressed ligand (e.g., cognate receptor protein, such as PD-L1) by the circulating checkpoint protein (e.g., PD-1), the tumor cell is unable to bind to cytotoxic T cell-expressed checkpoint protein. Consequently, cytotoxic T cells expressing checkpoint protein (e.g., PD-1) are not bound to and do not interact with cognate ligand on tumor cells (e.g., PD-L1), and the T cell cytotoxic activity is maintained and directed against the tumor cells, which are killed. Administration regimens for the checkpoint protein encoding viral vectors as described herein can be determined by a medical practitioner or clinician having skill in the art.

PD-1, the Programmed Death 1 (PD-1) protein, is a key immune checkpoint protein (receptor protein) that is expressed by activated T cells and mediates immunosuppression. PD-1 functions mainly in peripheral tissues where T cells may encounter the immunosuppressive PD-1 ligands PD-L1 (B7-H1) and PD-L2 that are expressed by tumor cells, stromal cells, or both. PD-1 produced in significant quantity by the Sindbis virus vector described herein serves to bind large quantities of PD-L1 on tumor cells, thus effectively inhibiting the normal interaction between cell-expressed PD-1 and PD-L1. Consequently, T-cell responses could be enhanced in vitro and could also mediate antitumor activity. Blockade of inhibitory receptors such as PD-L1 on tumors by the relatively large-scale, in vivo availability of Sindbis virus vector-produced, soluble checkpoint protein molecules encoded and expressed by the polynucleotides, Sindbis virus vectors and virus particles described herein offer a beneficial approach to prevent the inhibition of an anti-tumor immune response by T-cells and to augment the anti-tumor activity of T-cells whose inhibitory receptors are not blocked by binding to cognate ligand/receptors on tumor cells.

The soluble checkpoint proteins expressed by the viral vectors as described herein may further act as decoys that bind ligand/receptors on tumor cells and block binding of the tumor cell ligand/receptor to the same checkpoint proteins that are expressed on the surfaces of effector T cells, such as cytotoxic T cells ($CD8^+$ T cells). Such binding of the Sindbis virus vector-expressed checkpoint protein (or ligand binding portion thereof) to the cognate receptor protein expressed on tumor cells prevents a tumor cell from binding to the cytotoxic T cell that expresses the checkpoint protein, thereby preventing T cell anergy, which allows the cytotoxic T cell to kill the tumor.

In an embodiment, the immune response involves the activity of cytotoxic T cells which express checkpoint proteins on their surface, but are not made anergic by binding to cognate ligand expressed by tumor cells. In this embodiment, the checkpoint protein produced following administration of the Sindbis virus vector encoding the checkpoint protein binds to tumor cell-expressed ligand and prevents the tumor ligand from binding to and inactivating the anti-tumor activity that specifically kills the cancer or tumor cells. In an embodiment, the SV-encoded checkpoint protein-Ig fusion proteins as described and exemplified herein e.g., SV_PD-1, may facilitate binding to cells through the CH3 portion of the fusion protein, as well as trigger antibody dependent cell cytotoxicity (ADCC). Such checkpoint protein-Ig fusion proteins as described and exemplified herein may also be more stably expressed and have a longer half-life in vivo due to the Ig region components in the fusion protein.

The molecularly engineered viral vectors described herein provide an efficient and effective delivery system designed to harbor the genetic information of one or more checkpoint protein molecules and to promote a specific immune response, which ultimately allows cytotoxic T cells (e.g., effector $CD8^+$ T cells) to remain activated to specifically kill the cancer or tumor.

In an embodiment, a wild-type (non-mutated) checkpoint protein is encoded by the Sindbis virus vector. In an embodiment, the wild-type checkpoint protein may bind more effectively to its cognate ligand than a checkpoint protein that has been genetically mutated or altered. In a particular embodiment, a wild-type PD-1 checkpoint protein is encoded by the Sindbis virus vector.

The invention generally features virus vector-based compositions and methods that are useful for treating cancer and tumorigenesis and/or the symptoms thereof in a subject in need thereof, such as a patient having cancer. Methods utilizing viral vectors, which are designed to harbor polynucleotides encoding multiple, e.g., two or more, epitopes of one or more tumor associated antigens (TAAs) as described herein, involve administering a therapeutically effective amount of the viral vector, a viral particle, or a pharmaceutical composition comprising the viral vector or particle to a subject (e.g., a mammal such as a human), in particular, to elicit a T-cell-mediated immune response to the subject's cancer or tumor that expresses the tumor associated antigens and epitopes thereof.

The viral vectors described herein are designed to encode and express multiple epitopes, e.g., amino acid sequences, of tumor associated antigens that are recognized by T cell receptors, i.e., "T cell epitopes." The expression of multi-epitopes by the viral vectors of the invention can increase the likelihood of triggering an immune response to a variety of tumor antigens and also embraces treatment of subjects having different HLA haplotypes. Such viral vector products may also be designed to contain and express epitopes of tumor associated antigens that have optimal affinity for T cell receptors. Because the polynucleotides, viral vectors and viral particles described herein are designed to carry multiple epitopes of one or more than one tumor associated antigen(s), as well as immunostimulatory and immunomodulatory molecules, these products are capable of targeting multiple cancer and tumor types.

In an embodiment, particularly for the treatment and therapy of cancers, the polynucleotides, viral vectors and viral particles described herein may include one or more checkpoint inhibitor molecules, for example, antibodies directed against cell-expressed checkpoint proteins as described above, or fragments thereof that bind to the checkpoint proteins. As appreciated by the skilled practitioner in the art, human cancers, e.g., without limitation, breast cancers, melanomas, colon cancers and lung cancers, harbor numerous genetic and epigenetic alterations that generate neoantigens, which are potentially recognizable by the immune system. (S. L. Topalian et al., 2012, *N. Engl. J Med.,* 366:2443-2454). While an endogenous immune response to cancer is sometimes observed in preclinical models and patients, this response is ineffective, because tumors develop multiple resistance mechanisms, including local immune suppression, induction of tolerance, and systemic dysfunction in T-cell signaling. In addition, tumors are capable of exploiting several distinct pathways to evade immune destruction. Of particular importance in efforts to treat cancers and tumors is the ability of tumor cells to actively evade endogenous "immune checkpoints" that normally terminate immune responses after antigen activation. These observations have led to the development of immunotherapeutic approaches for cancer, including immune-checkpoint-pathway inhibitors such anti-checkpoint protein antibodies, e.g., anti-CTLA-4 antibody, anti-PD-1 antibody, or anti-PD-L1 antibody for the treatment of patients with cancers and tumors. As but one example, the anti-CTLA-4 antibody ipilimumab has undergone studies as a checkpoint inhibitor for treating advanced melanoma.

In an embodiment, one or more checkpoint protein inhibitors may be administered separately from and in conjunction with the polynucleotides, virus vectors, or viral particles and compositions thereof as described herein. For example, antibody checkpoint protein inhibitors, or binding fragments thereof, may be co-administered to a subject either at the same time as, or at a different at time from, the administration of the polynucleotides, virus vectors, or virus particles, or compositions thereof as described herein. Administration regimens can be determined by a medical practitioner or clinician having skill in the art.

Thus, viral vector products that encode and express multiple epitopes of tumor associated antigens according to the invention provide an approach for treating cancer and tumors that may mimic or augment whole-organism-induced immunity and prevent potential immunopathogenic or suppressive responses, in which the multiple epitopes of one or more tumor associated antigens are recognized by effector T cells to generate a potent immune response in a subject undergoing treatment. The viral vectors as described herein contain multiple epitopes of tumor associated antigens that are designed to be recognized by effector T cells, e.g., $CD4^+$ T cells, $CD8^+$ T cells, or both. The viral vectors can simultaneously induce responses against different cytotoxic lymphocyte (CTL) determinants, thereby optimizing and maximizing immunogenicity in vivo by inducing a $CD8^+$ CTL response of the breadth and strength needed to attack and kill cancer and tumor cells and protect against cancer growth and recurrence.

In accordance with the present invention, the design of polynucleotides, viral vectors, viral particles and cells and pharmaceutical compositions containing these products, which encode and express multiple epitopes, e.g., two or more epitopes, of one or more tumor associated antigens, provides biological products that can be used to expand the activated T cell repertoire. Such activated T cells are thus capable of reacting against (e.g., killing) cancer and tumor cells that express the tumor associated antigens and their associated epitopes, and thus broaden the therapeutic applicability and efficacy of the viral vectors described herein, e.g., alphavirus (e.g., Sindbis virus (SV)), lentivirus, retrovirus, or pseudotyped vectors, constructed to contain a polynucleotide encoding two or more epitopes of one or more tumor associated antigens. In an embodiment, each of the tumor associated antigen epitopes is separated by a processing site, such as an enzyme cleavage site, e.g., a furin cleavage site, for reproducible processing of the expressed epitopes.

According to the present invention, after administration to a subject having a cancer or tumor, the viral vectors and viral particles that encode multiple, e.g., two or more, epitopes derived from one or more tumor-associated antigens (TAAs), or pharmaceutical compositions thereof, deliver the multiple epitopes to cells in the form of RNA. The RNA is processed intracellularly into protein and protein fragments, e.g., epitope peptides, which are optimally presented by cells of the immune system, e.g., macrophages and dendritic cells, in the context of HLA/MHC antigens, to precursors of $CD8^+$ T cells. Such antigen presentation by the accessory cells of the immune system activates the $CD8^+$ T cells, which proliferate so as to produce large numbers of cytotoxic T cells that kill cancer and tumor cells that express the specific epitopes of the tumor associated antigens, including neo-antigens. Thus, the epitopes encoded by the polynucleotides and viral vectors described herein are optimally provided to elicit a heightened immune response, particularly a T-cell mediated immune response, specifically directed against a cancer cell or a solid tumor expressing one or more of the corresponding tumor associated antigens. In some embodiments, the polynucleotide contained in a viral vector of the invention is termed a minigene or a polynucleotide construct. In some embodiments, the polynucleotide, viral vector, or pharmaceutical composition of the invention may include one or more, preferably two or more, (e.g., 2, 3, 4, 5, 6, 7, 8, 9, 10, 15, 20, 25, 30, 35, 40, 45, 50, 55, 60, 65, 70, 75, 80, 85, 90, or more) epitopes derived from the same tumor associated antigen. For instance, a polynucleotide, viral vector, or pharmaceutical composition of the invention may include one or more copies of the same epitope. In some embodiments, the polynucleotide, viral vector, or pharmaceutical composition of the invention may include one or more, preferably two or more (e.g., 2, 3, 4, 5, 6, 7, 8, 9, 10, 15, 20, 25, 30, 35, 40, 45, 50, 55, 60, 65, 70, 75, 80, 85, 90, or more) epitopes derived from different tumor associated antigens.

Tumor Associated Antigens (TAAs)

The tumor associated antigens from which the epitopes expressed by polynucleotides and viral vectors of the invention are derived may be associated with, or expressed by, e.g., either extracellularly or intracellularly, a cancer or tumor, such as, without limitation, a/an ovarian cancer, breast cancer, testicular cancer, pancreatic cancer, liver cancer, colorectal cancer, thyroid cancer, lung cancer, prostate cancer, kidney cancer, melanoma, squamous cell carcinoma, chronic myeloid leukemia, acute lymphoblastic leukemia, acute myelogenous leukemia, chronic lymphocytic leukemia, promyelocytic leukemia, multiple myeloma, B-cell lymphoma, bladder carcinoma, head and neck cancer, esophageal cancer, brain cancer, pharynx cancer, tongue cancer, synovial cell carcinoma, neuroblastoma, uterine cancer, fibrosarcoma, myxosarcoma, liposarcoma, chondrosarcoma, osteogenic sarcoma, chordoma, angiosarcoma, endotheliosarcoma. lymphangiosarcoma, synovioma, mesothelioma, Ewing's tumor, leiomyosarcoma, rhabdomyosarcoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, small cell lung carcinoma, epithelial carcinoma, glioma, astrocytoma, medulloblastoma, craniopharyngioma, ependymoma, pinealoma. Hemangioblastoma, acoustic neuroma, oligodendroglioma, meningioma, neuroglioma, and retinoblastoma. Polynucleotides (minigenes), viral vectors and pharmaceutical compositions of the invention may thus be used to treat a subject, such as a human patient, suffering from one or more of the above conditions.

In an embodiment, two or more different epitopes of one or more tumor associated antigens may be associated with the same cancer or tumor type. In another embodiment, two or more epitopes may be associated with tumor associated antigens of different cancer types, e.g., two or more cancer types. For instance, in some embodiments, a polynucleotide, viral vector, or pharmaceutical composition of the invention includes one or more epitopes of a tumor associated antigen expressed by one type of cancer or tumor cell, e.g., an ovarian cancer cell, and one or more epitopes derived from a tumor associated antigen expressed by another type of cancer or tumor cell, e.g., a breast cancer cell. In some embodiments, a polynucleotide, viral vector, or pharmaceutical composition of the invention includes one or more epitopes, or two or more epitopes, of a tumor associated antigen expressed on the surface of one or more cancer types (e.g., 1, 2, 3, 4, 5, 6, 7, 8, 9, 10, 11, 12, 13, 14, 15, 16, 19, 18, 19, 20, 30, 40, 50, or more cancer or tumor types). In other embodiments, the one or more epitopes, or two or more epitopes, of a tumor associated antigen are expressed intracellularly in one or more cancer or tumor types.

In some embodiments, a polynucleotide, viral vector, or pharmaceutical composition of the invention includes two or more epitopes of one or more tumor associated antigens associated with the above cancer types. Tables 1-28, below, provide a non-limiting list of various tumor associated antigens and epitopes thereof that may be encoded by a polynucleotide, viral vector, or viral particle as described herein, or incorporated into a composition of the invention. Tumor associated antigens and their epitopes encompass human tumor associated antigens and epitopes thereof and human orthologs of tumor associated antigens and epitopes thereof. For instance, in some embodiments, a polynucleotide, viral vector, or pharmaceutical composition of the invention includes one or more, or two or more (e.g., 2, 3, 4, 5, 6, 7, 8, 9, 10, 15, 20, 25, 30, 35, 40, 45, 50, 55, 60, 65, 70, 75, 80, 85, 90, or more) epitopes of one or more of the tumor associated antigens listed in any one of Tables 1-28. In some embodiments, a polynucleotide, viral vector, or pharmaceutical composition of the invention includes one or more, or two or more, (e.g., 2, 3, 4, 5, 6, 7, 8, 9, 10, 15, 20, 25, 30, 35, 40, 45, 50, 55, 60, 65, 70, 75, 80, 85, 90, or more) of the amino acid sequences listed in any one of Tables 1-28.

In an embodiment, each of the epitopes of the tumor associated antigens encoded by a polynucleotide, viral vector, or viral particle of the invention is separated by an enzyme cleavage (or processing) site, for example, a furin cleavage site, or other enzyme cleavage or processing site as described herein. Non-limiting examples of additional processing enzymes for use in cleaving the epitope peptides encoded by the polynucleotides and viral vectors according to the present invention include serine protease, signalase, furin protease, and furin related endopeptidases, such as PC1/2, PC4/5, PACE4, and PC7. These enzymes recognize the processing signal (R/K)$X_n$(R/K), in which $X_n$ designates a spacer of any 0-6 amino acids, (SEQ ID NO: 6), (Seidah and Prat, 2012*, Nature Reviews Drug Discovery,* 11:367-383). The inclusion of an enzyme cleavage site that separates each of the encoded epitopes in the polynucleotide, viral vector, or viral particle as described herein, advantageously allows for reproducibility in processing the expressed epitopes following administration, which provides a safer product for use in treating subjects. For example, having the polynucleotide according to the invention contain enzyme cleavage sites interspersed between each of the nucleic acid sequences encoding the tumor associated antigen epitopes ensures that the processing and production of the epitopes is uniform, especially in cells in vivo, and that the designed polypeptide operates reproducibly to generate the appropriate immune response (e.g., a T cell response) directed against the encoded target antigens. In an embodiment, the tumor associated antigen epitopes are selected based on their binding to MHC/HLA molecules, e.g., for optimal presentation to effector T cells, thus providing reproducibility that ensures an optimal immune response, as described herein.

In other embodiments, the epitopes of the one or more tumor associated antigens are each separated by one enzyme cleavage site. In some embodiments, the epitopes are not separated by enzyme cleavage sites and the encoded sequences are cleaved intracellularly following delivery to cells by the viral vectors described herein.

TABLE 1

| Ovarian cancer | | | |
|---|---|---|---|
| No. | Tumor-associated antigen | Immunogenic epitopes | Sources |
| 1 | Kallikrein 4 | FLGYLILGV (SEQ ID NO: 22); SVSESDTIRSISIAS (SEQ ID NO: 23); LLANGRMPTVLQCVN (SEQ ID NO: 24); and RMPTVLQCVNVSVVS (SEQ ID NO: 25) | Wilkinson et al. Cancer Immunol. Immunother. 61(2):169-79 (2012). Hural et al. J. Immunol. 169(1):557-65 (2002). |
| 2 | PBF | CTACRWKKACQR (SEQ ID NO: 26) | Tsukahara et al. Cancer Res. 64(15):5442-8 (2004). |
| 3 | PRAME | VLDGLDVLL (SEQ ID NO: 27); SLYSFPEPEA (SEQ ID NO: 28); | Kessler et al. J. Exp. Med. 193(1):73-88 (2001). |

TABLE 1-continued

| No. | Tumor-associated antigen | Immunogenic epitopes | Sources |
|---|---|---|---|
| | | Ovarian cancer | |
| | | ALYVDSLFFL (SEQ ID NO: 29); SLLQHLIGL (SEQ ID NO: 30); and LYVDSLFFL (SEQ ID NO: 31) | Ikeda et al. Immunity 6(2)1 99-208 (1997). |
| 4 | WT1 | TSEKRPFMCAY (SEQ ID NO: 32); CMTWNQMNL (SEQ ID NO: 33); LSHLQMHSRKH (SEQ ID NO: 34); and KRYFKLSHLQMHSRKH (SEQ ID NO: 35) | Asemissen et al. Clin. Cancer Res. 12(24):7476-82 (2006) Ohminami et al. Blood. 95(1):286-93 (2000). Guo et al. Blood. 106(4)1 415-8 (2005). Lin et al. J. Immunother. 36(3)159-70 (2013). Fujiki et al. J. Immunother. 30(3):282-93 (2007). |
| 5 | HSDL1 | CYMEAVAL (SEQ ID NO: 36) | Wick et al. Clin. Cancer Res. 20(5):1125-34 (2014). |
| 6 | Mesothelin | SLLFLLFSL (SEQ ID NO: 37); VLPLTVAEV (SEQ ID NO: 38); ALQGGGPPY (SEQ ID NO: 39); LYPKARLAF (SEQ ID NO: 40); AFLPWHRLF (SEQ ID NO: 41); | Hassan et al. Appl. Immunohistochem. Mol. Morphol. 13(3):243-7 (2005). Thomas et al J Exp Med. 2004 Aug 2; 200(3): 297-306. |
| 7 | NY-ESO-1 | HLA-A2-restricted peptide p157-165 (SLLMWITQC) (SEQ ID NO: 42), HLA-Cw3-restricted p92-100 (LAMP-FATPM) (SEQ ID NO: 43) and HLA-Cw6-restricted p80-88 (ARGPESRLL) (SEQ ID NO: 44) MLMAQEALAFL (SEQ ID NO: 45) YLAMPFATPME (SEQ ID NO: 46) ASGPGGGAPR (SEQ ID NO: 47) LAAQERRVPR (SEQ ID NO: 48) TVSGNILTIR (SEQ ID NO: 49) APRGPHGGAASGL (SEQ ID NO: 50) MPFATPMEAEL (SEQ ID NO: 51) KEFTVSGNILTI (SEQ ID NO: 52) MPFATPMEA (SEQ ID NO: 53) FATPMEAEL (SEQ ID NO: 54) FATPMEAELAR (SEQ ID NO: 55) SLLMWITQCFLPVF (SEQ ID NO: 56) LLEFYLAMPFATPMEAEL-ARRSLAQ (SEQ ID NO: 57) EFYLAMPFATPM (SEQ ID NO: 58) PGVLLKEFTVSGNILTIRL-TAADHR (SEQ ID NO: 59) RLLEFYLAMPFA (SEQ ID NO: 60) QGAMLAAQERRVPRAAE-VPR (SEQ ID NO: 61) PFATPMEAELARR (SEQ ID NO: 62) PGVLLKEFTVSGNILTIRLT (SEQ ID NO: 63) VLLKEFTVSG (SEQ ID NO: 64) AADHRQLQLSISSCLQQL (SEQ ID NO: 65) LKEFTVSGNILTIRL (SEQ ID NO: 66) KEFTVSGNILT (SEQ ID NO: 67) LLEFYLAMPFATPM (SEQ ID NO: 68) AGATGGRGPRGAGA (SEQ ID NO: 69) | Jager et al. Proc. Natl. Acad. Scie. U.S.A. 103(39): 14453-8 (2006). Gnjatic et al. PNAS September 26, 2000 vol. 97 no. 20 p. 10919 Jager et al. J Exp Med. 187(2):265-70 (1998). Chen et al. J Immunol. 165(2):948-55 (2000). Valmori et al. Cancer Res. 60(16):4499-506 (2000). Aarnoudse et al. Int J Cancer. 82(3):442-8 (1999). Eikawa et al. Int J Cancer. 132(2):345-54 (2013). Wang et al. J Immunol. 161(7):3598-606 (1998). Matsuzaki et al. Cancer Immunol Immunother. 57(8)1185-95 (2008). Ebert et al. Cancer Res. 69(3):1046-54 (2009). Eikawa et al. Int J Cancer. 132(2):345-54 (2013). Knights et al. Cancer Immunol Immunother. 58(3):325-38 (2009). Jager et al. Cancer Immun. 2:12 (2002). Zeng et al. Proc Natl Acad Sci U S A. 98(7):3964-9 (2001). Mandic et al. J Immunol. 174(3):1751-9 (2005). Chen et al. Proc Natl Aced Sci U S A. 101(25):9363-8 (2004). Ayyoub et al. Clin Cancer Res. 16(18):4607-15 (2010). Sieger et al. J Immunol. 172(8):5095-102 (2004). Mizote et al. Vaccine. 28(32):5338-46 (2010). Jager et al. J Exp Med. 191(4):625-30 (2000). Zarour et al. Cancer Res. 60(17):4946-52 (2000). Zeng et al. J Immunol. 165(2):1153-9 (2000). Bioley et al. Clin Cancer Res. 15(13):4467-74 (2009). |

TABLE 1-continued

| Ovarian cancer | | | |
|---|---|---|---|
| No. | Tumor-associated antigen | Immunogenic epitopes | Sources |
| | | | Zarour et al. Cancer Res. 62(1):213-8 (2002).<br>Hasegawa et al. Clin Cancer Res. 12(6):1921-7 (2006). |
| 8 | CEA | TYYRPGVNLSLSC (SEQ ID NO: 70)<br>EIIYPNASLLIQN (SEQ ID NO: 71)<br>YACFVSNLATGRNNS (SEQ ID NO: 72)<br>LWWVNNQSLPVSP (SEQ ID NO: 73)<br>NSIVKSITVSASG (SEQ ID NO: 74)<br>KTWGQYWQV (SEQ ID NO: 75)<br>(A)MLGTHTMEV (SEQ ID NO: 76)<br>ITDQVPFSV (SEQ ID NO: 77)<br>YLEPGPVTA (SEQ ID NO: 78)<br>LLDGTATLRL (SEQ ID NO: 79)<br>VLYRYGSFSV (SEQ ID NO: 80)<br>SLADTNSLAV (SEQ ID NO: 81)<br>RLMKQDFSV (SEQ ID NO: 82)<br>RLPRIFCSC (SEQ ID NO: 83)<br>LIYRRRLMK (SEQ ID NO: 84)<br>ALLAVGATK (SEQ ID NO: 85)<br>IALNFPGSQK (SEQ ID NO: 86)<br>RSYVPLAHR (SEQ ID NO: 87) | Galanis et al. Cancer Res. 70(3):875-82 (2010).<br>Bast et al. Am. J. Obstet. Gynecol. 149(5)553-9 (1984).<br>Crosti et al. J Immunol. 176(8):5093-9 (2006).<br>Kobayashi et al. Clin Cancer Res. 8(10):3219-25 (2002).<br>Campi et al. Cancer Res. 63(23):8481-6 (2003).<br>Bakker et al. Int J Cancer. 62(1):97-102 (1995).<br>Tsai et al. J Immunol. 158(4):1796-802 (1997).<br>Kawakami et al. J Immunol. 154(8):3961-8 (1995).<br>Cox et al. Science. 264(5159):716-9 (1994).<br>Kawakami et al. J Immunol. 154(8):3961-8 (1995).<br>Kawakami et al. J Immunol. 161(12):6985-92 (1998).<br>Skipper et al. J Immunol. 157(11):5027-33 (1996).<br>Michaux et al. J Immunol. 192(4):1962-71(2014). |
| 9 | p53 | VVPCEPPEV (SEQ ID NO: 88) | Hung et al. Immunol. Rev. 222:43-69 (2008). |
| 10 | Her2/Neu | HLYQGCQVV (SEQ ID NO: 89)<br>YLVPQQGFFC (SEQ ID NO: 90)<br>PLQPEQLQV (SEQ ID NO: 91)<br>TLEEITGYL (SEQ ID NO: 92)<br>ALIHHNTHL (SEQ ID NO: 93)<br>PLTSIISAV (SEQ ID NO: 94)<br>VLRENTSPK (SEQ ID NO: 95)<br>TYLPTNASL (SEQ ID NO: 96) | Nakatsuka et al. Mod. Pathol. 19(6):804-814 (2006).<br>Pils et al. Br. J. Cancer 96(3):485-91 (2007).<br>Scardino et al. EurJ Immunol. 31(11):3261-70 (2001).<br>Scardino et al. J Immunol. 168(11):5900-6 (2002).<br>Kawashima et al. Cancer Res. 59(2):431-5 (1999).<br>Okugawa et al. EurJ Immunol. 30(11):3338-46 (2000). |
| 11 | EpCAM | RYQLDPKFI (SEQ ID NO: 97) | Spizzo et al. Gynecol. Oncol. 103(2):483-8 (2006).<br>Tajima et al. Tissue Antigens. 64(6):650-9 (2004). |
| 12 | CA125 | ILFTINFTI (SEQ ID NO: 98)<br>VLFTINFTI (SEQ ID NO: 99)<br>TLNFTITNL (SEQ ID NO: 100)<br>VLQGLLKPL (SEQ ID NO: 101)<br>VLQGLLRPV (SEQ ID NO: 102)<br>RLDPKSPGV (SEQ ID NO: 103)<br>QLYWELSKL (SEQ ID NO: 104)<br>KLTRGIVEL (SEQ ID NO: 105)<br>QLTNGITEL (SEQ ID NO: 106)<br>QLTHNITEL (SEQ ID NO: 107)<br>TLDRNSLYV (SEQ ID NO: 108) | Bast et al. Cancer 116(12):2850-2853 (2010). |
| 13 | Folate receptor α | FLLSLALML (SEQ ID NO: 109)<br>NLGPWIQQV (SEQ ID NO: 110) | Bagnoli et al. Gynecol. Oncol. 88:S140-4 (2003).<br>Pampeno et al. (2016) High-ranking In Silico epitopes by 3 algorithms: BISMAS, IEDB, RANKPEP unpublished |
| 14 | Sperm protein 17 | ILDSSEEDK (SEQ ID NO: 111) | Chiriva-Inernati et al. J. Immunother. 31(8):693-703 (2008). |

TABLE 1-continued

| Ovarian cancer | | | |
|---|---|---|---|
| No. | Tumor-associated antigen | Immunogenic epitopes | Sources |
| 15 | TADG-12 | YLPKSVVTIQV (SEQ ID NO: 112)<br>WIHEQMERDLKT (SEQ ID NO: 113) | Bellone et al. Cancer 115(4):800-11 (2009).<br>Underwood et al. BBA Mol. Basis of Disease. 1502(3):337-350 (2000). |
| 16 | MUC-16 | ILFTINFTI (SEQ ID NO: 114)<br>VLFTINFTI (SEQ ID NO: 115)<br>TLNFTITNL (SEQ ID NO: 116)<br>VLQGLLKPL (SEQ ID NO: 117)<br>VLQGLLRPV (SEQ ID NO: 118)<br>RLDPKSPGV (SEQ ID NO: 119)<br>QLYWELSKL (SEQ ID NO: 120)<br>KLTRGIVEL (SEQ ID NO: 121)<br>QLTNGITEL (SEQ ID NO: 122)<br>QLTHNITEL (SEQ ID NO: 123)<br>TLDRNSLYV (SEQ ID NO: 124) | Chekmasova et al. Clin. Cancer Res. 16(14):3594-606 (2010). |
| 17 | L1CAM | LLANAYIYV (SEQ ID NO: 125)<br>YLLCKAFGA (SEQ ID NO: 126)<br>KLSPYVHYT (SEQ ID NO: 127) | Hong et al. J. Immunother. 37(2):93-104 (2014).<br>Pampeno et al. (2016) High-ranking In Silico epitopes by 3 algorithms: BISMAS, IEDB, RANKPEP unpublished |
| 18 | Mannan-MUC-1 | PDTRPAPGSTAPPAHGVTSA (SEQ ID NO: 128)<br>STAPPVHNV (SEQ ID NO: 129)<br>LLLLTVLTV (SEQ ID NO: 130)<br>PGSTAPPAHGVT (SEQ ID NO: 131) | Loveland et al. Clin. Cancer Res. 12(3 Pt 1):869-77 (2006).<br>Godelaine et al. Cancer Immunol Immunother. 56(6)753-9 (2007).<br>Ma et al. Int J Cancer. 129(10):2427-34 (2011).<br>Wen et al. Cancer Sci. 102(8)1 455-61 (2011).<br>Jerome et al. J Immunol. 151(3):1654-62 (1993).<br>Brossart et al. Blood. 93(12):4309-17 (1999).<br>Hiltbold et al. Cancer Res. 58(22):5066-70 (1998). |
| 19 | HERV-K-MEL | MLAVISCAV (SEQ ID NO: 132) | Schiavetti et al. Cancer Res. 62(19):5510-6 (2002). |
| 20 | KK-LC-1 | RQKRILVNL (SEQ ID NO: 133) | Fukuyama et al. Cancer Res. 66(9):4922-8 (2006). |
| 21 | KM-HN-1 | NYNNFYRFL (SEQ ID NO: 134)<br>EYSKECLKEF (SEQ ID NO: 135)<br>EYLSLSDKI (SEQ ID NO: 136) | Fukuyama et al. Cancer Res. 66(9):4922-8 (2006).<br>Monji et al. Clin Cancer Res. 10(19 Pt 1): 6047-57 (2004). |
| 22 | LAGE-1 | MLMAQEALAFL (SEQ ID NO: 137)<br>SLLMWITQC (SEQ ID NO: 138)<br>LAAQERRVPR (SEQ ID NO: 139)<br>ELVRRILSR (SEQ ID NO: 140)<br>APRGVRMAV (SEQ ID NO: 141)<br>SLLMWITQCFLPVF (SEQ ID NO: 142)<br>QGAMLAAQERRVPRAAEVP-R (SEQ ID NO: 143)<br>AADHRQLQLSISSCLQQL (SEQ ID NO: 144)<br>CLSRRPWKRSWSAGSCPG-MPHL (SEQ ID NO: 145)<br>ILSRDAAPLPRPG (SEQ ID NO: 146)<br>AGATGGRGPRGAGA (SEQ ID NO: 147) | Aarnoudse et al. Int J Cancer. 82(3):442-8 (1999).<br>Rimoldi et al. J Immunol. 165(12):7253-61 (2000).<br>Wang et al. J Immunol. 161(7):3598-606 (1998).<br>Sun et al. Cancer Immunol Immunother. 55(6):644-52 (2006).<br>Sieger et al. Cancer Gene Ther. 11(3):227-36 (2004).<br>Zeng et al. Proc Natl Acad Sci U S A. 98(7):3964-9 (2001).<br>Sieger et al. J Immunol. 172(8):5095-102 (2004).<br>Jager et al. J Exp Med. 191(4):625-30 (2000).<br>Sieger et al. J Immunol. 170(3):1490-7 (2003).<br>Wang et al. Immunity. 20(1):107-18 (2004).<br>Hasegawa et al. Clin Cancer Res. 12(6):1921-7 (2006). |
| 23 | MAGE-A4 | EVDPASNTY (SEQ ID NO: 148)<br>GVYDGREHTV (SEQ ID NO: 149) | Kobayashi et al. Tissue Antigens. 62(5):426-32 (2003). |

TABLE 1-continued

| Ovarian cancer | | | |
|---|---|---|---|
| No. | Tumor-associated antigen | Immunogenic epitopes | Sources |
| | | NYKRCFPVI (SEQ ID NO: 150)<br>SESLKMIF (SEQ ID NO: 151) | Duffour et al. EurJ Immunol. 29(10):3329-37 (1999).<br>Miyahara et al. Clin Cancer Res. 11(15):5581-9 (2005).<br>Ottaviani et al. Cancer Immunol Immunother. 55(7):867-72 (2006)<br>Zhang et al. Tissue Antigens. 60(5):365-71(2002). |
| 24 | Sp17 | ILDSSEEDK (SEQ ID NO: 152) | Chiriva-Internati et al. Int J Cancer. 107(5):863-5 (2003). |
| 25 | SSX-4 | INKTSGPKRGKHAVVTHRLRE (SEQ ID NO: 153)<br>YFSKKEWEKMKSSEKIVYVY (SEQ ID NO: 154)<br>MKLNYEVMTKLGFKVTLPPF (SEQ ID NO: 155)<br>KHAVVTHRLRERKQLVVYEEI (SEQ ID NO: 156)<br>LGFKVTLPPFMRSKRAADFH (SEQ ID NO: 157)<br>KSSEKIVYVYMKLNYEVMTK (SEQ ID NO: 158) | Ayyoub et al. Clin Immunol. 114(1):70-8 (2005).<br>Valmori et al. Clin Cancer Res. 12(2):398-404 (2006). |
| 26 | TAG-1 | SLGWLFLLL (SEQ ID NO: 159)<br>LSRLSNRLL (SEQ ID NO: 160) | Adair et al. J Immunother. 31(1):7-17 (2008). |
| 27 | TAG-2 | LSRLSNRLL (SEQ ID NO: 161) | Adair et al. J Immunother. 31(1):7-17 (2008). |

TABLE 2

| Breast cancer | | | |
|---|---|---|---|
| No. | Tumor-associated antigen | Immunogenic epitopes | Sources |
| 1 | ENAH (hMena) | TMNGSKSPV (SEQ ID NO: 162) | Di Modugno et al. Int. J. Cancer. 109(6):909-18 (2004). |
| 2 | mammaglobin-A | PLLENVISK (SEQ ID NO: 163) | Jaramillo et al. Int. J. Cancer. 102(5):499-506 (2002). |
| 3 | NY-BR-1 | SLSKILDTV (SEQ ID NO: 164) | Wang et al. Cancer Res. 66(13):6826-33 (2006). |
| 4 | EpCAM | RYQLDPKFI (SEQ ID NO: 97) | Gasti et al. Lancet 356(9246):1981-2 (2000).<br>Tajima, 2004 |
| 5 | NY-ESO-1 | HLA-A2-restricted peptide p157-165 (SLLMWITQC) (SEQ ID NO: 42),<br>HLA-Cw3-restricted p92-100 (LAMP-FATPM) (SEQ ID NO: 43) and HLA-Cw6-restricted p80-88 (ARGPESRLL) (SEQ ID NO: 44)<br>MLMAQEALAFL (SEQ ID NO: 45)<br>YLAMPFATPME (SEQ ID NO: 46)<br>ASGPGGGAPR (SEQ ID NO: 47)<br>LAAQERRVPR (SEQ ID NO: 48)<br>TVSGNILTIR (SEQ ID NO: 49)<br>APRGPHGGAASGL (SEQ ID NO: 50)<br>MPFATPMEAEL (SEQ ID NO: 51)<br>KEFTVSGNILTI (SEQ ID NO: 52)<br>MPFATPMEA (SEQ ID NO: 53)<br>FATPMEAEL (SEQ ID NO: 54) | Jager et al. Proc. Natl. Acad. Scie. U.S.A. 103(39):14453-8 (2006).<br>Gnjatic et al. PNAS September 26, 2000 vol. 97 no. 20 p. 10919<br>Jager et al. J Exp Med. 187(2):265-70 (1998).<br>Chen et al. J Immunol. 165(2):948-55 (2000).<br>Valmori et al. Cancer Res. 60(16):4499-506 (2000).<br>Aarnoudse et al. Int J Cancer. 82(3):442-8 (1999).<br>Eikawa et al. Int J Cancer. 132(2):345-54 (2013).<br>Wang et al. J Immunol. 161(7):3598-606 (1998). |

TABLE 2-continued

| No. | Tumor-associated antigen | Immunogenic epitopes | Sources |
|---|---|---|---|
| | | **Breast cancer** | |
| | | FATPMEAELAR (SEQ ID NO: 55) SLLMWITQCFLPVF (SEQ ID NO: 56) LLEFYLAMPFATPMEAEL-ARRSLAQ (SEQ ID NO: 57) EFYLAMPFATPM (SEQ ID NO: 58) PGVLLKEFTVSGNILTIRL-TAADHR (SEQ ID NO: 59) RLLEFYLAMPFA (SEQ ID NO: 60) QGAMLAAQERRVPRAAE-VPR (SEQ ID NO: 61) PFATPMEAELARR (SEQ ID NO: 62) PGVLLKEFTVSGNILTIRLT (SEQ ID NO: 63) VLLKEFTVSG (SEQ ID NO: 64) AADHRQLQLSISSCLQQL (SEQ ID NO: 65) LKEFTVSGNILTIRL (SEQ ID NO: 66) KEFTVSGNILT (SEQ ID NO: 67) LLEFYLAMPFATPM (SEQ ID NO: 68) AGATGGRGPRGAGA (SEQ ID NO: 69) | Matsuzaki et al. Cancer Immunol Immunother. 57(8)1185-95 (2008). Ebert et al. Cancer Res. 69(3)1 046-54 (2009). Eikawa et al. Int J Cancer. 132(2):345-54 (2013). Knights et al. Cancer Immunol Immunother. 58(3):325-38 (2009). Jager et al. Cancer Immun. 2:12 (2002). Zeng et al. Proc Natl Acad Sci U S A. 98(7):3964-9 (2001). Mandic et al. J Immunol. 174(3):1751-9 (2005). Chen et al. Proc Natl Aced Sci U S A. 101(25):9363-8 (2004). Ayyoub et al. Clin Cancer Res. 16(18):4607-15 (2010). Sieger et al. J Immunol. 172(8):5095-102 (2004). Mizote et al. Vaccine. 28(32):5338-46 (2010). Jager et al. J Exp Med. 191(4):625-30 (2000). Zarour et al. Cancer Res. 60(17):4946-52 (2000). Zeng et al. J Immunol. 165(2):1153-9 (2000). Bioley et al. Clin Cancer Res. 15(13):4467-74 (2009). Zarour et al. Cancer Res. 62(1):213-8 (2002). Hasegawa et al. Clin Cancer Res. 12(6):1921-7 (2006). |
| 6 | BAGE-1 | AARAVFLAL (SEQ ID NO: 165) | Boel et al. Immunity. 2(2):167-75 (1995). |
| 7 | HERV-K-MEL | MLAVISCAV (SEQ ID NO: 132) | Schiavetti et al. Cancer Res. 62(19):5510-6 (2002). |
| 8 | KK-LC-1 | RQKRILVNL (SEQ ID NO: 133) | Fukuyama et al. Cancer Res. 66(9):4922-8 (2006). |
| 9 | KM-HN-1 | NYNNFYRFL (SEQ ID NO: 134) EYSKECLKEF (SEQ ID NO: 135) EYLSLSDKI (SEQ ID NO: 136) | Fukuyama et al. Cancer Res. 66(9):4922-8 (2006). Monji et al. Clin Cancer Res. 10(18 Pt 1):6047-57 (2004). |
| 10 | LAGE-1 | MLMAQEALAFL (SEQ ID NO: 137) SLLMWITQC (SEQ ID NO: 138) LAAQERRVPR (SEQ ID NO: 139) ELVRRILSR (SEQ ID NO: 140) APRGVRMAV (SEQ ID NO: 141) SLLMWITQCFLPVF (SEQ ID NO: 142) QGAMLAAQERRVPRAAEVP-R (SEQ ID NO: 143) AADHRQLQLSISSCLQQL (SEQ ID NO: 144) CLSRRPWKRSWSAGSCPG-MPHL (SEQ ID NO: 145) ILSRDAAPLPRPG (SEQ ID NO: 146) AGATGGRGPRGAGA (SEQ ID NO: 147) | Aarnoudse et al. Int J Cancer. 82(3):442-8 (1999). Rimoldi et al. J Immunol. 165(12):7253-61 (2000). Wang et al. J Immunol. 161(7):3598-606 (1998). Sun et al. Cancer Immunol Immunother. 55(6):644-52 (2006). Sieger et al. Cancer Gene Ther. 11(3):227-36 (2004). Zeng et al. Proc Natl Acad Sci U S A. 98(7):3964-9 (2001). Sieger et al. J Immunol. 172(8):5095-102 (2004). Jager et al. J Exp Med. 191(4):625-30 (2000). Sieger et al. J Immunol. 170(3):1490-7 (2003). Wang et al. Immunity. 20(1):107-18 (2004). Hasegawa et al. Clin Cancer Res. 12(6):1921-7 (2006). |
| 11 | MAGE-A1 | EADPTGHSY (SEQ ID NO: 166) KVLEYVIKV (SEQ ID NO: 167) SLFRAVITK (SEQ ID NO: 168) EVYDGREHSA (SEQ ID NO: 169) RVRFFFPSL (SEQ ID NO: 170) REPVTKAEML (SEQ ID NO: 171) | Traversari et al. J Exp Med. 176(5):1453-7 (1992). Ottaviani et al. Cancer Immunol Immunother. 54(12)1 214-20 (2005). Pascolo et al. Cancer Res. 61(10):4072-7 (2001). |

TABLE 2-continued

| Breast cancer | | | |
|---|---|---|---|
| No. | Tumor-associated antigen | Immunogenic epitopes | Sources |
| | | KEADPTGHSY (SEQ ID NO: 172)<br>DPARYEFLW (SEQ ID NO: 173)<br>ITKKVADLVGF (SEQ ID NO: 174)<br>SAFPTTINF (SEQ ID NO: 175)<br>SAYGEPRKL (SEQ ID NO: 176)<br>TSCILESLFRAVITK (SEQ ID NO: 177)<br>PRALAETSYVKVLEY (SEQ ID NO: 178)<br>FLLLKYRAREPVTKAE (SEQ ID NO: 179)<br>EYVIKVSARVRF (SEQ ID NO: 180) | Chaux et al. J Immunol. 163(5):2928-36 (1999).<br>Luiten et al. Tissue Anitgens. 55(2):49-52 (2000).<br>Luiten et al. Tissue Antigens. 56(1):77-81 (2000).<br>Tanzarella et al. Cancer Res. 59(11):2668-74 (1999).<br>Stroobant et al. EurJ Immunol. 42(6):1417-28 (2012).<br>Corbiere et al. Tissue Antigens. 63(5):453-7 (2004).<br>Goodyear et al. Cancer Immunol Immunother. 60(12)1 751-61 (2011).<br>van der Bruggen et al. EurJ Immunol. 24(9):2134-40 (1994).<br>Wang et al. Cancer Immunol Immunother. 56(6):807-18 (2007).<br>Chaux et al. J Exp Med. 189(5):767-78 (1999).<br>Chaux et al. EurJ Immunol. 31(6): 1910-6 (2001). |
| 12 | MAGE-A2 | YLQLVFGIEV (SEQ ID NO: 181)<br>EYLQLVFGI (SEQ ID NO: 182)<br>REPVTKAEML (SEQ ID NO: 183)<br>EGDCAPEEK (SEQ ID NO: 184)<br>LLKYRAREPVTKAE (SEQ ID NO: 185) | Kawashima et al. Hum Immunol. 59(1):1-14 (1998).<br>Tahara et al. Clin Cancer Res. 5(8):2236-41 (1999).<br>Tanzarella et al. Cancer Res. 59(11):2668-74 (1999).<br>Breckpot et al. J Immunol. 172(4):2232-7 (2004).<br>Chaux et al. J Exp Med. 89(5):767-78 (1999). |
| 13 | mucink | PDTRPAPGSTAPPAHGVTSA (SEQ ID NO: 128) | Jerome et al. J Immunol. 151(3):1654-62 (1993). |
| 14 | Sp17 | ILDSSEEDK (SEQ ID NO: 152) | Chiriya-Intemati et al. Int J Cancer. 107(5):863-5 (2003). |
| 15 | SSX-2 | KASEKIFYV (SEQ ID NO: 186)<br>EKIQKAFDDIAKYFSK (SEQ ID NO: 187)<br>FGRLQGISPKI (SEQ ID NO: 188)<br>WEKMKASEKIFYVYMKRK (SEQ ID NO: 189)<br>KIFYVYMKRKYEAMT (SEQ ID NO: 190)<br>KIFYVYMKRKYEAM (SEQ ID NO: 191) | Ayyoub et al. J Immunol. 168(4):1717-22 (2002).<br>Ayyoub et al. J Immunol. 172(11):7206-11 (2004).<br>Neumann et al. Cancer Immunol Immunother. 60(9)1 333-46 (2011).<br>Ayyoub et al. Clin Immunol. 114(1):70-8 (2005).<br>Neumann et al. Int J Cancer. 112(4):661-8 (2004).<br>Ayyoub et al. J Clin Invest. 113(8):1225-33 (2004). |
| 16 | TAG-1 | SLGWLFLLL (SEQ ID NO: 159)<br>LSRLSNRLL (SEQ ID NO: 160) | Adair et al. J Immunother. 31(1):7-17 (2008). |
| 17 | TAG-2 | LSRLSNRLL (SEQ ID NO: 161) | Adair et al. J Immunother. 31(1):7-17 (2008). |
| 18 | TRAG-3 | CEFHACWPAFTVLGE (SEQ ID NO: 192) | Janjic et al. J Immunol. 177(4):2717-27 (2006). |
| 19 | Her2/Neu | HLYQGCQVV (SEQ ID NO: 89)<br>YLVPQQGFFC (SEQ ID NO: 90)<br>PLQPEQLQV (SEQ ID NO: 91)<br>TLEEITGYL (SEQ ID NO: 92)<br>ALIHHNTHL (SEQ ID NO: 93)<br>PLTSIISAV (SEQ ID NO: 94)<br>VLRENTSPK (SEQ ID NO: 95)<br>TYLPTNASL (SEQ ID NO: 96) | Nakatsuka et al. Mod. Pathol. 19(6):804-814 (2006).<br>Pils et al. Br. J. Cancer 96(3):485-91 (2007).<br>Scardino et al. EurJ Immunol. 31(11):3261-70 (2001).<br>Scardino et al. J Immunol. 168(11):5900-6 (2002).<br>Kawashima et al. Cancer Res. 59(2):431-5 (1999).<br>Okugawa et al. EurJ Immunol. 30(11):3338-46 (2000). |

TABLE 2-continued

| Breast cancer | | | |
|---|---|---|---|
| No. | Tumor-associated antigen | Immunogenic epitopes | Sources |
| 20 | c-myc | SSPQGSPEPL (SEQ ID NO: 193) | Helm et al. PLoS ONE 8(10): e77375 (2013). |
| 21 | cyclin B1 | ILIDWLVQV (SEQ ID NO: 194) | Andersen et al. Cancer Immunol Immunother 60: 227 (2011). |
| 22 | MUC1 | STAPPVHNV (SEQ ID NO: 129)<br>LLLLTVLTV (SEQ ID NO: 130) | Brossart et al. Blood, 93(12), 4309-4317 (1999). |
| 23 | p53 | VVPCEPPEV (SEQ ID NO: 88) | Hung et al. Immunol. Rev. 222:43-69 (2008).<br>http://cancerimmunity.org/peptide/mutations/ |
| 24 | p62 | FLKNVGESV (SEQ ID NO: 195) | Pampeno et al. (2016) High-ranking In Silico epitopes by 3 algorithms:<br>BISMAS, IEDB, RANKPEP+unpublished |
| 25 | Survivin | ELTLGEFLKL (SEQ ID NO: 196) | Schmitz M Cancer Res. 60: 4845-9 (2000). |

TABLE 3

| Testicular cancer | | | |
|---|---|---|---|
| No. | Tumor-associated antigen | Immunogenic epitopes | Sources |
| 1 | CD45 | KFLDALISL (SEQ ID NO: 197) | Tomita et al. Cancer Sci. 102(4):697-705 (2011). |
| 2 | DKK1 | ALGGHPLLGV (SEQ ID NO: 198) | Qian et al. Blood. (5):1587-94 (2007). |
| 3 | PRAME | VLDGLDVLL (SEQ ID NO: 27), SLYSFPEPEA (SEQ ID NO: 28), ALYVDSLFFL (SEQ ID NO: 29), SLLQHLIGL (SEQ ID NO: 30), and LYVDSLFFL (SEQ ID NO: 31) | Kessler et al. J Exp Med. 193(1):73-88 (2001).<br>Ikeda et al. Immunity 6(2):199-208 (1997). |
| 4 | RU2AS | LPRWPPPQL (SEQ ID NO: 199) | Van Den Eynde et al. J. Exp. Med. 190(12):1793-800 (1999). |
| 5 | Telomerase | ILAKFLHWL (SEQ ID NO: 200); RLVDDFLLV; (SEQ ID NO: 201) RPGLLGASVLGLDDI (SEQ ID NO: 202); and LTDLQPYMRQFVAHL (SEQ ID NO: 203) | Vonderheide et al. Immunity 10(6):673-9 (1999).<br>Miney et al. Proc. Natl. Acad. Sci. U.S.A. 97(9):4796-801 (2000).<br>Schroers et al. Cancer Res. 62(9):2600-5 (2002).<br>Schroers et al. Clin. Cancer Res. 9(13):4743-55 (2003). |

TABLE 4

| Pancreatic cancer | | | |
|---|---|---|---|
| No. | Tumor-associated antigen | Immunogenic epitopes | Sources |
| 1 | ENAH (hMena) | TMNGSKSPV (SEQ ID NO: 162) | Di Modugno et al. Int. J. Cancer. 109(6):909-18 (2004). |
| 2 | PBF | CTACRWKKACQR (SEQ ID NO: 204) | Tsukahara et al. Cancer Res. 64(15):5442-8 (2004). |

TABLE 4-continued

| Pancreatic cancer | | | |
|---|---|---|---|
| No. | Tumor-associated antigen | Immunogenic epitopes | Sources |
| 3 | K-ras | VVVGAVGVG (SEQ ID NO: 205) | Gjertsen et al. Int. J. Cancer. 72(5):784-90 (1997). |
| 4 | Mesothelin | SLLFLLFSL (SEQ ID NO: 37) VLPLTVAEV (SEQ ID NO: 38) ALQGGGPPY (SEQ ID NO: 39) LYPKARLAF (SEQ ID NO: 40) AFLPWHRLF (SEQ ID NO: 41) | Le et al. Clin. Cancer Res. 18(3):858-68 (2012). Hassan et al. Appl. Immunohistochem. Mol. Morphol. 13(3):243-7 (2005). Thomas et al J Exp Med. 2004 Aug 2; 200(3): 297-306. |
| 5 | mucink | PDTRPAPGSTAPPAHGVTSA (SEQ ID NO: 128) | Jerome et al. J Immunol. 151(3):1654-62 (1993). |

TABLE 5

| Liver cancer | | | |
|---|---|---|---|
| No. | Tumor-associated antigen | Immunogenic epitopes | Sources |
| 1 | G250/MN/ CAIX | HLSTAFARV (SEQ ID NO: 206); KIFGSLAFL (SEQ ID NO: 207); IISAVVGIL (SEQ ID NO: 208); ALCRWGLLL (SEQ ID NO: 209); ILHNGAYSL (SEQ ID NO: 210); RLLQETELV (SEQ ID NO: 211); VVKGVVFGI (SEQ ID NO: 212); and YMIMVKCWMI (SEQ ID NO: 213) | Vissers et al. Cancer Res. 59(21):5554-9 (1999). Fisk et al. J Exp Med. 181(6):2109-17 (1995). Brossart et al. Cancer Res. 58(4):732-6 (1998). Kawashima et al. Hum Immunol. 59(1):1-14 (1998). Rongcun et al. J Immunol. 163(2):1037-44 (1999). |
| 2 | Hepsin | SLLSGDWVL (SEQ ID NO: 214); GLQLGVQAV (SEQ ID NO: 215); and PLTEYIQPV (SEQ ID NO: 216) | Guo et al. Scand J Immunol. 78(3):248-57 (2013). |
| 3 | Intestinal carboxyl esterase | SPRWWPTCL (SEQ ID NO: 217) | Ronsin et al. J Immunol. 163(1):483-90 (1999). |
| 4 | alpha-foetoprotein | GVALQTMKQ (SEQ ID NO: 218); FMNKFIYEI (SEQ ID NO: 219); and QLAVSVILRV (SEQ ID NO: 220) | Butterfield et al. Cancer Res. 59(13):3134-42 (1999). Pichard et al. J Immunother. 31(3):246-53 (2008) Alisa et al. Clin. Cancer Res. 11(18):6686-94 (2005). |
| 5 | M-CSF | LPAVVGLSPGEQEY (SEQ ID NO: 221) | Probst-Kepper et al. J Exp Med. 193(10):1189-98 (2001). |
| 6 | PBF | CTACRWKKACQR (SEQ ID NO: 222) | Tsukahara et al. Cancer Res. 64(15):5442-8 (2004). |
| 7 | PSMA | NYARTEDFF (SEQ ID NO: 223) | Horiguchi et al. Clin Cancer Res. 8(12):3885-92 (2002). |
| 8 | NY-ESO-1 | HLA-A2-restricted peptide p157-165 (SLLMWITQC) (SEQ ID NO: 42), HLA-Cw3-restricted p92-100 (LAMP-FATPM) (SEQ ID NO: 43) and HLA-Cw6-restricted p80-88 (ARGPESRLL) (SEQ ID NO: 44) MLMAQEALAFL (SEQ ID NO: 45) YLAMPFATPME (SEQ ID NO: 46) ASGPGGGAPR (SEQ ID NO: 47) LAAQERRVPR (SEQ ID NO: 48) | Jager et al. Proc. Natl. Acad. Scie. U.S.A. 103(39):14453-8 (2006). Gnjatic et al. PNAS September 26, 2000 vol. 97 no. 20 p. 10919 Jager et al. J Exp Med. 187(2):265-70 (1998). Chen et al. J Immunol. 165(2):948-55 (2000). Valmori et al. Cancer Res. 60(16):4499-506 (2000). |

TABLE 5-continued

| Liver cancer | | | |
|---|---|---|---|
| No. | Tumor-associated antigen | Immunogenic epitopes | Sources |
| | | TVSGNILTIR (SEQ ID NO: 49)<br>APRGPHGGAASGL (SEQ ID NO: 50)<br>MPFATPMEAEL (SEQ ID NO: 51)<br>KEFTVSGNILTI (SEQ ID NO: 52)<br>MPFATPMEA (SEQ ID NO: 53)<br>FATPMEAEL (SEQ ID NO: 54)<br>FATPMEAELAR (SEQ ID NO: 55)<br>SLLMWITQCFLPVF (SEQ ID NO: 56)<br>LLEFYLAMPFATPMEAEL-ARRSLAQ (SEQ ID NO: 57)<br>EFYLAMPFATPM (SEQ ID NO: 58)<br>PGVLLKEFTVSGNILTIRL-TAADHR (SEQ ID NO: 59)<br>RLLEFYLAMPFA (SEQ ID NO: 60)<br>QGAMLAAQERRVPRAAE-VPR (SEQ ID NO: 61)<br>PFATPMEAELARR (SEQ ID NO: 62)<br>PGVLLKEFTVSGNILTIRLT (SEQ ID NO: 63)<br>VLLKEFTVSG (SEQ ID NO: 64)<br>AADHRQLQLSISSCLQQL (SEQ ID NO: 65)<br>LKEFTVSGNILTIRL (SEQ ID NO: 66)<br>KEFTVSGNILT (SEQ ID NO: 67)<br>LLEFYLAMPFATPM (SEQ ID NO: 68)<br>AGATGGRGPRGAGA (SEQ ID NO: 69) | Aarnoudse et al. Int J Cancer. 82(3):442-8 (1999).<br>Eikawa et al. Int J Cancer. 132(2):345-54 (2013).<br>Wang et al. J Immunol. 161(7):3598-606 (1998).<br>Matsuzaki et al. Cancer Immunol Immunother. 57(8)1185-95 (2008).<br>Ebert et al. Cancer Res. 69(3):1046-54 (2009).<br>Eikawa et al. Int J Cancer. 132(2):345-54 (2013).<br>Knights et al. Cancer Immunol Immunother. 58(3):325-38 (2009).<br>Jager et al. Cancer Immun. 2:12 (2002).<br>Zeng et al. Proc Natl Acad Sci U S A. 98(7):3964-9 (2001).<br>Mandic et al. J Immunol. 174(3):1751-9 (2005).<br>Chen et al. Proc Natl Acad Sci U S A. 101(25):9363-8 (2004).<br>Ayyoub et al. Clin Cancer Res. 16(18):4607-15 (2010).<br>Slager et al. J Immunol. 172(8):5095-102 (2004).<br>Mizote et al. Vaccine. 28(32):5338-46 (2010).<br>Jager et al. J Exp Med. 191(4):625-30 (2000).<br>Zarour et al. Cancer Res. 60(17):4946-52 (2000).<br>Zeng et al. J Immunol. 165(2):1153-9 (2000).<br>Bioley et al. Clin Cancer Res. 15(13):4467-74 (2009).<br>Zarour et al. Cancer Res. 62(1):213-8 (2002).<br>Hasegawa et al. Clin Cancer Res. 12(6):1921-7 (2006). |
| 9 | LAGE-1 | MLMAQEALAFL (SEQ ID NO: 137)<br>SLLMWITQC (SEQ ID NO: 138)<br>LAAQERRVPR (SEQ ID NO: 139)<br>ELVRRILSR (SEQ ID NO: 140)<br>APRGVRMAV (SEQ ID NO: 141)<br>SLLMWITQCFLPVF (SEQ ID NO: 142)<br>QGAMLAAQERRVPRAAEVP-R (SEQ ID NO: 143)<br>AADHRQLQLSISSCLQQL (SEQ ID NO: 144)<br>CLSRRPWKRSWSAGSCPG-MPHL (SEQ ID NO: 145)<br>ILSRDAAPLPRPG (SEQ ID NO: 146)<br>AGATGGRGPRGAGA (SEQ ID NO: 147) | Aarnoudse et al. Int J Cancer. 82(3):442-8 (1999).<br>Rimoldi et al. J Immunol. 165(12):7253-61 (2000).<br>Wang et al. J Immunol. 161(7):3598-606 (1998).<br>Sun et al. Cancer Immunol Immunother. 55(6):644-52 (2006).<br>Sieger et al. Cancer Gene Ther. 11(3):227-36 (2004).<br>Zeng et al. Proc Natl Acad Sci U S A. 98(7):3964-9 (2001).<br>Sieger et al. J Immunol. 172(8):5095-102 (2004).<br>Jager et al. J Exp Med. 191(4):625-30 (2000).<br>Sieger et al. J Immunol. 170(3):1490-7 (2003).<br>Wang et al. Immunity. 20(1):107-18 (2004).<br>Hasegawa et al. Clin Cancer Res. 12(6):1921-7 (2006). |
| 10 | HERV-K-MEL | MLAVISCAV (SEQ ID NO: 132) | Schiavetti et al. Cancer Res. 62(19):5510-6 (2002). |
| 11 | KK-LC-1 | RQKRILVNL (SEQ ID NO: 133) | Fukuyama et al. Cancer Res. 66(9):4922-8 (2006). |
| 12 | KM-HN-1 | NYNNFYRFL (SEQ ID NO: 134)<br>EYSKECLKEF (SEQ ID NO: 135)<br>EYLSLSDKI (SEQ ID NO: 136) | Fukuyama et al. Cancer Res. 66(9):4922-8 (2006).<br>Monji et al. Clin Cancer Res. 10(18 Pt 1):6047-57 (2004). |
| 13 | Sp17 | ILDSSEEDK (SEQ ID NO: 152) | Chiriva-Internati et al. Int J Cancer. 107(5):863-5 (2003). |

TABLE 5-continued

| Liver cancer | | | |
|---|---|---|---|
| No. | Tumor-associated antigen | Immunogenic epitopes | Sources |
| 14 | c-myc | SSPQGSPEPL (SEQ ID NO: 193) | Helm et al. PLoS ONE 8(10): e77375 (2013). |
| 15 | cyclin B1 | ILIDWLVQV (SEQ ID NO: 194) | Andersen et al. Cancer Immunol Immunother 60: 227 (2011). |
| 16 | p53 | VVPCEPPEV (SEQ ID NO: 88) | Hung et al. Immunol. Rev. 222:43-69 (2008). http://cancerimmunity.org/peptide/mutations/ |
| 17 | p62 | FLKNVGESV (SEQ ID NO: 195) | Pampeno et al. (2016) High-ranking In Silico epitopes by 3 algorithms: BISMAS, IEDB, RANKPEP+unpublished |
| 18 | Survivin | ELTLGEFLKL (SEQ ID NO: 196) | Schmitz M Cancer Res. 60: 4845-9 (2000) |

TABLE 6

| Colorectal cancer | | | |
|---|---|---|---|
| No. | Tumor-associated antigen | Immunogenic epitopes | Sources |
| 1 | ENAH(hMena) | TMNGSKSPV (SEQ ID NO: 162) | Di Modugno et al. Int. J Cancer. 109(6):909-18 (2004). |
| 2 | Intestinal carboxyl esterase | SPRWWPTCL (SEQ ID NO: 217) | Ronsin et al. J Immunol. 163(1):483-90 (1999). |
| 3 | CASP-5 | FLIIWQNTM (SEQ ID NO: 224) | Schwitalle et al. Cancer Immun. 4: 14 (2004). |
| 4 | COA-1 | TLYQDDTLTLQAAG (SEQ ID NO: 225) | Maccalli et al. Cancer Res. 63(20):6735-43 (2003). |
| 5 | OGT | SLYKFSPFPL (SEQ ID NO: 226) | Ripberger. J Clin Immunol. 23(5):415-23 (2003). |
| 6 | OS-9 | KELEGILLL (SEQ ID NO: 227) | Vigneron et al. Cancer Immun. 2: 9 (2002). |
| 7 | TGF-betaRII | RLSSCVPVA (SEQ ID NO: 228) | Linnebacher et al. Int. J. Cancer. 93(1):6-11 (2001). |
| 8 | NY-ESO-1 | HLA-A2-restricted peptide p157-165 (SLLMWITQC) (SEQ ID NO: 42),<br>HLA-Cw3-restricted p92-100 (LAMP-FATPM) (SEQ ID NO: 43) and HLA-Cw6-restricted p80-88 (ARGPESRLL) (SEQ ID NO: 44)<br>MLMAQEALAFL (SEQ ID NO: 45)<br>YLAMPFATPME (SEQ ID NO: 46)<br>ASGPGGGAPR (SEQ ID NO: 47)<br>LAAQERRVPR (SEQ ID NO: 48)<br>TVSGNILTIR (SEQ ID NO: 49)<br>APRGPHGGAASGL (SEQ ID NO: 50)<br>MPFATPMEAEL (SEQ ID NO: 51)<br>KEFTVSGNILTI (SEQ ID NO: 52)<br>MPFATPMEA (SEQ ID NO: 53)<br>FATPMEAEL (SEQ ID NO: 54)<br>FATPMEAELAR (SEQ ID NO: 55)<br>SLLMWITQCFLPVF (SEQ ID NO: 56)<br>LLEFYLAMPFATPMEAEL-ARRSLAQ (SEQ ID NO: 57)<br>EFYLAMPFATPM (SEQ ID NO: 58)<br>PGVLLKEFTVSGNILTIRL-TAADHR (SEQ ID NO: 59) | Jager et al. Proc. Natl. Acad. Scie. U.S.A. 103(39):14453-8 (2006).<br>Gnjatic et al. PNAS September 26, 2000 vol. 97 no. 20 p. 10919<br>Jager et al. J Exp Med. 187(2):265-70 (1998).<br>Chen et al. J Immunol. 165(2):948-55 (2000).<br>Valmori et al. Cancer Res. 60(16):4499-506 (2000).<br>Aarnoudse et al. Int J Cancer. 82(3):442-8 (1999).<br>Eikawa et al. Int J Cancer. 132(2):345-54 (2013).<br>Wang et al. J Immunol. 161(7):3598-606 (1998).<br>Matsuzaki et al. Cancer Immunol Immunother. 57(8)1185-95 (2008).<br>Ebert et al. Cancer Res. 69(3)1 046-54 (2009).<br>Eikawa et al. Int J Cancer. 132(2):345-54 (2013).<br>Knights et al. Cancer Immunol Immunother. 58(3):325-38 (2009). |

TABLE 6-continued

| Colorectal cancer | | | |
|---|---|---|---|
| No. | Tumor-associated antigen | Immunogenic epitopes | Sources |
| | | RLLEFYLAMPFA (SEQ ID NO: 60)<br>QGAMLAAQERRVPRAAE-VPR (SEQ ID NO: 61)<br>PFATPMEAELARR (SEQ ID NO: 62)<br>PGVLLKEFTVSGNILTIRLT (SEQ ID NO: 63)<br>VLLKEFTVSG (SEQ ID NO: 64)<br>AADHRQLQLSISSCLQQL (SEQ ID NO: 65)<br>LKEFTVSGNILTIRL (SEQ ID NO: 66)<br>KEFTVSGNILT (SEQ ID NO: 67)<br>LLEFYLAMPFATPM (SEQ ID NO: 68)<br>AGATGGRGPRGAGA (SEQ ID NO: 69) | Jager et al. Cancer Immun. 2:12 (2002).<br>Zeng et al. Proc Natl Acad Sci U S A. 98(7):3964-9 (2001).<br>Mandic et al. J Immunol. 174(3):1751-9 (2005).<br>Chen et al. Proc Natl Aced Sci U S A. 101(25):9363-8 (2004).<br>Ayyoub et al. Clin Cancer Res. 16(18):4607-15 (2010).<br>Sieger et al. J Immunol. 172(8):5095-102 (2004).<br>Mizote et al. Vaccine. 28(32):5338-46 (2010).<br>Jager et al. J Exp Med. 191(4):625-30 (2000).<br>Zarour et al. Cancer Res. 60(17):4946-52 (2000).<br>Zeng et al. J Immunol. 165(2):1153-9 (2000).<br>Bioley et al. Clin Cancer Res. 15(13):4467-74 (2009).<br>Zarour et al. Cancer Res. 62(1):213-8 (2002).<br>Hasegawa et al. Clin Cancer Res. 12(6):1921-7 (2006). |
| 9 | CEA | TYYRPGVNLSLSC (SEQ ID NO: 70)<br>EIIYPNASLLIQN (SEQ ID NO: 71)<br>YACFVSNLATGRNNS (SEQ ID NO: 72)<br>LWWVNNQSLPVSP (SEQ ID NO: 73)<br>NSIVKSITVSASG (SEQ ID NO: 74)<br>KTWGQYWQV (SEQ ID NO: 75)<br>(A)MLGTHTMEV (SEQ ID NO: 76)<br>ITDQVPFSV (SEQ ID NO: 77)<br>YLEPGPVTA (SEQ ID NO: 78)<br>LLDGTATLRL (SEQ ID NO: 79)<br>VLYRYGSFSV (SEQ ID NO: 80)<br>SLADTNSLAV (SEQ ID NO: 81)<br>RLMKQDFSV (SEQ ID NO: 82)<br>RLPRIFCSC (SEQ ID NO: 83)<br>LIYRRRLMK (SEQ ID NO: 84)<br>ALLAVGATK (SEQ ID NO: 85)<br>IALNFPGSQK (SEQ ID NO: 86)<br>RSYVPLAHR (SEQ ID NO: 87) | Duffy, Clin. Chem. 47(4):624-30 (2001).<br>Parkhurst et al. Mol. Ther. 19(3):620-6 (2011).<br>Galanis et al. Cancer Res. 70(3):875-82 (2010).<br>Bast et al. Am. J. Obstet. Gynecol. 149(5):553-9 (1984).<br>Crosti et al. J Immunol. 176(8):5093-9 (2006).<br>Kobayashi et al. Clin Cancer Res. 8(10):3219-25 (2002).<br>Campi et al. Cancer Res. 63(23):8481-6 (2003).<br>Bakker et al. Int J Cancer. 62(1):97-102 (1995).<br>Tsai et al. J Immunol. 158(4)1 796-802 (1997).<br>Kawakami et al. J Immunol. 154(8):3961-8 (1995).<br>Cox et al. Science. 264(5159):716-9 (1994).<br>Kawakami et al. J Immunol. 154(8):3961-8 (1995).<br>Kawakami et al. J Immunol. 161(12):6985-92 (1998).<br>Skipper et al. J Immunol. 157(11):5027-33 (1996).<br>Michaux et al. J Immunol. 192(4):1962-71 (2014). |
| 10 | HERV-K-MEL | MLAVISCAV (SEQ ID NO: 132) | Schiavetti et al. Cancer Res. 62(19):5510-6 (2002). |
| 11 | KK-LC-1 | RQKRILVNL (SEQ ID NO: 133) | Fukuyama et al. Cancer Res. 66(9):4922-8 (2006). |
| 12 | KM-HN-1 | NYNNFYRFL (SEQ ID NO: 134)<br>EYSKECLKEF (SEQ ID NO: 135)<br>EYLSLSDKI (SEQ ID NO: 136) | Fukuyama et al. Cancer Res. 66(9):4922-8 (2006).<br>Monji et al. Clin Cancer Res. 10(18 Pt 1):6047-57 (2004). |
| 13 | LAGE-1 | MLMAQEALAFL (SEQ ID NO: 137)<br>SLLMWITQC (SEQ ID NO: 138)<br>LAAQERRVPR (SEQ ID NO: 139)<br>ELVRRILSR (SEQ ID NO: 140)<br>APRGVRMAV (SEQ ID NO: 141)<br>SLLMWITQCFLPVF (SEQ ID NO: 142) | Aarnoudse et al. Int J Cancer. 82(3):442-8 (1999).<br>Rimoldi et al. J Immunol. 165(12):7253-61 (2000).<br>Wang et al. J Immunol. 161(7):3598-606 (1998).<br>Sun et al. Cancer Immunol Immunother. |

TABLE 6-continued

| Colorectal cancer | | | |
|---|---|---|---|
| No. | Tumor-associated antigen | Immunogenic epitopes | Sources |
| | | QGAMLAAQERRVPRAAEVP-R (SEQ ID NO: 143)<br>AADHRQLQLSISSCLQQL (SEQ ID NO: 144)<br>CLSRRPWKRSWSAGSCPG-MPHL (SEQ ID NO: 145)<br>ILSRDAAPLPRPG (SEQ ID NO: 146)<br>AGATGGRGPRGAGA (SEQ ID NO: 147) | 55(6):644-52 (2006).<br>Slager et al. Cancer Gene Ther. 11(3):227-36 (2004).<br>Zeng et al. Proc Natl Acad Sci U S A. 98(7):3964-9 (2001).<br>Slager et al. J Immunol. 172(8):5095-102 (2004).<br>Jager et al. J Exp Med. 191(4):625-30 (2000).<br>Slager et al. J Immunol. 170(3):1490-7 (2003).<br>Wang et al. Immunity. 20(1):107-18 (2004).<br>Hasegawa et al. Clin Cancer Res. 12(6):1921-7 (2006). |
| 14 | MAGE-A2 | YLQLVFGIEV (SEQ ID NO: 181)<br>EYLQLVFGI (SEQ ID NO: 182)<br>REPVTKAEML (SEQ ID NO: 183)<br>EGDCAPEEK (SEQ ID NO: 184)<br>LLKYRAREPVTKAE (SEQ ID NO: 185) | Kawashima et al. Hum Immunol. 59(1):1-14 (1998).<br>Tahara et al. Olin Cancer Res. 5(8):2236-41 (1999).<br>Tanzarella et al. Cancer Res. 59(11):2668-74 (1999).<br>Breckpot et al. J Immunol. 172(4):2232-7 (2004).<br>Chaux et al. J Exp Med. 89(5):767-78 (1999). |
| 15 | Sp17 | ILDSSEEDK (SEQ ID NO: 152) | Chiriya-Internati et al. Int J Cancer. 107(5):863-5 (2003). |
| 16 | TAG-1 | SLGWLFLLL (SEQ ID NO: 159)<br>LSRLSNRLL (SEQ ID NO: 160) | Adair et al. J Immunother. 31(1):7-17 (2008). |
| 17 | TAG-2 | LSRLSNRLL (SEQ ID NO: 161) | Adair et al. J Immunother. 31(1):7-17 (2008). |
| 18 | c-myc | SSPQGSPEPL (SEQ ID NO: 193) | Helm et al. PLoS ONE 8(10): e77375 (2013). |
| 19 | cyclin B1 | ILIDWLVQV (SEQ ID NO: 194) | Andersen et al. Cancer Immunol Immunother 60: 227 (2011). |
| 20 | MUC1 | STAPPVHNV (SEQ ID NO: 129)<br>LLLLTVLTV (SEQ ID NO: 130) | Brossart et al. Blood, 93(12), 4309-4317 (1999). |
| 21 | p53 | VVPCEPPEV (SEQ ID NO: 88) | Hung et al. Immunol. Rev. 222:43-69 (2008).<br>http://cancerimmunity.org/peptide/mutations/ |
| 22 | p62 | FLKNVGESV (SEQ ID NO: 195) | Pampeno et al. (2016) High-ranking In Silico epitopes by 3 algorithms:<br>BISMAS, IEDB, RANKPEP+unpublished |
| 23 | Survivin | ELTLGEFLKL (SEQ ID NO: 196) | Schmitz M Cancer Res. 60: 4845-9 (2000). |
| 24 | gp70 | | Castle et al., BMC Genomics 15:190 (2014) |

TABLE 7

| Thyroid cancer | | | |
|---|---|---|---|
| No. | Tumor-associated antigen | Immunogenic epitopes | Sources |
| 1 | CALCA | VLLQAGSLHA (SEQ ID NO: 229) | El Hage et al. Proc. Natl. Acad. Sci. U.S.A. 105(29):10119-24 (2008). |
| 2 | NY-ESO-1 | HLA-A2-restricted peptide p157-165 (SLLMWITQC) (SEQ ID NO: 42),<br>HLA-Cw3-restricted p92-100 (LAMP-FATPM) (SEQ ID NO: 43) and HLA- | Jager et al. Proc. Natl. Acad. Scie. U.S.A. 103(39):14453-8 (2006).<br>Gnjatic et al. PNAS September 26, 2000 vol. 97 no. 20 p. |

TABLE 7-continued

| Thyroid cancer | | | |
|---|---|---|---|
| No. | Tumor-associated antigen | Immunogenic epitopes | Sources |
| | | Cw6-restricted p80-88 (ARGPESRLL) (SEQ ID NO: 44)<br>MLMAQEALAFL (SEQ ID NO: 45)<br>YLAMPFATPME (SEQ ID NO: 46)<br>ASGPGGGAPR (SEQ ID NO: 47)<br>LAAQERRVPR (SEQ ID NO: 48)<br>TVSGNILTIR (SEQ ID NO: 49)<br>APRGPHGGAASGL (SEQ ID NO: 50)<br>MPFATPMEAEL (SEQ ID NO: 51)<br>KEFTVSGNILTI (SEQ ID NO: 52)<br>MPFATPMEA (SEQ ID NO: 53)<br>FATPMEAEL (SEQ ID NO: 54)<br>FATPMEAELAR (SEQ ID NO: 55)<br>SLLMWITQCFLPVF (SEQ ID NO: 56)<br>LLEFYLAMPFATPMEAEL-ARRSLAQ (SEQ ID NO: 57)<br>EFYLAMPFATPM (SEQ ID NO: 58)<br>PGVLLKEFTVSGNILTIRL-TAADHR (SEQ ID NO: 59)<br>RLLEFYLAMPFA (SEQ ID NO: 60)<br>QGAMLAAQERRVPRAAE-VPR (SEQ ID NO: 61)<br>PFATPMEAELARR (SEQ ID NO: 62)<br>PGVLLKEFTVSGNILTIRLT (SEQ ID NO: 63)<br>VLLKEFTVSG (SEQ ID NO: 64)<br>AADHRQLQLSISSCLQQL (SEQ ID NO: 65)<br>LKEFTVSGNILTIRL (SEQ ID NO: 66)<br>KEFTVSGNILT (SEQ ID NO: 67)<br>LLEFYLAMPFATPM (SEQ ID NO: 68)<br>AGATGGRGPRGAGA (SEQ ID NO: 69) | 10919<br>Jager et al. J Exp Med. 187(2):265-70 (1998).<br>Chen et al. J Immunol. 165(2):948-55 (2000).<br>Valmori et al. Cancer Res. 60(16):4499-506 (2000).<br>Aarnoudse et al. Int J Cancer. 82(3):442-8 (1999).<br>Eikawa et al. Int J Cancer. 132(2)345-54 (2013).<br>Wang et al. J Immunol. 161(7):3598-606 (1998).<br>Matsuzaki et al. Cancer Immunol Immunother. 57(8)1185-95 (2008).<br>Ebert et al. Cancer Res. 69(3):1046-54 (2009).<br>Eikawa et al. Int J Cancer. 132(2):345-54 (2013).<br>Knights et al. Cancer Immunol Immunother. 58(3):325-38 (2009).<br>Jager et al. Cancer Immun. 2:12 (2002).<br>Zeng et al. Proc Natl Aced Sci U S A. 98(7):3964-9 (2001).<br>Mandic et al. J Immunol. 174(3):1751-9 (2005).<br>Chen et al. Proc Natl Acad Sci U S A. 101(25):9363-8 (2004).<br>Ayyoub et al. Clin Cancer Res. 16(18):4607-15 (2010).<br>Sieger et al. J Immunol. 172(8):5095-102 (2004).<br>Mizote et al. Vaccine. 28(32):5338-46 (2010).<br>Jager et al. J Exp Med. 191(4):625-30 (2000).<br>Zarour et al. Cancer Res. 60(17):4946-52 (2000).<br>Zeng et al. J Immunol. 165(2)1153-9 (2000).<br>Bioley et al. Clin Cancer Res. 15(13):4467-74 (2009).<br>Zarour et al. Cancer Res. 62(1):213-8 (2002).<br>Hasegawa et al. Clin Cancer Res. 12(6):1921-7 (2006). |
| 3 | HERV-K-MEL | MLAVISCAV (SEQ ID NO: 132) | Schiavetti et al. Cancer Res. 62(19):5510-6 (2002). |
| 4 | KK-LC-1 | RQKRILVNL (SEQ ID NO: 133) | Fukuyama et al. Cancer Res. 66(9):4922-8 (2006). |
| 5 | KM-HN-1 | NYNNFYRFL (SEQ ID NO: 134)<br>EYSKECLKEF (SEQ ID NO: 135)<br>EYLSLSDKI (SEQ ID NO: 136) | Fukuyama et al. Cancer Res. 66(9):4922-8 (2006).<br>Monji et al. Clin Cancer Res. 10(18 Pt 1):6047-57 (2004). |
| 6 | LAGE-1 | MLMAQEALAFL (SEQ ID NO: 137)<br>SLLMWITQC (SEQ ID NO: 138)<br>LAAQERRVPR (SEQ ID NO: 139)<br>ELVRRILSR (SEQ ID NO: 140)<br>APRGVRMAV (SEQ ID NO: 141)<br>SLLMWITQCFLPVF (SEQ ID NO: 142)<br>QGAMLAAQERRVPRAAEVP-R (SEQ ID NO: 143)<br>AADHRQLQLSISSCLQQL (SEQ ID NO: 144)<br>CLSRRPWKRSWSAGSCPG- | Aarnoudse et al. Int J Cancer. 82(3):442-8 (1999).<br>Rimoldi et al. J Immunol. 165(12):7253-61 (2000).<br>Wang et al. J Immunol. 161(7):3598-606 (1998).<br>Sun et al. Cancer Immunol Immunother. 55(6):644-52 (2006).<br>Sieger et al. Cancer Gene Ther. 11(3):227-36 (2004). |

TABLE 7-continued

| Thyroid cancer | | | |
|---|---|---|---|
| No. | Tumor-associated antigen | Immunogenic epitopes | Sources |
| | | MPHL (SEQ ID NO: 145) ILSRDAAPLPRPG (SEQ ID NO: 146) AGATGGRGPRGAGA (SEQ ID NO: 147) | Zeng et al. Proc Natl Aced Sci U S A. 98(7):3964-9 (2001). Sieger et al. J Immunol. 172(8):5095-102 (2004). Jager et al. J Exp Med. 191(4):625-30 (2000). Sieger et al. J Immunol. 170(3):1490-7 (2003). Wang et al. Immunity. 20(1):107-18 (2004). Hasegawa et al. Clin Cancer Res. 12(6):1921-7 (2006). |
| 7 | Sp17 | ILDSSEEDK (SEQ ID NO: 152) | Chiriya-Internati et al. Int J Cancer. 107(5):863-5 (2003). |

TABLE 8

| Lung cancer | | | |
|---|---|---|---|
| No. | Tumor-associated antigen | Immunogenic epitopes | Sources |
| 1 | CD274 | LLNAFTVTV (SEQ ID NO: 230) | Munir et al. Cancer Res. 73(6):1764-76 (2013). |
| 2 | mdm-2 | VLFYLGQY (SEQ ID NO: 231) | Asai et al. Cancer Immun. 2: 3 (2002). |
| 3 | alpha-actinin-4 | FIASNGVKLV (SEQ ID NO: 232) | Echchakir et al. Cancer Res. 61(10):4078-83 (2001). |
| 4 | Elongation factor 2 (squamous cell carcinoma of the lung) | ETVSEQSNV (SEQ ID NO: 233) | Hogan et al. Cancer Res. 58(22):5144-50 (1998). |
| 5 | ME1 (non-small cell lung carcinoma) | FLDEFMEGV (SEQ ID NO: 234) | Karanikas et al. Cancer Res. 61(9):3718-24 (2001). |
| 6 | NFYC (squamous cell carcinoma of the lung) | QQITKTEV (SEQ ID NO: 235) | Takenoyama et al. Int. J Cancer. 118(8):1992-7 (2006). |
| 7 | NY-ESO-1 | HLA-A2-restricted peptide p157-165 (SLLMWITQC) (SEQ ID NO: 42), HLA-Cw3-restricted p92-100 (LAMP-FATPM) (SEQ ID NO: 43) and HLA-Cw6-restricted p80-88 (ARGPESRLL) (SEQ ID NO: 44) MLMAQEALAFL (SEQ ID NO: 45) YLAMPFATPME (SEQ ID NO: 46) ASGPGGGAPR (SEQ ID NO: 47) LAAQERRVPR (SEQ ID NO: 48) TVSGNILTIR (SEQ ID NO: 49) APRGPHGGAASGL (SEQ ID NO: 50) MPFATPMEAEL (SEQ ID NO: 51) KEFTVSGNILTI (SEQ ID NO: 52) MPFATPMEA (SEQ ID NO: 53) FATPMEAEL (SEQ ID NO: 54) FATPMEAELAR (SEQ ID NO: 55) SLLMWITQCFLPVF (SEQ ID NO: 56) LLEFYLAMPFATPMEAEL-ARRSLAQ (SEQ ID NO: 57) | Jager et al. Proc. Natl. Acad. Scie. U.S.A. 103(39):14453-8 (2006). Gnjatic et al. PNAS September 26, 2000 vol. 97 no. 20 p. 10919 Jager et al. J Exp Med. 187(2):265-70 (1998). Chen et al. J Immunol. 165(2):948-55 (2000). Valmori et al. Cancer Res. 60(16):4499-506 (2000). Aarnoudse et al. Int J Cancer. 82(3):442-8 (1999). Eikawa et al. Int J Cancer. 132(2):345-54 (2013). Wang et al. J Immunol. 161(7):3598-606 (1998). Matsuzaki et al. Cancer Immunol Immunother. 57(8)1185-95 (2008). Ebert et al. Cancer Res. 69(3)1 046-54 (2009). Eikawa et al. Int J Cancer. 132(2):345-54 (2013). |

TABLE 8-continued

| Lung cancer | | | |
|---|---|---|---|
| No. | Tumor-associated antigen | Immunogenic epitopes | Sources |
| | | EFYLAMPFATPM (SEQ ID NO: 58)<br>PGVLLKEFTVSGNILTIRL-TAADHR (SEQ ID NO: 59)<br>RLLEFYLAMPFA (SEQ ID NO: 60)<br>QGAMLAAQERRVPRAAE-VPR (SEQ ID NO: 61)<br>PFATPMEAELARR (SEQ ID NO: 62)<br>PGVLLKEFTVSGNILTIRLT (SEQ ID NO: 63)<br>VLLKEFTVSG (SEQ ID NO: 64)<br>AADHRQLQLSISSCLQQL (SEQ ID NO: 65)<br>LKEFTVSGNILTIRL (SEQ ID NO: 66)<br>KEFTVSGNILT (SEQ ID NO: 67)<br>LLEFYLAMPFATPM (SEQ ID NO: 68)<br>AGATGGRGPRGAGA (SEQ ID NO: 69) | Knights et al. Cancer Immunol Immunother. 58(3):325-38 (2009).<br>Jager et al. Cancer Immun. 2:12 (2002).<br>Zeng et al. Proc Natl Acad Sci U S A. 98(7):3964-9 (2001).<br>Mandic et al. J Immunol. 174(3):1751-9 (2005).<br>Chen et al. Proc Natl Aced Sci U S A. 101(25):9363-8 (2004).<br>Ayyoub et al. Clin Cancer Res. 16(18):4607-15 (2010).<br>Sieger et al. J Immunol. 172(8):5095-102 (2004).<br>Mizote et al. Vaccine. 28(32):5338-46 (2010).<br>Jager et al. J Exp Med. 191(4):625-30 (2000).<br>Zarour et al. Cancer Res. 60(17):4946-52 (2000).<br>Zeng et al. J Immunol. 165(2):1153-9 (2000).<br>Bioley et al. Clin Cancer Res. 15(13):4467-74 (2009).<br>Zarour et al. Cancer Res. 62(1):213-8 (2002).<br>Hasegawa et al. Clin Cancer Res. 12(6):1921-7 (2006). |
| 8 | GAGE-1,2,8 | YRPRPRRY (SEQ ID NO: 236) | Van den Eynde et al. J Exp Med. 182(3):689-98 (1995). |
| 9 | HERV-K-MEL | MLAVISCAV (SEQ ID NO: 132) | Schiavetti et al. Cancer Res. 62(19):5510-6 (2002). |
| 10 | KK-LC-1 | RQKRILVNL (SEQ ID NO: 133) | Fukuyama et al. Cancer Res. 66(9):4922-8 (2006). |
| 11 | KM-HN-1 | NYNNFYRFL (SEQ ID NO: 134)<br>EYSKECLKEF (SEQ ID NO: 135)<br>EYLSLSDKI (SEQ ID NO: 136) | Fukuyama et al. Cancer Res. 66(9):4922-8 (2006).<br>Monji et al. Clin Cancer Res. 10(18 Pt 1):6047-57 (2004). |
| 12 | LAGE-1 | MLMAQEALAFL (SEQ ID NO: 137)<br>SLLMWITQC (SEQ ID NO: 138)<br>LAAQERRVPR (SEQ ID NO: 139)<br>ELVRRILSR (SEQ ID NO: 140)<br>APRGVRMAV (SEQ ID NO: 141)<br>SLLMWITQCFLPVF (SEQ ID NO: 142)<br>QGAMLAAQERRVPRAAEVP-R (SEQ ID NO: 143)<br>AADHRQLQLSISSCLQQL (SEQ ID NO: 144)<br>CLSRRPWKRSWSAGSCPG-MPHL (SEQ ID NO: 145)<br>ILSRDAAPLPRPG (SEQ ID NO: 146)<br>AGATGGRGPRGAGA (SEQ ID NO: 147) | Aarnoudse et al. Int J Cancer. 82(3):442-8 (1999).<br>Rimoldi et al. J Immunol. 165(12):7253-61 (2000).<br>Wang et al. J Immunol. 161(7):3598-606 (1998).<br>Sun et al. Cancer Immunol Immunother. 55(6):644-52 (2006).<br>Slager et al. Cancer Gene Ther. 11(3):227-36 (2004).<br>Zeng et al. Proc Natl Acad Sci U S A. 98(7):3964-9 (2001).<br>Slager et al. J Immunol. 172(8):5095-102 (2004).<br>Jager et al. J Exp Med. 191(4):625-30 (2000).<br>Slager et al. J Immunol. 170(3):1490-7 (2003).<br>Wang et al. Immunity. 20(1):107-18 (2004).<br>Hasegawa et al. Clin Cancer Res. 12(6):1921-7 (2006). |
| 13 | MAGE-A2 | YLQLVFGIEV (SEQ ID NO: 181)<br>EYLQLVFGI (SEQ ID NO: 182)<br>REPVTKAEML (SEQ ID NO: 183)<br>EGDCAPEEK (SEQ ID NO: 184)<br>LLKYRAREPVTKAE (SEQ ID NO: 185) | Kawashima et al. Hum Immunol. 59(1):1-14 (1998).<br>Tahara et al. Clin Cancer Res. 5(8):2236-41 (1999).<br>Tanzarella et al. Cancer Res. 59(11):2668-74 (1999).<br>Breckpot et al. J Immunol. 172(4):2232-7 (2004). |

TABLE 8-continued

| Lung cancer | | | |
|---|---|---|---|
| No. | Tumor-associated antigen | Immunogenic epitopes | Sources |
| | | | Chaux et al. J Exp Med. 89(5):767-78 (1999). |
| 14 | MAGE-A6 (squamous cell lung carcinoma) | MVKISGGPR (SEQ ID NO: 237)<br>EVDPIGHVY (SEQ ID NO: 238)<br>REPVTKAEML (SEQ ID NO: 239)<br>EGDCAPEEK (SEQ ID NO: 240)<br>ISGGPRISY (SEQ ID NO: 241)<br>LLKYRAREPVTKAE (SEQ ID NO: 242) | Zorn et al. EurJ Immunol. 29(2):602-7 (1999).<br>Benlalam et al. J Immunol. 171(11):6283-9 (2003).<br>Tanzarella et al. Cancer Res. 59(11):2668-74 (1999).<br>Breckpot et al. J Immunol. 172(4):2232-7 (2004).<br>Vantomme et al. Cancer Immun. 3:17 (2003).<br>Chaux et al. J Exp Med. 189(5):767-78 (1999). |
| 15 | Sp17 | ILDSSEEDK (SEQ ID NO: 152) | Chiriya-Internati et al. Int J Cancer. 107(5):863-5 (2003). |
| 16 | TAG-1 | SLGWLFLLL (SEQ ID NO: 159)<br>LSRLSNRLL (SEQ ID NO: 160) | Adair et al. J Immunother. 31(1):7-17 (2008). |
| 17 | TAG-2 | LSRLSNRLL (SEQ ID NO: 161) | Adair et al. J Immunother. 31(1):7-17 (2008). |
| 18 | TRAG-3 | CEFHACWPAFTVLGE (SEQ ID NO: 192) | Janjic et al. J Immunol. 177(4):2717-27 (2006). |
| 19 | XAGE-1b/ GAGED2a (non-small cell lung cancer) | RQKKIRIQL (SEQ ID NO: 243)<br>HLGSRQKKIRIQLRSQ (SEQ ID NO: 244)<br>CATWKVICKSCISQTPG (SEQ ID NO: 245) | Ohue etal. Int J Cancer. 131(5):E649-58 (2012).<br>Shimono et al. Int J Oncol. 30(4):835-40 (2007). |
| 20 | c-myc | SSPQGSPEPL (SEQ ID NO: 193) | Helm et al. PLoS ONE 8(10): e77375 (2013). |
| 21 | cyclin B1 | ILIDWLVQV (SEQ ID NO: 194) | Andersen et al. Cancer Immunol Immunother 60: 227 (2011). |
| 22 | Her2/Neu | HLYQGCQVV (SEQ ID NO: 89)<br>YLVPQQGFFC (SEQ ID NO: 90)<br>PLQPEQLQV (SEQ ID NO: 91)<br>TLEEITGYL (SEQ ID NO: 92)<br>ALIHHNTHL (SEQ ID NO: 93)<br>PLTSIISAV (SEQ ID NO: 94)<br>VLRENTSPK (SEQ ID NO: 95)<br>TYLPTNASL (SEQ ID NO: 96) | Nakatsuka et al. Mod. Pathol. 19(6):804-814 (2006).<br>PiIs et al. Br. J. Cancer 96(3):485-91 (2007).<br>Scardino et al. EurJ Immunol. 31(11):3261-70 (2001).<br>Scardino et al. J Immunol. 168(11):5900-6 (2002).<br>Kawashima et al. Cancer Res. 59(2):431-5 (1999).<br>Okugawa et al. EurJ Immunol. 30(11):3338-46 (2000). |
| 23 | MUC1 | STAPPVHNV (SEQ ID NO: 129)<br>LLLLTVLTV (SEQ ID NO: 130) | Brossart et al. Blood, 93(12), 4309-4317 (1999). |
| 24 | p53 | VVPCEPPEV (SEQ ID NO: 88) | Hung et al. Immunol. Rev. 222:43-69 (2008).<br>http://cancerimmunity.org/peptide/mutations/ |
| 25 | p62 | FLKNVGESV (SEQ ID NO: 195) | Reuschenbach et al. Cancer Immunol. Immunother. 58:1535-1544 (2009) |
| 26 | Survivin | ELTLGEFLKL (SEQ ID NO: 196) | Reuschenbach et al. Cancer Immunol. Immunother. 58:1535-1544 (2009) |

TABLE 9

| Prostate cancer | | | |
|---|---|---|---|
| No. | Tumor-associated antigen | Immunogenic epitopes | Sources |
| 1 | DKK1 | ALGGHPLLGV (SEQ ID NO: 198) | Qian et al. Blood. 110(5)1 587-94 (2007). |
| 2 | ENAH (hMena) | TMNGSKSPV (SEQ ID NO: 162) | Di Modugno et al. Int. J. Cancer. 109(6):909-18 (2004). |
| 3 | Kallikrein 4 | FLGYLILGV (SEQ ID NO: 22); SVSESDTIRSISIAS (SEQ ID NO: 23); LLANGRMPTVLQCVN (SEQ ID NO: 24); and RMPTVLQCVNVSVVS (SEQ ID NO: 25) | Wilkinson et al. Cancer Immunol Immunother. 61(2):169-79 (2012). Hural et al. J. Immunol. 169(1):557-65 (2002). |
| 4 | PSMA | NYARTEDFF (SEQ ID NO: 223) | Horiguchi et al. Clin Cancer Res. 8(12):3885-92 (2002). |
| 5 | STEAP1 | MIAVFLPIV (SEQ ID NO: 246) and HQQYFYKIPILVINK (SEQ ID NO: 247) | Rodeberg et al. Clin. Cancer Res. 11(12):4545-52 (2005). Kobayashi et al. Cancer Res. 67(11):5498-504 (2007). |
| 6 | PAP | FLFLLFFWL (SEQ ID NO: 248); TLMSAMTNL (SEQ ID NO: 249); and ALDVYNGLL (SEQ ID NO: 250) | Olson et al. Cancer Immunol Immunother. 59(6):943-53 (2010). |
| 7 | PSA (prostate carcinoma) | FLTPKKLQCV (SEQ ID NO: 251) and VISNDVCAQV (SEQ ID NO: 252) | Correale et al. J Natl. Cancer Inst. 89(4):293-300 (1997). |
| 8 | NY-ESO-1 | HLA-A2-restricted p157-165 (SLLMWITQC) (SEQ ID NO: 42), HLA-Cw3-restricted p92-100 (LAMP-FATPM) (SEQ ID NO: 43) and HLA-Cw6-restricted p80-88 (ARGPESRLL) (SEQ ID NO: 44) MLMAQEALAFL (SEQ ID NO: 45) YLAMPFATPME (SEQ ID NO: 46) ASGPGGGAPR (SEQ ID NO: 47) LAAQERRVPR (SEQ ID NO: 48) TVSGNILTIR (SEQ ID NO: 49) APRGPHGGAASGL (SEQ ID NO: 50) MPFATPMEAEL (SEQ ID NO: 51) KEFTVSGNILTI (SEQ ID NO: 52) MPFATPMEA (SEQ ID NO: 53) FATPMEAEL (SEQ ID NO: 54) FATPMEAELAR (SEQ ID NO: 55) SLLMWITQCFLPVF (SEQ ID NO: 56) LLEFYLAMPFATPMEAEL-ARRSLAQ (SEQ ID NO: 57) EFYLAMPFATPM (SEQ ID NO: 58) PGVLLKEFTVSGNILTIRL-TAADHR (SEQ ID NO: 59) RLLEFYLAMPFA (SEQ ID NO: 60) QGAMLAAQERRVPRAAE-VPR (SEQ ID NO: 61) PFATPMEAELARR (SEQ ID NO: 62) PGVLLKEFTVSGNILTIRLT (SEQ ID NO: 63) VLLKEFTVSG (SEQ ID NO: 64) AADHRQLQLSISSCLQQL (SEQ ID NO: 65) LKEFTVSGNILTIRL (SEQ ID NO: 66) KEFTVSGNILT (SEQ ID NO: 67) LLEFYLAMPFATPM (SEQ ID NO: 68) | peptide Jager et al. Proc. Natl. Acad. Scie. U.S.A. 103(39): 14453-8 (2006). Gnjatic et al. PNAS September 26, 2000 vol. 97 no. 20 p. 10919 Jager et al. J Exp Med. 187(2):265-70 (1998). Chen et al. J Immunol. 165(2):948-55 (2000). Valmori et al. Cancer Res. 60(16):4499-506 (2000). Aarnoudse et al. Int J Cancer. 82(3):442-8 (1999). Eikawa et al. Int J Cancer. 132(2):345-54 (2013). Wang et al. J Immunol. 161(7):3598-606 (1998). Matsuzaki et al. Cancer Immunol Immunother. 57(8)1185-95 (2008). Ebert et al. Cancer Res. 69(3):1046-54 (2009). Eikawa et al. Int J Cancer. 132(2):345-54 (2013). Knights et al. Cancer Immunol Immunother. 58(3):325-38 (2009). Jager et al. Cancer Immun. 2:12 (2002). Zeng et al. Proc Natl Acad Sci U S A. 98(7):3964-9 (2001). Mandic et al. J Immunol. 174(3):1751-9 (2005). Chen et al. Proc Natl Aced Sci U S A. 101(25):9363-8 (2004). Ayyoub et al. Clin Cancer Res. 16(18):4607-15 (2010). Sieger et al. J Immunol. 172(8):5095-102 (2004). Mizote et al. Vaccine. 28(32):5338-46 (2010). Jager et al. J Exp Med. 191(4):625-30 (2000). |

TABLE 9-continued

| Prostate cancer | | | |
|---|---|---|---|
| No. | Tumor-associated antigen | Immunogenic epitopes | Sources |
| | | AGATGGRGPRGAGA (SEQ ID NO: 69) | Zarour et al. Cancer Res. 60(17):4946-52 (2000). Zeng et al. J Immunol. 165(2):1153-9 (2000). Bioley et al. Clin Cancer Res. 15(13):4467-74 (2009). Zarour et al. Cancer Res. 62(1):213-8 (2002). Hasegawa et al. Clin Cancer Res. 12(6):1921-7 (2006). |
| 9 | BAGE-1 (non-small cell lung carcinoma) | AARAVFLAL (SEQ ID NO: 165) | Boel et al. Immunity. 2(2):167-75 (1995). |
| 10 | GAGE-1,2,8 (non-small cell lunch carcinoma) | YRPRPRRY (SEQ ID NO: 236) | Van den Eynde et al. J Exp Med. 182(3):689-98 (1995). |
| 11 | GAGE-3,4,5,6,7 (lung squamous cell carcinoma and lung adenocarcinoma) | YYWPRPRRY (SEQ ID NO: 427) | De Backer et al. Cancer Res. 59(13):3157-65 (1999). |
| 12 | HERV-K-MEL | MLAVISCAV (SEQ ID NO: 132) | Schiavetti et al. Cancer Res. 62(19):5510-6 (2002). |
| 13 | KK-LC-1 | RQKRILVNL (SEQ ID NO: 133) | Fukuyama et al. Cancer Res. 66(9):4922-8 (2006). |
| 14 | KM-HN-1 | NYNNFYRFL (SEQ ID NO: 134)<br>EYSKECLKEF (SEQ ID NO: 135)<br>EYLSLSDKI (SEQ ID NO: 136) | Fukuyama et al. Cancer Res. 66(9):4922-8 (2006). Monji et al. Clin Cancer Res. 10(18 Pt 1):6047-57 (2004). |
| 15 | LAGE-1 | MLMAQEALAFL (SEQ ID NO: 137)<br>SLLMWITQC (SEQ ID NO: 138)<br>LAAQERRVPR (SEQ ID NO: 139)<br>ELVRRILSR (SEQ ID NO: 140)<br>APRGVRMAV (SEQ ID NO: 141)<br>SLLMWITQCFLPVF (SEQ ID NO: 142)<br>QGAMLAAQERRVPRAAEVP-R (SEQ ID NO: 143)<br>AADHRQLQLSISSCLQQL (SEQ ID NO: 144)<br>CLSRRPWKRSWSAGSCPG-MPHL (SEQ ID NO: 145)<br>ILSRDAAPLPRPG (SEQ ID NO: 146)<br>AGATGGRGPRGAGA (SEQ ID NO: 147) | Aarnoudse et al. Int J Cancer. 82(3):442-8 (1999). Rimoldi et al. J Immunol. 165(12):7253-61 (2000). Wang et al. J Immunol. 161(7):3598-606 (1998). Sun et al. Cancer Immunol Immunother. 55(6):644-52 (2006). Sieger et al. Cancer Gene Ther. 11(3):227-36 (2004). Zeng et al. Proc Natl Acad Sci U S A. 98(7):3964-9 (2001). Sieger et al. J Immunol. 172(8):5095-102 (2004). Jager et al. J Exp Med. 191(4):625-30 (2000). Sieger et al. J Immunol. 170(3)1490-7 (2003). Wang et al. Immunity. 20(1):107-18 (2004). Hasegawa et al. Clin Cancer Res. 12(6):1921-7 (2006). |
| 16 | Sp17 | ILDSSEEDK (SEQ ID NO: 152) | Chiriva-Internati et al. Int J Cancer. 107(5):863-5 (2003). |

TABLE 10

| Kidney cancer | | | |
|---|---|---|---|
| No. | Tumor-associated antigen | Immunogenic epitopes | Sources |
| 1 | FGF5 | NTYASPRFK (SEQ ID NO: 253) | Hanada et al. Nature. 427(6971):252-6 (2004). |
| 2 | Hepsin | SLLSGDWVL (SEQ ID NO: 214); GLQLGVQAV (SEQ ID NO: 215); and PLTEYIQPV (SEQ ID NO: 216) | Guo et al. Scand J Immunol. 78(3):248-57 (2013). |
| 3 | Intestinal carboxyl esterase | SPRWWPTCL (SEQ ID NO: 217) | Ronsin et al. J Immunol. 163(1):483-90 (1999). |
| 4 | M-CSF | LPAVVGLSPGEQEY (SEQ ID NO: 221) | Probst-Kepper et al. J Exp Med. 193(10):1189-98 (2001). |
| 5 | RU2AS | LPRWPPPQL (SEQ ID NO: 199) | Van Den Eynde et al. J. Exp. Med. 190(12):1793-800 (1999). |
| 6 | h5p70-2 (renal cell carcinoma) | SLFEGIDIYT (SEQ ID NO: 254) | Gaudin et al. J. Immunol. 162(3):1730-8 (1999). |
| 7 | Mannan-MUC-1 (renal cell carcinoma) | PDTRPAPGSTAPPAHGVTSA (SEQ ID NO: 128) STAPPVHNV (SEQ ID NO: 129) LLLLTVLTV (SEQ ID NO: 130) PGSTAPPAHGVT (SEQ ID NO: 131) | Loveland et al. Clin. Cancer Res. 12(3 Pt 1):869-77 (2006). Loveland et al. Clin. Cancer Res. 12(3 Pt 1):869-77 (2006). Godelaine et al. Cancer Immunol Immunother. 56(6)753-9 (2007). Ma et al. Int J Cancer. 129(10):2427-34 (2011). Wen et al. Cancer Sci. 102(8):1455-61(2011). Jerome et al. J Immunol. 151(3):1654-62 (1993). Brossart et al. Blood. 93(12):4309-17 (1999). Hiltbold et al. Cancer Res. 58(22):5066-70 (1998). |
| 8 | MAGE-A9 (renal cell carcinoma) | ALSVMGVYV (SEQ ID NO: 255) | Oehlrich et al. Int J Cancer. 117(2):256-64 (2005). |

TABLE 11

| Melanoma | | | |
|---|---|---|---|
| No. | Tumor-associated antigen | Immunogenic epitopes | Sources |
| 1 | Hepsin | SLLSGDWVL (SEQ ID NO: 214); GLQLGVQA (SEQ ID NO: 215); and PLTEYIQPV (SEQ ID NO: 216) | Guo et al. Scand J Immunol. 78(3):248-57 (2013). |
| 2 | ARTC1 | YSVYFNLPADTIYTN (SEQ ID NO: 256) | Wang et al J Immunol. 174(5):2661-70 (2005). |
| 3 | B-RAF | EDLTVKIGDFGLATEKSRWSG (SEQ ID NO: 257) SHQFEQLS (SEQ ID NO: 258) | Sharkey et al. Cancer Res. 64(5):1595-9 (2004). |
| 4 | beta-catenin | SYLDSGIHF (SEQ ID NO: 259) | Robbins et al. J. Exp. Med. 183(3):1185-92 (1996). |
| 5 | Cdc27 | FSWAMDLDPKGA (SEQ ID NO: 260) | Wang et al. Science. 284(5418):1351-4 (1999). |
| 6 | CDK4 | ACDPHSGHFV (SEQ ID NO: 261) | Wölfel et al. Science. 269(5228):1281-4 (1995). |
| 7 | CDK12 | CILGKLFTK (SEQ ID NO: 262) | Robbins et al. Nat Med. 19(6):747-52. (2013). |

TABLE 11-continued

| Melanoma | | | |
|---|---|---|---|
| No. | Tumor-associated antigen | Immunogenic epitopes | Sources |
| 8 | CDKN2A | AVCPVVTWLR (SEQ ID NO: 263) | Huang et al. J Immunol. 172(10):6057-64 (2004). |
| 9 | CLPP | ILDKVLVHL (SEQ ID NO: 264) | Corbière et al. Cancer Res. 71(4):1253-62 (2011). |
| 10 | CSNK1A1 | GLFGDIYLA (SEQ ID NO: 265) | Robbins et al. Nat Med. 19(6):747-52 (2013). |
| 11 | FN1 | MIFEKHGFRRTTPP (SEQ ID NO: 266) | Wang et al. J Exp Med. 195(11)1 397-406 (2003). |
| 12 | GAS7 | SLADEAEVYL (SEQ ID NO: 267) | Robbins, et al. Nat Med. 19(6):747-52 (2013). |
| 13 | GPNMB | TLDWLLQTPK (SEQ ID NO: 268) | Lennerz et al. Proc. Natl. Acad. Sci. U.S.A. 102(44):16013-8 (2005). |
| 14 | HAUS3 | ILNAMIAKI (SEQ ID NO: 269) | Robbins et al. Nat Med. 19(6):747-52 (2013). |
| 15 | LDLR-fucosyltransferase | WRRAPAPGA (SEQ ID NO: 270) and PVTWRRAPA (SEQ ID NO: 271) | Wang et al. J Exp Med. 189(10)1 659-68 (1999). |
| 16 | MART2 | FLEGNEVGKTY (SEQ ID NO: 272) | Kawakami et al. J Immunol. 166(4):2871-7 (2001). |
| 17 | MATN | KTLTSVFQK (SEQ ID NO: 273) | Robbins et al. Nat Med. 19(6):747-52 (2013). |
| 18 | MUM-1 | EEKLIVVLF (SEQ ID NO: 274) | Coulie et al. Proc. Natl. Acad. Sci. U.S.A. 92(17):7976-80 (1995). |
| 19 | MUM-2 | SELFRSGLDSY (SEQ ID NO: 275) and FRSGLDSYV (SEQ ID NO: 276) | and Chiari et al. Cancer Res. 59(22):5785-92 (1999). |
| 20 | MUM-3 | EAFIQPITR (SEQ ID NO: 277) | Baurain et al. J. Immunol. 164(11):6057-66 (2000). |
| 21 | neo-PAP | RVIKNSIRLTL (SEQ ID NO: 278) | Topalian et al. Cancer Res. 62(19):5505-9 (2002). |
| 22 | Myosin class I | KINKNPKYK (SEQ ID NO: 279) | Zorn, et al. Eur. J. Immunol. 29(2):592-601 (1999). |
| 23 | PPP1R3B | YTDFHCQYV (SEQ ID NO: 280) | Robbins et al. Nat Med. 19(6):747-52 (2013). Lu et al. J Immunol. 190(12):6034-42 (2013). |
| 24 | PRDX5 | LLLDDLLVSI (SEQ ID NO: 281) | Sensi et al. Cancer Res. 65(2):632-40 (2005). |
| 25 | PTPRK | PYYFAAELPPRNLPEP (SEQ ID NO: 282) | Novellino et al. J. Immunol. 170(12):6363-70 (2003). |
| 26 | N-ras | ILDTAGREEY (SEQ ID NO: 283) | Linard et al. J. Immunol. 168(9):4802-8 (2002). |
| 27 | RBAF600 | RPHVPESAF (SEQ ID NO: 284) | Lennerz et al. Proc. Natl. Acad. Sci. U.S.A. 102(44):16013-8 (2005). |
| 28 | SIRT2 | KIFSEVTLK (SEQ ID NO: 285) | Lennerz et al. Proc. Natl. Acad. Sci. U.S.A. 102(44):16013-8 (2005). |
| 29 | SNRPD1 | SHETVIIEL (SEQ ID NO: 286) | Lennerz et al. Proc. Natl. Acad. Sci. U.S.A. 102(44):16013-8 (2005). |
| 30 | Triosephosphate isomerase | GELIGILNAAKVPAD (SEQ ID NO: 287) | Pieper et al. J Exp Med. 189(5):757-66 (1999). |
| 31 | OA1 | LYSACFWWL (SEQ ID NO: 288) | Touloukian et al. J. Immunol. 170(3):1579-85 (2003). |

TABLE 11-continued

Melanoma

| No. | Tumor-associated antigen | Immunogenic epitopes | Sources |
|---|---|---|---|
| 32 | RAB38/NY-MEL-1 | VLHWDPETV (SEQ ID NO: 289) | Walton et al. J Immunol. 177(11):8212-8 (2006). |
| 33 | TRP-1/gp75 | MSLQRQFLR (SEQ ID NO: 290); ISPNSVFSQWRVVCDSLEDY; (SEQ ID NO: 291) SLPYWNFATG (SEQ ID NO: 292); and SQWRVVCDSLEDYDT (SEQ ID NO: 293) | Touloukian et al. Cancer Res. 62(18):5144-7 (2002). Robbins et al. J. Immunol. (10):6036-47 (2002). Osen et al. PLoS One. 5(11):e14137 (2010). |
| 34 | TRP-2 | SVYDFFVWL (SEQ ID NO: 294); TLDSQVMSL (SEQ ID NO: 295); LLGPGRPYR (SEQ ID NO: 296); ANDPIFVVL (SEQ ID NO: 297); QCTEVRADTRPWSGP (SEQ ID NO: 298); and ALPYWNFATG (SEQ ID NO: 299) | Parkhurst et al. Cancer Res. 58(21):4895-901 (1998). Noppen et al. Int. J. Cancer. 87(2):241-6 (2000). Wang et al. J. Exp. Med. 1184(6):2207-16 (1996). Wang et al. J. Immunol. 160(2):890-7 (1998). Castelli et al. J. Immunol. 162(3):1739-48 (1999). Paschen et al. Clin. Cancer Res. (14):5241-7 (2005). Robbins et al. J. Immunol. 169(10):6036-47 (2002). |
| 35 | tyrosinase | KCDICTDEY (SEQ ID NO: 300); SSDYVIPIGTY (SEQ ID NO: 301); MLLAVLYCL (SEQ ID NO: 302); CLLWSFQTSA (SEQ ID NO: 303); YMDGTMSQV (SEQ ID NO: 304); AFLPWHRLF (SEQ ID NO: 305); IYMDGTADFSF (SEQ ID NO: 306); QCSGNFMGF (SEQ ID NO: 307); TPRLPSSADVEF (SEQ ID NO: 308); LPSSADVEF (SEQ ID NO: 309); LHHAFVDSIF (SEQ ID NO: 310); SEIWRDIDF (SEQ ID NO: 311); QNILLSNAPLGPQFP (SEQ ID NO: 312); SYLQDSDPDSFQD (SEQ ID NO: 313); and FLLHHAFVDSIFEQWLQRHRP (SEQ ID NO: 314) | Kittlesen et al. J. Immunol. 160(5):2099-106 (1998). Kawakami et al. J. Immunol. (12):6985-92 (1998). Wölfel et al. Eur. J. Immunol. 24(3):759-64 (1994). Riley et al. J. Immunother. 24(3):212-20 (2001). Skipper et al. J. Exp. Med. 183(2):527-34 (1996). Kang et al. J. Immunol. 155(3):1343-8 (1995). Dalet et al. Proc. Natl. Acad. Sci. U.S.A. 108(29):E323-31 (2011) Lennerz et al. Proc. Natl. Acad. Sci. U.S.A. 102(44)1 6013-8 (2005). Benlalam et al. J. Immunol. 171(11):6283-9 (2003). Morel et al. Int. J. Cancer. 83(6):755-9 (1999). Brichard et al. Eur. J. Immunol. 26(1):224-30 (1996). Topalian et al. J. Exp. Med. (5):1965-71 (1996). Kobayashi et al. Cancer Res. 58(2):296-301 (1998). |
| 36 | Melan-A/MART-1 | YTTAEEAAGIGILTVILGVLLLIG CWYCRR (SEQ ID NO: 315) | Meng et al. J. Immunother. 23:525-534 (2011) |
| 37 | gp100/Pmel17 | ALNFPGSQK (SEQ ID NO: 316) ALNFPGSQK (SEQ ID NO: 317) VYFFLPDHL (SEQ ID NO: 318) RTKQLYPEW (SEQ ID NO: 319) HTMEVTVYHR (SEQ ID NO: 320) SSPGCQPPA (SEQ ID NO: 321) VPLDCVLYRY (SEQ ID NO: 322) LPHSSSHWL (SEQ ID NO: 322) SNDGPTLI(SEQ ID NO: 323) GRAMLGTHTMEVTVY (SEQ ID NO: 324) WNRQLYPEVVTEAQRLD (SEQ ID NO: 325) TTEWVETTARELPIPEPE | El Hage et al. Proc. Natl. Acad. Sci. U.S.A. 105(29)10119-24 (2008). Kawashima et al. Hum Immunol. 59(1):1-14 (1998). Robbins et al. J Immunol. 159(1):303-8 (1997). Sensi et al. Tissue Antigens. 59(4):273-9 (2002). Lennerz et al. Proc Natl Aced Sci USA. 102(44):16013-8 (2005). Benlalam et al. J Immunol. 171(11):6283-9 (2003). Vigneron et al. Tissue Antigens. 65(2):156-62 (2005). Castelli et al. J Immunol. 162(3):1739-48 (1999). |

TABLE 11-continued

| Melanoma | | | |
|---|---|---|---|
| No. | Tumor-associated antigen | Immunogenic epitopes | Sources |
| | | (SEQ ID NO: 326) TGRAMLGTHTMEVTVYH (SEQ ID NO: 327) | Touloukian et al. J Immunol. 164(7):3535-42 (2000). Parkhurst et al. J Immunother. 27(2):79-91 (2004). Lapointe et al. J Immunol. 167(8):4758-64 (2001). Kobayashi et al. Cancer Res. 61(12):4773-8 (2001). |
| 38 | NY-ESO-1 | HLA-A2-restricted peptide p157-165 (SLLMWITQC) (SEQ ID NO: 42), HLA-Cw3-restricted p92-100 (LAMP-FATPM) (SEQ ID NO: 43) and HLA-Cw6-restricted p80-88 (ARGPESRLL) (SEQ ID NO: 44) MLMAQEALAFL (SEQ ID NO: 45) YLAMPFATPME (SEQ ID NO: 46) ASGPGGGAPR (SEQ ID NO: 47) LAAQERRVPR (SEQ ID NO: 48) TVSGNILTIR (SEQ ID NO: 49) APRGPHGGAASGL (SEQ ID NO: 50) MPFATPMEAEL (SEQ ID NO: 51) KEFTVSGNILTI (SEQ ID NO: 52) MPFATPMEA (SEQ ID NO: 53) FATPMEAEL (SEQ ID NO: 54) FATPMEAELAR (SEQ ID NO: 55) SLLMWITQCFLPVF (SEQ ID NO: 56) LLEFYLAMPFATPMEAELARRSLAQ (SEQ ID NO: 57) EFYLAMPFATPM (SEQ ID NO: 58) PGVLLKEFTVSGNILTIRLTAADHR (SEQ ID NO: 59) RLLEFYLAMPFA (SEQ ID NO: 60) QGAMLAAQERRVPRAAEVPR (SEQ ID NO: 61) PFATPMEAELARR (SEQ ID NO: 62) PGVLLKEFTVSGNILTIRLT (SEQ ID NO: 63) VLLKEFTVSG (SEQ ID NO: 64) AADHRQLQLSISSCLQQL (SEQ ID NO: 65) LKEFTVSGNILTIRL (SEQ ID NO: 66) KEFTVSGNILT (SEQ ID NO: 67) LLEFYLAMPFATPM (SEQ ID NO: 68) AGATGGRGPRGAGA (SEQ ID NO: 69) | Jager et al. Proc. Natl. Acad. Scie. U.S.A. 103(39):14453-8 (2006). Gnjatic et al. PNAS Sep. 26, 2000 vol. 97 no. 20 p. 10919 Jager et al. J Exp Med. 187(2):265-70 (1998). Chen et al. J Immunol. 165(2):948-55 (2000). Valmori et al. Cancer Res. 60(16):4499-506 (2000). Aarnoudse et al. Int J Cancer. 82(3):442-8 (1999). Eikawa et al. Int J Cancer. 132(2):345-54 (2013). Wang et al. J Immunol. 161(7):3598-606 (1998). Matsuzaki et al. Cancer Immunol Immunother. 57(8)1185-95 (2008). Ebert et al. Cancer Res. 69(3):1046-54 (2009). Eikawa et al. Int J Cancer. 132(2):345-54 (2013). Knights et al. Cancer Immunol Immunother. 58(3):325-38 (2009). Jäger et al. Cancer Immun. 2:12 (2002). Zeng et al. Proc Natl Acad Sci USA. 98(7):3964-9 (2001). Mandic et al. J Immunol. 174(3):1751-9 (2005). Chen et al. Proc Natl Aced Sci USA. 101(25):9363-8 (2004). Ayyoub et al. Clin Cancer Res. 16(18):4607-15 (2010). Slager et al. J Immunol. 172(8):5095-102 (2004). Mizote et al. Vaccine. 28(32):5338-46 (2010). Jager et al. J Exp Med. 191(4):625-30 (2000). Zarour et al. Cancer Res. 60(17):4946-52 (2000). Zeng et al. J Immunol. 165(2):1153-9 (2000). Bioley et al. Clin Cancer Res. 15(13):4467-74 (2009). Zarour et al. Cancer Res. 62(1):213-8 (2002). Hasegawa et al. Clin Cancer Res. 12(6):1921-7 (2006). |
| 39 | BAGE-1 | AARAVFLAL (SEQ ID NO: 165) | Boel et al. Immunity. 2(2):167-75 (1995). |
| 40 | GAGE-1, 2, 8 | YRPRPRRY (SEQ ID NO: 236) | Van den Eynde et al. J Exp Med. 182(3):689-98 (1995). |
| 41 | GAGE-3, 4, 5, 6, 7 (cutaneous melanoma) | YYWPRPRRY (SEQ ID NO: 427) | De Backer et al. Cancer Res. 59(13):3157-65 (1999). |
| 42 | GnTVf | VLPDVFIRC(V) (SEQ ID NO: 328) | Guilloux et al. J Exp Med. 183(3):1173-83 (1996). |

TABLE 11-continued

| Melanoma | | | |
|---|---|---|---|
| No. | Tumor-associated antigen | Immunogenic epitopes | Sources |
| 43 | HERV-K-MEL | MLAVISCAV (SEQ ID NO: 132) | Schiavetti et al. Cancer Res. 62(19):5510-6 (2002). |
| 44 | KK-LC-1 | RQKRILVNL (SEQ ID NO: 133) | Fukuyama et al. Cancer Res. 66(9):4922-8 (2006). |
| 45 | KM-HN-1 | NYNNFYRFL (SEQ ID NO: 134)<br>EYSKECLKEF (SEQ ID NO: 135)<br>EYLSLSDKI (SEQ ID NO: 136) | Fukuyama et al. Cancer Res. 66(9):4922-8 (2006).<br>Monji et al. Clin Cancer Res. 10(18 Pt 1):6047-57 (2004). |
| 46 | LAGE-1 | MLMAQEALAFL (SEQ ID NO: 137)<br>SLLMWITQC (SEQ ID NO: 138)<br>LAAQERRVPR (SEQ ID NO: 139)<br>ELVRRILSR (SEQ ID NO: 140)<br>APRGVRMAV (SEQ ID NO: 141)<br>SLLMWITQCFLPVF (SEQ ID NO: 142)<br>QGAMLAAQERRVPRAAEVPR (SEQ ID NO: 143)<br>AADHRQLQLSISSCLQQL (SEQ ID NO: 144)<br>CLSRRPWKRSWSAGSCPGMPHL (SEQ ID NO: 145)<br>ILSRDAAPLPRPG (SEQ ID NO: 146)<br>AGATGGRGPRGAGA (SEQ ID NO: 147) | Aarnoudse et al. Int J Cancer. 82(3):442-8 (1999).<br>Rimoldi et al. J Immunol. 165(12):7253-61 (2000).<br>Wang et al. J Immunol. 161(7):3598-606 (1998).<br>Sun et al. Cancer Immunol Immunother. 55(6):644-52 (2006).<br>Slager et al. Cancer Gene Ther. 11(3):227-36 (2004).<br>Zeng et al. Proc Natl Acad Sci USA. 98(7):3964-9 (2001).<br>Slager et al. J Immunol. 172(8):5095-102 (2004).<br>Jager et al. J Exp Med. 191(4):625-30 (2000).<br>Slager et al. J Immunol. 170(3):1490-7 (2003).<br>Wang et al. Immunity. 20(1):107-18 (2004).<br>Hasegawa et al. Clin Cancer Res. 12(6):1921-7 (2006). |
| 47 | LY6K | RYCNLEGPPI (SEQ ID NO: 329)<br>KVVTEPYCVIAAVKIFPRFFMVAKQ (SEQ ID NO: 330)<br>KCCKIRYCNLEGPPINSSVF (SEQ ID NO: 331) | Suda et al. Cancer Sci. 98(11)1 803-8 (2007).<br>Tomita et al. Oncoimmunology. 3:e28100 (2014). |
| 48 | MAGE-Al | EADPTGHSY (SEQ ID NO: 166)<br>KVLEYVIKV (SEQ ID NO: 167)<br>SLFRAVITK (SEQ ID NO: 168)<br>EVYDGREHSA (SEQ ID NO: 169)<br>RVRFFFPSL (SEQ ID NO: 170)<br>REPVTKAEML (SEQ ID NO: 171)<br>KEADPTGHSY (SEQ ID NO: 172)<br>DPARYEFLW (SEQ ID NO: 173)<br>ITKKVADLVGF (SEQ ID NO: 174)<br>SAFPTTINF (SEQ ID NO: 175)<br>SAYGEPRKL (SEQ ID NO: 176)<br>TSCILESLFRAVITK (SEQ ID NO: 177)<br>PRALAETSYVKVLEY (SEQ ID NO: 178)<br>FLLLKYRAREPVTKAE (SEQ ID NO: 179)<br>EYVIKVSARVRF (SEQ ID NO: 180) | Traversari et al. J Exp Med. 176(5):1453-7 (1992).<br>Ottaviani et al. Cancer Immunol Immunother. 54(12)1214-20 (2005).<br>Pascolo et al. Cancer Res. 61(10):4072-7 (2001).<br>Chaux et al. J Immunol. 163(5):2928-36 (1999).<br>Luiten et al. Tissue Antigens. 55(2):149-52 (2000).<br>Luiten et al. Tissue Antigens. 56(1):77-81 (2000).<br>Tanzarella et al. Cancer Res. 59(11):2668-74 (1999).<br>Stroobant et al. Eur J Immunol. 42(6):1417-28 (2012).<br>Corbière et al. Tissue Antigens. 63(5):453-7 (2004).<br>Goodyear et al. Cancer Immunol Immunother. 60(12)1751-61 (2011).<br>van der Bruggen et al. Eur J Immunol. 24(9):2134-40 (1994).<br>Wang et al. Cancer Immunol Immunother. 56(6):807-18 (2007).<br>Chaux et al. J Exp Med. 189(5):767-78 (1999).<br>Chaux et al. EurJ Immunol. 31(6)1 910-6 (2001). |
| 49 | MAGE-A6 | MVKISGGPR (SEQ ID NO: 237)<br>EVDPIGHVY (SEQ ID NO: 238)<br>REPVTKAEML (SEQ ID NO: 239)<br>EGDCAPEEK (SEQ ID NO: 240)<br>ISGGPRISY (SEQ ID NO: 241) | Zorn et al. EurJ Immunol. 29(2):602-7 (1999).<br>Benlalam et al. J Immunol. 171(11):6283-9 (2003).<br>Tanzarella et al. Cancer Res. |

TABLE 11-continued

| Melanoma | | | |
|---|---|---|---|
| No. | Tumor-associated antigen | Immunogenic epitopes | Sources |
| | | LLKYRAREPVTKAE (SEQ ID NO: 242) | 59(11):2668-74 (1999). Breckpot et al. J Immunol. 172(4):2232-7 (2004). Vantomme et al. Cancer Immun. 3:17 (2003). Chaux et al. J Exp Med. 189(5):767-78 (1999). |
| 50 | MAGE-A10 | GLYDGMEHL (SEQ ID NO: 332) DPARYEFLW (SEQ ID NO: 333) | Huang et al. J Immunol. 162(11):6849-54 (1999). Chaux et al. J Immunol. 163(5):2928-36 (1999). |
| 51 | MAGE-A12 | FLWGPRALV (SEQ ID NO: 334) VRIGHLYIL (SEQ ID NO: 335) EGDCAPEEK (SEQ ID NO: 336) REPFTKAEMLGSVIR (SEQ ID NO: 337) AELVHFLLLKYRAR (SEQ ID NO: 338) | van der Bruggen et al. Eur J Immunol. 24(12):3038-43 (1994). Heidecker et al. J Immunol. 164(11):6041-5 (2000). Panelli et al. J Immunol. 164(8):4382-92 (2000). Breckpot et al. J Immunol. 172(4):2232-7 (2004). Wang et al. Cancer Immunol Immunother. 56(6):807-18 (2007). Chaux et al. J Exp Med. 189(5):767-78 (1999). |
| 52 | MAGE-C2 | LLFGLALIEV (SEQ ID NO: 339) ALKDVEERV (SEQ ID NO: 340) SESIKKKVL (SEQ ID NO: 341) ASSTLYLVF (SEQ ID NO: 342) SSTLYLVFSPSSFST (SEQ ID NO: 343) | Ma et al. Int J Cancer. 109(5):698-702 (2004). Godelaine et al. Cancer Immunol Immunother. 56(6)753-9 (2007). Ma et al. Int J Cancer. 129(10):2427-34 (2011). Wen et al. Cancer Sc. 102(8)1 455-61 (2011). |
| 53 | NA88-A | QGQHFLQKV (SEQ ID NO: 344) | Moreau-Aubry et al. J Exp Med. 191(9):1617-24 (2000). |
| 54 | Sp17 | ILDSSEEDK (SEQ ID NO: 152) | Chiriva-Internati et al. Int J Cancer. 107(5):863-5 (2003). |
| 55 | SSX-2 | KASEKIFYV (SEQ ID NO: 186) EKIQKAFDDIAKYFSK (SEQ ID NO: 187) FGRLQGISPKI (SEQ ID NO: 188) WEKMKASEKIFYVYMKRK (SEQ ID NO: 189) KIFYVYMKRKYEAMT (SEQ ID NO: 190) KIFYVYMKRKYEAM (SEQ ID NO: 191) | Ayyoub et al. J Immunol. 168(4):1717-22 (2002). Ayyoub et al. J Immunol. 172(11):7206-11 (2004). Neumann et al. Cancer Immunol Immunother. 60(9): 1333-46 (2011). Ayyoub et al. Clin Immunol. 114(1):70-8 (2005). Neumann et al. Int J Cancer. 112(4):661-8 (2004). Ayyoub et al. J Clin Invest. 113(8):1225-33 (2004). |
| 56 | SSX-4 | INKTSGPKRGKHAVVTHRLRE (SEQ ID NO: 153) YFSKKEWEKMKSSEKIVYVY (SEQ ID NO: 154) MKLNYEVMTKLGFKVTLPPF (SEQ ID NO: 155) KHAVVTHRLRERKQLVVYEEI (SEQ ID NO: 156) LGFKVTLPPFMRSKRAADFH (SEQ ID NO: 157) KSSEKIVYVYMKLNYEVMTK (SEQ ID NO: 158) | Ayyoub et al. J Immunol. 174(8):5092-9 (2005). Valmori et al. Clin Cancer Res. 12(2):398-404 (2006). |
| 57 | TRAG-3 | CEFHACWPAFTVLGE (SEQ ID NO: 192) | Janjic et al. J Immunol. 177(4):2717-27 (2006). |

TABLE 11-continued

| Melanoma | | | |
|---|---|---|---|
| No. | Tumor-associated antigen | Immunogenic epitopes | Sources |
| 58 | TRP2-INT2g | EVISCKLIKR (SEQ ID NO: 345) | Lupetti et al. J Exp Med. 188(6):1005-16 (1998). |
| 59 | pbk | GSPFPAAVI (SEQ ID NO: 346) | Morgan et al., J. Immunol. 171:3287-3295 (2003) |

TABLE 12

| Squamous cell carcinoma | | | |
|---|---|---|---|
| No. | Tumor-associated antigen | Immunogenic epitopes | Sources |
| 1 | CASP-8 | FPSDSWCYF (SEQ ID NO: 347) | Mandruzzato et al. J. Exp. Med. 186(5):785-93 (1997). |
| 2 | p53 | VVPCEPPEV (SEQ ID NO: 88) | Ito et al. Int. J. Cancer. 120(12):2618-24 (2007). |

TABLE 12-continued

| Squamous cell carcinoma | | | |
|---|---|---|---|
| No. | Tumor-associated antigen | Immunogenic epitopes | Sources |
| 3 | SAGE | LYATVIHDI (SEQ ID NO: 348) | Miyahara et al. Clin Cancer Res. 11(15):5581-9 (2005). |

TABLE 13

| Chronic myeloid leukemia | | | |
|---|---|---|---|
| No. | Tumor-associated antigen | Immunogenic epitopes | Sources |
| 1 | BCR-ABL | SSKALQRPV (SEQ ID NO: 349); GFKQSSKAL (SEQ ID NO: 350); and ATGFKQSSKALQRPVAS (SEQ ID NO: 351); | Yotnda et al. J. Clin. Invest. 101(10)2290-6 (1998). Bosch et al. Blood. 88(9):3522-7 (1996). Makita et al. Leukemia. 16(12):2400-7 (2002). |
| 2 | dek-can | TMKQICKKEIRRLHQY (SEQ ID NO: 352) | Makita et al. Leukemia. 16(12):2400-7 (2002). |
| 3 | EFTUD2 | KILDAVVAQK (SEQ ID NO: 353) | Lennerz et al. Proc. Natl. Acad. Sci. U.S.A. 102(44):16013-8 (2005). |
| 4 | GAGE-3, 4, 5, 6, 7 | YYWPRPRRY (SEQ ID NO: 1427) | De Backer et al. Cancer Res. 59(13):3157-65 (1999). |

TABLE 14

| Acute lymphoblastic leukemia | | | |
|---|---|---|---|
| No. | Tumor-associated antigen | Immunogenic epitopes | Sources |
| 1 | ETV6-AML1 | RIAECILGM (SEQ ID NO: 354) and IGRIAECILGMNPSR (SEQ ID NO: 355) | Yotnda et al. J. Olin. Invest. (2):455-62 (1998). Yun et al. Tissue Antigens. 54(2):153-61 (1999). |
| 2 | GAGE-3, 4, 5, 6, 7 | YYWPRPRRY (SEQ ID NO: 427) | De Backer et al. Cancer Res. 59(13):3157-65 (1999). |

TABLE 15

| Acute myelogenous leukemia | | | |
|---|---|---|---|
| No. | Tumor-associated antigen | Immunogenic epitopes | Sources |
| 1 | FLT3-ITD | YVDFREYEYY (SEQ ID NO: 356) | Graf et al. Blood. 109(7):2985-8 (2007). |
| 2 | Cyclin-A1 | FLDRFLSCM (SEQ ID NO: 357) and SLIAAAAFCLA (SEQ ID NO: 358) | Ochsenreither et al. Blood. 119(23):5492-501 (2012). |
| 3 | GAGE-3, 4, 5, 6, 7 | YYWPRPRRY (SEQ ID NO: 427) | De Backer et al. Cancer Res. 59(13):3157-65 (1999). |

TABLE 16

| Chronic lymphocytic leukemia | | | |
|---|---|---|---|
| No. | Tumor-associated antigen | Immunogenic epitopes | Sources |
| 1 | FNDC3B | VVMSWAPPV (SEQ ID NO: 359) | Rajasagi et al. Blood. 124(3):453-62 (2014). |
| 2 | GAGE-3, 4, 5, 6, 7 | YYWPRPRRY (SEQ ID NO: 427) | De Backer et al. Cancer Res. 59(13):3157-65 (1999). |

TABLE 17

| Promyelocytic leukemia | | | |
|---|---|---|---|
| No. | Tumor-associated antigen | Immunogenic epitopes | Sources |
| 1 | pml-RARalpha | NSNHVASGAGEAAIETQSSSS EEIV (SEQ ID NO: 360) | Gambacorti-Passerini et al. Blood. 81(5):1369-75 (1993). |
| 2 | GAGE-3, 4, 5, 6, 7 | YYWPRPRRY (SEQ ID NO: 427) | De Backer et al. Cancer Res. 59(13):3157-65 (1999). |

TABLE 18

| Multiple myeloma | | | |
|---|---|---|---|
| No. | Tumor-associated antigen | Immunogenic epitopes | Sources |
| 1 | MAGE-C1 | ILFGISLREV (SEQ ID NO: 361) KVVEFLAML (SEQ ID NO: 362) SSALLSIFQSSPE (SEQ ID NO: 363) SFSYTLLSL (SEQ ID NO: 364) VSSFFSYTL (SEQ ID NO: 365) | Anderson et al. Cancer Immunol Immunother. 60(7):985-97 (2011). Nuber et al. Proc Natl Acad Sci USA. 107(34)1 5187-92 (2010). |
| 2 | NY-ESO-1 | HLA-A2-restricted peptide p157-165 (SLLMWITQC) (SEQ ID NO: 42), HLA-Cw3-restricted p92-100 (LAMP-FATPM) (SEQ ID NO: 43) and HLA-Cw6-restricted p80-88 (ARGPESRLL) (SEQ ID NO: 44) MLMAQEALAFL (SEQ ID NO: 45) | Jager et al. Proc. Natl. Acad. Scie. U.S.A. 103(39): 14453-8 (2006). Gnjatic et al. PNAS Sep. 26, 2000 vol. 97 no. 20 p. 10919 Jager et al. J Exp Med. 187(2):265-70 (1998). |

TABLE 18-continued

Multiple myeloma

| No. | Tumor-associated antigen | Immunogenic epitopes | Sources |
|---|---|---|---|
| | | YLAMPFATPME (SEQ ID NO: 46) | Chen et al. J Immunol. 165(2):948-55 |
| | | ASGPGGGAPR (SEQ ID NO: 47) | (2000). |
| | | LAAQERRVPR (SEQ ID NO: 48) | Valmori et al. Cancer Res. 60(16):4499-506 |
| | | TVSGNILTIR (SEQ ID NO: 49) | (2000). |
| | | APRGPHGGAASGL | Aarnoudse et al. Int J Cancer. |
| | | (SEQ ID NO: 50) | 82(3):442-8 (1999). |
| | | MPFATPMEAEL (SEQ ID NO: 51) | Eikawa et al. Int J Cancer. 132(2):345-54 |
| | | KEFTVSGNILTI | (2013). |
| | | (SEQ ID NO: 52) | Wang et al. J Immunol. 161(7):3598-606 |
| | | MPFATPMEA (SEQ ID NO: 53) | (1998). |
| | | FATPMEAEL (SEQ ID NO: 54) | Matsuzaki et al. Cancer Immunol |
| | | FATPMEAELAR | Immunother. 57(8)1185-95 (2008). |
| | | (SEQ ID NO: 55) | Ebert et al. Cancer Res. 69(3):1046-54 |
| | | SLLMWITQCFLPVF | (2009). |
| | | (SEQ ID NO: 56) | Eikawa et al. Int J Cancer. 132(2):345-54 |
| | | LLEFYLAMPFATPMEAELARRSLAQ | (2013). |
| | | (SEQ ID NO: 57) | Knights et al. Cancer Immunol |
| | | EFYLAMPFATPM | Immunother. 58(3):325-38 (2009). |
| | | (SEQ ID NO: 58) | Jäger et al. Cancer Immun. 2:12 (2002). |
| | | PGVLLKEFTVSGNILTIRLTAADHR | Zeng et al. Proc Natl Acad Sci U S A. |
| | | (SEQ ID NO: 59) | 98(7):3964-9 (2001). |
| | | RLLEFYLAMPFA | Mandic et al. J Immunol. 174(3):1751-9 |
| | | (SEQ ID NO: 60) | (2005). |
| | | QGAMLAAQERRVPRAAEVPR | Chen et al. Proc Natl Aced Sci U S A. |
| | | (SEQ ID NO: 61) | 101(25):9363-8 (2004). |
| | | PFATPMEAELARR | Ayyoub et al. Clin Cancer Res. |
| | | (SEQ ID NO: 62) | 16(18):4607-15 (2010). |
| | | PGVLLKEFTVSGNILTIRLT | Sieger et al. J Immunol. 172(8):5095-102 |
| | | (SEQ ID NO: 63) | (2004). |
| | | VLLKEFTVSG | Mizote et al. Vaccine. 28(32):5338-46 |
| | | (SEQ ID NO: 64) | (2010). |
| | | AADHRQLQLSISSCLQQL | Jager et al. J Exp Med. 191(4):625-30 |
| | | (SEQ ID NO: 65) | (2000). |
| | | LKEFTVSGNILTIRL | Zarour et al. Cancer Res. 60(17):4946-52 |
| | | (SEQ ID NO: 66) | (2000). |
| | | KEFTVSGNILT | Zeng et al. J Immunol. 165(2):1153-9 |
| | | (SEQ ID NO: 67) | (2000). |
| | | LLEFYLAMPFATPM | Bioley et al. Clin Cancer Res. |
| | | (SEQ ID NO: 68) | 15(13):4467-74 (2009). |
| | | AGATGGRGPRGAGA | Zarour et al. Cancer Res. 62(1):213-8 |
| | | (SEQ ID NO: 69) | (2002). |
| | | | Hasegawa et al. Clin Cancer Res. |
| | | | 12(6):1921-7 (2006). |
| 3 | LAGE-1 | MLMAQEALAFL | Aarnoudse et al. Int J Cancer. |
| | | (SEQ ID NO: 137) | 82(3):442-8 (1999). |
| | | SLLMWITQC | Rimoldi et al. J Immunol. 165(12):7253-61 |
| | | (SEQ ID NO: 138) | (2000). |
| | | LAAQERRVPR | Wang et al. J Immunol. 161(7):3598-606 |
| | | (SEQ ID NO: 139) | (1998). |
| | | ELVRRILSR | Sun et al. Cancer Immunol Immunother. |
| | | (SEQ ID NO: 140) | 55(6):644-52 (2006). |
| | | APRGVRMAV | Slager et al. Cancer Gene Ther. |
| | | (SEQ ID NO: 141) | 11(3):227-36 (2004). |
| | | SLLMWITQCFLPVF | Zeng et al. Proc Natl Acad Sci USA. |
| | | (SEQ ID NO: 142) | 98(7):3964-9 (2001). |
| | | QGAMLAAQERRVPRAAEVPR | Slager et al. J Immunol. 172(8):5095-102 |
| | | (SEQ ID NO: 143) | (2004). |
| | | AADHRQLQLSISSCLQQL | Jager et al. J Exp Med. 191(4):625-30 |
| | | (SEQ ID NO: 144) | (2000). |
| | | CLSRRPWKRSWSAGSCPGMPHL | Slager et al. J Immunol. 170(3):1490-7 |
| | | (SEQ ID NO: 145) | (2003). |
| | | ILSRDAAPLPRPG | Wang et al. Immunity. 20(1):107-18 |
| | | (SEQ ID NO: 146) | (2004). |
| | | AGATGGRGPRGAGA | Hasegawa et al. Clin Cancer Res. |
| | | (SEQ ID NO: 147) | 12(6):1921-7 (2006). |
| 4 | HERV-K-MEL | MLAVISCAV | Schiavetti et al. Cancer Res. |
| | | (SEQ ID NO: 132) | 62(19):5510-6 (2002). |
| 5 | KK-LC-1 | RQKRILVNL | Fukuyama et al. Cancer Res. |
| | | (SEQ ID NO: 133) | 66(9):4922-8 (2006). |
| 6 | KM-HN-1 | NYNNFYRFL | Fukuyama et al. Cancer Res. |
| | | (SEQ ID NO: 134) | 66(9):4922-8 (2006). |

TABLE 18-continued

| Multiple myeloma | | | |
|---|---|---|---|
| No. | Tumor-associated antigen | Immunogenic epitopes | Sources |
| | | EYSKECLKEF (SEQ ID NO: 135) EYLSLSDKI (SEQ ID NO: 136) | Monji et al. Clin Cancer Res. 10(18 Pt 1):6047-57 (2004). |
| 7 | Sp17 | ILDSSEEDK (SEQ ID NO: 152) | Chiriva-Internati et al. Int J Cancer. 107(5):863-5 (2003). |

TABLE 19

| B-cell lymphoma | | | |
|---|---|---|---|
| No. | Tumor-associated antigen | Immunogenic epitopes | Source |
| 1 | D393-CD20 | KPLFRRMSSLELVIA (SEQ ID NO: 366) | Vauchy et al. Int J Cancer. 137(1):116-26 (2015). |

TABLE 20

| Bladder carcinoma | | | |
|---|---|---|---|
| No. | Tumor-associated antigen | Immunogenic epitopes | Sources |
| 1 | BAGE-1 | AARAVFLAL (SEQ ID NO: 165) | Boel et al. Immunity. 2(2):167-75 (1995). |
| 2 | GAGE-1, 2, 8 | YRPRPRRY (SEQ ID NO: 236) | Van den Eynde et al. J Exp Med. 182(3):689-98 (1995). |
| 3 | GAGE-3, 4, 5, 6, 7 | YYWPRPRRY (SEQ ID NO: 427) | De Backer et al. Cancer Res. 59(13):3157-65 (1999). |
| 4 | MAGE-A4 (transitional cell carcinoma of urinary bladder) | EVDPASNTY (SEQ ID NO: 148) GVYDGREHTV (SEQ ID NO: 149) NYKRCFPVI (SEQ ID NO: 150) SESLKMIF (SEQ ID NO: 151) | Kobayashi et al. Tissue Antigens. 62(5):426-32 (2003). Duffour et al. Eur J Immunol. 29(10):3329-37 (1999). Miyahara et al. Clin Cancer Res. 11(15):5581-9 (2005). Ottaviani et al. Cancer Immunol Immunother. 55(7):867-72 (2006). Zhang et al. Tissue Antigens. 60(5):365-71 (2002). |
| 5 | MAGE-A6 | MVKISGGPR (SEQ ID NO: 237) EVDPIGHVY (SEQ ID NO: 238) REPVTKAEML (SEQ ID NO: 239) EGDCAPEEK (SEQ ID NO: 240) ISGGPRISY (SEQ ID NO: 241) LLKYRAREPVTKAE (SEQ ID NO: 242) | Zorn et al. Eur J Immunol. 29(2):602-7 (1999). Benlalam et al. J Immunol. 171(11):6283-9 (2003). Tanzarella et al. Cancer Res. 59(11):2668-74 (1999). Breckpot et al. J Immunol. 172(4):2232-7 (2004). Vantomme et al. Cancer Immun. 3:17 (2003). Chaux et al. J Exp Med. 189(5):767-78 (1999). |
| 6 | SAGE | LYATVIHDI (SEQ ID NO: 348) | Miyahara et al. Clin Cancer Res. 11(15):5581-9 (2005). |
| 7 | NY-ESO-1 | HLA-A2-restricted peptide p157-165 (SLLMWITQC) (SEQ ID NO: 42), HLA-Cw3-restricted p92-100 (LAMP-FATPM) (SEQ ID NO: 43) and HLA-Cw6-restricted p80-88 | Jager et al. Proc. Natl. Acad. Scie. U.S.A. 103(39): 14453-8 (2006). Gnjatic et al. PNAS Sep. 26, 2000 vol. 97 no. 20 p. 10919 |

TABLE 20-continued

Bladder carcinoma

| No. | Tumor-associated antigen | Immunogenic epitopes | Sources |
|---|---|---|---|
| | | (ARGPESRLL) | Jager et al. J Exp Med. 187(2):265-70 |
| | | (SEQ ID NO: 44) | (1998). |
| | | MLMAQEALAFL | Chen et al. J Immunol. 165(2):948-55 |
| | | (SEQ ID NO: 45) | (2000). |
| | | YLAMPFATPME | Valmori et al. Cancer Res. 60(16):4499-506 |
| | | (SEQ ID NO: 46) | (2000). |
| | | ASGPGGGAPR | Aarnoudse et al. Int J Cancer. |
| | | (SEQ ID NO: 47) | 82(3):442-8 (1999). |
| | | LAAQERRVPR (SEQ ID NO: 48) | Eikawa et al. Int J Cancer. 132(2):345-54 |
| | | TVSGNILTIR (SEQ ID NO: 49) | (2013). |
| | | APRGPHGGAASGL | Wang et al. J Immunol. 161(7):3598-606 |
| | | (SEQ ID NO: 50) | (1998). |
| | | MPFATPMEAEL | Matsuzaki et al. Cancer Immunol |
| | | (SEQ ID NO: 51) | Immunother. 57(8)1185-95 (2008). |
| | | KEFTVSGNILTI | Ebert et al. Cancer Res. 69(3):1046-54 |
| | | (SEQ ID NO: 52) | (2009). |
| | | MPFATPMEA (SEQ ID NO: 53) | Eikawa et al. Int J Cancer. 132(2):345-54 |
| | | FATPMEAEL (SEQ ID NO: 54) | (2013). |
| | | FATPMEAELAR | Knights et al. Cancer Immunol |
| | | (SEQ ID NO: 55) | Immunother. 58(3):325-38 (2009). |
| | | SLLMWITQCFLPVF | Jäger et al. Cancer Immun. 2:12 (2002). |
| | | (SEQ ID NO: 56) | Zeng et al. Proc Natl Acad Sci USA. |
| | | LLEFYLAMPFATPMEAELARRSLAQ | 98(7):3964-9 (2001). |
| | | (SEQ ID NO: 57) | Mandic et al. J Immunol. 174(3):1751-9 |
| | | EFYLAMPFATPM | (2005). |
| | | (SEQ ID NO: 58) | Chen et al. Proc Natl Aced Sci USA. |
| | | PGVLLKEFTVSGNILTIRLTAADHR | 101(25):9363-8 (2004). |
| | | (SEQ ID NO: 59) | Ayyoub et al. Clin Cancer Res. |
| | | RLLEFYLAMPFA | 16(18):4607-15 (2010). |
| | | (SEQ ID NO: 60) | Slager et al. J Immunol. 172(8):5095-102 |
| | | QGAMLAAQERRVPRAAEVPR | (2004). |
| | | (SEQ ID NO: 61) | Mizote et al. Vaccine. 28(32):5338-46 |
| | | PFATPMEAELARR | (2010). |
| | | (SEQ ID NO: 62) | Jager et al. J Exp Med. 191(4):625-30 |
| | | PGVLLKEFTVSGNILTIRLT | (2000). |
| | | (SEQ ID NO: 63) | Zarour et al. Cancer Res. 60(17):4946-52 |
| | | VLLKEFTVSG | (2000). |
| | | (SEQ ID NO: 64) | Zeng et al. J Immunol. 165(2):1153-9 |
| | | AADHRQLQLSISSCLQQL | (2000). |
| | | (SEQ ID NO: 65) | Bioley et al. Clin Cancer Res. |
| | | LKEFTVSGNILTIRL | 15(13):4467-74 (2009). |
| | | (SEQ ID NO: 66) | Zarour et al. Cancer Res. 62(1):213-8 |
| | | KEFTVSGNILT | (2002). |
| | | (SEQ ID NO: 67) | Hasegawa et al. Clin Cancer Res. |
| | | LLEFYLAMPFATPM | 12(6):1921-7 (2006). |
| | | (SEQ ID NO: 68) | |
| | | AGATGGRGPRGAGA | |
| | | (SEQ ID NO: 69) | |
| 8 | LAGE-1 | MLMAQEALAFL | Aarnoudse et al. Int J Cancer. |
| | | (SEQ ID NO: 137) | 82(3):442-8 (1999). |
| | | SLLMWITQC | Rimoldi et al. J Immunol. 165(12):7253-61 |
| | | (SEQ ID NO: 138) | (2000). |
| | | LAAQERRVPR | Wang et al. J Immunol. 161(7):3598-606 |
| | | (SEQ ID NO: 139) | (1998). |
| | | ELVRRILSR | Sun et al. Cancer Immunol Immunother. |
| | | (SEQ ID NO: 140) | 55(6):644-52 (2006). |
| | | APRGVRMAV | Slager et al. Cancer Gene Ther. |
| | | (SEQ ID NO: 141) | 11(3):227-36 (2004). |
| | | SLLMWITQCFLPVF | Zeng et al. Proc Natl Acad Sci USA. |
| | | (SEQ ID NO: 142) | 98(7):3964-9 (2001). |
| | | QGAMLAAQERRVPRAAEVPR | Slager et al. J Immunol. 172(8):5095-102 |
| | | (SEQ ID NO: 143) | (2004). |
| | | AADHRQLQLSISSCLQQL | Jager et al. J Exp Med. 191(4):625-30 |
| | | (SEQ ID NO: 144) | (2000). |
| | | CLSRRPWKRSWSAGSCPGMPHL | Slager et al. J Immunol. 170(3):1490-7 |
| | | (SEQ ID NO: 145) | (2003). |
| | | ILSRDAAPLPRPG | Wang et al. Immunity. 20(1):107-18 |
| | | (SEQ ID NO: 146) | (2004). |
| | | AGATGGRGPRGAGA | Hasegawa et al. Clin Cancer Res. |
| | | (SEQ ID NO: 147) | 12(6):1921-7 (2006). |
| 9 | HERV-K-MEL | MLAVISCAV | Schiavetti et al. Cancer Res. |
| | | (SEQ ID NO: 132) | 62(19):5510-6 (2002). |

TABLE 20-continued

| Bladder carcinoma | | | |
|---|---|---|---|
| No. | Tumor-associated antigen | Immunogenic epitopes | Sources |
| 10 | KK-LC-1 | RQKRILVNL (SEQ ID NO: 133) | Fukuyama et al. Cancer Res. 66(9):4922-8 (2006). |
| 11 | KM-HN-1 | NYNNFYRFL (SEQ ID NO: 134) EYSKECLKEF (SEQ ID NO: 135) EYLSLSDKI (SEQ ID NO: 136) | Fukuyama et al. Cancer Res. 66(9):4922-8 (2006). Monji et al. Clin Cancer Res. 10(18 Pt 1):6047-57 (2004). |
| 12 | Sp17 | ILDSSEEDK (SEQ ID NO: 152) | Chiriva-Internati et al. Int J Cancer. 107(5):863-5 (2003). |

TABLE 21

| Head and neck cancer | | | |
|---|---|---|---|
| No. | Tumor-associated antigen | Immunogenic epitopes | Sources |
| 1 | BAGE-1 (head and neck squamous cell carcinoma) | AARAVFLAL (SEQ ID NO: 165) | Boel et al. Immunity. 2(2):167-75 (1995). |
| 2 | GAGE-1, 2, 8 | YRPRPRRY (SEQ ID NO: 236) | Van den Eynde et al. J Exp Med. 182(3):689-98 (1995). |
| 3 | GAGE-3, 4, 5, 6, 7 | YYWPRPRRY (SEQ ID NO: 427) | De Backer et al. Cancer Res. 59(13):3157-65 (1999). |
| 4 | LY6K | RYCNLEGPPI (SEQ ID NO: 329) KVVTEPYCVIAAVKIFPRFFMVAKQ (SEQ ID NO: 330) KCCKIRYCNLEGPPINSSVF (SEQ ID NO: 331) | Suda et al. Cancer Sci. 98(11)1 803-8 (2007). Tomita et al. Oncoimmunology. 3:e28100 (2014). |
| 5 | MAGE-A3 (head and neck squamous cell carcinoma) | EVDPIGHLY (SEQ ID NO: 367) FLWGPRALV (SEQ ID NO: 368) KVAELVHFL (SEQ ID NO: 369) TFPDLESEF (SEQ ID NO: 370) VAELVHFLL (SEQ ID NO: 371) MEVDPIGHLY (SEQ ID NO: 372) REPVTKAEML (SEQ ID NO: 373) AELVHFLLL (SEQ ID NO: 374) WQYFFPVIF (SEQ ID NO: 375) EGDCAPEEK (SEQ ID NO: 376) KKLLTQHFVQENYLEY (SEQ ID NO: 377) RKVAELVHFLLLKYR (SEQ ID NO: 378) ACYEFLWGPRALVETS (SEQ ID NO: 379) VIFSKASSSLQL (SEQ ID NO: 380) VFGIELMEVDPIGHL (SEQ ID NO: 381) GDNQIMPKAGLLIIV (SEQ ID NO: 382) TSYVKVLHHMVKISG (SEQ ID NO: 383) RKVAELVHFLLLKYRA (SEQ ID NO: 384) | Gaugler et al. J Exp Med. 179(3):921-30 (1994). van der Bruggen et al. Eur J Immunol. 24(12):3038-43 (1994). Kawashima et al. Hum Immunol. 59(1):1-14 (1998). Oiso et al. Int J Cancer. 81(3):387-94 (1999). Miyagawa et al. Oncology. 70(1):54-62 (2006). Bilsborough et al. Tissue Antigens. 60(1):16-24 (2002). Schultz et al. Tissue Antigens. 57(2):103-9 (2001). Tanzarella et al. Cancer Res. 59(11):2668-74 (1999). Schultz et al. J Exp Med. 195(4):391-9 (2002). Herman et al. Immunogenetics. 43(6):377-83 (1996). Russo et al. Proc Natl Acad Sci USA. 97(5):2185-90 (2000). Breckpot et al. J Immunol. 172(4):2232-7 (2004). Schultz et al. Cancer Res. 60(22):6272-5 (2000). Cesson et al. Cancer Immunol Immunother. 60(1):23-35 (2011). Schultz et al. J Immunol. 172(2)1304-10 (2004). Zhang et al. J Immunol. 171(1):219-25 (2003). Cesson et al. Cancer Immunol Immunother. 60(1):23-35 (2010). Kobayashi et al. Cancer Res. 61(12):4773-8 (2001). |

TABLE 21-continued

Head and neck cancer

| No. | Tumor-associated antigen | Immunogenic epitopes | Sources |
|---|---|---|---|
| | | FLLLKYRAREPVTKAE (SEQ ID NO: 385) | Cesson et al. Cancer Immunol Immunother. 60(1):23-35 (2011). Consogno et al. Blood. 101(3):1038-44 (2003). Manici et al. J Exp Med. 189(5):871-6 (1999). Chaux et al. J Exp Med. 189(5):767-78 (1999). |
| 6 | MAGE-A6 | MVKISGGPR (SEQ ID NO: 237) EVDPIGHVY (SEQ ID NO: 238) REPVTKAEML (SEQ ID NO: 239) EGDCAPEEK (SEQ ID NO: 240) ISGGPRISY (SEQ ID NO: 241) LLKYRAREPVTKAE (SEQ ID NO: 242) | Zorn et al. Eur J Immunol. 29(2):602-7 (1999). Benlalam et al. J Immunol. 171(11):6283-9 (2003). Tanzarella et al. Cancer Res. 59(11):2668-74 (1999). Breckpot et al. J Immunol. 172(4):2232-7 (2004). Vantomme et al. Cancer Immun. 3:17 (2003). Chaux et al. J Exp Med. 189(5):767-78 (1999). |
| 7 | SAGE | LYATVIHDI (SEQ ID NO: 348) | Miyahara et al. Clin Cancer Res. 11(15):5581-9 (2005). |

TABLE 22

Esophageal cancer

| No. | Tumor-associated antigen | Immunogenic epitopes | Sources |
|---|---|---|---|
| 1 | GAGE-3, 4, 5, 6, 7 (Esophageal squamous cell carcinoma and esophageal adenocarcinoma) | YYWPRPRRY (SEQ ID NO: 427) | De Backer et al. Cancer Res. 59(13):3157-65 (1999). |
| 2 | MAGE-A2 | YLQLVFGIEV (SEQ ID NO: 181) EYLQLVFGI (SEQ ID NO: 182) REPVTKAEML (SEQ ID NO: 183) EGDCAPEEK (SEQ ID NO: 184) LLKYRAREPVTKAE (SEQ ID NO: 185) | Kawashima et al. Hum Immunol. 59(1):1-14 (1998). Tahara et al. Clin Cancer Res. 5(8):2236-41 (1999). Tanzarella et al. Cancer Res. 59(11):2668-74 (1999). Breckpot et al. J Immunol. 172(4):2232-7 (2004). Chaux et al. J Exp Med. 189(5):767-78 (1999). |
| 3 | MAGE-A6 | MVKISGGPR (SEQ ID NO: 237) EVDPIGHVY (SEQ ID NO: 238) REPVTKAEML (SEQ ID NO: 239) EGDCAPEEK (SEQ ID NO: 240) ISGGPRISY (SEQ ID NO: 241) LLKYRAREPVTKAE (SEQ ID NO: 242) | Zorn et al. Eur J Immunol. 29(2):602-7 (1999). Benlalam et al. J Immunol. 171(11):6283-9 (2003). Tanzarella et al. Cancer Res. 59(11):2668-74 (1999). Breckpot et al. J Immunol. 172(4):2232-7 (2004). Vantomme et al. Cancer Immun. 3:17 (2003). Chaux et al. J Exp Med. 189(5):767-78 (1999). |
| 4 | NY-ESO-1 | HLA-A2-restricted peptide p157-165 (SLLMWITQC) (SEQ ID NO: 42), HLA-Cw3-restricted p92-100 (LAMP-FATPM) (SEQ ID NO: 43)and HLA-Cw6-restricted p80-88 (ARGPESRLL) (SEQ ID NO: 44) | Jager et al. Proc. Natl. Acad. Scie. U.S.A. 103(39):14453-8 (2006). Gnjatic et al. PNAS Sep. 26, 2000 vol. 97 no. 20 p. 10919 Jager et al. J Exp Med. 187(2):265-70 (1998). |

TABLE 22-continued

Esophageal cancer

| No. | Tumor-associated antigen | Immunogenic epitopes | Sources |
|---|---|---|---|
| | | MLMAQEALAFL (SEQ ID NO: 45) | Chen et al. J Immunol. 165(2):948-55 (2000). |
| | | YLAMPFATPME (SEQ ID NO: 46) | Valmori et al. Cancer Res. 60(16):4499-506 (2000). |
| | | ASGPGGGAPR (SEQ ID NO: 47) | Aarnoudse et al. Int J Cancer. 82(3):442-8 (1999). |
| | | LAAQERRVPR (SEQ ID NO: 48) | Eikawa et al. Int J Cancer. 132(2):345-54 (2013). |
| | | TVSGNILTIR (SEQ ID NO: 49) | Wang et al. J Immunol. 161(7):3598-606 (1998). |
| | | APRGPHGGAASGL (SEQ ID NO: 50) | Matsuzaki et al. Cancer Immunol Immunother. 57(8)1185-95 (2008). |
| | | MPFATPMEAEL (SEQ ID NO: 51) | Ebert et al. Cancer Res. 69(3):1046-54 (2009). |
| | | KEFTVSGNILTI (SEQ ID NO: 52) | Eikawa et al. Int J Cancer. 132(2):345-54 (2013). |
| | | MPFATPMEA (SEQ ID NO: 53) | Knights et al. Cancer Immunol Immunother. 58(3):325-38 (2009). |
| | | FATPMEAEL (SEQ ID NO: 54) | Jäger et al. Cancer Immun. 2:12 (2002). |
| | | FATPMEAELAR (SEQ ID NO: 55) | Zeng et al. Proc Natl Acad Sci U S A. 98(7):3964-9 (2001). |
| | | SLLMWITQCFLPVF (SEQ ID NO: 56) | Mandic et al. J Immunol. 174(3):1751-9 (2005). |
| | | LLEFYLAMPFATPMEAELARRSLAQ (SEQ ID NO: 57) | Chen et al. Proc Natl Aced Sci U S A. 101(25):9363-8 (2004). |
| | | EFYLAMPFATPM (SEQ ID NO: 58) | Ayyoub et al. Clin Cancer Res. 16(18):4607-15 (2010). |
| | | PGVLLKEFTVSGNILTIRLTAADHR (SEQ ID NO: 59) | Slager et al. J Immunol. 172(8):5095-102 (2004). |
| | | RLLEFYLAMPFA (SEQ ID NO: 60) | Mizote et al. Vaccine. 28(32):5338-46 (2010). |
| | | QGAMLAAQERRVPRAAEVPR (SEQ ID NO: 61) | Jager et al. J Exp Med. 191(4):625-30 (2000). |
| | | PFATPMEAELARR (SEQ ID NO: 62) | Zarour et al. Cancer Res. 60(17):4946-52 (2000). |
| | | PGVLLKEFTVSGNILTIRLT (SEQ ID NO: 63) | Zeng et al. J Immunol. 165(2):1153-9 (2000). |
| | | VLLKEFTVSG (SEQ ID NO: 64) | Bioley et al. Clin Cancer Res. 15(13):4467-74 (2009). |
| | | AADHRQLQLSISSCLQQL (SEQ ID NO: 65) | Zarour et al. Cancer Res. 62(1):213-8 (2002). |
| | | LKEFTVSGNILTIRL (SEQ ID NO: 66) | Hasegawa et al. Clin Cancer Res. 12(6):1921-7 (2006). |
| | | KEFTVSGNILT (SEQ ID NO: 67) | |
| | | LLEFYLAMPFATPM (SEQ ID NO: 68) | |
| | | AGATGGRGPRGAGA (SEQ ID NO: 69) | |
| 5 | LAGE-1 | MLMAQEALAFL (SEQ ID NO: 137) | Aarnoudse et al. Int J Cancer. 82(3):442-8 (1999). |
| | | SLLMWITQC (SEQ ID NO: 138) | Rimoldi et al. J Immunol. 165(12):7253-61 (2000). |
| | | LAAQERRVPR (SEQ ID NO: 139) | Wang et al. J Immunol. 161(7):3598-606 (1998). |
| | | ELVRRILSR (SEQ ID NO: 140) | Sun et al. Cancer Immunol Immunother. 55(6):644-52 (2006). |
| | | APRGVRMAV (SEQ ID NO: 141) | Slager et al. Cancer Gene Ther. 11(3):227-36 (2004). |
| | | SLLMWITQCFLPVF (SEQ ID NO: 142) | Zeng et al. Proc Natl Acad Sci U S A. 98(7):3964-9 (2001). |
| | | QGAMLAAQERRVPRAAEVPR (SEQ ID NO: 143) | Slager et al. J Immunol. 172(8):5095-102 (2004). |
| | | AADHRQLQLSISSCLQQL (SEQ ID NO: 144) | Jager et al. J Exp Med. 191(4):625-30 (2000). |
| | | CLSRRPWKRSWSAGSCPGMPHL (SEQ ID NO: 145) | Slager et al. J Immunol. 170(3):1490-7 (2003). |
| | | ILSRDAAPLPRPG (SEQ ID NO: 146) | Wang et al. Immunity. 20(1):107-18 (2004). |
| | | AGATGGRGPRGAGA (SEQ ID NO: 147) | Hasegawa et al. Clin Cancer Res. 12(6):1921-7 (2006). |

TABLE 22-continued

| Esophageal cancer | | | |
|---|---|---|---|
| No. | Tumor-associated antigen | Immunogenic epitopes | Sources |
| 6 | HERV-K-MEL | MLAVISCAV (SEQ ID NO: 132) | Schiavetti et al. Cancer Res. 62(19):5510-6 (2002). |
| 7 | KK-LC-1 | RQKRILVNL (SEQ ID NO: 133) | Fukuyama et al. Cancer Res. 66(9):4922-8 (2006). |
| 8 | KM-HN-1 | NYNNFYRFL (SEQ ID NO: 134) EYSKECLKEF (SEQ ID NO: 135) EYLSLSDKI (SEQ ID NO: 136) | Fukuyama et al. Cancer Res. 66(9):4922-8 (2006). Monji et al. Clin Cancer Res. 10(18 Pt 1):6047-57 (2004). |
| 9 | Sp17 | ILDSSEEDK (SEQ ID NO: 152) | Chiriva-Internati et al. Int J Cancer. 107(5):863-5 (2003). |

TABLE 23

| Brain cancer | | | |
|---|---|---|---|
| No. | Tumor-associated antigen | Immunogenic epitopes | Sources |
| 1 | TAG-1 | SLGWLFLLL (SEQ ID NO: 159) LSRLSNRLL (SEQ ID NO: 160) | Adair et al. J Immunother. 31(1):7-17 (2008). |
| 2 | TAG-2 | LSRLSNRLL (SEQ ID NO: 161) | Adair et al. J Immunother. 31(1):7-17 (2008). |

TABLE 24

| Pharynx cancer | | | |
|---|---|---|---|
| No. | Tumor-associated antigen | Immunogenic epitopes | Sources |
| 1 | TAG-1 | SLGWLFLLL (SEQ ID NO: 159) LSRLSNRLL (SEQ ID NO: 160) | Adair et al. J Immunother. 31(1):7-17 (2008). |
| 2 | TAG-2 | LSRLSNRLL (SEQ ID NO: 161) | Adair et al. J Immunother. 31(1):7-17 (2008). |

TABLE 25

| Tumors of the tongue | | | |
|---|---|---|---|
| No. | Tumor-associated antigen | Immunogenic epitopes | Sources |
| 1 | TAG-1 | SLGWLFLLL (SEQ ID NO: 159) LSRLSNRLL (SEQ ID NO: 160) | Adair et al. J Immunother. 31(1):7-17 (2008). |

TABLE 25-continued

| Tumors of the tongue | | | |
|---|---|---|---|
| No. | Tumor-associated antigen | Immunogenic epitopes | Sources |
| 2 | TAG-2 | LSRLSNRLL (SEQ ID NO: 161) | Adair et al. J Immunother. 31(1):7-17 (2008). |

TABLE 26

| Synovial cell sarcoma | | | |
|---|---|---|---|
| No. | Tumor-associated antigen | Immunogenic epitopes | Sources |
| 1 | NY-ESO-1 | HLA-A2-restricted peptide p157-165 (SLLMWITQC) (SEQ ID NO: 42), HLA-Cw3-restricted p92-100 (LAMP-FATPM) (SEQ ID NO: 43) and HLA-Cw6-restricted p80-88 (ARGPESRLL) (SEQ ID NO: 44) MLMAQEALAFL (SEQ ID NO: 45) YLAMPFATPME (SEQ ID NO: 46) ASGPGGGAPR (SEQ ID NO: 47) LAAQERRVPR (SEQ ID NO: 48) TVSGNILTIR (SEQ ID NO: 49) APRGPHGGAASGL (SEQ ID NO: 50) MPFATPMEAEL (SEQ ID NO: 51) KEFTVSGNILTI (SEQ ID NO: 52) | Jager et al. Proc. Natl. Acad. Scie. U.S.A. 103(39): 14453-8 (2006). Gnjatic et al. PNAS Sept. 26, 2000 vol. 97 no. 20 p. 10919 Jager et al. J Exp Med. 187(2): 265-70 (1998). Chen et al. J Immunol. 165(2): 948-55 (2000). Valmori et al. Cancer Res. 60(16): 4499-506 (2000). Aarnoudse et al. Int J Cancer. 82(3):442-8 (1999). Eikawa et al. Int J Cancer. 132(2): 345-54 (2013). Wang et al. J Immunol. 161(7): 3598-606 (1998). Matsuzaki et al. |

TABLE 26-continued

Synovial cell sarcoma

| No. | Tumor-associated antigen | Immunogenic epitopes | Sources |
|---|---|---|---|
| | | MPFATPMEA (SEQ ID NO: 53)<br>FATPMEAEL (SEQ ID NO: 54)<br>FATPMEAELAR (SEQ ID NO: 55)<br>SLLMWITQCFLPVF (SEQ ID NO: 56)<br>LLEFYLAMPFATPMEAELARRSLAQ (SEQ ID NO: 57)<br>EFYLAMPFATPM (SEQ ID NO: 58)<br>PGVLLKEFTVSGNILTIRLTAADHR (SEQ ID NO: 59)<br>RLLEFYLAMPFA (SEQ ID NO: 60)<br>QGAMLAAQERRVPRAAEVPR (SEQ ID NO: 61)<br>PFATPMEAELARR (SEQ ID NO: 62)<br>PGVLLKEFTVSGNILTIRLT (SEQ ID NO: 63)<br>VLLKEFTVSG (SEQ ID NO: 64)<br>AADHRQLQLSISSCLQQL (SEQ ID NO: 65)<br>LKEFTVSGNILTIRL (SEQ ID NO: 66)<br>KEFTVSGNILT (SEQ ID NO: 67)<br>LLEFYLAMPFATPM (SEQ ID NO: 68)<br>AGATGGRGPRGAGA (SEQ ID NO: 69) | Cancer Immunol Immunother. 57(8)1185-95 (2008).<br>Ebert et al. Cancer Res. 69(3):1046-54 (2009).<br>Eikawa et al. Int J Cancer. 132(2):345-54 (2013).<br>Knights et al. Cancer Immunol Immunother. 58(3):325-38 (2009).<br>Jäger et al. Cancer Immun. 2:12 (2002).<br>Zeng et al. Proc Natl Acad Sci U S A. 98(7):3964-9 (2001).<br>Mandic et al. J Immunol. 174(3):1751-9 (2005).<br>Chen et al. Proc Natl Acad Sci U S A. 101(25):9363-8 (2004).<br>Ayyoub et al. Clin Cancer Res. 16(18):4607-15 (2010).<br>Slager et al. J Immunol. 172(8):5095-102 (2004).<br>Mizote et al. Vaccine. 28(32):5338-46 (2010).<br>Jager et al. J Exp Med. 191(4):625-30 (2000).<br>Zarour et al. Cancer Res. 60(17):4946-52 (2000).<br>Zeng et al. J Immunol. 165(2):1153-9 (2000).<br>Bioley et al. Clin Cancer Res. 15(13):4467-74 (2009).<br>Zarour et al. Cancer Res. 62(1):213-8(2002).<br>Hasegawa et al. Clin Cancer Res. 12(6):1921-7 (2006). |
| 2 | LAGE-1 | MLMAQEALAFL (SEQ ID NO: 137)<br>SLLMWITQC (SEQ ID NO: 138)<br>LAAQERRVPR (SEQ ID NO: 139)<br>ELVRRILSR (SEQ ID NO: 140)<br>APRGVRMAV (SEQ ID NO: 141)<br>SLLMWITQCFLPVF (SEQ ID NO: 142)<br>QGAMLAAQERRVPRAAEVPR (SEQ ID NO: 143)<br>AADHRQLQLSISSCLQQL (SEQ ID NO: 144)<br>CLSRRPWKRSWSAGSCPGMPHL (SEQ ID NO: 145)<br>ILSRDAAPLPRPG (SEQ ID NO: 146)<br>AGATGGRGPRGAGA (SEQ ID NO: 147) | Aarnoudse et al. Int J Cancer. 82(3):442-8 (1999).<br>Rimoldi et al. J Immunol. 165(12):7253-61 (2000).<br>Wang et al. J Immunol. 161(7):3598-606 (1998).<br>Sun et al. Cancer Immunol Immunother. 55(6):644-52 (2006).<br>Slager et al. Cancer Gene Ther. 11(3):227-36 (2004).<br>Zeng et al. Proc Natl Acad Sci U S A. 98(7):3964-9 (2001).<br>Slager et al. J Immunol. 172(8):5095-102 (2004).<br>Jager et al. J Exp Med. 191(4):625-30 (2000).<br>Slager et al. J Immunol. 170(3):1490-7 (2003).<br>Wang et al. Immunity. 20(1):107-18 (2004).<br>Hasegawa et al. Clin Cancer Res. 12(6):1921-7 (2006). |
| 3 | HERV-K-MEL | MLAVISCAV (SEQ ID NO: 132) | Schiavetti et al. Cancer Res. 62(19):5510-6 (2002). |
| 4 | KK-LC-1 | RQKRILVNL (SEQ ID NO: 133) | Fukuyama et al. Cancer Res. 66(9):4922-8 (2006). |
| 5 | KM-HN-1 | NYNNFYRFL (SEQ ID NO: 134)<br>EYSKECLKEF (SEQ ID NO: 135)<br>EYLSLSDKI (SEQ ID NO: 136) | Fukuyama et al. Cancer Res. 66(9):4922-8 (2006). |
| 6 | Sp17 | ILDSSEEDK (SEQ ID NO: 152) | Chiriva-Internati et al. Int J Cancer. 107(5):863-5 (2003). |

TABLE 27

Neuroblastoma

| No. | Tumor-associated antigen | Immunogenic epitopes | Sources |
|---|---|---|---|
| 1 | NY-ESO-1 | HLA-A2-restricted peptide p157-165 (SLLMWITQC) (SEQ ID NO: 42), HLA-Cw3-restricted p92-100 (LAMP-FATPM) (SEQ ID NO: 43) and HLA-Cw6-restricted p80-88 (ARGPESRLL) (SEQ ID NO: 44)<br>MLMAQEALAFL (SEQ ID NO: 45)<br>YLAMPFATPME (SEQ ID NO: 46)<br>ASGPGGGAPR (SEQ ID NO: 47)<br>LAAQERRVPR (SEQ ID NO: 48)<br>TVSGNILTIR (SEQ ID NO: 49)<br>APRGPHGGAASGL (SEQ ID NO: 50)<br>MPFATPMEAEL (SEQ ID NO: 51) | Jager et al. Proc. Natl. Acad. Scie. U.S.A. 103(39):14453-8 (2006).<br>Gnjatic et al. PNAS Sept. 26, 2000 vol. 97 no. 20 p. 10919<br>Jager et al. J Exp Med. 187(2):265-70 (1998).<br>Chen et al. J Immunol. 165(2):948-55 (2000).<br>Valmori et al. Cancer Res. 60(16):4499-506 (2000).<br>Aarnoudse et al. Int J Cancer. 82(3):442-8 (1999).<br>Eikawa et al. Int J Cancer. 132(2):345-54 (2013).<br>Wang et al. J Immunol. 161(7):3598-606 (1998).<br>Matsuzaki et al. Cancer Immunol Immunother. 57(8) |

TABLE 27-continued

| Neuroblastoma | | | |
|---|---|---|---|
| No. | Tumor-associated antigen | Immunogenic epitopes | Sources |
| | | KEFTVSGNILTI (SEQ ID NO: 52)<br>MPFATPMEA (SEQ ID NO: 53)<br>FATPMEAEL (SEQ ID NO: 54)<br>FATPMEAELAR (SEQ ID NO: 55)<br>SLLMWITQCFLPVF (SEQ ID NO: 56)<br>LLEFYLAMPFATPMEA-ELARRSLAQ (SEQ ID NO: 57)<br>EFYLAMPFATPM (SEQ ID NO: 58)<br>PGVLLKEFTVSGNILT-IRLTAADHR (SEQ ID NO: 59)<br>RLLEFYLAMPFA (SEQ ID NO: 60)<br>QGAMLAAQERRVPRAA-EVPR (SEQ ID NO: 61)<br>PFATPMEAELARR (SEQ ID NO: 62)<br>PGVLLKEFTVSGNIL-TIRLT (SEQ ID NO: 63)<br>VLLKEFTVSG (SEQ ID NO: 64)<br>AADHRQLQLSISSC-LQQL (SEQ ID NO: 65)<br>LKEFTVSGNILTIRL (SEQ ID NO: 66)<br>KEFTVSGNILT (SEQ ID NO: 67)<br>LLEFYLAMPFATPM (SEQ ID NO: 68)<br>AGATGGRGPRGAGA (SEQ ID NO: 69) | 1185-95 (2008).<br>Ebert et al. Cancer Res. 69(3):1046-54 (2009).<br>Eikawa et al. Int J Cancer. 132(2):345-54 (2013).<br>Knights et al. Cancer Immunol Immunother. 58(3): 325-38 (2009).<br>Jäger et al. Cancer Immun. 2:12 (2002).<br>Zeng et al. Proc Natl Acad Sci U S A. 98(7):3964-9 (2001).<br>Mandic et al. J Immunol. 174(3): 1751-9 (2005).<br>Chen et al. Proc Natl Acad Sci U S A. 101(25):9363-8 (2004).<br>Ayyoub et al. Clin Cancer Res. 16(18):4607-15 (2010).<br>Slager et al. J Immunol. 172(8):5095-102 (2004).<br>Mizote et al. Vaccine. 28(32):5338-46 (2010).<br>Jager et al. J Exp Med. 191(4):625-30 (2000).<br>Zarour et al. Cancer Res. 60(17):4946-52 (2000).<br>Zeng et al. J Immunol. 165(2):1153-9 (2000).<br>Bioley et al. Clin Cancer Res. 15(13):4467-74 (2009).<br>Zarour et al. Cancer Res. 62(1):213-8 (2002).<br>Hasegawa et al. Clin Cancer Res. 12(6):1921-7 (2006). |
| 2 | LAGE-1 | MLMAQEALAFL (SEQ ID NO: 137)<br>SLLMWITQC (SEQ ID NO: 138)<br>LAAQERRVPR (SEQ ID NO: 139)<br>ELVRRILSR (SEQ ID NO: 140)<br>APRGVRMAV (SEQ ID NO: 141)<br>SLLMWITQCFLPVF (SEQ ID NO: 142)<br>QGAMLAAQERRVPRAA-EVPR (SEQ ID NO: 143)<br>AADHRQLQLSISSCL-QQL (SEQ ID NO: 144)<br>CLSRRPWKRSWSAGSC-PGMPHL (SEQ ID NO: 145)<br>ILSRDAAPLPRPG (SEQ ID NO: 146)<br>AGATGGRGPRGAGA (SEQ ID NO: 147) | Aarnoudse et al. Int J Cancer. 82(3):442-8 (1999).<br>Rimoldi et al. J Immunol. 165(12): 7253-61 (2000).<br>Wang et al. J Immunol. 161(7):3598-606 (1998).<br>Sun et al. Cancer Immunol Immunother. 55(6):644-52 (2006).<br>Slager et al. Cancer Gene Ther. 11(3):227-36 (2004).<br>Zeng et al. Proc Natl Acad Sci U S A. 98(7):3964-9 (2001).<br>Slager et al. J Immunol. 172(8):5095-102 (2004).<br>Jager et al. J Exp Med. 191(4):625-30 (2000).<br>Slager et al. J Immunol. 170(3):1490-7 (2003).<br>Wang et al. Immunity. 20(1):107-18 (2004).<br>Hasegawa et al. Clin Cancer Res. 12(6):1921-7 (2006). |
| 3 | HERV-K-MEL | MLAVISCAV (SEQ ID NO: 132) | Schiavetti et al. Cancer Res. 62(19):5510-6 (2002). |
| 4 | KK-LC-1 | RQKRILVNL (SEQ ID NO: 133) | Fukuyama et al. Cancer Res. 66(9):4922-8 (2006). |
| 5 | KM-HN-1 | NYNNFYRFL (SEQ ID NO: 134)<br>EYSKECLKEF (SEQ ID NO: 135)<br>EYLSLSDKI (SEQ ID NO: 136) | Fukuyama et al. Cancer Res. 66(9):4922-8 (2006).<br>Monji et al. Clin Cancer Res. 10(18 Pt 1):6047-57 (2004). |
| 6 | Sp17 | ILDSSEEDK (SEQ ID NO: 152) | Chiriva-Internati et al. Int J Cancer. 107(5):863-5 (2003). |

TABLE 28

| Uterine cancer | | | |
|---|---|---|---|
| No. | Tumor-associated antigen | Immunogenic epitopes | Sources |
| 1 | NY-ESO-1 | HLA-A2-restricted peptide p157-165 (SLLMWITQC) (SEQ ID NO: 42), HLA-Cw3-restricted p92-100 (LAMP-FATPM) (SEQ ID NO: 43) and HLA-Cw6-restricted p80-88 (ARGPESRLL) (SEQ ID NO: 44)<br>MLMAQEALAFL (SEQ ID NO: 45)<br>YLAMPFATPME (SEQ ID NO: 46)<br>ASGPGGGAPR (SEQ ID NO: 47)<br>LAAQERRVPR (SEQ ID NO: 48)<br>TVSGNILTIR (SEQ ID NO: 49)<br>APRGPHGGAASGL (SEQ ID NO: 50)<br>MPFATPMEAEL (SEQ ID NO: 51)<br>KEFTVSGNILTI (SEQ ID NO: 52)<br>MPFATPMEA | Jager et al. Proc. Natl. Acad. Scie. U.S.A. 103(39): 14453-8 (2006).<br>Gnjatic et al. PNAS Sept. 26, 2000 vol. 97 no. 20 p. 10919<br>Jager et al. J Exp Med. 187(2):265-70 (1998).<br>Chen et al. J Immunol. 165(2):948-55 (2000).<br>Valmori et al. Cancer Res. 60(16):4499-506 (2000).<br>Aarnoudse et al. Int J Cancer. 82(3):442-8 (1999).<br>Eikawa et al. Int J Cancer. 132(2):345-54 (2013).<br>Wang et al. J Immunol. 161(7):3598-606 (1998).<br>Matsuzaki et al. Cancer Immunol Immunother. 57(8) 1185-95 (2008). |

TABLE 28-continued

| Uterine cancer | | | |
|---|---|---|---|
| No. | Tumor-associated antigen | Immunogenic epitopes | Sources |
| | | (SEQ ID NO: 53)<br>FATPMEAEL<br>(SEQ ID NO: 54)<br>FATPMEAELAR<br>(SEQ ID NO: 55)<br>SLLMWITQCFLPVF<br>(SEQ ID NO: 56)<br>LLEFYLAMPFATPMEA-ELARRSLAQ<br>(SEQ ID NO: 57)<br>EFYLAMPFATPM<br>(SEQ ID NO: 58)<br>PGVLLKEFTVSGNILT-IRLTAADHR<br>(SEQ ID NO: 59)<br>RLLEFYLAMPFA<br>(SEQ ID NO: 60)<br>QGAMLAAQERRVPRAA-EVPR<br>(SEQ ID NO: 61)<br>PFATPMEAELARR<br>(SEQ ID NO: 62)<br>PGVLLKEFTVSGNIL-TIRLT<br>(SEQ ID NO: 63)<br>VLLKEFTVSG<br>(SEQ ID NO: 64)<br>AADHRQLQLSISSCL-QQL<br>(SEQ ID NO: 65)<br>LKEFTVSGNILTIRL<br>(SEQ ID NO: 66)<br>KEFTVSGNILT<br>(SEQ ID NO: 67)<br>LLEFYLAMPFATPM<br>(SEQ ID NO: 68)<br>AGATGGRGPRGAGA<br>(SEQ ID NO: 69) | Ebert et al. Cancer Res. 69(3):1046-54 (2009).<br>Eikawa et al. Int J Cancer. 132(2):345-54 (2013).<br>Knights et al. Cancer Immunol Immunother. 58(3): 325-38 (2009).<br>Jäger et al. Cancer Immun. 2:12 (2002).<br>Zeng et al. Proc Natl Acad Sci U S A. 98(7):3964-9 (2001).<br>Mandic et al. J Immunol. 174(3): 1751-9 (2005).<br>Chen et al. Proc Natl Acad Sci U S A. 101(25):9363-8 (2004).<br>Ayyoub et al. Clin Cancer Res. 16(18):4607-15 (2010).<br>Slager et al. J Immunol. 172(8): 5095-102 (2004).<br>Mizote et al. Vaccine. 28(32):5338-46 (2010).<br>Jager et al. J Exp Med. 191(4):625-30 (2000).<br>Zarour et al. Cancer Res. 60(17): 4946-52 (2000).<br>Zeng et al. J Immunol. 165(2):1153-9 (2000).<br>Bioley et al. Clin Cancer Res. 15(13):4467-74 (2009).<br>Zarour et al. Cancer Res. 62(1):213-8 (2002).<br>Hasegawa et al. Clin Cancer Res. 12(6):1921-7 (2006). |
| 2 | LAGE-1 | MLMAQEALAFL<br>(SEQ ID NO: 137)<br>SLLMWITQC<br>(SEQ ID NO: 138)<br>LAAQERRVPR<br>(SEQ ID NO: 139)<br>ELVRRILSR<br>(SEQ ID NO: 140)<br>APRGVRMAV<br>(SEQ ID NO: 141)<br>SLLMWITQCFLPVF<br>(SEQ ID NO: 142)<br>QGAMLAAQERRVPRAA-EVPR<br>(SEQ ID NO: 143)<br>AADHRQLQLSISSCL-QQL<br>(SEQ ID NO: 144)<br>CLSRRPWKRSWSAGSC-PGMPHL<br>(SEQ ID NO: 145)<br>ILSRDAAPLPRPG<br>(SEQ ID NO: 146)<br>AGATGGRGPRGAGA<br>(SEQ ID NO: 147) | Aarnoudse et al. Int J Cancer. 82(3):442-8 (1999).<br>Rimoldi et al. J Immunol. 165(12): 7253-61 (2000).<br>Wang et al. J Immunol. 161(7):3598-606 (1998).<br>Sun et al. Cancer Immunol Immunother. 55(6):644-52 (2006).<br>Slager et al. Cancer Gene Ther. 11(3):227-36 (2004).<br>Zeng et al. Proc Natl Acad Sci U S A. 98(7):3964-9 (2001).<br>Slager et al. J Immunol. 172(8): 5095-102 (2004).<br>Jager et al. J Exp Med. 191(4): 625-30 (2000).<br>Slager et al. J Immunol. 170(3): 1490-7 (2003).<br>Wang et al. Immunity. 20(1):107-18 (2004).<br>Hasegawa et al. Clin Cancer Res. 12(6):1921-7 (2006). |
| 3 | HERV-K-MEL | MLAVISCAV<br>(SEQ ID NO: 132) | Schiavetti et al. Cancer Res. 62(19):5510-6 (2002). |
| 4 | KK-LC-1 | RQKRILVNL<br>(SEQ ID NO: 133) | Fukuyama et al. Cancer Res. 66(9):4922-8 (2006). |
| 5 | KM-HN-1 | NYNNFYRFL<br>(SEQ ID NO: 134)<br>EYSKECLKEF<br>(SEQ ID NO: 135)<br>EYLSLSDKI<br>(SEQ ID NO: 136) | Fukuyama et al. Cancer Res. 66(9):4922-8 (2006).<br>Monji et al. Clin Cancer Res. 10(18 Pt 1):6047-57 (2004). |
| 6 | Sp17 | ILDSSEEDK<br>(SEQ ID NO: 152) | Chiriva-Internati et al. Int J Cancer. 107(5):863-5 (2003). |

Additional examples of TAAs are known in the art and are described, for example, in Reuschenbach et al., *Cancer Immunol. Immunother.* 58:1535-1544 (2009); Parmiani et al., J. Nat. Cancer Inst. 94:805-818 (2002); Zarour et al., *Cancer Medicine*. (2003); Bright et al., Hum. *Vaccin. Immunother.* 10:3297-3305 (2014); Wurz et al., Ther. Adv. Med. Oncol. 8:4-31 (2016); Criscitiello, Breast Care 7:262-266 (2012); Chester et al., *J. Immunother. Cancer* 3:7 (2015); Li et al., *Mol. Med. Report* 1:589-594 (2008); Liu et al., *J. Hematol. Oncol.* 3:7 (2010); Bertino et al., *Biomed. Res. Int.* 731469 (2015); and Suri et al., *World J. Gastrointest. Oncol.* 7:492-502 (2015).

The polynucleotides (minigenes), viral vectors and viral particles of the invention encode two or more epitopes (e.g., 2, 3, 4, 5, 6, 7, 8, 9, 10, 11, 12, 13, 14, 15, 16, 17, 18, 19, 20, 30, 40, 50, 60, 70, 80, 90, or more), of one or more tumor associated antigens that are expressed by a tumor or cancer cell present within a patient in need of treatment for a cancer or a tumor. In embodiments, the two or more TAA-derived epitopes and the tumor associated antigens suitable for use in the polynucleotide and virus vector and particle products, and the compositions and methods of the invention are those listed in any one of Tables 1-28. In embodiments, the polynucleotides (minigenes), viral vectors, viral particles, and pharmaceutical compositions of the invention encode multiple, e.g., two or more, epitopes of one or more tumor associated antigens that are sufficiently immunologically cross-reactive with one or more tumor associated antigens or epitopes thereof expressed by a cancer or tumor to elicit an immune response directed against the cancer or tumor expressing the TAA epitopes upon administration to a subject, such as a patient afflicted with a cancer or tumor.

Any tumor associated antigen (TAA) having epitopes and expressed by a cancer cell or solid tumor can be utilized in conjunction with the compositions and methods of the invention. However, it is expected that variability may exist in the efficacy of different TAAs and their associated epitopes to induce or increase an immune response in a subject, because some TAAs and/or their epitopes may potentially induce more robust responses (i.e., immunodominant TAAs). Relevant reports, e.g., preclinical and clinical study reports, can be used to guide the choice of TAAs or epitopes thereof to be incorporated into a polynucleotide (minigene), viral vector, viral particle, or pharmaceutical composition of the invention. In some embodiments, coding sequences of TAAs or the epitopes thereof that are capable of inducing a robust immune response, that bind MHC class I proteins with high affinity, or that bind MHC class II proteins with high affinity are incorporated into the polynucleotide, viral vector, viral particle, or pharmaceutical composition of the invention. By way of example, NY-ESO-1, the cancer-testis antigen, is desirable for use as a tumor associated antigen for cancer immunotherapy, because it is expressed in several different cancer and tumor types, e.g., breast cancer, lung cancer, melanoma, as well as in the testis and placenta; however, it is not expressed in other normal adult tissues.

A variety of resources are available to inform the skilled practitioner about the selection of TAAs or multiple epitopes thereof for use in the viral vector-based, anti-cancer therapeutics described herein. For example, the National Cancer Institute (NCI) formed a committee of experts to evaluate cancer antigen data from clinical trials performed over a 5-year period. The NCI committee formulated criteria and ranked the 75 representative TAAs using a weighted analytical hierarchy process (Cheevers et al., *Clin Cancer Res.,* 15: 5323-5337, 2009). Those having skill in the pertinent art are familiar with the use of databases for the selection of TAAs or multiple epitopes thereof for inclusion in a polynucleotide, viral vector, viral particle, or pharmaceutical composition of the invention. Such references include, without limitation, van der Bruggen P. et al., Peptide database: T cell-defined tumor antigens. *Cancer Immun,* 2013. URL: http://www.cancerimmunity.org/peptide/; Vigneron et al. *Cancer Immun.* 2013; 13: 15; TANTIGEN: Tumor T cell Antigen Database, http://cvc.dfci.harvard.edu/tadb/; HPtaa database, http://www.bioinfo.org.cn/hptaa/; Backert, L. and Kohlbacher, O., 2015, *Genome Medicine,* 7:119; Nielsen, M. et al., 2010, *Immunology,* 130(3):319-328; Wang, P. et al., 2008, *PLoS Comput. Biol.,* 44(4):e10000048; Wang, P. et al., 2010, *BMC Bioinformatics,* 11:568; Chang, S. T. et al., 2006, *Bioinformatics,* 22(22):2761-2767; Guillaume, P. et al., 2009, *Cancer Immun.* (http://www.cancerimmunity.org/tetramers/); Chen, Y. T. et al., 2000, In: Rosenberg, S. A., Ed., Principles and practice of the biologic therapy of cancer, $3^{rd}$ ed. Philadelphia, PA: Lippincott Williams & Wilkins, pp. 557-570. In addition to available publications, putative epitopes can also analyzed for binding strength to T cell receptors using the algorithms available at different web-based sources presented in Table 29 below. An example of the use of the algorithms listed in Table 29 for epitope selection is set forth in Example 6, infra.

In a more personalized vaccine approach, the tumor associated antigens, and epitopes thereof, expressed by a patient's tumor can be identified from a biopsy or from a biological sample of the patient when a biopsy is not possible. A biological sample obtained from a subject (patient) may include, without limitation, blood, serum, plasma, urine, feces, sputum, saliva, tears, cerebrospinal fluid, peritoneal fluid, skin, tissue, cells, scrapings of tissue and skin, and processed, e.g., homogenized or reconstituted, forms thereof. Serological analysis of cDNA expression libraries (SEREX) has previously been used to identify human TAAs. A subject's serum sample can also be tested against panels of known TAA proteins by using either ELISA or Western blot assays. Epitopes of TAAs identified from the subject's serum can be further tested for the capacity to stimulate effector activity of the patient's T cells using methods known in the art, such as Elispot assays that measure T cell activation.

TABLE 29

URLs of Algorithms to Rank HLA/MHC Epitope Binding

| Name | URL |
|---|---|
| ANNPRED | http://www.imtech.res.in/raghava/nhlapred/neural.html |
| BIMAS | http://www-bimas.cit.nih.gov/molbio/hla_bind/ |
| EPIMHC | http://imed.med.ucm.es/epimhc/ |
| HLABIND | http://atom.research.microsoft.com/hlabinding/hlabinding.aspx |
| IEDB | http://tools.immuneepitope.org/analyze/html/mhc_binding.html |
| KISS | http://cbio.ensmp.fr/kiss |
| MOTIF_SCAN | http://www.hiv.lanl.gov/content/immunology/motif_scan/motif_scan |
| MULTIPRED | http://antigen.i2r.a-star.edu.sg/multipred/ |
| NetMHC | http://www.cbs.dtu.dk/services/NetMHC/ |
| NetMHCpan | http://www.cbs.dtu.dk/services/NetMHCpan/ |
| PEPVAC | http://imed.med.ucm.es/PEPVAC/ |
| POPI | http://iclab.life.nctu.edu.tw/POPI/ |
| PREDEP | http://margalit.huji.ac.il/Teppred/mhc-bind/index.html |
| RANKPEP | http://imed.med.ucm.es/Tools/rankpep.html |
| SVMHC | http://www-bs.informatik.uni-tuebingen.de/SVMHC/ |
| SVRMHC | http://SVRMHC.umn.edu/SVRMHCdb |
| SYFFPEITHI | http://www.syfpeithi.de/Scripts/MHCServer.dll/EpitopePrediction.htm |

Epitope Selection

In general, $CD8^+$ cytotoxic T cells are programmed to recognize peptides (epitope amino acid sequences) associated with the MHC class I molecules on all nucleated cells. These peptides or epitopes have certain general characteristics. Typically, epitopes that are capable of eliciting a $CD8^+$ T cell response are amino acid sequences or peptides that bind to MHC class I molecules and are about 3-50 amino acids in length, or about 3-30 amino acids in length, or about 5-30 amino acids in length, or about 5-25 amino acids in length, or about 7-20 amino acids in length, or about 8-10 amino acids in length. Without wishing to be bound by theory, the epitopic peptide lies in an elongated conformation along the MHC class I peptide-binding groove. However, variations in peptide length appear to be accommodated, in most cases, by a kinking in the peptide backbone. Therefore, some length variation in $CD8^+$ T cell activating epitopes is possible.

Epitopes that are capable of eliciting a $CD4^+$ T cell response are typically peptides (epitope amino acid sequences) that bind to MHC class II molecules. Peptides that bind to MHC class II molecules are at least 13 amino acids in length and can be much longer. The epitopic peptide lies in an extended conformation along the MHC class II peptide-binding groove. It is held in this groove both by peptide side chains that protrude into shallow and deep pockets lined by polymorphic residues and by interactions between the peptide backbone and the side chains of conserved amino acids that line the peptide-binding cleft in all MHC class II molecules. Because the peptide is bound by its backbone and allowed to emerge from both ends of the binding groove there is, in principle, no upper limit to the length of peptides that could bind to MHC class II molecules. However, longer peptides bound to MHC class II molecules are typically trimmed by peptidases to a length of 13-17 amino acids in most cases.

While selection of epitopes expected to elicit a T cell response can be guided by the literature, databases (Vigneron, N. et al., 2013, Database of T cell-defined tumor antigens. *Cancer Immun., Vol.* 13; and the Immune Epitope Database) and in silico algorithms (Table 29), such approaches are not intended to be limiting, and any means of detecting TAA epitopes generally consistent with the above description of epitopes found in association with tumor cells can be used. Databases curate data from the literature that indicate whether epitopes have been successful in eliciting immune responses. Many epitope prediction algorithms are available, some of which are listed in Table 29. Computer programs using various criteria are available to analyze amino acid sequences for peptide regions that are most likely to bind MHC receptors and T cells, including structure, physicochemical properties, flexibility, charge and protease processing (Yang and Yu, 2009, *Rev. Med. Virol.,* 19:77-96). Amino acid sequences of tumor associated antigen proteins can be analyzed using several algorithms to find the best consensus epitopes for eliciting anti-cancer/anti-tumor immune responses. An example of the use of epitope prediction algorithms to select epitopes for use in the present invention is set forth in Example 6, infra.

Experimental binding assays, such as the iTopia Epitope Discovery System (Beckman Coulter) further refine the selection of epitopes. The iTopia screening assay allows for prioritization of predicted epitopes based on MHC binding affinity and peptide:MHC complex stability. Epitopes restricted to HLA alleles that are present in the population at high frequencies can be chosen to broaden the applicability of the TAA-derived epitopes included in the polynucleotides (minigenes), viral vectors, viral particles, and compositions described herein. Frequencies of HLA I and HLA II alleles are compiled for worldwide populations and are available to the skilled practitioner, e.g., at www.allelefrequencies.net; bioinformatics.bethematchclinical.org. When several epitopes for a given TAA are under consideration, it may be useful to select those TAA epitopes that bind to the most frequent HLA alleles to allow for personalized treatment of an individual patient.

Polynucleotides Encoding Epitopes of Tumor Associated Antigens and Other Polypeptides The polynucleotides (minigenes) as described for incorporation into Sindbis viral vectors, for example, may further include sequences encoding molecules that augment peptide epitope-MHC interactions. For example, calreticulin and calnexin represent integral proteins in the production of MHC class I Proteins. Calnexin binds to newly synthesized MHC class I α-chains as they enter the endoplasmic reticulum, thus retaining them in a partly folded state. After $\beta_2$-microglobulin binds to the peptide-loading complex (PLC), calreticulin (along with ERp57) takes over the function of chaperoning the MHC class I protein, while tapasin links the complex to the transporter associated with antigen processing (TAP) complex. This association prepares the MHC class I molecule for binding an antigen for presentation on the cell surface. Thus, a Sindbis viral replicon particle can be constructed that encodes calreticulin (CRT) linked to the polynucleotide encoding multiple epitopes of one or more tumor associated antigens.

By way of example, a polynucleotide (minigene) can be constructed via polymerase chain reaction (PCR) using a series of overlapping DNA oligomer primers in a process known as gene 'Splicing by Overlap Extension' or gene "SOEing" (Horton, R. M., et al., 2013. BioTechniques, 8(5):528-535; (November 1990); Horton et al., Biotechniques. 2013; 54:129-133). Furin processing of multi-epitope polypeptides efficiently induces T cell activation. As Sindbis virus polypeptides are naturally processed by furin, the polynucleotides (minigenes), viral vectors, viral particles, and pharmaceutical compositions of the invention are designed to include furin cleavage sites to separate the multiple epitope coding sequences. For instance, compositions of the invention may include the Sindbis furin digestion sequence XRSKRX (SEQ ID NO: 5), in which X designates a hydrophobic residue. Non-limiting examples of additional processing enzymes for use in cleaving the epitope peptides encoded by the polynucleotides and viral vectors according to the present invention include furin related endopeptidases, such as PC1/2, PC4/5, PACE4, and PC7. These enzymes recognize the processing signal (R/K) $X_n$(R/K), in which $X_n$ designates a spacer of any 0-6 amino acids, (SEQ ID NO: 6), (Seidah and Prat, 2012, Nature Reviews Drug Discovery, 11:367-383). Nucleic acid sequences encoding contiguous epitopes (Thompson et al., 1998, J. Immunol., 160:1717-23) or epitopes with spacers, such as AAA or GGG, may be included in the polynucleotide (minigene) or viral vectors described herein, thus allowing for cellular processing. In some embodiments, a polynucleotide, viral vector, or pharmaceutical composition of the invention encodes contiguous epitopes without enzyme cleavage sites or spacers.

The cysteine protease cathepsin S (CAT S) is also suitable for use in the proteolytic processing of the peptides and polypeptides encoded by the polynucleotide (minigene) or viral vector of the invention. CAT S is located in the endosomal compartment of antigen presenting cells, such as dendritic cells, macrophages, and B-lymphocytes, and may play a role in antigen processing for presentation, particularly on MHC II. The endolytic cleavage sites for CAT S are PMGAP (SEQ ID NO: 386) and PMGLP (SEQ ID NO: 387).

A tumor associated antigen-derived epitope peptide encoded by the polynucleotides (minigenes) or viral vectors of the invention may contain, for example, from 5-50 amino acid residues. In embodiments, the epitopes of the tumor associated antigen comprise 5-30 amino acid residues, 5-25 amino acid residues, 5-20 amino acid residues, 7-25 amino acid residues, 7-20 amino acid residues, or 7-14 amino acid residues. By way of nonlimiting example, a polynucleotide of the invention encode from 21 to 42 residues. Since approximately 3700 nucleotides encoding Sindbis structural genes are removed from a replicon vector during the production of a Sindbis virus vector encoding multiple epitopes of one or more tumor associated antigens, it is estimated that from about 60 to 90 epitope-encoding sequences flanked by furin-cleavage sites can be inserted into a viral vector of the invention, e.g., a pT7StuI-R/epitope vector as described herein.

Polynucleotides and Viral Vectors Encoding Multiple Epitopes of One or More Tumor Associated Antigens In some embodiments, a viral vector, viral particle, or pharmaceutical composition containing a polynucleotide (minigene) that encodes two or more epitopes of one or more tumor associated antigens, in which the epitopes induce a robust immune response (such as a humoral or cell-mediated immune response) is provided. In an embodiment, the polynucleotide encodes an alphavirus protein, or a fragment thereof as described herein. In an embodiment, the polynucleotide encodes a Sindbis virus protein, or a fragment thereof as described herein. The immune response elicited may be assessed, for example, by determining the antibody titer generated against the tumor associated antigen or the extent of TAA-mediated T-cell activation in a patient in vivo, or in a biological sample obtained from the patient. Methods of selecting tumor associated antigens and epitopes thereof that induce a robust humoral or cell-mediated immune response and that may be incorporated into the polynucleotides, viral vectors, viral particles, or compositions of the invention are described in further detail herein.

In certain embodiments, and without wishing to be limiting, a polynucleotide (minigene), polynucleotide, viral vector, virus particle, or pharmaceutical composition of the invention contains a polynucleotide that encodes two or more epitopes of one or more of the following tumor associated antigens NY-ESO-1, CEA, k-Ras, c-myc, HPV-E6, HPV E7, cyclin B1, Her2, MUC1, p53, p62, survivin, WT1, sp17, and Pdz-Binding Kinase (PBK). For example, in some embodiments, the polynucleotide (minigene), viral vector, virus particle, or pharmaceutical composition comprises a polynucleotide that encodes one or more epitopes of the tumor associated antigen NY-ESO-1 (e.g., an epitope of NY-ESO-1 listed in any one of Tables 1-28), and one or more epitopes of the tumor associated antigen CEA (e.g., an epitope of CEA listed in any one of Tables 1-28). In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28), and one or more epitopes of the tumor associated antigen k-Ras (e.g., an epitope of k-Ras listed in any one of Tables 1-28). In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28), and one or more epitopes of the tumor associated antigen c-myc. In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28), and one or more epitopes of cyclin B1. In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28), and one or more epitopes of Her2 (e.g., an epitope of Her2 listed in any one of Tables 1-28). In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28), and one or more epitopes of MUC1. In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28), and one or more epitopes of p53 (e.g., an epitope of p53 listed in any one of Tables 1-28). In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28), and one or more epitopes of p62. In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28), and one or more epitopes of survivin or an epitope thereof. In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28), and one or more epitopes of WT1 (e.g., an epitope of WT1 listed in any one of Tables 1-28). In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28), and one or more epitopes of sp17 (e.g., an epitope of sp17 listed in any one of Tables 1-28). In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28), and one or more epitopes of gp70. In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28) and one or more epitopes of pbk (a PDZ binding kinase that is overexpressed in many tumors). In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28) and one or more epitopes of survivin.

In other embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28), one or more epitopes of p53 (e.g., an epitope of p53 listed in any one of Tables 1-28), one or more epitopes of sp17 (e.g., an epitope of sp17 listed in any one of Tables 1-28), one or more epitopes of survivin, and one or more epitopes of WT1 (e.g., an epitope of WT1 listed in any one of Tables 1-28). In some embodiments, the polynucleotide (minigene), viral vector, virus particle, or pharmaceutical composition comprises a polynucleotide that encodes one or more epitopes of NY-ESO-1 (e.g., an epitope of NY-ESO-1 listed in any one of Tables 1-28), one or more epitopes of gp70, and one or more epitopes of pbk, e.g., as described in Example 2, infra.

Viruses and Viral Vectors

Alphavirus, Sindbis Virus and Sindbis Virus Vectors

Alphaviruses belong to the group IV Togaviridae family of viruses that are small, spherical, enveloped, positive-sense, single-stranded RNA viruses. Most alphaviruses infect and replicate in vertebrate hosts and in hematophagous arthropods, such as mosquitoes. Alphavirus virions are spherical with an iscoahedral nucleocapsid enclosed in a lipid-protein envelope. Alphavirus RNA is a single 42S strand of approximately $4\times10^6$ daltons that is capped and polyadenylated. The alphavirus envelope comprises a lipid bilayer derived from the host cell plasma membrane and contains two viral glycoproteins, E1 (48,000 daltons) and E2 (52,000 daltons). A third, small E3 protein (10,000-12,000 daltons) is released from the virus as a soluble protein in alphaviruses other than Semliki Forest virus, where the E3 protein remains virus-associated.

As described herein, polynucleotides encoding an alphavirus protein, or a fragment thereof, and two or more epitopes of one or more tumor associated antigens, wherein each epitope is separated by an enzyme cleavage site are embraced by the invention. In addition, the present invention encompasses viral vectors and particles that are pseudotyped with proteins, e.g., envelope proteins, from other virus types. The polynucleotides, viral vectors and viral particles described herein encompass nucleic acid sequences and polypeptide sequences of members of the Alphavirus genus, including various strains, antigenic complexes, species and subtypes. Encompassed by the invention are alphaviruses, phylogenetically related alphaviruses, alphavirus complexes, and their structural components, such as envelope proteins, e.g., E1, as described, for example, in Powers, A. M. et al., 2011, *J. Virol.,* 75(21):10118-10131. Nonlimiting examples of alphaviruses, and polynucleotides and proteins thereof, as well as fragments of their polynucleotides and proteins, that may be used in the polynucleotides, viral vectors and viral particles as described herein include Barmah Forest virus, Barmah Forest virus complex, Eastern equine encephalitis virus (EEEV), Eastern equine encephalitis virus complex, Middelburg virus, Middelburg virus complex, Ndumu virus, Ndumu virus complex, Semliki Forest virus, Semliki Forest virus complex, Bebaru virus, Chikungunya virus, Mayaro virus, Subtype Una virus, O'Nyong Nyong virus, Subtype Igbo-Ora virus, Ross River virus, Subtype Getah virus, Subtype Bebaru virus, Subtype Sagiyama virus, Subtype Me Tri virus, Venezuelan equine encephalitis virus (VEEV), VEEV complex, Cabassou virus, Everglades virus, Mosso das Pedras virus, Mucambo virus, Paramana virus, Pixuna virus, Western equine encephalitis virus (WEEV), Rio Negro virus, Trocara virus, Subtype Bijou Bridge virus, Western equine encephalitis virus complex, Aura virus, Babanki virus, Kyzylagach virus, Sindbis virus, Ockelbo virus, Whataroa virus, Buggy Creek virus, Fort Morgan virus, Highlands J virus, Eilat virus, Salmon pancreatic disease virus (SPDV), Southern elephant seal virus (SESV), Tai Forest virus and Tonate virus.

As an alphavirus, Sindbis virus is a small, enveloped, positive-sense, single strand RNA virus. Other members of the alphavirus genus include, without limitation, Semliki Forest virus (SFV), Venezuelan equine encephalitis virus (VEEV) and Ross River Virus (RRV). Alphaviruses, including Sindbis virus, form spherical particles of 60-70 nm in diameter; the icosahedral structures of many alphaviruses have been defined to very high resolutions by cryo-electron microscopy (cryo-EM) and crystallographic studies, revealing details of the interactions between the structural proteins (Jose, J. et al., 2009, *Future Microbiol.,* 4:837-856). The genome is composed of a single strand of positive-sense RNA that is approximately 11 to 12 kb in length and encodes four nonstructural proteins (nsPl-nsP4) involved in virus replication and pathogenesis, and five structural proteins that compose the virion particle, i.e., the nucleocapsid protein C and the envelope proteins, P62 (proteolytically cleaved into the mature envelope proteins E2 and E3) and the E1 protein. Alphaviruses exhibit efficient replication and have broad range of susceptible and permissive hosts; therefore, these viruses are highly suitable for heterologous gene expression and as gene therapy delivery vectors. Alphavirus vectors are suitable for use in encoding the polynucleotides (minigenes) for delivering the multi-epitopes of tumor associated antigens as described herein.

Any Sindbis viral vector is suitable for use in conjunction with the polynucleotides, virus vectors, compositions and methods of the present invention, including replication-competent vectors (see, e.g., U.S. Pat. No. 8,282,916) and replication-defective vectors (see, e.g., U.S. Pat. Nos. 7,303,898, 7,306,792, and 8,093,021). Replication-defective vectors are preferred for use in the present invention, as they offer another layer of protection against infection of healthy tissues. Sindbis vectors can also be constructed to contain more than one subgenomic promoter to express more than one gene using methods known in the art.

By way of example, to produce the pT7StuI-R/epitope vector, the replicon plasmid encoding the Sindbis replicase genes (nsPl-nsP4) and a helper plasmid, encoding the viral structural genes (capsid protein C, E1, E2, E3, and 6K), were transcribed in vitro. To limit viral replication in vivo, the replicon genes have been separated from the structural genes, which additionally contain a mutated packaging signal to prevent incorporation into virus particles (Bredenbeek, P. J. et al., 1993, *J Virol* 67: 6439-6446). Virus particles were produced by transient transfection of baby hamster kidney (BHK) cells with in vitro synthesized Sindbis replicon RNA and helper RNA transcripts. Within the cell, genomic RNA was replicated by the Sindbis replicase and expressed from the capped replicon RNA transcript. Structural proteins were expressed from the helper RNA transcript. Only the replicon RNA was packaged into the capsid to form the nucleocapsid, which then associates with the viral glycoproteins E1 and E2 and buds out of the cell. The resulting virion contained the capped SV single-stranded RNA message for nsP1-nsP4 genes, which encode the viral replicase, a subgenomic promoter (Psg) from which the replicase can transcribe an inserted gene of interest and a poly A tail.

To formulate a Sindbis viral vector encoding multiple TAA epitopes ("SV/TAA") and exhibiting the potential to stimulate an anti-tumor T cell repertoire, a polynucleotide (e.g., a DNA minigene) encoding multiple T cell recognition epitopes, each separated by enzyme cleavage sites, was inserted into a Sindbis vector (e.g., pT7StuI-R LacZ #202; U.S. Pat. No. 8,093,021). Because SV/TAA virions induce a strong innate immune response and express TAA epitopes that activate $CD8^+$ T cells, the viral vectors of the invention do not require signal and immunogenic peptides, although such peptide may be included, if desired. If desired, vectors can be readily manipulated to include immune-enhancing elements as described below.

Lentivirus

Lentiviral vectors are particularly useful for long-term expression of genes, as they have the ability to infect both dividing and non-dividing cells. Third generation lentiviral systems are preferred for increased safety (Breckpot, K., et al., 2007, *Gene Ther,* 14: 847-862). These include, e.g., a transfer plasmid into which nucleic acid sequences encoding two or more epitopes of a tumor associated antigen is inserted, a packaging plasmid for gag and pol genes and another packaging plasmid for the rev gene. For optimal expression, the transfer expression vectors contain a splice donor, a packaging signal (psi), a Rev-responsive element (RRE), splice acceptor, central poly-purine tract (cPPT), and Wood chuck hepatitis virus transcriptional response element (WPRE) (Shaw and Cornetta, 2014, Biomedicines, 2:14-35). Transfer vector constructs may also contain a promoter for expression in mammalian cells. Constitutive promoters, such as the cytomegalovirus (CMV), mammalian beta-actin, or ubiquitin promoters may be incorporated into a composition of the invention. In some embodiments, tissue-specific promoters are utilized, such as $CD4^+$ T cell-specific promoters.

Plasmids for generating lentiviral vectors can be obtained from Addgene (Cambridge, MA, a non-profit plasmid repository) and modified, as necessary, using standard techniques in the art. Standard $3^{rd}$ generation packaging plasmids can be used. Suitable transfer vectors include, for example, pLX301, pFUGW, and pWPXL. These vectors contain all of the requisite characteristics mentioned above. To increase safety, the lentivirus transfer vectors can be mutated to decrease integration and increase episomal replication in infected cells. For instance, using standard techniques known in the field, the following modifications can be performed: a deletion within the U3 region of the 3' LTR to create a self-inactivating LTR (SIN-LTR) is made; LTR att sites within the U3 and U5 LTR regions are deleted or mutated; the 3' LTR-proximal polypurine tract (PPT) are deleted or modified (Shaw and Cornetta, 2014).

Pseudotyped viral vectors and virions are also suitable for use in connection with the polynucleotides and compositions of the invention. Such virions contain a viral particle and one or more foreign virus envelope proteins. (D. A. Sanders, 2002, *Curr. Opin. Biotechnol.,* 13:437-442). In some embodiments, a viral vector of the invention may be a lentivirus containing an alphavirus protein or a fragment thereof, e.g., an envelope protein or a functional fragment thereof. In some embodiments, a viral vector of the invention may be a lentivirus containing a Sindbis virus envelope glycoprotein, or certain Sindbis virus envelope glycoproteins. By way of example, to produce a construct (e.g., a pseudotyped viral vector) comprising a lentivirus backbone pseudotyped with one or more Sindbis envelope proteins, a Sindbis envelope plasmid, e.g., T7 DM helper #101 (U.S. Pat. No. 8,093,021) is transfected into BHK or 293 cells along with the lentiviral plasmids resulting in pseudotyped virions.

Retrovirus

Retroviral vectors are also suitable for use according to the invention. In some embodiments, the retroviral vector is Moloney murine leukemia virus (Mo-MuLV) pseudotyped with Sindbis envelope proteins. Pseudotyping can be performed using methods known in the art (see, e.g., Sharkey et al., 2001, *J. Virology,* 75(6):2653-2659). In some embodiments, the Mo-MuLV-based retrovirus particles are engineered to include and express the glycoproteins of the alphavirus Ross River virus (RRV) using methods known and practiced in the art.

Sindbis Virus Envelope Pseudotyped Vectors

The Sindbis virus (SV) envelope is advantageous for use as a gene or polynucleotide delivery vector. SV is a blood-borne virus with a relatively long half-life. Stable virus is easily produced and can be concentrated for administration. Modification of the Sindbis E2 envelope protein, which binds to cell surface molecules, does not affect the E1 fusogenic envelope protein that is required for cell entry, thus allowing for engineered targeting of the virus. Sindbis virus specifically targets tumors by interacting with the high-affinity laminin receptor (LAMR) (U.S. Pat. No. 7,306,792), which is found in the 40S ribosome and is over-expressed by many tumors (e.g., breast, thyroid, colon, prostate, stomach, pancreas, ovary, melanocytes, lung, liver, uterus), but does not infect normal tissues. As a blood-borne virus, Sindbis virus is capable of contacting disseminated metastatic tumor cells via the bloodstream.

Sindbis viral envelope structural proteins can pseudotype other viral vectors, such as lentivirus, retrovirus and Vesicular Stomatitis virus (VSV) to improve their targeting capabilities and increase virion stability. In particular, the Sindbis-ZZ protein, designed to contain the Fc binding domain of *S. aureus* protein A inserted into the E2 envelope protein (U.S. Pat. No. 6,432,699), is useful in conjunction with cell surface specific antibodies for redirecting the targeting of SV and other vectors.

In certain embodiments in which long-term, stable expression of multiple epitopes is desired, retroviral or lentiviral vectors pseudotyped with wild type or engineered Sindbis virus envelope proteins are employed. Lentiviral vectors are advantageous for infection of both dividing and non-dividing cells. Like the Sindbis virus genome, the lentivirus genome can be split into two or three vectors, and genes can be modified or deleted to improve safety. A retrovirus subtype lentivirus naturally integrates into the host genome. However, vectors containing either long terminal repeats (LTR) or integrase enzyme mutations can exist as stable, non-integrating episomes in the cell nucleus (Breckpot, K., et al., 2007, Gene Ther., 14:847-862).

In particular embodiments, a therapeutic composition of the invention comprises a replication defective Sindbis virus described in U.S. Pat. Nos. 7,303,898, 9,423,401; 8,530,232; or 8,093,021.

Enhancement of Immunogenicity of the Described Viral Vectors, e.g., Sindbis Viral Vector Augmentation of the immune response elicited by the multiple TAA-associated epitopes encoded by the viral vectors described herein, such as the pT7StuI-R/epitope vector, is encompassed by the invention. For example, promoting an increase in $CD4^+$ T cells (T cell help) can enhance cross-presentation of tumor antigens and stimulate the production of CD8+ memory T cells. Indeed, an immune response and anti-cancer therapy provided by a Sindbis viral vector encoding multiple epitopes of one or more tumor associated antigens (SV/TAA) was obviated when mice were depleted of CD4 T cells (FIG. 6A-6D).

The Pan HLA-DR reactive epitope, AKFVAAWTLKAAA (PADRE), (SEQ ID NO: 7), is capable of generating antigen-specific $CD4^+$ T cells that bind various HLA class II molecules with high affinity to stimulate T cell help (Alexander, J. et al., 1994, *Immunity,* 1:751-761). In certain embodiments, the polynucleotide (minigene), viral vector, or viral particle of the invention contains a sequence encoding the PADRE epitope in addition to sequences encoding multiple, e.g., two or more, epitopes of one or more tumor associated antigens in which the epitope sequences are separated by processing sites such as enzyme cleavage sites. In addition, sequences encoding cognate $CD4^+$ T cell epitopes and sequences encoding CD8+ T cell epitopes can be included in the polynucleotides and the viral vectors to potentiate efficacy.

Inclusion of an endoplasmic reticulum (ER) signal sequence can facilitate multi-epitope polypeptide translocation into the ER where furin digestion will take place. Potential ER signal peptides include sequences such as, the an alphavirus endoplasmic reticulum signal sequence (Garoff, H. et al., 1990, *J. Cell. Biol.,* 111:867-876), influenza virus matrix protein derived peptide, M57-68 (Anderson, K. et al., 1991, *J Exp Med,* 174: 489-492), or tissue plasminogen activator peptide (Aurisicchio, L. et al., 2014, *Oncoimmunology* 3:e27529). Signal sequences for use in the present invention are set forth below.

The additional ER signal-encoding nucleic acid sequences that can be incorporated into the polynucleotide (minigene) and viral vectors described herein to enhance intracellular processing of the multi-epitope polypeptide following administration include, without limitation, Adenovirus ER signal: MRYMILGLLALAAVCSA (SEQ ID NO: 388) and Tissue plasminogen activator peptide: MDAMLRGLCCVLLLCGAVFVSPS (SEQ ID NO: 389).

Nucleic acid sequences encoding immunogenic peptides can also be included in the polynucleotide (minigene) and viral vectors as described herein. Such sequences include, without limitation, *E. coli* heat labile enterotoxin subunit B (LTB):

(SEQ ID NO: 390)
MNKVKFYVLFTALLSSLCAHGAPQSITELCSEYHNTQIYTINDKILSYTE

SMAGKREMVIITFKSGATFQVEVPGSQHIDSQKKAIERMKDTLRITYLTE

TKIDKLCVWNNKTPNSIAAISMEN;

Influenza virus matrix protein M57-68

(SEQ ID NO: 391)
KGILGFVFTLLV;

Tetanus toxin fragment c:

(SEQ ID NO: 392)
IDKISDVSTIVPYIGPALNI;

Lysosome-associated membrane protein (LAMP):

(SEQ ID NO: 393)
MLIPIAVGGALAGLVLIVLIAYLVG;

and

Hsp70 peptide:

(SEQ ID NO: 394)
TKDNNLLGRFELSG.

In some embodiments, the inclusion of nucleic acid sequences encoding polypeptide adjuvants at the carboxyl terminus (3' end) of the polynucleotide (minigene) or viral vector described herein is employed to augment the immune response after administration and expression. Exemplary sequences useful for enhancement of the immune response include heat shock protein 70, lysosome-associated membrane protein (LAMP), the universal helper T cell (Th) epitope from tetanus toxin, and the *E. coli* heat-labile enterotoxin B subunit (Facciabene, A. et al., 2007, *Vaccine,* 26: 47-58; and 2006, *Hum Gene Ther.,* 17: 81-92).

In other embodiments, nucleic acid sequences encoding epitopes of mutated or overexpressed oncogenes, cytokines, chemokines, checkpoint inhibitor molecules, antibodies, and known immunogenic TAAs, separated by processing sites, such as enzyme, e.g., furin, cleavage sites, are included in the polynucleotides (minigenes) and viral vectors described herein. Mutated oncogenes may minimize self-genes that might trigger autoimmunity. By linking all these genes in tandem with only enzyme cleavage sites between them, the expression of all of these genes can be driven from one or more subgenomic promoter(s) in the vector. By way of nonlimiting example, polynucleotide sequences encoding multiple epitopes of one or more oncogenes, or mutated forms thereof, which may be included in the polynucleotides and viral vectors of the invention, include androgen receptor (Olson, B. M. et al., 2013, *Cancer Immunol. Immunother.,* 62(3):585-596), Her-2/neu (Parmiani, G. et al., 2002, *J. Natl. Cancer Inst.,* 94(11):805-818), P53 (Ito, D. et al., 2007, *Int. J. Cancer,* 120(12):2618-2624), EphA2 (Tandon, M. et al., 2011, *Expert Opin. Ther. Targets,* 15(1):31-51), K-Ras (Gjertsen, M. K. et al., 1997, *Int. J. Cancer,* 72(5):784-790) and H-Ras (Fossum, B. et al., 1993, *J. Immunol.,* 23:2687-2691). In other embodiments, nonlimiting examples of polynucleotide sequences encoding multiple epitopes of one or more immunotherapy enhancing genes that may be included in the polynucleotides and viral vectors of the invention include survivin (Siegel, S. A. et al., 2003, *Br. J. Haematol.,* 122:911-914; Yang, Z. et al., 2008, *Mol. Immunol.,* 45:1674-1681), WT1 (Miwa, H. et al., 1992, *Leukemia,* 6:405; Oji, Y. et al., 1999, *Japan. J Cancer. Res.,* 90:194; Oka Y. et al., 2000, *J. Immunol.* 2000, 164(4):1873-80; Li Z. et al., 2008, *Microbiol. Immunol.,* 52:551-558). HTERT (Bright, R. K., et al., 2014, *Human Vaccines & Immunotherapeutics,* 10(11): 3297-3305), tumor protein D52 (Bright, R. K., et al., 2014, Ibid.), IL-12 (Tseng, J. C. et al., 2004, *Cancer Res.,* 64:6684-6692; Tseng, J. C. et al., 2004, *Nature Biotechnol.,* 22:70-77; Granot, T. et al., 2013, *Mol. Ther.,* 22(1):112-122; Granot, T. et al., 2011, *PLoS One,* 6(6):e20598), interferon-gamma (Granot, T. et al., 2013, *Mol. Ther.,* 22(1):112-122; Granot, T. et al., 2011, *PLoS One,* 6(6):e20598) and calreticulin (Wang, H. T. et al., 2012, *Int. J. Cancer,* 130:2892-2902).

Further encompassed by the invention are polynucleotides, viral vectors and viral particles as described herein that contain sequences encoding checkpoint inhibitors. As described herein, checkpoint inhibitors are advantageous in the products of the invention as additional agents to stimulate cytotoxic T cell activity, particularly in those cancer subjects who do not show a tumor-specific T cell response because they inexplicably fail to generate cytotoxic T cells. The inclusion of sequences encoding one or more checkpoint inhibitors in the polynucleotides, viral vectors and viral particles of the invention, e.g., Sindbis viral vectors encoding multiple epitopes of one or more tumor associated antigens, would provide an added checkpoint blockade to enhance the anti-tumor or cancer immunity generated by the vector and its encoded tumor associated antigen epitopes. Examples of checkpoint inhibitors for the purpose of elevating and improving the anti-tumor effectiveness of the viral vectors described herein include, without limitation, anti-PD-1 antibody, anti-PD-L1 antibody, or a combination thereof. Thus, while the multi-TAA epitope encoding viral vectors, e.g., Sindbis viral vectors, of the invention effectively generate CD8+ T cells needed for a specific and effective anti-tumor response against multiple TAA epitopes, the blockade of active immune checkpoint molecules by encoded checkpoint inhibitors would further increase and enhance the anti-tumor immunity that generated by the multi-epitope encoding viral vectors and viral particles of the invention. As described above, the methods encompass the administration of one or more checkpoint protein inhibitors to a subject separately from and in conjunction with the polynucleotides, virus vectors, or viral particles and compositions thereof as described herein. For example, antibody checkpoint protein inhibitors, or binding fragments thereof, may be co-administered to a subject either at the same time as, or at a different at time from, the administration of the polynucleotides, virus vectors, or virus particles, or compositions thereof as described herein. Administration regimens can be determined by a medical practitioner or clinician having skill in the art.

Modulating the Immune Response Elicited by Sindbis Viral Vectors Encoding Multiple (two or more) Tumor Associated Antigen Epitopes In addition to activating CD8+ T cells and eliciting their responsiveness to tumor antigens and epitopes thereof, therapy with Sindbis viral vectors encoding multiple epitopes of tumor associated antigens can activate additional immune (or nonimmune) cells, including, but not limited to CD4+ T cells, natural killer (NK) cells, macrophages, monocytes, dendritic cells, neutrophils, and other cells, as well as the humoral immune response. Epitope spreading can occur not only in CD8+ T cells, but also in CD4+ T cells (Granot, T., and D. Meruelo, 2012, *Cancer Gene TheR.,* 19: 588-591; Granot, T. et al., 2011, *PLoS One* 6: e20598; Granot, T. et al., 2014, *Mol Ther,* 22:112-122). To create optimal conditions for T cell stimulation in the lymph nodes, an embodiment of the invention encompasses polynucleotides and viral vectors, such as Sindbis virus expression vectors, that contain and deliver nucleic acid sequences encoding multiple (e.g., two or more) epitopes of (one or more) tumor associated antigens in conjunction with nucleic acid sequences (genes) encoding certain immune stimulating cytokines. Such immune stimulating cytokines include, but are not limited to, the interleukins IL-1, IL-2, IL-3, IL-4, IL-5, IL-6 IL-7, IL-8, IL-9, IL-10, IL-11, IL-12, IL-13, IL-14, IL-15, IL-16, and IL-17. Additional cytokines include IL-18 through IL-36.

Nucleic acid sequences encoding chemokines can also be included in the polynucleotide and viral vector nucleic acid sequences, including, but not limited to, CCL1 through CCL27 and other CC chemokines; CXCL1 through CXCL13 and other CXC chemokines; C chemokines; and CX3C chemokines. Nucleic acid sequences encoding cytokine or chemokine receptors and soluble receptors can also be used. Nucleic acid sequences encoding additional immune modulators that can be used and incorporated in the nucleic acid sequences of the polynucleotides and viral vectors, e.g., SV/TAA, of the invention include, without limitation, TGF-β and TNFα. Different combinations of the above-mentioned (or alternative) cytokines can also be used. It will be appreciated that nucleic acid sequences (genes) encoding immune stimulating molecules can be expressed from an additional promoter inserted into, for example, a Sindbis virus vector encoding multiple TAA epitopes as described herein, or may be included in a separate vector that is co-administered.

Pharmaceutical Compositions

The present invention includes pharmaceutical compositions or formulations for treating subjects who are afflicted with cancer or a tumor, or who are at risk of developing cancer or a tumor. In an embodiment, the pharmaceutical composition includes a polynucleotide (minigene) encoding multiple epitopes, e.g., two or more, of a tumor associated antigen, wherein each epitope is separated by an enzyme cleavage site, e.g., a furin cleavage site, as well as other sequences for processing and expressing the encoded epitopes as described herein, and other coding sequences that may be included in the polynucleotide, e.g., immunostimulatory molecule coding sequence, and a pharmaceutically acceptable carrier, excipient, or diluent. In an embodiment, the pharmaceutical composition includes a viral vector or particle, e.g., a Sindbis viral vector or a pseudotyped viral vector as described herein, containing a polynucleotide (minigene) encoding multiple epitopes, e.g., two or more, of a tumor associated antigen, wherein each epitope is separated by an enzyme cleavage site, e.g., a furin cleavage site, as well as other sequences for processing and expressing the encoded epitopes as described herein, and other coding sequences that may be included in the polynucleotide, e.g., immunostimulatory molecule coding sequence, and a pharmaceutically acceptable carrier, excipient, or diluent. In an embodiment, the pharmaceutical composition includes viral vector, e.g., a Sindbis virus vector containing a polynucleotide encoding a checkpoint protein or a checkpoint protein minibody as described herein, or a cognate ligand binding portion thereof, and a pharmaceutically acceptable carrier, excipient, or diluent. In an embodiment, the pharmaceutical composition includes a Sindbis viral vector or a pseudotyped viral vector as described herein and a pharmaceutically acceptable carrier, excipient, or diluent. When formulated in a pharmaceutical composition, a therapeutic compound or product of the present invention can be admixed with a pharmaceutically acceptable carrier, diluent, or excipient.

The administration of a composition comprising a combination of agents herein for the treatment of a cancer or tumor may be by any suitable means that results in a concentration of the therapeutic that, combined with other components, is effective in ameliorating, reducing, or stabilizing a cancer in a subject. The composition may be administered systemically, for example, formulated in a pharmaceutically-acceptable buffer such as physiological saline. Routes of administration include, for example, subcutaneous (s.c.), intravenous (i.v.), intraperitoneal (i.p.), intramuscular (i.m.), or intradermal administration, e.g., by injection, that optimally provide continuous, sustained levels of the agent in the patient. The amount of the therapeutic agent to be administered varies depending upon the manner of administration, the age, physical condition and body weight of the patient, and with the clinical symptoms of the cancer or tumor. Generally, amounts will be in the range of those used for other viral vector-based agents employed in the treatment of a cancer or tumor, although in certain instances lower amounts will be needed if the agent exhibits increased specificity. A composition is administered at a dosage that shows a therapeutic effect, such as increasing immune cell (e.g., effector T cell; CD8+ T cell) levels, particular, TAA epitope-specific T cell levels, or that decreases cancer cell proliferation as determined by methods known to one skilled in the art.

The therapeutic agent(s) may be contained in any appropriate amount in any suitable carrier substance, and is/are generally present in an amount of 1-95% by weight of the total weight of the composition. The composition may be provided in a dosage form that is suitable for a parenteral (e.g., subcutaneous, intravenous, intramuscular, or intraperitoneal) administration route, such that the agent, such as a viral vector described herein, is systemically delivered. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active agent substantially immediately upon administration or at any predetermined time or time period after administration. The latter types of compositions are generally known as controlled release formulations, which include (i) formulations that create a substantially constant concentration of the agent within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with a tumor; (v) formulations that allow for convenient dosing, such that doses are administered, for example, once every one or two weeks; and (vi) formulations that target a cancer using carriers or chemical derivatives to deliver the therapeutic agent to a particular cell type (e.g., cancer or tumor cell). For some applications, controlled release formulations obviate the need for frequent dosing during the day to sustain the plasma level of the administered agent at a therapeutic level.

Methods by which to obtain controlled release in which the rate of release outweighs the rate of metabolism of the agent in question are not meant to be limiting. By way of example, controlled release is obtained by appropriate selection of various formulation parameters and ingredients, including, e.g., various types of controlled release compositions and coatings. Thus, the therapeutic agent is formulated with appropriate excipients into a pharmaceutical composition that, upon administration, releases the agent in a controlled manner. Examples include single or multiple unit tablet or capsule compositions, oil solutions, suspensions, emulsions, microcapsules, microspheres, molecular complexes, nanoparticles, patches, and liposomes.

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation, and can be found, for example, in Remington: The Science and Practice of Pharmacy, supra.

Compositions for parenteral delivery and administration may be provided in unit dosage forms (e.g., in single-dose ampules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent (e.g., a polynucleotide, viral vector or particle described herein), the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

In some embodiments, the composition comprising the active therapeutic(s) (i.e., a polynucleotide, viral vector or particle described herein) is formulated for intravenous delivery. As noted above, the pharmaceutical compositions according to the invention may be in the form suitable for sterile injection. To prepare such a composition, the suitable therapeutic(s) are dissolved or suspended in a parenterally acceptable liquid vehicle. Acceptable vehicles and solvents that may be employed include water, water adjusted to a suitable pH by addition of an appropriate amount of hydrochloric acid, sodium hydroxide or a suitable buffer, 1,3-butanediol, Ringer's solution, isotonic sodium chloride solution and dextrose solution. The aqueous formulation may also contain one or more preservatives (e.g., methyl, ethyl or n-propyl p-hydroxybenzoate). In cases where one of the agents is only sparingly or slightly soluble in water, a dissolution enhancing or solubilizing agent can be added, or the solvent may include 10-60% w/w of propylene glycol or the like.

Methods of Delivery

Administration of a polynucleotide (minigene), viral vector, or pharmaceutical composition of the invention to a subject, e.g., a patient having cancer, to treat one or more of the above cancers, may cause epitope spreading within the patient. One of the disadvantages of prior cancer vaccine strategies has been the heterogeneity and genomic instability of tumor cell populations, which, coupled with the selective pressure induced by treatment, can lead to tumor evasion by loss or modification of a tumor associated antigen used in the vaccine. In this context, an advantageous aspect of the present invention is the potential to induce epitope spreading, i.e., the expansion of an anti-tumor T cell response directed against epitopes of tumor associated antigens that are endogenous to a cancer or tumor cell, but not actively delivered by the vector during therapy with a cancer vaccine. Epitope spreading may be enhanced through the four stages of $CD8^+$ T cell activation: induction, cytotoxicity, diversification, and memory. For example, administration of a Sindbis/LacZ viral vector to a LacZ+ CT26 tumor-bearing mouse can enable the Sindbis to deliver LacZ to the mediastinal lymph node (LN), which can then induce a $CD8^+$ T cell response that targets LacZ(+) tumor cells. Lysis of LacZ(+) tumor cells by cytotoxic T cells can cause the LacZ(+) tumor cells to release gp70 and other TAAs, leading to the diversification of the $CD8^+$ T cell response and to the generation of a diverse repertoire of memory $CD8^+$ T cells. The diverse memory $CD8^+$ T cells are then capable of eliminating any re-emerging tumor cells that lost LacZ expression (i.e., LacZ(−) tumor escape variants). Clinical trials are increasingly incorporating the analysis of epitope spreading, and in some cases a positive correlation between the induction of epitope spreading and therapeutic efficacy has been shown.

In embodiments, the polynucleotide (minigene), viral vector, viral particle, or pharmaceutical composition of the invention, which is useful for eliciting a T cell response against the multiple epitopes of tumor associated antigens that are encoded by these agents, may be delivered, such as to a cell (particularly a cancer or tumor cell) in any manner such that the polynucleotide, viral vector, particle or composition is functional and active to express the encoded sequences. Illustratively, a polynucleotide encoding amino acid sequences of multiple tumor associated antigen epitopes may be delivered to cells for heterologous expression of the epitopes in the cells. Thus, the present invention features polynucleotides, viral vectors, or viral particles delivered to a cell by contacting the cell with a composition comprising the polynucleotides, viral vectors, or viral particles or by heterologously expressing the polynucleotides, viral vectors, or viral particles in the cell.

Polynucleotide Therapy

One therapeutic approach for treating a cancer or tumorigenesis is polynucleotide therapy using a polynucleotide encoding the tumor associated antigen epitopes, such as two or more epitopes of one or more tumor associated antigens, or using polynucleotide therapy using a polynucleotide encoding a checkpoint protein molecule as described herein. Expression of such polynucleotides or nucleic acid molecules in relevant cells is expected to stimulate an immune response, such as a cytotoxic T cell response, reduce survival of the cell and/or increase cell death. Such nucleic acid molecules can be delivered to cells of a subject having a cancer or tumor. The nucleic acid molecules must be delivered to the cells of a subject in a form in which they can be taken up so that therapeutically effective levels of the encoded products can be produced.

Transducing viral (e.g., retroviral, adenoviral, and adeno-associated viral) vectors can be used for delivering encoded proteins and peptide products to cells, especially because of their high efficiency of infection and stable integration and expression (see, e.g., Cayouette et al., *Human Gene Therapy,* 8:423-430, 1997; Kido et al., *Current Eye Research,* 15:833-844, 1996; Bloomer et al., *Journal of Virology,* 71:6641-6649, 1997; Naldini et al., *Science,* 272: 263-267, 1996; and Miyoshi et al., *Proc. Natl. Acad. Sci. U.S.A.,* 94:10319, 1997). For example, a polynucleotide encoding multiple epitopes of one or more tumor associated antigens, or a polynucleotide encoding a checkpoint protein or a ligand binding portion thereof, as well as a checkpoint protein minibody as described herein, can be cloned into a vector, e.g., a Sindbis virus vector or a pseudotyped virus vector, as described herein, and expression can be driven from its endogenous promoter, from a retroviral long terminal repeat, or from a promoter specific for a target cell type of interest. Other viral vectors that can be used include, for example, a vaccinia virus, a bovine papilloma virus, or a herpes virus (see, for example, the vectors of Miller, *Human Gene Therapy,* 15-14, 1990; Friedman, *Science,* 244:1275-1281, 1989; Eglitis et al., *BioTechniques,* 6:608-614, 1988; Tolstoshev et al., *Current Opinion in Biotechnology,* 1:55-61, 1990*; Sharp, The Lancet,* 337:1277-1278, 1991; Cornetta et al., *Nucleic Acid Research and Molecular Biology,* 36:311-322, 1987; Anderson, *Science,* 226:401-409, 1984; Moen, *Blood Cells,* 17:407-416, 1991; Miller et al., *Biotechnology,* 7:980-990, 1989; Le Gal La Salle et al., *Science,* 259:988-990, 1993; and Johnson, *Chest,* 107:77S-83S, 1995). Retroviral vectors are well developed and have been used, for example, as described in Rosenberg et al., *NEJM,* 323:370, 1990; Anderson et al., and U.S. Pat. No. 5,399,346. In some embodiments, the viral vector containing a polynucleotide or minigene encoding multiple tumor associated antigen epitopes is administered systemically. In some embodiments, the viral vector containing a polynucleotide encoding a checkpoint protein, a ligand binding portion thereof, or a checkpoint protein minibody is administered systemically.

As will be appreciated by the skilled practitioner, non-viral approaches can also be employed for the introduction of therapeutic polypeptide to a cell of a subject requiring induction of a T cell epitope immune response to inhibit growth of a cancer or tumor or to induce cancer or tumor cell death. For example, a nucleic acid molecule can be introduced into a cell by administering the nucleic acid in the presence of lipofection (Feigner et al., *Proc. Natl. Acad. Sci. U.S.A.* 84:7413, 1987; Ono et al., *Neuroscience Letters,* 17:259, 1990; Brigham et al., *Am. J Med. Sci.,* 298:278, 1989; Staubinger et al., *Methods in Enzymology,* 101:512, 1983), asialoorosomucoid-polylysine conjugation (Wu et al., *Journal of Biological Chemistry,* 263:14621, 1988; Wu et al., *Journal of Biological Chemistry,* 264:16985, 1989), or by micro-injection under surgical conditions (Wolff et al., *Science,* 247:1465, 1990). In addition, the nucleic acids can be administered in combination with a liposome and protamine.

Gene transfer can also be achieved using in vitro transfection methods. Such methods include the use of calcium phosphate, DEAE dextran, electroporation, and protoplast fusion. Liposomes can also be potentially beneficial for delivery of DNA into a cell.

cDNA expression for use in polynucleotide therapy methods can be directed from any suitable promoter (e.g., the Sindbis virus promoter, the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, regulation can be mediated by the cognate regulatory sequences or, if desired, by regulatory sequences derived from a heterologous source, including any of the promoters or regulatory elements described above.

Methods of Administration and Treatment Protocols

Provided are methods of administering a therapeutic agent to a subject in need, such as a subject having cancer or a tumor, or identified as being in need of such treatment), in which an effective amount of a polynucleotide, viral vector, or viral particle as described herein, or a composition described herein, is administered to a subject to produce a therapeutic effect. According to the present invention, a therapeutic effect includes, without limitation, an epitope-specific immune response against cancer and tumor cells expressing TAA-associated epitopes on their surface, e.g., by effector T cells (e.g., CD8+ T cells) activated by the multiple epitopes encoded by the polynucleotide or viral vector, such as a Sindbis virus vector encoding multiple epitopes of tumor associated antigens, optionally in association with MHC Class I or Class II molecules. Also according to the present invention, a therapeutic effect includes, without limitation, an immune response against cancer and tumor cells expressing checkpoint protein binding molecules (e.g., receptors that bind checkpoint protein) on their surface, e.g., by effector T cells (e.g., CD8+ T cells). Identifying a subject in need of such treatment can be in the judgment of a subject or a health or medical care professional and can be subjective (e.g. opinion) or objective (e.g. measurable by a test or diagnostic method).

The therapeutic methods of the invention (which include prophylactic treatment) in general comprise administration of a therapeutically effective amount of the agents described herein, such as a polynucleotide, a viral vector, a viral particle, or composition containing the aforementioned agents, to a subject (e.g., animal, human) in need thereof, including a mammal, particularly a human. Such treatment will be suitably administered to subjects, particularly humans, suffering from, having, susceptible to, or at risk for cancer or a tumor. Determination of those subjects "at risk" can be made by any objective or subjective determination by a diagnostic test or opinion of a subject or health care provider (e.g., genetic test, enzyme or protein marker or biomarker, family history, and the like). The polynucleotide and viral vector agents described herein may be also used in the treatment of any other diseases or disorders in which multiple epitopes of one or more tumor associated antigens may be implicated.

In preclinical studies using mice, a single intraperitoneal (i.p.) injection of a therapeutically effective amount of the Sindbis viral vector encoding multiple (e.g., two or more) epitopes of one or more tumor associated antigens (SV/TAA), (~$10^7$ virus particles), resulted in rapid immunogenic delivery to lymph nodes and elicited a detectable CD8+ mediated immune response directed against the tumor (Example 5, infra). In other preclinical studies using mice, intraperitoneal (i.p.) injections of a therapeutically effective amount of the Sindbis viral vector encoding the checkpoint protein (e.g., a checkpoint protein minibody), (~$10^5$ virus particle transforming units), resulted in an immune response directed against the tumor and a reduction in tumor growth and increased survival of treated animals (Example 11, infra). It will be appreciated by the skilled practitioner that other regimens may be necessary for achieving a maximal response in human subjects. For example, in human patients, therapeutically effective amounts of the vectors of the present invention can broadly range between about 6 and about 12 $Log_{10}$ vector particles/kg per treatment administered over time, e.g., between about 1 and about 8 i.p. injections over a time period of between about 1 week and many weeks, with the possibility of injecting one or more booster injections, week, months, or years, e.g., 1 or more years, later.

Viral vectors, polynucleotides (minigenes) and pharmaceutical compositions of the present invention can be used therapeutically to treat patients suffering from cancer or tumors, or prophylactically to vaccinate patients at risk for certain cancers or tumors, such as a prophylactic vaccine for cancer in the general population. A prophylactically effective amount of the vectors of the present invention may range between about $10^2$ TU (transducing units) per kilogram body weight of the recipient and about $10^6$ TU kilogram body weight, or about $10^8$ TU kilogram body weight, of the recipient. Mouse models of relevant cancers can be used to optimize dosages and regimens. To promote an effective, persistent immune response that includes both effector and memory CD8+ T cells, optimal dosage and immunization intervals are established. A CD8+ T cell response to an initial alphavirus vaccine quickly contracts, allowing development of memory T cells. Prior to this contraction, additional administration of the viral vector does not increase the immune response (Knudsen, M. L. et al., 2014, *J Virol.,* 88:12438-12451). The strong type I interferon (IFN) response to alphavirus RNA amplification stimulates the generation of memory T cells by activating dendritic cells to promote cross-priming (Fuertes, M. B. et al., *J Exp Med,* 208: 2005-2016).

A typical treatment regimen using a composition of the invention may include SV/multi-TAA epitope viral vector or SV_checkpoint protein viral vector administration followed by monitoring lymphocytes, several times per week, using flow cytometry to determine the peak and decline of effector CD8+ T cells ($CD62L^-$ $CD127^-$ phenotype). At this point, a boost of vector can be administered allowing an increase in effector memory T cells ($CD62L^-$ $CD127^+$), central memory T cells ($CD62L^+CD127^+$) and T cells with persistent high recall capacity ($CD27^+CD43^-$). Efficacy is determined by positive immune response and low tumor recurrence.

The present invention is not limited with respect to the vectors used for immunization and boost(s). The distribution of T cell subpopulations induced by a DNA-launched alphavirus replicon can be altered by heterologous boost (Knudsen, M. L. et al., 2-14, J. Virology, 88:12438-12451). For example, boosting with a poxvirus vector (Modified Vaccinia Ankara or MVA) can boost the expansion of T cell compartments that can greatly augment efficacy. In this embodiment, the viral vector employed in the booster administration encodes multiple (e.g., two or more) epitopes of one or more tumor associated antigens. Any antigen delivery system can be used to boost the immune response induced by the vectors of the present invention. Non-limiting examples include replication-defective adenoviruses, fowl pox viruses, vaccinia virus, influenza virus, Sendai virus, naked DNA, plasmids and peptides (Woodland, D. L., 2004, *TRENDS in Immunology*, Vol. 25(2):98-104).

Exemplary routes of vector administration include, without limitation, parenteral administration, such as by intraperitoneal, intravenous, subcutaneous, stereotactic, intramuscular, intranasal, intradermal, intraorbital, intranodular and intratumoral injection. Other modes of administration may include oral, intracranial, ocular, intraorbital, intra-aural, rectal, intravaginal, suppositories, intrathecal, inhalation, aerosol, and the like.

In a certain embodiment, the vector used for treatment is a defective Sindbis viral vector, the tumor is a cancer or tumor, such as ovarian cancer, and the two or more encoded epitopes of the tumor associated antigens include p53, SP17, survivin, WT1, and NY-ESO-1. In another embodiment the TAAs are NY-ESO-1, gp70, and pbk. In another embodiment the TAAs include NY-ESO-1 and survivin.

In another certain embodiment, the vector used for treatment is a defective Sindbis viral vector, the tumor is a cancer or tumor, such as colon cancer or ovarian cancer, and the checkpoint protein encoded by the viral vector is PD-1 or a cognate ligand binding portion thereof may be used.

Patients to whom the viral vectors of the present invention are administered may also benefit from adjunct or additional treatments, such as chemotherapy and or radiation treatments, as well known to those having skill in the art. In particular, the SV/TAA Sindbis viral vector can be combined with chemotherapy treatment. In certain cases, SV and chemotherapy synergize (e.g., US Patent Application Publication No. 2016/0008431), thus providing the potential for an improved treatment effect and/or outcome. Suitable chemotherapy includes, without limitation, chemotherapy treatment that stimulates the immune system, or that inhibits suppressor elements in the immune system, or that affects tumor cells and makes them more susceptible to T cell (or other immune cell) cytotoxicity. For example, there are certain chemotherapies that can facilitate treatment and therapy with the SV/TAA viral vector described herein because they attenuate the activity of immunosuppressive cells, thereby enhancing immunostimulation by the SV/TAA viral vector. In addition, chemotherapy may enhance tumor cell susceptibility to T cell mediated cytotoxicity.

Kits

The invention provides kits for the treatment or prevention of cancer or tumors, particularly those expressing multiple epitopes of one or more tumor associated antigens. In one embodiment, the kit includes a therapeutic or prophylactic composition containing an effective amount of a polynucleotide, viral vector, or viral particle as described herein, which comprises a polynucleotide that encodes two or more epitopes of one or more tumor associated antigens separated by enzymes cleavage sites. In another embodiment, the kit includes a therapeutic or prophylactic composition containing an effective amount of a polynucleotide, viral vector, or viral particle as described herein, which comprises a polynucleotide that encodes a checkpoint protein, a ligand binding portion of the checkpoint protein (e.g., an extracellular domain of the checkpoint protein), or a minibody checkpoint protein fusion protein. In an embodiment, the encoded checkpoint protein is PD-lor a cognate ligand binding portion thereof. In an embodiment, the polynucleotide encodes an alphavirus protein or a fragment thereof. In an embodiment, the alphavirus protein or a fragment thereof is a Sindbis virus protein or a fragment thereof. In embodiments, the epitopes and tumor associated antigens are those presented in Tables 1-28 supra. In some embodiments, the kit comprises a sterile container which contains the therapeutic or prophylactic composition; such containers can be boxes, ampoules, bottles, vials, tubes, bags, pouches, blister-packs, or other suitable container forms known in the art. The containers can be made of plastic, glass, laminated paper, metal foil, or other materials suitable for holding medicaments.

If desired, a composition comprising one or more TAA multiple epitope-encoding viral vector agents of the invention is provided together with instructions for administering the agent to a subject having or at risk of developing cancer or a tumor. The instructions will generally include information about the use of the composition for the treatment or prevention of the cancer or tumor. In other embodiments, the instructions include at least one of the following: description of the therapeutic agent; dosage schedule and administration for treatment or prevention of ischemia or symptoms thereof, precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides, viral vectors and viral particles of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1—Methods

Vector preparation: Construction of recombinant viral vectors was performed using standard techniques well known to those of ordinary skill in the field of molecular biology, including, but not limited to, plasmid purification, restriction endonuclease digestion, ligation, transformation, polymerase chain reaction and DNA sequencing (e.g., Current Protocols in Molecular Biology, EM. Ausubel et al. (Eds), John Wiley and Sons, Inc., NY, USA. (1998) and Molecular Cloning: A Laboratory Manual (2nd Ed.), J. Sambrook, E. F. Fritsch and T. Maniatis (Eds), Cold Spring Harbor Laboratory Press, NY, USA. (1989)).

For the experiments using Sindbis viral vector encoding LacZ (SV/LacZ) as an immunogenic SV/TAA agent, and SV/Fluc and SV/GFP as control vectors, the vectors were produced as previously described. (Tseng J. C. et al,., 2004, Nat. Biotechnol., 22:70-77). Briefly, plasmids carrying the replicon (SinRep5-LacZ, SinRep5-GFP, or SinRep5-Fluc) or DHBB helper RNAs (SinRep5-tBB) were linearized with XhoI (for SinRep5-LacZ, SinRep5-GFP, and SinRep5-tBB) or PacI (for SinRep5-Fluc). In vitro transcription was performed using the mMessage mMachine RNA transcription kit (Ambion, Austin, TX). Helper and replicon RNAs were then electroporated into BHK cells and incubated at 37° C. in α-MEM supplemented with 10% FBS. After 12 hours, the medium was replaced with OPTI-MEM I (Invitrogen, Carlsbad, CA), supplemented with $CaCl_2$ (100 μg/ml), and cells were incubated at 37° C. After 24 hours, the supernatant was collected, centrifuged to remove cellular debris, and frozen at −80° C. Vector titers were determined as known in the art (Tseng J. C., et al., 2002, *J Natl Cancer Inst.*, 94:1790-1802) and were similar in all three vectors (SV/LacZ, SV/Fluc, and SV/GFP).

Cell lines and Cell Culture: Baby hamster kidney (BHK), CT26.WT, and LacZ-expressing CT26.CL25 cells were obtained from the American Type Culture Collection (ATCC), (Manassas, VA). BHK cells were maintained in minimum essential α-modified media (α-MEM) (Mediatech, VA) with 10% fetal bovine serum (FBS) (Atlanta Biologicals, Norcross, GA). CT26.WT, CT26.CL25 cells were maintained in Dulbecco modified essential media (DMEM) containing 4.5 g/L glucose (Mediatech) supplemented with 10% FBS. All basal media was supplemented with 100 mg/mL of penicillin-streptomycin (Mediatech) and 0.5 mg/mL of amphotericin B (Mediatech).

Virion Production: Sindbis virus vectors were produced as described in U.S. Pat. Nos. 7,303,898, 7,306,792, and 8,093,021. Briefly, plasmids carrying the replicon pT7StuI-R or DHBB helper RNAs (SinRep5-tBB) were linearized with appropriate restriction enzymes. In vitro transcription was performed using the mMessage RNA transcription kit (Ambion, TX) according to the manufacturer's instructions. Helper and replicon RNAs were then electroporated into BHK cells and incubated at 37° C. in MEM supplemented with 10% FBS. After 12 hours, the medium was replaced with OPTIIEM I (Life Sciences, CA) supplemented with $CaCl_2$) (100 g/mL) and cells were incubated at 37° C. After 24 hours, the supernatant was collected, centrifuged to remove cellular debris, and frozen at −80° C. Titers of the vectors were determined using RT-qPCR as practiced in the art.

Mice, Tumor Inoculation and Therapeutic Efficacy: 4-8-week-old female BALB/c mice were purchased from Taconic (Germantown, NY). For an i.p. tumor model, $2.5\times10^4$ or $5\times10^4$ CT26.CL25 cells in 0.2 mL PBS were injected i.p. into each mouse. For the lung tumor model, $0.3\times10^6$ CT26.WT.Fluc or CT26.CL25.Fluc cells in 0.2 ml PBS were injected intravenously into each mouse. Therapeutic efficacy was monitored in three ways: tumor volume (for subcutaneous tumors, measured with mechanical calipers), tumor luminescence and survival. Noninvasive bioluminescent imaging was performed using the IVIS Spectrum imaging system (Caliper Life Sciences, Inc., MA), and tumor growth was quantified using the Living Image 3.0 software (Caliper Life Sciences). Survival of the animals was monitored and recorded daily.

Flow cytometry: Flow cytometry was used to analyze lymphocytes extracted from organs, peritoneum or peripheral blood. Cells were treated with 1×RBC lysis buffer (eBioscience) to eliminate red blood cells. Peritoneal cells were collected and stained with various Abs, washed twice with HBSS buffer (Mediatech), and analyzed using an LSR II machine (BD Biosciences, San Jose, CA). Data were analyzed using FlowJo (Tree Star, San Carlos, CA).

Bioluminescent imaging ofSVFluc: Tumor-bearing and tumor-free mice were injected with SV/Fluc (~$10^7$ plaque-forming units in 0.5 ml of OPTI-MEM I 0.5 ml) i.p. After the treatment, bioluminescence signal was detected by IVIS at the indicated time points (Tseng, J. C. et al., 2004).

Example 2—Construction of a Sindbis Viral Vector Expressing Multiple Epitopes for Inducing Anti-Tumor Immunity A polynucleotide (DNA sequence; minigene) encoding multiple T cell recognition epitopes separated by furin enzyme cleavage sites was synthesized by GeneArt® (Life Technologies Corp., Waltham MA) using standard molecular biology methods. The synthetic polynucleotide contained a ribosome binding site, a translation start codon, an endoplasmic reticulum signal sequence, followed by furin cleavage sites interspersed with the epitope-encoding sequences, a stop codon and restriction enzyme sites that allowed the polynucleotide sequence to be inserted into XbaI/ApaI restriction endonuclease sites of the Sindbis replicon pT7StuI-RLacZ #202 (WO 2015/035213 A2) to replace the LacZ gene. The Sindbis replicon contained a viral subgenomic promoter sequence upstream from the XbaI site and a mRNA poly A sequence located downstream of the ApaI site. This synthesized DNA sequence and its encoded amino acid sequences are as follows:

```
DNA Sequence
                                                  (SEQ ID NO: 10)
TCTAGAGCCACCATGCTGGTGACAGCCATGTGTCTGCTGGGCAATGTCAG

CTTCGTCCGGAGCAAGCGGCTGCGGGGACCAGAGTCTCGGCTCCTGGAGG

TGCGGAGCAAGCGGCTGTCCCCATCTTACGCCTACCACCAGTTCGTCCGG

AGCAAGCGGCTGGGCTGTGCCTTCCTGACCGTGAAGCAGATGCGGAGCAA

GCGGCTGTGAGGGCCC

Amino acid Sequence
                                                  (SEQ ID NO: 11)
MLVTAMCLLGNVSFVRSKRLRGPESRLLEVRSKRLSPSYAYHQFVRSKRL

GCAFLTVKQMRSKRL*
```

The synthesized polynucleotide sequence was inserted into the GeneArt pMX plasmid and provided as a DNA plasmid. The plasmid was transformed into NEB 5-alpha competent *E. coli* cells (New England BioLabs). Clones were grown and plasmid DNA was purified. The clones were verified by DNA sequencing (Macrogen USA). The restriction enzymes XbaI and ApaI were used to excise the DNA polynucleotide (minigene) from the pMX plasmid vector. Following extraction, the polynucleotide (minigene) was cloned into the pT7StuI-RLacZ #202 vector. Schematically, the minigene as described is illustrated in FIG. 1A and the exact sequence arrangement is shown in FIG. 1B.

Because Sindbis virus polypeptides are naturally processed by furin, a nucleic acid sequence encoding the Sindbis furin digestion motif, XRSKRX, where X is a hydrophobic residue (SEQ ID NO: 5), was incorporated into the polynucleotide to allow proper processing of the encoded epitopes of the tumor associated antigens. A ribosomal binding site, start codon and an alphavirus endoplasmic reticulum (ER) signal sequence were also encoded at the 5' flanking region of the furin-epitope-furin sequences. The ER signal sequence was included to facilitate multi-epitope polypeptide translocation into the ER where furin digestion occurs. A stop codon was included at the 3' end of the polynucleotide (minigene). The restriction enzyme sites, XbaI and ApaI, were molecularly engineered into the 5' and 3' ends, respectively, of the polynucleotide in order to clone the synthesized polynucleotide sequence into the Sindbis virus vector nucleic acid directly downstream of the viral subgenomic promoter that drives high levels of transcription.

In this Example, two or more epitopes, i.e., 3 different epitopes, of different tumor associated antigens were incorporated into the Sindbis viral vector, namely, an epitope of human NY-ESO-1, as described herein, which is a tumor associated antigen expressed in human ovarian cancers and other human cancers; an epitope of gp70, an endogenous murine leukemia virus antigen; and an epitope of survivin, an anti-apoptotic protein that is highly expressed in many tumors. The three epitopes are presented in Table 30 and are highly expressed in CT26 tumors, but have low expression in normal mouse tissues.

TABLE 30

Epitopes included in SV/MG

| Antigen | Epitope | Amino acids | MHC I | Reference |
|---|---|---|---|---|
| GP70 | SPSYAY-HQF (SEQ ID NO: 395) | 423-431 | H-2$L^d$ | Slansky, J. E. et al., 2000, Immunity, 13: 529-538 |
| NY-ESO-1 | RGPESR-LLE (SEQ ID NO: 3) | 81-89 | H-2$D^d$ | Muraoka, D., et al., 2013, Vaccine, 31: 2110-2118 |
| Survivin | AFLTVK-KQM (SEQ ID NO: 4) | 83-91 | H-2$K^d$ | Siegel, S. et al., 2003, Br. J. Haematol., 122:911-914; Yang, Z. et al., 2008, Mol. Immunol., 45:1674-1681. |

Determining in vivo anti-tumor efficacy: To test the anti-tumor efficacy of the Sindbis viral vector encoding multiple (3) epitopes of different tumor associated antigens (TAAs), as described above, (denoted "SV/MG" or "SV/MG-CT26" herein), a Balb/c CT26 colon carcinoma tumor model was used in which CT26/NY-ESO-1 cells were injected intraperitoneally into BALB/c mice. CT26 is a murine colon cancer cell line that was transfected with human NY-ESO-1 cDNA and stably expresses human NY-ESO-1 and its epitopes, and is available from the American Type Culture Collection (ATCC, Manassas, VA). When injected into susceptible mice, the cells form solid tumors in the animals. CT26 cells can also be transfected with proteins, e.g., LacZ, luciferase, GFP, to aid in detecting tumors in animal studies. An exemplary administration regimen is shown FIG. 2A. Imaging of tumors: Bioluminescence signals were periodically monitored using the IVIS system. Living Image software (Xenogen Corp., Alameda, CA) was used to grid the imaging data and integrate the total bioluminescence signals (RLU) in each boxed region to obtain the data shown in FIG. 2B. Wild-type CT26 cells and LacZ-expressing CT26 cells (CT26.CL25 (LacZ) cells) were obtained from the American Type Culture Collection (Manassas, VA).

The CT26.CL.25 (LacZ) cells express several tumor associated antigens. (Castle, J. C. et al., 2014, *BMC Genomics,* 15:190). CT26.CL25 cells expressing the NY-ESO-1 epitope are as described in Gnjatic, S. et al., 2006, *Adv Cancer Res,* 95:1-30. Firefly luciferase (Fluc)-expressing CT26 cells (CT26.WT.Fluc and CT26.CL25.Fluc) for non-invasive bioluminescent imaging were generated by stable transfection of a Fluc-expressing plasmid into the CT26.WT and CT26.CL25 cells. The Fluc-expressing plasmid was constructed by introducing an SV40 promoter sequence into the multi-cloning site of the pGL4.20 vector (Promega, WI) (Granot, T. et al., 2014, *Mol. Ther.,* 22:112-122).

Figure 2B:
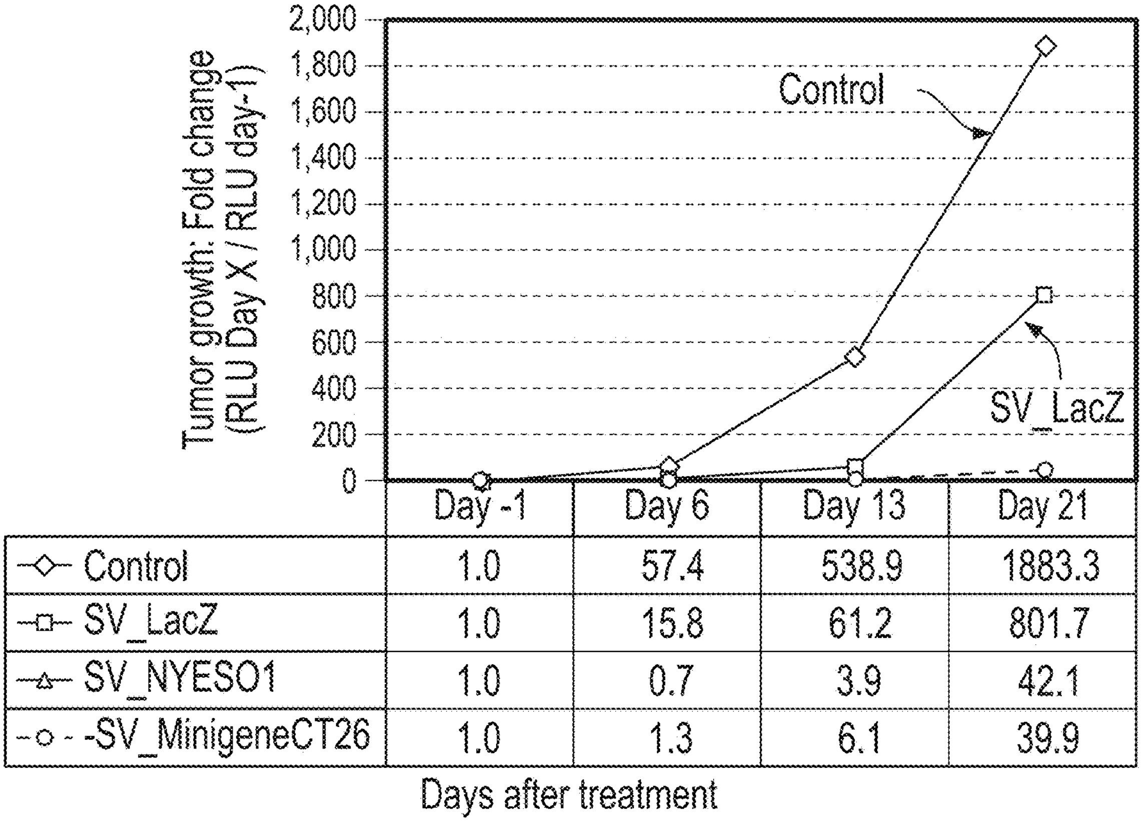

As shown in FIG. 2B, the growth of CT26/NY-ESO-1 tumor cells in animals treated with the multi-TAA epitope Sindbis virus vector (SV/MG) was strikingly lower compared to that in animals treated with the negative control and irrelevant control Sindbis viral vectors for an extended time period, e.g., to Day 27 post administration. Controls shown in FIG. 2B were mice that had not received Sindbis viral vectors (control), mice that had received SV/LacZ, a Sindbis viral vector that encodes the bacterial enzyme beta-galactosidase (LacZ), an irrelevant tumor associated antigen; and a positive control Sindbis viral vector, SV/NY-ESO-1, which encodes the NY-ESO-1 tumor associated antigen and which effectively reduced the growth of CT26/NY-ESO-1 tumor cells in animals harboring the tumors.

In a related example, another Sindbis viral vector encoding multiple epitopes of tumor associated antigens (e.g., called the SV/MG vector) can be prepared using the same techniques described above for testing in the CT26 tumor mouse model. The Sindbis viral vector created to treat tumors in the CT26 mouse model encodes an epitope of the tumor associated antigen NY-ESO-1, an epitope of the viral antigen gp70, and an epitope from the tumor associated antigen Pbk, also termed TOPK for T-cell-originated protein kinase. Advantageously, these epitopes are highly expressed in CT26.CL25 tumor cells, but have low expression in mouse tissues. The epitope sequences included in the SV/MG vector are shown in the below Table 31. In an embodiment, epitope sequences of HIV gp120 or gp41 and an epitope sequence from human pbk or a human pbk ortholog may be included in the SV vector.

TABLE 31

Epitopes used in the Sindbis virus multi-TAA epitope vector

| Antigen | MHC 1 | Epitope |
| --- | --- | --- |
| NY-ESO-1 | H2Dd | LLMWITQCF (SEQ ID NO: 1) |
| MuLV gp70 | H2Ld | SPSYVYHQF (SEQ ID NO: 396) |
| Pbk | H2Dd | GSPFPAAVI (SEQ ID NO: 2) |

The polynucleotide comprising multiple epitope sequences of tumor associated antigens NY-ESO-1, gp70 and pbk for Sindbis viral vector expression was prepared by synthesizing double-stranded oligomers and DNA primers (GeneLink Inc.) as set forth below. Routine PCR technology was used to generate two fragments which have their ends modified by mis-priming so that they shared a region of homology. When these two fragments were mixed, denatured and reannealed, the 3'-end of the top strand of fragment annealed onto the 3'-end of the bottom strand of fragment, and this overlap was extended to form the recombinant product. This process was reiterated until all epitope fragments were incorporated.

A. Oligomers

```
Gp70        R S K R L S P S Y V Y H Q F
            AGG AGC AAA AGA GTG AGC CCC AGC TAC
            GTG TAC CAC CAG TTC TCC TCG TTT TCT
            CAC TCG GGG TCG ATG CAC ATG GTG GTC
            AAG (SEQ ID NO: 398)

NY-ESO-1    R S K R L L M W I T Q C F
            AGG AGC AAA AGA CTG CTG ATG TGG ATC
            ACC CAG TGC TTC TCC TCG TTT TCT GAC
            GAC TAC ACC TAG TGG GTC ACG AAG
            (SEQ ID NO: 400)
```

```
Pbk         R S K R G S P F P A A V T
            AGG AGC AAA AGA GGC AGC CCC TTC CCC
            GCC GCT GTG ACC TCC TCG TTT TCT CCG
            TCG GGG AAG GGG CGG CGA
            CAC TGG
            (SEQ ID NO: 402)
RSKR = Furin sequence
```

B. Primers

```
Primer 1:   5' agg agc aaa aga cac agc ccc agc 3'
            (SEQ ID NO: 403)

Primer 2:   5' tct ttt gct cct gaa ctg gtg gta 3'
            (SEQ ID NO: 404)

Primer 3:   5' tac cac cag ttc agg agc aaa aga 3'
            (SEQ ID NO: 405)

Primer 4:   5' tct ttt gct cct gaa gca ctg ggt 3'
            (SEQ ID NO: 406)

Primer 5:   5' acc cag tgc ttc agg agc aaa aga 3'
            (SEQ ID NO: 407)

Primer 6:   5' ggt cac agc ggc ggg gaa 3'
            (SEQ ID NO: 408)
```

PCR and splicing by overhang extension (SOE) PCR reactions were carried out in a thermocycler for 25 cycles, each consisting of 1 min at 94° C., 2 min at 50° C., and 3 min at 72° C. Taq-PCR reactions were performed with reaction buffer containing dNTP's (200 µM), forward and reverse primers (0.5 µM/each) and 1µ Taq-DNA polymerase in a final volume of 20 µl. PCR products were analyzed by electrophoresis in agarose gels and DNA bands were excised from the gel and purified with a gel extraction kit (Zymo Research). The completed multi-epitope fragment was blunt-end ligated into the NaeI site of the pT7StuI-R ALacZ #202 plasmid vector, transformed into *E. coli*, purified and sequenced.

Example 3—Sindbis Viral Vector Encoding Multiple Epitopes of Tumor Associated Antigens Produces Polyepitope mRNA An experiment was conducted to determine whether the Sindbis viral vector (SV/MG-CT26) encoding multiple epitopes of tumor associated antigens, namely, NY-ESO-1, gp70 and survivin as described in Example 2 supra, produced the correct multiple epitope mRNA. For the experiment, ten-fold serial dilutions of the Sindbis virus vector encoding multiple epitopes, called "SV/MG-CT.26" herein ($10^0$-$10^{11}$) were used to infect $2 \times 10^4$ baby hamster kidney cells. After an overnight incubation, the cells were collected by centrifugation, and RNA was isolated using a Qiagen kit (Qiagen, Hilden, Germany) according to the manufacturer's instructions. RNA was quantified using a nanodrop spectrophotometer.

One microgram (1 µg) of each sample was reversed transcribed using ThermoScript (Life Technologies, CA) according to the manufacturer's instructions. The cDNA5_R reverse primer 5' TTTTTGAAATGTTAAAAACAAAAT-TTTGTTG (SEQ ID NO: 409) was used at a concentration of 50 M to transcribe the RNA into cDNA. Quantitative PCR (qPCR) was performed using 5 µl out of the 30 µl total cDNA reaction. Syber green master reaction mix was used according to the manufacturer's instructions (BioRad, CA). A standard curve was generated using 10-fold dilutions of pT7StuI-R-MG_CT26 plasmid DNA from which the viral vector was made. For performing qPCR, the Forward primer was: Sindbis position 7692: TGATCCGACCAGCAAAACTC (SEQ ID NO: 410), and the Reverse primer was cDNA5_R pos. 7990: TTTTTGAAATGTTAAAAACAAAATTTTGTTG (SEQ ID NO: 409). The primer concentration used was 10 μM. qPCR was performed using a MyiQ cycler (BioRad, CA). The dilution factors and picograms (pg) of transcript produced are presented in the table below.

TABLE 32

| Dilution Factor | Transcript (in pg) |
|---|---|
| $10^0$ | 1122 |
| $10^{-2}$ | 26.5 |
| $10^{-4}$ | 1.39 |

Figure 3:
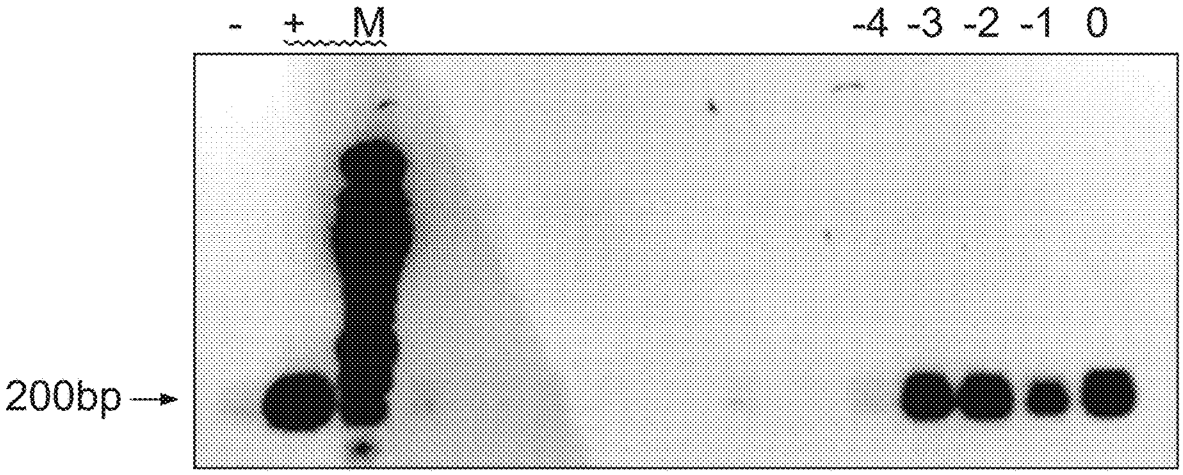
FIG. 3 shows a UV image of a stained agarose gel containing DNA samples following qPCR as described in Example 3, infra. The qPCR was performed with oligonucleotide primers specific for the SV RNA genome. In the gel, Lane (−) contained cDNA from uninfected BHK (control); Lane (+) contained a pSV/MG-CT.26 DNA plasmid (control); Lane M contained a 100 base pair ladder marker (control). The Lanes marked −4, −3, −2, −1 and 0 reflect the dilutions $10^{-4}$, $10^{-3}$, $10^{-2}$, $10^{-1}$ and $10^{0}$, respectively, of SV/MG-CT.26 virus used to infect BHK cells. The size of the qPCR fragment (~200 bp) agrees with that obtained with the plasmid DNA control. Because 100 μl of virus was added to the cells, the appearance of viral RNA in a $10^{-4}$ dilution indicated a titer of $10^5$ virus particles/ml. This titer coincided with the titer determined by qPCR CT (threshold cycle) values.

FIG. 3 presents a UV image of stained qPCR DNA products subjected to agarose gel electrophoresis. In the UV image of stained DNA samples from qPCR, the Lanes are identified as follows: Lane (−): cDNA from uninfected BHK; Lane (+): RNA/cDNA from pSV/MG plasmid; Lane M, 100 base pair ladder marker; Lane (−4), Lane (−3), Lane (−2), Lane (−1) and Lane (0) show qPCR products at the $10^{-4}$, $10^{-3}$, $10^{-2}$, $10^{-1}$, and $10^0$, respectively, dilutions, respectively, of RNA from baby hamster kidney (BHK) cells infected with SV/MG-CT.26 at the stated dilutions. The results from the qPCR experiment as presented in Table 32 indicate that the polynucleotide encoding multiple epitopes of the NY-ESO-1, gp70 and survivin tumor associated antigens was transcribed in BHK cells. Agarose gel electrophoresis indicates that the qPCR transcript is the expected size of 204 base pairs (bp). (FIG. 3).

Example 4—Preclinical Prophylactic and Therapeutic Treatment with SV/Multi-Epitope Vector The treatment protocol presented in Table 33 was used in testing the prophylactic, therapeutic and combined treatment of CT26/NY-ESO-1 tumor cells by administering a Sindbis viral vector encoding multiple epitopes of tumor associated antigens, in particular, the NY-ESO-1 cancer antigen, as described in Example 2, supra, and shown in FIG. 2A. The protocol was designed to determine the effects of prophylactic treatment of animals with a Sindbis viral vector expressing epitopes from multiple tumor associated antigens, i.e., SV/NY-ESO-1-gp70-survivin prior to inoculation of tumor cells (e.g., a Sindbis viral vector vaccine). The protocol was also designed to determine the effects of additional boosting inoculations administered at two time intervals; the effects of vector therapy only after tumor inoculation; and the effects of combined vaccine and therapeutic vector treatment.

TABLE 33

Treatment protocols using a SV/multi-epitope vector

| | Immunization | Boost | Inject tumor cells | Treat with SV/multi-epitope vector | Treat with SV/multi-epitope vector |
|---|---|---|---|---|---|
| Day | 1 | 7 | 17 | None | None |
| | 1 | 7 | 17 | 24 | 31 |
| | None | None | 17 | 24 | 31 |
| | None | None | 17 | None | None |
| | 1 | 21 | 31 | None | None |
| | 1 | 21 | 31 | 38 | 45 |
| | None | None | 31 | 38 | 45 |
| | None | None | 31 | None | None |

Example 5—Clinical Treatment with a Sindbis Virus-Multi Epitope Vector

A Sindbis virus vector encoding multiple epitopes of ovarian cancer tumor associated antigens (SV/Multi-epitope vector), including, for example, two or more of NY-ESO-1, CEA or CA-125 (Schwab, C. L. et al., 2014, *Immunotherapy,* 6:1279-1293) would be advantageous for use in treating ovarian cancer. Screening of tumors from patients who have undergone tumor debulking surgery can be used to determine whether treatment with a Sindbis viral vector encoding multiple epitopes of tumor associated antigens will be beneficial based on the presence of TAAs on cancer or tumor cells of the patients and on the patient's specific antigen presenting HLA haplotypes, e.g., as described in Example 6, infra. Following administration of the Sindbis viral vector encoding multiple epitopes of one or more tumor associated antigens, a body fluid sample, e.g., blood, serum, or plasma, of selected patients can be obtained to monitor blood lymphocytes in order to examine the patient's immune response and guide the treatment regimen. For example, a patient's blood can be analyzed over time for the presence of effector $CD8^+$ T cells, and to determine if the effector cells decline and memory ($CD27^+CD43^-CD8^+$) T cells appear. Routine techniques in the art are suitable for analyzing the patient's blood sample for the presence of the appropriate T cells, e.g., flow cytometry, immunohistochemistry, staining (e.g., immunofluorescent staining). When a memory cell response is detected, a second administration of the Sindbis viral vector encoding tumor associated antigen epitopes can be administered to boost the patient's immune response.

Figure 4A:
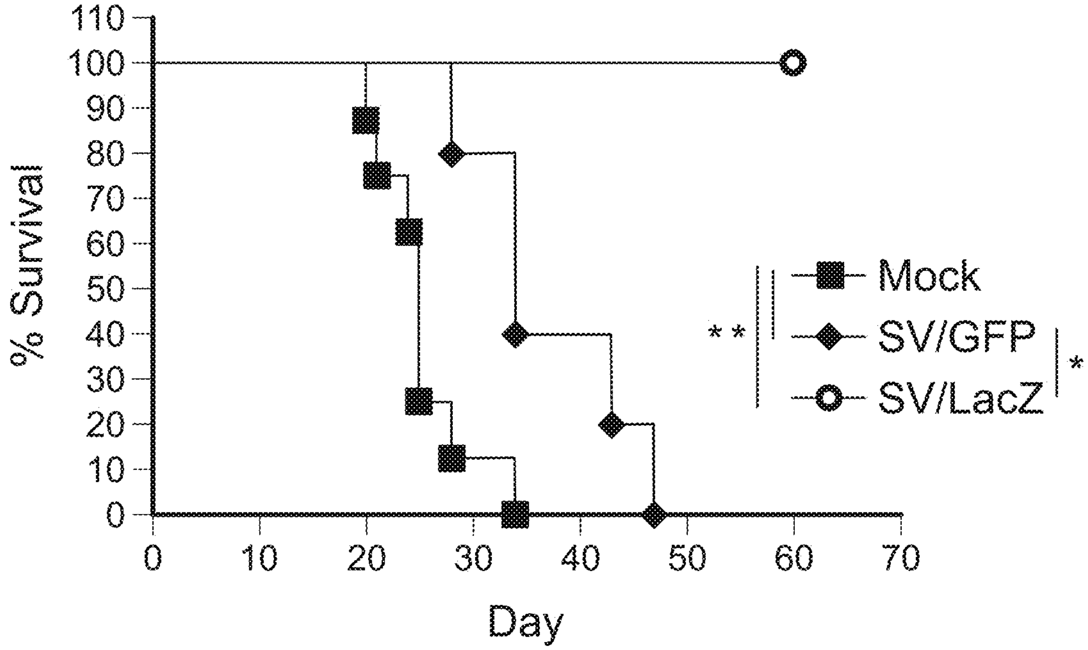
FIGS. 4A-4C show that treatment of tumored (LacZ+ CT26 tumors) mice with a Sindbis viral vector encoding LacZ, a representative tumor associated antigen ("SV/TAA" herein), substantially prolongs survival relative to controls, induces epitope spreading, and circumvents TAA loss.
Figure 4B:
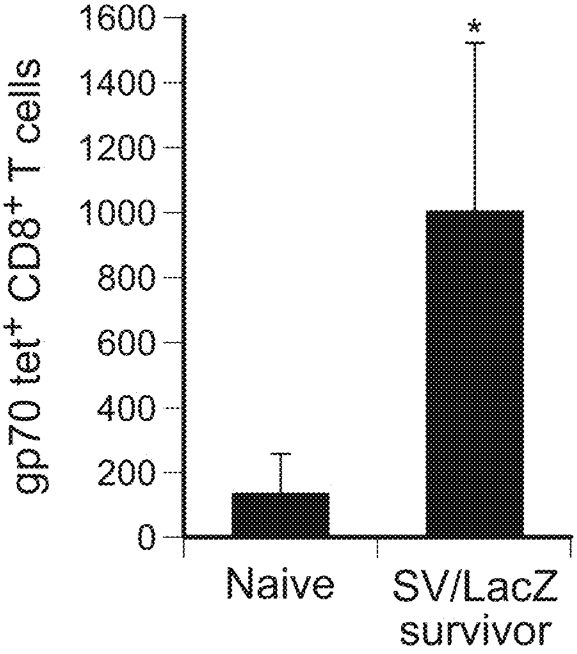
Figure 4C:
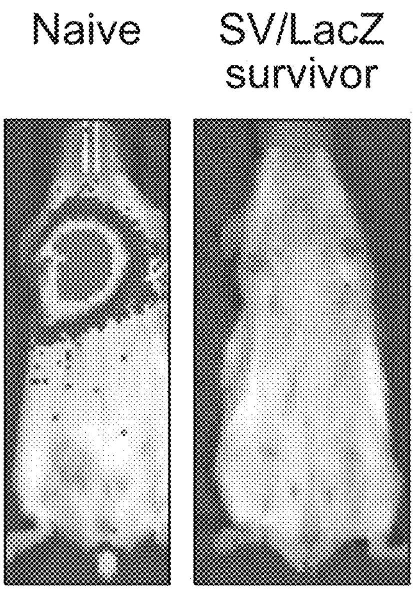

That a SV vector expressing the exemplary tumor associated antigen (TAA) LacZ was effective in the CT26 tumor mouse model and maintained the survival of mice having LacZ-expressing CT26 tumors, (FIG. 4A), as well as induced the diversification of the $CD8^+$ T cell response to a tumor model (FIG. 4B), has been demonstrated by the inventors' studies using a Sindbis viral vector encoding the bacterial β-galactosidase (LacZ) enzyme, (SV/LacZ), and a comparator control Sindbis viral vector encoding green fluorescence protein (GFP), (SV/GFP). FIG. 4A shows a survival plot of mice treated with the different Sindbis viral vectors described above. For these studies, CT26 tumor-bearing mice were treated, 4 days after tumor inoculation, with either the SV/LacZ vector, the control SV/GFP vector, or media (Mock). Intraperitoneal inoculations of $10^7$ virus particles in 0.5 ml Optimem (Mediatech, VA) were administered to the mice. Only the SV/LacZ vector was found to induce complete tumor remission for at least 60 days. FIG. 4B involved the use of tetramers, labeled tetrameric MHIC molecules, (Altman, J. D. et al., 1996, *Science,* 274(5284): 94-96) as a sensitive means for identifying specific T cells in mice treated with the Sindbis vector SV/LacZ. Following treatment with the Sindbis vector encoding LacZ, splenocytes from the SV/LacZ-treated mice were found to contain $CD8^+$ T cells specific for both LacZ and gp70, an endogenous CT26 tumor associated antigen. The production of effector T cells directed against an antigen different from that produced by the SV/LacZ vector administered to the mice thus indicated that epitope spreading had occurred in the SV/LacZ treated animals. FIG. 4C presents photographs of representative mice imaged 14 days post-treatment with the SV/LacZ vector or naïve controls, in which tumors (CT26 colon tumors) were found to grow in naïve mice (i.e., those not treated with SV/LacZ), but not in mice treated with the SV/LacZ vector expressing LacZ antigen (SV/LacZ survivor mice).

Figure 5A:
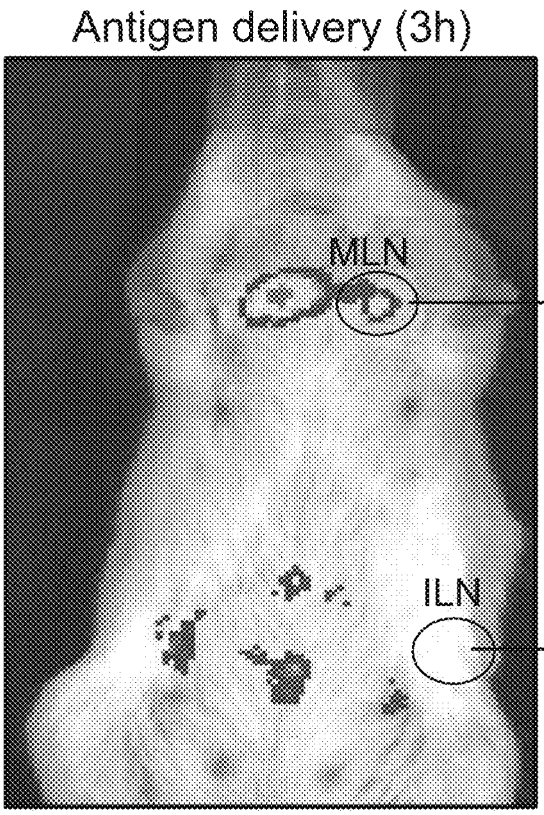
FIGS. 5A and 5B show a combination of imaging and flow cytometry to evaluate the effects of treatment/immunotherapy of animals with a Sindbis viral vector encoding at least one tumor associated antigen (SV/luciferase as "SV/TAA").
Figure 5B:
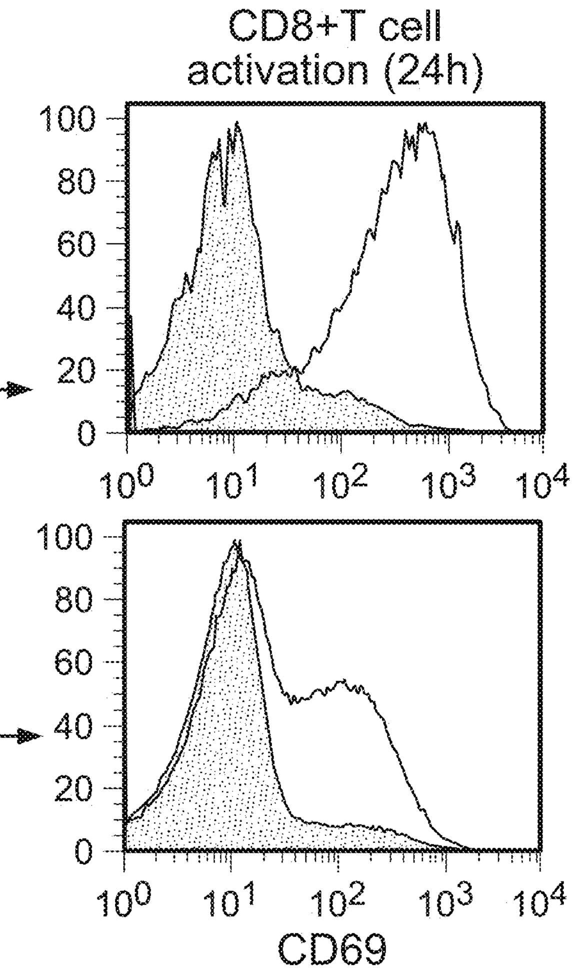

The results presented in FIG. 5B demonstrate that SV/LacZ-induced epitope spreading was successful in countering the loss of LacZ expression. Such SV/LacZ-dependent epitope spreading generated by administering the SV/LacZ vector to mice in the CT26 tumor mouse model contributed significantly to the complete suppression of growth of tumors in the mice treated with the SV/LacZ Sindbis viral vector, and their survival, as evidenced by the negative tumor cell growth in the SV/LacZ-treated mouse (FIG. 4C). These results evidence that SV vectors carrying R galactosidase (LacZ) had a remarkable therapeutic effect in mice bearing LacZ-expressing CT26 tumors.

FIGS. 5A and 5B show the combination of imaging and flow cytometry used to assess the results of in vivo treatment (immunotherapy) using a Sindbis viral vector expressing at least one epitope derived from a tumor associated antigen (SV/TAA), i.e., LacZ polypeptide, and firefly luciferase for imaging of virus delivery. FIG. 5A shows representative results of in vivo imaging that was used to non-invasively and longitudinally determine in mice the sites of expression of the luciferase tumor associated antigen encoded by a Sindbis viral vector, as described herein, after injection of the mice with the SV/TAA vector. At 3 hours after SV/TAA vector inoculation the mice were imaged. At 24 hours, the mediastinal and inguinal lymph nodes were extracted and T cells were isolated and assessed for the presence of the T-cell activation marker CD69. Compared with the expression levels of the control T-cell activation marker CD69 in inguinal lymph nodes (ILN) (FIGS. 5A and 5B), the mediastinal lymph node (MLN) was identified as a site of delivery of the luciferase antigen (FIG. 5A) and was also found to be a site of potent $CD8^+$ T cell activation after 24 hours (FIG. 5B).

Figure 6A:
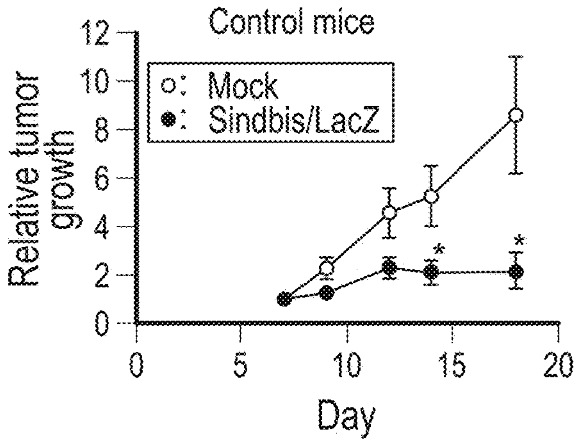
FIGS. 6A-6D show graphs of tumor growth versus time (days) following injection of mice having LacZ+CT26 tumors with PBS (control, FIG. 6A) or with the Sindbis viral vector encoding LacZ as tumor associated antigen (SV/LacZ), (FIGS. 6B-6D). The therapeutic effects of SV/LacZ on subcutaneous tumors (i.e., reduced tumor growth as measured by calipers) was not observed in mice depleted of CD4+ T cells (FIG. 6B), CD8+ T cells (FIG. 6C), or both (FIG. 6D), when compared with the results seen for control mice (FIG. 6A).
Figure 6B:
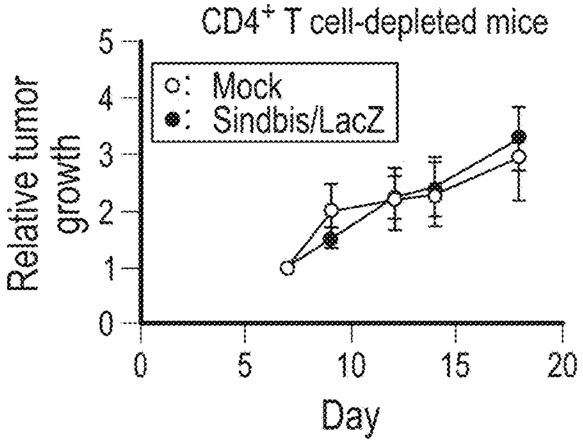
Figure 6C:
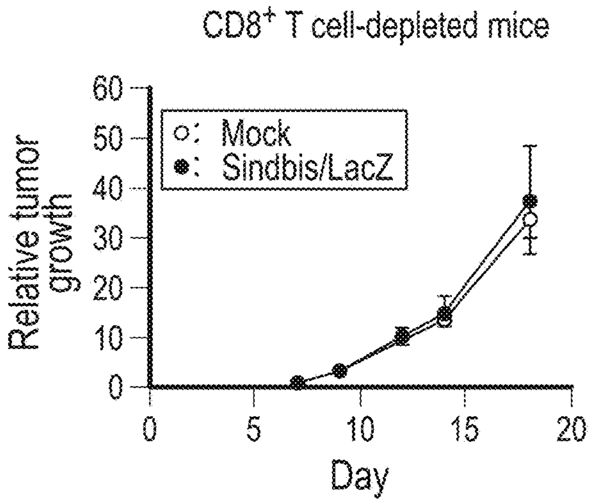
Figure 6D:
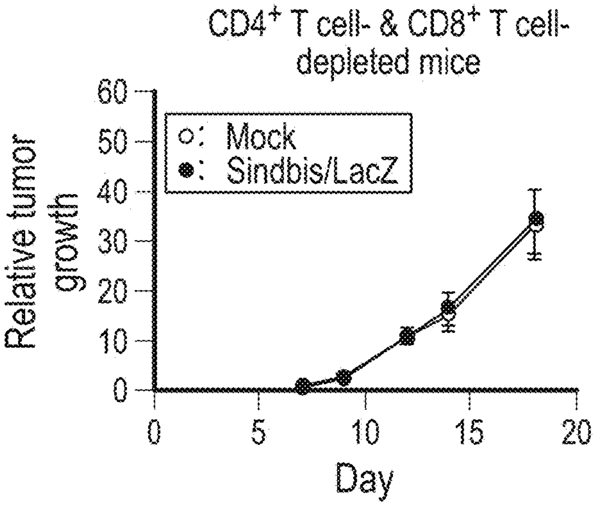

FIGS. 6A-6D present graphs of relative tumor growth in mice having subcutaneous LacZ+CT26 tumors versus the number of days following treatment with a Sindbis viral vector encoding the LacZ polypeptide (e.g., SV/LacZ) as described above. The results presented in the graphs were obtained from experiments in which control or vector-treated tumored mice were depleted of CD8+ and $CD4^+$ T cells using an anti-CD8 antibody and an anti-CD4 antibody, as follows: 0.4 mg of each type of antibody in 0.2 ml PBS were injected into each mouse, starting 1 day before the first treatment with the SV/LacZ viral vector or mock control, and the antibodies were then injected every 2-3 days for 2 weeks thereafter. Mock control mice were injected with PBS. LacZ+ CT26 tumor-bearing mice were treated with either the SV/LacZ viral vector (Sindbis/LacZ) or with PBS (Mock). Tumor growth was determined by caliper measurement. FIG. 6A shows the results using control tumored mice, either mock-treated or treated with the SV/LacZ vector. FIG. 6B shows the results using tumored mice depleted of $CD4^+$ T cells, either mock-treated or treated with the SV/LacZ vector. FIG. 6C shows the results using tumored mice depleted of $CD8^+$ T cells, either mock-treated or treated with the SV/LacZ vector. FIG. 6D shows the results using tumored mice depleted of both $CD4^+$ T cells and $CD8^+$ T cells, either mock-treated or treated with the SV/LacZ vector.

The results depicted in FIGS. 6B-6D demonstrate that a therapeutic effect of the SV/LacZ vector on decreasing the growth of subcutaneous tumors was observed in the control mice having a normal complement of T cells, while a therapeutic effect was not observed in T cell-depleted mice. In accordance with the present invention, the therapeutic benefit obtained from treatment with a Sindbis viral vector encoding at least one, preferably two or more, epitopes of one or more tumor associated antigens, i.e., a SV/TAA viral vector, does not necessarily require the direct targeting of tumor cells. As supported by the Examples herein, SV/TAA therapy involved transient early delivery of the tumor associated antigen to lymph nodes draining the injection site, in particular, the mediastinal lymph nodes (MLN) in the case of intraperitoneal injection of the SV/TAA viral vector as demonstrated in FIG. 5A. Treatment with a SV/TAA viral vector also induced a potent TAA-specific $CD8^+$ T cell response that was subsequently redirected against tumor cells expressing the cognate TAA. Further, SV/TAA therapy led to epitope spreading, providing a possible solution to the problem of tumor escape by TAA loss or modification, and SV/TAA therapy ultimately led to long-term survival of tumor-bearing mice, and to the generation of long-lasting memory $CD8^+$ T cells against multiple TAAs. FIGS. 6A-6D provide evidence that the in vivo therapeutic effect of treatment with a Sindbis viral vector encoding at least one, preferably two or more, tumor associated antigen epitopes is T-cell-dependent, as tumor reduction following administration of the SV/LacZ viral vector was not observed in T-cell-depleted mice (FIGS. 6B-6D).

The results from the in vivo experiments utilizing the SV vector encoding multiple tumor associated epitopes evidence that SV provides an effective therapeutic platform for the immunogenic delivery of multiple TAA epitopes. Moreover, the therapeutic benefit obtained from SV/TAA generated an anti-tumor immune response that results in tumor cell killing, even if the tumor cells themselves are not directly targeted by the vector. SV/TAA therapy involves transient early delivery of the TAA epitopes to lymph nodes draining the injection site, in particular, the MLN in the case of i.p. SV injection. In addition, SV/TAA therapy induced a potent TAA-specific $CD8^+$ T-cell response that is subsequently redirected against tumor cells expressing the cognate TAA and leads to epitope spreading, thus providing a possible solution to the problem of tumor escape by TAA loss or modification. As shown by the experimental results herein, SV/TAA therapy ultimately leads to long-term survival of tumor-bearing mice and to the generation of long-lasting memory $CD8^+$ T cells against multiple TAAs.

Example 6—Prediction of Tumor Associated Antigen Epitopes for Use in Sindbis Viral Vectors Multiple epitopic amino acid sequences of one or more tumor associated antigens for incorporation into the Sindbis viral vector according to the invention can be analyzed using the Immune Epitope Database, (www.IEDB.org), e.g., to rank epitope binding to BALB/c $H2^d$ class I MHC.

This Example provides different epitope prediction algorithms for use in the selection of multiple epitopes encoded and expressed by the polynucleotides and viral vectors described herein. The amino acid sequence of the tumor associated antigen NY-ESO-1 was analyzed by the three predictions programs, namely, BIMAS: BioInformatics and Molecular Analysis Section, ranks peptides by predicted dissociation constants from HLA alleles; IEDB: Immune Epitope Database (IEDB.org); and Rankpep for the prediction of peptide binding to MHC molecules as described below.

The NY-ESO-1 sequence analyzed for determining epitopes to generate an optimal T cell response is presented below.

NY-ESO-1 sequence > gi|14503119|ref|NP_001318.1| cancer/testis antigen 1 [*Homo sapiens*]

(SEQ ID NO: 21)

MQAEGRGTGGSTGDADGPGGPGIPDGPGGNAGGPGEAGATGGRGPRGAGA

ARASGPGGGAPRGPHGGAASGLNGCCRCGARGPESRLLEFYLAMPFATPM

EAELARRSLAQDAPPLPVPGVLLKEFTVSGNILTIRLTAADHRQLQLSIS

SCLQQLSLLMWITQCFLPVFLAQPPSGQRR

HLA-A0201, a common human allele, was used for screening epitopes.

BIMAS: BioInformatics and Molecular Analysis Section (BIMAS), Center for Information Technology, National Institutes of Health, (http://www-bimas.cit.nih.gov). This web site allows users to locate and rank 8-mer, 9-mer, or 10-mer peptides that contain peptide-binding motifs for HLA class I molecules. The rankings employ amino acid/position coefficient tables deduced from the literature by Dr. Kenneth Parker, of Boston's Children's Hospital, Harvard Medical School, and of the National Institute of Allergy and Infectious Diseases (NIAID) at the National Institutes of Health (NIH) in Bethesda, Maryland. The Web site was created by Ronald Taylor of BIMAS, Computational Bioscience and Engineering Laboratory (CBEL), Division of Computer Research & Technology (CIT), National Institutes of Health, in collaboration with Dr. Parker. Information and Background on the HLA peptide motif searches that can be conducted via BISMAS is available via (https://www-bimas.cit.nih.gov/molbio/hla_bind/hla_motif_search_info.html). BISMAS provides HLA Peptide Binding Predictions and (an) algorithm(s) that ranks peptides by predicted dissociation constants from HLA alleles. HLA Peptide Binding Predictions ranks potential 8- to 10-mer peptides based on a predicted half-time of dissociation to HLA class 1 molecules. References for analysis of peptide/MHC Class I peptide binding motifs and ranking HLA-binding peptides include, e.g., Maier, R. et al., 1994, *Immunogenetics,* 40:306-308; Raghavan, et al., 1996, *Protein Science,* 5:2080-2088; Parker, K. C. et al., 1994, *J. Immunol.,* 152: 163-175; and Rammensee, H. G. et al., 1999, *Immunogenetics,* 50:213-219. Another database and computer software source (H. G. Rammensee) for obtaining information on epitope sequences based on analysis of peptide sequences and MHC specificity is SYFPEITHI (BMI Biomedical Informatics, SYFPEITHI@BMI-Heidelberg.com).

Table 34 shows HLA peptide motif search results, and associated user parameters and scoring information obtainable via BIMAS.

TABLE 34

| HLA peptide motif search results<br>User Parameters and Scoring Information | |
|---|---|
| method selected to limit number of results | explicit number |
| number of results requested | 20 |
| HLA molecule type selected | A_0201 |
| length selected for subsequences to be scored | 9 |
| echoing mode selected for input sequence | Y |
| echoing format | numbered lines |
| length of user's input peptide sequence | 180 |
| number of subsequence scores calculated | 172 |
| number of top-scoring subsequences reported back in scoring output table | 20 |

Scoring Results

| Rank | Start Position | Subsequence Residue Listing | Score (Estimate of Half Time of Disassociation of a Molecule Containing This Subsequence) |
|---|---|---|---|
| 1 | 159 | LMWITQCFL | 1197.321 |
| 2 | 86 | RLLEFYLAM | 429.578 |
| 3 | 120 | GVLLKEFTV | 130.601 |
| 4 | 161 | WITQCFLPV | 83.584 |
| 5 | 155 | QLSLLMWIT | 52.704 |
| 6 | 154 | QQLSLLMWI | 49.509 |
| 7 | 157 | SLLMWITQC | 42.278 |
| 8 | 108 | SLAQDAPPL | 21.362 |
| 9 | 132 | ILTIRLTAA | 19.425 |
| 10 | 145 | LQLSISSCL | 13.624 |

IEDB: Immune Epitope Database (IEDB.org). The IEDB prediction tool uses a consensus of different algorithms that predict epitope binding to HLA alleles. The epitopes are then ranked—lower percentiles predict higher binding. The results of the prediction of MHC-1 binding are shown in the below Table 35.

TABLE 35

| Allele | # | Start | End | Length | Peptide | Method used | Percentile Rank |
|---|---|---|---|---|---|---|---|
| HLA-A*02:01 | 1 | 108 | 116 | 9 | SLAQDAPPL (SEQ ID NO: 411) | Consensus (ann/smm/comblib_sidney2008) | 0.8 |
| HLA-A*02:01 | 1 | 159 | 167 | 9 | LMWITQCFL (SEQ ID NO: 412) | Consensus (ann/smm/comblib_sidney2008) | 1.1 |
| HLA-A*02:01 | 1 | 86 | 94 | 9 | RLLEFYLAM (SEQ ID NO: 413) | Consensus (ann/smm/comblib_sidney2008) | 1.4 |

TABLE 35-continued

| Allele | # | Start | End | Length | Peptide | Method used | Percentile Rank |
|---|---|---|---|---|---|---|---|
| HLA-A*02:01 | 1 | 161 | 169 | 9 | WITQCFLPV (SEQ ID NO: 414) | Consensus (ann/smm/comblib_sidney2008) | 2 |
| HLA-A*02:01 | 1 | 120 | 128 | 9 | GVLLKEFTV (SEQ ID NO: 415) | Consensus (ann/smm/comblib_sidney2008) | 3 |
| HLA-A*02:01 | 1 | 110 | 118 | 9 | AQDAPPLPV (SEQ ID NO: 416) | Consensus (ann/smm/comblib_sidney2008) | 3.2 |
| HLA-A*02:01 | 1 | 154 | 162 | 9 | QQLSLLMWI (SEQ ID NO: 417) | Consensus (ann/smm/comblib_sidney2008) | 3.6 |
| HLA-A*02:01 | 1 | 158 | 166 | 9 | LLMWITQCF (SEQ ID NO: 1) | Consensus (ann/smm/comblib_sidney2008) | 4 |
| HLA-A*02:01 | 1 | 145 | 153 | 9 | LQLSISSCL (SEQ ID NO: 418) | Consensus (ann/smm/comblib_sidney2008) | 4.9 |
| HLA-A*02:01 | 1 | 157 | 165 | 9 | SLLMWITQC (SEQ ID NO: 42) | Consensus (ann/smm/comblib_sidney2008) | 5.3 |
| HLA-A*02:01 | 1 | 132 | 140 | 9 | ILTIRLTAA (SEQ ID NO: 419) | Consensus (ann/smm/comblib_sidney2008) | 5.6 |
| HLA-A*02:01 | 1 | 148 | 156 | 9 | SISSCLQQL (SEQ ID NO: 420) | Consensus (ann/smm/comblib_sidney2008) | 5.6 |
| HLA-A*02:01 | 1 | 92 | 100 | 9 | LAMPFATPM (SEQ ID NO: 43) | Consensus (ann/smm/comblib_sidney2008) | 6.5 |
| HLA-A*02:01 | 1 | 96 | 104 | 9 | FATPMEAEL (SEQ ID NO: 54) | Consensus (ann/smm/comblib_sidney2008) | 6.7 |
| HLA-A*02:01 | 1 | 152 | 160 | 9 | CLQQLSLLM (SEQ ID NO: 421) | Consensus (ann/smm/comblib_sidney2008) | 6.9 |
| HLA-A*02:01 | 1 | 126 | 134 | 9 | FTVSGNILT (SEQ ID NO: 422) | Consensus (ann/smm/comblib_sidney2008) | 7.5 |
| HLA-A*02:01 | 1 | 90 | 98 | 9 | FYLAMPFAT (SEQ ID NO: 423) | Consensus (ann/smm/comblib_sidney2008) | 7.7 |

Rankpep: This epitope experimental tool uses experimental data from known peptides that bind MHC/HLA and then compares sequences using a position specific scoring matrix. Rankpep uses Position Specific Scoring Matrices (PSSMs) or profiles from a set of aligned peptides (e.g., peptides aligned by structural or sequence similarity) known to bind to a given MHC molecule as the predictor of MHC-peptide binding. (http://imed.med.ucm.es/Tools/rankpep_help.html). It also takes into account which peptides are likely to be processed by proteases. (Reche P. A. et al., 2002, Prediction of MHC Class I Binding Peptides Using Profile Motifs, *Human Immunology,* 63: 701-709; Reche P. A. et al., 2004, Enhancement to the RANKPEP resource for the prediction of peptide binding to MHC molecules using profiles, *Immunogenetics,* 56:405-419; Reche P. A. and Reinherz E. L., 2007, Prediction of peptide-MHC binding using profiles. *Methods Mol-Biol.,* 409:185-200. Nonlimiting examples of MHC databases, including gene sequence, polymorphisms, etc., include IMGT (ImMunoGene Tics database); IMGT/HLA database, dbMHC (database at NCBI), Allele Frequencies database; HLA Informatics group; IHWG (International Histocompatibility Working Group); Genetics and Molecular Genetics of the MHC; and the Tumor Gene Database. Nonlimiting examples of peptide databases include MHC-PEP, SYFPEITHI, HIV Molecular Immunology Database, MHCPEP HLA Ligand/Motif Database; MHCBN Database (comprehensive database of MHC binding and nonbinding peptides); HLA Ligand/Motif Database; JenPep Database (MHC and TAP ligands, T and B cell epitopes); FINMIV Database (T and B cell epitopes); and MIPID (IVIIC-peptide interaction database).

The results of the prediction of peptides binding to MHC molecules based on Rankpep output is shown in the below Table 36.

TABLE 36

| RANK | POS | N | SEQUENCE | C | MW (Da) | SCORE | % OPT |
|---|---|---|---|---|---|---|---|
| 1 | 127 | KEF | TVSGNILTI (SEQ ID NO: 424) | RLT | 899.04 | 85.0 | 66.41% |
| 2 | 148 | LQL | SISSCLQQL (SEQ ID NO: 420) | SLL | 960.12 | 84.0 | 65.62% |
| 3 | 86 | PES | RLLEFYLAM (SEQ ID NO: 413) | PFA | 1137.42 | 78.0 | 60.94% |
| 4 | 152 | ISS | CLQQLSLLM (SEQ ID NO: 421) | WIT | 1030.31 | 74.0 | 57.81% |
| 5 | 108 | ARR | SLAQDAPPL (SEQ ID NO: 411) | PVP | 893.02 | 64.0 | 50.00% |
| 6 | 157 | QQL | SLLMWITQC (SEQ ID NO: 42) | FLP | 1053.33 | 62.0 | 48.44% |
| 7 | 151 | SIS | SCLQQLSLL (SEQ ID NO: 425) | MWI | 986.2 | 60.0 | 46.88% |
| 8 | 132 | SGN | ILTIRLTAA (SEQ ID NO: 419) | DHR | 953.19 | 59.0 | 46.09% |
| 9 | 144 | DHR | QLQLSISSC (SEQ ID NO: 426) | LQQ | 960.12 | 56.0 | 43.75% |

TABLE 36-continued

| RANK | POSN | SEQUENCE | C | MW (Da) | SCORE | % OPT |
|---|---|---|---|---|---|---|
| 10 | 161LLM | WITQCFLPV (SEQ ID NO: 414) | FLA | 1065.33 | 55.0 | 42.97% |

In the above Table 36, the light-gray highlighted rows 1-5 represent predicted binders. Rows 2, 5 and 7 of the table provide information about peptides with C-termini predicted by cleavage models.

Analysis of Results

The results of the epitope analysis of the NY-ESO-1 tumor associated antigen showed the ranking of several different epitopes in the protein using the above-described algorithms. A NY-ESO-1 epitope frequently used for cancer immunotherapy is SLLMWITQC (SEQ ID NO: 42). The rank of this epitope as determined by the use of the three algorithms was as follows:

BIMAS: 7, IEDB: 10; Rankpep: 7 (10+7+7=24), as shown in Table 37 below.

The results indicate that peptide RLLEFYLAM (SEQ TD NO: 413) may also be a good epitope as it is ranked highly by all three algorithms.

TABLE 37

| Ranking of Epitopes Based on BIMAS, IEDB and RANKPEP algorithms | | | |
|---|---|---|---|
| EPITOPE | BIMAS | IEDB | RANKPEP |
| SLAQDAPPL (SEQ ID NO: 411) | 8 | 1 | 5 |
| LMWITQCFL (SEQ ID NO: 412) | 1 | 2 | — |
| RLLEFYLAM (SEQ ID NO: 413) | 2 | 3 | 3 |
| WITQCFLPV (SEQ ID NO: 414) | 4 | 4 | 10 |
| GVLLKEFTV (SEQ ID NO: 415) | 3 | 5 | — |
| SLLMWITQC (SEQ ID NO: 42) | 7 | 10 | 7 |

Example 7—Improved Survivability of Tumored Mammalian Subjects Using a Combination Treatment Involving a Checkpoint Inhibitor and Sindbis Viral Vector Encoding a Tumor-Associated Antigen Immune checkpoints are a specific subtype of membrane-bound molecules that provide fine-tuning of the immune response. In normal tissues, immune checkpoints are inhibitory signals and play an important role by preventing autoimmunity. However, in a tumored subject, up-regulation of immune checkpoint proteins allows tumors to escape immune surveillance and evade anti-tumor immunity. Two immune checkpoint proteins that have been the focus of clinical cancer immunotherapeutics are cytotoxic T-lymphocyte-associated antigen 4 (CTLA-4) and programmed cell death protein 1 (PD-1). CTLA-4, also known as CD152, is essential for the activation of $CD4^+$ T cells and the priming phase of the immune response. PD-1, also known as CD279, is a key immune checkpoint receptor expressed by activated T and B cells and mediates immunosuppression. While immunotherapy with the antagonistic checkpoint blocking antibodies anti-CTLA-4 or anti-PD-1 has been a recent approach to enhance the immune response and treat diseases, such checkpoint inhibitors do not target tumor cells directly. Rather, these checkpoint inhibitors target lymphocyte receptors or their ligands.

Figure 7A:
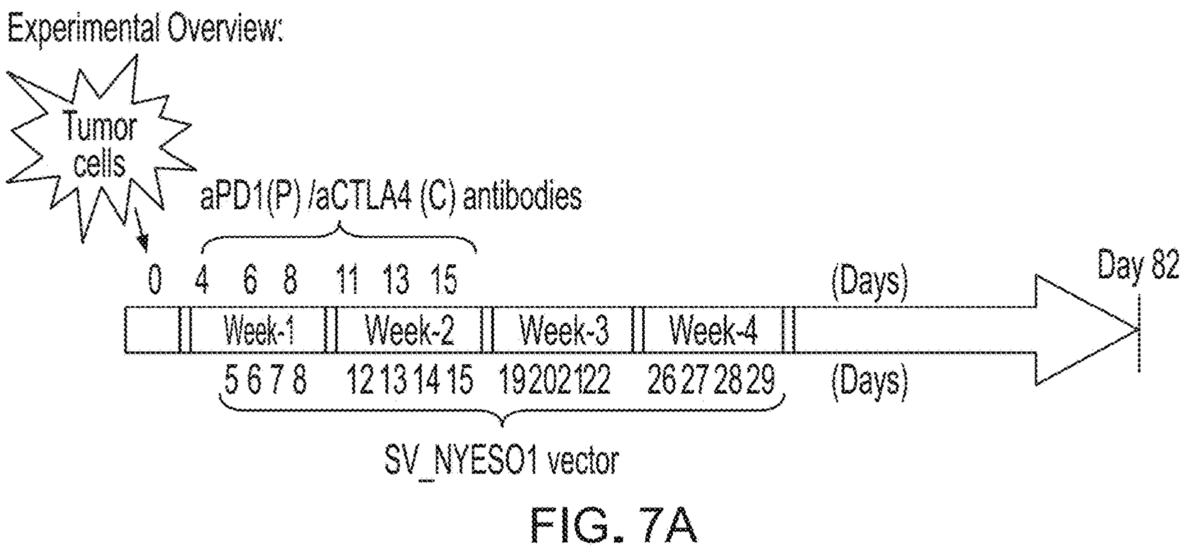
FIG. 7A is a schematic showing an experimental overview of the Sindbis checkpoint inhibitors experiment. CT26 tumor cells expressing firefly luciferase (Fluc) and NY-ESO-1 were injected at time 0. Anti-PD1 and antiCTLA4 antibodies were administered to the mice at days 4, 6, 8, 11, 13, and 15 and the Sindbis virus NYESO1 in accordance with the timeline of checkpoint inhibitor or vector administration.
Figure 7B:
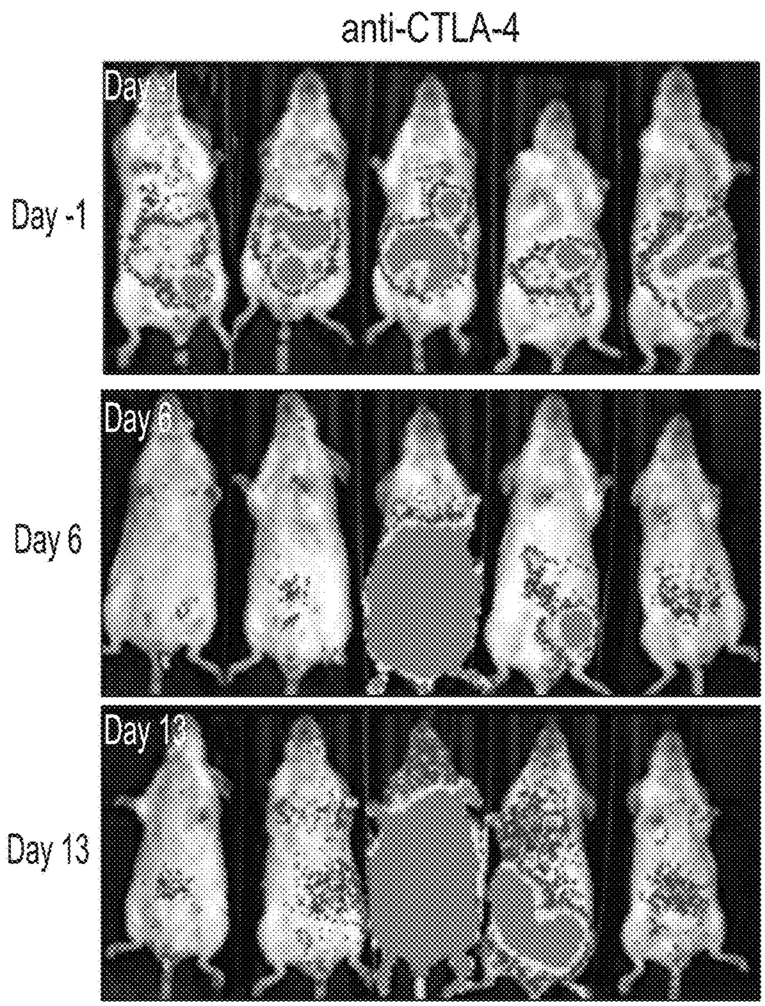
FIGS. 7B-7Q show in vivo images of Balb/C mice that had CT26-derived tumors expressing both firefly luciferase (Fluc) and NY-ESO-1 injected intraperitoneally (i.p.) into each mouse on Day 0, followed by administration according to the timeline in FIG. 7A of anti-CTLA4 antibody (FIG. 7B, FIG. 7C, FIG. 7D, and FIG. 7E) (10 mg/kg; 3 mice per group), or a combination of anti-CTLA4 antibody and a SV/NY-ESO-1 vector (FIG. 7F, FIG. 7G, FIG. 7H, and FIG. 7I), or anti-PD-1 antibody (FIG. 7J and FIG. 7K), or a combination of anti-PD-1 antibody and a SV/NY-ESO-1 vector (FIG. 7L and FIG. 7M), or a combination of anti-PD-1 antibody and anti-CTLA4 antibody (FIG. 7N and FIG. 7O), or a combination of anti-PD-1 antibody and anti-CTLA4 antibody and a SV/NY-ESO-1 vector (FIG. 7P and FIG. 7Q). The SV/NY-ESO-1 vector was administered at about $10^7$ transducing units per ml (TU per ml), in a volume of about 0.3 ml each time per mouse according to the timeline in FIG. 7A (3 mice per group). Survival of mice was monitored.
Figure 7C:
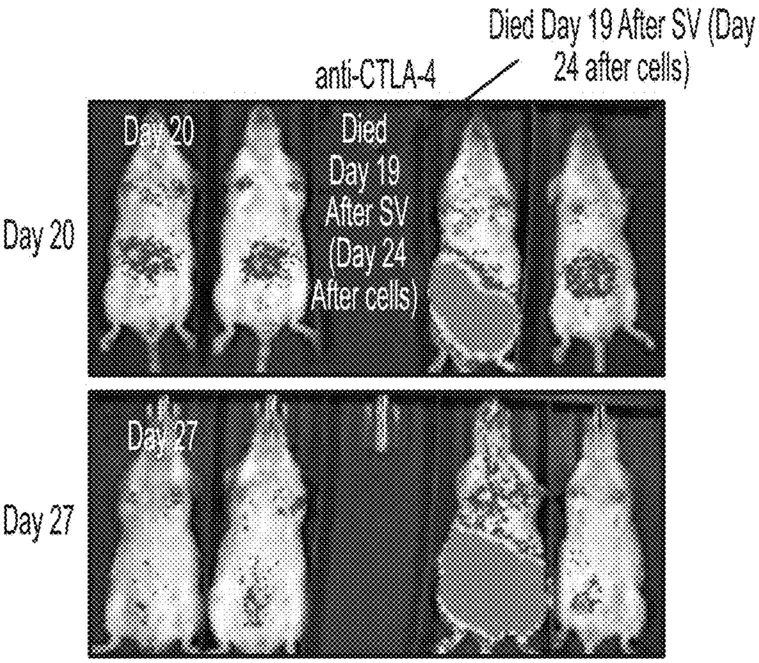
Figure 7D:
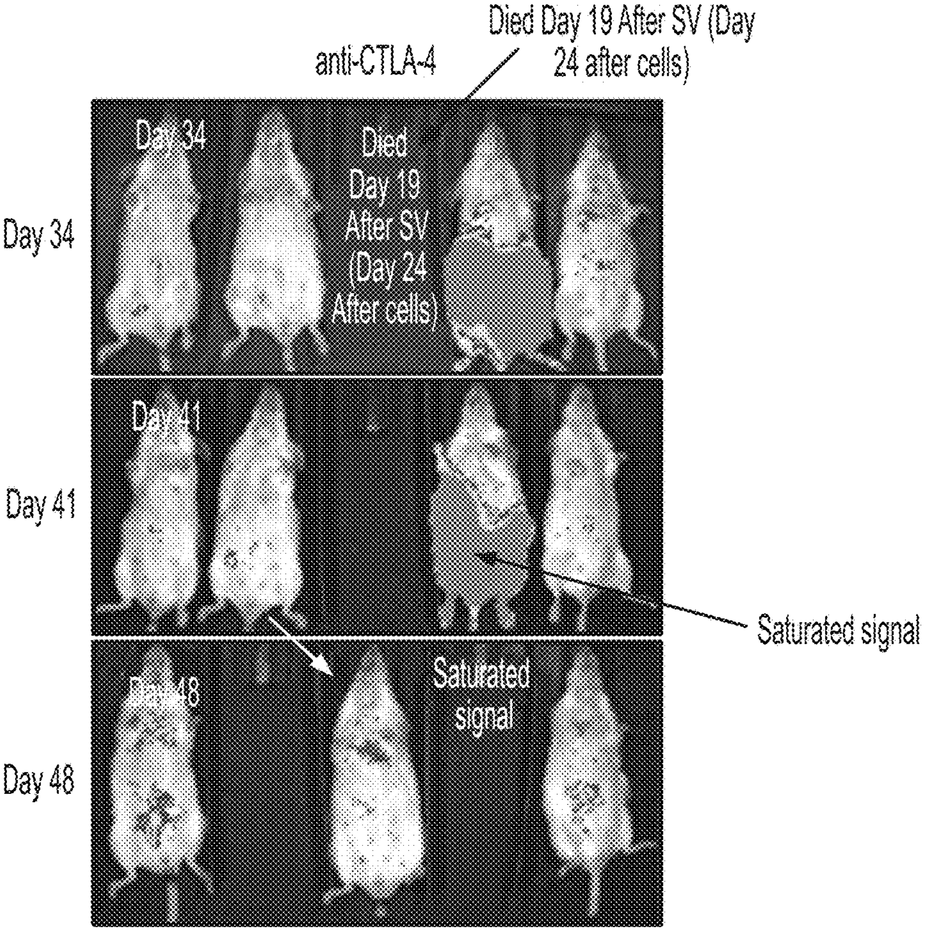
Figure 7E:
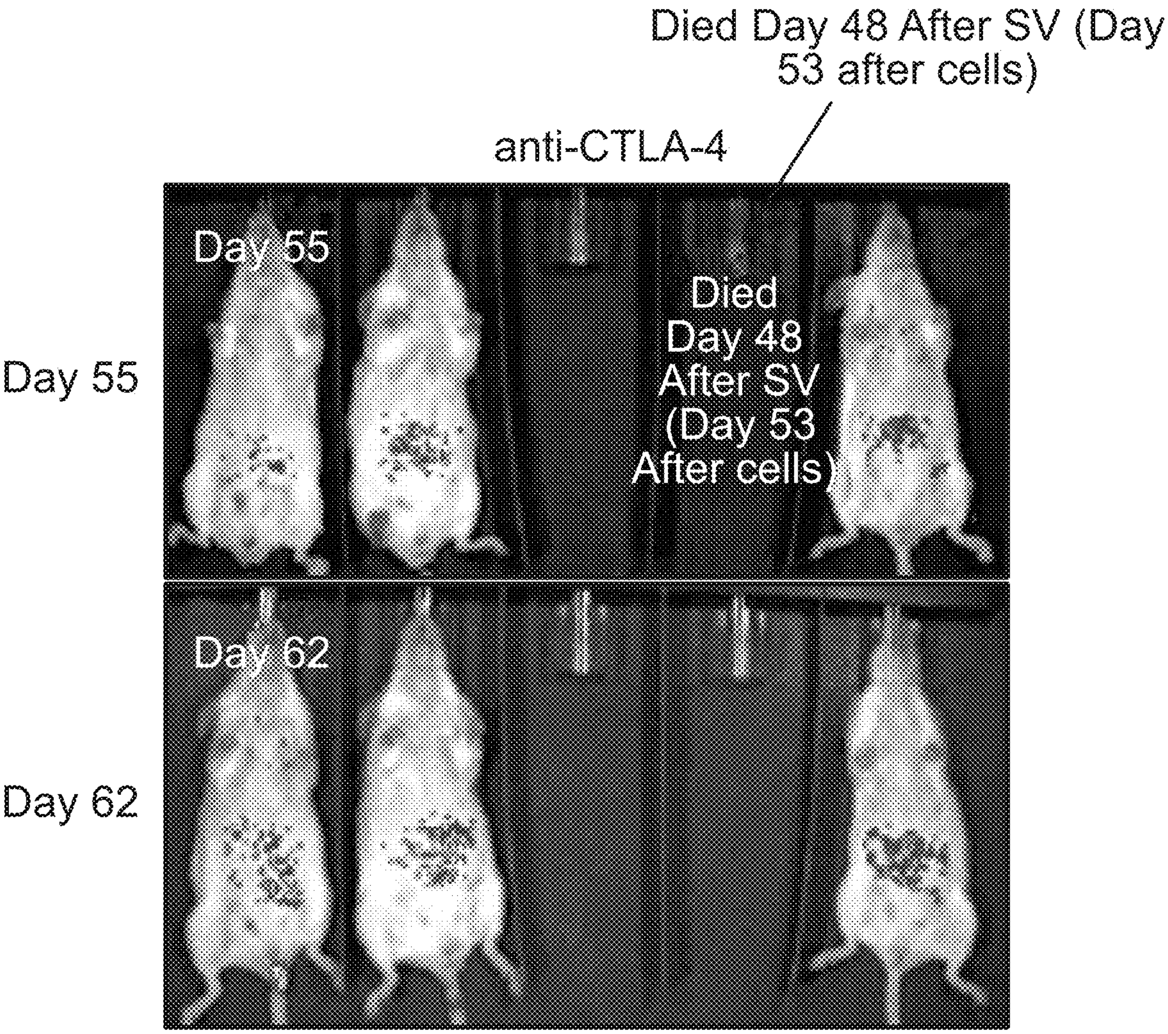
Figure 7F:
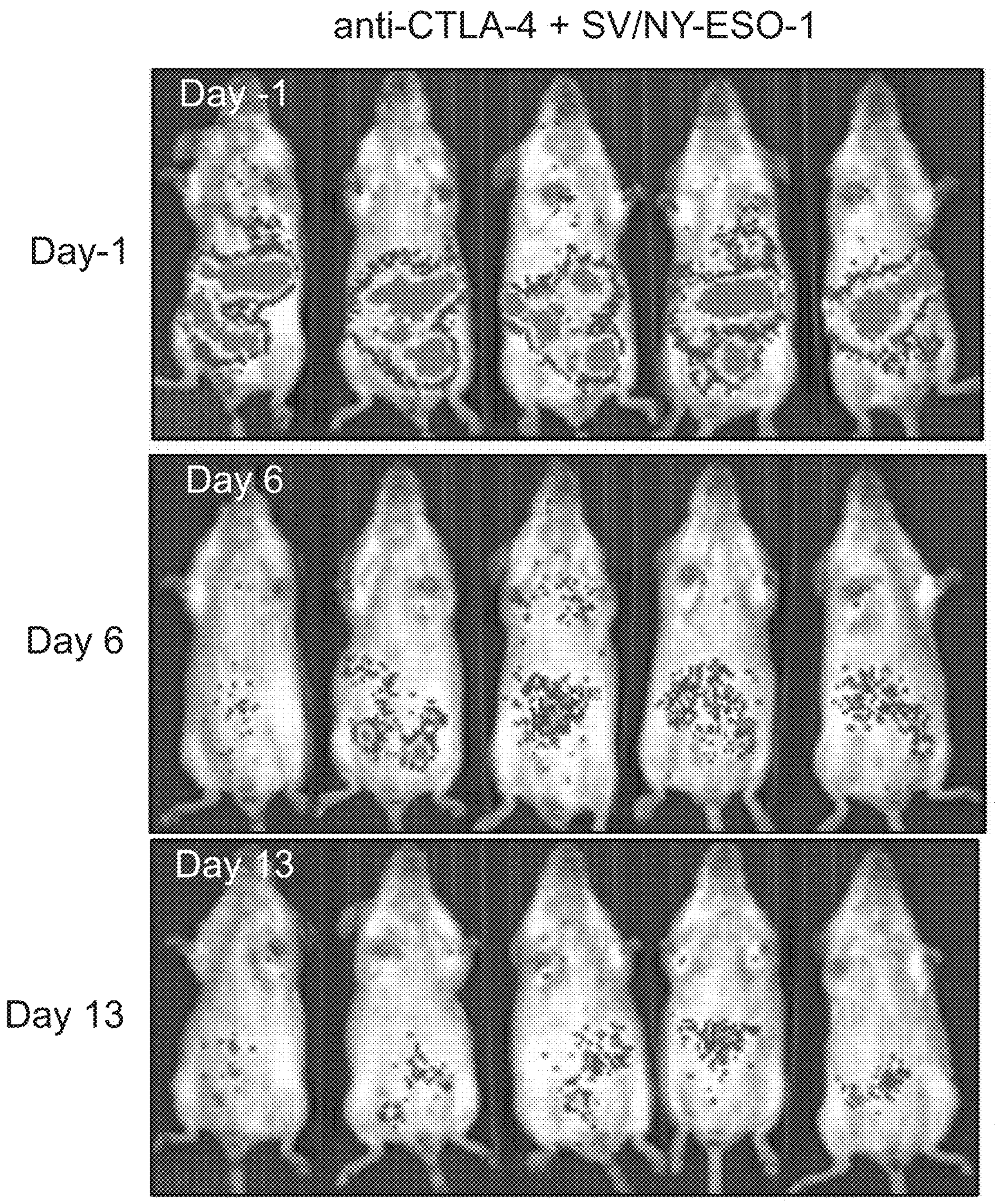
Figure 7G:
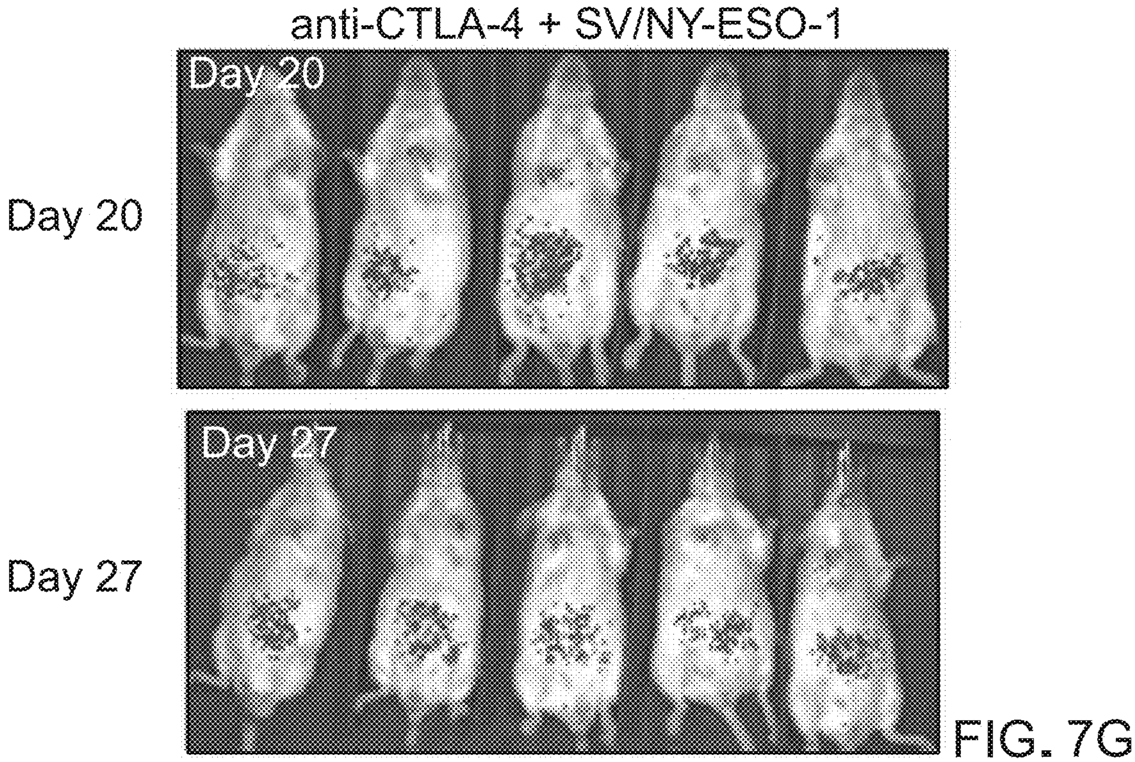
Figure 7H:
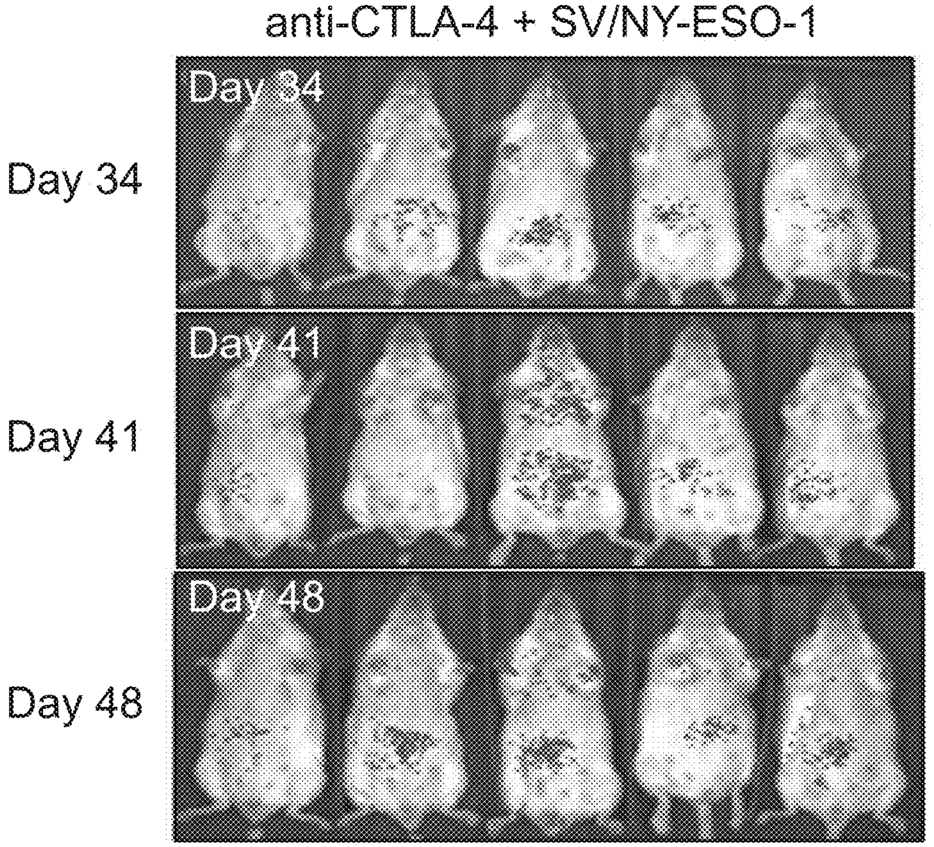
Figure 7I:
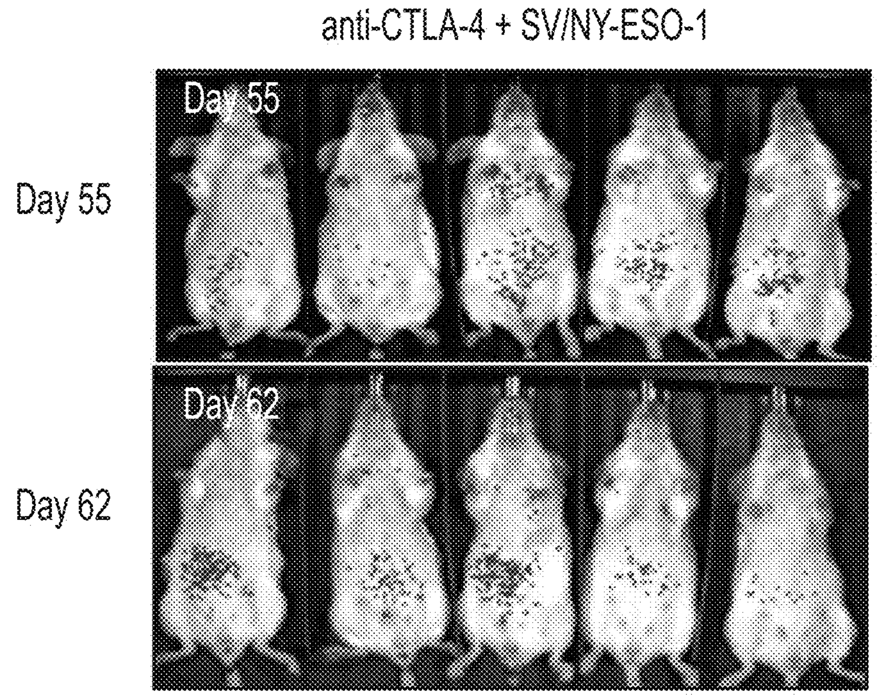
Figure 7J:
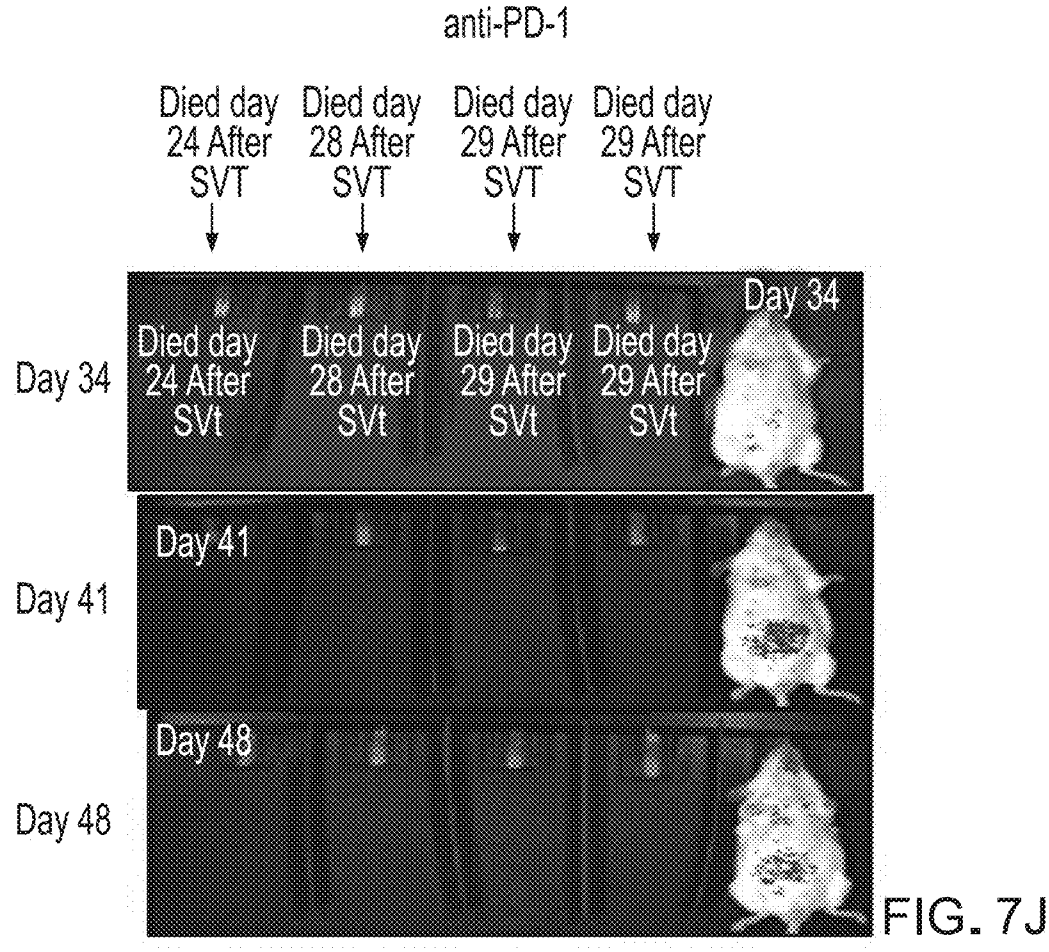
Figure 7K:
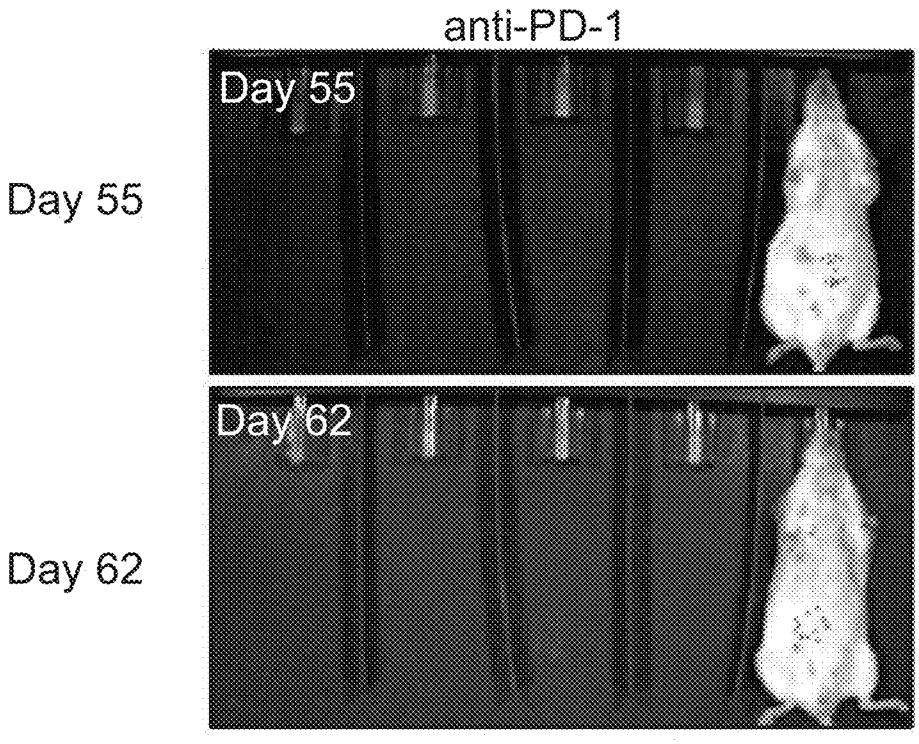
Figure 7L:
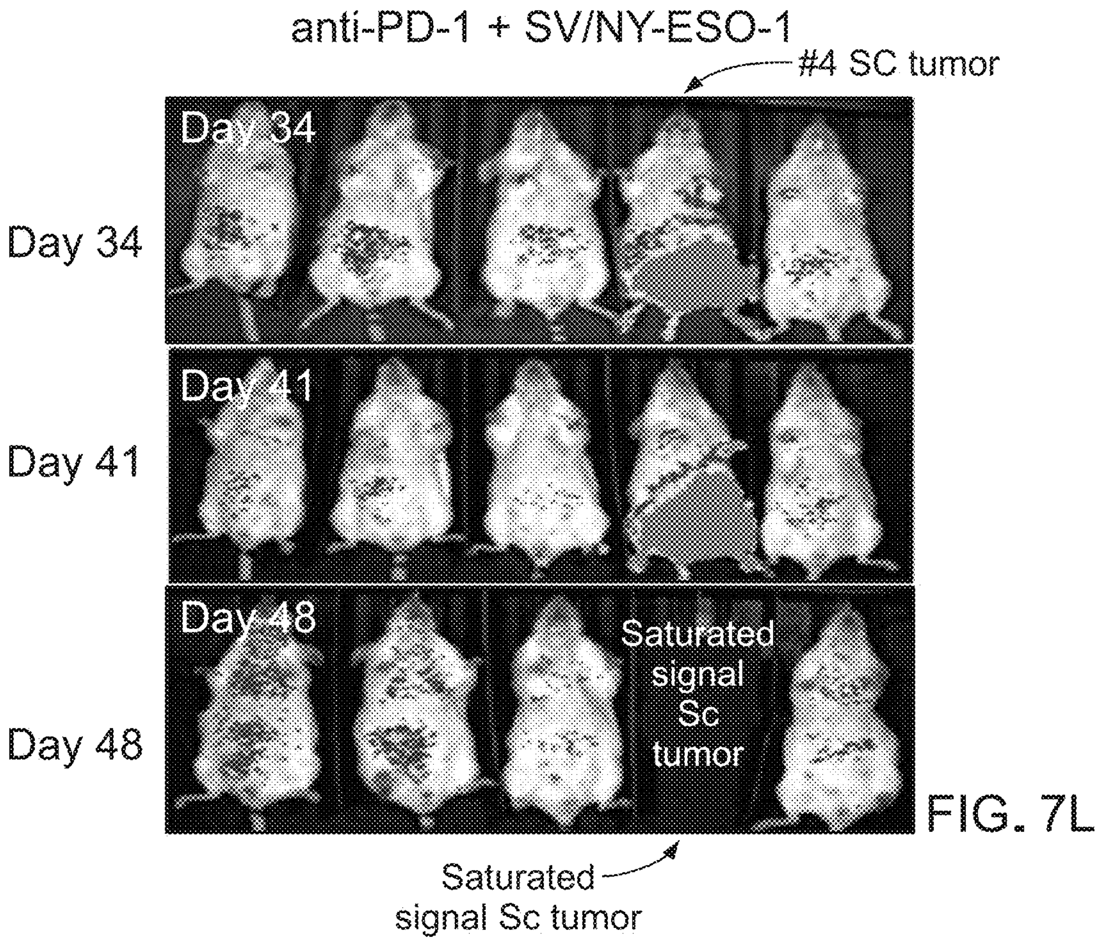
Figure 7M:
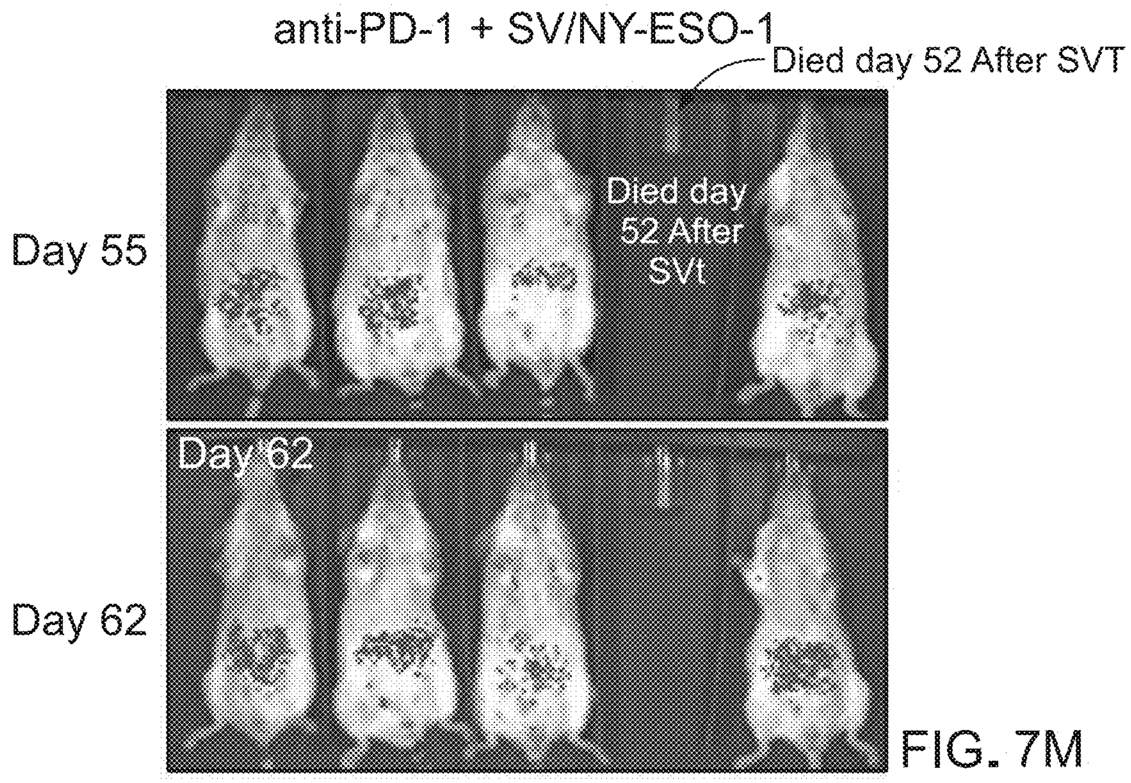
Figure 7N:
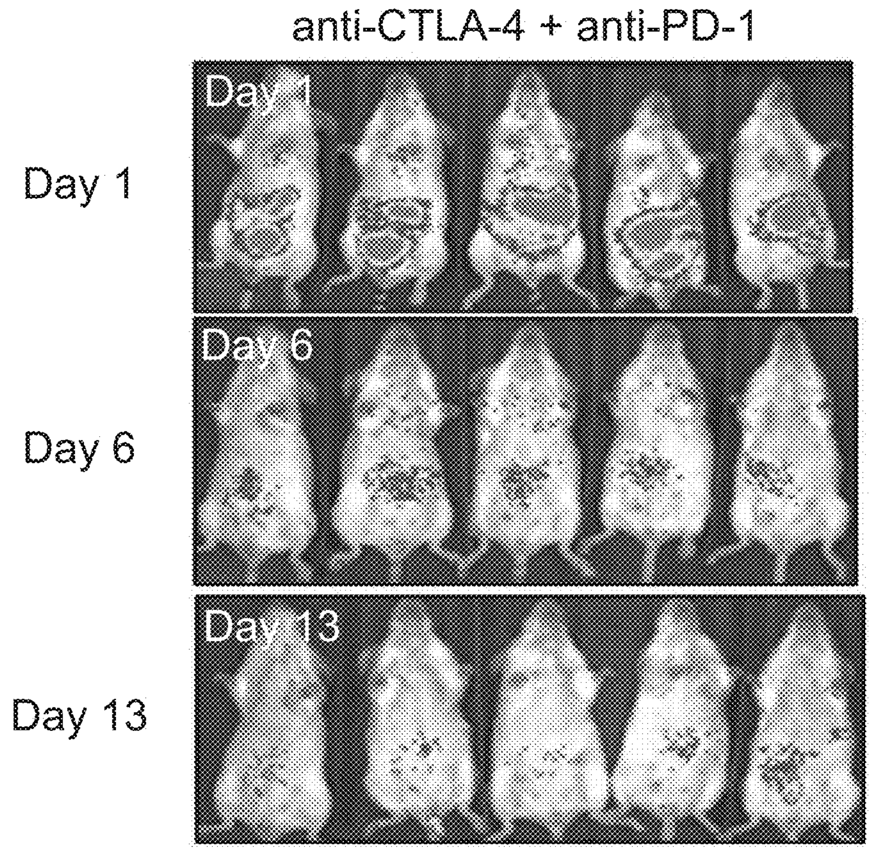
Figure 7O:
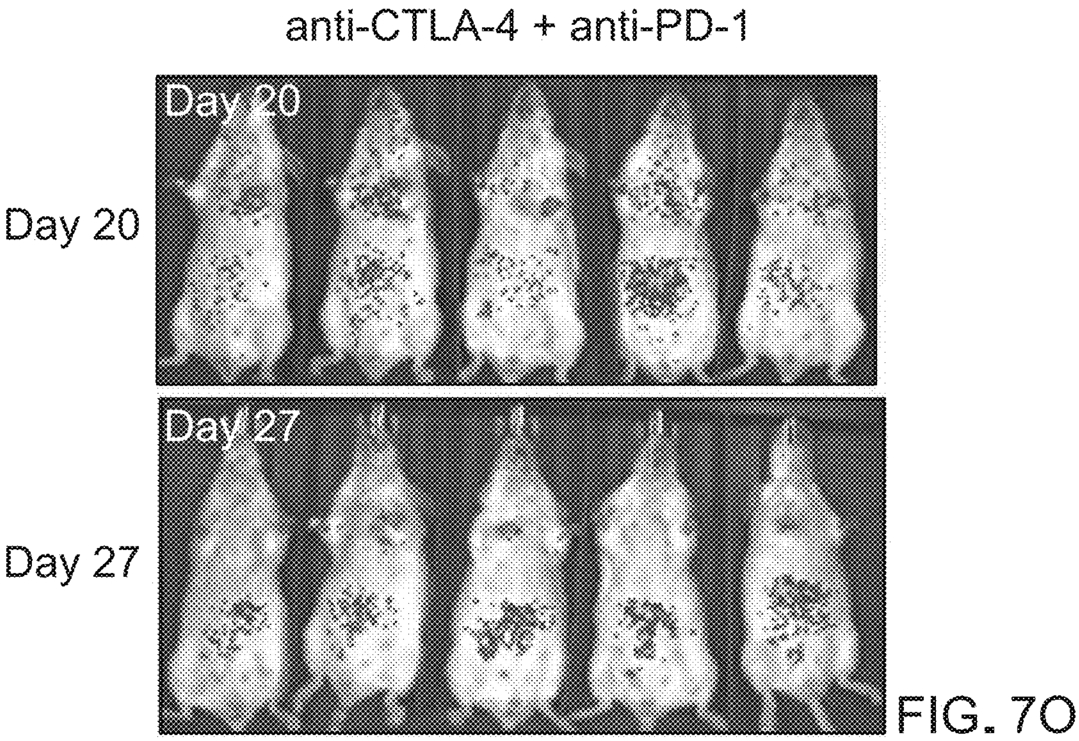
Figure 7P:
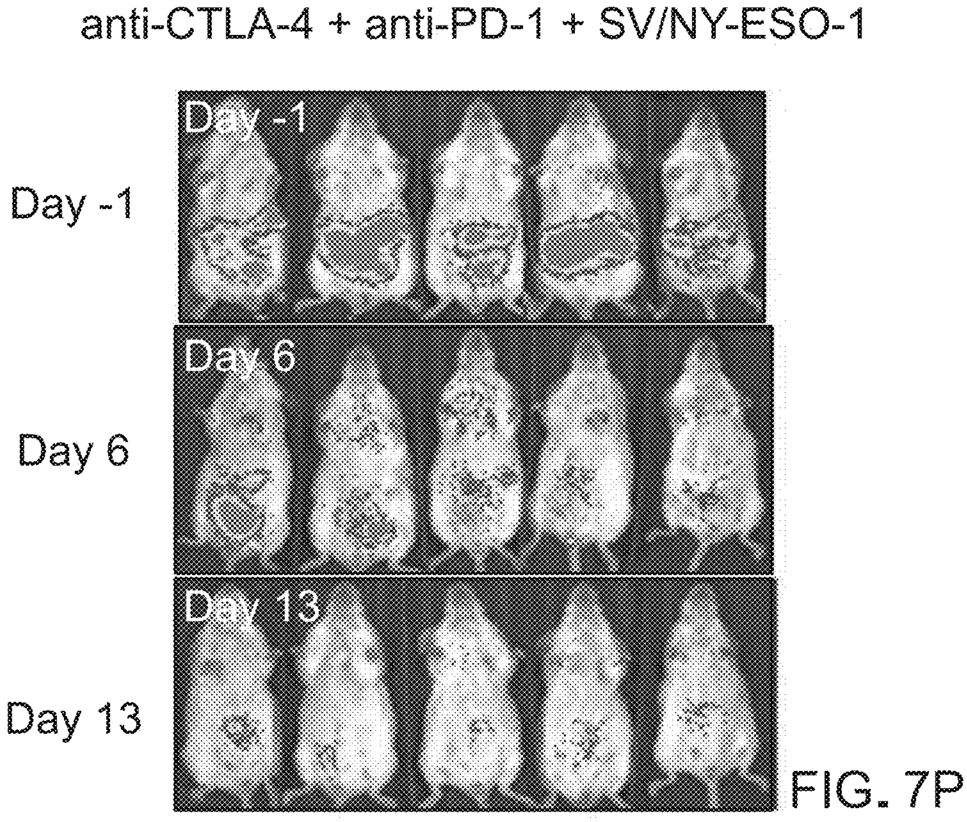
Figure 7Q:
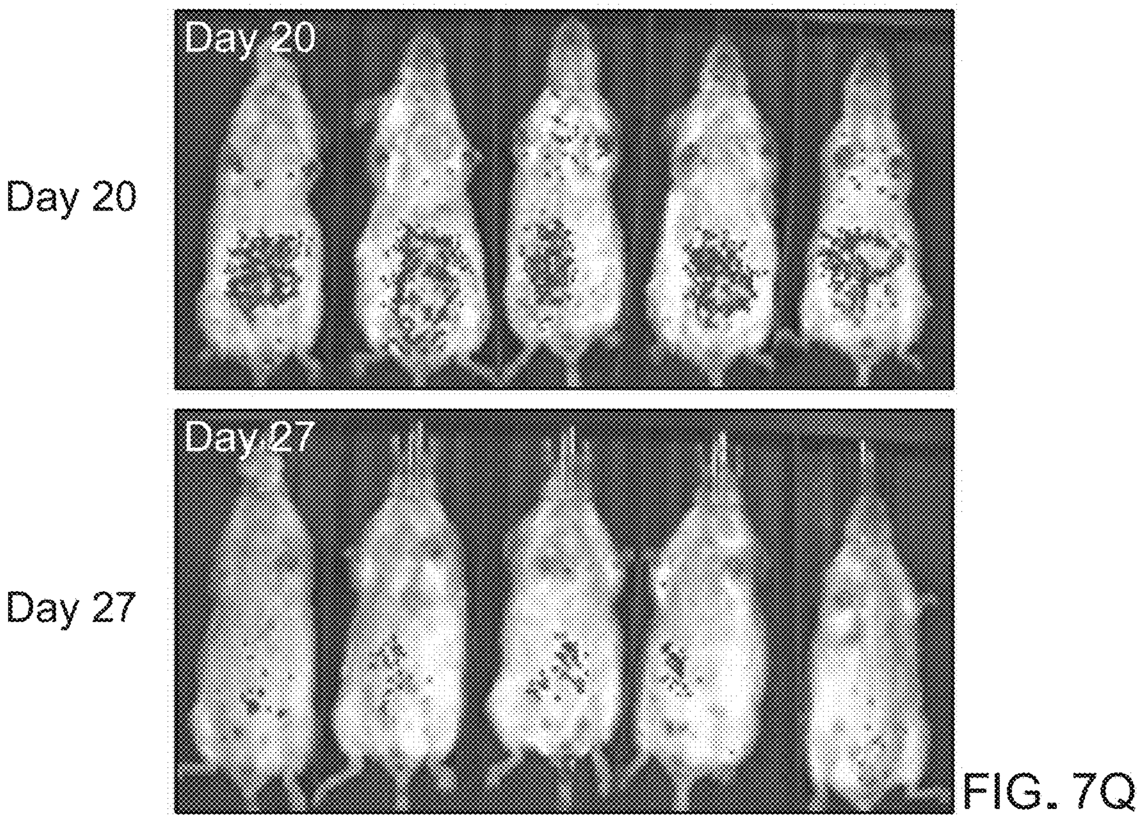
Figure 8:
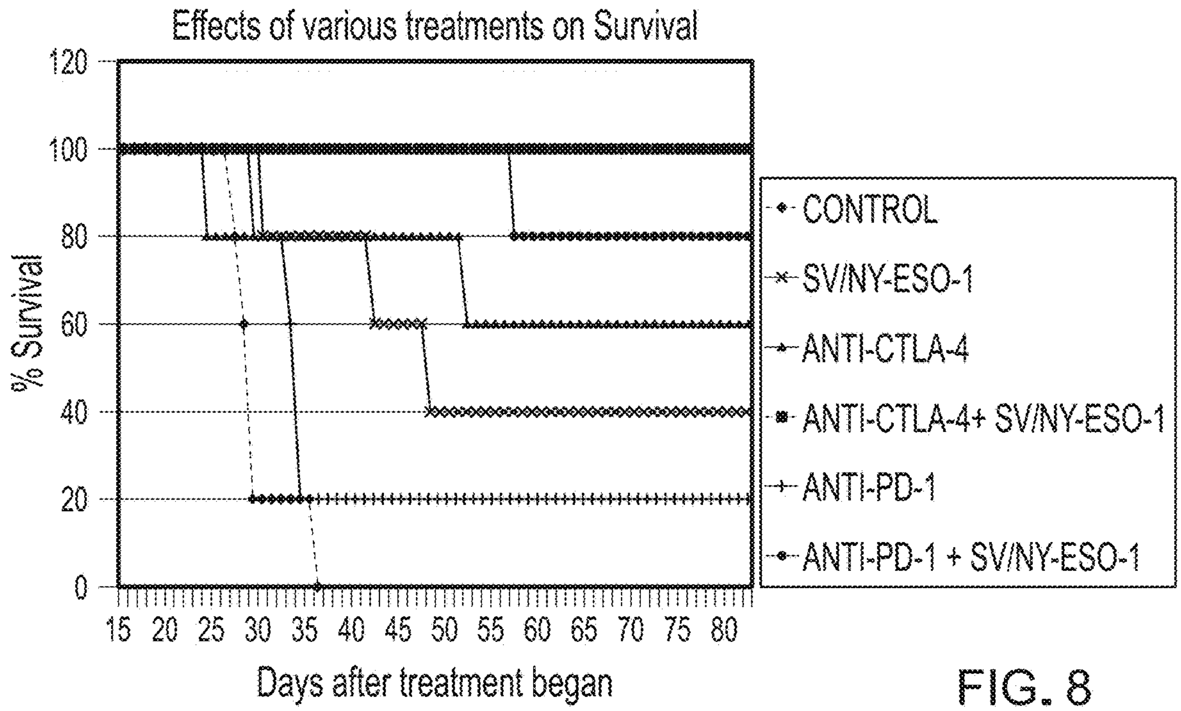
FIG. 8 is a graph showing percent survival of Balb/C mice that had CT26 derived tumors expressing NY-ESO-1. The treatments included administration of anti-CTLA-4 antibody or anti-PD-1 antibody alone or in combination with vector SV/NY-ESO-1. These combinations were administered to mice according to the time line in FIG. 7A.
Figure 9:
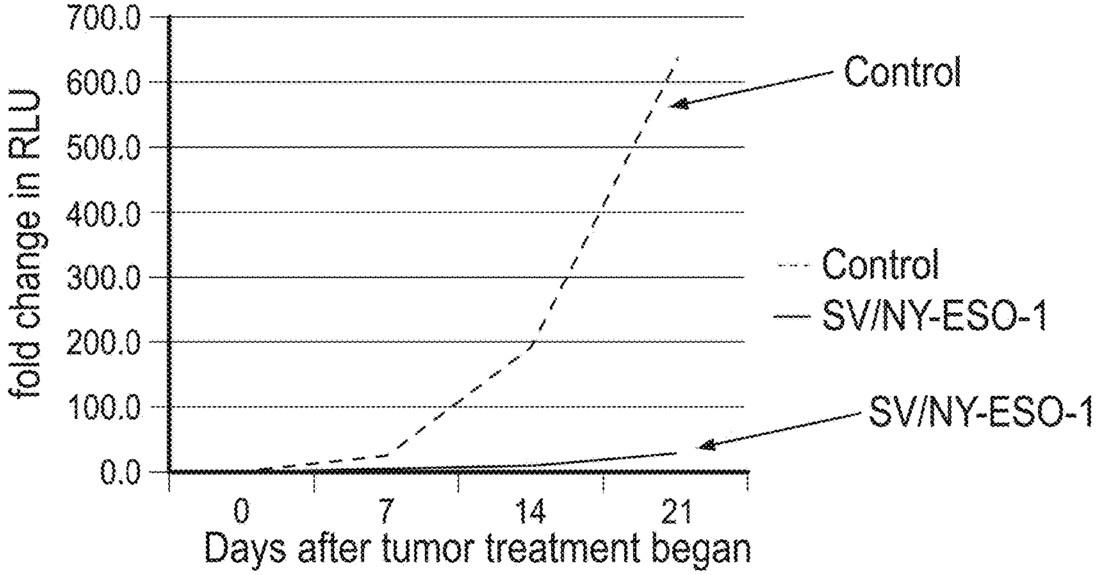
FIG. 9 is a graph showing tumor growth as a function of days after treatment of tumored mice with a Sindbis viral vector encoding NY-ESO-1 compared to control mice (BALBc/CT26:NY-ESO-1). The growth of the tumor was measured in relative light unit (RLU) values indicating tumor growth in the control and experimental groups of mice treated as described above.
Figure 10A:
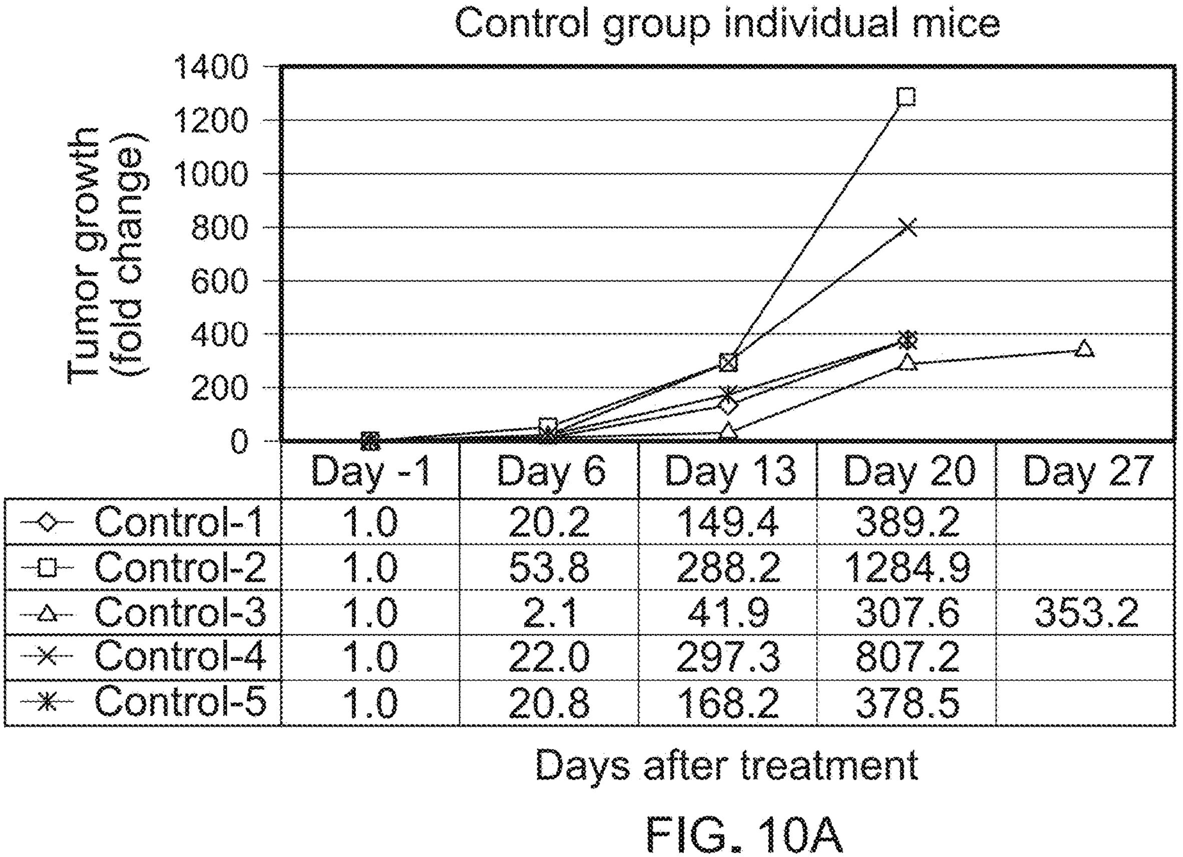
FIGS. 10A-10E are graphs and tables showing tumor growth over time in tumored and control mice (control group, FIG. 10A), anti-CTLA4 antibody (FIG. 10B), anti-CTLA4 antibody and a SV/NY-ESO-1 vector (FIG. 10C), anti-PD-1 antibody (FIG. 10D), anti-PD-1 antibody and a SV/NY-ESO-1 vector (FIG. 10E). Shown below each graph in FIG. 10A, FIG. 10B, FIG. 10C, FIG. 10D, and FIG. 10E are tables showing the relative light unit (RLU) values indicating tumor growth in the control and experimental groups of mice treated as described above.
Figure 10B:
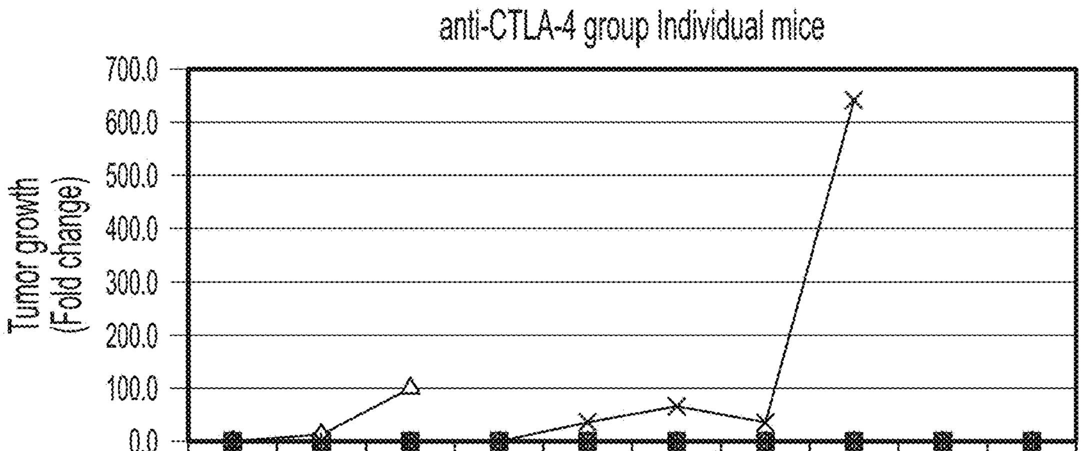
Figure 10C:
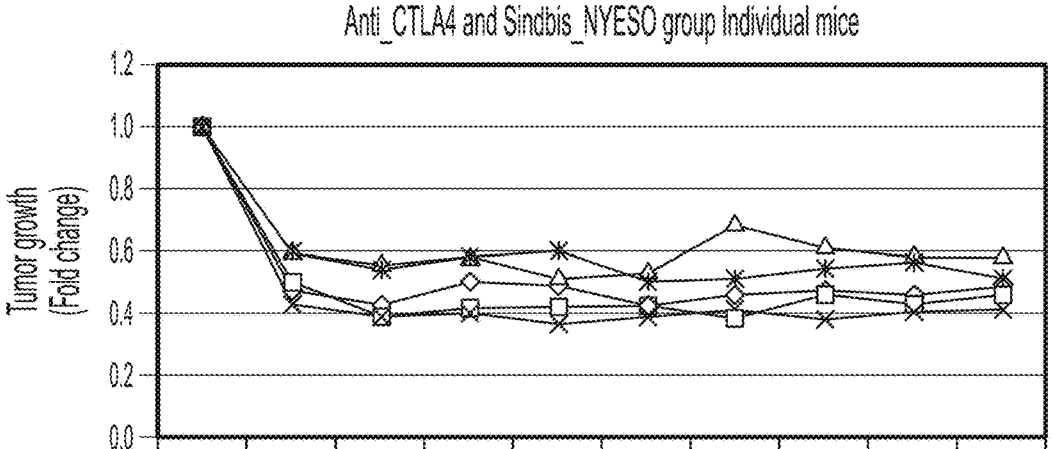
Figure 10D:
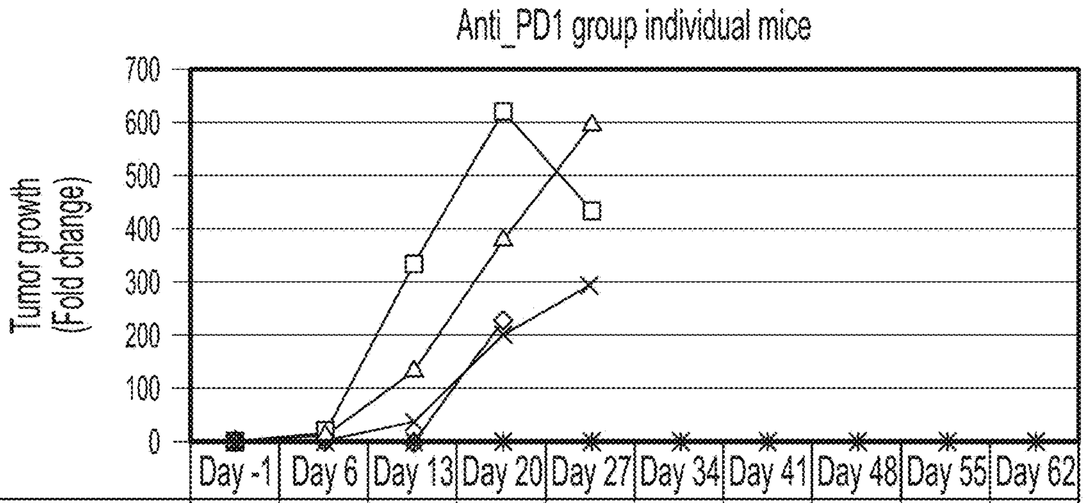
Figure 10E:
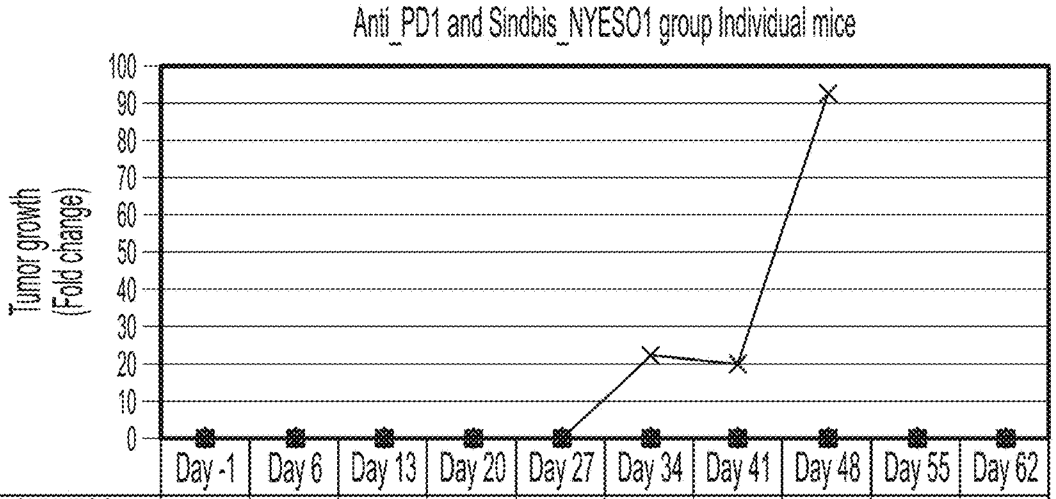

To see if a combination treatment involving a checkpoint inhibitor and a Sindbis viral vector encoding a tumor-associated antigen could enhance the endogenous antitumor activity and improve the survivability of tumored mammalian subjects, different treatment combinations were administered to tumor-bearing mice, and the mice were monitored for more than 11 weeks to evaluate treatment efficacy. As shown in the experimental overview in FIG. 7A, on Day 0, four to eight week-old female Balb/C mice received an i.p. injection of colon carcinoma cells, CT26, expressing luciferase and the tumor associated antigen, NYESO1 (CT26.Fluc.NYESO1 #4B9) ($7\times10^4$ cells per i.p.). Then, according to the timeline in FIG. 7A, the tumor-bearing mice received i.p. injections of the SV/NY-ESO-1 vector alone, checkpoint inhibitor alone (anti-CTLA-4 antibody or anti-PD-1 antibody), or a combination of a checkpoint inhibitor (anti-CTLA-4 antibody or anti-PD-1 antibody) with the SV/NY-ESO-1 vector (FIG. 8). After treatment, therapeutic efficacy and survival of the tumor-bearing mice was monitored in vivo by tumor luminescence. The bioluminescence signals were detected by IVIS at the indicated time points for the anti-CTLA4 antibody (FIG. 7B, FIG. 7C, FIG. 7D, and FIG. 7E), the combination of anti-CTLA4 antibody and SV/NY-ESO-1 vector (FIG. 7F, FIG. 7G, FIG. 7H, and FIG. 7I), the anti-PD-1 antibody (FIG. 7J, FIG. 7K), or a combination of anti-PD-1 antibody and a SV/NY-ESO-1 vector (FIG. 7L, FIG. 7M), or a combination of anti-PD-1 antibody and anti-CTLA4 antibody (FIG. 7N, FIG. 7O), or a combination of anti-PD-1 antibody and anti-CTLA4 antibody and a SV/NY-ESO-1 vector (FIG. 7P, FIG. 7Q). Percent survival over time is shown at FIG. 8. A mouse isotype control was used as the control in the experiment. A Sindbis viral vector encoding NY-ESO-1 is shown to reduce tumor growth in treated mice compared to untreated control mice in FIG. 9. Also, tumor growth is shown as a function of days after treatment (FIG. 10B, FIG. 10C, FIG. 10D, and FIG. 10E) or no treatment (control, FIG. 10). These data indicate that the combination of a checkpoint inhibitor and Sindbis virus vector encoding a tumor associated antigen, NYESO-1, increases survival and reduces tumor growth in mice with cancer. Surprisingly, treatment with an anti-CTLA4 antibody a Sindbis virus expressing NY-ESO-1 results in 100% survival of the tumor bearing mice. The anti-PDL1 antibody

Example 8—Systemically Administrated Sindbis Viral Vectors Markedly Improve the Efficacy of Immune Checkpoint Inhibition of Solid Tumor Growth This Example presents results showing that Sindbis virus vectors administered in combination with an anti-PD-1 antibody induced complete clearance of a solid tumor in a tumored animal model and protected treated mice from tumor recurrences.

Cancer immunotherapy requires the elicitation of an immune response that recognizes, targets, and eliminates cancer cells. Several methods, including immune checkpoint blockade, cancer vaccine and chimeric antigen receptor T cell treatment, have already been approved for the treatment of some cancers J. D. Wolchok et al., 2017, *NEnglJ Med,* 377:1345-1356; D. Pettitt et al., 2018, *Mol Ther,* 26, 342-353; G. G. Kenter et al., 2009, *N Engl J Med,* 361:1838-1847; and F. Massari et al., 2018, *Cancer Treat Rev,* 64:11-20). However, the benefits of such methods are often observed for only a minority of patients.

Oncolytic virus (OV) immunotherapy is an alternative therapeutic approach for treating cancer. The therapeutic efficacy of OVs is achieved by a combination of selective tumor cell killing and the establishment of a local, anti-tumor immune response, which can have a systemic effect (R. H. Andtbacka et al., 2015, *J Clin Oncol,* 33:2780-2788; H. L. Kaufman et al., 2015, *Nat Rev Drug Discov,* 14:642-662; Z. S. Guo et al., 2017, Biomedicines 5; D. Zamarin et al., 2014, *Sci TranslMed* 6, 226ra232; and A. K. Moesta et al., 2017, *C/in Cancer Res,* 23:6190-6202). Moreover, oncolytic viruses (OVs) can be genetically engineered for optimization of tumor selectivity and enhanced stimulation of the immune response. The use of viruses for cancer treatment is not new, but in past decades, researchers were mainly focused on enhancing the oncolytic potential of OVs. Recently however, clinical investigations involving OVs have been more focused on the immunostimulatory properties of these viruses. The studies in this Example demonstrate that a combined therapy involving the use of Sindbis virus as OV and immune checkpoint blockade show effective results.

As is appreciated by the practitioner in the art, Sindbis virus is a member of the Alphavirus genus and is an oncolytic virus (OV) with marked oncolytic activity. A Sindbis virus vector (SV) has several advantages that make it a good candidate for cancer therapy. First, SV has a positive sense single stranded RNA genome, rendering the vector safer than DNA-based OVs, as the vector cannot incorporate its genome into the host's DNA. Furthermore, in humans, Sindbis virus infection is considered to be asymptomatic, although, infrequently, it can lead to mild fever, rash and arthralgia that resolves promptly. More rarely, primarily in some DRB1*01 positive individuals, arthritic symptoms can persist longer. To further enhance its safety, SV was genetically modified to be replication-defective by splitting its genome to separate the replicon and a protein-encoding gene of interest from the viral structural genes and the packaging signal deleted from the later genome strand (P. J. Bredenbeek et al., 1993, *J Virol,* 67:6439-6446). In addition, because Sindbis virus is a blood-born pathogen, it can be administrated systemically in the bloodstream, thus facilitating its delivery as a therapeutic.

To test the therapeutic efficacy of SV in a clinically relevant tumor model, a tumor cell line expressing a tumor associated antigen (TAA), namely, the human cancer testis antigen NYESO-1, was used as described in this Example. NYESO-1 is an advantageous TAA for use in clinical immunotherapy due to its lack of expression in tissues outside of the testes and its frequent occurrence in numerous cancers, as well as its immunogenicity and its safety, which have been demonstrated in numerous clinical trials. The presence and expression of NYESO-1 are observed in approximately one-third to one-fourth of all melanoma, lung, esophageal, liver, gastric, prostate, ovarian and bladder cancers. Over 80% of synovial sarcomas, which are considered rare cancers, express NYESO-1. In this Example, the therapeutic efficacy of a SV vector expressing the tumor associated antigen (TAA) NYESO-1 (SV-NYESO1) was studied in immunocompetent mice. The results demonstrated that a combination treatment involving the administration of SV and a checkpoint protein inhibitor, i.e., an anti-programmed death 1 (anti-PD-1) antibody induced a potent systemic and intratumoral anti-tumor immune response in a tumored animal model, which led to total tumor clearance in the majority of treated animals, as well as the rejection of tumor re-challenge. Thus, the described treatment strategy is likely to serve as an improved and advantageous treatment therapy for subjects having a number of types of NYESO-1-expressing tumors.

Materials and Methods

Study Design

The study described in this Example was designed to investigate the therapeutic efficacy of SV-NYESO1 treatment administered either with or without a checkpoint protein inhibitor, an anti-PD-1 antibody (called "checkpoint blockade anti-PD-1" herein) in mice bearing NYESO-1 expressing tumors. Experiments were designed to evaluate the immune response to SV therapy. In all experiments, mice were randomized only after tumors were established and before SV treatment (day 0), to ensure similar tumor sizes in all groups. Mice inoculated with tumor cells, but which showed a tumor signal below $10^5$ relative luminescence units (RLU) before treatment, were excluded from the study. The numbers of mice, statistical tests and numbers of experimental replicates performed for each experiment are described in the description of the figures. Data included all outliers, and investigators were not blinded during evaluation of the in vivo experiments.

Cell Lines

Baby hamster kidney (BHK), BALB/c colon carcinoma (CT26) and the CT26 expressing LacZ (CT26.LacZ) cell lines were obtained from the American Type Culture Collection (ATCC). Firefly luciferase (Fluc)-expressing CT26 cells (CT26.Fluc and CT26.LacZ.Fluc) were generated by stable transfection of pGL4.20_Fluc plasmid. The CT26 cell line expressing both Fluc and NYESO-1 (CT26.Fluc.NYESO1) was generated by stably transfecting the CT26.Fluc cell line with the expression plasmid pReceiver-M02 (GeneCopoeia) that contains a gene encoding NYESO-1 (Accession no. NM_001327.1).

BHK cells were maintained in minimum essential α-modified media (α-MEM), (Corning CellGro), with 5% fetal bovine serum (FCS, Gibco) and 100 mg/ml penicillin-streptomycin (Corning CellGro). CT26.Fluc.NYESO1 and CT26.Fluc.LacZ cells were maintained in Dulbecco's modified Eagles medium containing 4.5 g/L Glucose (DMEM, Corning CellGro), supplemented with 10% FCS, 100 mg/mL penicillin-streptomycin, 7.5 μg/mL Puromycin and 800 or 400 μg/mL Geneticin, respectively. All cell lines were cultured at 37° C. and in 5% $CO_2$.

Sindbis Viral Vector Production

Sindbis virus vector (replicon) expressing NYESO-1 cDNA (SV-NYESO1) was made by PCR amplification of the NYESO-1 gene from the pReceiver-M02 plasmid. Expression of the NYESO-1 gene was confirmed by Western blot as described below for vector titering. Sindbis virus vector expressing the LacZ gene (SV-LacZ) has been described previously (J. C. Tseng et al., 2002, *J Natl Cancer Inst,* 94, 1790-1802). SV vector and SV replicon are used interchangeably herein.

Sindbis viral vectors expressing LacZ cDNA (SV-LacZ) or NYESO-1 (SV-NYESO1) were produced as previously described (A. Hurtado et al., 2005, *Mol Ther,* 12, 813-823).

Briefly, DNA plasmids containing the Sindbis replicon comprising the gene of interest or Sindbis virus helper sequences were linearized before in vitro transcription using the mMACHINE RNA transcription kit (Ambion, Austin, TX) following the manufacturer's protocol. Helper and SV replicon RNAs were mixed at a 1:1 ratio and were then electroporated into BHK cells. Culture medium was replaced with OPTI-MEM (Invitrogen), supplemented with 100 μg/mL $CaCl_2$). Supernatant isolated from infected BHK cells was collected 24 hours later and stored at −80° C.

Sindbis Viral Vector Quantification

Virus titers were determined by making serial dilutions of the SV vector in Optimem-$CaCl_2$) and infecting BHK cells for an hour at room temperature (RT). Cells were washed with α-MEM media and incubated overnight (o/n) at 37° C. and in 5% $CO_2$. For SV-LacZ production, $1\times10^4$ BHK cells in 96 well plates were infected with the SV vector (50 L/well). For SV-NYESO1 production, $1\times10^5$ BHK cells in 12 well plates were infected with the SV vector (250 μL/well). In both cases, protein extraction was performed using M-PER Mammalian Protein Extraction Reagent (Pierce). LacZ was detected using the All in one ß-Gal Assay reagent kit (Pierce) following the manufacturer's protocol. NYESO-1 was detected by Western blot using standard protocols. Anti-NYESO-1 antibody clone E978 (Upstate) was used as a primary antibody at a dilution 1/5,000 in TBS-T with 5% non-fat milk. Vector titers refer to the number of infectious particles, transducing units, per milliliter of supernatant (TU/ml) and were estimated as the last dilution having detectable reporter activity.

Because different detection sensitivities are obtained in the ß-Gal assay and NYESO-1 Western blot, vectors were also titered by RT-PCR on total RNA obtained from infected BHK cells (Table 38 below). Both vectors were used at an RT-PCR titer of $10^7$-$10^8$ TU/ml, equivalent to $10^4$-$10^5$ TU/ml NYESO1 Western blot or $10^6$-$10^7$ TU/ml ß-Gal Assay.

TABLE 38

Primers and conditions for RT-PCR used to titer vectors

| primer | Sequence | cDNA Cycle |
|---|---|---|
| cDNA (ThermoScript ™ RNaseH-reverse transcriptase, Invitrogen) | | |
| cDNA5R | 5'-TTTTTGAAATGTTAAAAACA AAATTTTGTTG (SEQ ID NO: 409) | 2 hours at 60° C. |
| QPCR (IQ SYBR Green Supermix. BioRad)) | | |
| 7692F | 5'-TGATCCGACCAGCAAAACTC (SEQ ID NO: 410) | 5 min at 95° C. |
| cDNA5R | 5'-TTTTTGAAATGTTAAAAACA AAATTTTGTTG (SEQ ID NO: 409) | 40 x [95° C. 20 sec; 60° C. 30 sec; 72° C. 30 sec] |

In Vivo Experiments and Animal Tumor Models

All in vivo experiments were performed in accordance with the Institute of Animal Care and Use Committee at New York University Health. Six to 12-week old female BALB/c mice were purchased from Taconic (Germantown, NY). For the animal tumor model, $7\times10^4$ CT26.Fluc.NYESO1 cells in 500 μL OPTI-MEM were injected intraperitoneally (i.p.) into the right side of the animal on day −4. For treatments with SV vector, the virus ($10^7$-$10^8$ TU/ml) in a total volume of 500 μL was injected i.p. into the left side of the animal, 4 days a week (days 1, 2, 3, 4), for a total of 4 weeks. The immune checkpoint inhibitor anti-PD-1 antibody (clone RMPI-14, BioXCell) was injected i.p. into the left side of the animal at a dose of 250 μg per injection. Anti-PD-1 was administrated 3 days a week (days 0, 2, 4) for a total of 2 weeks. For the tumor rechallenge model, $7\times10^4$ CT26.Fluc.NYESO1 cells or $5\times10^4$ CT26.Fluc.LacZ cells were injected i.p. into the left side of the animal. The therapeutic efficacy of the treatment was monitored in two ways: by determining tumor luminescence and animal survival. Noninvasive bioluminescent imaging was done using the IVIS Spectrum imaging system (Caliper Life Science), and tumor growth was quantified using the Living Image 3.0 software (Caliper Life Science) as previously described (J. C. Tseng et al., 2004), *Nat Biotechnol.,* 22:70-77. Relative tumor growth for each mouse was calculated by dividing total body counts on a given day by total body counts of the first IVIS image. Animal survival (mortality) was monitored and recorded daily.

Flow Cytometry

For flow cytometry analysis, spleens, lymph nodes (LNs) and tumors were Harvested from mice. The extracted LNs and tumors were chopped in small pieces and incubated with a digestive mix containing RPMI with collagenase IV (50 μg/mL) and DNAseI (20 U/mL) for 1 hour at 37° C. Additional hyaluronidase V (50 μg/ml) was included in the digestive mix for tumor samples.

Spleens, digested tumors and LNs were mashed through a 70-μm strainer before red blood cells were lysed using ACK (ammonium-chloride-potassium) lysis buffer (Gibco). Cells were washed with PBS containing 1% FCS and surface receptors were stained using various antibodies and fluorescence activated cell sorting (FACS) techniques (Table 39).

TABLE 39

FACS panel for surface markers

| Antibody | Clone | Fluorochrome | Vendor |
|---|---|---|---|
| CD3 | 17A2 | BV786 | Biolegend |
| CD3 | 17A2 | BV605 | Biolegend |
| CD4 | RM4-4 | PerCP-Cy5.5 | Biolegend |
| CD8 | 53-6.7 | APC-H7 | BD Bioscience |
| CD11b | MI/70 | BV786 | Biolegend |
| CD11c | N418 | PerCP-Cy5.5 | Biolegend |
| CD19 | 6D5 | PE-Cy7 | Biolegend |
| CD44 | IM7 | BV605 | Biolegend |
| CD49 | DX5 | PE | Biolegend |
| CD62L | MEL-14 | Alexa Fluor 700 | Biolegend |
| CD69 | H1.2F3 | FITC | Biolegend |
| Ly6C | HK1.4 | PE-Cy7 | Biolegend |
| Ly6G | 1A8 | BV421 | Biolegend |
| PD-1 | 29F.1A12 | APC | Biolegend |
| PD-L1 | 10F.9G2 | PE | Biolegend |
| F4/80 | T45-2342 | PE-CF594 | BD Bioscience |
| IA/IB | M5/114.15.2 | V500 | BD Bioscience |

Stained cells were then fixed with PBS containing 4% formaldehyde. For intracellular staining, anti-FOXP3 antibody (Clone 259D/C7) and fluorochrome PE-CF594 (BD Bioscience) and the FOXP3 staining buffer set was used (eBioscience). Flow cytometry analysis was performed on a LSR II machine (BD Bioscience) and data were analyzed using FlowJo (Tree Star). In some cases, anti-Ki-67 antibody (Clone 16A8) and fluorochrome BV412 (Biolegend) were used for staining.

Enzyme-Linked Immunospot

Splenocytes were isolated as described for flow cytometry. To isolate tumor infiltrating cells, digested tumors were mashed through a 70-μm strainer and incubated for 4 hours at 37° C. until most tumor cells adhered to the flask. Floating cells were collected and used to characterize tumor infiltrating cells. Splenocytes and tumor infiltrating cells were prepared at various time points during treatment, and mouse IFN-γ ELISPOT was performed according to the manufacturer's protocol (BD Bioscience). $4\times10^5$ cells were plated per well o/n in RPMI medium supplemented with 10% FCS and stimulated with NYESO-1 peptide (RGPESRLLE, (SEQ ID NO: 3)) at a final concentration of 5 μg/ml.

Ex Vivo Cytotoxic Assay

Splenocytes were collected from animals 14 days after treatment had started. Splenocytes ($4\times10^6$/mL) were co-cultured with CT26.Fluc.NYESO1 ($2\times10^4$/ml) or CT26.Fluc.LacZ ($2\times10^4$/ml) in a 24 well plate for 2 days in 1 ml RPMI supplemented with 10% fetal calf serum (FCS). Cells were washed with phosphate buffered saline (PBS) and were lysed with 100 μL of M-PER Mammalian Protein Extraction Reagent (Pierce) per well. Cell cytotoxicity was assessed based on the viability of CT26 cells, which was determined by measuring the luciferase activity in each well. Luciferase activity was measured by adding 100 μL of Steady-Glo reagent (Promega) to each cell lysate and measuring the luminescence using a GLOMAX portable luminometer (Promega).

Statistical Analysis

All statistical analyses were performed using GraphPad Prism 6.0. Data are presented as means+/−SEM.

Results

SV Vectors Expressing the TAA NYESO-1 Exhibit Antitumor Efficacy In Vivo

Figure 11A:
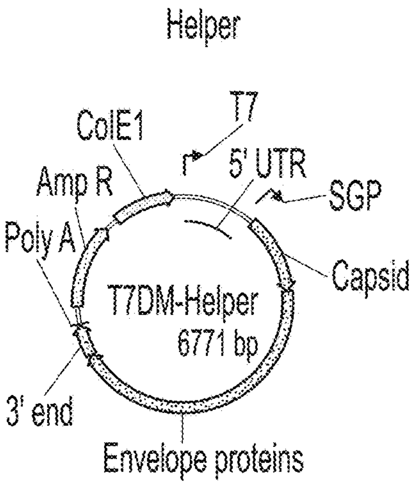
FIGS. 11A-11G show vector maps, Western blots and bar graphs related to Sindbis virus vector production, infection of cells and expression of protein from a gene encoded by the vector.
Figure 11B:
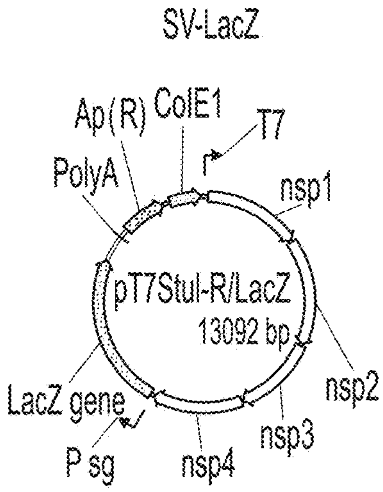
Figure 11C:
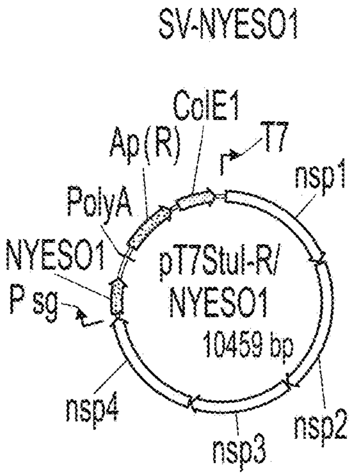

To exploit the therapeutic effect of the TAA-encoding Sindbis virus vector (SV vector) against human cancers, a replication-deficient SV vector was genetically modified to express the human cancer testis antigen NYESO-1 (SV-NYESO1), (FIG. 11A). As noted above, NYESO-1 is an advantageous candidate for eliciting a tumor specific immune response due to its restricted expression in normal tissues but frequent occurrence in numerous cancers, such as ovarian cancer where it is expressed in 43% of cases.

Figure 11D:
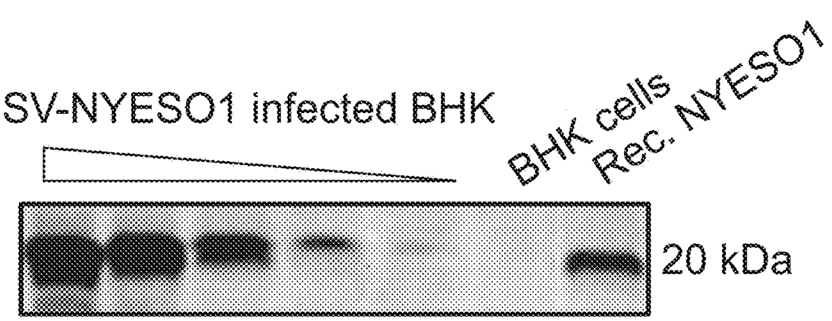
Figure 11E:
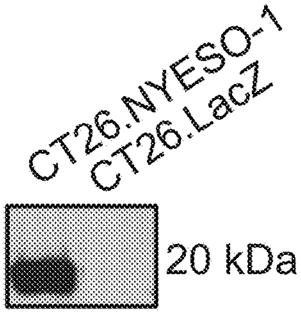
Figure 11F:
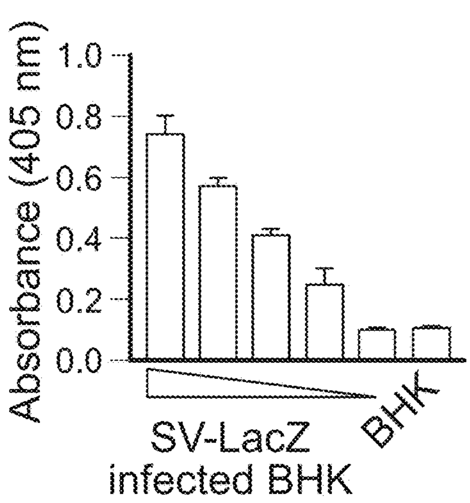
Figure 11G:
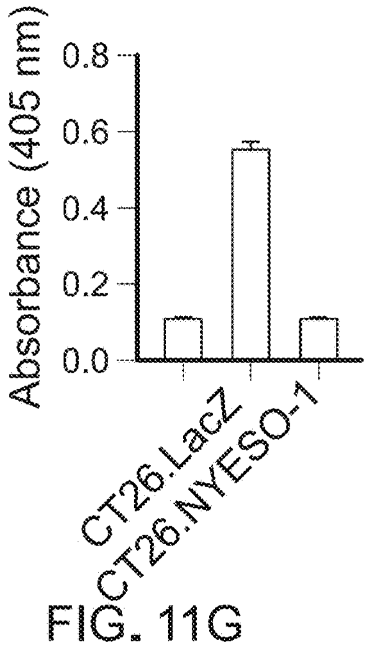
Figure 12A:
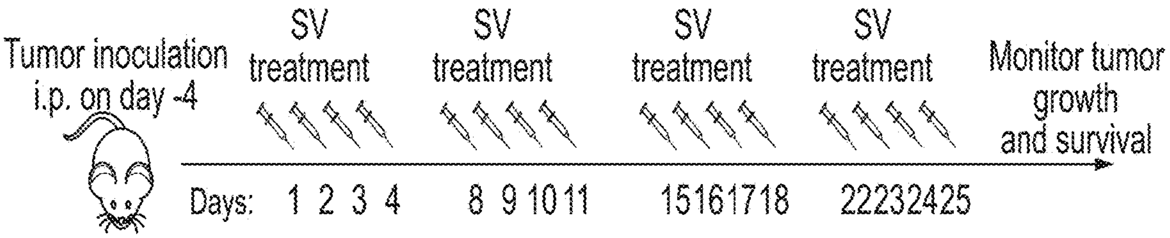
FIGS. 12A-12D present treatment schema, graphs of tumor growth curves, bioluminescence images and survival plots of in vivo experiments showing that SV expressing the NYESO-1 tumor associated antigen (TAA) exhibited anti-tumor efficacy.
Figure 12B:
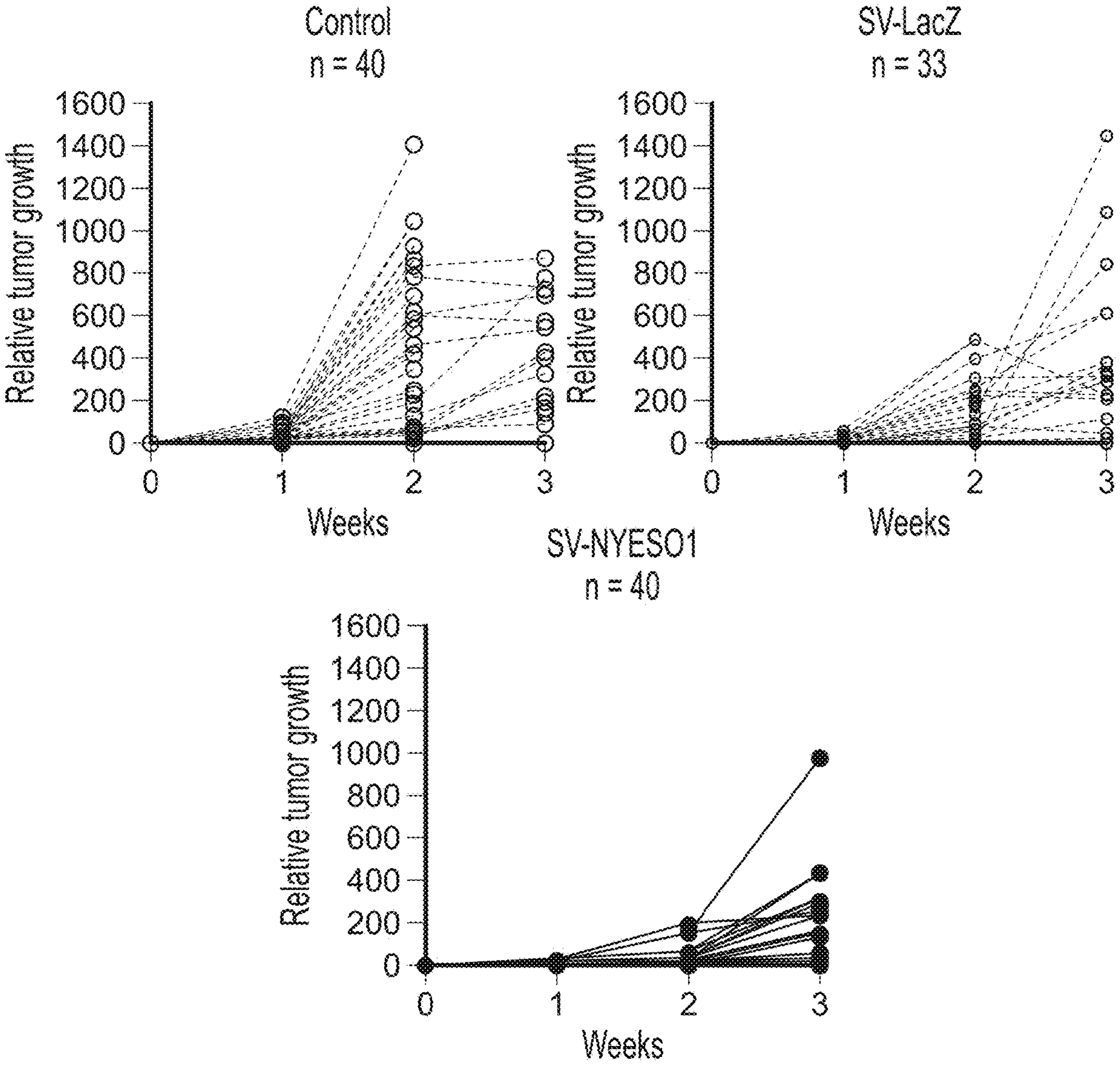
Figure 12C:
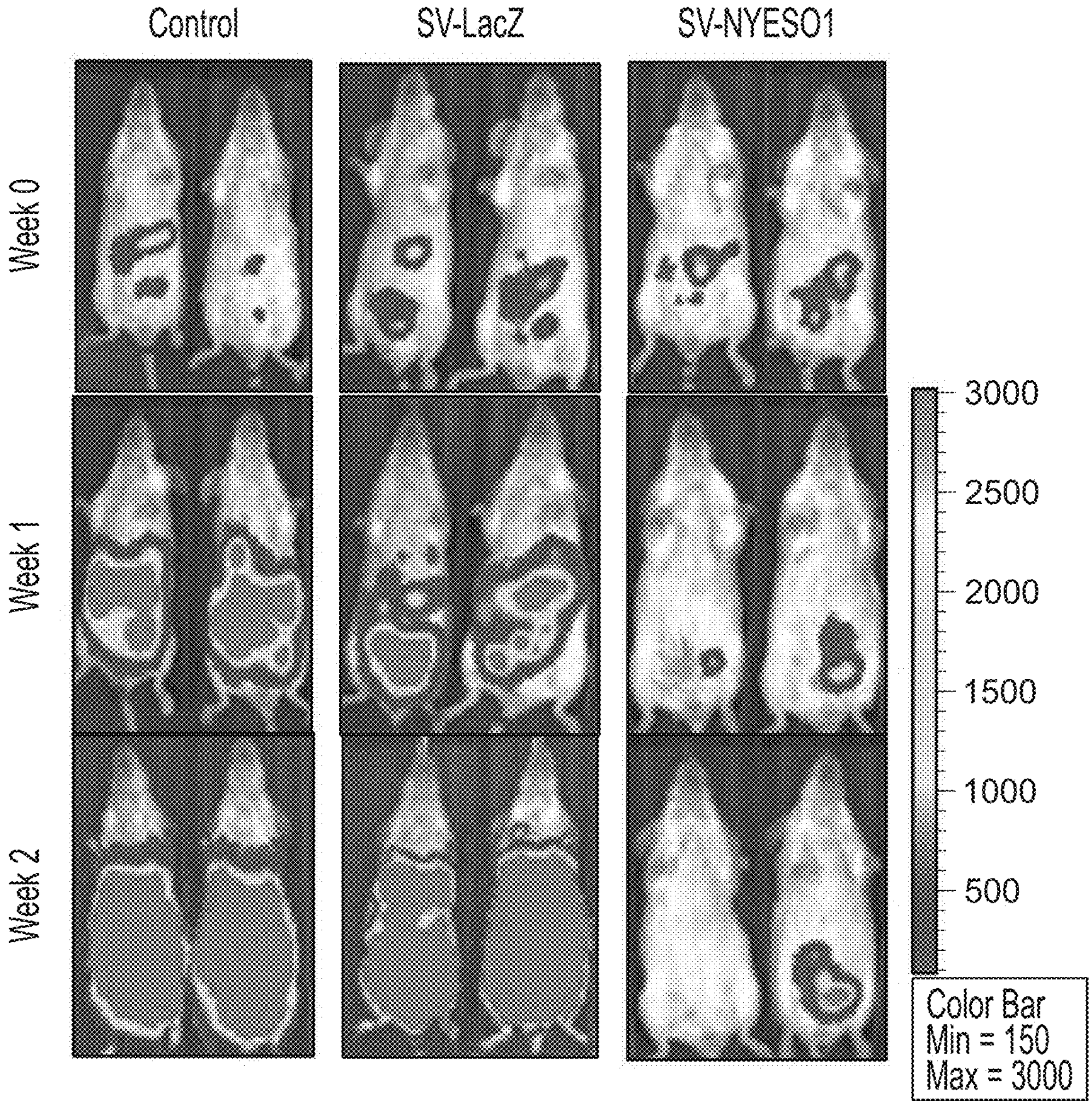
Figure 12D:
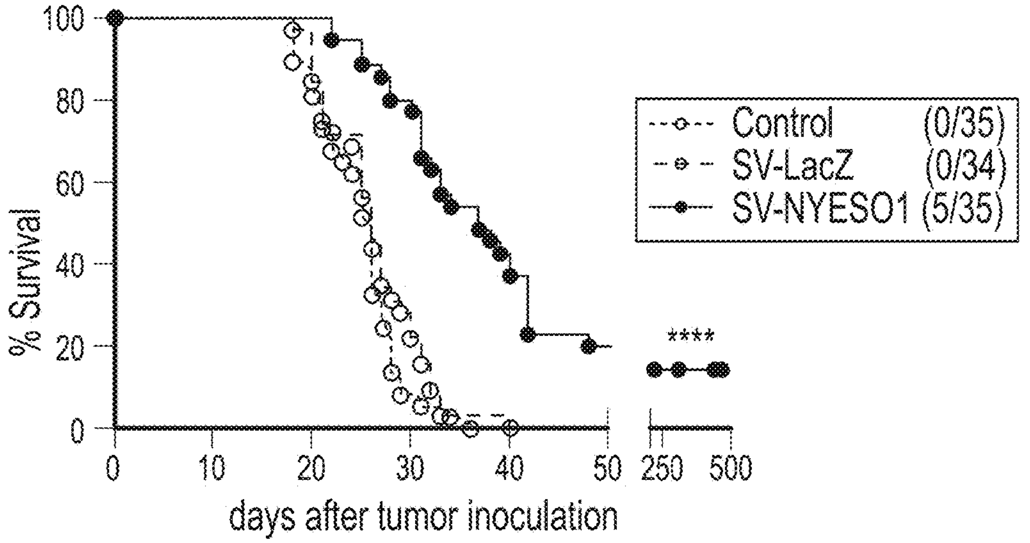

To test the SV vector SV-NYESO1 for cancer therapy, a tumor cell line expressing NYESO-1 and firefly luciferase (CT26.Fluc.NYESO1) was administered by i.p. injection to immuno-competent female mice. Expression of NYESO-1 by SV-NYESO1 and CT26.Fluc.NYESO1 was previously confirmed by Western Blot (FIGS. 11D and 11E). After the tumor was established in the animals (day 0), SV-NYESO1 vector was systemically injected on 4 consecutive days (day 1, 2, 3 and 4) for a total of 4 weeks (FIG. 12A). To investigate the importance and effect of the tumor-associated antigen (TAA) NYESO-1 in the vector, SV vector expressing an unrelated antigen, 3-Galactosidase (LacZ), (SV-LacZ), was used (FIGS. 11A and 11G). Tumor growth was measured once a week using noninvasive bioluminescent imaging (FIGS. 12B and 12C). Tumors were found to grow progressively in both untreated animals (control) and mice treated with the SV-LacZ vector. In contrast, in tumored animals that had been treated by systemic injection with SV-NYESO1, the SV-NYESO1 induced a delay in tumor growth and, in some cases, resulted in complete tumor regression. Tumor growth was inversely correlated with long-term survival, as all control and SV-LacZ treated animals died after 3 weeks, and 15 to 20% of the animals treated with SV-NYESO1 showed complete tumor clearance response, depending on the experimental conditions. (FIG. 12D).

Figure 13A:
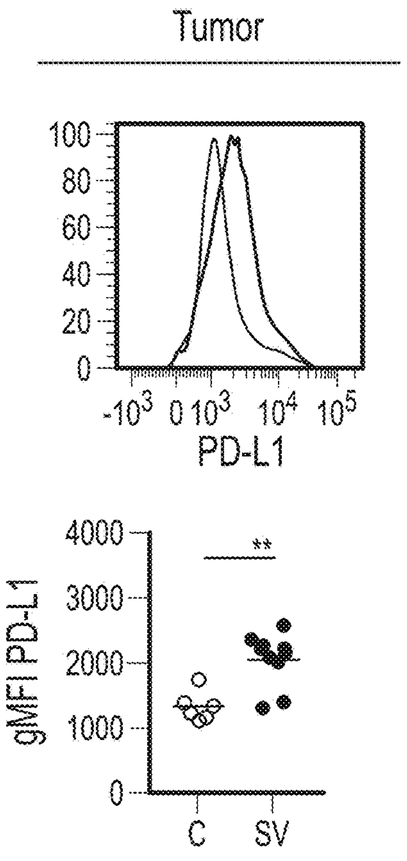
FIGS. 13A-13F present results from experiments showing that SV-NYESO1 vector in combination with anti-PD-1 antibody completely inhibits tumor growth and cures mice from established tumors.

SV-NYESO1 in Combination with Anti-PD-1 Antibody Completely Inhibits Tumor Growth and Cures Mice from Established Tumors The inventors had previously demonstrated the crucial role of T cells in eradicating tumors in response to SV treatment (T. Granot et al., 2014, *Mol Ther,* 22:112-122). In those studies, LacZ, a foreign antigen, was used, while in the studies described in this Example, the cancer-testis-antigen NYESO-1 was used in the animal model. Based on the results of the experiments described in this Example, SV-NYESO1 treatment may have been less efficacious due to the mitigation of the therapeutic activity of T cells by the tumor-specific expression of the immune checkpoint molecule programmed death ligand 1 (PD-L1), as well as by the expression of programmed death protein 1 (PD-1) on T cells. Indeed, SV-NYESO1 therapy induced a significant increase of PD-L1 and PD-1 expression on tumor cells and on tumor-infiltrating T cells, respectively (FIGS. 13A and 13B).

Figure 13B:
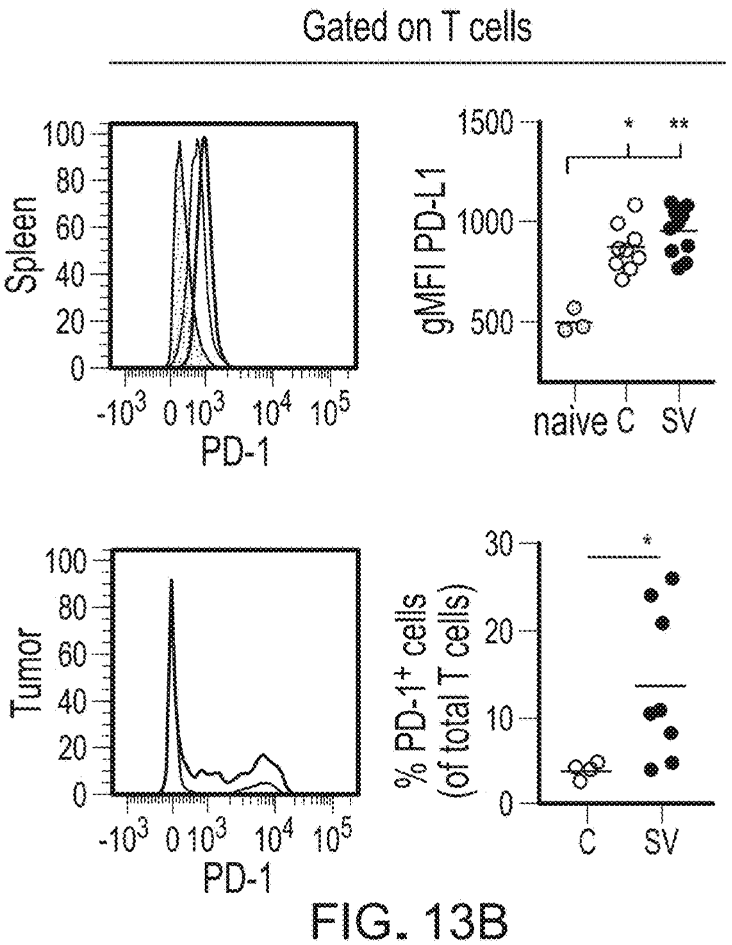
Figure 13C:
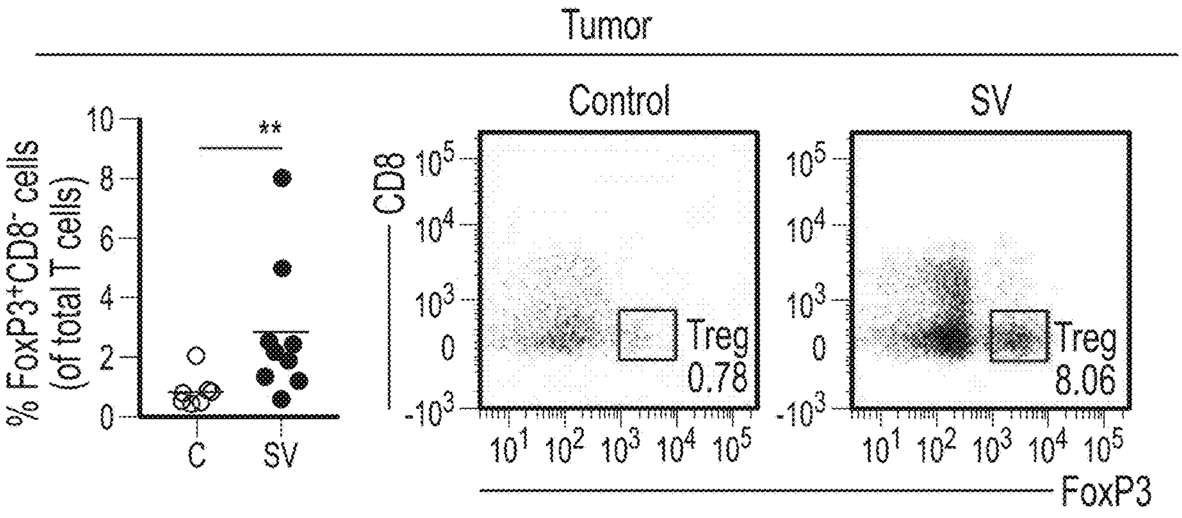
Figure 13D:
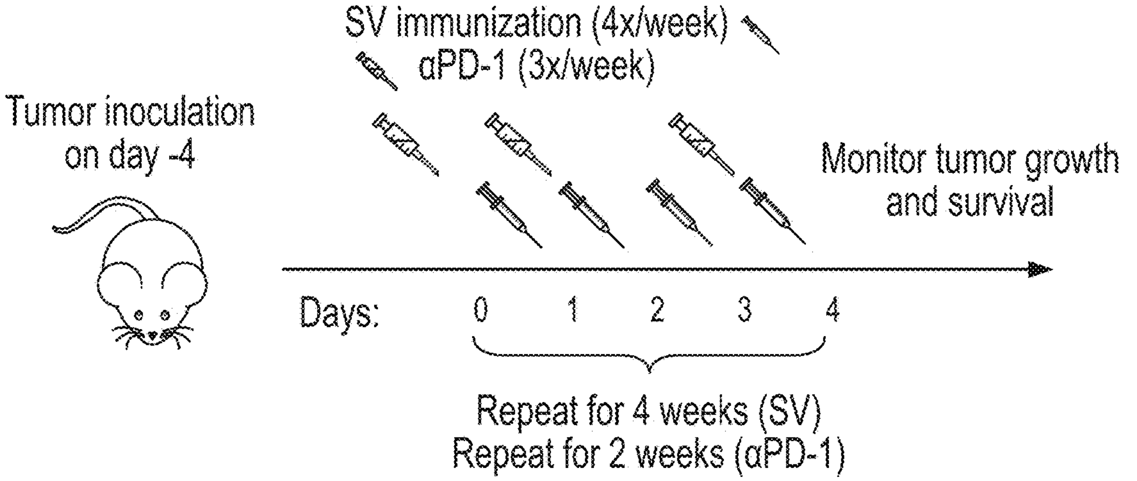
Figure 13E:
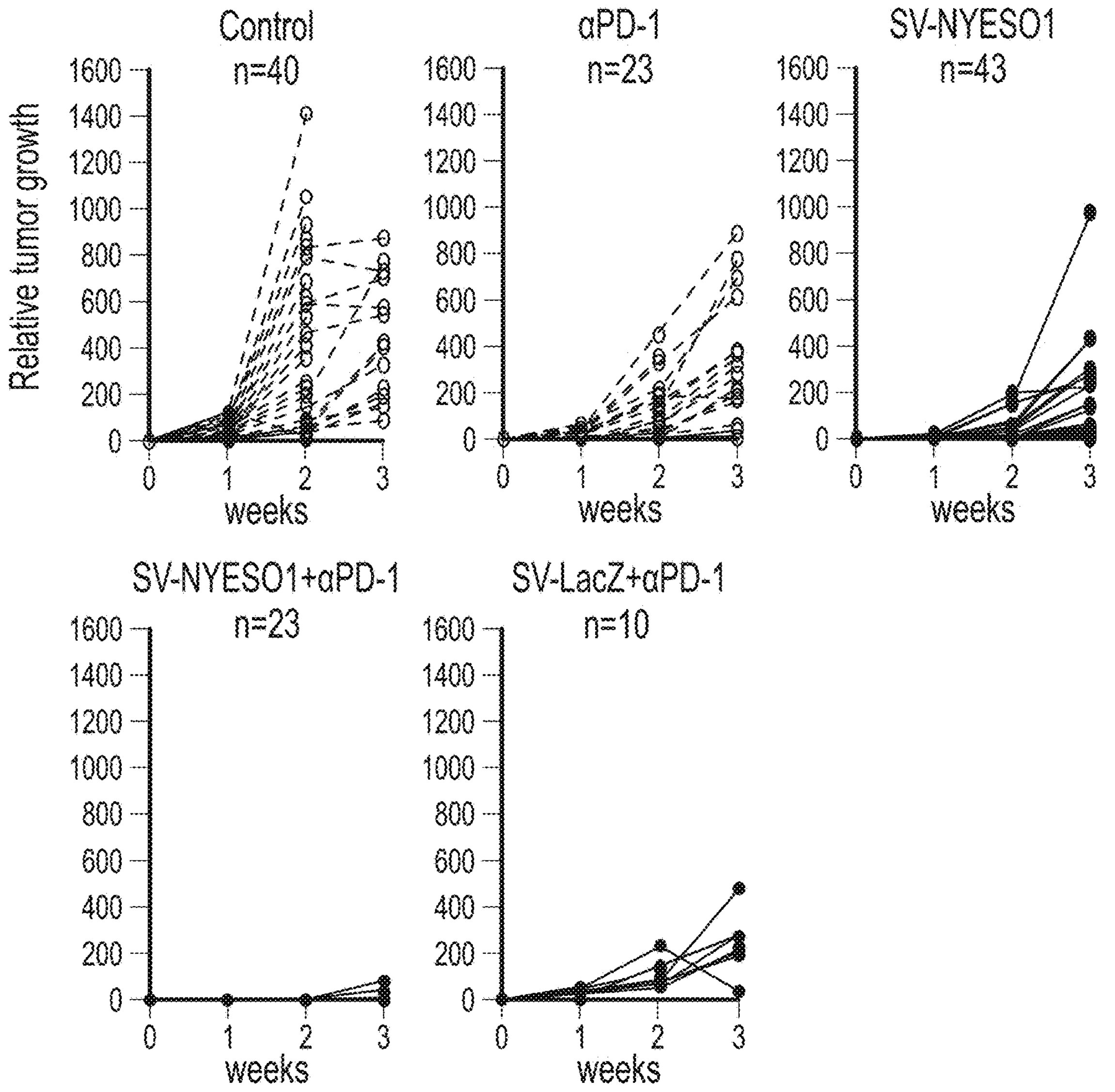
Figure 14:
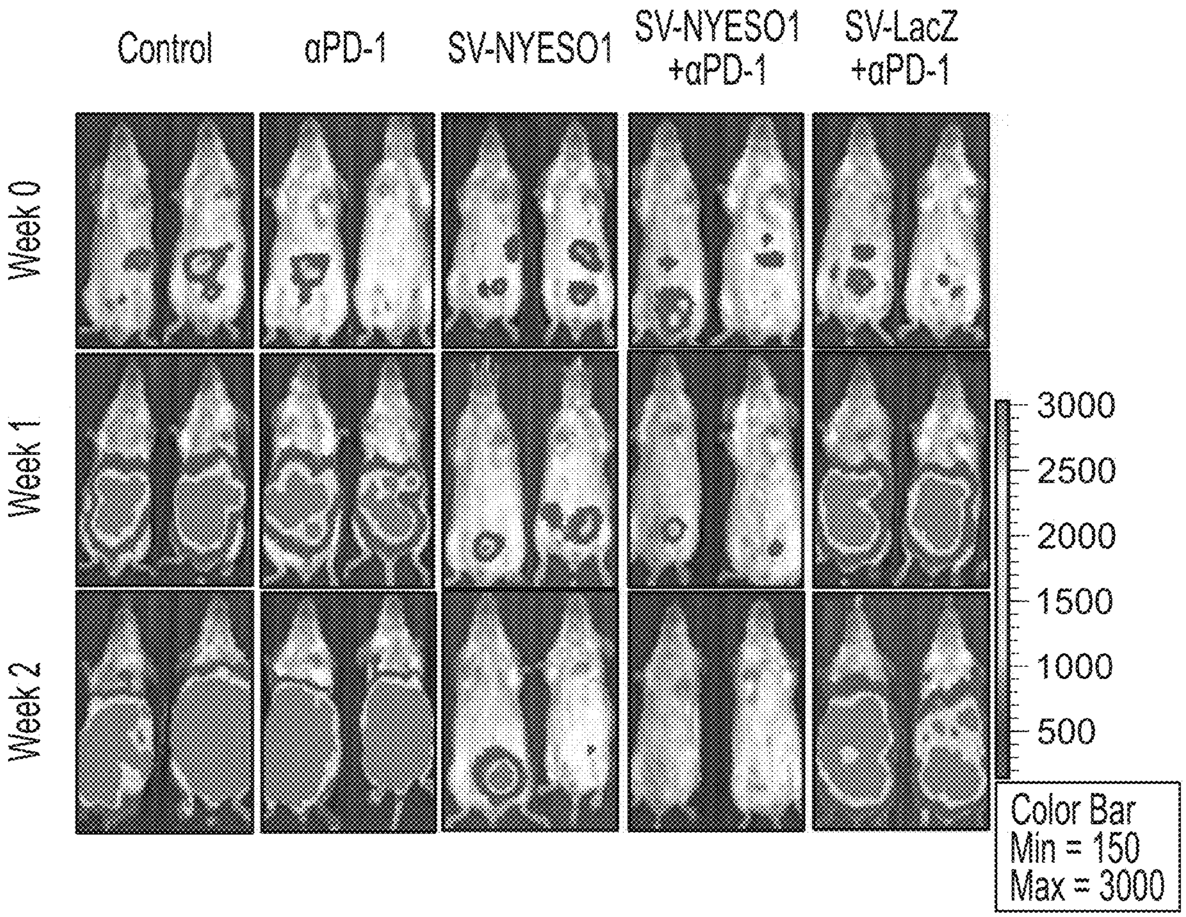
FIG. 14 shows representative noninvasive bioluminescence images of three independent experiments showing control and treated mice bearing CT26.Fluc.NYESO1 tumors during treatment with SV NYESO1 vector. Images were taken one day before starting SV treatment (day 0) and at weeks 1 and 2.

The expression of PD-1 on splenic T cells was similar in tumor bearing mice with and without viral therapy (FIG. 13B). In addition, an increase of regulatory T cells was observed in tumors from SV-NYESO1-treated mice when compared with control mice (FIG. 13C). These results suggest that SV-NYESO1 therapy may be augmented by anti-PD-1 treatment, because blockade of the PD-1/PD-L1 interaction reduces the number and/or suppressive activity of regulatory T cells and restores the activity of effector T cells. To test this, tumor bearing mice were treated with SV-NYESO1 together with the checkpoint inhibitor anti-PD-1 antibody. Anti-PD-1 antibody was injected into tumored animals three times a week (day 0, 2 and 4) for a total of two weeks (FIG. 13D). The animals were then monitored for tumor growth once a week using noninvasive bioluminescent imaging (FIG. 13E and FIG. 14). Again, it was found that tumors in untreated mice grew progressively and that all mice succumbed to their tumor burden after 3 weeks. SV-NYESO1 and anti-PD-1 antibody treatments alone induced a delay in tumor growth with moderate therapeutic efficacy of 15 to 20%, depending on the experimental conditions.

Figure 13F:
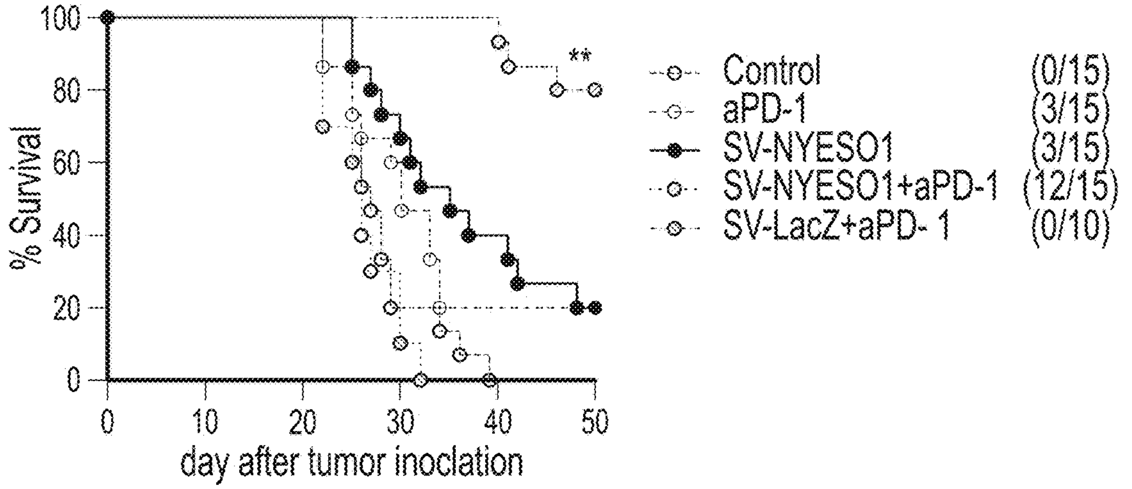

However, SV-NYESO1 and anti-PD-1 antibody administered in combination ("combination treatment") resulted in complete regression of tumors in almost all mice (12 of 15 mice) (FIG. 13F). This effect was dependent on the expression of NYESO-1 by the SV vector, as 1 out of 10 mice treated with SV-LacZ and anti-PD-1 antibody were unable to control tumor growth and succumbed to cancer. Thus, efficacy is dependent upon SV initially expressing the TAA, i.e., NYESO-1, in the tumor.

Figure 15A:
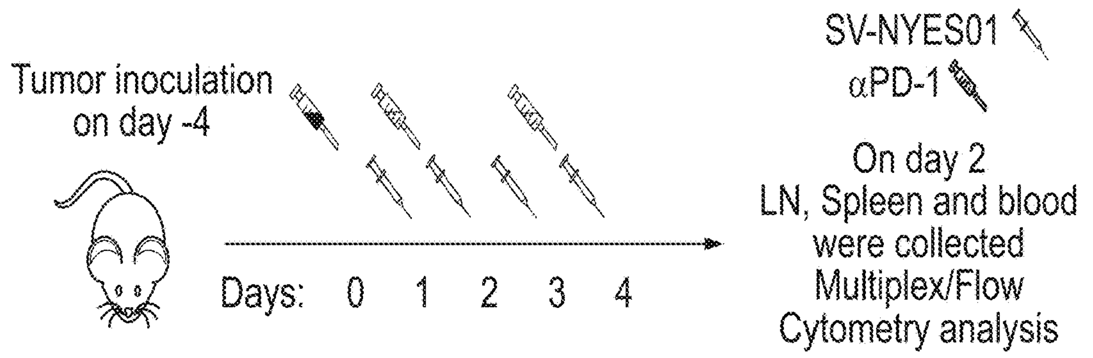
FIGS. 15A-15I present results demonstrating that SV-NYESO1 acted as an immunostimulatory agent and induced a rapid and systemic T cell activation in peripheral lymphoid organs.
Figure 15B:
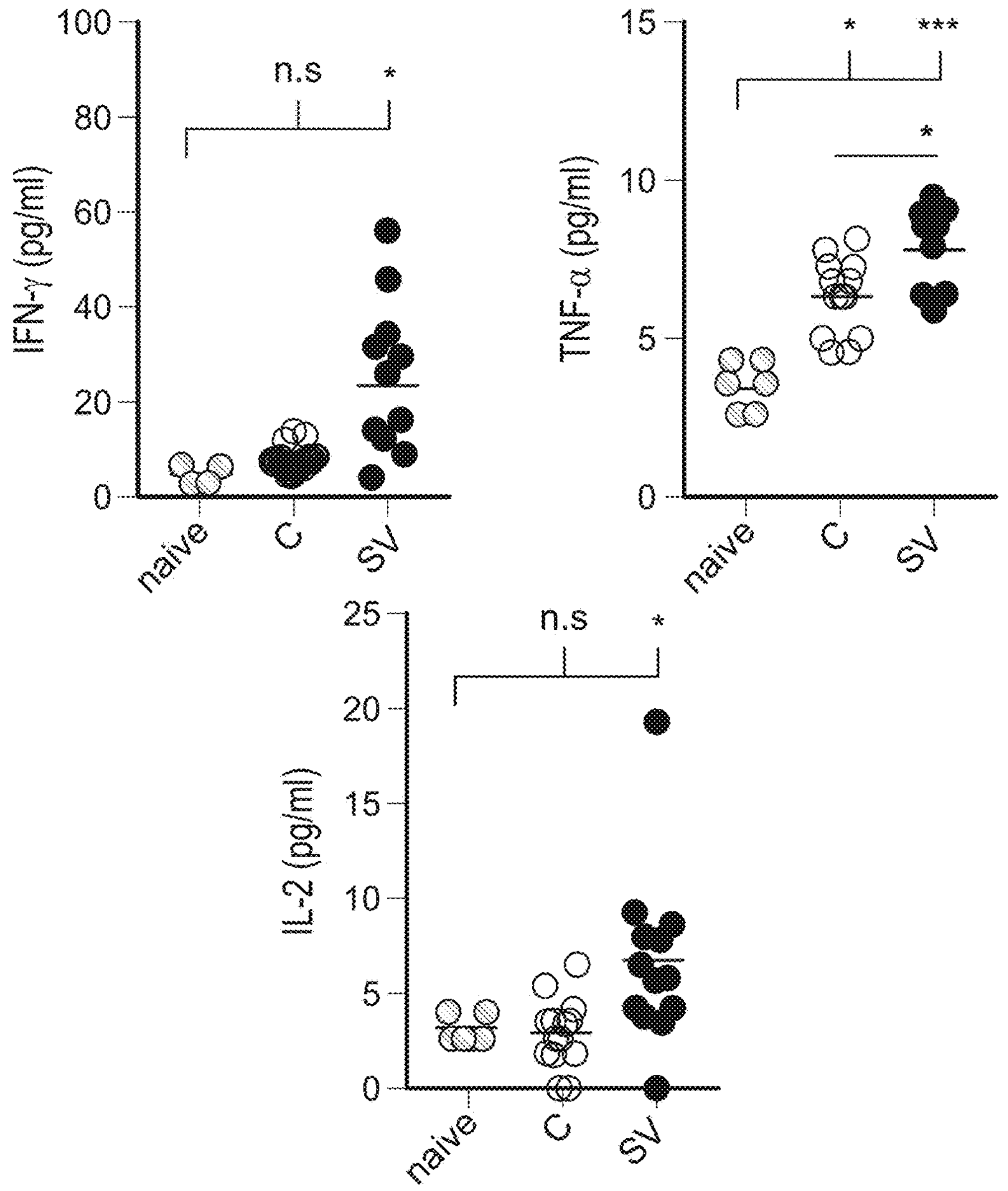
Figure 15C:
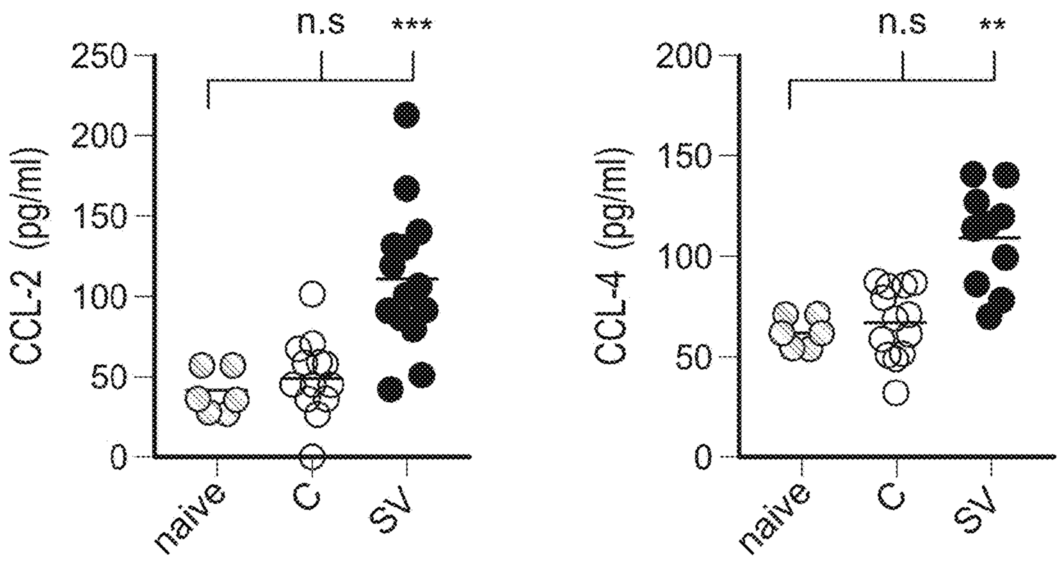
Figure 15D:
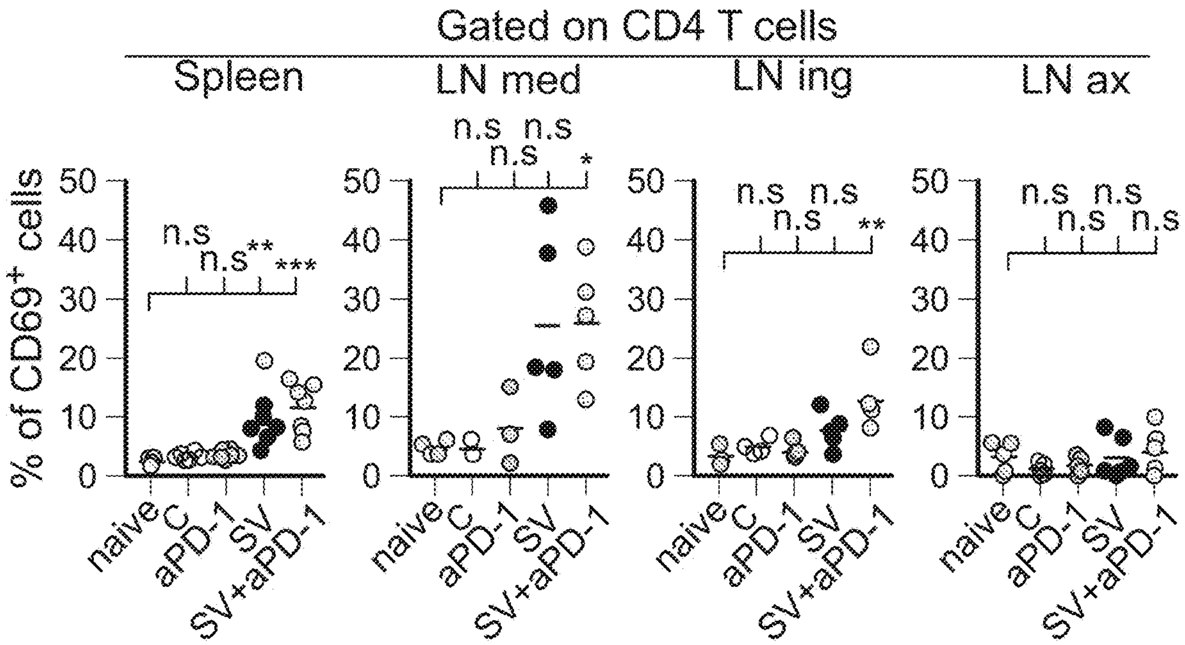
Figure 15E:
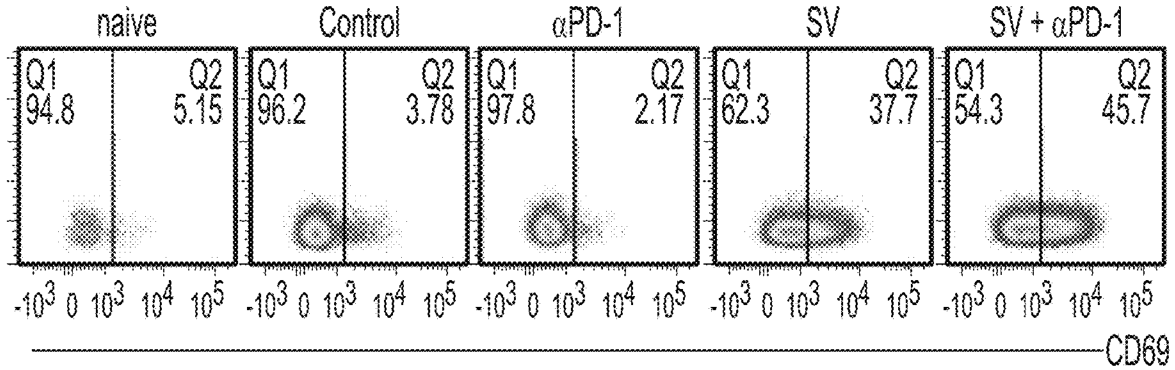
Figure 15F:
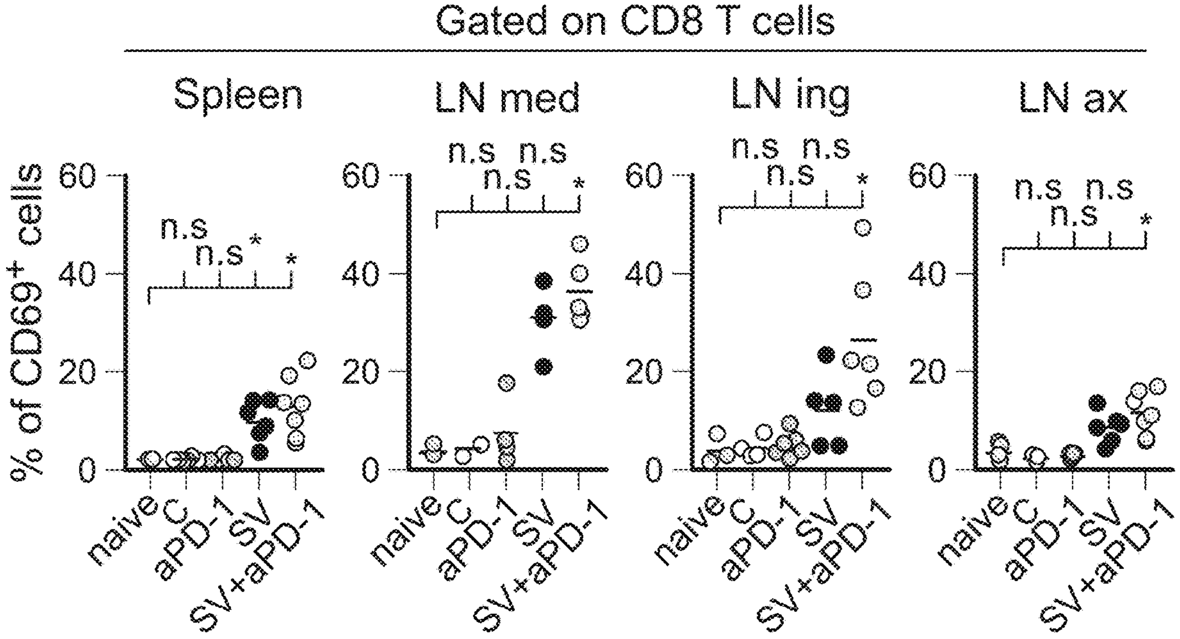
Figure 15G:
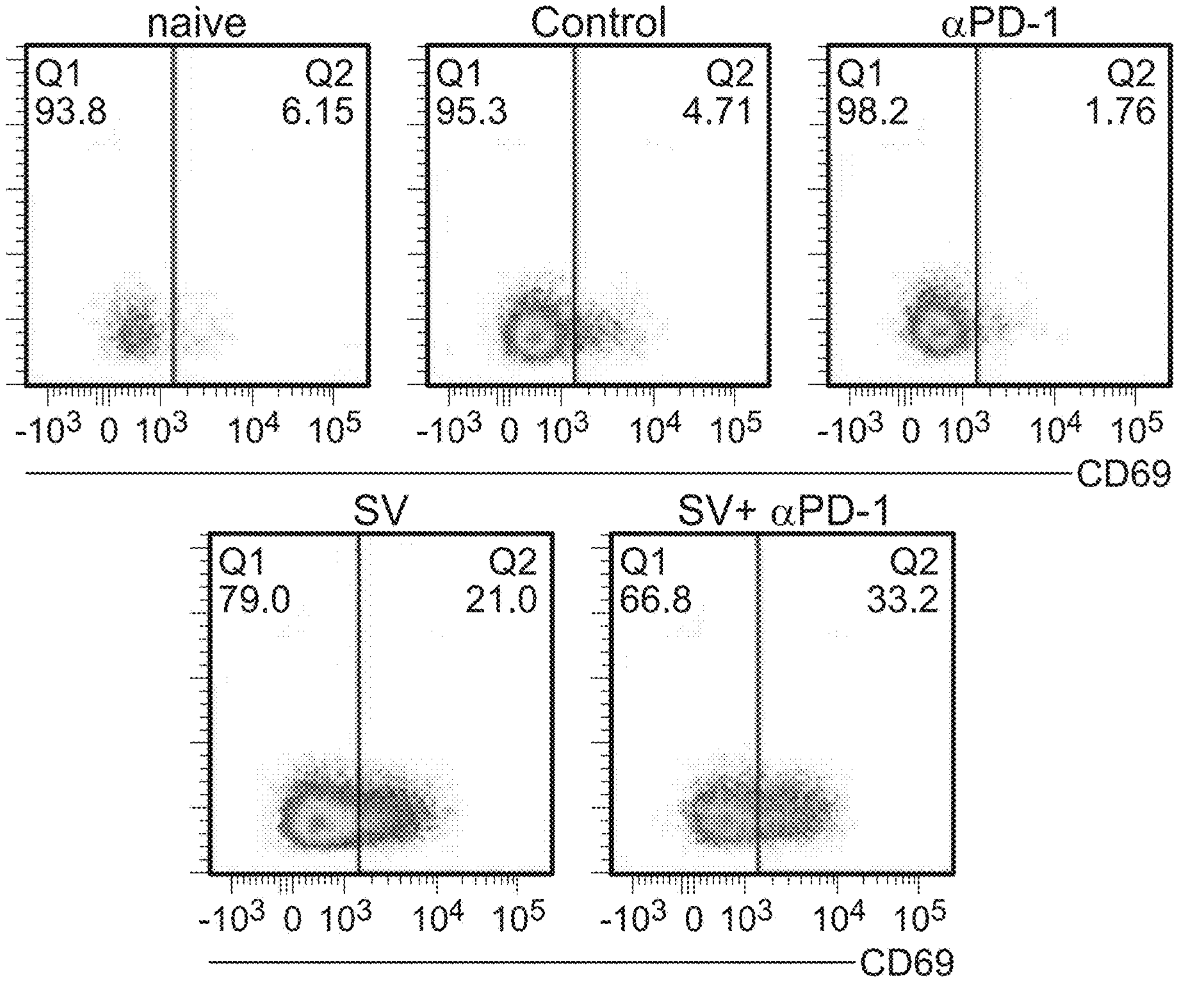

SV-NYESO1 Acts as an Immunostimulatory Agent and Induces a Rapid and Systemic Lymphocyte Activation Oncolytic viruses can stimulate the immune response and trigger inflammation, which can enhance an anti-tumor response. To analyze the effect of SV therapy on the immune response in treated animals, the spleen, LNs and plasma from animals in all groups were collected on several days during treatment. First, the effect of one SV-NYESO1 injection on the immune response was investigated (FIG. 15A). Plasma was collected on day 2 (24 and 48 hours after the first SV-NYESO1 and/or anti-PD-1 antibody injection, respectively, and pro-inflammatory cytokines and chemokines were analyzed (FIG. 15B). The levels of the pro-inflammatory cytokines IFN-γ, TNF-α, and IL-2 showed a significant increase in SV-NYESO1 treated mice compared with those in control and naïve mice. The same trend was observed for the levels of the chemokines CCL-2 and CCL-4, which have been shown to promote leukocyte recruitment to the site of inflammation/infection (FIG. 15C). No difference in cytokine and chemokine levels was detected in animals treated with SV-NYESO1 with and without anti-PD-1 antibody (data not shown).

To determine whether the pro-inflammatory condition observed in the blood after one injection of SV-NYESO1 reflected the activation status of lymphocytes in the treated animals, spleen and LNs were collected on day 2, and lymphocyte activation (assessed by the expression of the early activation marker CD69) was analyzed by flow cytometry. The expression of CD69 on $CD4^+$ and $CD8^+$ T cells (FIGS. 15D-15G), as well as on NK and B cells (FIGS. 16A-16D), was markedly upregulated in spleen, mediastinal, inguinal and axillary LNs of animals that had received one injection of SV-NYESO1, compared with control mice and mice treated with anti-PD-1 antibody alone. Even though a slight difference was observed, there was no significant difference in T cell activation between mice treated with the combined therapy and mice treated with SV-NYESO-1 alone.

Figure 15H:
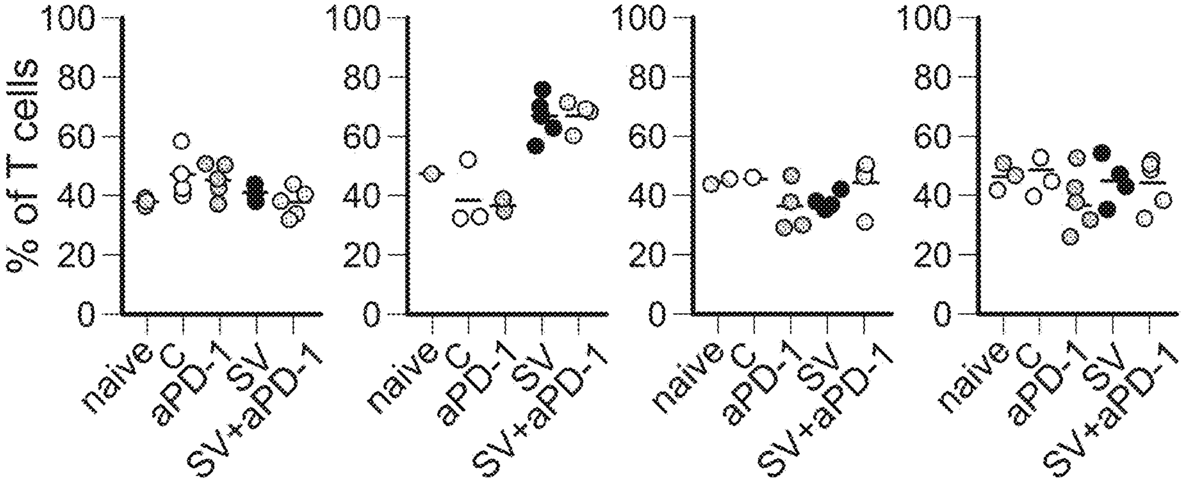
Figure 15I:
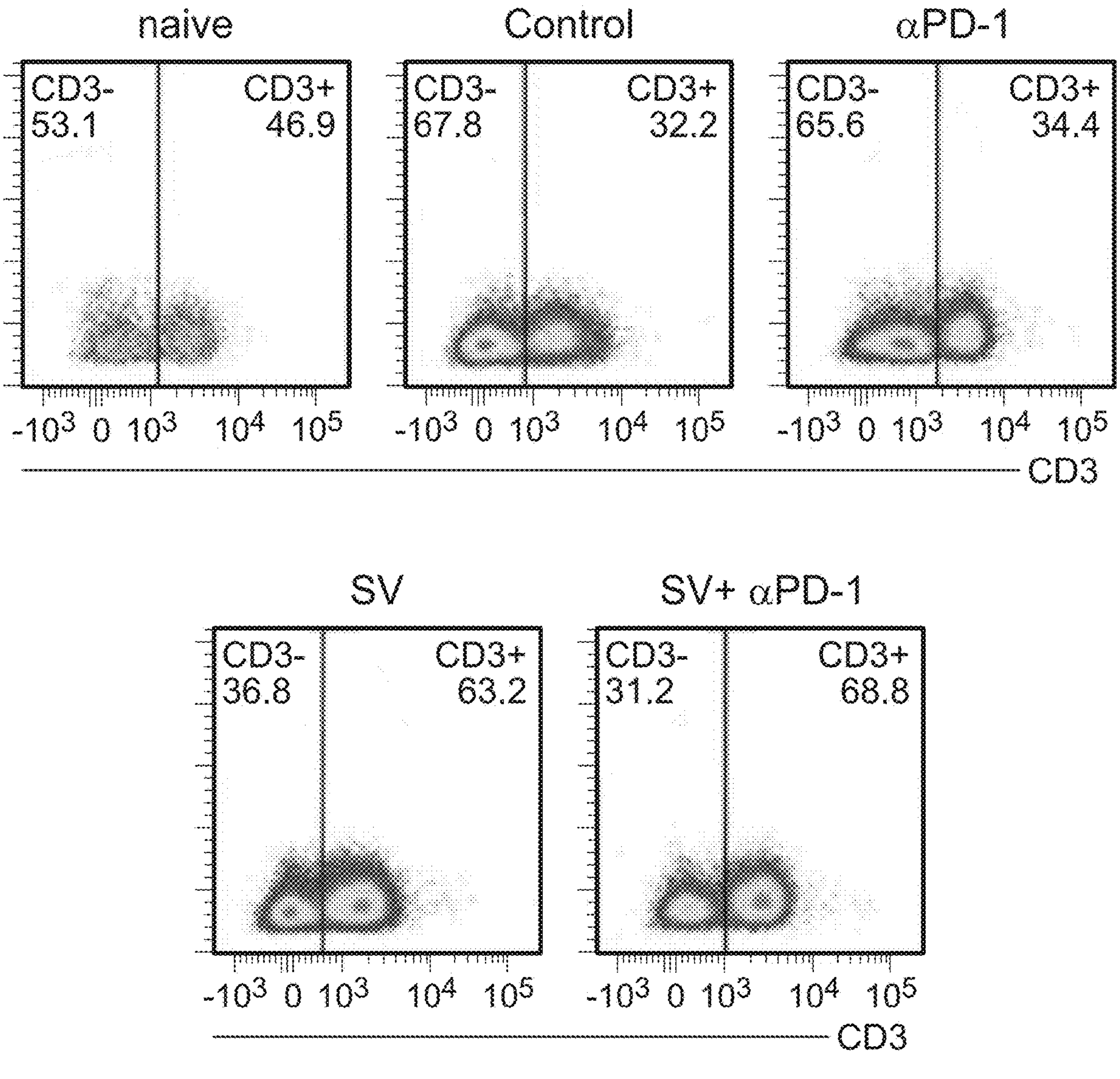
Figure 16A:
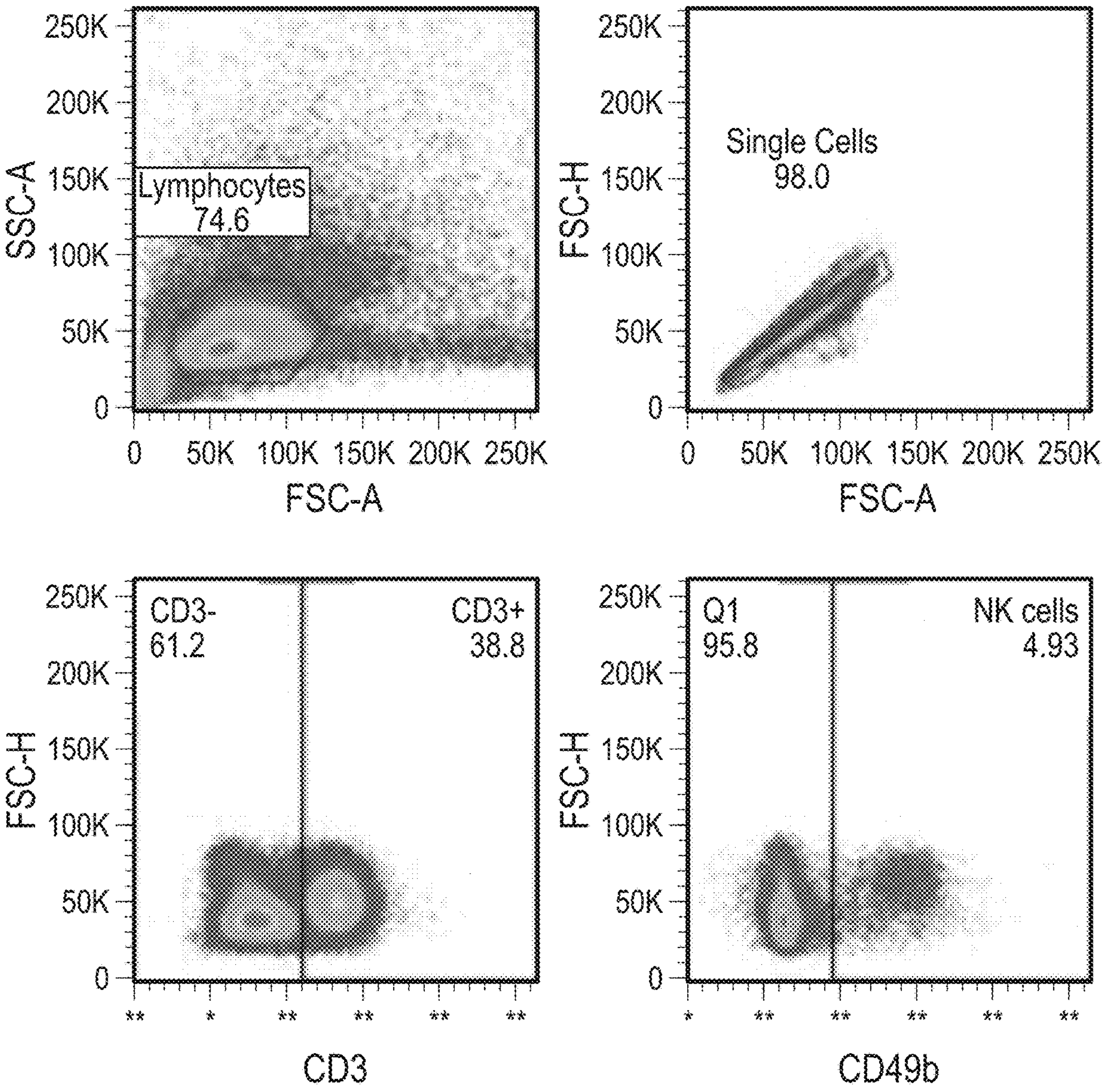
FIGS. 16A-16D present results demonstrating that the SV-NYESO1 vector induced an early and systemic activation of NK and B cells. CT26.FlucNYESO1 tumor cells were injected into BALB/c mice on day −4. One injection of anti-PD-1 antibody (250 μg) and/or the SV-NYESO1 vector was administered to the respective groups of animals on day 0 and 1, respectively. On day 2, mice were sacrificed and their organs were removed and prepared for flow cytometry analysis.
Figure 16B:
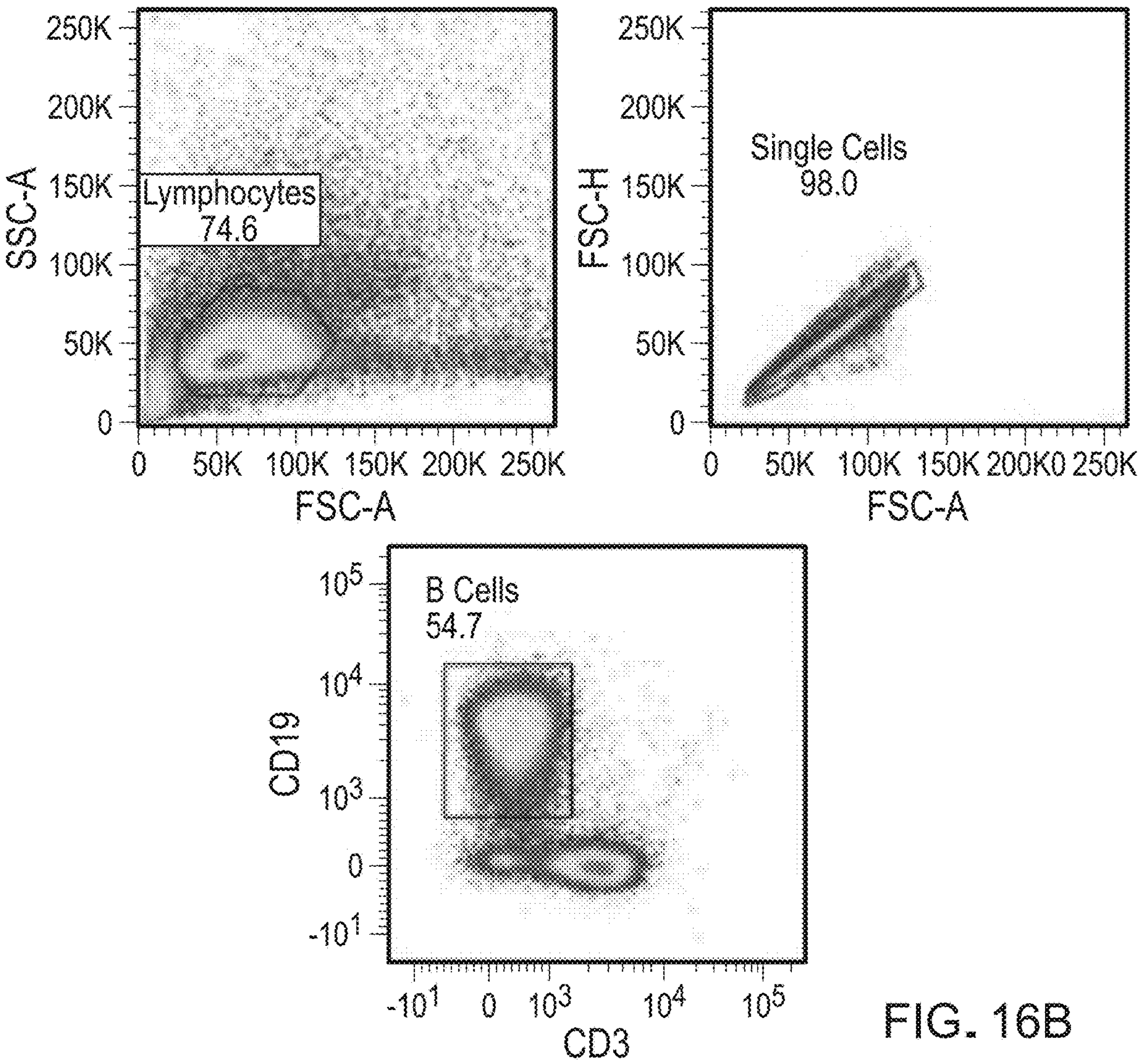
Figure 16C:
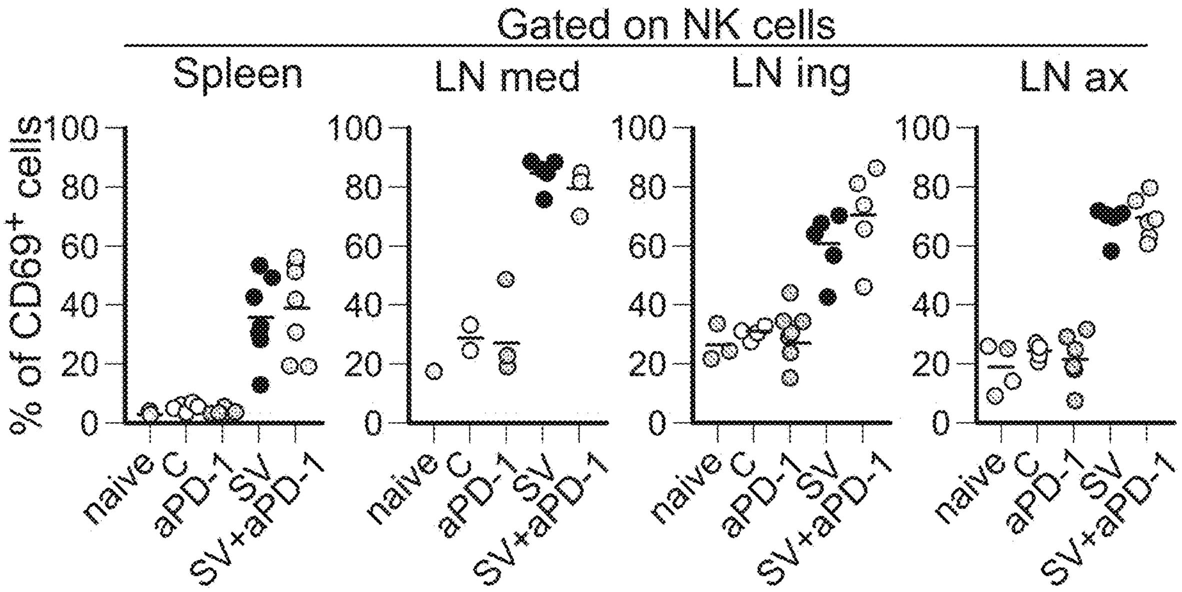
Figure 16D:
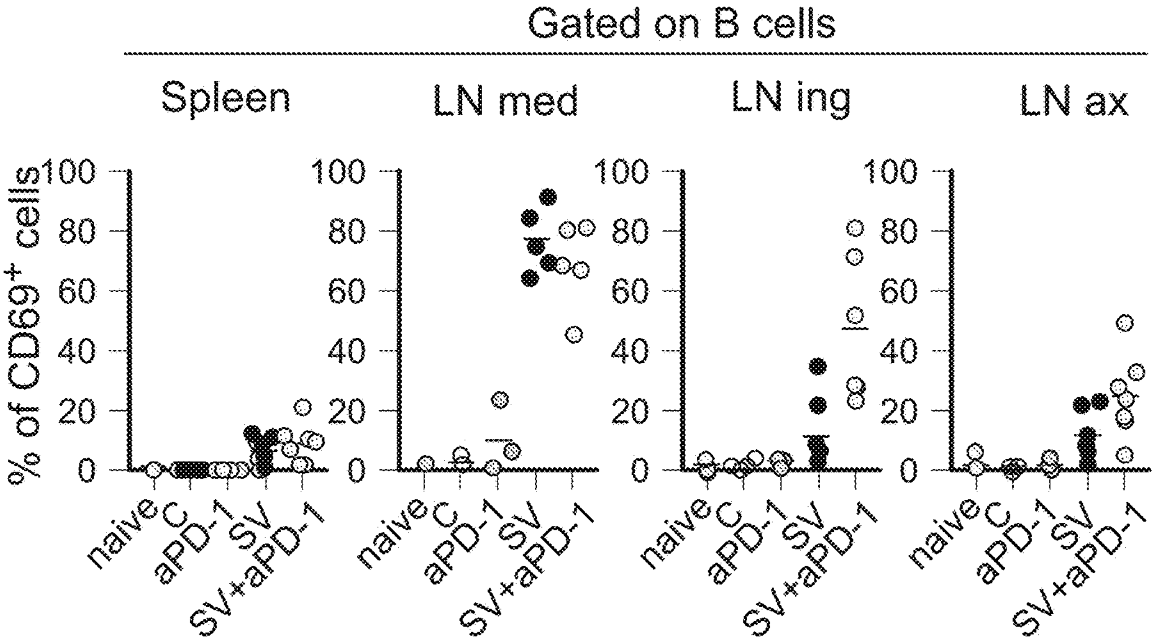

Interestingly, the strongest lymphocyte activation was detected in mediastinal LN. This finding is consistent with the inventors' studies demonstrating that SV rapidly localizes in the mediastinal LN after i.p. injection (T. Granot et al., 2014, *Mol Ther,* 22:112-122). In a similar manner, a strong infiltration of T cells in mediastinal LN was observed in mice treated with SV-NYESO1 with and without anti-PD-1 antibody (FIGS. 15H and 15I). These results demonstrate that replication-deficient SV-NYESO1 viral vector is a potent immunostimulatory agent, which quickly induces a systemic pro-inflammatory environment and lymphocyte activation in animals treated with the vector.

Figure 17A:
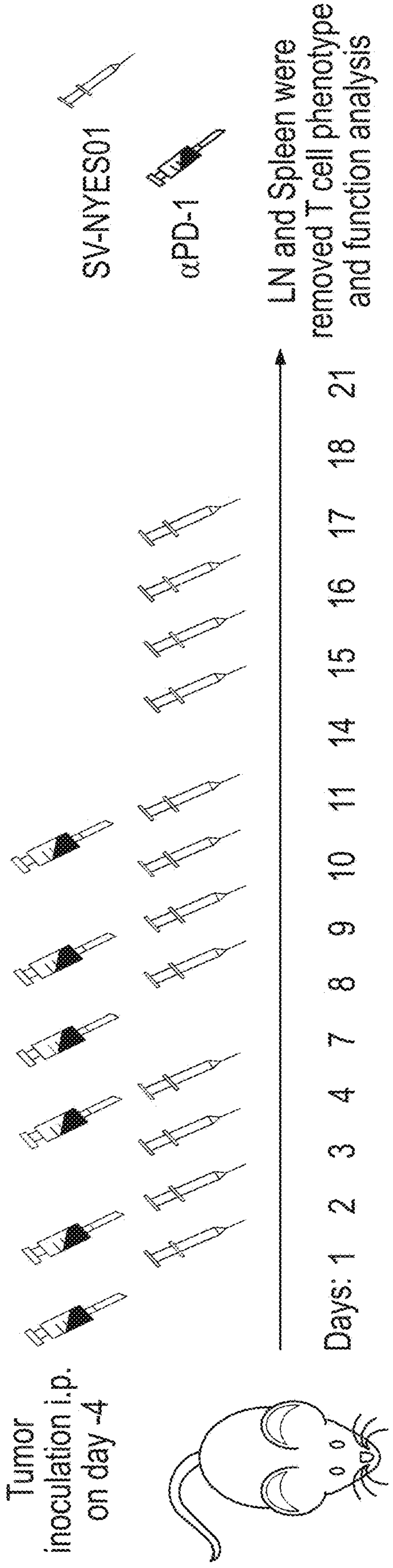
Figure 17B:
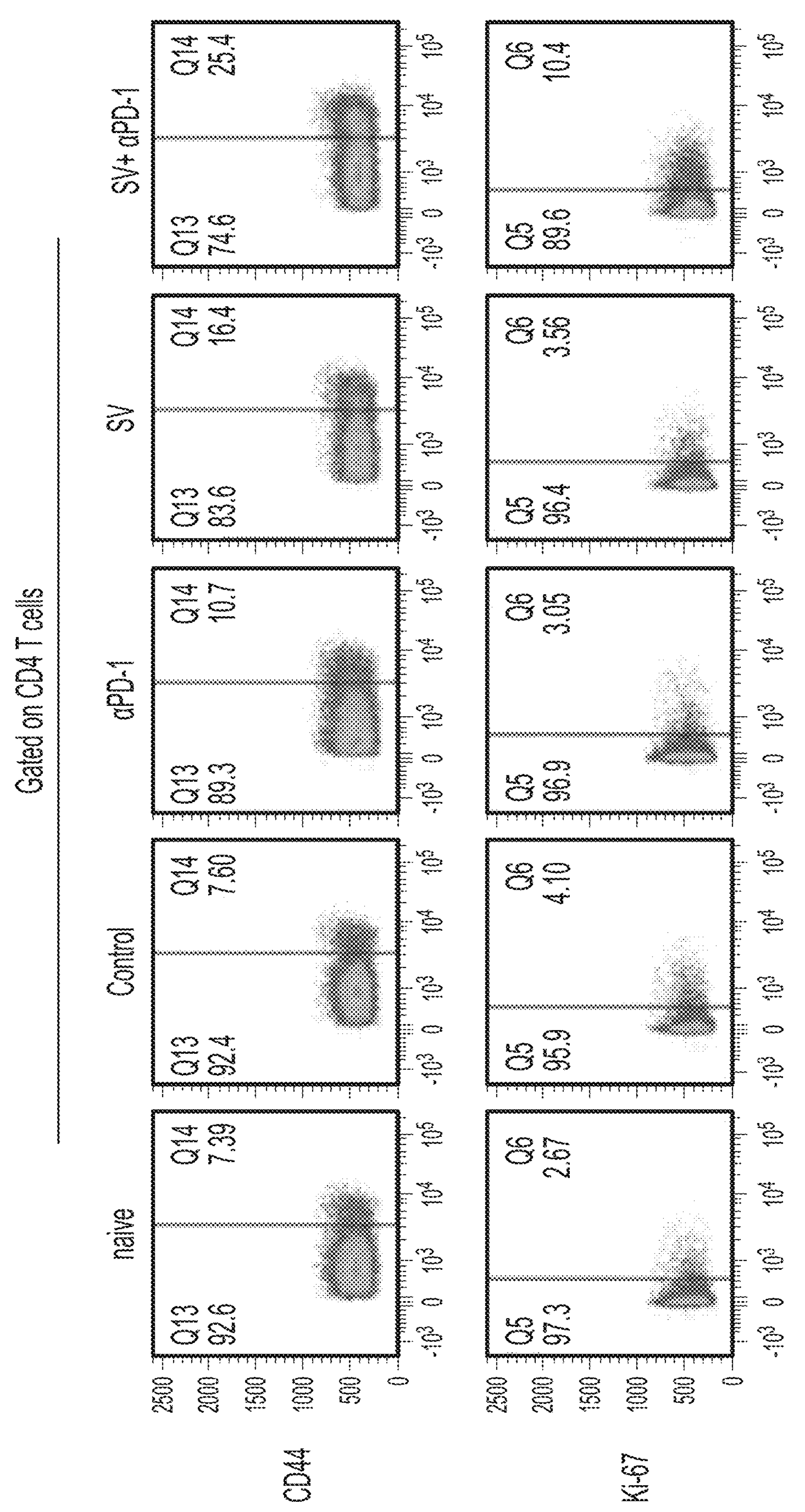
FIGS. 17B and 17C: Percentage of CD44 and Ki-67 expression by $CD4^+$ T cells (FIG. 171B) and CD8+ T cells (FIG. 17C) in naive mice as well as control and treated tumor-bearing mice using flow cytometry (n:=8 mice per group). Top graphs: Representative flow cytometry plots from day 14. Bottom graphs: Symbols summarizing data from two independent experiments. Statistical significance between groups treated with SV vector construct in the presence or absence of anti-PD-1 antibody was determined with the Mann-Whitney test.
Figure 17C:
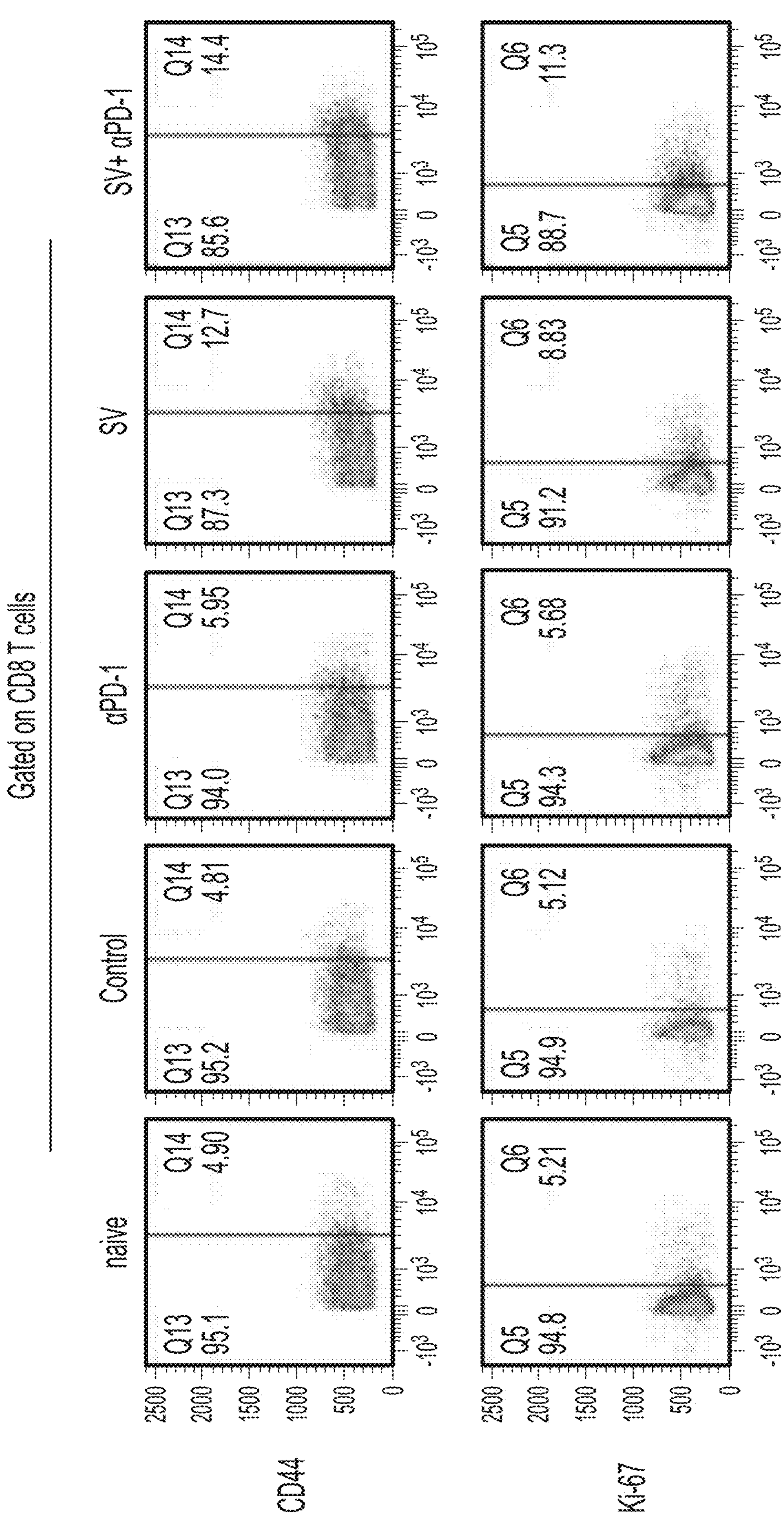
Figure 18A:
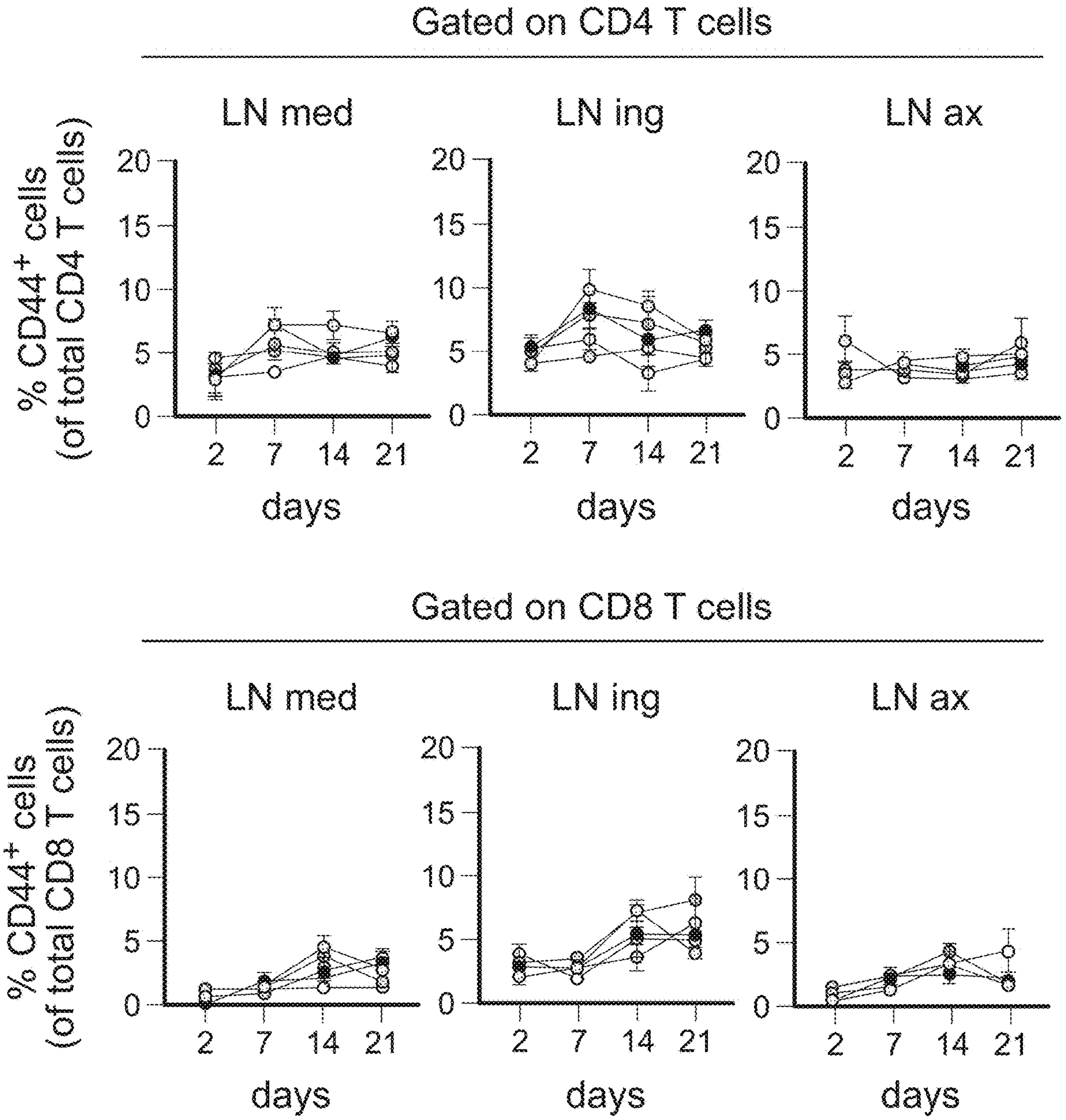
FIGS. 18A-18C demonstrate results showing T cell activation in peripheral lymphoid organs over the course of treatment of animals with the SV-NYESO1 vector in the presence or absence of anti-PD-1 antibody. Tumor bearing BALB/c mice were left untreated or were treated with SV vector with or without anti-PD-1 antibody. Mice were sacrificed on day 2, 7, 14 or 21 to analyze the T cell immune response in spleen and mediastinal (med), inguinal (ing) and axillary (ax) lymph nodes (LN).
Figure 18B:
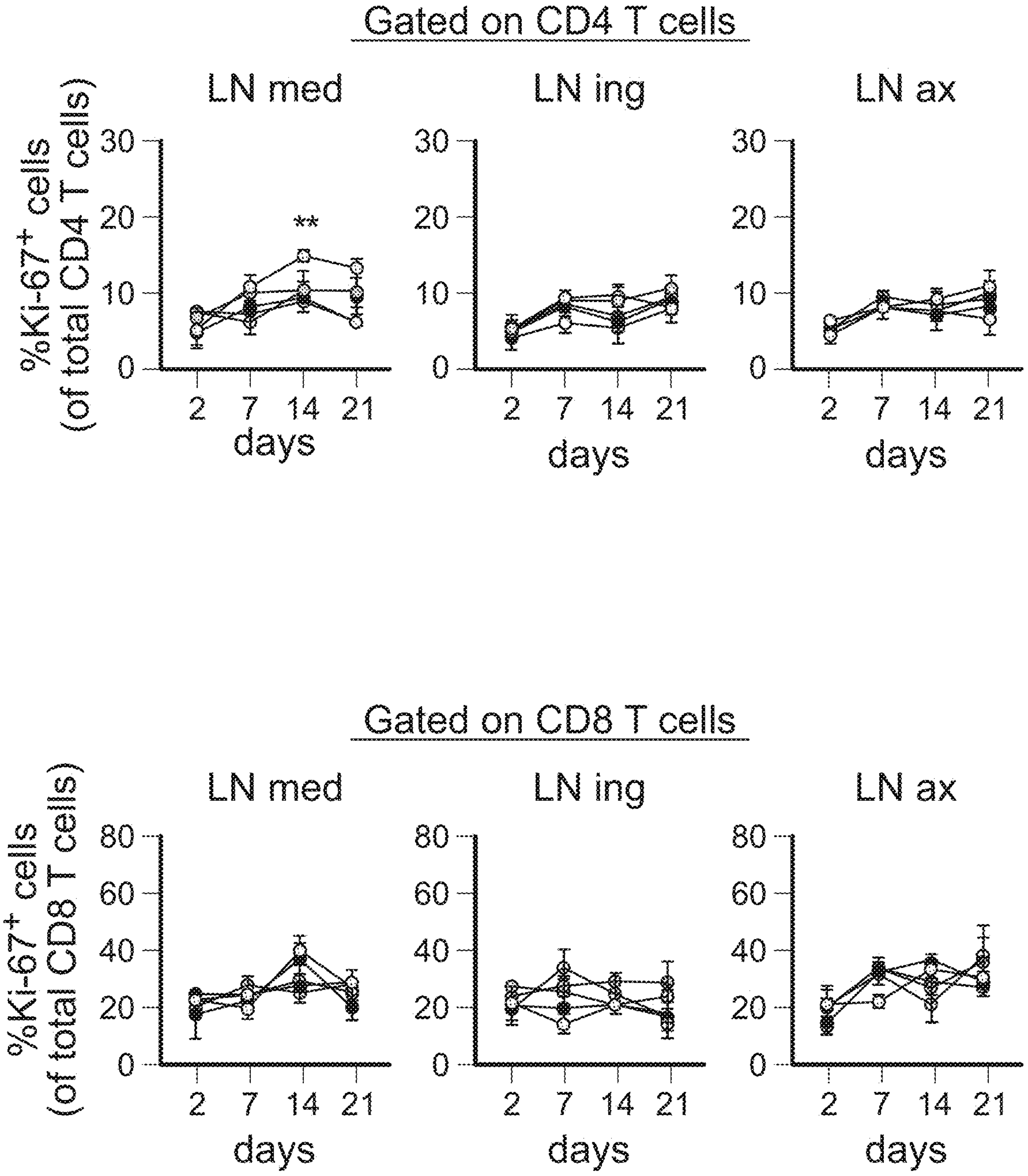

Combined Therapy Enhances T Cell Activation and Function Over the Course of Treatment To better understand the role of anti-PD-1 antibody in the combined therapy, T cell activation in peripheral lymphoid organs of treated mice was determined over a three-week period. After tumor inoculation (day −4), mice were treated with SV-NYESO1 four times a week (day 1, 2, 3 and 4) for a total of four weeks (FIG. 17A). Anti-PD-1 antibody was administered to the respective groups three times a week (day 0, 2 and 4) for a total of two weeks. Spleens and LNs were collected from mice on days 7, 14 and 21, and T cell activation was determined by assaying the expression of the activation and proliferation markers CD44 and Ki-67, respectively, on cells from these organs and tissues. The expression of CD44 and Ki-67 was substantially and continuously upregulated on splenic $CD4^+$ and $CD8^+$ T cells in animals treated with combined therapy compared with animals treated with SV-NYESO1 alone (FIGS. 17B and 17C). T cell activation was not observed in LNs, except for a slight increase in mediastinal LNs on day 14 (FIGS. 18A and 18B). In contrast to the results found in mice that had received treatment with SV-NYESO1, control mice and mice treated with anti-PD-1 antibody alone showed no significant differences in T cell activation when compared with naïve mice.

Figure 17D:
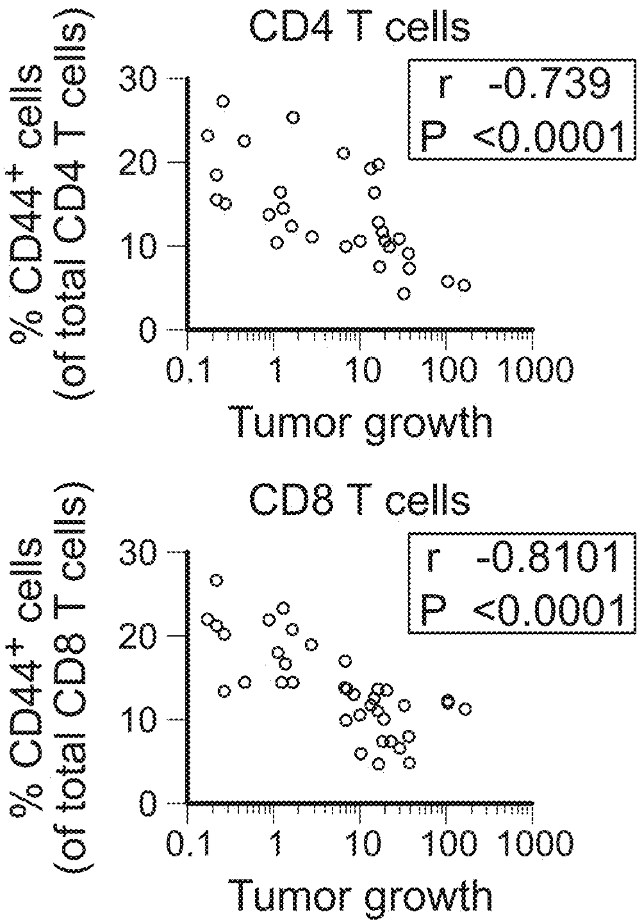
FIG. 17D: Correlation of splenic $CD4^+$ T cells' or $CD8^+$ T cells' CD44 expression against tumor growth on day 14 by the Spearman-rank correlation test.
Figure 17E:
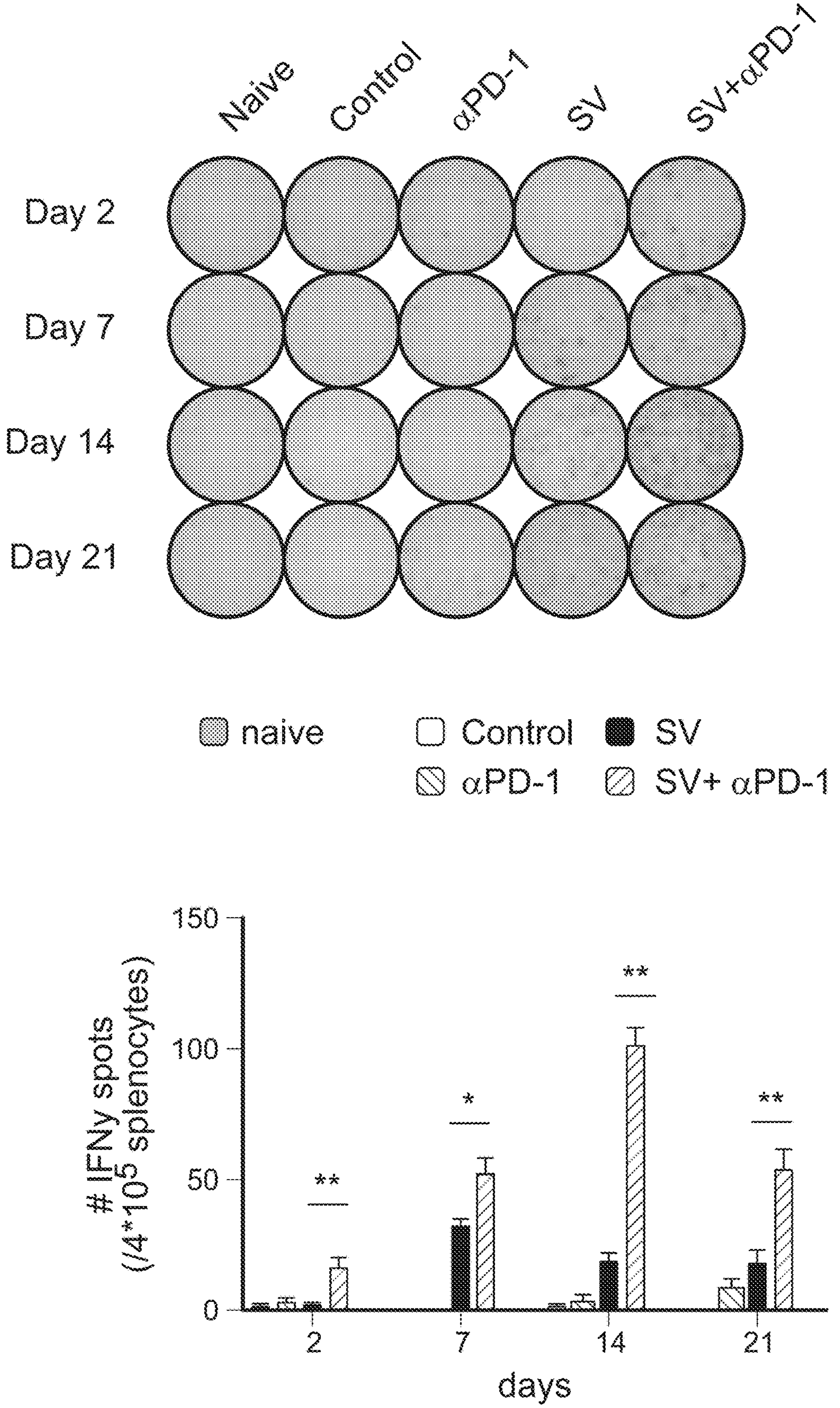
FIG. 17E: Interferon-γ (IFN-γ) enzyme-linked immunospot analysis of splenocytes harvested on day 14 from control and treated mice (n=8 mice per group).
Figure 18C:
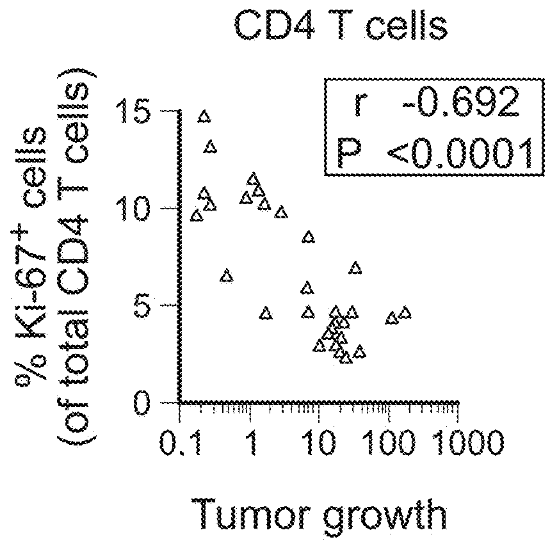

Furthermore, a highly significant negative correlation between splenic T cell activation, as assessed by CD44 and Ki-67 expression on splenic cells, and tumor growth was observed, suggesting that T cells have an important role in controlling tumor growth (FIG. 17D and FIG. 18C). In line with these results, ELISPOT analysis of IFN-7 production and secretion by splenocytes isolated from treated mice revealed that combined therapy accelerated and augmented IFN-7 secretion compared with treatment with SV-NYESO1 alone, with peak IFN-7 secretion occurring on day 14 (FIG. 17E). Splenocytes from mice treated with SV-NYESO1 alone produced a constant low level of IFN-7 over the course of treatment.

Figure 17F:
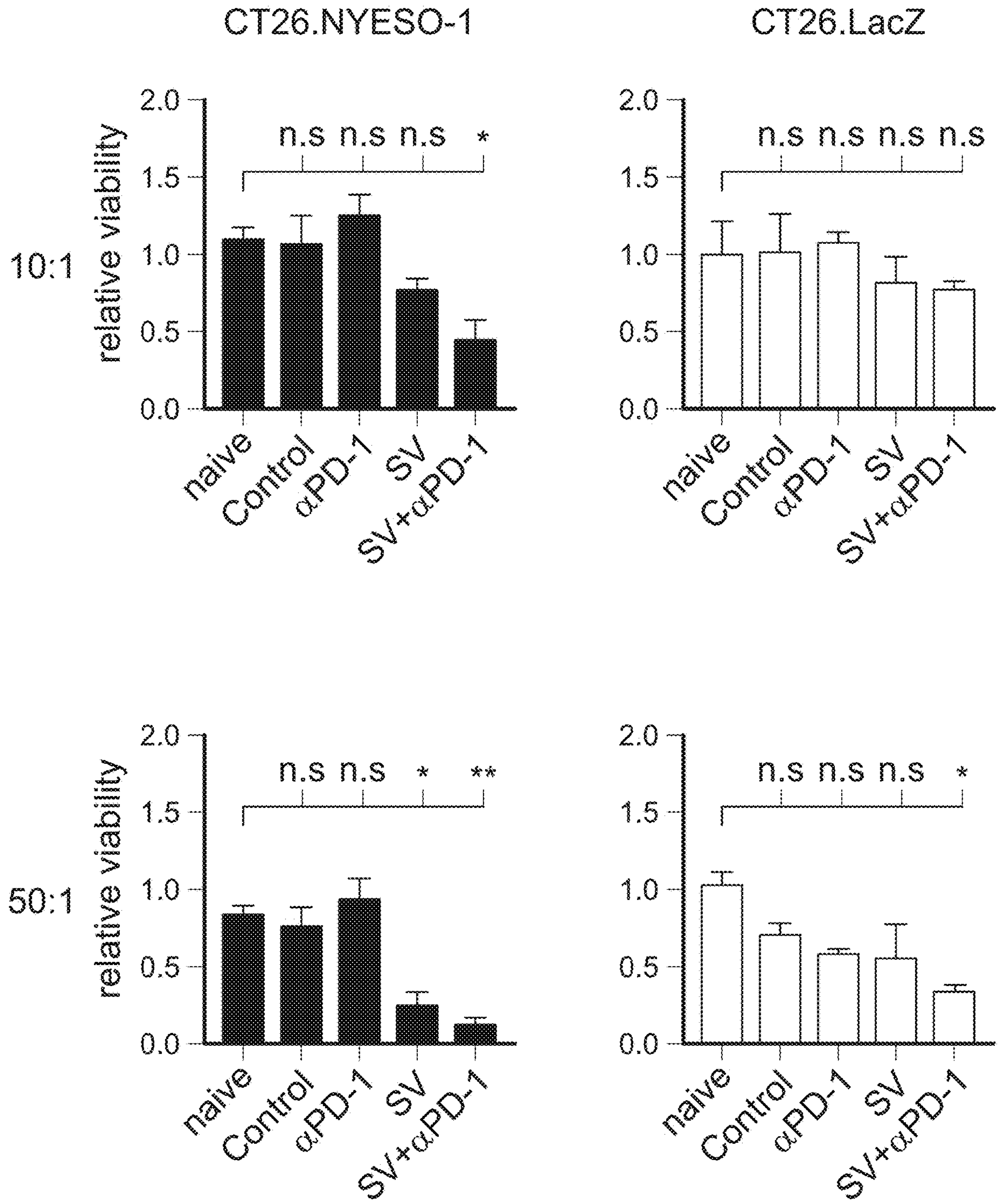

Because enhanced T cell activation and cytokine production were observed in mice treated with the combination therapy, the function of T cells was investigated using an ex vivo cytotoxic assay. Splenocytes obtained from mice in all treatment groups were co-cultured at various effector-to-target (E/T) cell ratios with the tumor cell line CT26.Fluc that expressed the TAA NYESO-1 (CT26.NYESO1) or that expressed an unrelated antigen, LacZ (CT26.LacZ) (FIG. 17F). The cytotoxic potential of splenocytes was determined by measuring the luciferase activity of the CT26 cells, which correlates with the tumor cell viability. Viability of CT26.NYESO1 was markedly reduced at both E/T ratios (10:1 and 50:1) when co-cultured with splenocytes from mice that had received combined therapy (SV-NSYEO-1 and anti-PD-1 antibody) compared with splenocytes from naïve, control mice and mice that had received anti-PD-1 antibody alone. The cytotoxic potential of splenocytes from mice treated with SV-NYESO1 alone was weaker than that of splenocytes from mice that had received the combined therapy. The results also indicated that cytotoxicity was TAA-dependent, as the viability of CT26 expressing LacZ remained stable across all groups. Only splenocytes from animals that had received the combined therapy showed some killing potential toward CT26.LacZ at an E/T ratio of 50:1, suggesting that SV-NYESO1 in combination with anti-PD-1 antibody may induce a broader immune response and favor epitope spreading.

Together, these results demonstrate that the combination of anti-PD-1 antibody administration and SV-NYESO1 administration enhances T cell activation over the course of treatment, which results in improved IFN-7 production and cytotoxic activity. In line with these results, a highly significant negative correlation between T cell activation and tumor growth was demonstrated, indicating a crucial role of activated T cells in controlling tumor growth. Thus, SV-NYESO1 acts as an initial stimulus to activate the immune response, such as an activated T cell response, in animals treated with SV-NYESO-1 and anti-PD-1 antibody. The presence of anti-PD-1 antibody keeps T cells activated and to further enhances T cell function.

Mice Treated with SV-NYESO1 in Combination with Anti-PD-1 Display Enhanced Intratumoral Immunity Not only does the SV-NYESO1 viral vector enter peripheral lymphoid organs and induce a systemic immune response, it can directly infect cancer cells and provide a local immune response in the tumor microenviroment, similar to the activity of other oncolytic viruses. However, it has been reported that CT26 cells are not infected by SV in vitro or in vivo, thus suggesting that the powerful therapeutic effect observed from combined therapy is not a direct result of tumor cell targeting. It was further investigated whether the treatment of animals with SV-NYESO1 in combination with treating the animals with anti-PD-1 antibody could alter the local tumor microenvironment and favor an intra-tumoral immunity.

Figure 19A:
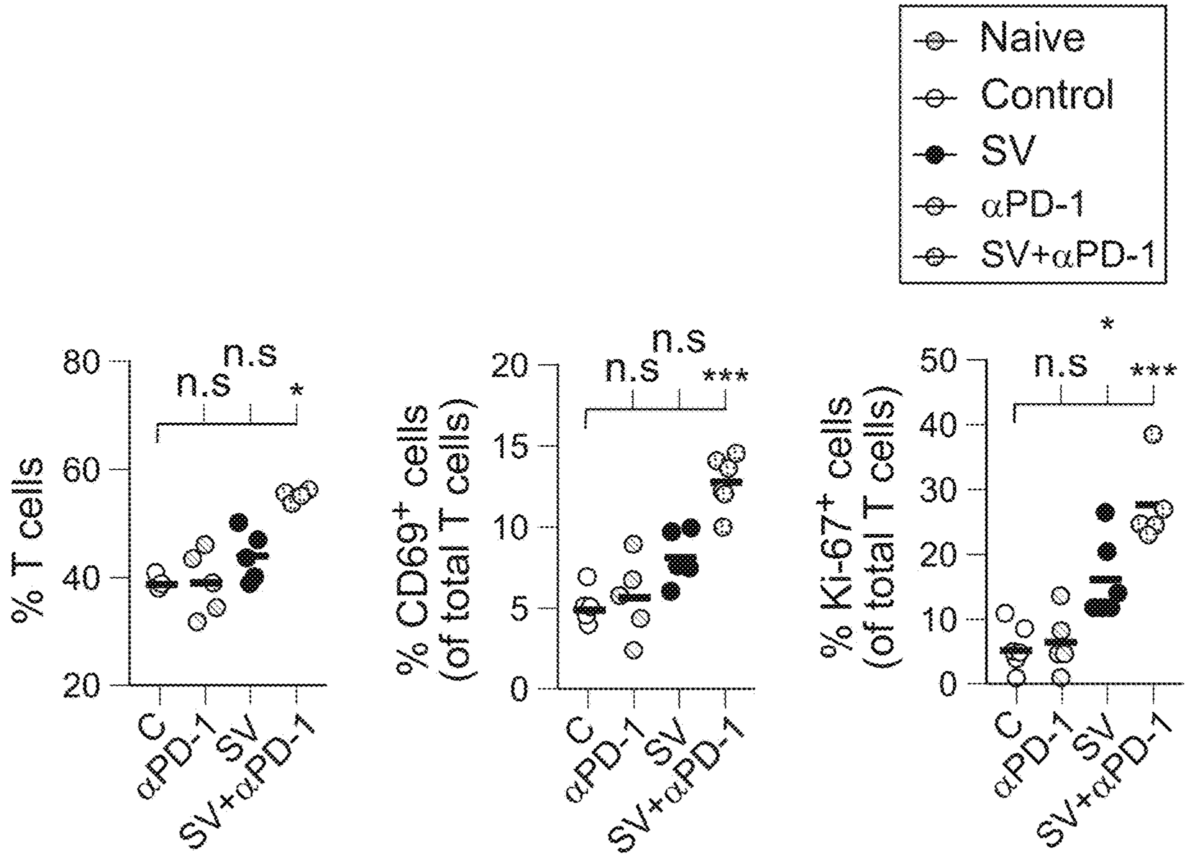
FIGS. 19A-19G present results of experiments showing that mice treated with SV-NYESO1 in combination with anti-PD-1 antibody displayed enhanced intratumoral T cell immunity. Tumors were harvested on day 14 and 21 from control and treated mice (n=5-8 mice per group).
Figure 19B:
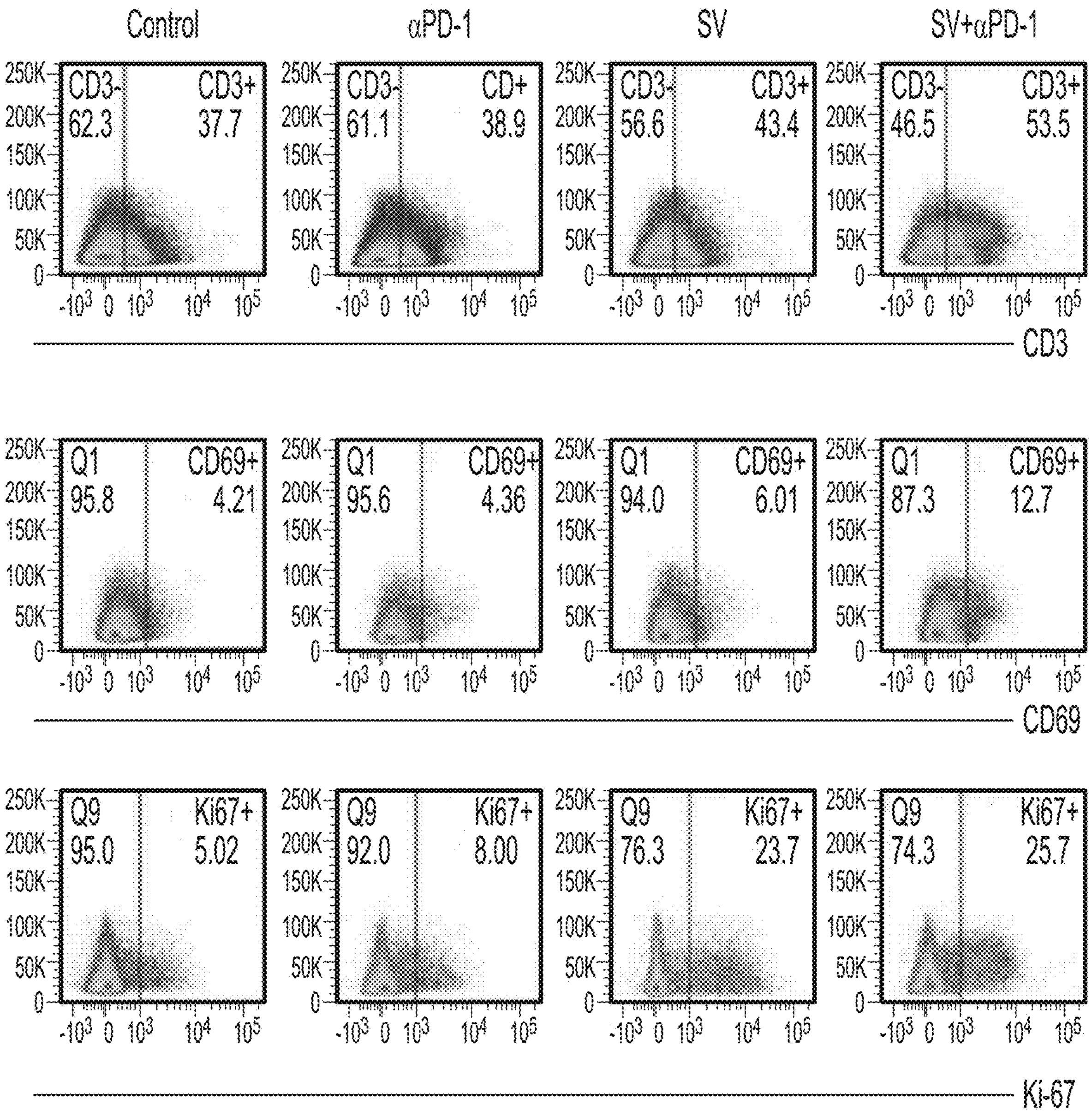
Figure 19C:
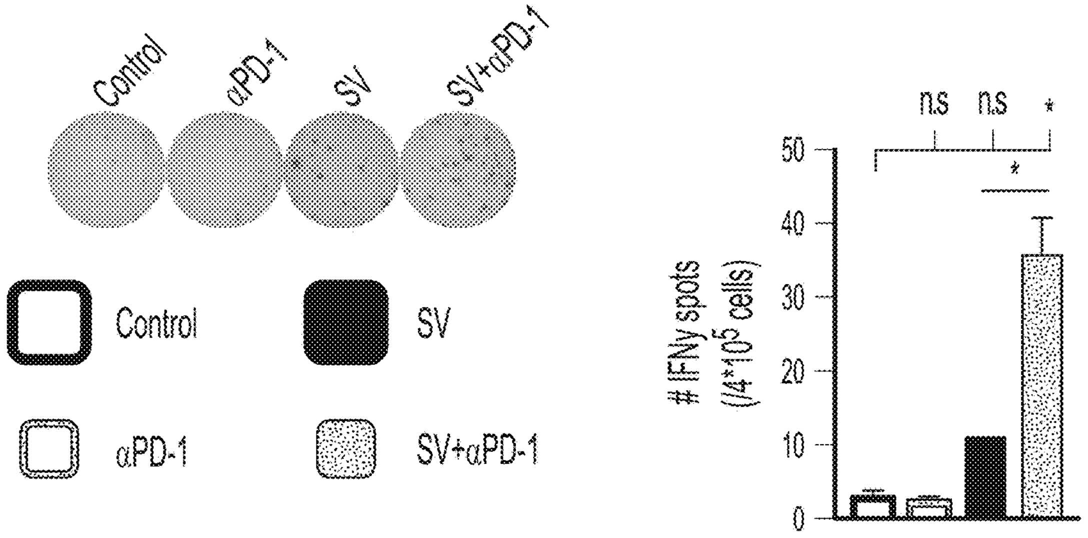

To assess the immune response in the tumor microenviroment, tumors were harvested from animals in all groups on day 14 and 21, and immune cells were analyzed by flow cytometry. A strong T cell infiltration was observed in animals treated with the combined therapy (FIGS. 19A and 19B). Furthermore, as assessed by CD69 and Ki-67 expression, T cell activation was markedly enhanced in mice treated with SV-NYESO1 and with anti-PD-1 antibody compared with naïve mice as well as control mice and mice treated with anti-PD-1 antibody alone. T cell activation was also observed in mice treated with SV-NYESO1 alone, although to a lesser extent. These results were supported by the IFN-7 production from tumor infiltrating cells as measured by ELISPOT (FIG. 19C).

Figure 19D:
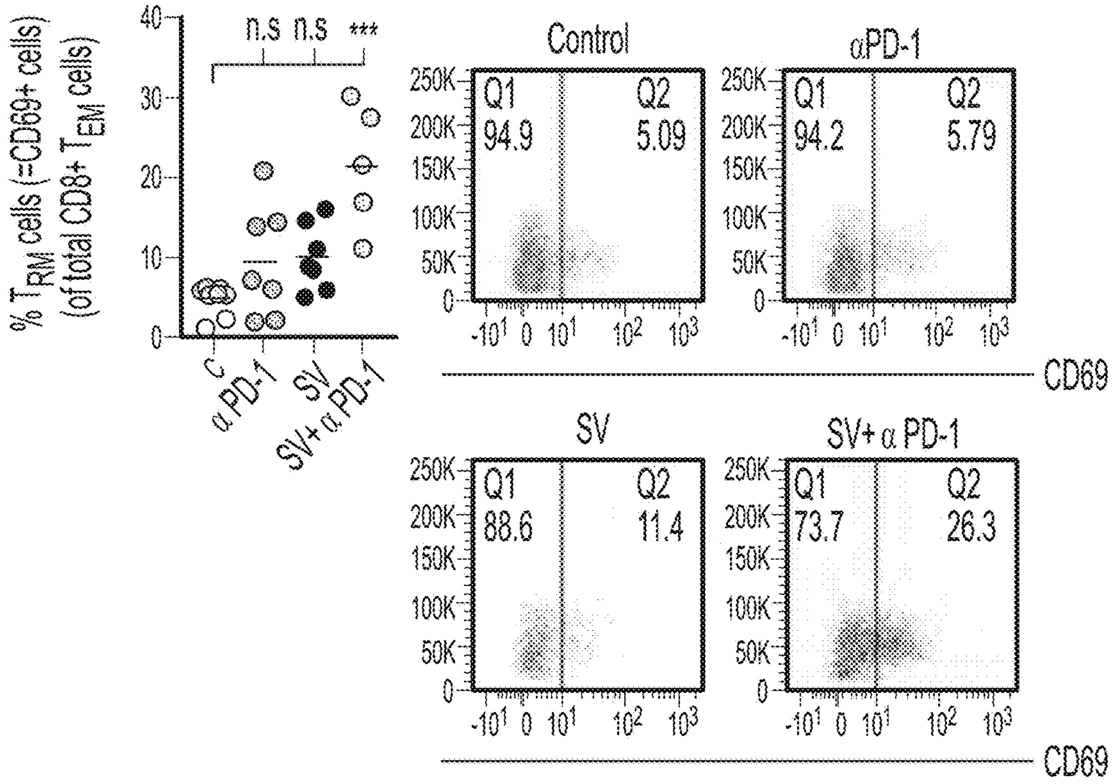
Figure 19E:
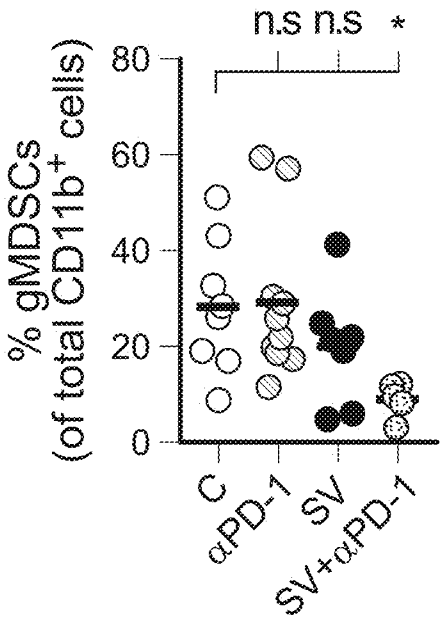
Figure 19F:
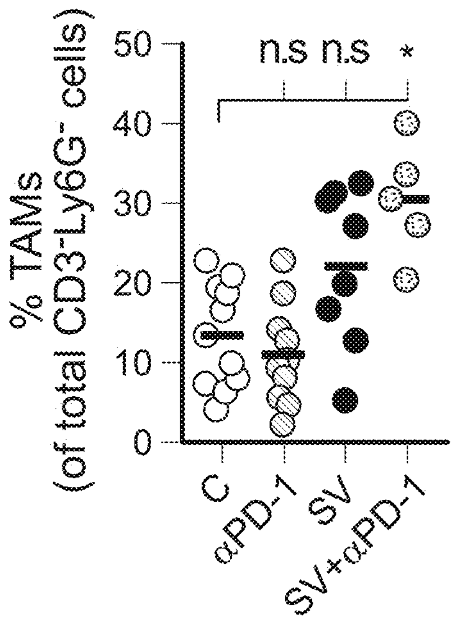
Figure 19G:
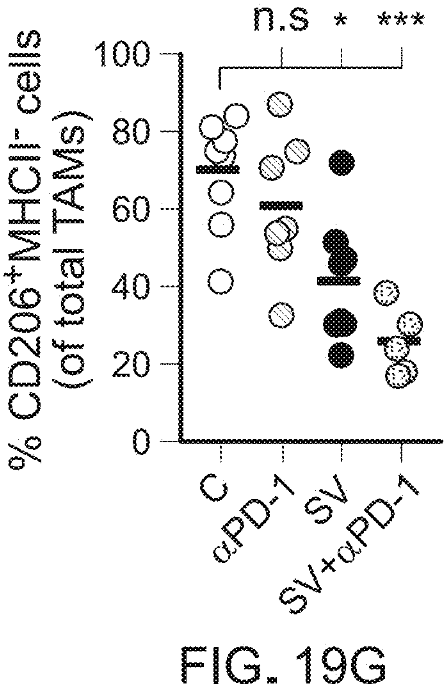
Figure 20A:
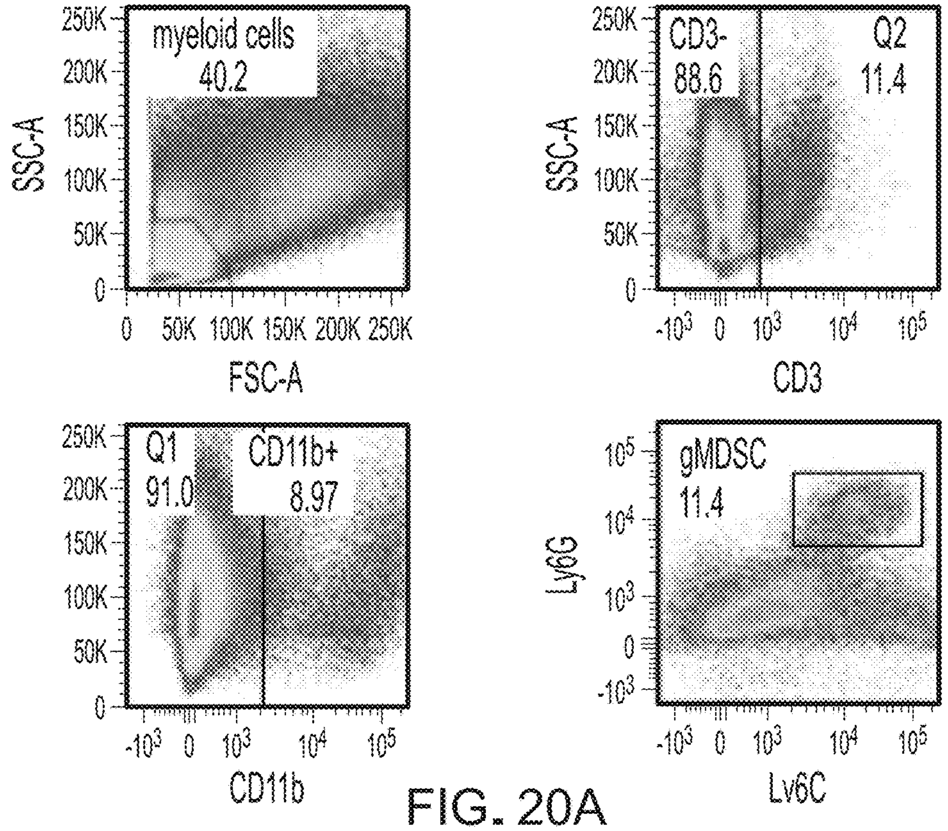
FIGS. 20A-20C present flow cytometry gating strategies for granulocytic-myeloid derived suppressor cell and tumor-associated macrophages in tumors.
Figure 20B:
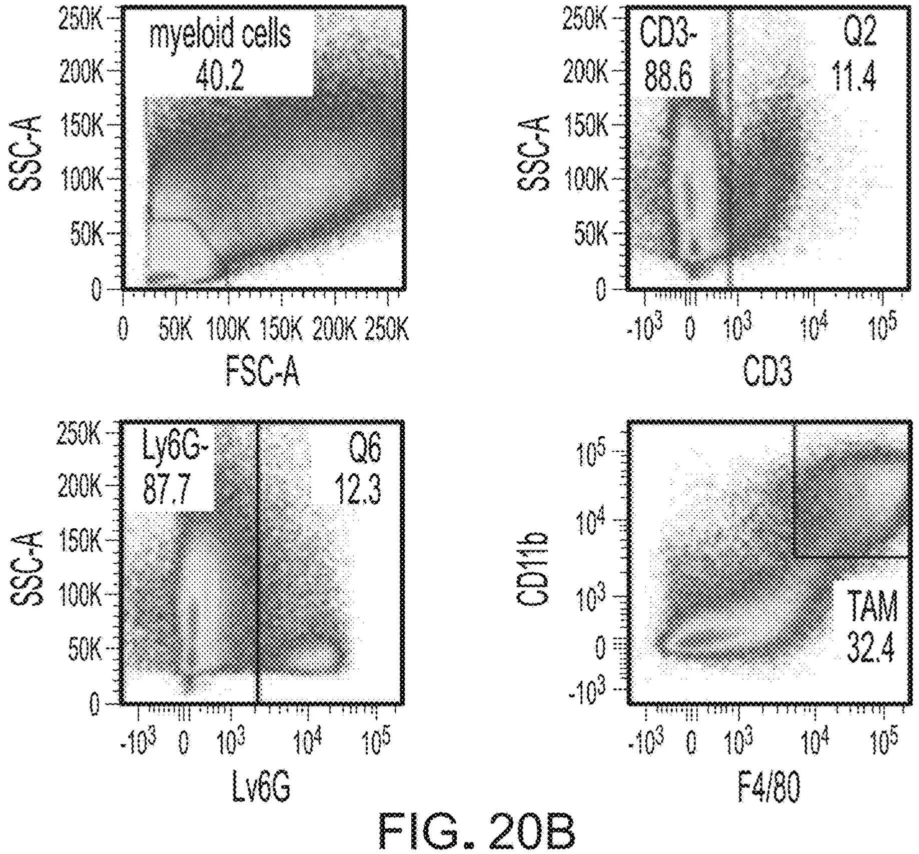
Figure 20C:
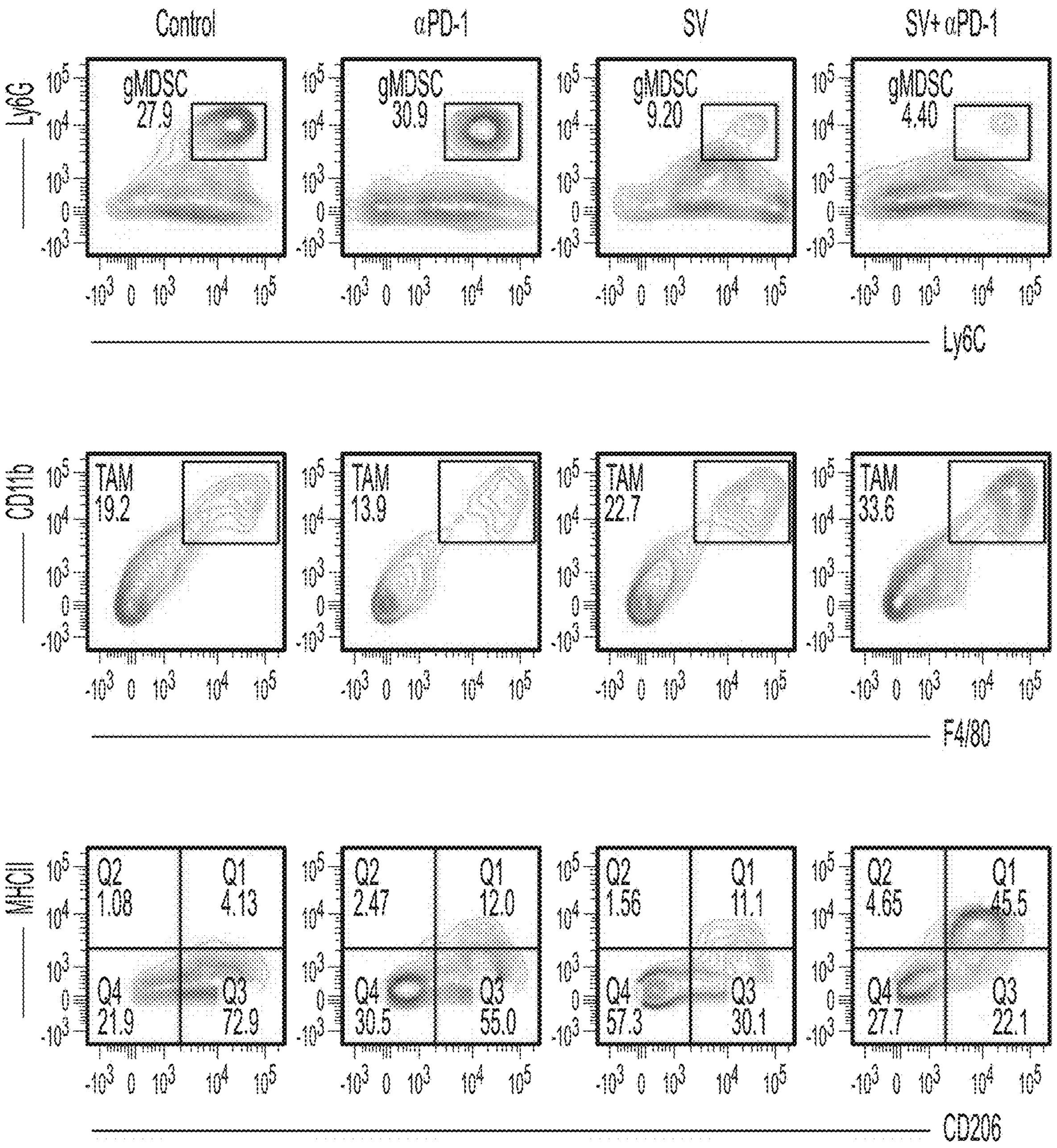

The presence of tissue-resident memory T cells ($T_{RM}$) in tumors has been linked with improved overall survival in both mice and humans. Consistent with this, a four-fold increase in $T_{RM}$ cells was detected in tumors from mice treated with the combined therapy compared with naïve mice (FIG. 19D). The overall increase in the intratumoral T cell response in mice treated with SV-NYESO1 and anti-PD-1 antibody, in combination, is also in accordance with a significant reduction of granulocytic myeloid-derived suppressor cells (gMDSC) and tumor-associated macrophages (TAMs) with a pro-tumor 'M2' state (FIGS. 19E and 19GC). Reduction of both cell types in tumors was also observed in mice treated with SV-NYESO1 alone, although to a lesser extent. Interestingly, an overall increase in TAMs was detected during SV-NYESO1 treatment (FIG. 19F and FIGS. 20A-C). This indicates an increase in inflammatory 'M1'-like TAMs in tumors; M1 TAMs have been correlated with a reduction in tumor growth and prolonged survival time in humans and mice.

Collectively, these findings revealed that treatment of animals with SV-NYESO1 produced a favorable intratumoral immune response in the treated animals, which were shown to have an increased number of activated T cells and an increased percentage of $T_{RM}$ cells, as well as more inflammatory M1 TAMs and fewer suppressor cells, such as gMDSC and M2 TAMs. The treatment of tumored animals with a combination of anti-PD-1 antibody and SV-NYESO1 strongly enhanced these trends and induced a better immune response within the tumor microenvironment.

Figure 21A:
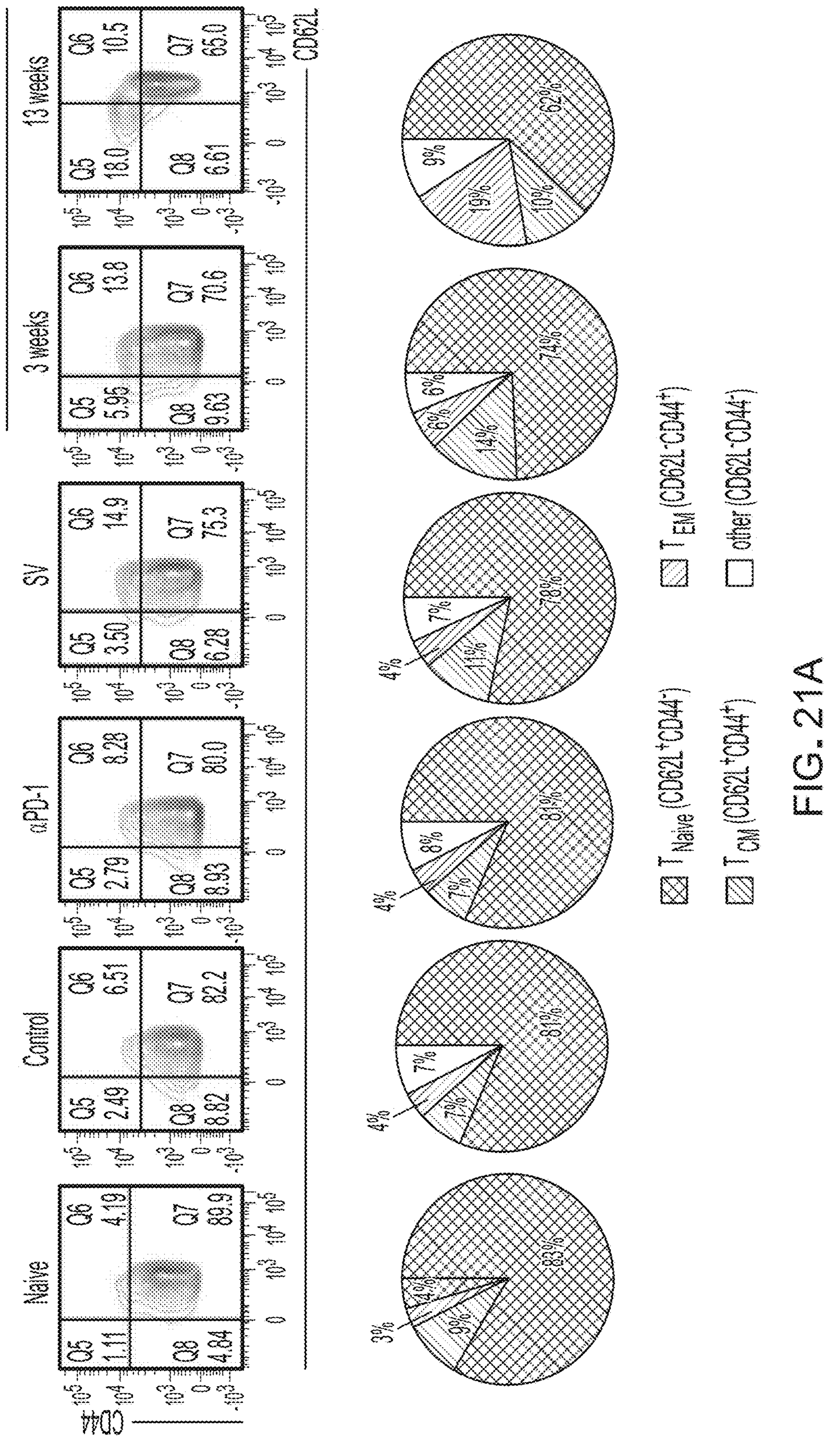
FIGS. 21A-21D present results of experiments showing that memory T cells were enriched in spleen and tumor of mice treated with SV-NYESO1 vector in combination with anti-PD-1 antibody, providing long term immunity against closely related tumors.
Figure 21B:
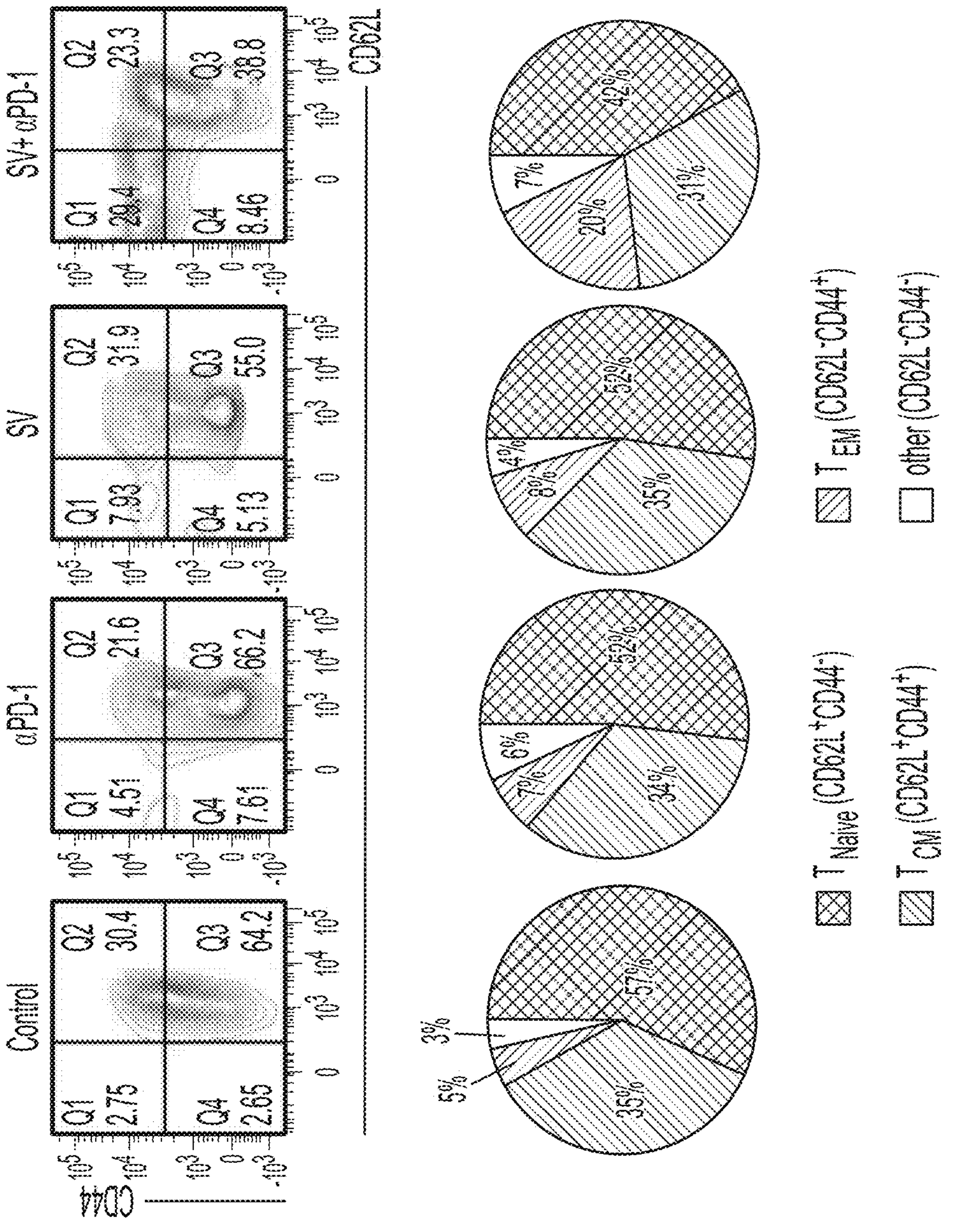

Combined Therapy Favors the Formation of Effector Memory T Cells, Providing Long-Term Immunity Against Recurrence An important goal of successful anti-tumoral immunity is the development of long-term protective immunity to prevent relapse metastases and recurrences in treated animals. To investigate whether SV-NYESO1 treatment induced memory T cell production, the phenotype of T cells in the spleens and tumors obtained from mice in all treatment groups was investigated by flow cytometry after three weeks of treatment (FIGS. 21A-21D). Splenocytes from untreated (control) mice and mice treated with anti-PD-1 antibody alone demonstrated percentages of central-memory ($T_{CM}$) and effector-memory ($T_{EM}$) T cells similar to those of splenocytes from naïve mice (percentages of 7% and 4%, respectively), (FIG. 21A). Treatment of mice with SV-NYESO1 alone, or with SV-NYESO-1 in combination with anti-PD-1 antibody, resulted in a slight enhancement of $T_{CM}$ (11% or 14%, respectively), but not of $T_{EM}$ (4% and 6%, respectively). After 3 months, surviving mice which had received the combined treatment therapy showed enhanced production of $T_{EM}$ (19%) with a similar percentage of $T_{CM}$ (10%). The same observations were made in tumors. Tumors in mice that had received the combination treatment showed induced 20% $T_{EM}$ compared with control, while mice treated with anti-PD-1 antibody alone or SV-NYESO1 alone showed 5%, 7% and 8% respectively (FIG. 21B). The percentage of $T_{CM}$ remained stable in all groups.

Figure 21C:
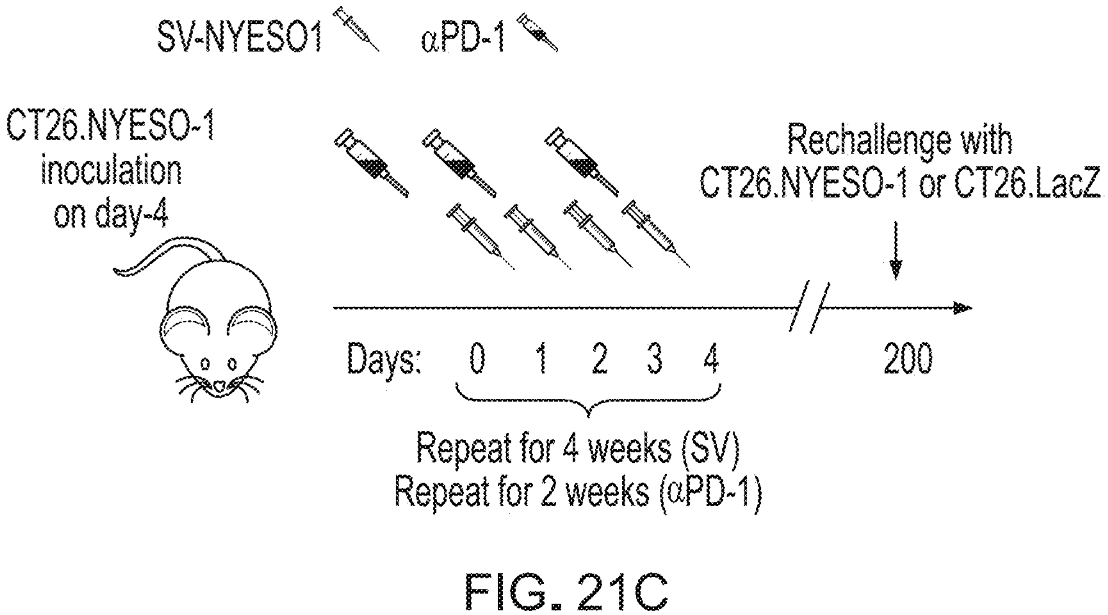
Figure 21D:
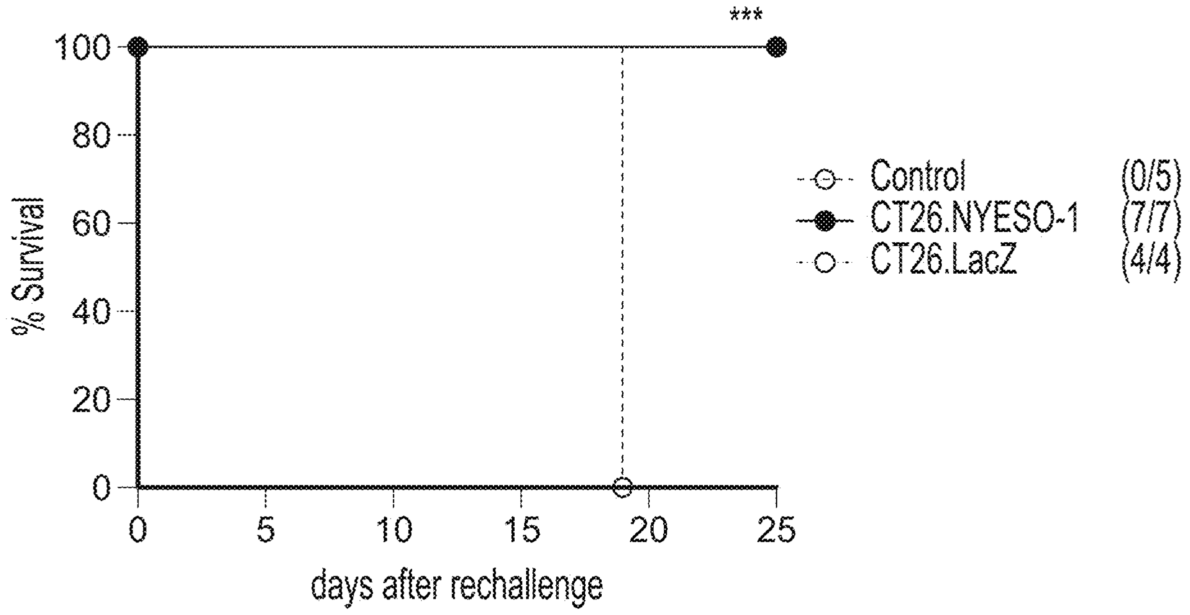
Figure 22A:
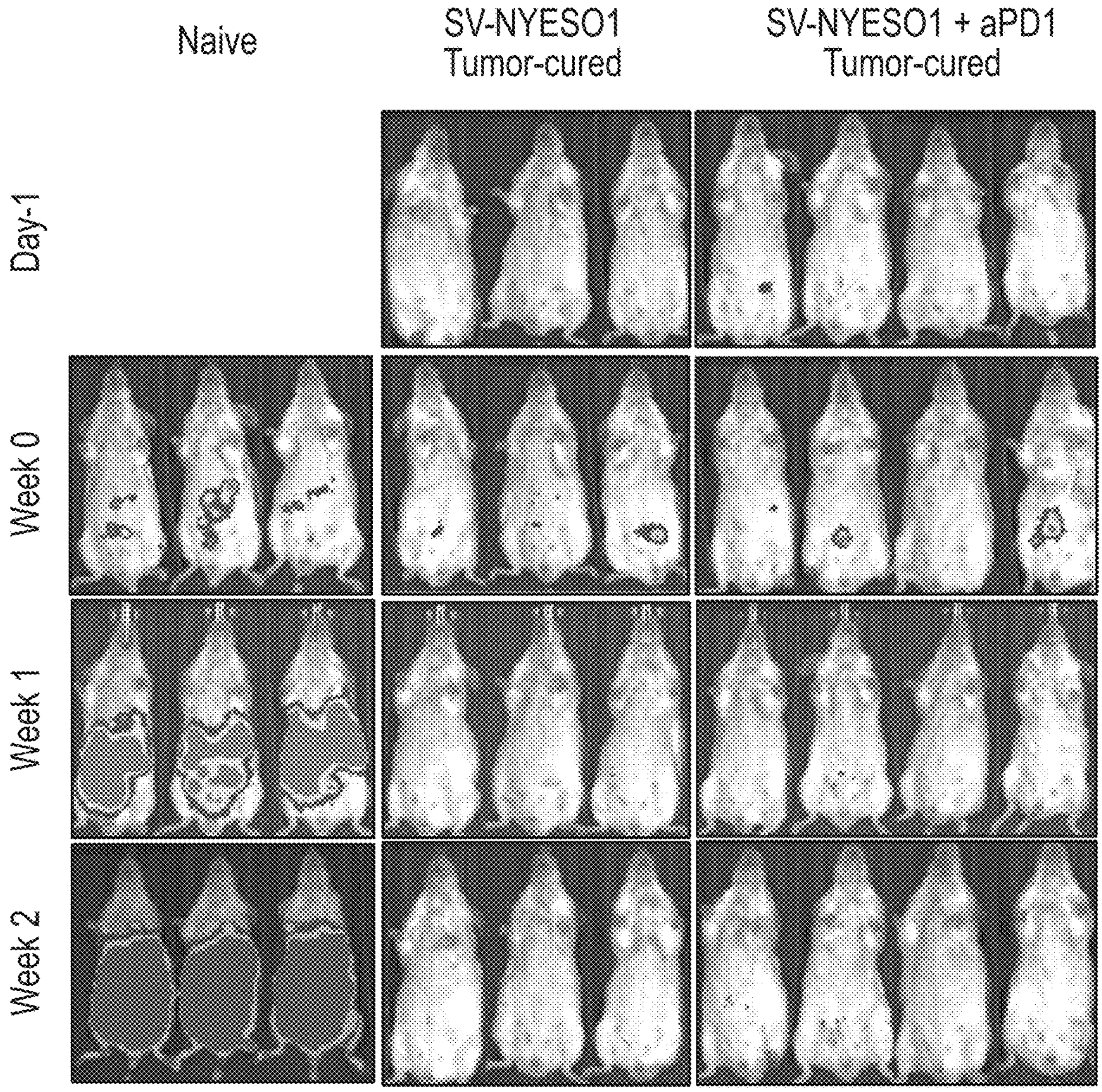
FIGS. 22A and 22B present results showing whole body bioluminescent images of rechallenged tumor-cured mice. Tumor cured mice (n=7) were injected i.p. with $7\times10^4$ CT26.Fluc.NYESO1 cells (FIG. 22A) or with $5\times10^4$ CT26.Fluc.LacZ cells (FIG. 22B), n=4, at 200 days after treatment with SV-NYESO1 vector or with SV-NYESO1 vector in combination with anti-PD-1 antibody. Bioluminescence was recorded one day before re-challenge for tumor cured mice as background signal control; one day after cell inoculation (Week 0) and then weekly. The scale used to prepare FIGS. 22A and B is shown in FIG. 22B.
Figure 22B:
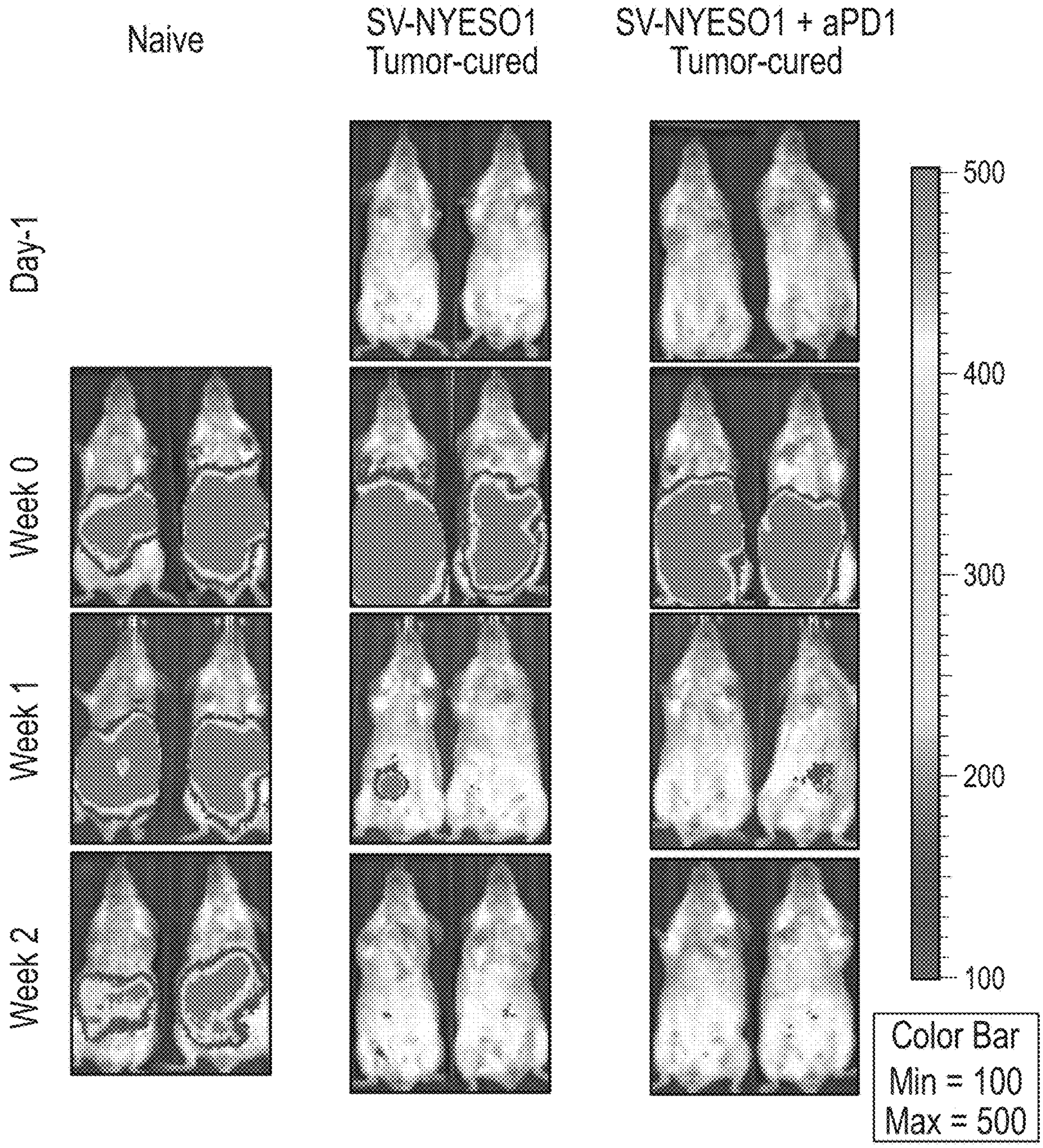

To test whether enhanced T cell memory formation correlated with long-lived protection against the same cancers, mice were re-challenged with tumors after 200 days using CT26.Fluc.NYESO1 (FIGS. 21C and 21D; FIGS. 22A and 22B). As epitope spreading was previously observed to occur during SV treatment, mice were rechallenged with a closely-related tumor that lacked NYESO-1, CT26.Fluc.LacZ. Indeed, mice cured by the combination treatment were immune to rechallenge with the same tumor, as well as with the closely related tumor. These results demonstrate that SV-NYESO1 administered in combination with anti-PD-1 antibody enhanced the formation of $T_{EM}$ immune cells in the spleen and tumor, which provided long-term immunity against the same tumor.

Study Conclusions

The results presented in this Example demonstrated a potent therapeutic effect of treatment with SV NYESO-1 (an SV vector expressing the TAANYESO-1) in combination with anti-PD-1 antibody in tumor bearing mice whose tumors expressed the NYESO-1 TAA. The results also demonstrated a systemic lymphocyte activation and induction of pro-inflammatory cytokines/chemokines after a single SV-NYESO1 injection. In a model system in which anti-PD-1 antibody induces a moderate therapeutic effect, the introduction of SV vector leads to a curative result, as well as protection against tumor relapses. Anti-PD-1 antibody contributes to SV therapy by enhancing T cell activation, as assessed by IFN-7 production and cytotoxic activity, in spleen and tumors during treatment. An inverse correlation observed between T cell activation and tumor growth supports the role of T cell responses in tumor treatment. These findings account for total tumor clearance in mice treated with SV-NYESO1 and anti-PD-1 antibody. Thus, SV-NYESO1 acts as an immunostimulatory agent that induces a strong systemic inflammatory response while anti-PD-1 antibody improves the magnitude of the anti-tumor T cell response in spleen for increased reactivity against the tumor.

The results of the studies described herein indicate that the therapeutic efficacy of a tumor associated antigen (TAA) expressed by SV, for example, the cancer testis antigen NYESO-1, may also depend on the nature of the animal tumor model and the antigen(s) expressed by the tumor cells. By way of example, an SV vector containing and expressing LacZ (SV-LacZ) was unable to cure mice bearing CT26.NYESO1 tumors. These observations indicate that the TAA expressed by the SV vector plays a crucial role for initiating an adequate anti-tumor immune response in an animal receiving the SV-TAA vector. Subsequent to the administration of the SV-TAA, such as SV-NYESO-1 in a tumored animal, a diversified T cell response develops that contributes to long-term protection.

Treatment with anti-PD-1 or anti-PD-L1 antibodies results in long lasting antitumor responses in patients with various cancers (P. Sharma et al., 2015, *Cell,* 161:205-214; J. Larkin et al., 2015, *NEngl J Med,* 373:23-34; E. B. Garon et al., 2015, *NEngl J Med,* 372:2018-2028; R. J. Motzer et al., 2015, *J Clin Oncol,* 33:1430-1437). It was observed that patients who did not respond to treatment with these antibodies were more likely to lack $CD8^+$ T cells inside tumors (P. C. Tumeh et al., 2014, *Nature,* 515:568-571; R. S. Herbst et al., 2014, *Nature,* 515:563-567); if no $CD8^+$ T cells were present that could be inhibited by the PD-1/PD-L1 interaction, then PD-1 blockade therapy was unlikely to work as well (A. Ribas, 2015, *Cancer Discov,* 5:915-919; S. Spranger et al., 2013, *Sci TranslMed,* 5:200rai16; D. M. Pardoll, 2012, *Nat Rev Cancer,* 12:252-264). Another reason that patients may not respond to PD-1 blockade therapy is the low expression of PD-L1 and PD-1 on tumor cells and tumor infiltrating T cells, respectively. PD-L1 expression on tumor cells is induced by IFN-γ, a mechanism that appears to have evolved to evade destruction by the immune system.

In the experiments described in this Example, it was demonstrated that SV-NYESO1 therapy increases T cell infiltration in tumors as well as enhances IFN-γ production by tumor infiltrating lymphocytes. In addition, SV-NYESO1 induces PD-L1 and PD-1 expression on tumor cells and on tumor infiltrating T cells, respectively. Thus, the experiments described herein were designed to study the potential for enhancement of antitumor immune responses initiated by SV infection when combined with immune checkpoint therapy, e.g., treatment with immune checkpoint inhibitors, such as anti-PD-1 antibody. Indeed, the results obtained showed that T cell response in the spleen and tumors was strongly enhanced in presence of the immune checkpoint blockade anti-PD-1 antibody.

This Example further showed that SV-NYESO1 vector treatment in tumored animals led to long-term protection against recurrences of closely related tumors, as demonstrated by rechallenging tumor cured mice after 200 days. This observation is consistent with the finding of enhanced formation of $T_{EM}$ cells in the spleen after treatment. Increased frequency of $T_{EM}$ and $T_{RM}$ cells was also observed in tumors during combination treatment with SV-NYESO-1 and anti-PD-1 antibody. $T_{RM}$ cells are characterized by stable surface expression of CD69 and an enhanced effector ability that functionally provides a tissue-wide alert state against local reinfection. These results are in accordance with previous studies in humans and mice showing a correlation between tumor infiltration of T cells with a $T_{RM}$ cell like phenotype and improved overall survival (B. T. Malik et al., 2017, *Sci Immunol,* 2(10); J. R. Webb et al., 2014, *Clin Cancer Res,* 20:434-444; F. Djenidi et al., 2015, *J Immunol,* 194:3475-3486; J. Y Kho et al., 2017, *Hand* (NY), 12:246-251; M. Enamorado et al., 2017, *Nat Commun,* 8:6073). In murine studies, the presence of $T_{RM}$ cells was also shown to improve the anti-tumor response and provide long-term immunity to cancer. Furthermore, anti-PD-1 antibody treatment promoted the infiltration of $T_{CM}$ cells, which can differentiate into $T_{RM}$ cells following viral infection. Therefore, the combination of a SV-TAA vector and anti-PD-1 is needed for increased $T_{RM}$ presence in tumors.

In general, most oncolytic viruses are administrated intratumorally, which limits the possibility of cancer treatment to easily accessible cancers and tumors, such as melanoma. The studies presented in this Example showed that i.p. injections of SV-NYESO1 vector induced an intratumoral immune response and changed the tumor microenvironment by promoting T cell recruitment and activation, as well as deflection of M2 to M1 macrophages in tumors. In the tumor model described in this Example, the SV-NYESO-1 vector did not directly infect tumor cells, thus indicating that the therapeutic treatment effect (tumor reduction) observed in animals bearing tumors was not a direct result of tumor cell targeting. Rather, the SV-NYESO-1 vector quickly localizes in LNs and infects monocytes/macrophages; in the LNs, T cells are primed against the NYESO-1 TAA expressed by SV The recruitment of T cells to the mediastinal LN on day 2, as well as the increased T cell activation therein, compared with spleen and other LNs, indicate that the SV-NYESO-1 vector is inducing a T cell response in the mediastinal LN. The targeting of LNs, e.g., mediastinal LNs, by SV vectors (and other alphaviruses) is particularly advantageous, because TAAs harbored by the SV vectors used in treatment are directly delivered to LNs, thus providing more efficient and rapid T cell priming.

The treatment of tumored animals with the TAA-encoding SV vector (SV-NYESO-1) and checkpoint inhibitor (anti-PD-1) combination therapy described herein allows for a broad window of treatment success using SV. In the studies of this Example, the combination treatment can overcome a narrow window of opportunity for OV treatment often encountered when rapid tumor growth outstrips the generation of effective anti-tumor immune responses in tumored subjects. In studies involving the SV-NYESO1 vector as the OV combined with anti-PD-1 treatment, no reduced therapeutic efficacy was found when tumor growth was accelerated in control mice.

As observed from the results described herein, once animals completely cleared tumors after SV-NYESO1 vector treatment, the animals could withstand rechallenge of the originally seeded tumor without any additional treatment, indicating the both a therapeutic and a prophylactic effect was achieved using SV-NYESO1. After treatment with the SV vector encoding the NYESO1 TAA (SV-NYESO1 vector), tumor cured mice were also protected against a closely related tumor, called CT26.LacZ, which lacks the TAANYESO-1. Similar to these results, the results of experiments described herein showed that splenocytes from mice treated with the combined SV-NYESO1 and anti-PD-1 therapy exhibited cytotoxicity against not only CT26.NYESO1 cells but also against CT26.LacZ cells. These results suggest that an immune response to endogenous CT26 tumor antigens developed as a consequence of SV-NYESO1 therapy, a phenomenon known as epitope spreading. Due to the heterogeneity and genomic instability of the tumor cell population, the selective pressure of a treatment, based on the expression of a given TAA, can lead to tumor escape by loss or modification of the TAA used in the treatment. Thus, SV vector treatment and combined SV vector and anti-PD-1 antibody treatment offers a solution to this problem.

Because the majority of ovarian cancer patients are diagnosed at disease stage III or IV, the standard of care for these patients involves a combination of cytoreductive surgery and systemic platinum-based chemotherapy. However, in most cases, total cytoreductive surgery may not be technically or fully possible, and the majority of patients experience recurrence. Thus, there is an urgent need for new therapeutic approaches for the treatment of ovarian cancer. The use of SV-NYESO1 is attractive for this purpose for several reasons. One reason is that approximately 43% of ovarian cancers/tumors express the NYESO-1 TAA, and SVs have been shown, once they trigger an antigen specific T cell response, to subsequently induce a diversified T cell response that can recognize additional TAAs present in the tumor (T. Granot et al., 2014, *Mol Ther,* 22:112-122). One of the immunotherapeutic challenges in ovarian cancer treatment relates to the relatively low numbers of tumor-infiltrating lymphocytes (TILs) and cells that express PD-L1. The mutational burden or neoantigen levels in these tumors tend to also be low.

The studies described in this example demonstrate that treatment with a combination of SV-NYESO-1 and anti-PD-1 antibody has the potential to overcome the limitations of prior studies and are very effective in murine models of ovarian cancer. Furthermore, the fact that SV-NYESO1 treatment can be administrated intraperitoneally or intravenously rather than intratumorally is an additional advantage that facilitates eliciting a strong cellular immune response.

Example 9—Sindbis Virus Vector Encoding a Single Chain Anti-CTLA4 Binding Molecule Shows Anti-Tumor Efficacy In Vivo This Example describes studies conducted utilizing a Sindbis virus vector which contained a polynucleotide encoding a single chain binding molecule (antibody) that binds to cytotoxic T lymphocyte associated protein 4 (CTLA4), i.e., an anti-CTLA4 binding molecule, also termed a single chain antibody. CTLA4, also known as "cluster of differentiation 152," is a receptor protein expressed by T cells, which functions as an immune checkpoint protein and plays a role in downregulating the immune response. The single chain anti-CTLA4 antibody is a CTLA4 checkpoint protein inhibitor encoded by the Sindbis virus vector as described herein.

Materials and Methods

Cell Lines

Baby hamster kidney cells (BHK-21; ATTC CCL-10) were maintained in minimum essential α-modified medium (α-MEM) (Corning CellGro) supplemented to contain 5% fetal bovine serum (FCS, Gibco) and 100 mg/mL penicillin-streptomycin (Corning CellGro). BHKSINLuc2 cells (ATCC CRL12071) were cultured in a manner similar to that of BHK cells, and 400 μg/mL Geneticin was included in the culture medium.

The BALB/c colon carcinoma (CT26) cell line was obtained from the American Type Culture Collection (ATCC: CRL 2638). Firefly luciferase (Fluc)-expressing CT26 cells (CT26.Fluc) were generated by stable transfection of pGL4.20_Fluc plasmid that expresses luciferase from a SV40 promoter and has puromycin as a selection marker. The CT26 cell line expressing both Firefly luciferase and NYESO1 (CT26.Fluc.NYESO1) was generated by stably transfecting the CT26.Fluc cell line with the expression plasmid pReceiver-M02 (GeneCopoeia) that contains the polynucleotide encoding NYESO1 (NM_001327.1) under the control of the CMV promoter and that contains neomycin as a selection marker. The CT26.Fluc.NYESO1 cell line was maintained in Dulbecco's modified Eagles medium (DMEM) containing 4.5 g/L Glucose (Corning CellGro) supplemented with 10% FCS, 100 mg/mL penicillin-streptomycin, 7.5 μg/mL Puromycin and 800 μg/mL Geneticin. All cell lines were cultured at 37° C. and 5% $CO_2$.

pT7StuIR-antiCTLA4 Vector

The anti-CTLA4 binding molecule (anti-CTLA4) sequence was derived from the published sequence (Jin et al., 2013, *Cell Biochem Biophys,* 67:1067) and was optimized for expression in humans and mouse. The sequence was fused, minus the stop codon, to the human immunoglobulin kappa light chain variable region amino acids, 6-108 (GenBank, AOV81894.1), (Igκ, $V_H$). A synthetic linker sequence was placed between the anti-CTLA4 and IgG kappa sequences, as shown in FIG. 23A. The sequence was synthesized by GenArt (Lifetechnologies.com). An XbaI site was included at the 5' end of the sequence. An ApaI sequence at the 3' end of the sequence facilitated subcloning from the GenArt pMK-RQ-Bb vector.

The synthesized sequence was released from the pMK-RQ-Bb plasmid using the restriction enzymes XbaI and ApaI. The restriction enzyme digest was run on an agarose electrophoresis gel, and the anti-CTLA band was visualized and excised. Sindbis virus vector plasmid, pT7StuIR, was also digested with XbaI/ApaI enzymes and the fragments were ligated with the fragment containing the polynucleotide encoding the anti-CTLA-4 binding molecule. Bacteria were transformed with DNA from the ligation reactions. Plasmid DNA isolated from transformed bacteria was analyzed by restriction digestion and positive plasmids were sequenced.

Sindbis anti-CTLA4 viral vector (SV_aCTLA4) was produced by linearizing the DNA plasmids pT7StuIR1-anti-CTLA4 and pT7DM-Helper (plasmid/vector maps shown in FIG. 23B with PacI and XhoI restriction enzymes, respectively, prior to in vitro transcription using the mMACHINE RNA transcription kit (Ambion, Austin, TX) following the manufacturer's protocol. Helper and replicon RNAs were mixed at a 1:1 ratio and were then electroporated into BHK cells. After 8 to 10 hours, the culture medium was replaced with OPTI-MEM (Invitrogen), supplemented to contain 100 μg/mL $CaCl_2$). After 24 hours, the supernatant was collected, centrifuged to remove cellular debris and stored at −80° C.

The vector titer was determined by infecting BHK-SINLuc2 cells that expressed Firefly luciferase under the Sindbis virus promoter, which allowed a Luciferase signal only in infected cells in which Sindbis replicase was expressed. Briefly, $10^5$ BHKSINLUC2 cells in 12 well plates were infected with serial dilutions of vector (250 μL/well) in Optimem-$CaCl_2$) for an hour at room temperature (RT). Cells were washed with α-MEM medium and were incubated overnight (O/N) at 37° C. and in 5% CO2. The medium was then removed, and cells were lysed with M-PER Mammalian Protein Extraction Reagent (100 L/well) for 10 min at RT. Thereafter, 100 μL of SteadyGlo Reagent (Promega E2520) was added. Following shaking at RT for 10 min, bioluminescence was measured in a Glomax Biorad luminometer. The SV_aCTLA4 vector was titered in parallel to Sindbis vector expressing GFP (Sindbis GFP) to establish a correlation between the visual titer (GFP positive cells) and the Luminescent signal. Vector titers refer to the number of infectious particles, transducing units (TU), per milliliter of supernatant (TU/mL). In this study SV_aCTLA4 vector was used at titer 107 TU/ml.

In Vivo Studies Using the SV_aCTLA4 Vector

All experiments were performed in accordance with the Institute of Animal Care and Use Committee at New York University Health.

Figure 24A:
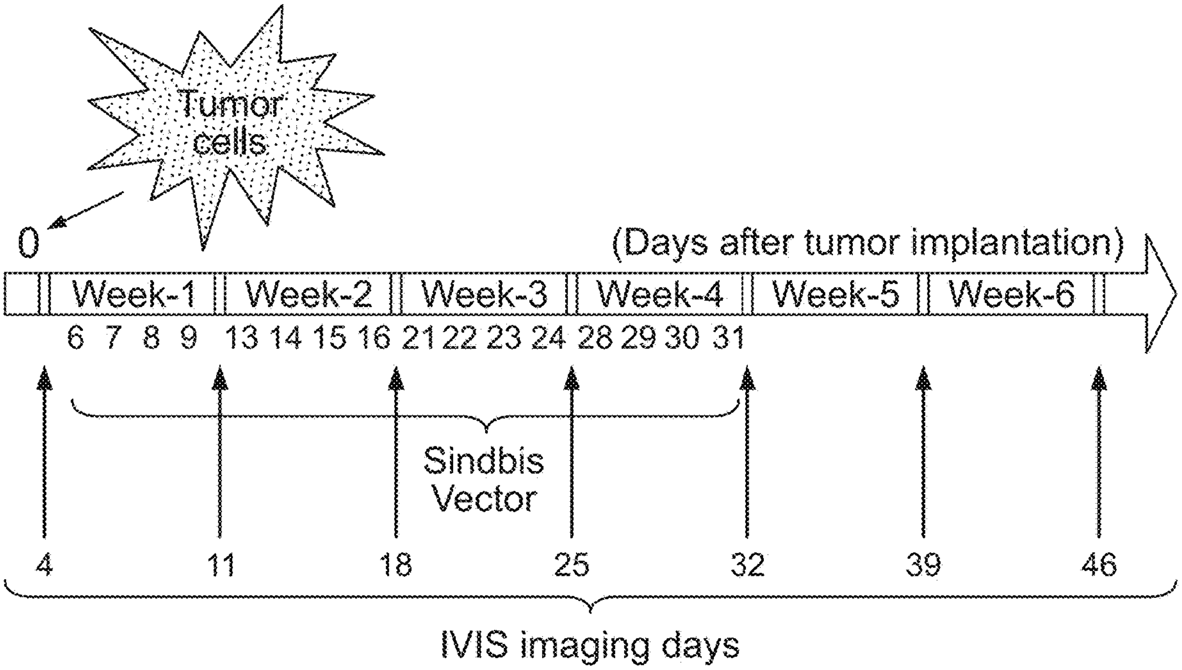

Four to eight week old female BALB/c mice were purchased from Taconic (Germantown, NY). For the animal tumor model, $7\times10^4$ CT26.Fluc.NYESO1 cells in 500 μL OPTI-MEM medium were injected (i.p. administration) into animals 6 days before treatment with the Sindbis vector (SV_aCTLA4), (day 0). Four days after the cells were injected into animals, tumor implantation in the mice was assessed by IVIS imaging. Six days after tumor inoculation, mice received a first dose of $10^7$ TU of SV_aCTLA4 vector in a total volume of 500 μL administered by i.p. injection. The treatment was carried out for 4 days a week for a total of 4 weeks; days after cell inoculation: 6, 7, 8, 9 (Week one); 13, 14, 15, 16 (week 2); 21, 22, 23, 24 (week 3); and 28, 29, 30, 31 (Week 4). A schematic diagram of the experiment design is shown in FIG. 24A. The therapeutic efficacy of the treatment was monitored in two ways: by tumor luminescence and by animal survival.

Noninvasive bioluminescent imaging was performed using the IVIS Spectrum imaging system (Caliper Life Science) and tumor growth was quantified using the Living Image 3.0 software (Caliper Life Science). The first tumor bioluminescent image was collected on day 4 after tumor cell inoculation, and then imaging was continued weekly for 6 weeks. Relative tumor growth for each mouse was calculated by dividing total body counts on a given day by total body counts on the first day of IVIS imaging (on day 4).

Figure 24B:
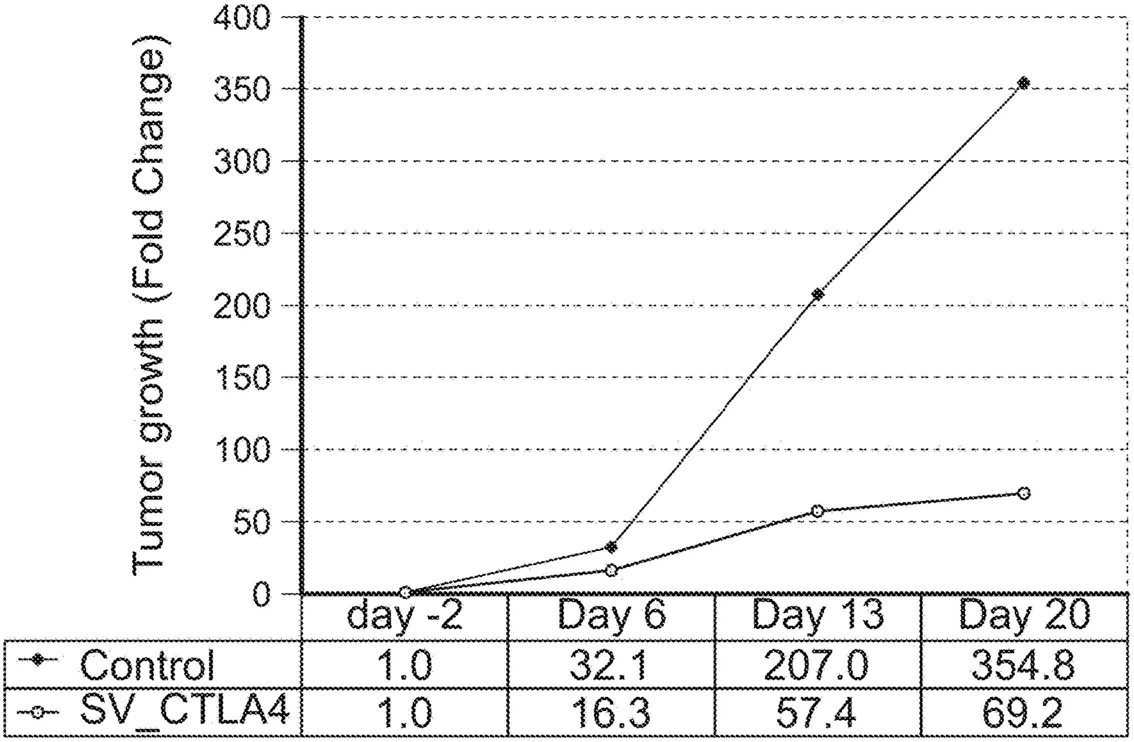

Graphs showing relative tumor growth (fold change) at different days after treatment graphs are shown in FIG. 24B. Animal survival was monitored and recorded daily; survival plots of untreated and SV_aCTLA4 treated mice are shown in FIG. 24C.

Example 10—Sindbis Virus Vector Encoding TAA Survivin Shows Anti-Tumor Efficacy In Vivo This Example describes studies conducted utilizing a Sindbis viral vector containing a polynucleotide sequence encoding Survivin protein. Survivin is a representative tumor associated antigen. It is a member of the "inhibitor of apoptosis" (IAP) protein family that inhibits caspases and blocks cell death. Survivin is highly expressed in most cancers and is associated with a poor clinical outcome.

Materials and Methods

Cell Lines

Baby hamster kidney cells (BHK-21; ATTC CCL-10) were maintained in minimum essential α-modified medium (α-MEM), (Corning CellGro), supplemented to contain 5% fetal bovine serum (FCS, Gibco) and 100 mg/ml penicillin-streptomycin (Corning CellGro). BHKSINLuc2 cells (ATCC CRL12071) were cultured in a manner similar to that of BHK cells, and 400 μg/mL Geneticin was included in the culture medium.

The BALB/c colon carcinoma (CT26) cell line was obtained from the American Type Culture Collection (ATCC: CRL 2638). Firefly luciferase (Fluc)-expressing CT26 cells (CT26.Fluc) were generated by stable transfection of pGL4.20_Fluc plasmid that expresses luciferase from a SV40 promoter and has puromycin as a selection marker. The CT26 cell line expressing both Firefly luciferase and NYESO1 (CT26.Fluc.NYESO1) was generated by stably transfecting the CT26.Fluc cell line with the expression plasmid pReceiver-M02 (GeneCopoeia) that contains the polynucleotide encoding NYESO1 (NM_001327.1) under the control of the CMV promoter and that contains neomycin as a selection marker. The CT26.Fluc.NYESO1 cell line was maintained in Dulbecco's modified Eagles medium (DMEM) containing 4.5 g/L Glucose (Corning CellGro) supplemented with 10% FCS, 100 mg/mL penicillin-streptomycin, 7.5 μg/mL Puromycin and 800 μg/mL Geneticin. All cell lines were cultured at 37° C. and 5% CO2.

PT7StuIR-survivin Vector

The polynucleotide sequence encoding mouse survivin was derived from the GenBank protein sequence under Accession No. AAD34225. Nucleotides that encode the sequence were optimized for mouse expression as shown in FIG. 25A. The underlined nucleotides at the 5' and 3' ends of the polynucleotide sequence in FIG. 25A are restriction enzyme sites added to the survivin coding sequence as described herein.

The survivin-encoding polynucleotide sequence was synthesized by GenArt (Lifetechnologies.com). A 5' XbaI restriction site and a 3' ApaI restriction site were included at the ends of the sequence to facilitate subcloning from the GenArt vector into the XbaI/ApaI restriction sites of the pT7StuIR1 vector. Plasmid DNAs, isolated from bacterial colonies obtained following transformation with the ligation reactions were analyzed by restriction digestion and positive plasmids were sequenced.

The Sindbis_Survivin viral vector (SV_Survivin) was produced by linearizing the DNA plasmids pT7StuIR1-Survivin and pT7DM-Helper vector (maps in FIG. 25B) with restriction enzymes PacI and XhoI, respectively, prior to in vitro transcription using the mMACHINE RNA transcription kit (Ambion, Austin, TX) following the manufacturer's protocol. Helper and replicon RNAs were mixed at a 1:1 ratio and were then electroporated into BHK cells. After 8 to 10 hours, the culture medium was replaced with OPTI-MEM (Invitrogen), supplemented to contain 100 μg/mL $CaCl_2$). After 24 hours, the supernatant was collected, centrifuged to remove cellular debris and stored at −80° C.

The vector titer was determined by infecting BHK-SINLuc2 cells that expressed the Firefly luciferase under Sindbis promoter, which allowed a Luciferase signal only in infected cells in which Sindbis replicase is expressed. Briefly, $10^5$ BHKSINLUC2 cells in 12 well plates were infected with serial dilutions of vector (250 l/well of vector) in Optimem-$CaCl_2$) for an hour at room temperature (RT). Cells were washed with α-MEM medium and were incubated overnight (O/N) at 37° C. and at 5% CO2. Then medium was removed and cells were lysed using M-PER Mammalian Protein Extraction Reagent (100 L/well) for 10 min at RT. Thereafter, 100 μL of SteadyGlo Reagent (Promega E2520) was added. Bioluminescence was measured in a Glomax Biorad luminometer after cell lysate was shaken for 10 min at RT. SV_Survivin vector was titered in parallel to Sindbis virus vector carrying and expressing GFP to establish a correlation between the visual titer (GFP positives cells) and the Luminescent signal. Vector titers refer to the number of infectious particles, transducing units (TU), per milliliter of supernatant (TU/mL). In this study, the SV_Survivin vector was used at titer 5-$10^6$ TU/ml.

In Vivo Studies Using the SV Survivin Vector

All experiments were performed in accordance with the Institute of Animal Care and Use Committee at New York University Health.

Figure 26A:
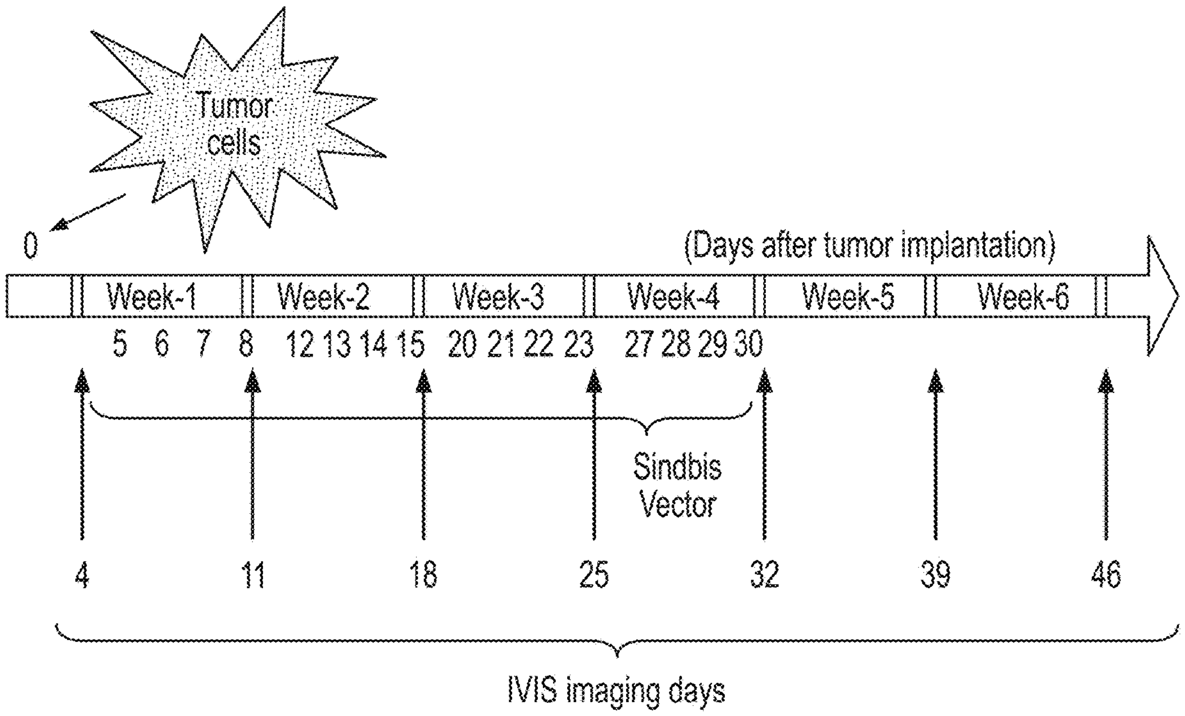
FIGS. 26A-26C: Schematic depiction of the in vivo experimental design, graph of tumor growth and survival curves as described in Example 10 herein.

Four to eight week old female BALB/c mice were purchased from Taconic (Germantown, NY). For the animal tumor model, $7\times10^4$ CT26.Fluc.NYESO1 cells in 500 μL OPTI-MEM medium were injected into animals (i.p. administration) 5 days before treatment with the Sindbis vector (SV_Survivin), (day 0). Four days after the cells were injected into animals, tumor implantation in mice was assessed by IVIS imaging. At day 5 after tumor inoculation, mice received a first dose of $10^6$ TU of SV_Survivin vector in a total volume of 500 μL administered by i.p. injection. The treatment was carried out for 4 days a week for a total of 4 weeks; days after cell inoculation: 5, 6, 7, 8 (Week one); 12, 13, 14, 15 (week 2); 20, 21, 22, 23 (week 3); and 27, 28, 29, 30 (Week 4). A schematic diagram of the experimental design is shown in FIG. 26A. The therapeutic efficacy of the treatment was monitored in two ways: by tumor luminescence and by animal survival.

Figure 26B:
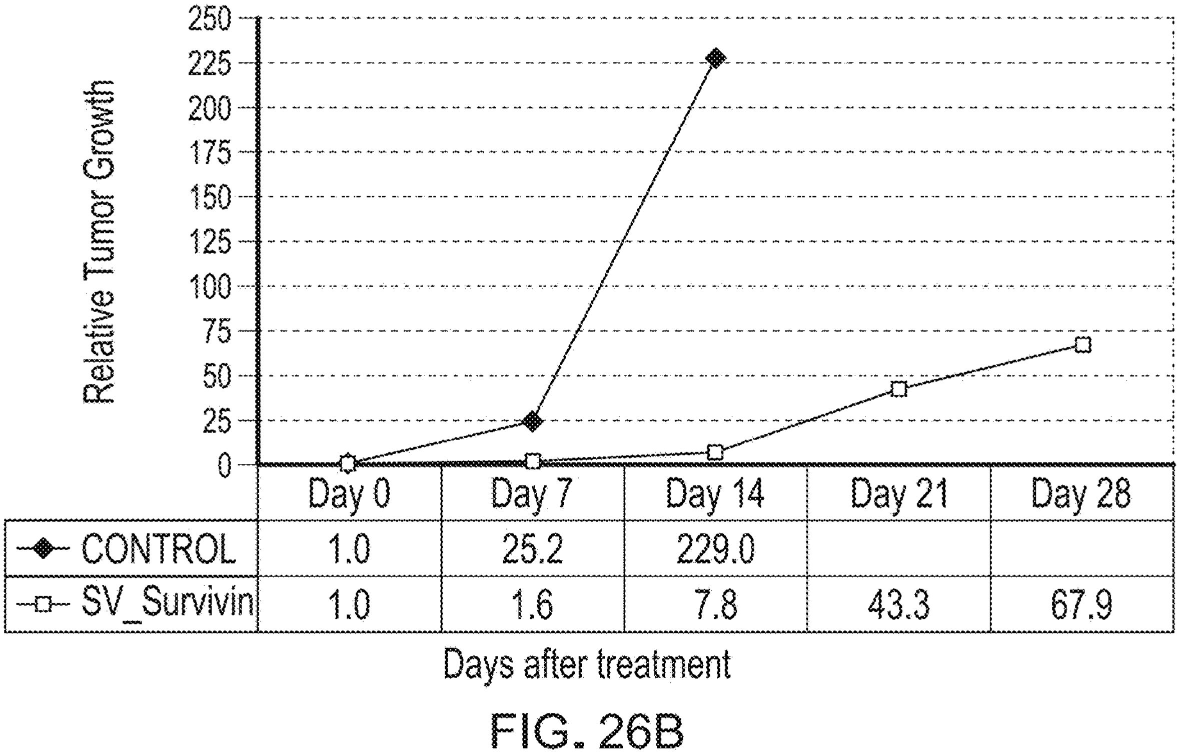
Figure 26C:
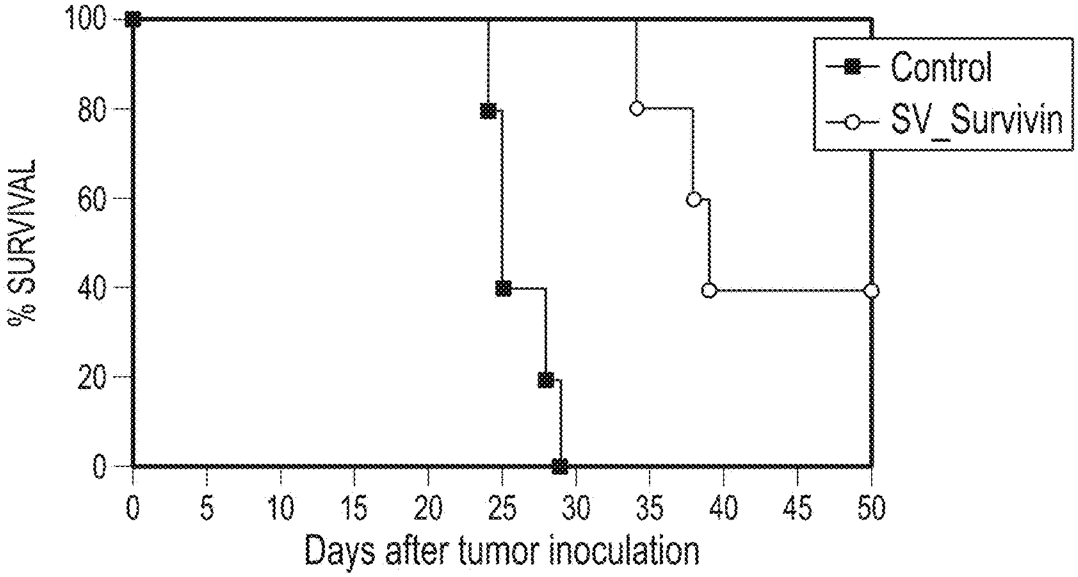

Noninvasive bioluminescent imaging was performed using the IVIS Spectrum imaging system (Caliper Life Science), and tumor growth was quantified using the Living Image 3.0 software (Caliper Life Science). The first tumor bioluminescence image was collected at day 4 after cell inoculation, and then weekly thereafter for 6 weeks. Relative tumor growth for each mouse was calculated by dividing total body counts on a given day by total body counts on the day of the first IVIS image (at day 4). Graphs showing relative tumor growth (fold change) at different days after treatment graphs are shown in FIG. 26B. Animal survival was monitored and recorded daily; survival plots of untreated and SV_Survivin treated mice are shown in FIG. 26C. Compared with control animals, a larger percentage of tumored animals treated with the SV_survivin virus vector survived for a longer period of time.

Example 11—Sindbis Virus Vector Encoding the Immune Checkpoint Protein PD-1 Provided Anti-Tumor Efficacy In Vivo This Example describes studies conducted utilizing a Sindbis virus vector which contained a polynucleotide encoding the extracellular portion of PD-1, a checkpoint protein (receptor protein) expressed by T cells, which plays a role in downregulating the immune response.

Materials and Methods

Cell Lines

Baby hamster kidney cells (BHK-21; ATTC CCL-10) were maintained in minimum essential α-modified medium (α-MEM) (Corning CellGro) supplemented to contain 5% fetal bovine serum (FCS, Gibco) and 100 mg/mL penicillin-streptomycin (Corning CellGro). BHKSINLuc2 cells (ATCC CRL12071) were cultured in a manner similar to that of BHK cells, and 400 μg/mL Geneticin was included in the culture medium.

The BALB/c colon carcinoma (CT26) cell line was obtained from the American Type Culture Collection (ATCC: CRL 2638). Firefly luciferase (Fluc)-expressing CT26 cells (CT26.Fluc) were generated by stable transfection of the pGL4.20_Fluc plasmid that expresses luciferase from an SV40 promoter and has puromycin as a selection marker. The CT26 cell line expressing both Firefly luciferase and NYESO1 (CT26.Fluc.NYESO1) was generated by stably transfecting the CT26.Fluc cell line with the expression plasmid pReceiver-M02 (GeneCopoeia) that contains the polynucleotide encoding NYESO1 (NM_001327.1) under the control of the CMV promoter and that contains neomycin as a selection marker. The CT26.Fluc.NYESO1 cell line was maintained in Dulbecco's modified Eagles medium (DMEM) containing 4.5 g/L Glucose (Corning CellGro) supplemented to contain 10% FCS, 100 mg/mL penicillin-streptomycin, 7.5 μg/mL Puromycin and 800 μg/mL Geneticin. All cell lines were cultured at 37° C. and 5% CO2.

Preparation of pT7StuIR-WT PD-1 Minibody Vector

The extracellular domain of the human PD-1 protein is encoded by nucleotides 69-576 of the GenBank-NCBI sequence, Ref. Seq. NM_005018.2 (FIG. 27A, top). The encoded polypeptide is 59% identical and 69% similar to the mouse sequence. To produce the Sindbis virus vector encoding PD-1 protein, the wild-type human PD-1 sequence was fused to the hinge region and the CH3 heavy chain constant region domain of human immunoglobulin (Ig) G isotype 1, IgG1 (GenBank, P01857.1). (FIG. 27A). A glycine-rich, artificial spacer or linker sequence was added between the hinge and CH3 domains to provide greater flexibility between the protein domains. Amino acid sequences were optimized for expression and function in the mouse. The sequence was synthesized by GenArt (Lifetechnologies). The PD-1 sequence fused to the IgG1 hinge region and the heavy chain constant region CH3 domain is termed a "minibody" or "minibody fragment" herein. An XbaIrestriction enyme site was included to facilitate subcloning from the GenArt pMK-RQ-Bb vector. The synthesized sequence was excised from the pMK-RQ-Bb plasmid using the restriction enzymes XbaI and PmeI. The Sindbis virus plasmid, pT7StuIR, was also digested with the XbaIPmeI enzymes and was ligated with the PD-1 minibody fragment. Plasmid DNAs, isolated from bacterial colonies obtained following transformation with the ligation reactions, were analyzed by restriction enzyme digestion and positive plasmids were sequenced. FIG. 27B shows an amino acid sequence comparison (alignment) of the human WT-PD-1 amino acid sequence to PD-1 amino acid sequences of other species, e.g., mouse and monkey.

To produce the Sindbis virus_PD-1WT minibody viral vector (SV_PD-1WT), the DNA plasmids pT7StuIR1-PD-1 WT Minibody and T7DM-Helper (maps in FIG. 28) were linearized with PacI and XhoI restriction enzymes, respectively, before performing in vitro transcription using the mMACHINE RNA transcription kit (Ambion, Austin, TX) following the manufacturer's protocol. Helper and replicon RNAs were mixed at a 1:1 ratio and then were electroporated into BHK cells. After 8 to 10 hours, the cell culture medium was replaced with OPTI-MEM (Invitrogen), supplemented to contain 100 μg/mL $CaCl_2$). After 24 hours, the supernatant was collected, centrifuged to remove cellular debris and stored at −80° C.

The vector titer was determined by infecting BHK-SINLuc2 cells that expressed Firefly luciferase under the Sindbis promoter, which produced Luciferase signal only in infected cells in which the Sindbis replicase wa expressed. Briefly, $10^5$ BHKSINLUC2 cells in 12 well plates were infected with serial dilutions of vector (250 μL/well) in Optimem-$CaCl_2$) for an hour at room temperature (RT). Cells were washed with α-MEM medium and were incubated overnight (O/N) at 37° C. and in 5% $CO_2$. Thereafter, the medium was removed and the cells were lysed using M-PER Mammalian Protein Extraction Reagent (100 μL/well) for 10 min at RT. Thereafter, 100 μL of SteadyGlo Reagent (Promega E2520) was added. Following shaking at RT for 10 min, bioluminescence was measured in a Glomax Biorad luminometer. The SV_PD1WT vector was titered in parallel to Sindbis virus vector expressing GFP (Sindbis-GFP) to establish a correlation between the visual titer (GFP positive cells) and the Luminescent signal. Vector titers refer to the number of infectious particles, transducing units (TU), per milliliter of supernatant (TU/mL). In this study the SV_PD-1WT vector was used at titer of 5-$10^5$ TU/ml.

In Vivo Studies Using the SV PD-1WT Vector

All experiments were performed in accordance with the Institute of Animal Care and Use Committee at New York University Health.

Figure 29:
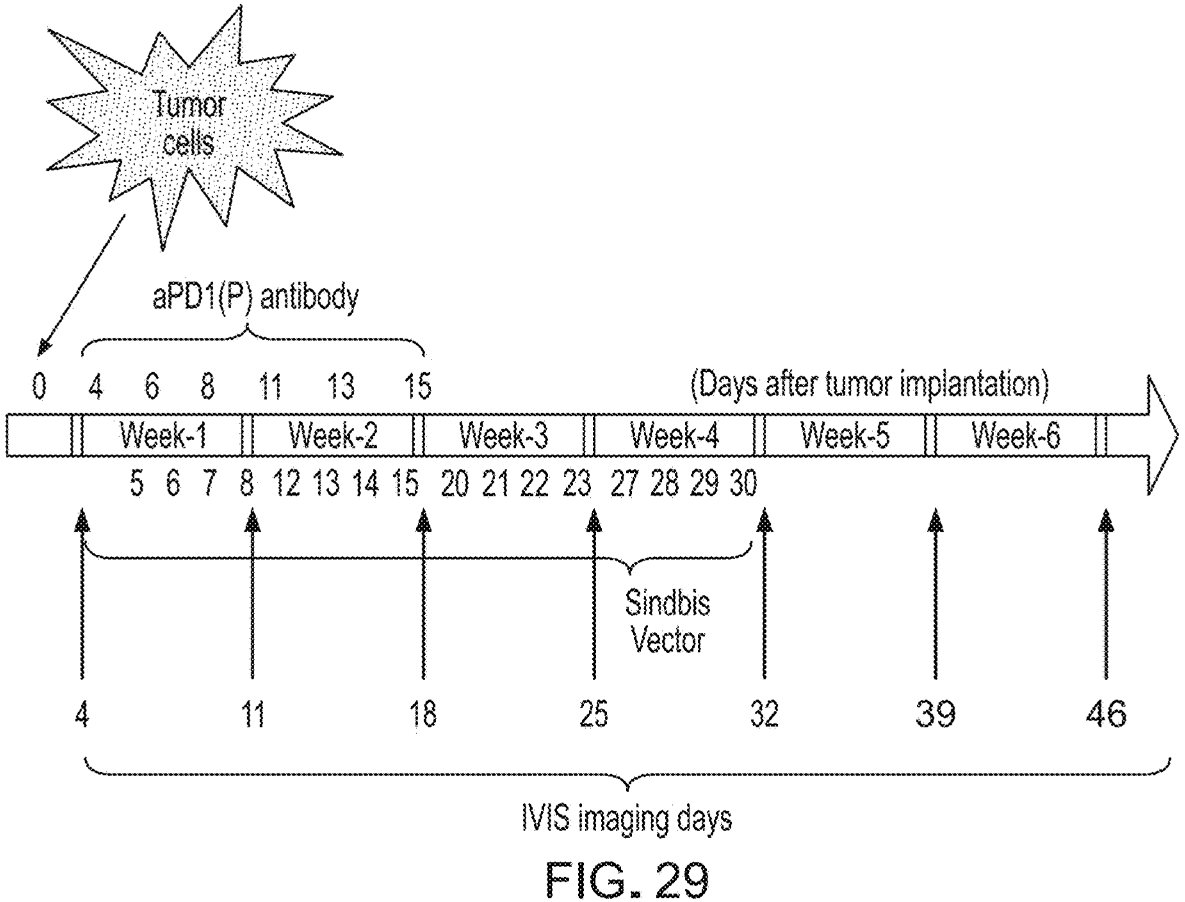
FIG. 29: presents a schematic depiction of the design of the in vivo experiments described herein. For animals that received treatment with the immune checkpoint inhibitor, anti-PD-1 antibody, (αPD-1), the mice were dosed at days 4, 6, 8, 11, 13, 15; as shown the diagram. For animals that received treatment with the SV vector, SV_PD-1WT, Sindbis virus vector treatment was administered to the animals 4 times a week for 4 weeks, at days 5, 6, 7, 8 (week 1); 12, 13, 14, 15 (week 2); 20, 21, 22, 23 (week 3) and 27, 28, 29, 30 (week 4), as indicated. Tumor growth analysis was performed once a week bioluminescence was measured in the mice using IVIS at days 4, 11, 18, 25, 32, 39 and 46.

Four to eight week old female BALB/c mice were purchased from Taconic (Germantown, NY). For the animal tumor model, $7\times10^4$ CT26.Fluc.NYESO1 cells in 500 L OPTI-MEM medium were injected (i.p. administration) into animals 5 days before treatment with the Sindbis vector (SV_PD-1WT), (day 0). Four days after the cells were injected, tumor implantation in mice was assessed by IVIS imaging, and mice in the group receiving anti-PD-1 antibody received a first dose (250 μg/mouse) of anti-PD-1 antibody (clone RPMI-14, BioXCell) via i.p. injection. Anti-PD-1 antibody was administrated 3 days a week for a total of 2 weeks: days 4, 6, 8 and 11, 13 15 after tumor cell implantation. For treatments, $10^5$ TU of SV_PD-1WT vector in a total volume of 500 μL was injected into mice (i.p.) 4 days a week for a total of 4 weeks. Days after cells inoculation: 5, 6, 7, 8 (week one); 12, 13, 14, 15 (week 2); 20, 21, 22, 23 (week 3); and 27, 28, 29, 30 (week 4). The schematic diagram of the experiment design is shown in FIG. 29. The therapeutic efficacy of the treatment was monitored in two ways: by tumor luminescence and by animal survival.

Figure 30:
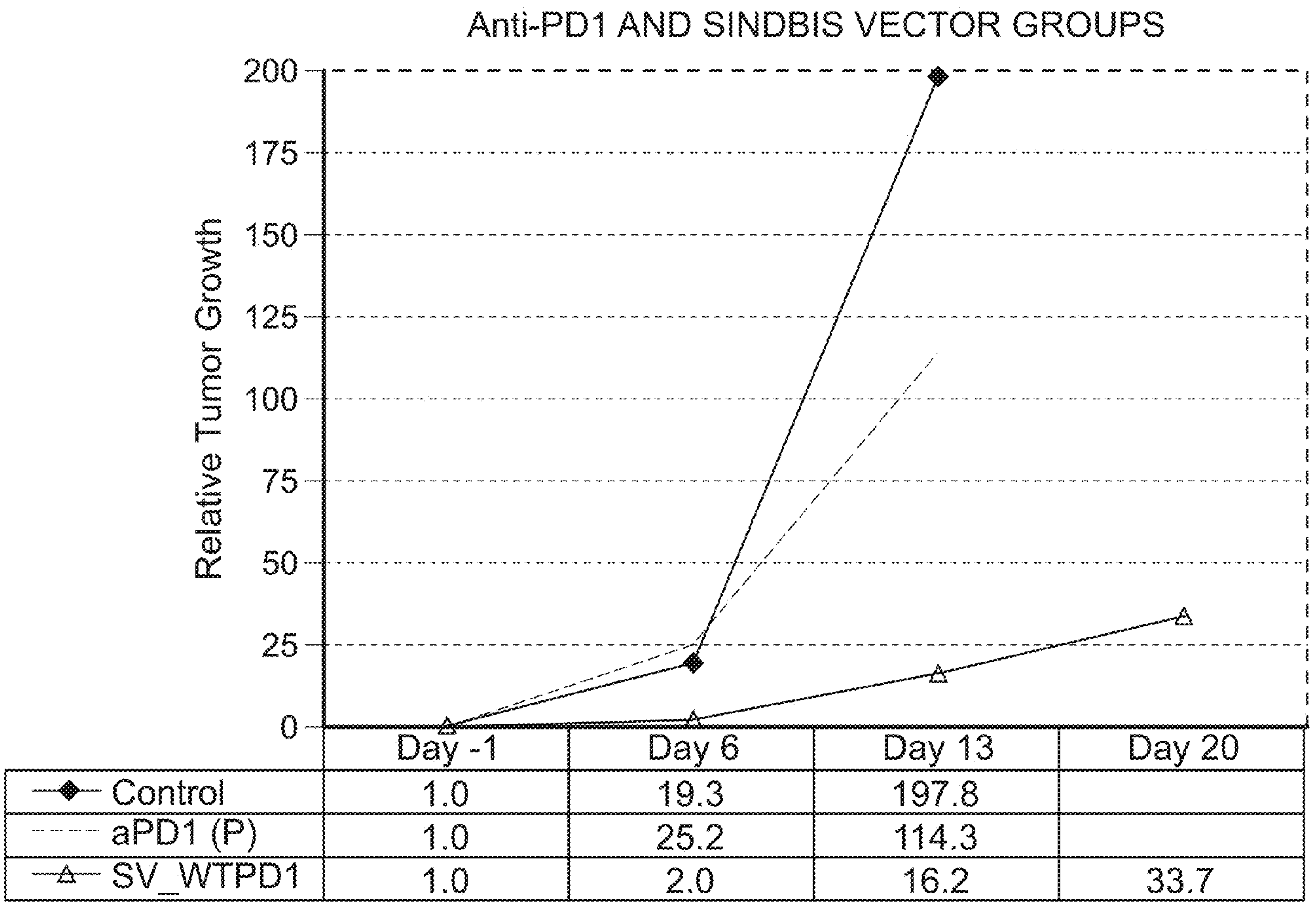
FIG. 30 presents graphs of tumor growth curves of mice treated with SV_PD-1WT Sindbis vector and of untreated (control) mice. Tumor growth is shown as fold changes relative to bioluminescence on the day before treatment of the same mouse with the Sindbis virus vecot: (day-1/day-1); (day 6/day −1); (day 13/day −1) and (day 20/day −1). Each time point shows the tumor growth average of the 5 mice in each group. Day 13 is the last day, with 5 mice/group for control (untreated) and PD1 antibody treated groups.
Figure 31:
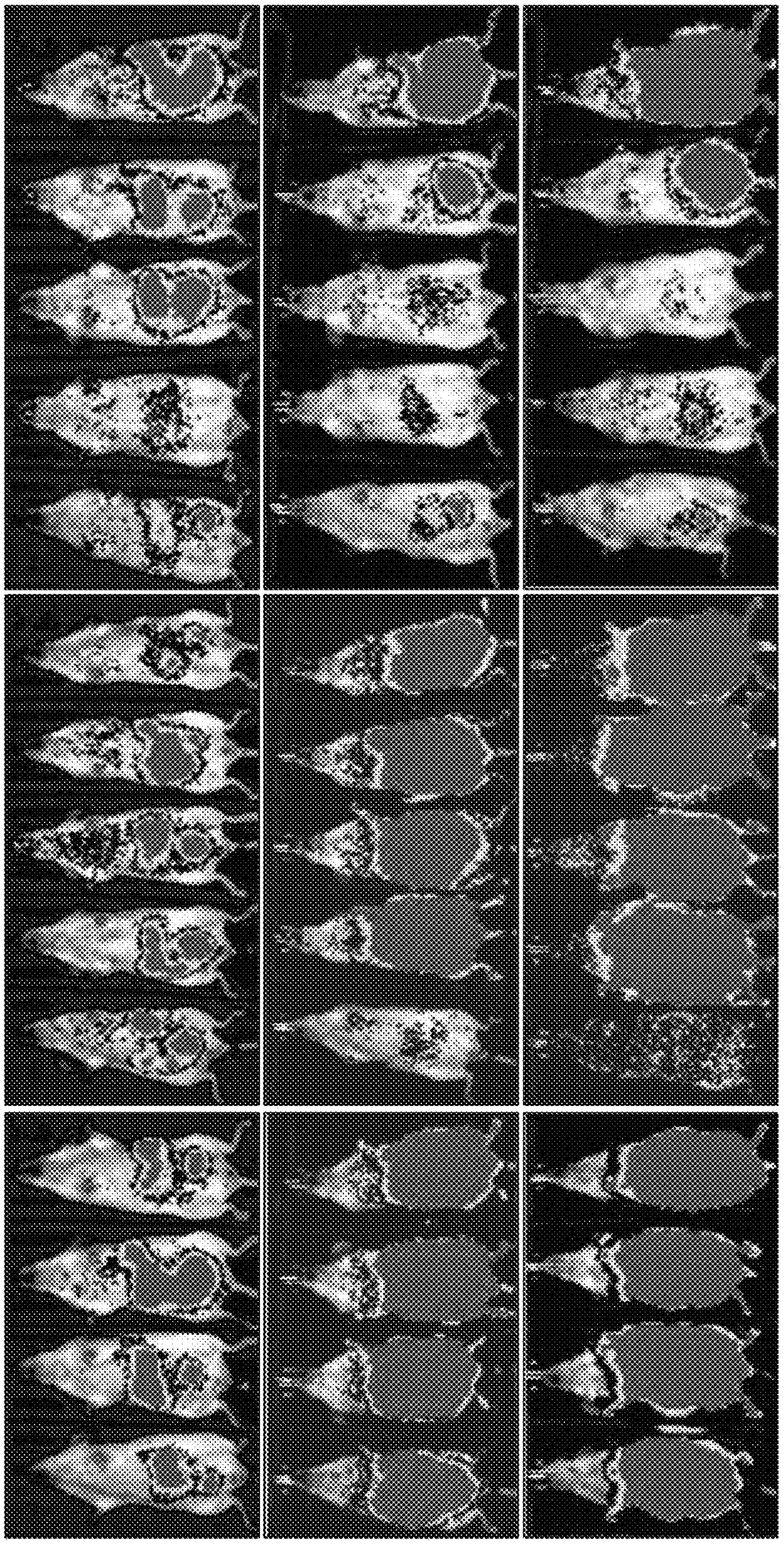
FIG. 31 shows representative bioluminescence images of control mice, anti-PD1 antibody-treated mice and SV_PD-1WT vector-treated mice bearing CT26.Fluc.NYESO1 tumors. Images correspond to days 4, 11 and 18 after tumor inoculation. Image scale min=50 Max=150 counts.
Figure 32:
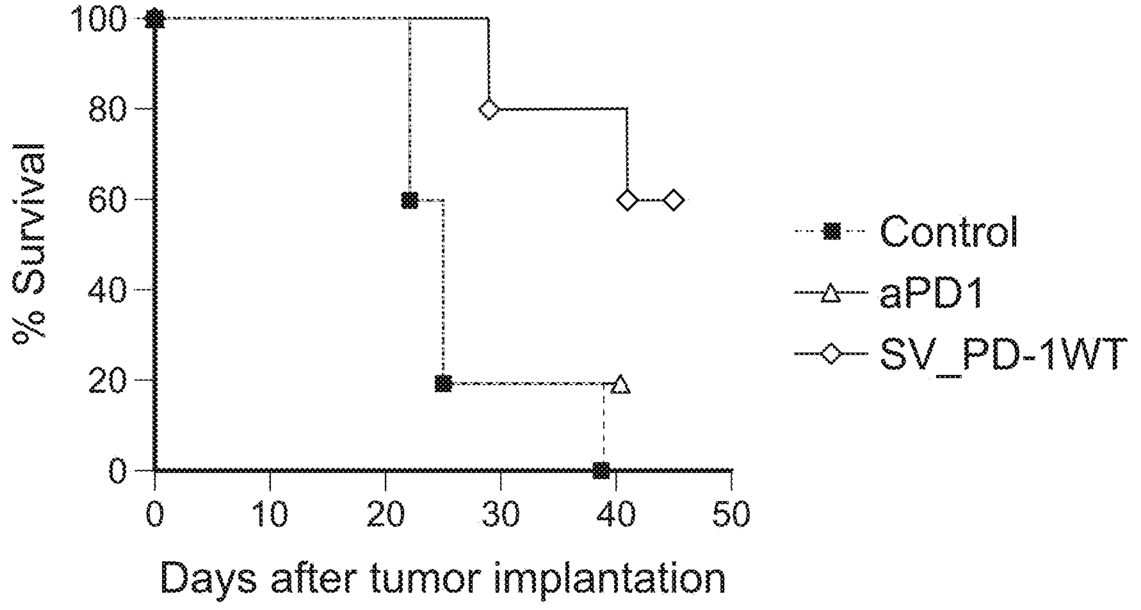
FIG. 32 shows survival curves of untreated Control animals (n=5), animals treated with anti-PD-1 antibody, (αPD1), (n=5) and animals treated with the Sindbis virus vector SV_PD-1WT, (n=5).

Noninvasive bioluminescent imaging was performed using the IVIS Spectrum imaging system (Caliper Life Science) and tumor growth was quantified using the Living Image 3.0 software (Caliper Life Science). The first tumor bioluiminescent image was collected on day 4 after tumor cell inoculation, and then imaging was continued weekly for 6 weeks. Relative tumor growth for each mouse was calculated by dividing total body counts on a given day by total body counts on the first day of IVIS imaging (at day 4). Graphs showing relative tumor growth (fold change) at different days after treatment are shown in FIG. 30. Representative bioluminescence images of control, anti-PD1 antibody treated and SV_PD-1WT vector-treated mice bearing establishe dCT26.Fluc.NYESO1 tumors are shown in FIG. 31. Animal survival was monitored and recorded daily; survival plots of untreated and SV_PD-1WT treated mice are shown in FIG. 32.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of, for treating a subject having cancer, the method comprising administering to the subject a combination consisting of a Sindbis virus encoding an NY-ESO-1 polypeptide, and an anti-PD-1 antibody, wherein administering the combination eliminates an established tumor comprising cancer cells that express the NY-ESO-1 polypeptide.

* * * * *

SEQUENCE LISTING

```
<160> NUMBER OF SEQ ID NOS: 427

<210> SEQ ID NO 1
<211> LENGTH: 9
<212> TYPE: PRT
<213> ORGANISM: Artificial Sequence
<220> FEATURE:
<223> OTHER INFORMATION: Epitope from tumor associated antigen NY-ESO-1

<400> SEQUENCE: 1

Leu Leu Met Trp Ile Thr Gln Cys Phe
1               5


<210> SEQ ID NO 2
<211> LENGTH: 9
<212> TYPE: PRT
<213> ORGANISM: Artificial Sequence
<220> FEATURE:
<223> OTHER INFORMATION: Epitope from tumor associated antigen pbk

<400> SEQUENCE: 2

Gly Ser Pro Phe Pro Ala Ala Val Ile
1               5


<210> SEQ ID NO 3
<211> LENGTH: 9
<212> TYPE: PRT
<213> ORGANISM: Artificial Sequence
<220> FEATURE:
<223> OTHER INFORMATION: Epitope from tumor associated antigen NY-ESO-1

<400> SEQUENCE: 3

Arg Gly Pro Glu Ser Arg Leu Leu Glu
1               5


<210> SEQ ID NO 4
<211> LENGTH: 9
<212> TYPE: PRT
<213> ORGANISM: Artificial Sequence
<220> FEATURE:
<223> OTHER INFORMATION: Epitope from tumor associated antigen Survivin

<400> SEQUENCE: 4

Ala Phe Leu Thr Val Lys Lys Gln Met
```

1 5

<210> SEQ ID NO 5
<211> LENGTH: 6
<212> TYPE: PRT
<213> ORGANISM: Artificial Sequence
<220> FEATURE:
<223> OTHER INFORMATION: Enzyme cleavage site
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 5

Xaa Arg Ser Lys Arg Xaa
1 5

<210> SEQ ID NO 6
<211> LENGTH: 8
<212> TYPE: PRT
<213> ORGANISM: Artificial Sequence
<220> FEATURE:
<223> OTHER INFORMATION: Enzyme cleavage site
<220> FEATURE:
<221> NAME/KEY: MISC_FEATURE
<222> LOCATION: (1)..(1)
<223> OTHER INFORMATION: X1 is either Arginine or Lysine
<220> FEATURE:
<221> NAME/KEY: MISC_FEATURE
<222> LOCATION: (2)..(7)
<223> OTHER INFORMATION: an integer from 0 to 6 representing any amino acid
<220> FEATURE:
<221> NAME/KEY: MISC_FEATURE
<222> LOCATION: (8)..(8)
<223> OTHER INFORMATION: X8 is either Arginine or Lysine

<400> SEQUENCE: 6

Xaa Xaa Xaa Xaa Xaa Xaa Xaa Xaa
1 5

<210> SEQ ID NO 7
<211> LENGTH: 13
<212> TYPE: PRT
<213> ORGANISM: Artificial Sequence
<220> FEATURE:
<223> OTHER INFORMATION: HLA-DR reactive epitope

<400> SEQUENCE: 7

Ala Lys Phe Val Ala Ala Trp Thr Leu Lys Ala Ala Ala
1 5 10

<210> SEQ ID NO 8
<211> LENGTH: 726
<212> TYPE: DNA
<213> ORGANISM: Artificial Sequence
<220> FEATURE:
<223> OTHER INFORMATION: Polynucleotide sequence encoding the anti-CTLA4 binding molecule

<400> SEQUENCE: 8
gaggaattca tgcaggtgca gctggtggag tctgggggag gcgtggtcca gcctgggagg 60
tccctgagac tctcctgtgt ggcttctgga ttcaccttca gcagccatgg catgcactgg 120
gtccgccagg ctccaggcaa gggactggag tgggtggcag ttatctggta tgatggaaga 180

-continued

```
aataaatact atgcagactc cgtgaagggc cggttcacca tctccagaga caattccaag    240

aacacactgt ttctgcagat gaacagcctg agagccgagg acactgctgt gtattactgt    300

gctagaggag gccacttcgg tccttttgac tactggggcc agggaaccct ggtcaccgtc    360

tcctctggag gcggtggcag cggaggcgga ggcagcggag gcggcggcag ccagtctcca    420

ggcaccctgt ctctgtctcc aggggaaaga gccaccctgt cctgcagggc cagccagagc    480

attagcagca gcttcctggc ctggtaccag cagagacctg gccaggctcc caggctgctt    540

atctatggtg catccagcag ggccactggc atcccagaca ggttcagcgg cagcgggtct    600

gggacagact tcactctcac catcagcaga ctggagcctg aagattttgc agtgtattac    660

tgtcagcagt atggcacctc tccctggaca ttcggccaag ggaccaaggt ggaaatcaaa    720

agatga                                                               726
```

```
<210> SEQ ID NO 9
<211> LENGTH: 238
<212> TYPE: PRT
<213> ORGANISM: Artificial Sequence
<220> FEATURE:
<223> OTHER INFORMATION: Amino acid sequence encoding the anti-CTLA4
      binding molecule

<400> SEQUENCE: 9

Met Gln Val Gln Leu Val Glu Ser Gly Gly Gly Val Val Gln Pro Gly
1               5                   10                  15

Arg Ser Leu Arg Leu Ser Cys Val Ala Ser Gly Phe Thr Phe Ser Ser
            20                  25                  30

His Gly Met His Trp Val Arg Gln Ala Pro Gly Lys Gly Leu Glu Trp
        35                  40                  45

Val Ala Val Ile Trp Tyr Asp Gly Arg Asn Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Phe Leu Gln Met Asn Ser Leu Arg Ala Glu Asp Thr Ala Val Tyr Tyr
                85                  90                  95

Cys Ala Arg Gly Gly His Phe Gly Pro Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Ser Pro Gly Thr Leu Ser Leu Ser Pro
    130                 135                 140

Gly Glu Arg Ala Thr Leu Ser Cys Arg Ala Ser Gln Ser Ile Ser Ser
145                 150                 155                 160

Ser Phe Leu Ala Trp Tyr Gln Gln Arg Pro Gly Gln Ala Pro Arg Leu
                165                 170                 175

Leu Ile Tyr Gly Ala Ser Ser Arg Ala Thr Gly Ile Pro Asp Arg Phe
            180                 185                 190

Ser Gly Ser Gly Ser Gly Thr Asp Phe Thr Leu Thr Ile Ser Arg Leu
        195                 200                 205

Glu Pro Glu Asp Phe Ala Val Tyr Tyr Cys Gln Gln Tyr Gly Thr Ser
    210                 215                 220

Pro Trp Thr Phe Gly Gln Gly Thr Lys Val Glu Ile Lys Arg
225                 230                 235


<210> SEQ ID NO 10
<211> LENGTH: 216
```

<212> TYPE: DNA
<213> ORGANISM: Artificial Sequence
<220> FEATURE:
<223> OTHER INFORMATION: A polynucleotide encoding multiple T cell recognition epitopes separated by furin enzyme cleavage sites

<400> SEQUENCE: 10
tctagagcca ccatgctggt gacagccatg tgtctgctgg gcaatgtcag cttcgtccgg 60
agcaagcggc tgcggggacc agagtctcgg ctcctggagg tgcggagcaa gcggctgtcc 120
ccatcttacg cctaccacca gttcgtccgg agcaagcggc tgggctgtgc cttcctgacc 180
gtgaagcaga tgcggagcaa gcggctgtga gggccc 216

<210> SEQ ID NO 11
<211> LENGTH: 65
<212> TYPE: PRT
<213> ORGANISM: Artificial Sequence
<220> FEATURE:
<223> OTHER INFORMATION: An amino acid sequence encoding multiple T cell recognition epitopes separated by furin enzyme cleavage sites

<400> SEQUENCE: 11

Met Leu Val Thr Ala Met Cys Leu Leu Gly Asn Val Ser Phe Val Arg
1 5 10 15

Ser Lys Arg Leu Arg Gly Pro Glu Ser Arg Leu Leu Glu Val Arg Ser
20 25 30

Lys Arg Leu Ser Pro Ser Tyr Ala Tyr His Gln Phe Val Arg Ser Lys
35 40 45

Arg Leu Gly Cys Ala Phe Leu Thr Val Lys Gln Met Arg Ser Lys Arg
50 55 60

Leu
65

<210> SEQ ID NO 12
<211> LENGTH: 516
<212> TYPE: DNA
<213> ORGANISM: Artificial Sequence
<220> FEATURE:
<223> OTHER INFORMATION: Polynucleotide sequence encoding the survivin protein

<400> SEQUENCE: 12
tctagagccg gcatgggtgc cccgacgttg ccccctgcct ggcagccctt tctcaaggac 60
caccgcatct ctacattcaa gaactggccc ttcttggagg gctgcgcctg caccccggag 120
cggatggccg aggctggctt catccactgc cccactgaga acgagccaga cttggcccag 180
tgtttcttct gcttcaagga gctggaaggc tgggagccag atgacgaccc cattgggccg 240
ggcacggtgg cttacgcctg taataccagc actttgggag gccgaggcgg gcggatcacg 300
agagaggaac ataaaaagca ttcgtccggt tgcgctttcc tttctgtcaa gaagcagttt 360
gaagaattaa cccttggtga atttttgaaa ctggacagag aaagagccaa gaacaaaatt 420
gcaaaggaaa ccaacaataa gaagaaagaa tttgaggaaa ctgcggagaa agtgcgccgt 480
gccatcgagc agctggctgc catggattga gggccc 516

<210> SEQ ID NO 13
<211> LENGTH: 165
<212> TYPE: PRT
<213> ORGANISM: Artificial Sequence
<220> FEATURE:
<223> OTHER INFORMATION: Amino acid sequence encoding the survivin protein

<400> SEQUENCE: 13

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asp Pro Ile Gly Pro Gly Thr Val Ala
65                  70                  75                  80

Tyr Ala Cys Asn Thr Ser Thr Leu Gly Gly Arg Gly Gly Arg Ile Thr
                85                  90                  95

Arg Glu Glu His Lys Lys His Ser Ser Gly Cys Ala Phe Leu Ser Val
            100                 105                 110

Lys Lys Gln Phe Glu Glu Leu Thr Leu Gly Glu Phe Leu Lys Leu Asp
        115                 120                 125

Arg Glu Arg Ala Lys Asn Lys Ile Ala Lys Glu Thr Asn Asn Lys Lys
    130                 135                 140

Lys Glu Phe Glu Glu Thr Ala Glu Lys Val Arg Arg Ala Ile Glu Gln
145                 150                 155                 160

Leu Ala Ala Met Asp
                165

<210> SEQ ID NO 14
<211> LENGTH: 900
<212> TYPE: DNA
<213> ORGANISM: Artificial Sequence
<220> FEATURE:
<223> OTHER INFORMATION: PD-1 precursor

<400> SEQUENCE: 14
gccaccatgc agatcccaca ggcgccctgg ccagtcgtct gggcggtgct acaactgggc 60
tggcggccag gatggttctt agactcccca gacaggccct ggaacccccc caccttctcc 120
ccagccctgc tcgtggtgac cgaaggggac aacgccacct tcacctgcag cttctccaac 180
acatcggaga gcttcgtgct aaactggtac cgcatgagcc ccagcaacca gacggacaag 240
ctggccgcct tccccgagga ccgcagccag cccggccagg actgccgctt ccgtgtcaca 300
caactgccca acgggcgtga cttccacatg agcgtggtca gggcccggcg caatgacagc 360
ggcacctacc tctgtggggc catctccctg gcccccaagg cgcagatcaa agagagcctg 420
cgggcagagc tcagggtgac agagagaagg gcagaagtgc ccacagccca ccccagcccc 480
tcacccaggc cagccggcca gttccaaacc ctggtggagc ctaagagctg cgacaaaaca 540
cacacttgcc caccctgcgg aggaggctct agcggaggag ggtctggagg ccagccaaga 600
gagccccagg tgtacacact gcctccctct cgagacgagc ttacaaagaa ccaggtgtct 660
ctgacctgtc tggttaaagg cttctatcct agcgacattg ctgtggagtg ggaaagcaac 720
ggccagccag agaataacta caagactaca ccacctgtgc tggactctga tggcagcttc 780
tttctttaca gcaaactgac agttgacaag tctaggtggc agcaaggcaa cgtgttctct 840
tgcagcgtga tgcacaacca ctacacacag aagtctctta gcctgagccc tggcaaatga 900

<210> SEQ ID NO 15
<211> LENGTH: 297

```
<212> TYPE: PRT
<213> ORGANISM: Artificial Sequence
<220> FEATURE:
<223> OTHER INFORMATION: PD-1 precursor

<400> SEQUENCE: 15

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Glu Pro Lys Ser Cys Asp
                165                 170                 175

Lys Thr His Thr Cys Pro Pro Cys Gly Gly Gly Ser Ser Gly Gly Gly
            180                 185                 190

Ser Gly Gly Gln Pro Arg Glu Pro Gln Val Tyr Thr Leu Pro Pro Ser
        195                 200                 205

Arg Asp Glu Leu Thr Lys Asn Gln Val Ser Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Asn His Tyr Thr Gln
        275                 280                 285

Lys Ser Leu Ser Leu Ser Pro Gly Lys
    290                 295


<210> SEQ ID NO 16
<211> LENGTH: 288
<212> TYPE: PRT
<213> ORGANISM: Homo sapiens

<400> SEQUENCE: 16

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
```

```
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285


<210> SEQ ID NO 17
<211> LENGTH: 287
<212> TYPE: PRT
<213> ORGANISM: Mus musculus

<400> SEQUENCE: 17

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125
```

```
His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro
        275                 280                 285


<210> SEQ ID NO 18
<211> LENGTH: 288
<212> TYPE: PRT
<213> ORGANISM: Macaca nemestrina

<400> SEQUENCE: 18

Met Gln Ile Pro Gln Ala Pro Trp Pro Val Val Trp Ala Val Leu Gln
1               5                   10                  15

Leu Gly Trp Arg Pro Gly Trp Phe Leu Glu Ser Pro Asp Arg Pro Trp
            20                  25                  30

Asn Pro Pro Thr Phe Ser Pro Ala Leu Leu Leu Val Thr Glu Gly Asp
        35                  40                  45

Asn Ala Thr Phe Thr Cys Ser Phe Ser Asn Ala Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Gln Gly Thr Ile Glu Ala Arg Arg Thr Gly Gln Pro
        195                 200                 205

Leu Lys Glu Asp Pro Ser Ala Val Pro Val Phe Ser Val Asp Tyr Gly
    210                 215                 220
```

```
Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
                245                 250                 255

Leu Gly Thr Ser Ser Pro Ala Arg Arg Gly Ser Ala Asp Gly Pro Arg
            260                 265                 270

Ser Pro Arg Pro Leu Arg Pro Glu Asp Gly His Cys Ser Trp Pro Leu
        275                 280                 285


<210> SEQ ID NO 19
<211> LENGTH: 11
<212> TYPE: PRT
<213> ORGANISM: Artificial Sequence
<220> FEATURE:
<223> OTHER INFORMATION: Glycine-rich linker

<400> SEQUENCE: 19

Gly Gly Gly Ser Ser Gly Gly Gly Ser Gly Gly
1               5                   10


<210> SEQ ID NO 20
<211> LENGTH: 752
<212> TYPE: DNA
<213> ORGANISM: Homo sapiens

<400> SEQUENCE: 20

atcctcgtgg gccctgacct tctctctgag agccgggcag aggctccgga gccatgcagg      60

ccgaaggccg gggcacaggg ggttcgacgg gcgatgctga tggcccagga ggccctggca     120

ttcctgatgg cccagggggc aatgctggcg gcccaggaga ggcgggtgcc acgggcggca     180

gaggtccccg gggcgcaggg gcagcaaggg cctcggggcc gggaggaggc gccccgcggg     240

gtccgcatgg cggcgcggct tcagggctga atggatgctg cagatgcggg gccagggggc     300

cggagagccg cctgcttgag ttctacctcg ccatgccttt cgcgacaccc atggaagcag     360

agctggcccg caggagcctg gcccaggatg ccccaccgct tcccgtgcca ggggtgcttc     420

tgaaggagtt cactgtgtcc ggcaacatac tgactatccg actgactgct gcagaccacc     480

gccaactgca gctctccatc agctcctgtc tccagcagct ttccctgttg atgtggatca     540

cgcagtgctt tctgcccgtg tttttggctc agcctccctc agggcagagg cgctaagccc     600

agcctggcgc cccttcctag gtcatgcctc ctcccctagg gaatggtccc agcacgagtg     660

gccagttcat tgtgggggcc tgattgtttg tcgctggagg aggacggctt acatgtttgt     720

ttctgtagaa aataaaactg agctacgaaa aa                                  752


<210> SEQ ID NO 21
<211> LENGTH: 180
<212> TYPE: PRT
<213> ORGANISM: Homo sapiens

<400> SEQUENCE: 21

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60
```

```
His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180


<210> SEQ ID NO 22
<211> LENGTH: 9
<212> TYPE: PRT
<213> ORGANISM: Artificial Sequence
<220> FEATURE:
<223> OTHER INFORMATION: Kallikrein 4 Immunogenic Epitope

<400> SEQUENCE: 22

Phe Leu Gly Tyr Leu Ile Leu Gly Val
1               5


<210> SEQ ID NO 23
<211> LENGTH: 15
<212> TYPE: PRT
<213> ORGANISM: Artificial Sequence
<220> FEATURE:
<223> OTHER INFORMATION: Kallikrein 4 Immunogenic Epitope

<400> SEQUENCE: 23

Ser Val Ser Glu Ser Asp Thr Ile Arg Ser Ile Ser Ile Ala Ser
1               5                   10                  15


<210> SEQ ID NO 24
<211> LENGTH: 15
<212> TYPE: PRT
<213> ORGANISM: Artificial Sequence
<220> FEATURE:
<223> OTHER INFORMATION: Kallikrein 4 Immunogenic Epitope

<400> SEQUENCE: 24

Leu Leu Ala Asn Gly Arg Met Pro Thr Val Leu Gln Cys Val Asn
1               5                   10                  15


<210> SEQ ID NO 25
<211> LENGTH: 15
<212> TYPE: PRT
<213> ORGANISM: Artificial Sequence
<220> FEATURE:
<223> OTHER INFORMATION: Kallikrein 4 Immunogenic Epitope

<400> SEQUENCE: 25

Arg Met Pro Thr Val Leu Gln Cys Val Asn Val Ser Val Val Ser
1               5                   10                  15


<210> SEQ ID NO 26
```

<211> LENGTH: 12
<212> TYPE: PRT
<213> ORGANISM: Artificial Sequence
<220> FEATURE:
<223> OTHER INFORMATION: PBF Immunogenic Epitope

<400> SEQUENCE: 26

Cys Thr Ala Cys Arg Trp Lys Lys Ala Cys Gln Arg
1 5 10

<210> SEQ ID NO 27
<211> LENGTH: 9
<212> TYPE: PRT
<213> ORGANISM: Artificial Sequence
<220> FEATURE:
<223> OTHER INFORMATION: PRAME Immunogenic Epitope

<400> SEQUENCE: 27

Val Leu Asp Gly Leu Asp Val Leu Leu
1 5

<210> SEQ ID NO 28
<211> LENGTH: 10
<212> TYPE: PRT
<213> ORGANISM: Artificial Sequence
<220> FEATURE:
<223> OTHER INFORMATION: PRAME Immunogenic Epitope

<400> SEQUENCE: 28

Ser Leu Tyr Ser Phe Pro Glu Pro Glu Ala
1 5 10

<210> SEQ ID NO 29
<211> LENGTH: 10
<212> TYPE: PRT
<213> ORGANISM: Artificial Sequence
<220> FEATURE:
<223> OTHER INFORMATION: PRAME Immunogenic Epitope

<400> SEQUENCE: 29

Ala Leu Tyr Val Asp Ser Leu Phe Phe Leu
1 5 10

<210> SEQ ID NO 30
<211> LENGTH: 9
<212> TYPE: PRT
<213> ORGANISM: Artificial Sequence
<220> FEATURE:
<223> OTHER INFORMATION: PRAME Immunogenic Epitope

<400> SEQUENCE: 30

Ser Leu Leu Gln His Leu Ile Gly Leu
1 5

<210> SEQ ID NO 31
<211> LENGTH: 9
<212> TYPE: PRT
<213> ORGANISM: Artificial Sequence
<220> FEATURE:
<223> OTHER INFORMATION: PRAME Immunogenic Epitope

<400> SEQUENCE: 31

Leu Tyr Val Asp Ser Leu Phe Phe Leu
1 5

<210> SEQ ID NO 32
<211> LENGTH: 11

<212> TYPE: PRT
<213> ORGANISM: Artificial Sequence
<220> FEATURE:
<223> OTHER INFORMATION: WT1 Immunogenic Epitope

<400> SEQUENCE: 32

Thr Ser Glu Lys Arg Pro Phe Met Cys Ala Tyr
1 5 10

<210> SEQ ID NO 33
<211> LENGTH: 9
<212> TYPE: PRT
<213> ORGANISM: Artificial Sequence
<220> FEATURE:
<223> OTHER INFORMATION: WT1 Immunogenic Epitope

<400> SEQUENCE: 33

Cys Met Thr Trp Asn Gln Met Asn Leu
1 5

<210> SEQ ID NO 34
<211> LENGTH: 11
<212> TYPE: PRT
<213> ORGANISM: Artificial Sequence
<220> FEATURE:
<223> OTHER INFORMATION: WT1 Immunogenic Epitope

<400> SEQUENCE: 34

Leu Ser His Leu Gln Met His Ser Arg Lys His
1 5 10

<210> SEQ ID NO 35
<211> LENGTH: 16
<212> TYPE: PRT
<213> ORGANISM: Artificial Sequence
<220> FEATURE:
<223> OTHER INFORMATION: WT1 Immunogenic Epitope

<400> SEQUENCE: 35

Lys Arg Tyr Phe Lys Leu Ser His Leu Gln Met His Ser Arg Lys His
1 5 10 15

<210> SEQ ID NO 36
<211> LENGTH: 8
<212> TYPE: PRT
<213> ORGANISM: Artificial Sequence
<220> FEATURE:
<223> OTHER INFORMATION: HSDL1 Immunogenic Epitope

<400> SEQUENCE: 36

Cys Tyr Met Glu Ala Val Ala Leu
1 5

<210> SEQ ID NO 37
<211> LENGTH: 9
<212> TYPE: PRT
<213> ORGANISM: Artificial Sequence
<220> FEATURE:
<223> OTHER INFORMATION: Mesothelin Immunogenic Epitope

<400> SEQUENCE: 37

Ser Leu Leu Phe Leu Leu Phe Ser Leu
1 5

<210> SEQ ID NO 38
<211> LENGTH: 9
<212> TYPE: PRT

<213> ORGANISM: Artificial Sequence
<220> FEATURE:
<223> OTHER INFORMATION: Mesothelin Immunogenic Epitope

<400> SEQUENCE: 38

Val Leu Pro Leu Thr Val Ala Glu Val
1               5

<210> SEQ ID NO 39
<211> LENGTH: 9
<212> TYPE: PRT
<213> ORGANISM: Artificial Sequence
<220> FEATURE:
<223> OTHER INFORMATION: Mesothelin Immunogenic Epitope

<400> SEQUENCE: 39

Ala Leu Gln Gly Gly Gly Pro Pro Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: Mesothelin Immunogenic Epitope

<400> SEQUENCE: 40

Leu Tyr Pro Lys Ala Arg Leu Ala Phe
1               5

<210> SEQ ID NO 41
<211> LENGTH: 9
<212> TYPE: PRT
<213> ORGANISM: Artificial Sequence
<220> FEATURE:
<223> OTHER INFORMATION: Mesothelin Immunogenic Epitope

<400> SEQUENCE: 41

Ala Phe Leu Pro Trp His Arg Leu Phe
1               5

<210> SEQ ID NO 42
<211> LENGTH: 9
<212> TYPE: PRT
<213> ORGANISM: Artificial Sequence
<220> FEATURE:
<223> OTHER INFORMATION: NY-ESO-1 Immunogenic Epitope

<400> SEQUENCE: 42

Ser Leu Leu Met Trp Ile Thr Gln Cys
1               5

<210> SEQ ID NO 43
<211> LENGTH: 9
<212> TYPE: PRT
<213> ORGANISM: Artificial Sequence
<220> FEATURE:
<223> OTHER INFORMATION: NY-ESO-1 Immunogenic Epitope

<400> SEQUENCE: 43

Leu Ala Met Pro Phe Ala Thr Pro Met
1               5

<210> SEQ ID NO 44
<211> LENGTH: 9
<212> TYPE: PRT
<213> ORGANISM: Artificial Sequence
<220> FEATURE:
<223> OTHER INFORMATION: NY-ESO-1 Immunogenic Epitope

<400> SEQUENCE: 44

Ala Arg Gly Pro Glu Ser Arg Leu Leu
1 5

<210> SEQ ID NO 45
<211> LENGTH: 11
<212> TYPE: PRT
<213> ORGANISM: Artificial Sequence
<220> FEATURE:
<223> OTHER INFORMATION: NY-ESO-1 Immunogenic Epitope

<400> SEQUENCE: 45

Met Leu Met Ala Gln Glu Ala Leu Ala Phe Leu
1 5 10

<210> SEQ ID NO 46
<211> LENGTH: 11
<212> TYPE: PRT
<213> ORGANISM: Artificial Sequence
<220> FEATURE:
<223> OTHER INFORMATION: NY-ESO-1 Immunogenic Epitope

<400> SEQUENCE: 46

Tyr Leu Ala Met Pro Phe Ala Thr Pro Met Glu
1 5 10

<210> SEQ ID NO 47
<211> LENGTH: 10
<212> TYPE: PRT
<213> ORGANISM: Artificial Sequence
<220> FEATURE:
<223> OTHER INFORMATION: NY-ESO-1 Immunogenic Epitope

<400> SEQUENCE: 47

Ala Ser Gly Pro Gly Gly Gly Ala Pro Arg
1 5 10

<210> SEQ ID NO 48
<211> LENGTH: 10
<212> TYPE: PRT
<213> ORGANISM: Artificial Sequence
<220> FEATURE:
<223> OTHER INFORMATION: NY-ESO-1 Immunogenic Epitope

<400> SEQUENCE: 48

Leu Ala Ala Gln Glu Arg Arg Val Pro Arg
1 5 10

<210> SEQ ID NO 49
<211> LENGTH: 10
<212> TYPE: PRT
<213> ORGANISM: Artificial Sequence
<220> FEATURE:
<223> OTHER INFORMATION: NY-ESO-1 Immunogenic Epitope

<400> SEQUENCE: 49

Thr Val Ser Gly Asn Ile Leu Thr Ile Arg
1 5 10

<210> SEQ ID NO 50
<211> LENGTH: 13
<212> TYPE: PRT
<213> ORGANISM: Artificial Sequence
<220> FEATURE:

-continued

<223> OTHER INFORMATION: NY-ESO-1 Immunogenic Epitope

<400> SEQUENCE: 50

Ala Pro Arg Gly Pro His Gly Gly Ala Ala Ser Gly Leu
1 5 10

<210> SEQ ID NO 51
<211> LENGTH: 11
<212> TYPE: PRT
<213> ORGANISM: Artificial Sequence
<220> FEATURE:
<223> OTHER INFORMATION: NY-ESO-1 Immunogenic Epitope

<400> SEQUENCE: 51

Met Pro Phe Ala Thr Pro Met Glu Ala Glu Leu
1 5 10

<210> SEQ ID NO 52
<211> LENGTH: 12
<212> TYPE: PRT
<213> ORGANISM: Artificial Sequence
<220> FEATURE:
<223> OTHER INFORMATION: NY-ESO-1 Immunogenic Epitope

<400> SEQUENCE: 52

Lys Glu Phe Thr Val Ser Gly Asn Ile Leu Thr Ile
1 5 10

<210> SEQ ID NO 53
<211> LENGTH: 9
<212> TYPE: PRT
<213> ORGANISM: Artificial Sequence
<220> FEATURE:
<223> OTHER INFORMATION: NY-ESO-1 Immunogenic Epitope

<400> SEQUENCE: 53

Met Pro Phe Ala Thr Pro Met Glu Ala
1 5

<210> SEQ ID NO 54
<211> LENGTH: 9
<212> TYPE: PRT
<213> ORGANISM: Artificial Sequence
<220> FEATURE:
<223> OTHER INFORMATION: NY-ESO-1 Immunogenic Epitope

<400> SEQUENCE: 54

Phe Ala Thr Pro Met Glu Ala Glu Leu
1 5

<210> SEQ ID NO 55
<211> LENGTH: 11
<212> TYPE: PRT
<213> ORGANISM: Artificial Sequence
<220> FEATURE:
<223> OTHER INFORMATION: NY-ESO-1 Immunogenic Epitope

<400> SEQUENCE: 55

Phe Ala Thr Pro Met Glu Ala Glu Leu Ala Arg
1 5 10

<210> SEQ ID NO 56
<211> LENGTH: 14
<212> TYPE: PRT
<213> ORGANISM: Artificial Sequence
<220> FEATURE:
<223> OTHER INFORMATION: NY-ESO-1 Immunogenic Epitope

<400> SEQUENCE: 56

Ser Leu Leu Met Trp Ile Thr Gln Cys Phe Leu Pro Val Phe
1 5 10

<210> SEQ ID NO 57
<211> LENGTH: 25
<212> TYPE: PRT
<213> ORGANISM: Artificial Sequence
<220> FEATURE:
<223> OTHER INFORMATION: NY-ESO-1 Immunogenic Epitope

<400> SEQUENCE: 57

Leu Leu Glu Phe Tyr Leu Ala Met Pro Phe Ala Thr Pro Met Glu Ala
1 5 10 15

Glu Leu Ala Arg Arg Ser Leu Ala Gln
20 25

<210> SEQ ID NO 58
<211> LENGTH: 12
<212> TYPE: PRT
<213> ORGANISM: Artificial Sequence
<220> FEATURE:
<223> OTHER INFORMATION: NY-ESO-1 Immunogenic Epitope

<400> SEQUENCE: 58

Glu Phe Tyr Leu Ala Met Pro Phe Ala Thr Pro Met
1 5 10

<210> SEQ ID NO 59
<211> LENGTH: 25
<212> TYPE: PRT
<213> ORGANISM: Artificial Sequence
<220> FEATURE:
<223> OTHER INFORMATION: NY-ESO-1 Immunogenic Epitope

<400> SEQUENCE: 59

Pro Gly Val Leu Leu Lys Glu Phe Thr Val Ser Gly Asn Ile Leu Thr
1 5 10 15

Ile Arg Leu Thr Ala Ala Asp His Arg
20 25

<210> SEQ ID NO 60
<211> LENGTH: 12
<212> TYPE: PRT
<213> ORGANISM: Artificial Sequence
<220> FEATURE:
<223> OTHER INFORMATION: NY-ESO-1 Immunogenic Epitope

<400> SEQUENCE: 60

Arg Leu Leu Glu Phe Tyr Leu Ala Met Pro Phe Ala
1 5 10

<210> SEQ ID NO 61
<211> LENGTH: 20
<212> TYPE: PRT
<213> ORGANISM: Artificial Sequence
<220> FEATURE:
<223> OTHER INFORMATION: NY-ESO-1 Immunogenic Epitope

<400> SEQUENCE: 61

Gln Gly Ala Met Leu Ala Ala Gln Glu Arg Arg Val Pro Arg Ala Ala
1 5 10 15

Glu Val Pro Arg
20

-continued

<210> SEQ ID NO 62
<211> LENGTH: 13
<212> TYPE: PRT
<213> ORGANISM: Artificial Sequence
<220> FEATURE:
<223> OTHER INFORMATION: NY-ESO-1 Immunogenic Epitope

<400> SEQUENCE: 62

Pro Phe Ala Thr Pro Met Glu Ala Glu Leu Ala Arg Arg
1 5 10

<210> SEQ ID NO 63
<211> LENGTH: 20
<212> TYPE: PRT
<213> ORGANISM: Artificial Sequence
<220> FEATURE:
<223> OTHER INFORMATION: NY-ESO-1 Immunogenic Epitope

<400> SEQUENCE: 63

Pro Gly Val Leu Leu Lys Glu Phe Thr Val Ser Gly Asn Ile Leu Thr
1 5 10 15

Ile Arg Leu Thr
20

<210> SEQ ID NO 64
<211> LENGTH: 10
<212> TYPE: PRT
<213> ORGANISM: Artificial Sequence
<220> FEATURE:
<223> OTHER INFORMATION: NY-ESO-1 Immunogenic Epitope

<400> SEQUENCE: 64

Val Leu Leu Lys Glu Phe Thr Val Ser Gly
1 5 10

<210> SEQ ID NO 65
<211> LENGTH: 18
<212> TYPE: PRT
<213> ORGANISM: Artificial Sequence
<220> FEATURE:
<223> OTHER INFORMATION: NY-ESO-1 Immunogenic Epitope

<400> SEQUENCE: 65

Ala Ala Asp His Arg Gln Leu Gln Leu Ser Ile Ser Ser Cys Leu Gln
1 5 10 15

Gln Leu

<210> SEQ ID NO 66
<211> LENGTH: 15
<212> TYPE: PRT
<213> ORGANISM: Artificial Sequence
<220> FEATURE:
<223> OTHER INFORMATION: NY-ESO-1 Immunogenic Epitope

<400> SEQUENCE: 66

Leu Lys Glu Phe Thr Val Ser Gly Asn Ile Leu Thr Ile Arg Leu
1 5 10 15

<210> SEQ ID NO 67
<211> LENGTH: 11
<212> TYPE: PRT
<213> ORGANISM: Artificial Sequence
<220> FEATURE:
<223> OTHER INFORMATION: NY-ESO-1 Immunogenic Epitope

<400> SEQUENCE: 67

Lys Glu Phe Thr Val Ser Gly Asn Ile Leu Thr
1 5 10

<210> SEQ ID NO 68
<211> LENGTH: 14
<212> TYPE: PRT
<213> ORGANISM: Artificial Sequence
<220> FEATURE:
<223> OTHER INFORMATION: NY-ESO-1 Immunogenic Epitope

<400> SEQUENCE: 68

Leu Leu Glu Phe Tyr Leu Ala Met Pro Phe Ala Thr Pro Met
1 5 10

<210> SEQ ID NO 69
<211> LENGTH: 14
<212> TYPE: PRT
<213> ORGANISM: Artificial Sequence
<220> FEATURE:
<223> OTHER INFORMATION: NY-ESO-1 Immunogenic Epitope

<400> SEQUENCE: 69

Ala Gly Ala Thr Gly Gly Arg Gly Pro Arg Gly Ala Gly Ala
1 5 10

<210> SEQ ID NO 70
<211> LENGTH: 13
<212> TYPE: PRT
<213> ORGANISM: Artificial Sequence
<220> FEATURE:
<223> OTHER INFORMATION: CEA Immunogenic Epitope

<400> SEQUENCE: 70

Thr Tyr Tyr Arg Pro Gly Val Asn Leu Ser Leu Ser Cys
1 5 10

<210> SEQ ID NO 71
<211> LENGTH: 13
<212> TYPE: PRT
<213> ORGANISM: Artificial Sequence
<220> FEATURE:
<223> OTHER INFORMATION: CEA Immunogenic Epitope

<400> SEQUENCE: 71

Glu Ile Ile Tyr Pro Asn Ala Ser Leu Leu Ile Gln Asn
1 5 10

<210> SEQ ID NO 72
<211> LENGTH: 15
<212> TYPE: PRT
<213> ORGANISM: Artificial Sequence
<220> FEATURE:
<223> OTHER INFORMATION: CEA Immunogenic Epitope

<400> SEQUENCE: 72

Tyr Ala Cys Phe Val Ser Asn Leu Ala Thr Gly Arg Asn Asn Ser
1 5 10 15

<210> SEQ ID NO 73
<211> LENGTH: 13
<212> TYPE: PRT
<213> ORGANISM: Artificial Sequence
<220> FEATURE:
<223> OTHER INFORMATION: CEA Immunogenic Epitope

<400> SEQUENCE: 73

Leu Trp Trp Val Asn Asn Gln Ser Leu Pro Val Ser Pro
1 5 10

<210> SEQ ID NO 74
<211> LENGTH: 13
<212> TYPE: PRT
<213> ORGANISM: Artificial Sequence
<220> FEATURE:
<223> OTHER INFORMATION: CEA Immunogenic Epitope

<400> SEQUENCE: 74

Asn Ser Ile Val Lys Ser Ile Thr Val Ser Ala Ser Gly
1 5 10

<210> SEQ ID NO 75
<211> LENGTH: 9
<212> TYPE: PRT
<213> ORGANISM: Artificial Sequence
<220> FEATURE:
<223> OTHER INFORMATION: CEA Immunogenic Epitope

<400> SEQUENCE: 75

Lys Thr Trp Gly Gln Tyr Trp Gln Val
1 5

<210> SEQ ID NO 76
<211> LENGTH: 10
<212> TYPE: PRT
<213> ORGANISM: Artificial Sequence
<220> FEATURE:
<223> OTHER INFORMATION: CEA Immunogenic Epitope

<400> SEQUENCE: 76

Ala Met Leu Gly Thr His Thr Met Glu Val
1 5 10

<210> SEQ ID NO 77
<211> LENGTH: 9
<212> TYPE: PRT
<213> ORGANISM: Artificial Sequence
<220> FEATURE:
<223> OTHER INFORMATION: CEA Immunogenic Epitope

<400> SEQUENCE: 77

Ile Thr Asp Gln Val Pro Phe Ser Val
1 5

<210> SEQ ID NO 78
<211> LENGTH: 9
<212> TYPE: PRT
<213> ORGANISM: Artificial Sequence
<220> FEATURE:
<223> OTHER INFORMATION: CEA Immunogenic Epitope

<400> SEQUENCE: 78

Tyr Leu Glu Pro Gly Pro Val Thr Ala
1 5

<210> SEQ ID NO 79
<211> LENGTH: 10
<212> TYPE: PRT
<213> ORGANISM: Artificial Sequence
<220> FEATURE:
<223> OTHER INFORMATION: CEA Immunogenic Epitope

<400> SEQUENCE: 79

Leu Leu Asp Gly Thr Ala Thr Leu Arg Leu
1 5 10

<210> SEQ ID NO 80
<211> LENGTH: 10
<212> TYPE: PRT
<213> ORGANISM: Artificial Sequence
<220> FEATURE:
<223> OTHER INFORMATION: CEA Immunogenic Epitope

<400> SEQUENCE: 80

Val Leu Tyr Arg Tyr Gly Ser Phe Ser Val
1 5 10

<210> SEQ ID NO 81
<211> LENGTH: 10
<212> TYPE: PRT
<213> ORGANISM: Artificial Sequence
<220> FEATURE:
<223> OTHER INFORMATION: CEA Immunogenic Epitope

<400> SEQUENCE: 81

Ser Leu Ala Asp Thr Asn Ser Leu Ala Val
1 5 10

<210> SEQ ID NO 82
<211> LENGTH: 9
<212> TYPE: PRT
<213> ORGANISM: Artificial Sequence
<220> FEATURE:
<223> OTHER INFORMATION: CEA Immunogenic Epitope

<400> SEQUENCE: 82

Arg Leu Met Lys Gln Asp Phe Ser Val
1 5

<210> SEQ ID NO 83
<211> LENGTH: 9
<212> TYPE: PRT
<213> ORGANISM: Artificial Sequence
<220> FEATURE:
<223> OTHER INFORMATION: CEA Immunogenic Epitope

<400> SEQUENCE: 83

Arg Leu Pro Arg Ile Phe Cys Ser Cys
1 5

<210> SEQ ID NO 84
<211> LENGTH: 9
<212> TYPE: PRT
<213> ORGANISM: Artificial Sequence
<220> FEATURE:
<223> OTHER INFORMATION: CEA Immunogenic Epitope

<400> SEQUENCE: 84

Leu Ile Tyr Arg Arg Arg Leu Met Lys
1 5

<210> SEQ ID NO 85
<211> LENGTH: 9
<212> TYPE: PRT
<213> ORGANISM: Artificial Sequence
<220> FEATURE:
<223> OTHER INFORMATION: CEA Immunogenic Epitope

<400> SEQUENCE: 85

Ala Leu Leu Ala Val Gly Ala Thr Lys 1 5

<210> SEQ ID NO 86
<211> LENGTH: 10
<212> TYPE: PRT
<213> ORGANISM: Artificial Sequence
<220> FEATURE:
<223> OTHER INFORMATION: CEA Immunogenic Epitope

<400> SEQUENCE: 86

Ile Ala Leu Asn Phe Pro Gly Ser Gln Lys
1 5 10

<210> SEQ ID NO 87
<211> LENGTH: 9
<212> TYPE: PRT
<213> ORGANISM: Artificial Sequence
<220> FEATURE:
<223> OTHER INFORMATION: CEA Immunogenic Epitope

<400> SEQUENCE: 87

Arg Ser Tyr Val Pro Leu Ala His Arg
1 5

<210> SEQ ID NO 88
<211> LENGTH: 9
<212> TYPE: PRT
<213> ORGANISM: Artificial Sequence
<220> FEATURE:
<223> OTHER INFORMATION: p53 Immunogenic Epitope

<400> SEQUENCE: 88

Val Val Pro Cys Glu Pro Pro Glu Val
1 5

<210> SEQ ID NO 89
<211> LENGTH: 9
<212> TYPE: PRT
<213> ORGANISM: Artificial Sequence
<220> FEATURE:
<223> OTHER INFORMATION: Her2/Neu Immunogenic Epitope

<400> SEQUENCE: 89

His Leu Tyr Gln Gly Cys Gln Val Val
1 5

<210> SEQ ID NO 90
<211> LENGTH: 10
<212> TYPE: PRT
<213> ORGANISM: Artificial Sequence
<220> FEATURE:
<223> OTHER INFORMATION: Her2/Neu Immunogenic Epitope

<400> SEQUENCE: 90

Tyr Leu Val Pro Gln Gln Gly Phe Phe Cys
1 5 10

<210> SEQ ID NO 91
<211> LENGTH: 9
<212> TYPE: PRT
<213> ORGANISM: Artificial Sequence
<220> FEATURE:
<223> OTHER INFORMATION: Her2/Neu Immunogenic Epitope

<400> SEQUENCE: 91

Pro Leu Gln Pro Glu Gln Leu Gln Val
1 5

<210> SEQ ID NO 92
<211> LENGTH: 9
<212> TYPE: PRT
<213> ORGANISM: Artificial Sequence
<220> FEATURE:
<223> OTHER INFORMATION: Her2/Neu Immunogenic Epitope

<400> SEQUENCE: 92

Thr Leu Glu Glu Ile Thr Gly Tyr Leu
1 5

<210> SEQ ID NO 93
<211> LENGTH: 9
<212> TYPE: PRT
<213> ORGANISM: Artificial Sequence
<220> FEATURE:
<223> OTHER INFORMATION: Her2/Neu Immunogenic Epitope

<400> SEQUENCE: 93

Ala Leu Ile His His Asn Thr His Leu
1 5

<210> SEQ ID NO 94
<211> LENGTH: 9
<212> TYPE: PRT
<213> ORGANISM: Artificial Sequence
<220> FEATURE:
<223> OTHER INFORMATION: Her2/Neu Immunogenic Epitope

<400> SEQUENCE: 94

Pro Leu Thr Ser Ile Ile Ser Ala Val
1 5

<210> SEQ ID NO 95
<211> LENGTH: 9
<212> TYPE: PRT
<213> ORGANISM: Artificial Sequence
<220> FEATURE:
<223> OTHER INFORMATION: Her2/Neu Immunogenic Epitope

<400> SEQUENCE: 95

Val Leu Arg Glu Asn Thr Ser Pro Lys
1 5

<210> SEQ ID NO 96
<211> LENGTH: 9
<212> TYPE: PRT
<213> ORGANISM: Artificial Sequence
<220> FEATURE:
<223> OTHER INFORMATION: Her2/Neu Immunogenic Epitope

<400> SEQUENCE: 96

Thr Tyr Leu Pro Thr Asn Ala Ser Leu
1 5

<210> SEQ ID NO 97
<211> LENGTH: 9
<212> TYPE: PRT
<213> ORGANISM: Artificial Sequence
<220> FEATURE:
<223> OTHER INFORMATION: EpCAM Immunogenic Epitope

<400> SEQUENCE: 97

Arg Tyr Gln Leu Asp Pro Lys Phe Ile
1 5

<210> SEQ ID NO 98
<211> LENGTH: 9
<212> TYPE: PRT
<213> ORGANISM: Artificial Sequence
<220> FEATURE:
<223> OTHER INFORMATION: CA125 Immunogenic Epitope

<400> SEQUENCE: 98

Ile Leu Phe Thr Ile Asn Phe Thr Ile
1 5

<210> SEQ ID NO 99
<211> LENGTH: 9
<212> TYPE: PRT
<213> ORGANISM: Artificial Sequence
<220> FEATURE:
<223> OTHER INFORMATION: CA125 Immunogenic Epitope

<400> SEQUENCE: 99

Val Leu Phe Thr Ile Asn Phe Thr Ile
1 5

<210> SEQ ID NO 100
<211> LENGTH: 9
<212> TYPE: PRT
<213> ORGANISM: Artificial Sequence
<220> FEATURE:
<223> OTHER INFORMATION: CA125 Immunogenic Epitope

<400> SEQUENCE: 100

Thr Leu Asn Phe Thr Ile Thr Asn Leu
1 5

<210> SEQ ID NO 101
<211> LENGTH: 9
<212> TYPE: PRT
<213> ORGANISM: Artificial Sequence
<220> FEATURE:
<223> OTHER INFORMATION: CA125 Immunogenic Epitope

<400> SEQUENCE: 101

Val Leu Gln Gly Leu Leu Lys Pro Leu
1 5

<210> SEQ ID NO 102
<211> LENGTH: 9
<212> TYPE: PRT
<213> ORGANISM: Artificial Sequence
<220> FEATURE:
<223> OTHER INFORMATION: CA125 Immunogenic Epitope

<400> SEQUENCE: 102

Val Leu Gln Gly Leu Leu Arg Pro Val
1 5

<210> SEQ ID NO 103
<211> LENGTH: 9
<212> TYPE: PRT
<213> ORGANISM: Artificial Sequence
<220> FEATURE:
<223> OTHER INFORMATION: CA125 Immunogenic Epitope

<400> SEQUENCE: 103

Arg Leu Asp Pro Lys Ser Pro Gly Val
1 5

<210> SEQ ID NO 104
<211> LENGTH: 9
<212> TYPE: PRT
<213> ORGANISM: Artificial Sequence
<220> FEATURE:
<223> OTHER INFORMATION: CA125 Immunogenic Epitope

<400> SEQUENCE: 104

Gln Leu Tyr Trp Glu Leu Ser Lys Leu
1 5

<210> SEQ ID NO 105
<211> LENGTH: 9
<212> TYPE: PRT
<213> ORGANISM: Artificial Sequence
<220> FEATURE:
<223> OTHER INFORMATION: CA125 Immunogenic Epitope

<400> SEQUENCE: 105

Lys Leu Thr Arg Gly Ile Val Glu Leu
1 5

<210> SEQ ID NO 106
<211> LENGTH: 9
<212> TYPE: PRT
<213> ORGANISM: Artificial Sequence
<220> FEATURE:
<223> OTHER INFORMATION: CA125 Immunogenic Epitope

<400> SEQUENCE: 106

Gln Leu Thr Asn Gly Ile Thr Glu Leu
1 5

<210> SEQ ID NO 107
<211> LENGTH: 9
<212> TYPE: PRT
<213> ORGANISM: Artificial Sequence
<220> FEATURE:
<223> OTHER INFORMATION: CA125 Immunogenic Epitope

<400> SEQUENCE: 107

Gln Leu Thr His Asn Ile Thr Glu Leu
1 5

<210> SEQ ID NO 108
<211> LENGTH: 9
<212> TYPE: PRT
<213> ORGANISM: Artificial Sequence
<220> FEATURE:
<223> OTHER INFORMATION: CA125 Immunogenic Epitope

<400> SEQUENCE: 108

Thr Leu Asp Arg Asn Ser Leu Tyr Val
1 5

<210> SEQ ID NO 109
<211> LENGTH: 9
<212> TYPE: PRT
<213> ORGANISM: Artificial Sequence
<220> FEATURE:
<223> OTHER INFORMATION: Folate receptor ? Immunogenic Epitope

<400> SEQUENCE: 109

Phe Leu Leu Ser Leu Ala Leu Met Leu
1 5

<210> SEQ ID NO 110

<211> LENGTH: 9
<212> TYPE: PRT
<213> ORGANISM: Artificial Sequence
<220> FEATURE:
<223> OTHER INFORMATION: Folate receptor ? Immunogenic Epitope

<400> SEQUENCE: 110

Asn Leu Gly Pro Trp Ile Gln Gln Val
1               5

<210> SEQ ID NO 111
<211> LENGTH: 9
<212> TYPE: PRT
<213> ORGANISM: Artificial Sequence
<220> FEATURE:
<223> OTHER INFORMATION: Sperm protein 17 Immunogenic Epitope

<400> SEQUENCE: 111

Ile Leu Asp Ser Ser Glu Glu Asp Lys
1               5

<210> SEQ ID NO 112
<211> LENGTH: 10
<212> TYPE: PRT
<213> ORGANISM: Artificial Sequence
<220> FEATURE:
<223> OTHER INFORMATION: TADG-12 Immunogenic Epitope

<400> SEQUENCE: 112

Tyr Leu Pro Lys Ser Trp Thr Ile Gln Val
1               5                   10

<210> SEQ ID NO 113
<211> LENGTH: 12
<212> TYPE: PRT
<213> ORGANISM: Artificial Sequence
<220> FEATURE:
<223> OTHER INFORMATION: TADG-12 Immunogenic Epitope

<400> SEQUENCE: 113

Trp Ile His Glu Gln Met Glu Arg Asp Leu Lys Thr
1               5                   10

<210> SEQ ID NO 114
<211> LENGTH: 9
<212> TYPE: PRT
<213> ORGANISM: Artificial Sequence
<220> FEATURE:
<223> OTHER INFORMATION: MUC-16 Immunogenic Epitope

<400> SEQUENCE: 114

Ile Leu Phe Thr Ile Asn Phe Thr Ile
1               5

<210> SEQ ID NO 115
<211> LENGTH: 9
<212> TYPE: PRT
<213> ORGANISM: Artificial Sequence
<220> FEATURE:
<223> OTHER INFORMATION: MUC-16 Immunogenic Epitope

<400> SEQUENCE: 115

Val Leu Phe Thr Ile Asn Phe Thr Ile
1               5

<210> SEQ ID NO 116
<211> LENGTH: 9

<212> TYPE: PRT
<213> ORGANISM: Artificial Sequence
<220> FEATURE:
<223> OTHER INFORMATION: MUC-16 Immunogenic Epitope

<400> SEQUENCE: 116

Thr Leu Asn Phe Thr Ile Thr Asn Leu
1 5

<210> SEQ ID NO 117
<211> LENGTH: 9
<212> TYPE: PRT
<213> ORGANISM: Artificial Sequence
<220> FEATURE:
<223> OTHER INFORMATION: MUC-16 Immunogenic Epitope

<400> SEQUENCE: 117

Val Leu Gln Gly Leu Leu Lys Pro Leu
1 5

<210> SEQ ID NO 118
<211> LENGTH: 9
<212> TYPE: PRT
<213> ORGANISM: Artificial Sequence
<220> FEATURE:
<223> OTHER INFORMATION: MUC-16 Immunogenic Epitope

<400> SEQUENCE: 118

Val Leu Gln Gly Leu Leu Arg Pro Val
1 5

<210> SEQ ID NO 119
<211> LENGTH: 9
<212> TYPE: PRT
<213> ORGANISM: Artificial Sequence
<220> FEATURE:
<223> OTHER INFORMATION: MUC-16 Immunogenic Epitope

<400> SEQUENCE: 119

Arg Leu Asp Pro Lys Ser Pro Gly Val
1 5

<210> SEQ ID NO 120
<211> LENGTH: 9
<212> TYPE: PRT
<213> ORGANISM: Artificial Sequence
<220> FEATURE:
<223> OTHER INFORMATION: MUC-16 Immunogenic Epitope

<400> SEQUENCE: 120

Gln Leu Tyr Trp Glu Leu Ser Lys Leu
1 5

<210> SEQ ID NO 121
<211> LENGTH: 9
<212> TYPE: PRT
<213> ORGANISM: Artificial Sequence
<220> FEATURE:
<223> OTHER INFORMATION: MUC-16 Immunogenic Epitope

<400> SEQUENCE: 121

Lys Leu Thr Arg Gly Ile Val Glu Leu
1 5

<210> SEQ ID NO 122
<211> LENGTH: 9
<212> TYPE: PRT

<213> ORGANISM: Artificial Sequence
<220> FEATURE:
<223> OTHER INFORMATION: MUC-16 Immunogenic Epitope

<400> SEQUENCE: 122

Gln Leu Thr Asn Gly Ile Thr Glu Leu
1               5

<210> SEQ ID NO 123
<211> LENGTH: 9
<212> TYPE: PRT
<213> ORGANISM: Artificial Sequence
<220> FEATURE:
<223> OTHER INFORMATION: MUC-16 Immunogenic Epitope

<400> SEQUENCE: 123

Gln Leu Thr His Asn Ile Thr Glu Leu
1               5

<210> SEQ ID NO 124
<211> LENGTH: 9
<212> TYPE: PRT
<213> ORGANISM: Artificial Sequence
<220> FEATURE:
<223> OTHER INFORMATION: MUC-16 Immunogenic Epitope

<400> SEQUENCE: 124

Thr Leu Asp Arg Asn Ser Leu Tyr Val
1               5

<210> SEQ ID NO 125
<211> LENGTH: 9
<212> TYPE: PRT
<213> ORGANISM: Artificial Sequence
<220> FEATURE:
<223> OTHER INFORMATION: L1CAM Immunogenic Epitope

<400> SEQUENCE: 125

Leu Leu Ala Asn Ala Tyr Ile Tyr Val
1               5

<210> SEQ ID NO 126
<211> LENGTH: 9
<212> TYPE: PRT
<213> ORGANISM: Artificial Sequence
<220> FEATURE:
<223> OTHER INFORMATION: L1CAM Immunogenic Epitope

<400> SEQUENCE: 126

Tyr Leu Leu Cys Lys Ala Phe Gly Ala
1               5

<210> SEQ ID NO 127
<211> LENGTH: 9
<212> TYPE: PRT
<213> ORGANISM: Artificial Sequence
<220> FEATURE:
<223> OTHER INFORMATION: L1CAM Immunogenic Epitope

<400> SEQUENCE: 127

Lys Leu Ser Pro Tyr Val His Tyr Thr
1               5

<210> SEQ ID NO 128
<211> LENGTH: 20
<212> TYPE: PRT
<213> ORGANISM: Artificial Sequence -continued
<220> FEATURE:
<223> OTHER INFORMATION: Mannan-MUC-1 Immunogenic Epitope

<400> SEQUENCE: 128

Pro Asp Thr Arg Pro Ala Pro Gly Ser Thr Ala Pro Pro Ala His Gly
1 5 10 15

Val Thr Ser Ala
20

<210> SEQ ID NO 129
<211> LENGTH: 9
<212> TYPE: PRT
<213> ORGANISM: Artificial Sequence
<220> FEATURE:
<223> OTHER INFORMATION: Mannan-MUC-1 Immunogenic Epitope

<400> SEQUENCE: 129

Ser Thr Ala Pro Pro Val His Asn Val
1 5

<210> SEQ ID NO 130
<211> LENGTH: 9
<212> TYPE: PRT
<213> ORGANISM: Artificial Sequence
<220> FEATURE:
<223> OTHER INFORMATION: Mannan-MUC-1 Immunogenic Epitope

<400> SEQUENCE: 130

Leu Leu Leu Leu Thr Val Leu Thr Val
1 5

<210> SEQ ID NO 131
<211> LENGTH: 12
<212> TYPE: PRT
<213> ORGANISM: Artificial Sequence
<220> FEATURE:
<223> OTHER INFORMATION: Mannan-MUC-1 Immunogenic Epitope

<400> SEQUENCE: 131

Pro Gly Ser Thr Ala Pro Pro Ala His Gly Val Thr
1 5 10

<210> SEQ ID NO 132
<211> LENGTH: 9
<212> TYPE: PRT
<213> ORGANISM: Artificial Sequence
<220> FEATURE:
<223> OTHER INFORMATION: HERV-K-MEL Immunogenic Epitope

<400> SEQUENCE: 132

Met Leu Ala Val Ile Ser Cys Ala Val
1 5

<210> SEQ ID NO 133
<211> LENGTH: 9
<212> TYPE: PRT
<213> ORGANISM: Artificial Sequence
<220> FEATURE:
<223> OTHER INFORMATION: KK-LC-1 Immunogenic Epitope

<400> SEQUENCE: 133

Arg Gln Lys Arg Ile Leu Val Asn Leu
1 5

<210> SEQ ID NO 134
<211> LENGTH: 9

<212> TYPE: PRT
<213> ORGANISM: Artificial Sequence
<220> FEATURE:
<223> OTHER INFORMATION: KM-HN-1 Immunogenic Epitope

<400> SEQUENCE: 134

Asn Tyr Asn Asn Phe Tyr Arg Phe Leu
1               5

<210> SEQ ID NO 135
<211> LENGTH: 10
<212> TYPE: PRT
<213> ORGANISM: Artificial Sequence
<220> FEATURE:
<223> OTHER INFORMATION: KM-HN-1 Immunogenic Epitope

<400> SEQUENCE: 135

Glu Tyr Ser Lys Glu Cys Leu Lys Glu Phe
1               5                   10

<210> SEQ ID NO 136
<211> LENGTH: 9
<212> TYPE: PRT
<213> ORGANISM: Artificial Sequence
<220> FEATURE:
<223> OTHER INFORMATION: KM-HN-1 Immunogenic Epitope

<400> SEQUENCE: 136

Glu Tyr Leu Ser Leu Ser Asp Lys Ile
1               5

<210> SEQ ID NO 137
<211> LENGTH: 11
<212> TYPE: PRT
<213> ORGANISM: Artificial Sequence
<220> FEATURE:
<223> OTHER INFORMATION: LAGE-1 Immunogenic Epitope

<400> SEQUENCE: 137

Met Leu Met Ala Gln Glu Ala Leu Ala Phe Leu
1               5                   10

<210> SEQ ID NO 138
<211> LENGTH: 9
<212> TYPE: PRT
<213> ORGANISM: Artificial Sequence
<220> FEATURE:
<223> OTHER INFORMATION: LAGE-1 Immunogenic Epitope

<400> SEQUENCE: 138

Ser Leu Leu Met Trp Ile Thr Gln Cys
1               5

<210> SEQ ID NO 139
<211> LENGTH: 10
<212> TYPE: PRT
<213> ORGANISM: Artificial Sequence
<220> FEATURE:
<223> OTHER INFORMATION: LAGE-1 Immunogenic Epitope

<400> SEQUENCE: 139

Leu Ala Ala Gln Glu Arg Arg Val Pro Arg
1               5                   10

<210> SEQ ID NO 140
<211> LENGTH: 9
<212> TYPE: PRT

<213> ORGANISM: Artificial Sequence
<220> FEATURE:
<223> OTHER INFORMATION: LAGE-1 Immunogenic Epitope

<400> SEQUENCE: 140

Glu Leu Val Arg Arg Ile Leu Ser Arg
1 5

<210> SEQ ID NO 141
<211> LENGTH: 9
<212> TYPE: PRT
<213> ORGANISM: Artificial Sequence
<220> FEATURE:
<223> OTHER INFORMATION: LAGE-1 Immunogenic Epitope

<400> SEQUENCE: 141

Ala Pro Arg Gly Val Arg Met Ala Val
1 5

<210> SEQ ID NO 142
<211> LENGTH: 14
<212> TYPE: PRT
<213> ORGANISM: Artificial Sequence
<220> FEATURE:
<223> OTHER INFORMATION: LAGE-1 Immunogenic Epitope

<400> SEQUENCE: 142

Ser Leu Leu Met Trp Ile Thr Gln Cys Phe Leu Pro Val Phe
1 5 10

<210> SEQ ID NO 143
<211> LENGTH: 20
<212> TYPE: PRT
<213> ORGANISM: Artificial Sequence
<220> FEATURE:
<223> OTHER INFORMATION: LAGE-1 Immunogenic Epitope

<400> SEQUENCE: 143

Gln Gly Ala Met Leu Ala Ala Gln Glu Arg Arg Val Pro Arg Ala Ala
1 5 10 15

Glu Val Pro Arg
20

<210> SEQ ID NO 144
<211> LENGTH: 18
<212> TYPE: PRT
<213> ORGANISM: Artificial Sequence
<220> FEATURE:
<223> OTHER INFORMATION: LAGE-1 Immunogenic Epitope

<400> SEQUENCE: 144

Ala Ala Asp His Arg Gln Leu Gln Leu Ser Ile Ser Ser Cys Leu Gln
1 5 10 15

Gln Leu

<210> SEQ ID NO 145
<211> LENGTH: 22
<212> TYPE: PRT
<213> ORGANISM: Artificial Sequence
<220> FEATURE:
<223> OTHER INFORMATION: LAGE-1 Immunogenic Epitope

<400> SEQUENCE: 145

Cys Leu Ser Arg Arg Pro Trp Lys Arg Ser Trp Ser Ala Gly Ser Cys
1 5 10 15

Pro Gly Met Pro His Leu
20

<210> SEQ ID NO 146
<211> LENGTH: 13
<212> TYPE: PRT
<213> ORGANISM: Artificial Sequence
<220> FEATURE:
<223> OTHER INFORMATION: LAGE-1 Immunogenic Epitope

<400> SEQUENCE: 146

Ile Leu Ser Arg Asp Ala Ala Pro Leu Pro Arg Pro Gly
1 5 10

<210> SEQ ID NO 147
<211> LENGTH: 14
<212> TYPE: PRT
<213> ORGANISM: Artificial Sequence
<220> FEATURE:
<223> OTHER INFORMATION: LAGE-1 Immunogenic Epitope

<400> SEQUENCE: 147

Ala Gly Ala Thr Gly Gly Arg Gly Pro Arg Gly Ala Gly Ala
1 5 10

<210> SEQ ID NO 148
<211> LENGTH: 9
<212> TYPE: PRT
<213> ORGANISM: Artificial Sequence
<220> FEATURE:
<223> OTHER INFORMATION: MAGE-A4 Immunogenic Epitope

<400> SEQUENCE: 148

Glu Val Asp Pro Ala Ser Asn Thr Tyr
1 5

<210> SEQ ID NO 149
<211> LENGTH: 10
<212> TYPE: PRT
<213> ORGANISM: Artificial Sequence
<220> FEATURE:
<223> OTHER INFORMATION: MAGE-A4 Immunogenic Epitope

<400> SEQUENCE: 149

Gly Val Tyr Asp Gly Arg Glu His Thr Val
1 5 10

<210> SEQ ID NO 150
<211> LENGTH: 9
<212> TYPE: PRT
<213> ORGANISM: Artificial Sequence
<220> FEATURE:
<223> OTHER INFORMATION: MAGE-A4 Immunogenic Epitope

<400> SEQUENCE: 150

Asn Tyr Lys Arg Cys Phe Pro Val Ile
1 5

<210> SEQ ID NO 151
<211> LENGTH: 8
<212> TYPE: PRT
<213> ORGANISM: Artificial Sequence
<220> FEATURE:
<223> OTHER INFORMATION: MAGE-A4 Immunogenic Epitope

<400> SEQUENCE: 151

Ser Glu Ser Leu Lys Met Ile Phe 1 5

<210> SEQ ID NO 152
<211> LENGTH: 9
<212> TYPE: PRT
<213> ORGANISM: Artificial Sequence
<220> FEATURE:
<223> OTHER INFORMATION: Sp17 Immunogenic Epitope

<400> SEQUENCE: 152

Ile Leu Asp Ser Ser Glu Glu Asp Lys
1 5

<210> SEQ ID NO 153
<211> LENGTH: 20
<212> TYPE: PRT
<213> ORGANISM: Artificial Sequence
<220> FEATURE:
<223> OTHER INFORMATION: SSX-4 Immunogenic Epitope

<400> SEQUENCE: 153

Ile Asn Lys Thr Ser Gly Pro Lys Arg Gly Lys His Ala Trp Thr His
1 5 10 15

Arg Leu Arg Glu
20

<210> SEQ ID NO 154
<211> LENGTH: 20
<212> TYPE: PRT
<213> ORGANISM: Artificial Sequence
<220> FEATURE:
<223> OTHER INFORMATION: SSX-4 Immunogenic Epitope

<400> SEQUENCE: 154

Tyr Phe Ser Lys Lys Glu Trp Glu Lys Met Lys Ser Ser Glu Lys Ile
1 5 10 15

Val Tyr Val Tyr
20

<210> SEQ ID NO 155
<211> LENGTH: 20
<212> TYPE: PRT
<213> ORGANISM: Artificial Sequence
<220> FEATURE:
<223> OTHER INFORMATION: SSX-4 Immunogenic Epitope

<400> SEQUENCE: 155

Met Lys Leu Asn Tyr Glu Val Met Thr Lys Leu Gly Phe Lys Val Thr
1 5 10 15

Leu Pro Pro Phe
20

<210> SEQ ID NO 156
<211> LENGTH: 20
<212> TYPE: PRT
<213> ORGANISM: Artificial Sequence
<220> FEATURE:
<223> OTHER INFORMATION: SSX-4 Immunogenic Epitope

<400> SEQUENCE: 156

Lys His Ala Trp Thr His Arg Leu Arg Glu Arg Lys Gln Leu Val Val
1 5 10 15

Tyr Glu Glu Ile
20

<210> SEQ ID NO 157
<211> LENGTH: 20
<212> TYPE: PRT
<213> ORGANISM: Artificial Sequence
<220> FEATURE:
<223> OTHER INFORMATION: SSX-4 Immunogenic Epitope

<400> SEQUENCE: 157

```
Leu Gly Phe Lys Val Thr Leu Pro Pro Phe Met Arg Ser Lys Arg Ala
1               5                   10                  15

Ala Asp Phe His
            20
```

<210> SEQ ID NO 158
<211> LENGTH: 20
<212> TYPE: PRT
<213> ORGANISM: Artificial Sequence
<220> FEATURE:
<223> OTHER INFORMATION: SSX-4 Immunogenic Epitope

<400> SEQUENCE: 158

```
Lys Ser Ser Glu Lys Ile Val Tyr Val Tyr Met Lys Leu Asn Tyr Glu
1               5                   10                  15

Val Met Thr Lys
            20
```

<210> SEQ ID NO 159
<211> LENGTH: 9
<212> TYPE: PRT
<213> ORGANISM: Artificial Sequence
<220> FEATURE:
<223> OTHER INFORMATION: TAG-1 Immunogenic Epitope

<400> SEQUENCE: 159

```
Ser Leu Gly Trp Leu Phe Leu Leu Leu
1               5
```

<210> SEQ ID NO 160
<211> LENGTH: 9
<212> TYPE: PRT
<213> ORGANISM: Artificial Sequence
<220> FEATURE:
<223> OTHER INFORMATION: TAG-1 Immunogenic Epitope

<400> SEQUENCE: 160

```
Leu Ser Arg Leu Ser Asn Arg Leu Leu
1               5
```

<210> SEQ ID NO 161
<211> LENGTH: 9
<212> TYPE: PRT
<213> ORGANISM: Artificial Sequence
<220> FEATURE:
<223> OTHER INFORMATION: TAG-2 Immunogenic Epitope

<400> SEQUENCE: 161

```
Leu Ser Arg Leu Ser Asn Arg Leu Leu
1               5
```

<210> SEQ ID NO 162
<211> LENGTH: 9
<212> TYPE: PRT
<213> ORGANISM: Artificial Sequence
<220> FEATURE:
<223> OTHER INFORMATION: ENAH(hMena) Immunogenic Epitope

<400> SEQUENCE: 162

Thr Met Asn Gly Ser Lys Ser Pro Val
1 5

<210> SEQ ID NO 163
<211> LENGTH: 9
<212> TYPE: PRT
<213> ORGANISM: Artificial Sequence
<220> FEATURE:
<223> OTHER INFORMATION: mammaglobin-A Immunogenic Epitope

<400> SEQUENCE: 163

Pro Leu Leu Glu Asn Val Ile Ser Lys
1 5

<210> SEQ ID NO 164
<211> LENGTH: 9
<212> TYPE: PRT
<213> ORGANISM: Artificial Sequence
<220> FEATURE:
<223> OTHER INFORMATION: NY-BR-1 Immunogenic Epitope

<400> SEQUENCE: 164

Ser Leu Ser Lys Ile Leu Asp Thr Val
1 5

<210> SEQ ID NO 165
<211> LENGTH: 9
<212> TYPE: PRT
<213> ORGANISM: Artificial Sequence
<220> FEATURE:
<223> OTHER INFORMATION: BAGE-1 Immunogenic Epitope

<400> SEQUENCE: 165

Ala Ala Arg Ala Val Phe Leu Ala Leu
1 5

<210> SEQ ID NO 166
<211> LENGTH: 9
<212> TYPE: PRT
<213> ORGANISM: Artificial Sequence
<220> FEATURE:
<223> OTHER INFORMATION: MAGE-A1 Immunogenic Epitope

<400> SEQUENCE: 166

Glu Ala Asp Pro Thr Gly His Ser Tyr
1 5

<210> SEQ ID NO 167
<211> LENGTH: 9
<212> TYPE: PRT
<213> ORGANISM: Artificial Sequence
<220> FEATURE:
<223> OTHER INFORMATION: MAGE-A1 Immunogenic Epitope

<400> SEQUENCE: 167

Lys Val Leu Glu Tyr Val Ile Lys Val
1 5

<210> SEQ ID NO 168
<211> LENGTH: 9
<212> TYPE: PRT
<213> ORGANISM: Artificial Sequence
<220> FEATURE:
<223> OTHER INFORMATION: MAGE-A1 Immunogenic Epitope

<400> SEQUENCE: 168

Ser Leu Phe Arg Ala Val Ile Thr Lys
1 5

<210> SEQ ID NO 169
<211> LENGTH: 10
<212> TYPE: PRT
<213> ORGANISM: Artificial Sequence
<220> FEATURE:
<223> OTHER INFORMATION: MAGE-A1 Immunogenic Epitope

<400> SEQUENCE: 169

Glu Val Tyr Asp Gly Arg Glu His Ser Ala
1 5 10

<210> SEQ ID NO 170
<211> LENGTH: 9
<212> TYPE: PRT
<213> ORGANISM: Artificial Sequence
<220> FEATURE:
<223> OTHER INFORMATION: MAGE-A1 Immunogenic Epitope

<400> SEQUENCE: 170

Arg Val Arg Phe Phe Phe Pro Ser Leu
1 5

<210> SEQ ID NO 171
<211> LENGTH: 10
<212> TYPE: PRT
<213> ORGANISM: Artificial Sequence
<220> FEATURE:
<223> OTHER INFORMATION: MAGE-A1 Immunogenic Epitope

<400> SEQUENCE: 171

Arg Glu Pro Val Thr Lys Ala Glu Met Leu
1 5 10

<210> SEQ ID NO 172
<211> LENGTH: 10
<212> TYPE: PRT
<213> ORGANISM: Artificial Sequence
<220> FEATURE:
<223> OTHER INFORMATION: MAGE-A1 Immunogenic Epitope

<400> SEQUENCE: 172

Lys Glu Ala Asp Pro Thr Gly His Ser Tyr
1 5 10

<210> SEQ ID NO 173
<211> LENGTH: 9
<212> TYPE: PRT
<213> ORGANISM: Artificial Sequence
<220> FEATURE:
<223> OTHER INFORMATION: MAGE-A1 Immunogenic Epitope

<400> SEQUENCE: 173

Asp Pro Ala Arg Tyr Glu Phe Leu Trp
1 5

<210> SEQ ID NO 174
<211> LENGTH: 11
<212> TYPE: PRT
<213> ORGANISM: Artificial Sequence
<220> FEATURE:
<223> OTHER INFORMATION: MAGE-A1 Immunogenic Epitope

<400> SEQUENCE: 174

Ile Thr Lys Lys Val Ala Asp Leu Val Gly Phe
1 5 10

<210> SEQ ID NO 175
<211> LENGTH: 9
<212> TYPE: PRT
<213> ORGANISM: Artificial Sequence
<220> FEATURE:
<223> OTHER INFORMATION: MAGE-A1 Immunogenic Epitope

<400> SEQUENCE: 175

Ser Ala Phe Pro Thr Thr Ile Asn Phe
1 5

<210> SEQ ID NO 176
<211> LENGTH: 9
<212> TYPE: PRT
<213> ORGANISM: Artificial Sequence
<220> FEATURE:
<223> OTHER INFORMATION: MAGE-A1 Immunogenic Epitope

<400> SEQUENCE: 176

Ser Ala Tyr Gly Glu Pro Arg Lys Leu
1 5

<210> SEQ ID NO 177
<211> LENGTH: 15
<212> TYPE: PRT
<213> ORGANISM: Artificial Sequence
<220> FEATURE:
<223> OTHER INFORMATION: MAGE-A1 Immunogenic Epitope

<400> SEQUENCE: 177

Thr Ser Cys Ile Leu Glu Ser Leu Phe Arg Ala Val Ile Thr Lys
1 5 10 15

<210> SEQ ID NO 178
<211> LENGTH: 15
<212> TYPE: PRT
<213> ORGANISM: Artificial Sequence
<220> FEATURE:
<223> OTHER INFORMATION: MAGE-A1 Immunogenic Epitope

<400> SEQUENCE: 178

Pro Arg Ala Leu Ala Glu Thr Ser Tyr Val Lys Val Leu Glu Tyr
1 5 10 15

<210> SEQ ID NO 179
<211> LENGTH: 16
<212> TYPE: PRT
<213> ORGANISM: Artificial Sequence
<220> FEATURE:
<223> OTHER INFORMATION: MAGE-A1 Immunogenic Epitope

<400> SEQUENCE: 179

Phe Leu Leu Leu Lys Tyr Arg Ala Arg Glu Pro Val Thr Lys Ala Glu
1 5 10 15

<210> SEQ ID NO 180
<211> LENGTH: 12
<212> TYPE: PRT
<213> ORGANISM: Artificial Sequence
<220> FEATURE:
<223> OTHER INFORMATION: MAGE-A1 Immunogenic Epitope

<400> SEQUENCE: 180

Glu Tyr Val Ile Lys Val Ser Ala Arg Val Arg Phe 1 5 10

<210> SEQ ID NO 181
<211> LENGTH: 10
<212> TYPE: PRT
<213> ORGANISM: Artificial Sequence
<220> FEATURE:
<223> OTHER INFORMATION: MAGE-A2 Immunogenic Epitope

<400> SEQUENCE: 181

Tyr Leu Gln Leu Val Phe Gly Ile Glu Val
1 5 10

<210> SEQ ID NO 182
<211> LENGTH: 9
<212> TYPE: PRT
<213> ORGANISM: Artificial Sequence
<220> FEATURE:
<223> OTHER INFORMATION: MAGE-A2 Immunogenic Epitope

<400> SEQUENCE: 182

Glu Tyr Leu Gln Leu Val Phe Gly Ile
1 5

<210> SEQ ID NO 183
<211> LENGTH: 10
<212> TYPE: PRT
<213> ORGANISM: Artificial Sequence
<220> FEATURE:
<223> OTHER INFORMATION: MAGE-A2 Immunogenic Epitope

<400> SEQUENCE: 183

Arg Glu Pro Val Thr Lys Ala Glu Met Leu
1 5 10

<210> SEQ ID NO 184
<211> LENGTH: 9
<212> TYPE: PRT
<213> ORGANISM: Artificial Sequence
<220> FEATURE:
<223> OTHER INFORMATION: MAGE-A2 Immunogenic Epitope

<400> SEQUENCE: 184

Glu Gly Asp Cys Ala Pro Glu Glu Lys
1 5

<210> SEQ ID NO 185
<211> LENGTH: 14
<212> TYPE: PRT
<213> ORGANISM: Artificial Sequence
<220> FEATURE:
<223> OTHER INFORMATION: MAGE-A2 Immunogenic Epitope

<400> SEQUENCE: 185

Leu Leu Lys Tyr Arg Ala Arg Glu Pro Val Thr Lys Ala Glu
1 5 10

<210> SEQ ID NO 186
<211> LENGTH: 9
<212> TYPE: PRT
<213> ORGANISM: Artificial Sequence
<220> FEATURE:
<223> OTHER INFORMATION: SSX-2 Immunogenic Epitope

<400> SEQUENCE: 186

Lys Ala Ser Glu Lys Ile Phe Tyr Val
1 5

<210> SEQ ID NO 187
<211> LENGTH: 16
<212> TYPE: PRT
<213> ORGANISM: Artificial Sequence
<220> FEATURE:
<223> OTHER INFORMATION: SSX-2 Immunogenic Epitope

<400> SEQUENCE: 187

Glu Lys Ile Gln Lys Ala Phe Asp Asp Ile Ala Lys Tyr Phe Ser Lys
1 5 10 15

<210> SEQ ID NO 188
<211> LENGTH: 11
<212> TYPE: PRT
<213> ORGANISM: Artificial Sequence
<220> FEATURE:
<223> OTHER INFORMATION: SSX-2 Immunogenic Epitope

<400> SEQUENCE: 188

Phe Gly Arg Leu Gln Gly Ile Ser Pro Lys Ile
1 5 10

<210> SEQ ID NO 189
<211> LENGTH: 18
<212> TYPE: PRT
<213> ORGANISM: Artificial Sequence
<220> FEATURE:
<223> OTHER INFORMATION: SSX-2 Immunogenic Epitope

<400> SEQUENCE: 189

Trp Glu Lys Met Lys Ala Ser Glu Lys Ile Phe Tyr Val Tyr Met Lys
1 5 10 15

Arg Lys

<210> SEQ ID NO 190
<211> LENGTH: 15
<212> TYPE: PRT
<213> ORGANISM: Artificial Sequence
<220> FEATURE:
<223> OTHER INFORMATION: SSX-2 Immunogenic Epitope

<400> SEQUENCE: 190

Lys Ile Phe Tyr Val Tyr Met Lys Arg Lys Tyr Glu Ala Met Thr
1 5 10 15

<210> SEQ ID NO 191
<211> LENGTH: 14
<212> TYPE: PRT
<213> ORGANISM: Artificial Sequence
<220> FEATURE:
<223> OTHER INFORMATION: SSX-2 Immunogenic Epitope

<400> SEQUENCE: 191

Lys Ile Phe Tyr Val Tyr Met Lys Arg Lys Tyr Glu Ala Met
1 5 10

<210> SEQ ID NO 192
<211> LENGTH: 15
<212> TYPE: PRT
<213> ORGANISM: Artificial Sequence
<220> FEATURE:
<223> OTHER INFORMATION: TRAG-3 Immunogenic Epitope

<400> SEQUENCE: 192

Cys Glu Phe His Ala Cys Trp Pro Ala Phe Thr Val Leu Gly Glu 1 5 10 15

<210> SEQ ID NO 193
<211> LENGTH: 10
<212> TYPE: PRT
<213> ORGANISM: Artificial Sequence
<220> FEATURE:
<223> OTHER INFORMATION: c-myc Immunogenic Epitope

<400> SEQUENCE: 193

Ser Ser Pro Gln Gly Ser Pro Glu Pro Leu
1 5 10

<210> SEQ ID NO 194
<211> LENGTH: 9
<212> TYPE: PRT
<213> ORGANISM: Artificial Sequence
<220> FEATURE:
<223> OTHER INFORMATION: cyclin B1 Immunogenic Epitope

<400> SEQUENCE: 194

Ile Leu Ile Asp Trp Leu Val Gln Val
1 5

<210> SEQ ID NO 195
<211> LENGTH: 9
<212> TYPE: PRT
<213> ORGANISM: Artificial Sequence
<220> FEATURE:
<223> OTHER INFORMATION: p62 Immunogenic Epitope

<400> SEQUENCE: 195

Phe Leu Lys Asn Val Gly Glu Ser Val
1 5

<210> SEQ ID NO 196
<211> LENGTH: 10
<212> TYPE: PRT
<213> ORGANISM: Artificial Sequence
<220> FEATURE:
<223> OTHER INFORMATION: Survivin Immunogenic Epitope

<400> SEQUENCE: 196

Glu Leu Thr Leu Gly Glu Phe Leu Lys Leu
1 5 10

<210> SEQ ID NO 197
<211> LENGTH: 9
<212> TYPE: PRT
<213> ORGANISM: Artificial Sequence
<220> FEATURE:
<223> OTHER INFORMATION: CD45 Immunogenic Epitope

<400> SEQUENCE: 197

Lys Phe Leu Asp Ala Leu Ile Ser Leu
1 5

<210> SEQ ID NO 198
<211> LENGTH: 10
<212> TYPE: PRT
<213> ORGANISM: Artificial Sequence
<220> FEATURE:
<223> OTHER INFORMATION: DKK1 Immunogenic Epitope

<400> SEQUENCE: 198

Ala Leu Gly Gly His Pro Leu Leu Gly Val
1 5 10

<210> SEQ ID NO 199
<211> LENGTH: 9
<212> TYPE: PRT
<213> ORGANISM: Artificial Sequence
<220> FEATURE:
<223> OTHER INFORMATION: RU2AS Immunogenic Epitope

<400> SEQUENCE: 199

Leu Pro Arg Trp Pro Pro Pro Gln Leu
1               5

<210> SEQ ID NO 200
<211> LENGTH: 9
<212> TYPE: PRT
<213> ORGANISM: Artificial Sequence
<220> FEATURE:
<223> OTHER INFORMATION: Telomerase Immunogenic Epitope

<400> SEQUENCE: 200

Ile Leu Ala Lys Phe Leu His Trp Leu
1               5

<210> SEQ ID NO 201
<211> LENGTH: 9
<212> TYPE: PRT
<213> ORGANISM: Artificial Sequence
<220> FEATURE:
<223> OTHER INFORMATION: Telomerase Immunogenic Epitope

<400> SEQUENCE: 201

Arg Leu Val Asp Asp Phe Leu Leu Val
1               5

<210> SEQ ID NO 202
<211> LENGTH: 15
<212> TYPE: PRT
<213> ORGANISM: Artificial Sequence
<220> FEATURE:
<223> OTHER INFORMATION: Telomerase Immunogenic Epitope

<400> SEQUENCE: 202

Arg Pro Gly Leu Leu Gly Ala Ser Val Leu Gly Leu Asp Asp Ile
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Telomerase Immunogenic Epitope

<400> SEQUENCE: 203

Leu Thr Asp Leu Gln Pro Tyr Met Arg Gln Phe Val Ala His Leu
1               5                   10                  15

<210> SEQ ID NO 204
<211> LENGTH: 12
<212> TYPE: PRT
<213> ORGANISM: Artificial Sequence
<220> FEATURE:
<223> OTHER INFORMATION: PBF Immunogenic Epitope

<400> SEQUENCE: 204

Cys Thr Ala Cys Arg Trp Lys Lys Ala Cys Gln Arg
1               5                   10

<210> SEQ ID NO 205
<211> LENGTH: 9
<212> TYPE: PRT
<213> ORGANISM: Artificial Sequence
<220> FEATURE:
<223> OTHER INFORMATION: K-ras Immunogenic Epitope

<400> SEQUENCE: 205

Val Val Val Gly Ala Val Gly Val Gly
1 5

<210> SEQ ID NO 206
<211> LENGTH: 9
<212> TYPE: PRT
<213> ORGANISM: Artificial Sequence
<220> FEATURE:
<223> OTHER INFORMATION: G250 / MN / CAIX Immunogenic Epitope

<400> SEQUENCE: 206

His Leu Ser Thr Ala Phe Ala Arg Val
1 5

<210> SEQ ID NO 207
<211> LENGTH: 9
<212> TYPE: PRT
<213> ORGANISM: Artificial Sequence
<220> FEATURE:
<223> OTHER INFORMATION: G250 / MN / CAIX Immunogenic Epitope

<400> SEQUENCE: 207

Lys Ile Phe Gly Ser Leu Ala Phe Leu
1 5

<210> SEQ ID NO 208
<211> LENGTH: 9
<212> TYPE: PRT
<213> ORGANISM: Artificial Sequence
<220> FEATURE:
<223> OTHER INFORMATION: G250 / MN / CAIX Immunogenic Epitope

<400> SEQUENCE: 208

Ile Ile Ser Ala Val Val Gly Ile Leu
1 5

<210> SEQ ID NO 209
<211> LENGTH: 9
<212> TYPE: PRT
<213> ORGANISM: Artificial Sequence
<220> FEATURE:
<223> OTHER INFORMATION: G250 / MN / CAIX Immunogenic Epitope

<400> SEQUENCE: 209

Ala Leu Cys Arg Trp Gly Leu Leu Leu
1 5

<210> SEQ ID NO 210
<211> LENGTH: 9
<212> TYPE: PRT
<213> ORGANISM: Artificial Sequence
<220> FEATURE:
<223> OTHER INFORMATION: G250 / MN / CAIX Immunogenic Epitope

<400> SEQUENCE: 210

Ile Leu His Asn Gly Ala Tyr Ser Leu
1 5

<210> SEQ ID NO 211
<211> LENGTH: 9
<212> TYPE: PRT
<213> ORGANISM: Artificial Sequence
<220> FEATURE:
<223> OTHER INFORMATION: G250 / MN / CAIX Immunogenic Epitope

<400> SEQUENCE: 211

Arg Leu Leu Gln Glu Thr Glu Leu Val
1               5

<210> SEQ ID NO 212
<211> LENGTH: 9
<212> TYPE: PRT
<213> ORGANISM: Artificial Sequence
<220> FEATURE:
<223> OTHER INFORMATION: G250 / MN / CAIX Immunogenic Epitope

<400> SEQUENCE: 212

Val Val Lys Gly Val Val Phe Gly Ile
1               5

<210> SEQ ID NO 213
<211> LENGTH: 10
<212> TYPE: PRT
<213> ORGANISM: Artificial Sequence
<220> FEATURE:
<223> OTHER INFORMATION: G250 / MN / CAIX Immunogenic Epitope

<400> SEQUENCE: 213

Tyr Met Ile Met Val Lys Cys Trp Met Ile
1               5                   10

<210> SEQ ID NO 214
<211> LENGTH: 9
<212> TYPE: PRT
<213> ORGANISM: Artificial Sequence
<220> FEATURE:
<223> OTHER INFORMATION: Hepsin Immunogenic Epitope

<400> SEQUENCE: 214

Ser Leu Leu Ser Gly Asp Trp Val Leu
1               5

<210> SEQ ID NO 215
<211> LENGTH: 8
<212> TYPE: PRT
<213> ORGANISM: Artificial Sequence
<220> FEATURE:
<223> OTHER INFORMATION: Hepsin Immunogenic Epitope

<400> SEQUENCE: 215

Gly Leu Gln Leu Gly Val Gln Ala
1               5

<210> SEQ ID NO 216
<211> LENGTH: 9
<212> TYPE: PRT
<213> ORGANISM: Artificial Sequence
<220> FEATURE:
<223> OTHER INFORMATION: Hepsin Immunogenic Epitope

<400> SEQUENCE: 216

Pro Leu Thr Glu Tyr Ile Gln Pro Val
1               5

<210> SEQ ID NO 217

<211> LENGTH: 9
<212> TYPE: PRT
<213> ORGANISM: Artificial Sequence
<220> FEATURE:
<223> OTHER INFORMATION: Intestinal carboxyl esterase Immunogenic Epitope

<400> SEQUENCE: 217

Ser Pro Arg Trp Trp Pro Thr Cys Leu
1               5

<210> SEQ ID NO 218
<211> LENGTH: 9
<212> TYPE: PRT
<213> ORGANISM: Artificial Sequence
<220> FEATURE:
<223> OTHER INFORMATION: alpha-foetoprotein Immunogenic Epitope

<400> SEQUENCE: 218

Gly Val Ala Leu Gln Thr Met Lys Gln
1               5

<210> SEQ ID NO 219
<211> LENGTH: 9
<212> TYPE: PRT
<213> ORGANISM: Artificial Sequence
<220> FEATURE:
<223> OTHER INFORMATION: alpha-foetoprotein Immunogenic Epitope

<400> SEQUENCE: 219

Phe Met Asn Lys Phe Ile Tyr Glu Ile
1               5

<210> SEQ ID NO 220
<211> LENGTH: 10
<212> TYPE: PRT
<213> ORGANISM: Artificial Sequence
<220> FEATURE:
<223> OTHER INFORMATION: alpha-foetoprotein Immunogenic Epitope

<400> SEQUENCE: 220

Gln Leu Ala Val Ser Val Ile Leu Arg Val
1               5                   10

<210> SEQ ID NO 221
<211> LENGTH: 14
<212> TYPE: PRT
<213> ORGANISM: Artificial Sequence
<220> FEATURE:
<223> OTHER INFORMATION: M-CSF Immunogenic Epitope

<400> SEQUENCE: 221

Leu Pro Ala Val Val Gly Leu Ser Pro Gly Glu Gln Glu Tyr
1               5                   10

<210> SEQ ID NO 222
<211> LENGTH: 12
<212> TYPE: PRT
<213> ORGANISM: Artificial Sequence
<220> FEATURE:
<223> OTHER INFORMATION: PBF Immunogenic Epitope

<400> SEQUENCE: 222

Cys Thr Ala Cys Arg Trp Lys Lys Ala Cys Gln Arg
1               5                   10

<210> SEQ ID NO 223

<211> LENGTH: 9
<212> TYPE: PRT
<213> ORGANISM: Artificial Sequence
<220> FEATURE:
<223> OTHER INFORMATION: PSMA Immunogenic Epitope

<400> SEQUENCE: 223

Asn Tyr Ala Arg Thr Glu Asp Phe Phe
1               5

<210> SEQ ID NO 224
<211> LENGTH: 9
<212> TYPE: PRT
<213> ORGANISM: Artificial Sequence
<220> FEATURE:
<223> OTHER INFORMATION: CASP-5 Immunogenic Epitope

<400> SEQUENCE: 224

Phe Leu Ile Ile Trp Gln Asn Thr Met
1               5

<210> SEQ ID NO 225
<211> LENGTH: 14
<212> TYPE: PRT
<213> ORGANISM: Artificial Sequence
<220> FEATURE:
<223> OTHER INFORMATION: COA-1 Immunogenic Epitope

<400> SEQUENCE: 225

Thr Leu Tyr Gln Asp Asp Thr Leu Thr Leu Gln Ala Ala Gly
1               5                   10

<210> SEQ ID NO 226
<211> LENGTH: 10
<212> TYPE: PRT
<213> ORGANISM: Artificial Sequence
<220> FEATURE:
<223> OTHER INFORMATION: OGT Immunogenic Epitope

<400> SEQUENCE: 226

Ser Leu Tyr Lys Phe Ser Pro Phe Pro Leu
1               5                   10

<210> SEQ ID NO 227
<211> LENGTH: 9
<212> TYPE: PRT
<213> ORGANISM: Artificial Sequence
<220> FEATURE:
<223> OTHER INFORMATION: OS-9 Immunogenic Epitope

<400> SEQUENCE: 227

Lys Glu Leu Glu Gly Ile Leu Leu Leu
1               5

<210> SEQ ID NO 228
<211> LENGTH: 9
<212> TYPE: PRT
<213> ORGANISM: Artificial Sequence
<220> FEATURE:
<223> OTHER INFORMATION: TGF-betaRII Immunogenic Epitope

<400> SEQUENCE: 228

Arg Leu Ser Ser Cys Val Pro Val Ala
1               5

<210> SEQ ID NO 229
<211> LENGTH: 10

<212> TYPE: PRT
<213> ORGANISM: Artificial Sequence
<220> FEATURE:
<223> OTHER INFORMATION: CALCA Immunogenic Epitope

<400> SEQUENCE: 229

Val Leu Leu Gln Ala Gly Ser Leu His Ala
1 5 10

<210> SEQ ID NO 230
<211> LENGTH: 9
<212> TYPE: PRT
<213> ORGANISM: Artificial Sequence
<220> FEATURE:
<223> OTHER INFORMATION: CD274 Immunogenic Epitope

<400> SEQUENCE: 230

Leu Leu Asn Ala Phe Thr Val Thr Val
1 5

<210> SEQ ID NO 231
<211> LENGTH: 8
<212> TYPE: PRT
<213> ORGANISM: Artificial Sequence
<220> FEATURE:
<223> OTHER INFORMATION: mdm-2 Immunogenic Epitope

<400> SEQUENCE: 231

Val Leu Phe Tyr Leu Gly Gln Tyr
1 5

<210> SEQ ID NO 232
<211> LENGTH: 10
<212> TYPE: PRT
<213> ORGANISM: Artificial Sequence
<220> FEATURE:
<223> OTHER INFORMATION: alpha-actinin-4 Immunogenic Epitope

<400> SEQUENCE: 232

Phe Ile Ala Ser Asn Gly Val Lys Leu Val
1 5 10

<210> SEQ ID NO 233
<211> LENGTH: 9
<212> TYPE: PRT
<213> ORGANISM: Artificial Sequence
<220> FEATURE:
<223> OTHER INFORMATION: Elongation factor 2 (squamous cell carcinoma of the lung) Immunogenic Epitope

<400> SEQUENCE: 233

Glu Thr Val Ser Glu Gln Ser Asn Val
1 5

<210> SEQ ID NO 234
<211> LENGTH: 9
<212> TYPE: PRT
<213> ORGANISM: Artificial Sequence
<220> FEATURE:
<223> OTHER INFORMATION: ME1 (non-small cell lung carcinoma) Immunogenic Epitope

<400> SEQUENCE: 234

Phe Leu Asp Glu Phe Met Glu Gly Val
1 5

<210> SEQ ID NO 235

<211> LENGTH: 8
<212> TYPE: PRT
<213> ORGANISM: Artificial Sequence
<220> FEATURE:
<223> OTHER INFORMATION: NFYC (squamous cell carcinoma of the lung)
Immunogenic Epitope

<400> SEQUENCE: 235

Gln Gln Ile Thr Lys Thr Glu Val
1 5

<210> SEQ ID NO 236
<211> LENGTH: 8
<212> TYPE: PRT
<213> ORGANISM: Artificial Sequence
<220> FEATURE:
<223> OTHER INFORMATION: GAGE-1,2,8 Immunogenic Epitope

<400> SEQUENCE: 236

Tyr Arg Pro Arg Pro Arg Arg Tyr
1 5

<210> SEQ ID NO 237
<211> LENGTH: 9
<212> TYPE: PRT
<213> ORGANISM: Artificial Sequence
<220> FEATURE:
<223> OTHER INFORMATION: MAGE-A6 Immunogenic Epitope

<400> SEQUENCE: 237

Met Val Lys Ile Ser Gly Gly Pro Arg
1 5

<210> SEQ ID NO 238
<211> LENGTH: 9
<212> TYPE: PRT
<213> ORGANISM: Artificial Sequence
<220> FEATURE:
<223> OTHER INFORMATION: MAGE-A6 Immunogenic Epitope

<400> SEQUENCE: 238

Glu Val Asp Pro Ile Gly His Val Tyr
1 5

<210> SEQ ID NO 239
<211> LENGTH: 10
<212> TYPE: PRT
<213> ORGANISM: Artificial Sequence
<220> FEATURE:
<223> OTHER INFORMATION: MAGE-A6 Immunogenic Epitope

<400> SEQUENCE: 239

Arg Glu Pro Val Thr Lys Ala Glu Met Leu
1 5 10

<210> SEQ ID NO 240
<211> LENGTH: 9
<212> TYPE: PRT
<213> ORGANISM: Artificial Sequence
<220> FEATURE:
<223> OTHER INFORMATION: MAGE-A6 Immunogenic Epitope

<400> SEQUENCE: 240

Glu Gly Asp Cys Ala Pro Glu Glu Lys
1 5

<210> SEQ ID NO 241

<211> LENGTH: 9
<212> TYPE: PRT
<213> ORGANISM: Artificial Sequence
<220> FEATURE:
<223> OTHER INFORMATION: MAGE-A6 Immunogenic Epitope

<400> SEQUENCE: 241

Ile Ser Gly Gly Pro Arg Ile Ser Tyr
1 5

<210> SEQ ID NO 242
<211> LENGTH: 14
<212> TYPE: PRT
<213> ORGANISM: Artificial Sequence
<220> FEATURE:
<223> OTHER INFORMATION: MAGE-A6 Immunogenic Epitope

<400> SEQUENCE: 242

Leu Leu Lys Tyr Arg Ala Arg Glu Pro Val Thr Lys Ala Glu
1 5 10

<210> SEQ ID NO 243
<211> LENGTH: 9
<212> TYPE: PRT
<213> ORGANISM: Artificial Sequence
<220> FEATURE:
<223> OTHER INFORMATION: XAGE-1b/GAGED2a (non-small cell lung cancer)
Immunogenic Epitope

<400> SEQUENCE: 243

Arg Gln Lys Lys Ile Arg Ile Gln Leu
1 5

<210> SEQ ID NO 244
<211> LENGTH: 16
<212> TYPE: PRT
<213> ORGANISM: Artificial Sequence
<220> FEATURE:
<223> OTHER INFORMATION: XAGE-1b/GAGED2a (non-small cell lung cancer)
Immunogenic Epitope

<400> SEQUENCE: 244

His Leu Gly Ser Arg Gln Lys Lys Ile Arg Ile Gln Leu Arg Ser Gln
1 5 10 15

<210> SEQ ID NO 245
<211> LENGTH: 17
<212> TYPE: PRT
<213> ORGANISM: Artificial Sequence
<220> FEATURE:
<223> OTHER INFORMATION: XAGE-1b/GAGED2a (non-small cell lung cancer)
Immunogenic Epitope

<400> SEQUENCE: 245

Cys Ala Thr Trp Lys Val Ile Cys Lys Ser Cys Ile Ser Gln Thr Pro
1 5 10 15

Gly

<210> SEQ ID NO 246
<211> LENGTH: 9
<212> TYPE: PRT
<213> ORGANISM: Artificial Sequence
<220> FEATURE:
<223> OTHER INFORMATION: STEAP1 Immunogenic Epitope

<400> SEQUENCE: 246

Met Ile Ala Val Phe Leu Pro Ile Val 1 5

<210> SEQ ID NO 247
<211> LENGTH: 15
<212> TYPE: PRT
<213> ORGANISM: Artificial Sequence
<220> FEATURE:
<223> OTHER INFORMATION: STEAP1 Immunogenic Epitope

<400> SEQUENCE: 247

His Gln Gln Tyr Phe Tyr Lys Ile Pro Ile Leu Val Ile Asn Lys
1 5 10 15

<210> SEQ ID NO 248
<211> LENGTH: 9
<212> TYPE: PRT
<213> ORGANISM: Artificial Sequence
<220> FEATURE:
<223> OTHER INFORMATION: PAP Immunogenic Epitope

<400> SEQUENCE: 248

Phe Leu Phe Leu Leu Phe Phe Trp Leu
1 5

<210> SEQ ID NO 249
<211> LENGTH: 9
<212> TYPE: PRT
<213> ORGANISM: Artificial Sequence
<220> FEATURE:
<223> OTHER INFORMATION: PAP Immunogenic Epitope

<400> SEQUENCE: 249

Thr Leu Met Ser Ala Met Thr Asn Leu
1 5

<210> SEQ ID NO 250
<211> LENGTH: 9
<212> TYPE: PRT
<213> ORGANISM: Artificial Sequence
<220> FEATURE:
<223> OTHER INFORMATION: PAP Immunogenic Epitope

<400> SEQUENCE: 250

Ala Leu Asp Val Tyr Asn Gly Leu Leu
1 5

<210> SEQ ID NO 251
<211> LENGTH: 10
<212> TYPE: PRT
<213> ORGANISM: Artificial Sequence
<220> FEATURE:
<223> OTHER INFORMATION: PSA (prostate carcinoma) Immunogenic Epitope

<400> SEQUENCE: 251

Phe Leu Thr Pro Lys Lys Leu Gln Cys Val
1 5 10

<210> SEQ ID NO 252
<211> LENGTH: 10
<212> TYPE: PRT
<213> ORGANISM: Artificial Sequence
<220> FEATURE:
<223> OTHER INFORMATION: PSA (prostate carcinoma) Immunogenic Epitope

<400> SEQUENCE: 252

Val Ile Ser Asn Asp Val Cys Ala Gln Val
1 5 10

<210> SEQ ID NO 253
<211> LENGTH: 9
<212> TYPE: PRT
<213> ORGANISM: Artificial Sequence
<220> FEATURE:
<223> OTHER INFORMATION: FGF5 Immunogenic Epitope

<400> SEQUENCE: 253

Asn Thr Tyr Ala Ser Pro Arg Phe Lys
1               5

<210> SEQ ID NO 254
<211> LENGTH: 10
<212> TYPE: PRT
<213> ORGANISM: Artificial Sequence
<220> FEATURE:
<223> OTHER INFORMATION: hsp70-2 (renal cell carcinoma) Immunogenic
      Epitope

<400> SEQUENCE: 254

Ser Leu Phe Glu Gly Ile Asp Ile Tyr Thr
1               5                   10

<210> SEQ ID NO 255
<211> LENGTH: 9
<212> TYPE: PRT
<213> ORGANISM: Artificial Sequence
<220> FEATURE:
<223> OTHER INFORMATION: MAGE-A9 (renal cell carcinoma) Immunogenic
      Epitope

<400> SEQUENCE: 255

Ala Leu Ser Val Met Gly Val Tyr Val
1               5

<210> SEQ ID NO 256
<211> LENGTH: 15
<212> TYPE: PRT
<213> ORGANISM: Artificial Sequence
<220> FEATURE:
<223> OTHER INFORMATION: ARTC1 Immunogenic Epitope

<400> SEQUENCE: 256

Tyr Ser Val Tyr Phe Asn Leu Pro Ala Asp Thr Ile Tyr Thr Asn
1               5                   10                  15

<210> SEQ ID NO 257
<211> LENGTH: 29
<212> TYPE: PRT
<213> ORGANISM: Artificial Sequence
<220> FEATURE:
<223> OTHER INFORMATION: B-RAF Immunogenic Epitope

<400> SEQUENCE: 257

Glu Asp Leu Thr Val Lys Ile Gly Asp Phe Gly Leu Ala Thr Glu Lys
1               5                   10                  15

Ser Arg Trp Ser Gly Ser His Gln Phe Glu Gln Leu Ser
            20                  25

<210> SEQ ID NO 258
<211> LENGTH: 8
<212> TYPE: PRT
<213> ORGANISM: Artificial Sequence
<220> FEATURE:
<223> OTHER INFORMATION: B-RAF Immunogenic Epitope

<400> SEQUENCE: 258

Ser His Gln Phe Glu Gln Leu Ser
1 5

<210> SEQ ID NO 259
<211> LENGTH: 9
<212> TYPE: PRT
<213> ORGANISM: Artificial Sequence
<220> FEATURE:
<223> OTHER INFORMATION: beta-catenin Immunogenic Epitope

<400> SEQUENCE: 259

Ser Tyr Leu Asp Ser Gly Ile His Phe
1 5

<210> SEQ ID NO 260
<211> LENGTH: 12
<212> TYPE: PRT
<213> ORGANISM: Artificial Sequence
<220> FEATURE:
<223> OTHER INFORMATION: Cdc27 Immunogenic Epitope

<400> SEQUENCE: 260

Phe Ser Trp Ala Met Asp Leu Asp Pro Lys Gly Ala
1 5 10

<210> SEQ ID NO 261
<211> LENGTH: 10
<212> TYPE: PRT
<213> ORGANISM: Artificial Sequence
<220> FEATURE:
<223> OTHER INFORMATION: CDK4 Immunogenic Epitope

<400> SEQUENCE: 261

Ala Cys Asp Pro His Ser Gly His Phe Val
1 5 10

<210> SEQ ID NO 262
<211> LENGTH: 9
<212> TYPE: PRT
<213> ORGANISM: Artificial Sequence
<220> FEATURE:
<223> OTHER INFORMATION: CDK12 Immunogenic Epitope

<400> SEQUENCE: 262

Cys Ile Leu Gly Lys Leu Phe Thr Lys
1 5

<210> SEQ ID NO 263
<211> LENGTH: 9
<212> TYPE: PRT
<213> ORGANISM: Artificial Sequence
<220> FEATURE:
<223> OTHER INFORMATION: CDKN2A Immunogenic Epitope

<400> SEQUENCE: 263

Ala Val Cys Pro Trp Thr Trp Leu Arg
1 5

<210> SEQ ID NO 264
<211> LENGTH: 9
<212> TYPE: PRT
<213> ORGANISM: Artificial Sequence
<220> FEATURE:
<223> OTHER INFORMATION: CLPP Immunogenic Epitope

<400> SEQUENCE: 264

Ile Leu Asp Lys Val Leu Val His Leu
1               5

<210> SEQ ID NO 265
<211> LENGTH: 9
<212> TYPE: PRT
<213> ORGANISM: Artificial Sequence
<220> FEATURE:
<223> OTHER INFORMATION: CSNK1A1 Immunogenic Epitope

<400> SEQUENCE: 265

Gly Leu Phe Gly Asp Ile Tyr Leu Ala
1               5

<210> SEQ ID NO 266
<211> LENGTH: 14
<212> TYPE: PRT
<213> ORGANISM: Artificial Sequence
<220> FEATURE:
<223> OTHER INFORMATION: FN1 Immunogenic Epitope

<400> SEQUENCE: 266

Met Ile Phe Glu Lys His Gly Phe Arg Arg Thr Thr Pro Pro
1               5                   10

<210> SEQ ID NO 267
<211> LENGTH: 10
<212> TYPE: PRT
<213> ORGANISM: Artificial Sequence
<220> FEATURE:
<223> OTHER INFORMATION: GAS7 Immunogenic Epitope

<400> SEQUENCE: 267

Ser Leu Ala Asp Glu Ala Glu Val Tyr Leu
1               5                   10

<210> SEQ ID NO 268
<211> LENGTH: 10
<212> TYPE: PRT
<213> ORGANISM: Artificial Sequence
<220> FEATURE:
<223> OTHER INFORMATION: GPNMB Immunogenic Epitope

<400> SEQUENCE: 268

Thr Leu Asp Trp Leu Leu Gln Thr Pro Lys
1               5                   10

<210> SEQ ID NO 269
<211> LENGTH: 9
<212> TYPE: PRT
<213> ORGANISM: Artificial Sequence
<220> FEATURE:
<223> OTHER INFORMATION: HAUS3 Immunogenic Epitope

<400> SEQUENCE: 269

Ile Leu Asn Ala Met Ile Ala Lys Ile
1               5

<210> SEQ ID NO 270
<211> LENGTH: 9
<212> TYPE: PRT
<213> ORGANISM: Artificial Sequence
<220> FEATURE:
<223> OTHER INFORMATION: LDLR-fucosyltransferase Immunogenic Epitope

<400> SEQUENCE: 270

Trp Arg Arg Ala Pro Ala Pro Gly Ala
1 5

<210> SEQ ID NO 271
<211> LENGTH: 9
<212> TYPE: PRT
<213> ORGANISM: Artificial Sequence
<220> FEATURE:
<223> OTHER INFORMATION: LDLR-fucosyltransferase Immunogenic Epitope

<400> SEQUENCE: 271

Pro Val Thr Trp Arg Arg Ala Pro Ala
1 5

<210> SEQ ID NO 272
<211> LENGTH: 11
<212> TYPE: PRT
<213> ORGANISM: Artificial Sequence
<220> FEATURE:
<223> OTHER INFORMATION: MART2 Immunogenic Epitope

<400> SEQUENCE: 272

Phe Leu Glu Gly Asn Glu Val Gly Lys Thr Tyr
1 5 10

<210> SEQ ID NO 273
<211> LENGTH: 9
<212> TYPE: PRT
<213> ORGANISM: Artificial Sequence
<220> FEATURE:
<223> OTHER INFORMATION: MATN Immunogenic Epitope

<400> SEQUENCE: 273

Lys Thr Leu Thr Ser Val Phe Gln Lys
1 5

<210> SEQ ID NO 274
<211> LENGTH: 9
<212> TYPE: PRT
<213> ORGANISM: Artificial Sequence
<220> FEATURE:
<223> OTHER INFORMATION: MUM-1 Immunogenic Epitope

<400> SEQUENCE: 274

Glu Glu Lys Leu Ile Val Val Leu Phe
1 5

<210> SEQ ID NO 275
<211> LENGTH: 11
<212> TYPE: PRT
<213> ORGANISM: Artificial Sequence
<220> FEATURE:
<223> OTHER INFORMATION: MUM-2 Immunogenic Epitope

<400> SEQUENCE: 275

Ser Glu Leu Phe Arg Ser Gly Leu Asp Ser Tyr
1 5 10

<210> SEQ ID NO 276
<211> LENGTH: 9
<212> TYPE: PRT
<213> ORGANISM: Artificial Sequence
<220> FEATURE:
<223> OTHER INFORMATION: MUM-2 Immunogenic Epitope

<400> SEQUENCE: 276

Phe Arg Ser Gly Leu Asp Ser Tyr Val 1 5

<210> SEQ ID NO 277
<211> LENGTH: 9
<212> TYPE: PRT
<213> ORGANISM: Artificial Sequence
<220> FEATURE:
<223> OTHER INFORMATION: MUM-3 Immunogenic Epitope

<400> SEQUENCE: 277

Glu Ala Phe Ile Gln Pro Ile Thr Arg
1 5

<210> SEQ ID NO 278
<211> LENGTH: 11
<212> TYPE: PRT
<213> ORGANISM: Artificial Sequence
<220> FEATURE:
<223> OTHER INFORMATION: neo-PAP Immunogenic Epitope

<400> SEQUENCE: 278

Arg Val Ile Lys Asn Ser Ile Arg Leu Thr Leu
1 5 10

<210> SEQ ID NO 279
<211> LENGTH: 9
<212> TYPE: PRT
<213> ORGANISM: Artificial Sequence
<220> FEATURE:
<223> OTHER INFORMATION: Myosin class I Immunogenic Epitope

<400> SEQUENCE: 279

Lys Ile Asn Lys Asn Pro Lys Tyr Lys
1 5

<210> SEQ ID NO 280
<211> LENGTH: 9
<212> TYPE: PRT
<213> ORGANISM: Artificial Sequence
<220> FEATURE:
<223> OTHER INFORMATION: PPP1R3B Immunogenic Epitope

<400> SEQUENCE: 280

Tyr Thr Asp Phe His Cys Gln Tyr Val
1 5

<210> SEQ ID NO 281
<211> LENGTH: 10
<212> TYPE: PRT
<213> ORGANISM: Artificial Sequence
<220> FEATURE:
<223> OTHER INFORMATION: PRDX5 Immunogenic Epitope

<400> SEQUENCE: 281

Leu Leu Leu Asp Asp Leu Leu Val Ser Ile
1 5 10

<210> SEQ ID NO 282
<211> LENGTH: 16
<212> TYPE: PRT
<213> ORGANISM: Artificial Sequence
<220> FEATURE:
<223> OTHER INFORMATION: PTPRK Immunogenic Epitope

<400> SEQUENCE: 282

Pro Tyr Tyr Phe Ala Ala Glu Leu Pro Pro Arg Asn Leu Pro Glu Pro
1 5 10 15

<210> SEQ ID NO 283
<211> LENGTH: 10
<212> TYPE: PRT
<213> ORGANISM: Artificial Sequence
<220> FEATURE:
<223> OTHER INFORMATION: N-ras Immunogenic Epitope

<400> SEQUENCE: 283

Ile Leu Asp Thr Ala Gly Arg Glu Glu Tyr
1 5 10

<210> SEQ ID NO 284
<211> LENGTH: 9
<212> TYPE: PRT
<213> ORGANISM: Artificial Sequence
<220> FEATURE:
<223> OTHER INFORMATION: RBAF600 Immunogenic Epitope

<400> SEQUENCE: 284

Arg Pro His Val Pro Glu Ser Ala Phe
1 5

<210> SEQ ID NO 285
<211> LENGTH: 9
<212> TYPE: PRT
<213> ORGANISM: Artificial Sequence
<220> FEATURE:
<223> OTHER INFORMATION: SIRT2 Immunogenic Epitope

<400> SEQUENCE: 285

Lys Ile Phe Ser Glu Val Thr Leu Lys
1 5

<210> SEQ ID NO 286
<211> LENGTH: 9
<212> TYPE: PRT
<213> ORGANISM: Artificial Sequence
<220> FEATURE:
<223> OTHER INFORMATION: SNRPD1 Immunogenic Epitope

<400> SEQUENCE: 286

Ser His Glu Thr Val Ile Ile Glu Leu
1 5

<210> SEQ ID NO 287
<211> LENGTH: 15
<212> TYPE: PRT
<213> ORGANISM: Artificial Sequence
<220> FEATURE:
<223> OTHER INFORMATION: Triosephosphate isomerase Immunogenic Epitope

<400> SEQUENCE: 287

Gly Glu Leu Ile Gly Ile Leu Asn Ala Ala Lys Val Pro Ala Asp
1 5 10 15

<210> SEQ ID NO 288
<211> LENGTH: 9
<212> TYPE: PRT
<213> ORGANISM: Artificial Sequence
<220> FEATURE:
<223> OTHER INFORMATION: OA1 Immunogenic Epitope

<400> SEQUENCE: 288

Leu Tyr Ser Ala Cys Phe Trp Trp Leu
1 5

<210> SEQ ID NO 289
<211> LENGTH: 9
<212> TYPE: PRT
<213> ORGANISM: Artificial Sequence
<220> FEATURE:
<223> OTHER INFORMATION: RAB38 / NY-MEL-1 Immunogenic Epitope

<400> SEQUENCE: 289

Val Leu His Trp Asp Pro Glu Thr Val
1               5

<210> SEQ ID NO 290
<211> LENGTH: 9
<212> TYPE: PRT
<213> ORGANISM: Artificial Sequence
<220> FEATURE:
<223> OTHER INFORMATION: TRP-1 / gp75 Immunogenic Epitope

<400> SEQUENCE: 290

Met Ser Leu Gln Arg Gln Phe Leu Arg
1               5

<210> SEQ ID NO 291
<211> LENGTH: 20
<212> TYPE: PRT
<213> ORGANISM: Artificial Sequence
<220> FEATURE:
<223> OTHER INFORMATION: TRP-1 / gp75 Immunogenic Epitope

<400> SEQUENCE: 291

Ile Ser Pro Asn Ser Val Phe Ser Gln Trp Arg Val Val Cys Asp Ser
1               5                   10                  15

Leu Glu Asp Tyr
            20

<210> SEQ ID NO 292
<211> LENGTH: 10
<212> TYPE: PRT
<213> ORGANISM: Artificial Sequence
<220> FEATURE:
<223> OTHER INFORMATION: TRP-1 / gp75 Immunogenic Epitope

<400> SEQUENCE: 292

Ser Leu Pro Tyr Trp Asn Phe Ala Thr Gly
1               5                   10

<210> SEQ ID NO 293
<211> LENGTH: 15
<212> TYPE: PRT
<213> ORGANISM: Artificial Sequence
<220> FEATURE:
<223> OTHER INFORMATION: TRP-1 / gp75 Immunogenic Epitope

<400> SEQUENCE: 293

Ser Gln Trp Arg Val Val Cys Asp Ser Leu Glu Asp Tyr Asp Thr
1               5                   10                  15

<210> SEQ ID NO 294
<211> LENGTH: 9
<212> TYPE: PRT
<213> ORGANISM: Artificial Sequence
<220> FEATURE:
<223> OTHER INFORMATION: TRP-2 Immunogenic Epitope

<400> SEQUENCE: 294

Ser Val Tyr Asp Phe Phe Val Trp Leu 1 5

<210> SEQ ID NO 295
<211> LENGTH: 9
<212> TYPE: PRT
<213> ORGANISM: Artificial Sequence
<220> FEATURE:
<223> OTHER INFORMATION: TRP-2 Immunogenic Epitope

<400> SEQUENCE: 295

Thr Leu Asp Ser Gln Val Met Ser Leu
1 5

<210> SEQ ID NO 296
<211> LENGTH: 9
<212> TYPE: PRT
<213> ORGANISM: Artificial Sequence
<220> FEATURE:
<223> OTHER INFORMATION: TRP-2 Immunogenic Epitope

<400> SEQUENCE: 296

Leu Leu Gly Pro Gly Arg Pro Tyr Arg
1 5

<210> SEQ ID NO 297
<211> LENGTH: 9
<212> TYPE: PRT
<213> ORGANISM: Artificial Sequence
<220> FEATURE:
<223> OTHER INFORMATION: TRP-2 Immunogenic Epitope

<400> SEQUENCE: 297

Ala Asn Asp Pro Ile Phe Val Val Leu
1 5

<210> SEQ ID NO 298
<211> LENGTH: 15
<212> TYPE: PRT
<213> ORGANISM: Artificial Sequence
<220> FEATURE:
<223> OTHER INFORMATION: TRP-2 Immunogenic Epitope

<400> SEQUENCE: 298

Gln Cys Thr Glu Val Arg Ala Asp Thr Arg Pro Trp Ser Gly Pro
1 5 10 15

<210> SEQ ID NO 299
<211> LENGTH: 10
<212> TYPE: PRT
<213> ORGANISM: Artificial Sequence
<220> FEATURE:
<223> OTHER INFORMATION: TRP-2 Immunogenic Epitope

<400> SEQUENCE: 299

Ala Leu Pro Tyr Trp Asn Phe Ala Thr Gly
1 5 10

<210> SEQ ID NO 300
<211> LENGTH: 9
<212> TYPE: PRT
<213> ORGANISM: Artificial Sequence
<220> FEATURE:
<223> OTHER INFORMATION: tyrosinase Immunogenic Epitope

<400> SEQUENCE: 300

Lys Cys Asp Ile Cys Thr Asp Glu Tyr
1 5

<210> SEQ ID NO 301
<211> LENGTH: 11
<212> TYPE: PRT
<213> ORGANISM: Artificial Sequence
<220> FEATURE:
<223> OTHER INFORMATION: tyrosinase Immunogenic Epitope

<400> SEQUENCE: 301

Ser Ser Asp Tyr Val Ile Pro Ile Gly Thr Tyr
1 5 10

<210> SEQ ID NO 302
<211> LENGTH: 9
<212> TYPE: PRT
<213> ORGANISM: Artificial Sequence
<220> FEATURE:
<223> OTHER INFORMATION: tyrosinase Immunogenic Epitope

<400> SEQUENCE: 302

Met Leu Leu Ala Val Leu Tyr Cys Leu
1 5

<210> SEQ ID NO 303
<211> LENGTH: 10
<212> TYPE: PRT
<213> ORGANISM: Artificial Sequence
<220> FEATURE:
<223> OTHER INFORMATION: tyrosinase Immunogenic Epitope

<400> SEQUENCE: 303

Cys Leu Leu Trp Ser Phe Gln Thr Ser Ala
1 5 10

<210> SEQ ID NO 304
<211> LENGTH: 9
<212> TYPE: PRT
<213> ORGANISM: Artificial Sequence
<220> FEATURE:
<223> OTHER INFORMATION: tyrosinase Immunogenic Epitope

<400> SEQUENCE: 304

Tyr Met Asp Gly Thr Met Ser Gln Val
1 5

<210> SEQ ID NO 305
<211> LENGTH: 9
<212> TYPE: PRT
<213> ORGANISM: Artificial Sequence
<220> FEATURE:
<223> OTHER INFORMATION: tyrosinase Immunogenic Epitope

<400> SEQUENCE: 305

Ala Phe Leu Pro Trp His Arg Leu Phe
1 5

<210> SEQ ID NO 306
<211> LENGTH: 11
<212> TYPE: PRT
<213> ORGANISM: Artificial Sequence
<220> FEATURE:
<223> OTHER INFORMATION: tyrosinase Immunogenic Epitope

<400> SEQUENCE: 306

Ile Tyr Met Asp Gly Thr Ala Asp Phe Ser Phe
1 5 10

<210> SEQ ID NO 307
<211> LENGTH: 9
<212> TYPE: PRT
<213> ORGANISM: Artificial Sequence
<220> FEATURE:
<223> OTHER INFORMATION: tyrosinase Immunogenic Epitope

<400> SEQUENCE: 307

Gln Cys Ser Gly Asn Phe Met Gly Phe
1 5

<210> SEQ ID NO 308
<211> LENGTH: 12
<212> TYPE: PRT
<213> ORGANISM: Artificial Sequence
<220> FEATURE:
<223> OTHER INFORMATION: tyrosinase Immunogenic Epitope

<400> SEQUENCE: 308

Thr Pro Arg Leu Pro Ser Ser Ala Asp Val Glu Phe
1 5 10

<210> SEQ ID NO 309
<211> LENGTH: 9
<212> TYPE: PRT
<213> ORGANISM: Artificial Sequence
<220> FEATURE:
<223> OTHER INFORMATION: tyrosinase Immunogenic Epitope

<400> SEQUENCE: 309

Leu Pro Ser Ser Ala Asp Val Glu Phe
1 5

<210> SEQ ID NO 310
<211> LENGTH: 10
<212> TYPE: PRT
<213> ORGANISM: Artificial Sequence
<220> FEATURE:
<223> OTHER INFORMATION: tyrosinase Immunogenic Epitope

<400> SEQUENCE: 310

Leu His His Ala Phe Val Asp Ser Ile Phe
1 5 10

<210> SEQ ID NO 311
<211> LENGTH: 9
<212> TYPE: PRT
<213> ORGANISM: Artificial Sequence
<220> FEATURE:
<223> OTHER INFORMATION: tyrosinase Immunogenic Epitope

<400> SEQUENCE: 311

Ser Glu Ile Trp Arg Asp Ile Asp Phe
1 5

<210> SEQ ID NO 312
<211> LENGTH: 15
<212> TYPE: PRT
<213> ORGANISM: Artificial Sequence
<220> FEATURE:
<223> OTHER INFORMATION: tyrosinase Immunogenic Epitope

<400> SEQUENCE: 312

Gln Asn Ile Leu Leu Ser Asn Ala Pro Leu Gly Pro Gln Phe Pro
1 5 10 15

<210> SEQ ID NO 313
<211> LENGTH: 13
<212> TYPE: PRT
<213> ORGANISM: Artificial Sequence
<220> FEATURE:
<223> OTHER INFORMATION: tyrosinase Immunogenic Epitope

<400> SEQUENCE: 313

Ser Tyr Leu Gln Asp Ser Asp Pro Asp Ser Phe Gln Asp
1               5                   10

<210> SEQ ID NO 314
<211> LENGTH: 21
<212> TYPE: PRT
<213> ORGANISM: Artificial Sequence
<220> FEATURE:
<223> OTHER INFORMATION: tyrosinase Immunogenic Epitope

<400> SEQUENCE: 314

Phe Leu Leu His His Ala Phe Val Asp Ser Ile Phe Glu Gln Trp Leu
1               5                   10                  15

Gln Arg His Arg Pro
            20

<210> SEQ ID NO 315
<211> LENGTH: 30
<212> TYPE: PRT
<213> ORGANISM: Artificial Sequence
<220> FEATURE:
<223> OTHER INFORMATION: Melan-A/MART-1 Immunogenic Epitope

<400> SEQUENCE: 315

Tyr Thr Thr Ala Glu Glu Ala Ala Gly Ile Gly Ile Leu Thr Val Ile
1               5                   10                  15

Leu Gly Val Leu Leu Leu Ile Gly Cys Trp Tyr Cys Arg Arg
            20                  25                  30

<210> SEQ ID NO 316
<211> LENGTH: 9
<212> TYPE: PRT
<213> ORGANISM: Artificial Sequence
<220> FEATURE:
<223> OTHER INFORMATION: gp100 / Pmel17 Immunogenic Epitope

<400> SEQUENCE: 316

Ala Leu Asn Phe Pro Gly Ser Gln Lys
1               5

<210> SEQ ID NO 317
<211> LENGTH: 9
<212> TYPE: PRT
<213> ORGANISM: Artificial Sequence
<220> FEATURE:
<223> OTHER INFORMATION: gp100 / Pmel17 Immunogenic Epitope

<400> SEQUENCE: 317

Val Tyr Phe Phe Leu Pro Asp His Leu
1               5

<210> SEQ ID NO 318
<211> LENGTH: 9
<212> TYPE: PRT
<213> ORGANISM: Artificial Sequence
<220> FEATURE:
<223> OTHER INFORMATION: gp100 / Pmel17 Immunogenic Epitope

<400> SEQUENCE: 318

Arg Thr Lys Gln Leu Tyr Pro Glu Trp
1 5

<210> SEQ ID NO 319
<211> LENGTH: 10
<212> TYPE: PRT
<213> ORGANISM: Artificial Sequence
<220> FEATURE:
<223> OTHER INFORMATION: gp100 / Pmel17 Immunogenic Epitope

<400> SEQUENCE: 319

His Thr Met Glu Val Thr Val Tyr His Arg
1 5 10

<210> SEQ ID NO 320
<211> LENGTH: 9
<212> TYPE: PRT
<213> ORGANISM: Artificial Sequence
<220> FEATURE:
<223> OTHER INFORMATION: gp100 / Pmel17 Immunogenic Epitope

<400> SEQUENCE: 320

Ser Ser Pro Gly Cys Gln Pro Pro Ala
1 5

<210> SEQ ID NO 321
<211> LENGTH: 10
<212> TYPE: PRT
<213> ORGANISM: Artificial Sequence
<220> FEATURE:
<223> OTHER INFORMATION: gp100 / Pmel17 Immunogenic Epitope

<400> SEQUENCE: 321

Val Pro Leu Asp Cys Val Leu Tyr Arg Tyr
1 5 10

<210> SEQ ID NO 322
<211> LENGTH: 9
<212> TYPE: PRT
<213> ORGANISM: Artificial Sequence
<220> FEATURE:
<223> OTHER INFORMATION: gp100 / Pmel17 Immunogenic Epitope

<400> SEQUENCE: 322

Leu Pro His Ser Ser Ser His Trp Leu
1 5

<210> SEQ ID NO 323
<211> LENGTH: 8
<212> TYPE: PRT
<213> ORGANISM: Artificial Sequence
<220> FEATURE:
<223> OTHER INFORMATION: gp100 / Pmel17 Immunogenic Epitope

<400> SEQUENCE: 323

Ser Asn Asp Gly Pro Thr Leu Ile
1 5

<210> SEQ ID NO 324
<211> LENGTH: 15
<212> TYPE: PRT
<213> ORGANISM: Artificial Sequence
<220> FEATURE:
<223> OTHER INFORMATION: gp100 / Pmel17 Immunogenic Epitope

<400> SEQUENCE: 324

Gly Arg Ala Met Leu Gly Thr His Thr Met Glu Val Thr Val Tyr
1 5 10 15

<210> SEQ ID NO 325
<211> LENGTH: 16
<212> TYPE: PRT
<213> ORGANISM: Artificial Sequence
<220> FEATURE:
<223> OTHER INFORMATION: gp100 / Pmel17 Immunogenic Epitope

<400> SEQUENCE: 325

Trp Asn Arg Gln Leu Tyr Pro Glu Trp Thr Glu Ala Gln Arg Leu Asp
1 5 10 15

<210> SEQ ID NO 326
<211> LENGTH: 18
<212> TYPE: PRT
<213> ORGANISM: Artificial Sequence
<220> FEATURE:
<223> OTHER INFORMATION: gp100 / Pmel17 Immunogenic Epitope

<400> SEQUENCE: 326

Thr Thr Glu Trp Val Glu Thr Thr Ala Arg Glu Leu Pro Ile Pro Glu
1 5 10 15

Pro Glu

<210> SEQ ID NO 327
<211> LENGTH: 17
<212> TYPE: PRT
<213> ORGANISM: Artificial Sequence
<220> FEATURE:
<223> OTHER INFORMATION: gp100 / Pmel17 Immunogenic Epitope

<400> SEQUENCE: 327

Thr Gly Arg Ala Met Leu Gly Thr His Thr Met Glu Val Thr Val Tyr
1 5 10 15

His

<210> SEQ ID NO 328
<211> LENGTH: 10
<212> TYPE: PRT
<213> ORGANISM: Artificial Sequence
<220> FEATURE:
<223> OTHER INFORMATION: GnTVf Immunogenic Epitope

<400> SEQUENCE: 328

Val Leu Pro Asp Val Phe Ile Arg Cys Val
1 5 10

<210> SEQ ID NO 329
<211> LENGTH: 20
<212> TYPE: PRT
<213> ORGANISM: Artificial Sequence
<220> FEATURE:
<223> OTHER INFORMATION: LY6K Immunogenic Epitope

<400> SEQUENCE: 329

Lys Cys Cys Lys Ile Arg Tyr Cys Asn Leu Glu Gly Pro Pro Ile Asn
1 5 10 15

Ser Ser Val Phe
20

<210> SEQ ID NO 330
<211> LENGTH: 24
<212> TYPE: PRT

<213> ORGANISM: Artificial Sequence
<220> FEATURE:
<223> OTHER INFORMATION: LY6K Immunogenic Epitope

<400> SEQUENCE: 330

Lys Trp Thr Glu Pro Tyr Cys Val Ile Ala Ala Val Lys Ile Phe Pro
1 5 10 15

Arg Phe Phe Met Val Ala Lys Gln
20

<210> SEQ ID NO 331
<211> LENGTH: 10
<212> TYPE: PRT
<213> ORGANISM: Artificial Sequence
<220> FEATURE:
<223> OTHER INFORMATION: LY6K Immunogenic Epitope

<400> SEQUENCE: 331

Arg Tyr Cys Asn Leu Glu Gly Pro Pro Ile
1 5 10

<210> SEQ ID NO 332
<211> LENGTH: 9
<212> TYPE: PRT
<213> ORGANISM: Artificial Sequence
<220> FEATURE:
<223> OTHER INFORMATION: MAGE-A10 Immunogenic Epitope

<400> SEQUENCE: 332

Gly Leu Tyr Asp Gly Met Glu His Leu
1 5

<210> SEQ ID NO 333
<211> LENGTH: 9
<212> TYPE: PRT
<213> ORGANISM: Artificial Sequence
<220> FEATURE:
<223> OTHER INFORMATION: MAGE-A10 Immunogenic Epitope

<400> SEQUENCE: 333

Asp Pro Ala Arg Tyr Glu Phe Leu Trp
1 5

<210> SEQ ID NO 334
<211> LENGTH: 9
<212> TYPE: PRT
<213> ORGANISM: Artificial Sequence
<220> FEATURE:
<223> OTHER INFORMATION: MAGE-A12 Immunogenic Epitope

<400> SEQUENCE: 334

Phe Leu Trp Gly Pro Arg Ala Leu Val
1 5

<210> SEQ ID NO 335
<211> LENGTH: 9
<212> TYPE: PRT
<213> ORGANISM: Artificial Sequence
<220> FEATURE:
<223> OTHER INFORMATION: MAGE-A12 Immunogenic Epitope

<400> SEQUENCE: 335

Val Arg Ile Gly His Leu Tyr Ile Leu
1 5

<210> SEQ ID NO 336

<211> LENGTH: 9
<212> TYPE: PRT
<213> ORGANISM: Artificial Sequence
<220> FEATURE:
<223> OTHER INFORMATION: MAGE-A12 Immunogenic Epitope

<400> SEQUENCE: 336

Glu Gly Asp Cys Ala Pro Glu Glu Lys
1               5

<210> SEQ ID NO 337
<211> LENGTH: 15
<212> TYPE: PRT
<213> ORGANISM: Artificial Sequence
<220> FEATURE:
<223> OTHER INFORMATION: MAGE-A12 Immunogenic Epitope

<400> SEQUENCE: 337

Arg Glu Pro Phe Thr Lys Ala Glu Met Leu Gly Ser Val Ile Arg
1               5                   10                  15

<210> SEQ ID NO 338
<211> LENGTH: 14
<212> TYPE: PRT
<213> ORGANISM: Artificial Sequence
<220> FEATURE:
<223> OTHER INFORMATION: MAGE-A12 Immunogenic Epitope

<400> SEQUENCE: 338

Ala Glu Leu Val His Phe Leu Leu Leu Lys Tyr Arg Ala Arg
1               5                   10

<210> SEQ ID NO 339
<211> LENGTH: 10
<212> TYPE: PRT
<213> ORGANISM: Artificial Sequence
<220> FEATURE:
<223> OTHER INFORMATION: MAGE-C2 Immunogenic Epitope

<400> SEQUENCE: 339

Leu Leu Phe Gly Leu Ala Leu Ile Glu Val
1               5                   10

<210> SEQ ID NO 340
<211> LENGTH: 9
<212> TYPE: PRT
<213> ORGANISM: Artificial Sequence
<220> FEATURE:
<223> OTHER INFORMATION: MAGE-C2 Immunogenic Epitope

<400> SEQUENCE: 340

Ala Leu Lys Asp Val Glu Glu Arg Val
1               5

<210> SEQ ID NO 341
<211> LENGTH: 9
<212> TYPE: PRT
<213> ORGANISM: Artificial Sequence
<220> FEATURE:
<223> OTHER INFORMATION: MAGE-C2 Immunogenic Epitope

<400> SEQUENCE: 341

Ser Glu Ser Ile Lys Lys Lys Val Leu
1               5

<210> SEQ ID NO 342
<211> LENGTH: 9

<212> TYPE: PRT
<213> ORGANISM: Artificial Sequence
<220> FEATURE:
<223> OTHER INFORMATION: MAGE-C2 Immunogenic Epitope

<400> SEQUENCE: 342

Ala Ser Ser Thr Leu Tyr Leu Val Phe
1 5

<210> SEQ ID NO 343
<211> LENGTH: 15
<212> TYPE: PRT
<213> ORGANISM: Artificial Sequence
<220> FEATURE:
<223> OTHER INFORMATION: MAGE-C2 Immunogenic Epitope

<400> SEQUENCE: 343

Ser Ser Thr Leu Tyr Leu Val Phe Ser Pro Ser Ser Phe Ser Thr
1 5 10 15

<210> SEQ ID NO 344
<211> LENGTH: 9
<212> TYPE: PRT
<213> ORGANISM: Artificial Sequence
<220> FEATURE:
<223> OTHER INFORMATION: NA88-A Immunogenic Epitope

<400> SEQUENCE: 344

Gln Gly Gln His Phe Leu Gln Lys Val
1 5

<210> SEQ ID NO 345
<211> LENGTH: 10
<212> TYPE: PRT
<213> ORGANISM: Artificial Sequence
<220> FEATURE:
<223> OTHER INFORMATION: TRP2-INT2g Immunogenic Epitope

<400> SEQUENCE: 345

Glu Val Ile Ser Cys Lys Leu Ile Lys Arg
1 5 10

<210> SEQ ID NO 346
<211> LENGTH: 9
<212> TYPE: PRT
<213> ORGANISM: Artificial Sequence
<220> FEATURE:
<223> OTHER INFORMATION: pbk Immunogenic Epitope

<400> SEQUENCE: 346

Gly Ser Pro Phe Pro Ala Ala Val Ile
1 5

<210> SEQ ID NO 347
<211> LENGTH: 9
<212> TYPE: PRT
<213> ORGANISM: Artificial Sequence
<220> FEATURE:
<223> OTHER INFORMATION: CASP-8 Immunogenic Epitope

<400> SEQUENCE: 347

Phe Pro Ser Asp Ser Trp Cys Tyr Phe
1 5

<210> SEQ ID NO 348
<211> LENGTH: 9
<212> TYPE: PRT

<213> ORGANISM: Artificial Sequence
<220> FEATURE:
<223> OTHER INFORMATION: SAGE Immunogenic Epitope

<400> SEQUENCE: 348

Leu Tyr Ala Thr Val Ile His Asp Ile
1 5

<210> SEQ ID NO 349
<211> LENGTH: 9
<212> TYPE: PRT
<213> ORGANISM: Artificial Sequence
<220> FEATURE:
<223> OTHER INFORMATION: BCR-ABL Immunogenic Epitope

<400> SEQUENCE: 349

Ser Ser Lys Ala Leu Gln Arg Pro Val
1 5

<210> SEQ ID NO 350
<211> LENGTH: 9
<212> TYPE: PRT
<213> ORGANISM: Artificial Sequence
<220> FEATURE:
<223> OTHER INFORMATION: BCR-ABL Immunogenic Epitope

<400> SEQUENCE: 350

Gly Phe Lys Gln Ser Ser Lys Ala Leu
1 5

<210> SEQ ID NO 351
<211> LENGTH: 17
<212> TYPE: PRT
<213> ORGANISM: Artificial Sequence
<220> FEATURE:
<223> OTHER INFORMATION: BCR-ABL Immunogenic Epitope

<400> SEQUENCE: 351

Ala Thr Gly Phe Lys Gln Ser Ser Lys Ala Leu Gln Arg Pro Val Ala
1 5 10 15

Ser

<210> SEQ ID NO 352
<211> LENGTH: 16
<212> TYPE: PRT
<213> ORGANISM: Artificial Sequence
<220> FEATURE:
<223> OTHER INFORMATION: dek-can Immunogenic Epitope

<400> SEQUENCE: 352

Thr Met Lys Gln Ile Cys Lys Lys Glu Ile Arg Arg Leu His Gln Tyr
1 5 10 15

<210> SEQ ID NO 353
<211> LENGTH: 10
<212> TYPE: PRT
<213> ORGANISM: Artificial Sequence
<220> FEATURE:
<223> OTHER INFORMATION: EFTUD2 Immunogenic Epitope

<400> SEQUENCE: 353

Lys Ile Leu Asp Ala Val Val Ala Gln Lys
1 5 10

<210> SEQ ID NO 354
<211> LENGTH: 9

<212> TYPE: PRT
<213> ORGANISM: Artificial Sequence
<220> FEATURE:
<223> OTHER INFORMATION: ETV6-AML1 Immunogenic Epitope

<400> SEQUENCE: 354

Arg Ile Ala Glu Cys Ile Leu Gly Met
1 5

<210> SEQ ID NO 355
<211> LENGTH: 15
<212> TYPE: PRT
<213> ORGANISM: Artificial Sequence
<220> FEATURE:
<223> OTHER INFORMATION: ETV6-AML1 Immunogenic Epitope

<400> SEQUENCE: 355

Ile Gly Arg Ile Ala Glu Cys Ile Leu Gly Met Asn Pro Ser Arg
1 5 10 15

<210> SEQ ID NO 356
<211> LENGTH: 10
<212> TYPE: PRT
<213> ORGANISM: Artificial Sequence
<220> FEATURE:
<223> OTHER INFORMATION: FLT3-ITD Immunogenic Epitope

<400> SEQUENCE: 356

Tyr Val Asp Phe Arg Glu Tyr Glu Tyr Tyr
1 5 10

<210> SEQ ID NO 357
<211> LENGTH: 9
<212> TYPE: PRT
<213> ORGANISM: Artificial Sequence
<220> FEATURE:
<223> OTHER INFORMATION: Cyclin-A1 Immunogenic Epitope

<400> SEQUENCE: 357

Phe Leu Asp Arg Phe Leu Ser Cys Met
1 5

<210> SEQ ID NO 358
<211> LENGTH: 11
<212> TYPE: PRT
<213> ORGANISM: Artificial Sequence
<220> FEATURE:
<223> OTHER INFORMATION: Cyclin-A1 Immunogenic Epitope

<400> SEQUENCE: 358

Ser Leu Ile Ala Ala Ala Ala Phe Cys Leu Ala
1 5 10

<210> SEQ ID NO 359
<211> LENGTH: 9
<212> TYPE: PRT
<213> ORGANISM: Artificial Sequence
<220> FEATURE:
<223> OTHER INFORMATION: FNDC3B Immunogenic Epitope

<400> SEQUENCE: 359

Val Val Met Ser Trp Ala Pro Pro Val
1 5

<210> SEQ ID NO 360
<211> LENGTH: 25
<212> TYPE: PRT

<213> ORGANISM: Artificial Sequence
<220> FEATURE:
<223> OTHER INFORMATION: pml-RARalpha Immunogenic Epitope

<400> SEQUENCE: 360

Asn Ser Asn His Val Ala Ser Gly Ala Gly Glu Ala Ala Ile Glu Thr
1               5                   10                  15

Gln Ser Ser Ser Ser Glu Glu Ile Val
            20                  25

<210> SEQ ID NO 361
<211> LENGTH: 10
<212> TYPE: PRT
<213> ORGANISM: Artificial Sequence
<220> FEATURE:
<223> OTHER INFORMATION: MAGE-C1 Immunogenic Epitope

<400> SEQUENCE: 361

Ile Leu Phe Gly Ile Ser Leu Arg Glu Val
1               5                   10

<210> SEQ ID NO 362
<211> LENGTH: 9
<212> TYPE: PRT
<213> ORGANISM: Artificial Sequence
<220> FEATURE:
<223> OTHER INFORMATION: MAGE-C1 Immunogenic Epitope

<400> SEQUENCE: 362

Lys Val Val Glu Phe Leu Ala Met Leu
1               5

<210> SEQ ID NO 363
<211> LENGTH: 13
<212> TYPE: PRT
<213> ORGANISM: Artificial Sequence
<220> FEATURE:
<223> OTHER INFORMATION: MAGE-C1 Immunogenic Epitope

<400> SEQUENCE: 363

Ser Ser Ala Leu Leu Ser Ile Phe Gln Ser Ser Pro Glu
1               5                   10

<210> SEQ ID NO 364
<211> LENGTH: 9
<212> TYPE: PRT
<213> ORGANISM: Artificial Sequence
<220> FEATURE:
<223> OTHER INFORMATION: MAGE-C1 Immunogenic Epitope

<400> SEQUENCE: 364

Ser Phe Ser Tyr Thr Leu Leu Ser Leu
1               5

<210> SEQ ID NO 365
<211> LENGTH: 9
<212> TYPE: PRT
<213> ORGANISM: Artificial Sequence
<220> FEATURE:
<223> OTHER INFORMATION: MAGE-C1 Immunogenic Epitope

<400> SEQUENCE: 365

Val Ser Ser Phe Phe Ser Tyr Thr Leu
1               5

<210> SEQ ID NO 366

<211> LENGTH: 15
<212> TYPE: PRT
<213> ORGANISM: Artificial Sequence
<220> FEATURE:
<223> OTHER INFORMATION: D393-CD20 Immunogenic Epitope

<400> SEQUENCE: 366

Lys Pro Leu Phe Arg Arg Met Ser Ser Leu Glu Leu Val Ile Ala
1 5 10 15

<210> SEQ ID NO 367
<211> LENGTH: 9
<212> TYPE: PRT
<213> ORGANISM: Artificial Sequence
<220> FEATURE:
<223> OTHER INFORMATION: MAGE-A3 (head and neck squamous cell carcinoma) Immunogenic Epitope

<400> SEQUENCE: 367

Glu Val Asp Pro Ile Gly His Leu Tyr
1 5

<210> SEQ ID NO 368
<211> LENGTH: 9
<212> TYPE: PRT
<213> ORGANISM: Artificial Sequence
<220> FEATURE:
<223> OTHER INFORMATION: MAGE-A3 (head and neck squamous cell carcinoma) Immunogenic Epitope

<400> SEQUENCE: 368

Phe Leu Trp Gly Pro Arg Ala Leu Val
1 5

<210> SEQ ID NO 369
<211> LENGTH: 9
<212> TYPE: PRT
<213> ORGANISM: Artificial Sequence
<220> FEATURE:
<223> OTHER INFORMATION: MAGE-A3 (head and neck squamous cell carcinoma) Immunogenic Epitope

<400> SEQUENCE: 369

Lys Val Ala Glu Leu Val His Phe Leu
1 5

<210> SEQ ID NO 370
<211> LENGTH: 9
<212> TYPE: PRT
<213> ORGANISM: Artificial Sequence
<220> FEATURE:
<223> OTHER INFORMATION: MAGE-A3 (head and neck squamous cell carcinoma) Immunogenic Epitope

<400> SEQUENCE: 370

Thr Phe Pro Asp Leu Glu Ser Glu Phe
1 5

<210> SEQ ID NO 371
<211> LENGTH: 9
<212> TYPE: PRT
<213> ORGANISM: Artificial Sequence
<220> FEATURE:
<223> OTHER INFORMATION: MAGE-A3 (head and neck squamous cell carcinoma) Immunogenic Epitope

<400> SEQUENCE: 371

Val Ala Glu Leu Val His Phe Leu Leu 1 5

<210> SEQ ID NO 372
<211> LENGTH: 10
<212> TYPE: PRT
<213> ORGANISM: Artificial Sequence
<220> FEATURE:
<223> OTHER INFORMATION: MAGE-A3 (head and neck squamous cell carcinoma)
Immunogenic Epitope

<400> SEQUENCE: 372

Met Glu Val Asp Pro Ile Gly His Leu Tyr
1 5 10

<210> SEQ ID NO 373
<211> LENGTH: 10
<212> TYPE: PRT
<213> ORGANISM: Artificial Sequence
<220> FEATURE:
<223> OTHER INFORMATION: MAGE-A3 (head and neck squamous cell carcinoma)
Immunogenic Epitope

<400> SEQUENCE: 373

Arg Glu Pro Val Thr Lys Ala Glu Met Leu
1 5 10

<210> SEQ ID NO 374
<211> LENGTH: 9
<212> TYPE: PRT
<213> ORGANISM: Artificial Sequence
<220> FEATURE:
<223> OTHER INFORMATION: MAGE-A3 (head and neck squamous cell carcinoma)
Immunogenic Epitope

<400> SEQUENCE: 374

Ala Glu Leu Val His Phe Leu Leu Leu
1 5

<210> SEQ ID NO 375
<211> LENGTH: 9
<212> TYPE: PRT
<213> ORGANISM: Artificial Sequence
<220> FEATURE:
<223> OTHER INFORMATION: MAGE-A3 (head and neck squamous cell carcinoma)
Immunogenic Epitope

<400> SEQUENCE: 375

Trp Gln Tyr Phe Phe Pro Val Ile Phe
1 5

<210> SEQ ID NO 376
<211> LENGTH: 9
<212> TYPE: PRT
<213> ORGANISM: Artificial Sequence
<220> FEATURE:
<223> OTHER INFORMATION: MAGE-A3 (head and neck squamous cell carcinoma)
Immunogenic Epitope

<400> SEQUENCE: 376

Glu Gly Asp Cys Ala Pro Glu Glu Lys
1 5

<210> SEQ ID NO 377
<211> LENGTH: 16
<212> TYPE: PRT
<213> ORGANISM: Artificial Sequence
<220> FEATURE:
<223> OTHER INFORMATION: MAGE-A3 (head and neck squamous cell carcinoma)

Immunogenic Epitope

<400> SEQUENCE: 377

Lys Lys Leu Leu Thr Gln His Phe Val Gln Glu Asn Tyr Leu Glu Tyr
1 5 10 15

<210> SEQ ID NO 378
<211> LENGTH: 15
<212> TYPE: PRT
<213> ORGANISM: Artificial Sequence
<220> FEATURE:
<223> OTHER INFORMATION: MAGE-A3 (head and neck squamous cell carcinoma) Immunogenic Epitope

<400> SEQUENCE: 378

Arg Lys Val Ala Glu Leu Val His Phe Leu Leu Leu Lys Tyr Arg
1 5 10 15

<210> SEQ ID NO 379
<211> LENGTH: 16
<212> TYPE: PRT
<213> ORGANISM: Artificial Sequence
<220> FEATURE:
<223> OTHER INFORMATION: MAGE-A3 (head and neck squamous cell carcinoma) Immunogenic Epitope

<400> SEQUENCE: 379

Ala Cys Tyr Glu Phe Leu Trp Gly Pro Arg Ala Leu Val Glu Thr Ser
1 5 10 15

<210> SEQ ID NO 380
<211> LENGTH: 12
<212> TYPE: PRT
<213> ORGANISM: Artificial Sequence
<220> FEATURE:
<223> OTHER INFORMATION: MAGE-A3 (head and neck squamous cell carcinoma) Immunogenic Epitope

<400> SEQUENCE: 380

Val Ile Phe Ser Lys Ala Ser Ser Ser Leu Gln Leu
1 5 10

<210> SEQ ID NO 381
<211> LENGTH: 15
<212> TYPE: PRT
<213> ORGANISM: Artificial Sequence
<220> FEATURE:
<223> OTHER INFORMATION: MAGE-A3 (head and neck squamous cell carcinoma) Immunogenic Epitope

<400> SEQUENCE: 381

Val Phe Gly Ile Glu Leu Met Glu Val Asp Pro Ile Gly His Leu
1 5 10 15

<210> SEQ ID NO 382
<211> LENGTH: 15
<212> TYPE: PRT
<213> ORGANISM: Artificial Sequence
<220> FEATURE:
<223> OTHER INFORMATION: MAGE-A3 (head and neck squamous cell carcinoma) Immunogenic Epitope

<400> SEQUENCE: 382

Gly Asp Asn Gln Ile Met Pro Lys Ala Gly Leu Leu Ile Ile Val
1 5 10 15

<210> SEQ ID NO 383

<211> LENGTH: 15
<212> TYPE: PRT
<213> ORGANISM: Artificial Sequence
<220> FEATURE:
<223> OTHER INFORMATION: MAGE-A3 (head and neck squamous cell carcinoma) Immunogenic Epitope

<400> SEQUENCE: 383

Thr Ser Tyr Val Lys Val Leu His His Met Val Lys Ile Ser Gly
1 5 10 15

<210> SEQ ID NO 384
<211> LENGTH: 16
<212> TYPE: PRT
<213> ORGANISM: Artificial Sequence
<220> FEATURE:
<223> OTHER INFORMATION: MAGE-A3 (head and neck squamous cell carcinoma) Immunogenic Epitope

<400> SEQUENCE: 384

Arg Lys Val Ala Glu Leu Val His Phe Leu Leu Leu Lys Tyr Arg Ala
1 5 10 15

<210> SEQ ID NO 385
<211> LENGTH: 16
<212> TYPE: PRT
<213> ORGANISM: Artificial Sequence
<220> FEATURE:
<223> OTHER INFORMATION: MAGE-A3 (head and neck squamous cell carcinoma) Immunogenic Epitope

<400> SEQUENCE: 385

Phe Leu Leu Leu Lys Tyr Arg Ala Arg Glu Pro Val Thr Lys Ala Glu
1 5 10 15

<210> SEQ ID NO 386
<211> LENGTH: 5
<212> TYPE: PRT
<213> ORGANISM: Artificial Sequence
<220> FEATURE:
<223> OTHER INFORMATION: Endolytic cleavage site

<400> SEQUENCE: 386

Pro Met Gly Ala Pro
1 5

<210> SEQ ID NO 387
<211> LENGTH: 5
<212> TYPE: PRT
<213> ORGANISM: Artificial Sequence
<220> FEATURE:
<223> OTHER INFORMATION: Endolytic cleavage site

<400> SEQUENCE: 387

Pro Met Gly Leu Pro
1 5

<210> SEQ ID NO 388
<211> LENGTH: 17
<212> TYPE: PRT
<213> ORGANISM: Artificial Sequence
<220> FEATURE:
<223> OTHER INFORMATION: Adenovirus ER signal

<400> SEQUENCE: 388

Met Arg Tyr Met Ile Leu Gly Leu Leu Ala Leu Ala Ala Val Cys Ser
1 5 10 15

Ala

<210> SEQ ID NO 389
<211> LENGTH: 23
<212> TYPE: PRT
<213> ORGANISM: Artificial Sequence
<220> FEATURE:
<223> OTHER INFORMATION: Tissue plasminogen activator peptide

<400> SEQUENCE: 389

Met Asp Ala Met Leu Arg Gly Leu Cys Cys Val Leu Leu Leu Cys Gly
1               5                   10                  15

Ala Val Phe Val Ser Pro Ser
            20

<210> SEQ ID NO 390
<211> LENGTH: 124
<212> TYPE: PRT
<213> ORGANISM: Artificial Sequence
<220> FEATURE:
<223> OTHER INFORMATION: E. coli heat labile enterotoxin subunit B

<400> SEQUENCE: 390

Met Asn Lys Val Lys Phe Tyr Val Leu Phe Thr Ala Leu Leu Ser Ser
1               5                   10                  15

Leu Cys Ala His Gly Ala Pro Gln Ser Ile Thr Glu Leu Cys Ser Glu
            20                  25                  30

Tyr His Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
    50                  55                  60

Ser Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn
        115                 120

<210> SEQ ID NO 391
<211> LENGTH: 12
<212> TYPE: PRT
<213> ORGANISM: Artificial Sequence
<220> FEATURE:
<223> OTHER INFORMATION: Influenza virus matrix protein M57-68

<400> SEQUENCE: 391

Lys Gly Ile Leu Gly Phe Val Phe Thr Leu Leu Val
1               5                   10

<210> SEQ ID NO 392
<211> LENGTH: 20
<212> TYPE: PRT
<213> ORGANISM: Artificial Sequence
<220> FEATURE:
<223> OTHER INFORMATION: Tetanus toxin fragment c

<400> SEQUENCE: 392

Ile Asp Lys Ile Ser Asp Val Ser Thr Ile Val Pro Tyr Ile Gly Pro
1               5                   10                  15

Ala Leu Asn Ile

20

<210> SEQ ID NO 393
<211> LENGTH: 25
<212> TYPE: PRT
<213> ORGANISM: Artificial Sequence
<220> FEATURE:
<223> OTHER INFORMATION: Lysosome-associated membrane protein

<400> SEQUENCE: 393

Met Leu Ile Pro Ile Ala Val Gly Gly Ala Leu Ala Gly Leu Val Leu
1 5 10 15

Ile Val Leu Ile Ala Tyr Leu Val Gly
20 25

<210> SEQ ID NO 394
<211> LENGTH: 14
<212> TYPE: PRT
<213> ORGANISM: Artificial Sequence
<220> FEATURE:
<223> OTHER INFORMATION: Hsp70 peptide

<400> SEQUENCE: 394

Thr Lys Asp Asn Asn Leu Leu Gly Arg Phe Glu Leu Ser Gly
1 5 10

<210> SEQ ID NO 395
<211> LENGTH: 9
<212> TYPE: PRT
<213> ORGANISM: Artificial Sequence
<220> FEATURE:
<223> OTHER INFORMATION: GP70

<400> SEQUENCE: 395

Ser Pro Ser Tyr Ala Tyr His Gln Phe
1 5

<210> SEQ ID NO 396
<211> LENGTH: 9
<212> TYPE: PRT
<213> ORGANISM: Artificial Sequence
<220> FEATURE:
<223> OTHER INFORMATION: MuLV gp70

<400> SEQUENCE: 396

Ser Pro Ser Tyr Val Tyr His Gln Phe
1 5

<210> SEQ ID NO 397
<211> LENGTH: 14
<212> TYPE: PRT
<213> ORGANISM: Artificial Sequence
<220> FEATURE:
<223> OTHER INFORMATION: Gp70

<400> SEQUENCE: 397

Arg Ser Lys Arg Leu Ser Pro Ser Tyr Val Tyr His Gln Phe
1 5 10

<210> SEQ ID NO 398
<211> LENGTH: 84
<212> TYPE: DNA
<213> ORGANISM: Artificial Sequence
<220> FEATURE:
<223> OTHER INFORMATION: Gp70

<400> SEQUENCE: 398
aggagcaaaa gagtgagccc cagctacgtg taccaccagt tctcctcgtt ttctcactcg 60
gggtcgatgc acatggtggt caag 84

<210> SEQ ID NO 399
<211> LENGTH: 13
<212> TYPE: PRT
<213> ORGANISM: Artificial Sequence
<220> FEATURE:
<223> OTHER INFORMATION: NY-ESO-1

<400> SEQUENCE: 399

Arg Ser Lys Arg Leu Leu Met Trp Ile Thr Gln Cys Phe
1 5 10

<210> SEQ ID NO 400
<211> LENGTH: 78
<212> TYPE: DNA
<213> ORGANISM: Artificial Sequence
<220> FEATURE:
<223> OTHER INFORMATION: NY-ESO-1

<400> SEQUENCE: 400
aggagcaaaa gactgctgat gtggatcacc cagtgcttct cctcgttttc tgacgactac 60
acctagtggg tcacgaag 78

<210> SEQ ID NO 401
<211> LENGTH: 13
<212> TYPE: PRT
<213> ORGANISM: Artificial Sequence
<220> FEATURE:
<223> OTHER INFORMATION: pbk

<400> SEQUENCE: 401

Arg Ser Lys Arg Gly Ser Pro Phe Pro Ala Ala Val Thr
1 5 10

<210> SEQ ID NO 402
<211> LENGTH: 78
<212> TYPE: DNA
<213> ORGANISM: Artificial Sequence
<220> FEATURE:
<223> OTHER INFORMATION: pbk

<400> SEQUENCE: 402
aggagcaaaa gaggcagccc cttccccgcc gctgtgacct cctcgttttc tccgtcgggg 60
aaggggcggc gacactgg 78

<210> SEQ ID NO 403
<211> LENGTH: 24
<212> TYPE: DNA
<213> ORGANISM: Artificial Sequence
<220> FEATURE:
<223> OTHER INFORMATION: Primer 1

<400> SEQUENCE: 403
aggagcaaaa gacacagccc cagc 24

<210> SEQ ID NO 404
<211> LENGTH: 24
<212> TYPE: DNA
<213> ORGANISM: Artificial Sequence
<220> FEATURE:
<223> OTHER INFORMATION: Primer 2

<400> SEQUENCE: 404
tcttttgctc ctgaactggt ggta 24

<210> SEQ ID NO 405
<211> LENGTH: 24
<212> TYPE: DNA
<213> ORGANISM: Artificial Sequence
<220> FEATURE:
<223> OTHER INFORMATION: Primer 3

<400> SEQUENCE: 405
taccaccagt tcaggagcaa aaga 24

<210> SEQ ID NO 406
<211> LENGTH: 24
<212> TYPE: DNA
<213> ORGANISM: Artificial Sequence
<220> FEATURE:
<223> OTHER INFORMATION: Primer 4

<400> SEQUENCE: 406
tcttttgctc ctgaagcact gggt 24

<210> SEQ ID NO 407
<211> LENGTH: 24
<212> TYPE: DNA
<213> ORGANISM: Artificial Sequence
<220> FEATURE:
<223> OTHER INFORMATION: Primer 5

<400> SEQUENCE: 407
acccagtgct tcaggagcaa aaga 24

<210> SEQ ID NO 408
<211> LENGTH: 18
<212> TYPE: DNA
<213> ORGANISM: Artificial Sequence
<220> FEATURE:
<223> OTHER INFORMATION: Primer 6

<400> SEQUENCE: 408
ggtcacagcg gcggggaa 18

<210> SEQ ID NO 409
<211> LENGTH: 31
<212> TYPE: DNA
<213> ORGANISM: Artificial Sequence
<220> FEATURE:
<223> OTHER INFORMATION: cDNA5_R reverse primer

<400> SEQUENCE: 409
tttttgaaat gttaaaaaca aaattttgtt g 31

<210> SEQ ID NO 410
<211> LENGTH: 20
<212> TYPE: DNA
<213> ORGANISM: Artificial Sequence
<220> FEATURE:
<223> OTHER INFORMATION: Forward primer

<400> SEQUENCE: 410
tgatccgacc agcaaaactc 20

<210> SEQ ID NO 411
<211> LENGTH: 9

<212> TYPE: PRT
<213> ORGANISM: Artificial Sequence
<220> FEATURE:
<223> OTHER INFORMATION: HLA allele

<400> SEQUENCE: 411

Ser Leu Ala Gln Asp Ala Pro Pro Leu
1               5

<210> SEQ ID NO 412
<211> LENGTH: 9
<212> TYPE: PRT
<213> ORGANISM: Artificial Sequence
<220> FEATURE:
<223> OTHER INFORMATION: HLA allele

<400> SEQUENCE: 412

Leu Met Trp Ile Thr Gln Cys Phe Leu
1               5

<210> SEQ ID NO 413
<211> LENGTH: 9
<212> TYPE: PRT
<213> ORGANISM: Artificial Sequence
<220> FEATURE:
<223> OTHER INFORMATION: HLA allele

<400> SEQUENCE: 413

Arg Leu Leu Glu Phe Tyr Leu Ala Met
1               5

<210> SEQ ID NO 414
<211> LENGTH: 9
<212> TYPE: PRT
<213> ORGANISM: Artificial Sequence
<220> FEATURE:
<223> OTHER INFORMATION: HLA allele

<400> SEQUENCE: 414

Trp Ile Thr Gln Cys Phe Leu Pro Val
1               5

<210> SEQ ID NO 415
<211> LENGTH: 9
<212> TYPE: PRT
<213> ORGANISM: Artificial Sequence
<220> FEATURE:
<223> OTHER INFORMATION: HLA allele

<400> SEQUENCE: 415

Gly Val Leu Leu Lys Glu Phe Thr Val
1               5

<210> SEQ ID NO 416
<211> LENGTH: 9
<212> TYPE: PRT
<213> ORGANISM: Artificial Sequence
<220> FEATURE:
<223> OTHER INFORMATION: HLA allele

<400> SEQUENCE: 416

Ala Gln Asp Ala Pro Pro Leu Pro Val
1               5

<210> SEQ ID NO 417
<211> LENGTH: 9
<212> TYPE: PRT

<213> ORGANISM: Artificial Sequence
<220> FEATURE:
<223> OTHER INFORMATION: HLA allele

<400> SEQUENCE: 417

Gln Gln Leu Ser Leu Leu Met Trp Ile
1 5

<210> SEQ ID NO 418
<211> LENGTH: 9
<212> TYPE: PRT
<213> ORGANISM: Artificial Sequence
<220> FEATURE:
<223> OTHER INFORMATION: HLA allele

<400> SEQUENCE: 418

Leu Gln Leu Ser Ile Ser Ser Cys Leu
1 5

<210> SEQ ID NO 419
<211> LENGTH: 9
<212> TYPE: PRT
<213> ORGANISM: Artificial Sequence
<220> FEATURE:
<223> OTHER INFORMATION: HLA allele

<400> SEQUENCE: 419

Ile Leu Thr Ile Arg Leu Thr Ala Ala
1 5

<210> SEQ ID NO 420
<211> LENGTH: 9
<212> TYPE: PRT
<213> ORGANISM: Artificial Sequence
<220> FEATURE:
<223> OTHER INFORMATION: HLA allele

<400> SEQUENCE: 420

Ser Ile Ser Ser Cys Leu Gln Gln Leu
1 5

<210> SEQ ID NO 421
<211> LENGTH: 9
<212> TYPE: PRT
<213> ORGANISM: Artificial Sequence
<220> FEATURE:
<223> OTHER INFORMATION: HLA allele

<400> SEQUENCE: 421

Cys Leu Gln Gln Leu Ser Leu Leu Met
1 5

<210> SEQ ID NO 422
<211> LENGTH: 9
<212> TYPE: PRT
<213> ORGANISM: Artificial Sequence
<220> FEATURE:
<223> OTHER INFORMATION: HLA allele

<400> SEQUENCE: 422

Phe Thr Val Ser Gly Asn Ile Leu Thr
1 5

<210> SEQ ID NO 423
<211> LENGTH: 9
<212> TYPE: PRT
<213> ORGANISM: Artificial Sequence -continued

```
<220> FEATURE:
<223> OTHER INFORMATION: HLA allele

<400> SEQUENCE: 423

Phe Tyr Leu Ala Met Pro Phe Ala Thr
1               5


<210> SEQ ID NO 424
<211> LENGTH: 9
<212> TYPE: PRT
<213> ORGANISM: Artificial Sequence
<220> FEATURE:
<223> OTHER INFORMATION: HLA allele

<400> SEQUENCE: 424

Thr Val Ser Gly Asn Ile Leu Thr Ile
1               5


<210> SEQ ID NO 425
<211> LENGTH: 9
<212> TYPE: PRT
<213> ORGANISM: Artificial Sequence
<220> FEATURE:
<223> OTHER INFORMATION: HLA allele

<400> SEQUENCE: 425

Ser Cys Leu Gln Gln Leu Ser Leu Leu
1               5


<210> SEQ ID NO 426
<211> LENGTH: 9
<212> TYPE: PRT
<213> ORGANISM: Artificial Sequence
<220> FEATURE:
<223> OTHER INFORMATION: HLA allele

<400> SEQUENCE: 426

Gln Leu Gln Leu Ser Ile Ser Ser Cys
1               5


<210> SEQ ID NO 427
<211> LENGTH: 9
<212> TYPE: PRT
<213> ORGANISM: Artificial Sequence
<220> FEATURE:
<223> OTHER INFORMATION: GAGE-3,4,5,6,7 (Esophageal squamous cell
      carcinoma and esophageal adenocarcinoma)

<400> SEQUENCE: 427

Tyr Tyr Trp Pro Arg Pro Arg Arg Tyr
1               5
```